(12) United States Patent
Keller et al.

(10) Patent No.: US 9,702,008 B2
(45) Date of Patent: Jul. 11, 2017

(54) MIRNA FINGERPRINT IN THE DIAGNOSIS OF DISEASES

(71) Applicant: Comprehensive Biomarker Center GmbH, Heidelberg (DE)

(72) Inventors: Andreas Keller, Puettlingen (DE); Eckart Meese, Huetschenhausen (DE); Anne Borries, Heidelberg (DE); Peer Friedrich Staehler, Mannheim (DE); Markus Beier, Weinheim (DE)

(73) Assignee: HUMMINGBIRD DIAGNOSTICS GMBH, Heidelberg (DE)

(*) Notice: Subject to any disclaimer, the term of this patent is extended or adjusted under 35 U.S.C. 154(b) by 0 days.

(21) Appl. No.: 14/867,174

(22) Filed: Sep. 28, 2015

(65) Prior Publication Data

US 2016/0076103 A1    Mar. 17, 2016

Related U.S. Application Data

(62) Division of application No. 13/376,225, filed as application No. PCT/EP2010/057944 on Jun. 7, 2010, now Pat. No. 9,194,002.

(60) Provisional application No. 61/184,452, filed on Jun. 5, 2009, provisional application No. 61/213,971, filed on Aug. 3, 2009, provisional application No. 61/287,521, filed on Dec. 17, 2009.

(30) Foreign Application Priority Data

Dec. 17, 2009 (EP) .................................. 09015668

(51) Int. Cl.
*C12Q 1/68* (2006.01)
*G06F 19/20* (2011.01)
*G06F 19/24* (2011.01)

(52) U.S. Cl.
CPC ......... *C12Q 1/6883* (2013.01); *C12Q 1/6809* (2013.01); *C12Q 1/6886* (2013.01); *G06F 19/20* (2013.01); *G06F 19/24* (2013.01); *C12Q 2600/106* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 9,194,002 B2 * | 11/2015 | Keller ................ | C12Q 1/6809 |
| 2002/0172968 A1 | 11/2002 | Liu et al. | |
| 2006/0019258 A1 | 1/2006 | Yearkley | |
| 2007/0050146 A1 | 3/2007 | Bentwich et al. | |
| 2007/0161004 A1 | 7/2007 | Brown et al. | |
| 2011/0143948 A1 | 6/2011 | Perera | |

FOREIGN PATENT DOCUMENTS

| | | |
|---|---|---|
| EP | 2133431 A1 | 12/2009 |
| EP | 2327800 A1 | 6/2011 |
| WO | WO 2008/104984 A2 | 9/2008 |
| WO | WO 2008/117278 A2 | 10/2008 |
| WO | WO 2009/025790 A1 | 2/2009 |
| WO | WO 2009/033185 A1 | 3/2009 |
| WO | WO 2009/036332 A1 | 3/2009 |
| WO | WO 2009/055979 A1 | 5/2009 |
| WO | WO 2009/057113 A2 | 5/2009 |
| WO | WO 2009/070653 A1 | 6/2009 |
| WO | WO 2009/099905 A2 | 8/2009 |
| WO | WO 2009/108866 A2 | 9/2009 |
| WO | WO 2009/147525 A1 | 12/2009 |

OTHER PUBLICATIONS

Achiron et al., "Peripheral blood gene expression signature mirrors central nervous system disease: the model of multiple sclerosis." Autoimmunity Reviews, vol. 5, No. 8, Oct. 2006 (Oct. 2006), pp. 517-522, XP002596358 ISSN: 1568-9972 the whole document.
Arnett et al., "Microrna Expression Profiling in Multiple Sclerosis and Eae" Journal of Neurochemistry, vol. 108, No. Suppl. Mar. 1, 2009 (Mar. 2009), p. 81, XP002596357 & 40th Annual Meeting of The American-Society-For-Neurochemistry; Charleston, SC, USA ISSN: 0022-3042 the whole document.
Chen et al., "Characterization of microRNAs in serum: a novel class of biomarkers for diagnosis of cancer and other diseases" Cell Research—Xibao Yanjiu, Nature Publishing Group, GB, CN LNO D01:10.1038/CR.2008.282, vol. 18, No. 10, Oct. 1, 2008 (Oct. 1, 2008), pp. 997-1006, XP00255942 ISSN: 1001-0602 [retrieved on 2008-09-002] the whole document.
Guo et al., Confirmation of gene expression-based prediction of survival in non-small cell lung cancer. Clinical Cancer Research, vol. 14, No. 24, Dec. 15, 2008, pp. 8213-8220.
Keller et al., "Multiple Sclerosis: MicroRNA Expression Profiles Accurately Differentiate Patients with Relapsing-Remitting Disease from Healthy Controls" Plos One, vol. 4, No. 10, Oct. 2009 (Oct. 2009), XP002596072 ISSN: 1932-6203 the whole document.
Krell et al., "MicroRNAs in the cancer clinic". Frontiers in Bioscience (Elite Edition), vol. 5, Jan. 2013, pp. 204-213.
Kruhøffer et al Isolation of microarray-grade total RNA, MicroRNA, and DNA from a single PAXgene Blood RNA tube. Journal of Molecular Diagnostics, vol. 9, No. 4, Sep. 2007, pp. 452-458.
Leidinger et al., "High-throughput miRNA profiling of human melanoma blood samples." BMC Cancer 2010 LNKD-PUBMED:20529253, vol. 10, Jun. 7, 2010 (Jun. 7, 2010), p. 262, XP002597623 ISSN: 1471-2407 the whole document.
Lu et al., "An Analysis of Human MicroRNA and Disease Associations" Plos One, vol. 3, No. 10, Oct. 2008 (Oct. 2008), XP002596074 ISSN: 1932-6203 the whole document.
McShane et al., "Reporting recommendations for tumor MARKer prognostic studies (REMARK)". British Journal of Cancer, vol. 93, 2005, pp. 387-391.

(Continued)

*Primary Examiner* — Jim Ketter
(74) *Attorney, Agent, or Firm* — Wenderoth, Lind & Ponack, L.L.P.

(57) ABSTRACT

The present invention provides novel methods for diagnosing a state of health based on the determination of specific miRNAs that have altered expression levels in different conditions, e.g. disease states compared to healthy controls.

15 Claims, 218 Drawing Sheets

(56) References Cited

OTHER PUBLICATIONS

Figure 1:
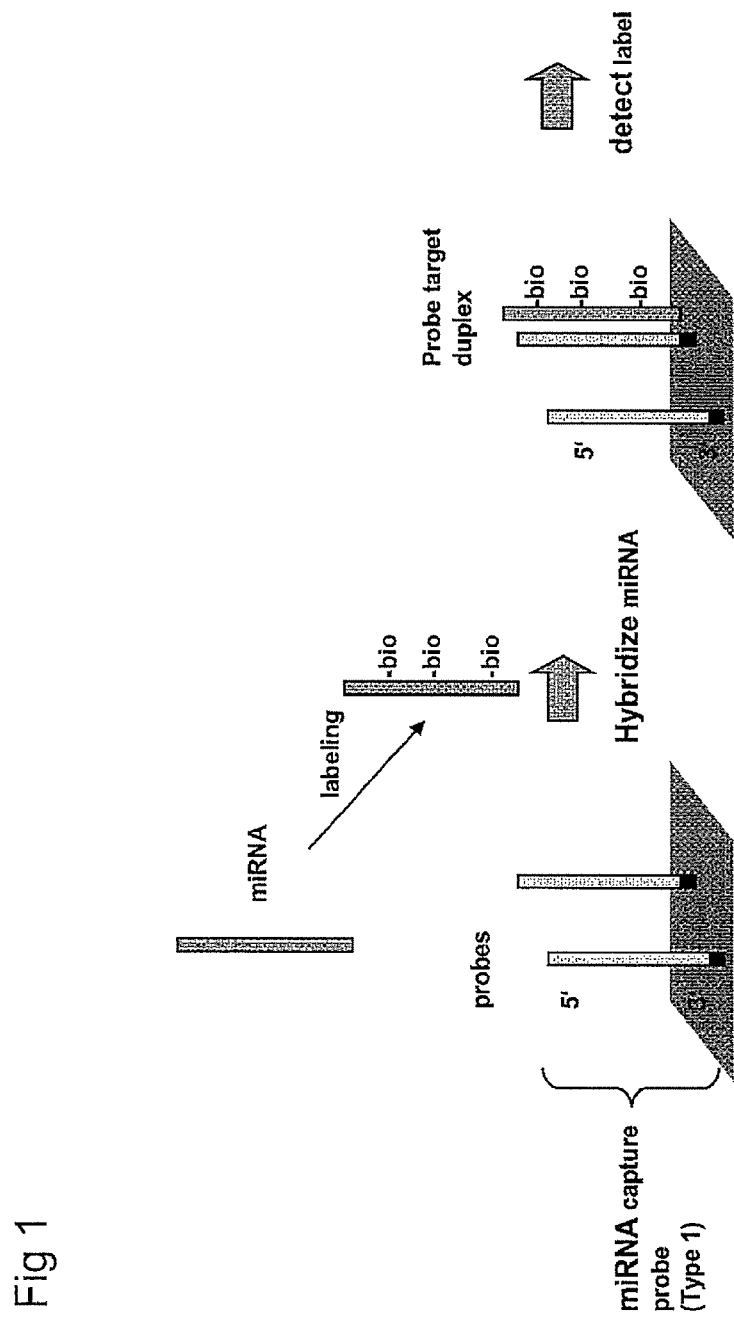

Mitchell et al., "Circulating microRNAs as stable blood-based markers for cancer detection" Jul. 29, 2008 (Jul. 29, 2008), Proceedings of the National Academy of Sciences of The United States (PNAS), National Academy of Science, US LNKD D01:10.1073/PNAS.0804549105, pp. 10513-10518, XP002518102 ISSN: 0027-8424 [retrieved on Jul. 29, 2008] the whole document.
Molnar et al., "Changes in miRNA expression in solid tumors: An miRNA profiling in melanomas" Seminars in Cancer Biology, Saunders Scientific Publications, Philadelphia, PA, US LNKD D01:10.1016/J. SEMCANCER.2008.01.001, vol. 18, No. 2, Jan. 15, 2008 (Jan. 15, 2008), pp. 111-122, XP022517940 ISSN: 1044-579X the whole document.
Office Action dated Nov. 6, 2014 in U.S. Appl. No. 13/376,281, 22 pages.
Office Action dated Nov. 6, 2014 in U.S. Appl. No. 13/376,225, 28 pages.
Otaegui et al., "Differential Micro RNA Expression in PBMC from Multiple Sclerosis Patients" Plos One, vol. 4, No. 7, Jul. 2009 (Jul. 2009), XP002596073 ISSN: 1932-6203 table 2.
Pauley et al., "Unregulated miR_146a expression in peripheral blood mononuclear cells from rheumatoid arthritis patients." Arthritis Research & Therapy, vol. 10, No. 4, R101, Aug. 29, 2008 (Aug. 29, 2008), pp. 1-10 XP002596359 ISSN: 1478-6362 the whole document.
PAXgene® Blood RNA Kit Handbook, Jun. 2005, printed as pp. 1-36.
PAXgene® Blood RNA Kit Handbook, Version 2, Mar. 2009, printed as pp. 1-56.
Rabinowitz et al., "Exosomal microRNA: a diagnostic marker for lung cancer." Clinical Lung Cancer Jan. 2009 LNKD—PUBMED:19289371, vol. 10, No. 1, Jan. 2009 (Jan. 2009), pp. 42-46, XP002595815 ISSN: 1525-7304 the whole document.
Schneider, Non-small cell hung cancer staging: proposed revisions to the TNM system. Cancer Imaging, vol. 8, Aug. 2008, pp. 181-185.
Volinia et al., A microRNA expression signature of human solid tumors defines cancer gene targets, Proceedings of the National Academy of Sciences, USA, vol. 103, No. 7, pp. 2257-2261, Feb. 2006, including Supporting Information printed as pp. 1-17.
Young et al., Wheater's Functional Histology: A Text and Colour Atlas, 5th edition, Churchhill Livingstone, Elsevier, 2006, pages on "Blood cell types," printed as p. 1.
U.S. Appl. No. 13/376,243, filed Feb. 28, 2012.
U.S. Appl. No. 13/376,281, filed Jan. 19, 2012.
Keller et al., "miRNAs in hung cancer—Studying complex fingerprings in patient's blood cells by microarray experiments", BMC Cancer, BioMed Central, London, GB LNKD-D01:10.1186/1471/2407-9-353, vol. 9, No. 1, Oct. 6, 2009, p. 353, XP021062692 ISSN: 1471-2407 the whole document.
PAXgene Blood RNA, Prenalytics, Processing, Centrifugation, May 2009, 4 pages.
Panomics, QuantiGene® Technical Note, Factors Affecting Blood Gene Expression, 4 pages, 2007.
Debey-Pascher S. et al. Blood-Based miRNA Preparation for Non-invasive Biomarker Development. Methods Mol Biol. 822:307-338 (2012).

\* cited by examiner

Fig 5

Example: human mature miRNA let-7a
ID: hsa-let-7a
Accession-Nr.: MIMAT0000062
Sequence: 5'-UGAGGUAGUAGGUUGUAUAGUU-3' miRNA capture probes :

■ Type 1 (miRNA Hybridization Assay)

surface-3'-ACTCCATCATCCAACATATCAA-5'
surface-5'-AACTATACAACCTACTACCTCA-3'

■ Type 2 (miRNA Tandem Hybridization Assay)

surface-3'-ACTCCATCATCCAACATATCAA-SP-ACTCCATCATCCAACATATCAA-5'
surface-5'-AACTATACAACCTACTACCTCA-SP-AACTATACAACCTACTACCTCA-3'

■ Type 3 (miRNA RAKE-Assay)

surface-5'-EL-AACTATACAACCTACTACCTCA-3'

■ Type 4 (miRNA MPEA-Assay)

surface-3'-ACTCCATCATCCAACATATCAA-EL-5'

Figure 6

Type 2 (miRNA Tandem Hybridization Assay)

surface-3'-ACTCCATCATCCAACATATCAA-SP-ACTCCATCATCCAACATATCAA-5'
surface-5'-AACTATACAACCTACTACCTCA-SP-AACTATACAACCTACTACCTCA-3'

With SP:

- nucleotide sequence with n = 0 –12 nucleotides chosen on the basis of showing low complementarity to potential target sequences, therefore resulting in no to low degree of crosshybridisation to target mixture preferentially : n = 0, no spacer between the 2 miRNA probe sequence stretches

Fig 7

Type 3 (miRNA RAKE-Assay)

surface-5'-EL-AACTATACAACCTACTACCTCA-3'

Type 4 (miRNA MPEA-Assay)

surface-3'-ACTCCATCATCCAACATATCAA-EL-5'

With EL:

- nucleotide sequence with n = 0 – 30 nucleotides chosen on the basis of showing low complementarity to potential target sequences, therefore resulting in no to low degree of crosshybridisation to target mixture preferentially: homomeric sequence stretch, $-N_n-$ with n = 1-30, N = A or C, or T, or G especially preferentially: homomeric sequence stretch, $-N_n-$ with n = 1-12, N = A or C, or T, or G

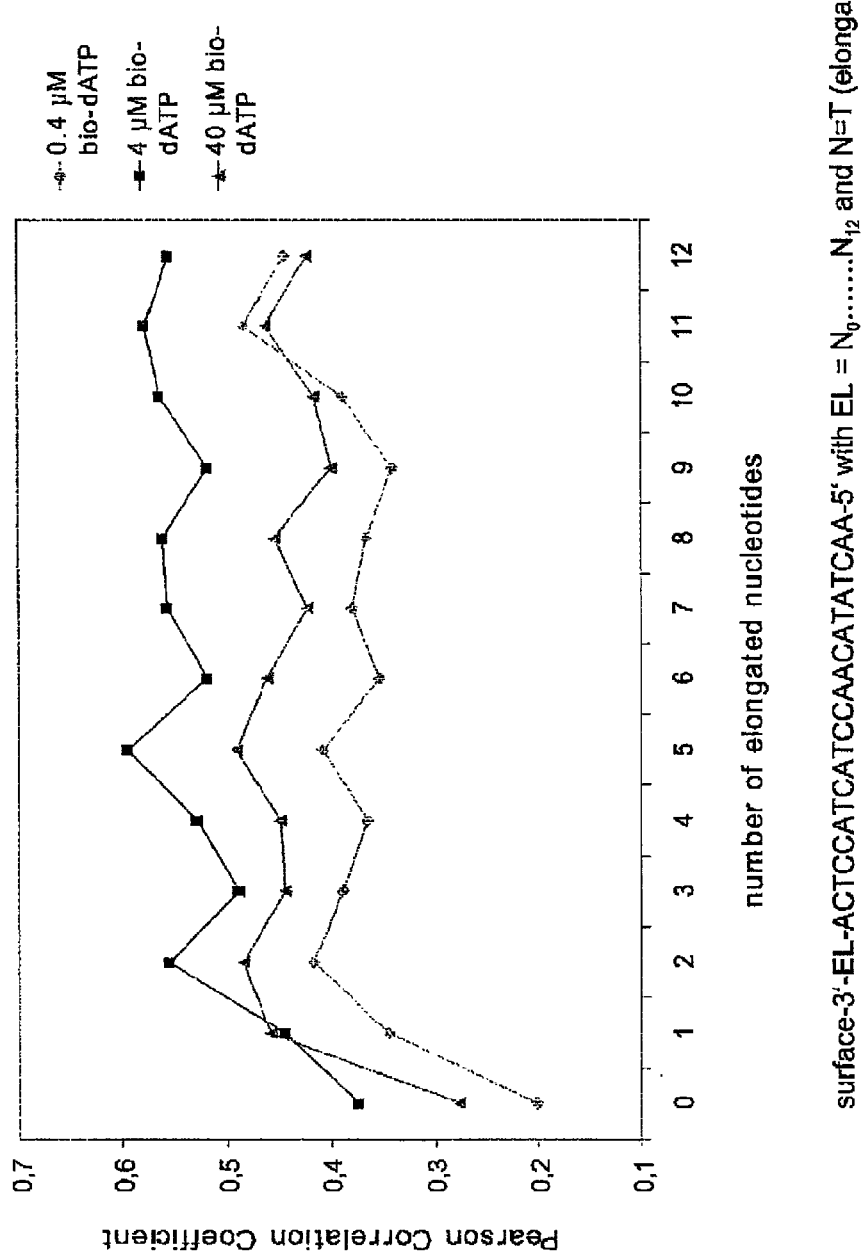

FIG. 10A

| SEQ ID NO: | No. | microRNA | Sequence | Median Cancer | Median Normal | Fold Quotient | Mutual Information |
|---|---|---|---|---|---|---|---|
| SEQ ID NO: 431 | 1 | hsa-miR-361-5p | uuaucagaauccuccaggguac | 606,46 | 53 | 11,44 | 0,45 |
| SEQ ID NO: 531 | 2 | hsa-miR-23b | aucacauugccagggauuacc | 3976,97 | 2099,43 | 1,89 | 0,42 |
| SEQ ID NO: 805 | 3 | hsa-miR-126 | ucguaccgugaguaauaaugcg | 606,46 | 3428,42 | 0,18 | 0,42 |
| SEQ ID NO: 250 | 4 | hsa-miR-527 | cugcaaaggaagcccuuuc | 74,78 | 68,44 | 1,09 | 0,42 |
| SEQ ID NO: 507 | 5 | hsa-miR-29a | uagcaccaucugaaaucgguua | 447 | 108,56 | 4,12 | 0,36 |
| SEQ ID NO: 888 | 6 | hsa-let-7i | ugagguaguaguuugugcuguu | 4106,11 | 6349,31 | 0,65 | 0,34 |
| SEQ ID NO: 602 | 7 | hsa-miR-19a | ugugcaaaucuaugcaaaacuga | 420,06 | 1 | 420,06 | 0,34 |
| SEQ ID NO: 514 | 8 | hsa-miR-28-5p | aaggagcucacagucuauugag | 454,22 | 108,56 | 4,18 | 0,33 |
| SEQ ID NO: 657 | 9 | hsa-miR-185* | aggggcugguuuccucugguc | 55,56 | 47,06 | 1,18 | 0,31 |
| SEQ ID NO: 533 | 10 | hsa-miR-23a | aucacauugccaggaguuuuc | 3428,42 | 1797,04 | 1,91 | 0,3 |
| SEQ ID NO: 633 | 11 | hsa-miR-1914* | ggaggggucccgcacuggagg | 249,39 | 153 | 1,63 | 0,3 |
| SEQ ID NO: 502 | 12 | hsa-miR-29c | uagcaccauuugaaaucgguua | 340,89 | 36,11 | 9,44 | 0,29 |
| SEQ ID NO: 320 | 13 | hsa-miR-505* | gggagccaggaaguauugagu | 280,11 | 90,78 | 3,09 | 0,29 |
| SEQ ID NO: 897 | 14 | hsa-let-7d | agagguaguagguugcauaguu | 6795,89 | 13307,74 | 0,51 | 0,29 |
| SEQ ID NO: 403 | 15 | hsa-miR-378 | acuggacuuggaguucagaagg | 284,22 | 21,56 | 13,19 | 0,29 |
| SEQ ID NO: 505 | 16 | hsa-miR-29b | uagcaccauuugaaaucaguguu | 337,83 | 82,06 | 4,12 | 0,29 |
| SEQ ID NO: 155 | 17 | hsa-miR-604 | aggcugcgaauucaggac | 245 | 90,78 | 2,7 | 0,29 |
| SEQ ID NO: 549 | 18 | hsa-miR-22 | aagcugccaguugaagaacugu | 7978,5 | 3868,5 | 2,06 | 0,28 |
| SEQ ID NO: 901 | 19 | hsa-let-7b | ugagguaguagguugugugguu | 6349,31 | 9746,17 | 0,65 | 0,28 |
| SEQ ID NO: 509 | 20 | hsa-miR-299-3p | uauguggauggaaccgcuu | 58,78 | 55,22 | 1,06 | 0,28 |
| SEQ ID NO: 385 | 21 | hsa-miR-423-3p | agcucggucugaggcccccagu | 1797,04 | 463,22 | 3,88 | 0,27 |
| SEQ ID NO: 649 | 22 | hsa-miR-18a* | acugccauagugucccuuucugg | 1040,44 | 119,89 | 8,68 | 0,27 |
| SEQ ID NO: 644 | 23 | hsa-miR-1909 | cgcaggggccgggugcucaccg | 154,22 | 132,56 | 1,16 | 0,26 |
| SEQ ID NO: 899 | 24 | hsa-let-7c | ugagguaguagguuguaugguu | 5660,31 | 8969,72 | 0,63 | 0,26 |
| SEQ ID NO: 682 | 25 | hsa-miR-15a | uagcagcacauaaugguuugug | 3428,42 | 5944,79 | 0,58 | 0,25 |
| SEQ ID NO: 381 | 26 | hsa-miR-425 | aaugacacgaucacuccguuga | 11838,82 | 7392,17 | 1,6 | 0,25 |
| SEQ ID NO: 21 | 27 | hsa-miR-93* | acugcugagcuagcacuccg | 480,44 | 30,44 | 15,78 | 0,25 |
| SEQ ID NO: 85 | 28 | hsa-miR-665 | accaggaggcugaggccccu | 212 | 191,33 | 1,11 | 0,25 |
| SEQ ID NO: 478 | 29 | hsa-miR-30e | uguaaacauccuugacugaag | 369,89 | 129,44 | 2,86 | 0,25 |
| SEQ ID NO: 450 | 30 | hsa-miR-339-3p | ugagcgccucgacgacagaccg | 209,67 | 109,67 | 1,91 | 0,25 |
| SEQ ID NO: 750 | 31 | hsa-miR-1307 | acucgccggcguggcgucgug | 82,06 | 70,67 | 1,16 | 0,25 |
| SEQ ID NO: 130 | 32 | hsa-miR-625* | gacuauagaacuuucccuca | 52 | 21,89 | 2,38 | 0,23 |

FIG. 10A (Cont.)

| SEQ ID NO | # | miRNA | Sequence | | | |
|---|---|---|---|---|---|---|
| SEQ ID NO: 627 | 33 | hsa-miR-193a-5p | ugggucuuugcggcgagauga | 46,89 | 30,44 | 1,54 | 0,23 |
| SEQ ID NO: 746 | 34 | hsa-miR-130b | cagugcaaugaugaaagggcau | 388 | 185,22 | 2,09 | 0,23 |
| SEQ ID NO: 674 | 35 | hsa-miR-17* | acugcagugaaggcacuuguag | 194 | 90,78 | 2,14 | 0,23 |
| SEQ ID NO: 189 | 36 | hsa-miR-574-5p | ugagugugugugugugagugugu | 108,56 | 30,22 | 3,59 | 0,22 |
| SEQ ID NO: 466 | 37 | hsa-miR-324-3p | acugcccaguucagcgcaugg | 1221,94 | 700,5 | 1,74 | 0,22 |
| SEQ ID NO: 529 | 38 | hsa-miR-24 | uggcucaguucagcaggaacag | 511,89 | 331,06 | 1,55 | 0,21 |
| SEQ ID NO: 125 | 39 | hsa-miR-629 | ugggcuuuacguugggagaacu | 106,11 | 63,11 | 1,68 | 0,21 |
| SEQ ID NO: 740 | 40 | hsa-miR-1323 | ucaaaaacugagggcauuuucu | 68,22 | 44 | 1,55 | 0,21 |
| SEQ ID NO: 890 | 41 | hsa-let-7g | ugagguaguaguuuguacaguu | 3428,42 | 6795,89 | 0,5 | 0,21 |
| SEQ ID NO: 825 | 42 | hsa-miR-1246 | aauggauuuuuggagcagg | 4915,83 | 3572,67 | 1,38 | 0,21 |
| SEQ ID NO: 559 | 43 | hsa-miR-215 | augaccuagauaaugacagac | 1085,22 | 463,22 | 2,34 | 0,21 |
| SEQ ID NO: 693 | 44 | hsa-miR-151-3p | cuagacuagaagcucuugagg | 344,56 | 90,78 | 3,8 | 0,21 |
| SEQ ID NO: 703 | 45 | hsa-miR-1471 | gccccgcgugugggaggcaggugu | 37,89 | 33,78 | 1,12 | 0,21 |
| SEQ ID NO: 101 | 46 | hsa-miR-652 | aauggcgccacuaggguugug | 1388,26 | 961,58 | 1,44 | 0,21 |
| SEQ ID NO: 679 | 47 | hsa-miR-15b* | cgaaucauuauuugcucucucua | 46,89 | 1 | 46,89 | 0,21 |
| SEQ ID NO: 573 | 48 | hsa-miR-210 | cugugcgugugacagcggcuga | 412,67 | 58,89 | 7,01 | 0,21 |
| SEQ ID NO: 449 | 49 | hsa-miR-339-5p | uccccugucuccaggagcucacg | 312,11 | 12,44 | 25,08 | 0,21 |
| SEQ ID NO: 577 | 50 | hsa-miR-20b | caaagugcuuauagugcagguag | 1118,35 | 2947,83 | 0,38 | 0,2 |
| SEQ ID NO: 98 | 51 | hsa-miR-654-5p | ugguggccgcagaacaugugc | 124,11 | 98,56 | 1,26 | 0,2 |
| SEQ ID NO: 462 | 52 | hsa-miR-328 | cuggccccucugccccuucccgu | 72,22 | 68,44 | 1,06 | 0,19 |
| SEQ ID NO: 93 | 53 | hsa-miR-859 | cuugguucagggagggucccca | 150,56 | 133,11 | 1,13 | 0,19 |
| SEQ ID NO: 579 | 54 | hsa-miR-20a | uaaagugcuuauagugcagguag | 2319,9 | 4202,14 | 0,55 | 0,19 |
| SEQ ID NO: 893 | 55 | hsa-let-7f | ugagguaguaguuguauaguu | 5382,15 | 9746,17 | 0,55 | 0,19 |
| SEQ ID NO: 521 | 56 | hsa-miR-26b | uucaaguaacagcaggauuaggu | 1085,22 | 2058,85 | 0,53 | 0,18 |
| SEQ ID NO: 510 | 57 | hsa-miR-298 | agcagaagcagggagguucuccca | 71,56 | 53,33 | 1,34 | 0,18 |
| SEQ ID NO: 205 | 58 | hsa-miR-557 | guuugcacggguggcuuuguucu | 114,67 | 132 | 0,87 | 0,18 |
| SEQ ID NO: 723 | 59 | hsa-miR-140-3p | uaccacagggguagaaccacgg | 9312,5 | 4621,29 | 2,02 | 0,18 |
| SEQ ID NO: 86 | 60 | hsa-miR-864* | acuggcuaggugaaaaugauuggau | 61,56 | 39,44 | 1,56 | 0,18 |
| SEQ ID NO: 5 | 61 | hsa-miR-98 | ugagguaguaagguuguauguu | 322,44 | 1440,75 | 0,22 | 0,18 |
| SEQ ID NO: 754 | 62 | hsa-miR-1303 | uuuagagacggggucuugcucu | 41,89 | 31,33 | 1,34 | 0,18 |
| SEQ ID NO: 70 | 63 | hsa-miR-744 | ugcggggcuaggcuaacagca | 364,22 | 388 | 0,94 | 0,18 |
| SEQ ID NO: 402 | 64 | hsa-miR-378* | cuccugacuccagguccugugu | 111,78 | 28 | 3,99 | 0,18 |
| SEQ ID NO: 851 | 65 | hsa-miR-1207-3p | ucagcuggcccucauuuc | 1 | 18,11 | 0,06 | 0,18 |
| SEQ ID NO: 86 | 66 | hsa-miR-864* | cauuauuacuuuuggacgcg | 1 | 33,78 | 0,03 | 0,18 |
| SEQ ID NO: 804 | 67 | hsa-miR-126* | uggacugccugaucugggaga | 1 | 1 | 1 | 0,18 |
| SEQ ID NO: 771 | 68 | hsa-miR-145* | ggauucugccugaaauacuguucu | 1 | 1 | 1 | 0,18 |
| SEQ ID NO: 712 | 69 | hsa-miR-18a | uaaggugcaucuagugcagauag | 143,78 | 58,89 | 2,44 | 0,18 |

FIG. 10A (Cont.)

| SEQ ID NO | # | name | sequence | | | |
|---|---|---|---|---|---|---|
| SEQ ID NO: 451 | 70 | hsa-miR-338-5p | aacaauauccugguqcugagug | 1 | 1 | 0,18 |
| SEQ ID NO: 414 | 71 | hsa-miR-374a | uuauaauacaaccugauaagug | 225,11 | 692,94 | 0,32 | 0,18 |
| SEQ ID NO: 360 | 72 | hsa-miR-454 | uagugcgguauugcuuaaagggu | 90,44 | 26,56 | 3,41 | 0,18 |
| SEQ ID NO: 323 | 73 | hsa-miR-503 | uagcagcgggaacaguucugcag | 68,67 | 73,33 | 0,94 | 0,18 |
| SEQ ID NO: 200 | 74 | hsa-miR-563 | aggugacauacguuucc | 1 | 1 | 1 | 0,18 |
| SEQ ID NO: 384 | 75 | hsa-miR-423-5p | ugagggcagagagcgagacuuu | 6795,89 | 3976,97 | 1,71 | 0,17 |
| SEQ ID NO: 678 | 76 | hsa-miR-16 | uagcagcacguaaauauuggcg | 20349,58 | 24783,94 | 0,82 | 0,17 |
| SEQ ID NO: 116 | 77 | hsa-miR-637 | acugggggcuuucgggcucugcgu | 90,11 | 70,89 | 1,27 | 0,17 |
| SEQ ID NO: 526 | 78 | hsa-miR-25 | cauugcacuugucucggucuga | 12517,64 | 7639,53 | 1,64 | 0,17 |
| SEQ ID NO: 863 | 79 | hsa-miR-1182 | gagguculuggggauggaggugac | 708,06 | 674,69 | 1,05 | 0,17 |
| SEQ ID NO: 845 | 80 | hsa-miR-1224-5p | gugaggacucgggaggug | 586,78 | 388 | 1,51 | 0,17 |
| SEQ ID NO: 714 | 81 | hsa-miR-144* | ggauaucaucauaucuguaag | 340,89 | 450,61 | 0,76 | 0,16 |
| SEQ ID NO: 432 | 82 | hsa-miR-361-3p | uccccagguguguauucugauuu | 367,06 | 256,44 | 1,43 | 0,16 |
| SEQ ID NO: 692 | 83 | hsa-miR-151-5p | ucgaggagcucacagucuagu | 1732,86 | 1024,56 | 1,69 | 0,16 |
| SEQ ID NO: 895 | 84 | hsa-let-7e | ugagguaggagguuguauaguu | 1297,51 | 2947,83 | 0,44 | 0,15 |
| SEQ ID NO: 904 | 85 | hsa-let-7a | ugagguaguagguuguauaguu | 6795,89 | 12517,64 | 0,54 | 0,15 |
| SEQ ID NO: 624 | 86 | hsa-miR-194 | uguaacagcaacuccaugugga | 1853,1 | 1440,75 | 1,29 | 0,15 |
| SEQ ID NO: 30 | 87 | hsa-miR-921 | cuagagggacagaaccaggauuc | 260,22 | 207,33 | 1,26 | 0,15 |
| SEQ ID NO: 680 | 88 | hsa-miR-15b | uagcagcacaucaugguuuaca | 20349,58 | 23734,72 | 0,86 | 0,15 |
| SEQ ID NO: 653 | 89 | hsa-miR-187* | ggcuacaacacagagccggc | 88,56 | 68,44 | 1,29 | 0,14 |
| SEQ ID NO: 540 | 90 | hsa-miR-223 | uguacaguuugcaaauaccca | 3080,08 | 5660,31 | 0,54 | 0,14 |
| SEQ ID NO: 816 | 91 | hsa-miR-1255a | agguagcaaagaaagaaguagauu | 46,44 | 28,44 | 1,63 | 0,14 |
| SEQ ID NO: 814 | 92 | hsa-miR-1256 | aggcauugacuucucacuagcu | 1 | 1 | 1 | 0,14 |
| SEQ ID NO: 776 | 93 | hsa-miR-1283 | ucuacaaaggaaagcgcuuucu | 2,33 | 22,22 | 0,11 | 0,14 |
| SEQ ID NO: 731 | 94 | hsa-miR-136 | acuccauuguuuugaugauga | 1 | 1,56 | 0,64 | 0,14 |
| SEQ ID NO: 716 | 95 | hsa-miR-143* | gggugcagugcuggcaucucuggu | 1 | 1 | 1 | 0,14 |
| SEQ ID NO: 655 | 96 | hsa-miR-186* | gccaaaggugaauuuuuggg | 1 | 1 | 1 | 0,14 |
| SEQ ID NO: 652 | 97 | hsa-miR-188-3p | cuccacugccaggguuugca | 1 | 4,44 | 0,23 | 0,14 |
| SEQ ID NO: 601 | 98 | hsa-miR-19a* | aguuuugcaugguugcacuaca | 1 | 1 | 1 | 0,14 |
| SEQ ID NO: 580 | 99 | hsa-miR-208b | auaagacgaacaaaaguuugu | 6,78 | 1 | 6,78 | 0,14 |
| SEQ ID NO: 516 | 100 | hsa-miR-27b* | agccuuagcugaugguqaac | 8,44 | 4,22 | 2 | 0,14 |
| SEQ ID NO: 511 | 101 | hsa-miR-297 | auguaugugcuuccaugcaug | 1 | 12,11 | 0,08 | 0,14 |
| SEQ ID NO: 495 | 102 | hsa-miR-302b | uaagugcuuccaugguuuagauag | 1 | 1 | 1 | 0,14 |
| SEQ ID NO: 477 | 103 | hsa-miR-30e* | cuuucagucggauguuuuacagc | 20,56 | 8,33 | 2,47 | 0,14 |
| SEQ ID NO: 441 | 104 | hsa-miR-342-5p | aggggugcuaucuguqauga | 82,44 | 73,33 | 1,12 | 0,14 |
| SEQ ID NO: 374 | 105 | hsa-miR-433 | aucaugaugggcuccucggugu | 1 | 1 | 1 | 0,14 |
| SEQ ID NO: 361 | 106 | hsa-miR-453 | aggugcuccugguqucgca | 6,78 | 57 | 0,12 | 0,14 |

FIG. 10A (Cont.)

| | | | | | | |
|---|---|---|---|---|---|---|
| SEQ ID NO: 249 | 107 | hsa-miR-532-3p | ccucccacacccaaggcuugca | 88,11 | 114,67 | 0,77 | 0,14 |
| SEQ ID NO: 244 | 108 | hsa-miR-542-3p | ugugacagauugauaaacugaaa | 1 | 18,72 | 0,05 | 0,14 |
| SEQ ID NO: 232 | 109 | hsa-miR-548d-3p | caaaaaccacaguuuccuuuugc | 1 | 1 | 1 | 0,14 |
| SEQ ID NO: 108 | 110 | hsa-miR-645 | ucuaggcugguacugcuga | 1 | 1 | 1 | 0,14 |
| SEQ ID NO: 106 | 111 | hsa-miR-647 | guggcugcacucucccuuc | 1 | 1 | 1 | 0,14 |
| SEQ ID NO: 88 | 112 | hsa-miR-663b | ggugccggccgugccugagg | 5,56 | 4,44 | 1,25 | 0,14 |
| SEQ ID NO: 487 | 113 | hsa-miR-30a | uguaaacauccucgacuggaag | 1175,03 | 1056,33 | 1,11 | 0,14 |
| SEQ ID NO: 426 | 114 | hsa-miR-365 | uaaugcccuaaaaauccuuau | 24 | 42,78 | 0,56 | 0,14 |
| SEQ ID NO: 82 | 115 | hsa-miR-671-3p | uccgguucucaggcuccacc | 21,11 | 13,72 | 1,54 | 0,13 |
| SEQ ID NO: 896 | 116 | hsa-let-7d* | cuauacgaccugcugccuuucu | 39,44 | 6 | 6,57 | 0,13 |
| SEQ ID NO: 823 | 117 | hsa-miR-1248 | accuucuuguauaagcacugugcuaaa | 154,22 | 31,33 | 4,92 | 0,13 |
| SEQ ID NO: 795 | 118 | hsa-miR-1268 | cgggcgugugugggg | 901,96 | 1056,33 | 0,85 | 0,13 |
| SEQ ID NO: 713 | 119 | hsa-miR-145 | guccaguuuccaggaauccccu | 571,78 | 101,11 | 5,66 | 0,13 |
| SEQ ID NO: 607 | 120 | hsa-miR-198 | ggucagaggggagauaagguuc | 428,39 | 382 | 1,12 | 0,13 |
| SEQ ID NO: 605 | 121 | hsa-miR-199a-5p | cccagugu uucagacuaccucuuc | 145,33 | 36,11 | 4,02 | 0,13 |
| SEQ ID NO: 467 | 122 | hsa-miR-323-5p | agguggucccugcgcguugc | 58,33 | 67,44 | 0,86 | 0,13 |
| SEQ ID NO: 600 | 123 | hsa-miR-19b | ugugcaaauccaugcaaaacuga | 3428,42 | 1853,1 | 1,85 | 0,13 |
| SEQ ID NO: 876 | 124 | hsa-miR-106a | aaaagugcuuacagugcagguag | 4462,58 | 6349,31 | 0,7 | 0,13 |
| SEQ ID NO: 46 | 125 | hsa-miR-885-3p | agcagcggauuguaguggaua | 463,22 | 1040,44 | 0,45 | 0,12 |
| SEQ ID NO: 622 | 126 | hsa-miR-195 | uagcagcacagaaauauuggc | 2575,72 | 4462,58 | 0,58 | 0,12 |
| SEQ ID NO: 883 | 127 | hsa-miR-101 | uacaguacuguguauaaacugaa | 94,56 | 138,61 | 0,68 | 0,12 |
| SEQ ID NO: 748 | 128 | hsa-miR-130a | cagugcaauguuaaaagggcau | 746,29 | 874,97 | 0,85 | 0,12 |
| SEQ ID NO: 630 | 129 | hsa-miR-192 | cugaccuaugcgucucagugcagagc | 3080,08 | 1675,67 | 1,84 | 0,12 |
| SEQ ID NO: 115 | 130 | hsa-miR-638 | agggaucgcgggcgguggcgggccu | 4915,83 | 5944,79 | 0,83 | 0,12 |
| SEQ ID NO: 831 | 131 | hsa-miR-1238 | cuuccucugucacagugccc | 52 | 58,89 | 0,88 | 0,11 |
| SEQ ID NO: 874 | 132 | hsa-miR-106b | uaaagugcugacagugcagau | 3080,08 | 2319,9 | 1,33 | 0,11 |
| SEQ ID NO: 886 | 133 | hsa-miR-1 | uggaauguaaagaaguauguau | 1 | 1 | 1 | 0,11 |
| SEQ ID NO: 870 | 134 | hsa-miR-10a* | caaauucguaucuaggggaaua | 1 | 4,44 | 0,23 | 0,11 |
| SEQ ID NO: 858 | 135 | hsa-miR-1200 | cucugagcaaucugagcccuc | 1 | 5,11 | 0,2 | 0,11 |
| SEQ ID NO: 854 | 136 | hsa-miR-1204 | ucguggccuguagucccauuau | 1 | 4,44 | 0,23 | 0,11 |
| SEQ ID NO: 852 | 137 | hsa-miR-1206 | uguucauguagauguuaagc | 20,56 | 10,44 | 0,1 | 0,11 |
| SEQ ID NO: 830 | 138 | hsa-miR-124 | uaaggcacgcggugaaugcc | 1 | 11,33 | 1,81 | 0,11 |
| SEQ ID NO: 826 | 139 | hsa-miR-1245 | aagugaucuaaaggccuacau | 1 | 1 | 1 | 0,11 |
| SEQ ID NO: 811 | 140 | hsa-miR-1259 | auauaugauucaaggcucuuggau | 112,44 | 106,11 | 1,06 | 0,11 |
| SEQ ID NO: 806 | 141 | hsa-miR-125b-2* | ucaaguaaggcucuuggac | 1 | 3,67 | 0,27 | 0,11 |
| SEQ ID NO: 802 | 142 | hsa-miR-1261 | auggauaaggcuuuggcuu | 1 | 10,44 | 0,1 | 0,11 |
| SEQ ID NO: 797 | 143 | hsa-miR-1266 | ccucagggcuuagaaacagggcu | 17,11 | 29,94 | 0,57 | 0,11 |

FIG. 10A (Cont.)

| | | | | | | |
|---|---|---|---|---|---|---|
| SEQ ID NO: 782 | 144 | hsa-miR-1278 | uaguacugugcauaaucaucuau | | | |
| SEQ ID NO: 759 | 145 | hsa-miR-1297 | uucaaguaauacuuauucagguug | 1 | 1 | 0,11 |
| SEQ ID NO: 755 | 146 | hsa-miR-1302 | uugggacauacuuuagcuaaa | 1 | 1 | 0,11 |
| SEQ ID NO: 753 | 147 | hsa-miR-1304 | uuugaggcuacaguaugaugug | 20,56 | 28 | 0,11 |
| SEQ ID NO: 733 | 148 | hsa-miR-135b | uauggcuuuucauuccuauguga | 1 | 1 | 0,11 |
| SEQ ID NO: 672 | 149 | hsa-miR-181a* | accaucgaccguugauuguacc | 1 | 1 | 0,11 |
| SEQ ID NO: 669 | 150 | hsa-miR-181c | aacauucaaccugucggugagu | 130,44 | 21,78 | 0,11 |
| SEQ ID NO: 599 | 151 | hsa-miR-19b-1* | aguuuugcagguuugcauccagu | 1 | 1 | 0,11 |
| SEQ ID NO: 587 | 152 | hsa-miR-205 | uccuucauuccaccggagucug | 1 | 1 | 0,11 |
| SEQ ID NO: 576 | 153 | hsa-miR-20b* | acuguagauggcacuuccag | 4,44 | 0,23 | 0,11 |
| SEQ ID NO: 553 | 154 | hsa-miR-218-2* | cauggaguucugucaagcaccgcg | 1 | 1 | 0,11 |
| SEQ ID NO: 546 | 155 | hsa-miR-220b | ccaccacgguucugacacu | 2,67 | 2,67 | 0,11 |
| SEQ ID NO: 543 | 156 | hsa-miR-221* | accuggcauacaauguagauuu | 1 | 1 | 0,11 |
| SEQ ID NO: 530 | 157 | hsa-miR-23b* | ugggucccuggaaugcugugaa | 1 | 1 | 0,11 |
| SEQ ID NO: 527 | 158 | hsa-miR-24-2* | ugccuacugagcugaaacacag | 1 | 1 | 0,11 |
| SEQ ID NO: 515 | 159 | hsa-miR-28-3p | cacuagauugugagcugcugga | 29,11 | 21,11 | 1,38 |
| SEQ ID NO: 494 | 160 | hsa-miR-302b* | acuuuaacauggaagugcuuuc | 1 | 1 | 0,11 |
| SEQ ID NO: 455 | 161 | hsa-miR-335* | uuuuucauuauugcuccugcc | 1 | 1,56 | 0,64 |
| SEQ ID NO: 436 | 162 | hsa-miR-34b | caaucuaacuccacugccau | 2,67 | 19,78 | 0,13 |
| SEQ ID NO: 419 | 163 | hsa-miR-371-3p | aagugccgccaucuuuugagugu | 1 | 1 | 0,11 |
| SEQ ID NO: 412 | 164 | hsa-miR-374b | auauaacaaccugcuaagug | 126,44 | 21,56 | 5,87 |
| SEQ ID NO: 405 | 165 | hsa-miR-377 | aucacacaaggcaacuuuugu | 1 | 1 | 0,11 |
| SEQ ID NO: 390 | 166 | hsa-miR-411 | uaguagaccguauagcguau | 1 | 1 | 0,11 |
| SEQ ID NO: 362 | 167 | hsa-miR-424* | caaaacgugagcgucugcuau | 34 | 46,11 | 0,74 |
| SEQ ID NO: 380 | 168 | hsa-miR-425* | aucgggaaugucgugucgccc | 98 | 33,78 | 2,9 |
| SEQ ID NO: 372 | 169 | hsa-miR-449a | uggcaguguauuguuagcuggu | 1 | 1 | 0,11 |
| SEQ ID NO: 364 | 170 | hsa-miR-451 | aaaccguuaccauuacugaguu | 1118,35 | 4106,11 | 0,27 |
| SEQ ID NO: 313 | 171 | hsa-miR-509-5p | uacugcagacaguggcaauca | 1 | 1 | 0,11 |
| SEQ ID NO: 298 | 172 | hsa-miR-516b* | ugcuucucuuucagagggu | 9,56 | 31,33 | 0,3 |
| SEQ ID NO: 296 | 173 | hsa-miR-517a | aucugcauccccuuuagagugu | 1 | 1 | 0,11 |
| SEQ ID NO: 261 | 174 | hsa-miR-522 | aaaaugguuccccuuuugugu | 1 | 8,33 | 0,12 |
| SEQ ID NO: 254 | 175 | hsa-miR-525-5p | cucagagggaugugucacuuucu | 1,89 | 4,22 | 0,45 |
| SEQ ID NO: 248 | 176 | hsa-miR-532-5p | caucuugaguaggaccgu | 121,44 | 92,56 | 1,31 |
| SEQ ID NO: 229 | 177 | hsa-miR-548f | aaaaacuguaauuacuuuu | 1 | 1 | 0,11 |
| SEQ ID NO: 227 | 178 | hsa-miR-548h | aaaaguaaugcgguuuuugugc | 1 | 1 | 0,11 |
| SEQ ID NO: 213 | 179 | hsa-miR-551b | gcgacccauacuuggguuucag | 1 | 1 | 0,11 |
| SEQ ID NO: 209 | 180 | hsa-miR-554 | gcuaguccguagacucagccagu | 1 | 1 | 0,11 |

FIG. 10A (Cont.)

| | | | | | | | |
|---|---|---|---|---|---|---|---|
| SEQ ID NO: 162 | 181 | hsa-miR-597 | ugugucacugaugaccacugu | | 1 | 1 | 0,11 |
| SEQ ID NO: 160 | 182 | hsa-miR-599 | guuugucaguuuuaucaaac | | 1 | 1 | 0,11 |
| SEQ ID NO: 157 | 183 | hsa-miR-602 | gacacgggcgacagcugcggcc | 20,56 | 44 | 0,47 | 0,11 |
| SEQ ID NO: 156 | 184 | hsa-miR-603 | cacacacugcaauuacuuuugc | 1 | 1,56 | 0,64 | 0,11 |
| SEQ ID NO: 152 | 185 | hsa-miR-607 | guucaaaucagaucuauaac | 1 | 1 | 1 | 0,11 |
| SEQ ID NO: 138 | 186 | hsa-miR-619 | gaccuggaccauguuuugugcccagu | 1 | 1 | 1 | 0,11 |
| SEQ ID NO: 122 | 187 | hsa-miR-631 | agaccugccccagaccucagc | 2,67 | 13,72 | 0,19 | 0,11 |
| SEQ ID NO: 53 | 188 | hsa-miR-874 | cugcccuggcccgaggacga | 34 | 35,83 | 0,95 | 0,11 |
| SEQ ID NO: 37 | 189 | hsa-miR-891a | ugcaacgaaccugagccacuga | 6,78 | 6,56 | 1,03 | 0,11 |
| SEQ ID NO: 29 | 190 | hsa-miR-922 | gcagagaauaggacuacguc | 1 | 18,72 | 0,05 | 0,11 |
| SEQ ID NO: 28 | 191 | hsa-miR-933 | ugugcagggagaccucucc | 18,11 | 28,44 | 0,64 | 0,11 |
| SEQ ID NO: 20 | 192 | hsa-miR-99b | caccguagaaccgaccuugcg | 73,33 | 33,56 | 2,19 | 0,11 |
| SEQ ID NO: 2 | 193 | hsa-miR-106b* | ccgcacuguggguacuugcugc | 901,96 | 137,56 | 6,56 | 0,11 |
| SEQ ID NO: 873 | 194 | hsa-miR-29c* | ugaccgauuucccugugguuc | 61,11 | 1 | 61,11 | 0,11 |
| SEQ ID NO: 501 | 195 | hsa-miR-493* | uugaauggagcuuuuccaccag | 1,56 | 3,11 | 0,5 | 0,1 |
| SEQ ID NO: 338 | 196 | hsa-miR-886-5p | cgggucggagugacuccaagagc | 126,44 | 87,67 | 1,44 | 0,1 |
| SEQ ID NO: 43 | 197 | hsa-miR-197 | uucaccaccuucuccacccagc | 143,78 | 111,78 | 1,29 | 0,1 |
| SEQ ID NO: 616 | 198 | hsa-miR-183 | uauggcacuggaauucacu | 90,11 | 26,56 | 3,39 | 0,1 |
| SEQ ID NO: 661 | 199 | hsa-miR-500 | uaaucuuugcuaccugggugaga | 136,17 | 58,78 | 2,32 | 0,1 |
| SEQ ID NO: 329 | 200 | hsa-miR-484 | ucaggcucagucccuccccgau | 3778,89 | 2575,72 | 1,47 | 0,1 |
| SEQ ID NO: 354 | 201 | hsa-miR-185 | uggagagaaaggcaguuccuga | 15421,86 | 13307,74 | 1,16 | 0,09 |
| SEQ ID NO: 658 | 202 | hsa-miR-668 | ugucacucggcucggcccacuac | 276,44 | 92,56 | 2,99 | 0,09 |
| SEQ ID NO: 84 | 203 | hsa-miR-936 | acaguagaggaggaaucgcag | 683,82 | 660,47 | 1,04 | 0,09 |
| SEQ ID NO: 17 | 204 | hsa-miR-331-3p | gcccuggccuauccuagaa | 723,61 | 403,89 | 1,79 | 0,09 |
| SEQ ID NO: 458 | 205 | hsa-miR-611 | gcgaggaccccucgggguucgac | 30,44 | 18,11 | 1,68 | 0,09 |
| SEQ ID NO: 148 | 206 | hsa-miR-1469 | cucggcgcggggcgcgggcucc | 961,58 | 1297,51 | 0,74 | 0,1 |
| SEQ ID NO: 710 | 207 | hsa-miR-564 | aggcacggugucagcaggc | 56,78 | 47,06 | 1,21 | 0,09 |
| SEQ ID NO: 199 | 208 | hsa-miR-103 | agcagcauuguacagggcuauga | 3868,5 | 5382,15 | 0,72 | 0,09 |
| SEQ ID NO: 881 | 209 | hsa-miR-1273 | gggcgacaaagcaagacucuuucuu | 26,44 | 31,33 | 0,84 | 0,09 |
| SEQ ID NO: 790 | 210 | hsa-miR-181b | aacauucauuguagucgggguu | 61,11 | 27,78 | 2,2 | 0,09 |
| SEQ ID NO: 670 | 211 | hsa-miR-658 | ggcggugaaguaguccguuggu | 2425,74 | 1118,35 | 2,17 | 0,09 |
| SEQ ID NO: 94 | 212 | hsa-miR-125a-3p | acagguaguuccuuggagcc | 58,33 | 39,22 | 1,49 | 0,08 |
| SEQ ID NO: 810 | 213 | hsa-miR-140-5p | caguguuuuaccuauggua | 1 | 1 | 1 | 0,08 |
| SEQ ID NO: 722 | 214 | hsa-miR-301a | cagugcaauaguauugucaaagc | 16,78 | 21,56 | 0,78 | 0,08 |
| SEQ ID NO: 499 | 215 | hsa-miR-1253 | agagaagaagaucagccugca | 1 | 1 | 1 | 0,08 |
| SEQ ID NO: 818 | 216 | hsa-miR-663 | aggcggggcgccgcgggaccgc | 715,83 | 1175,03 | 0,61 | 0,08 |
| SEQ ID NO: 89 | 217 | hsa-let-7c* | uagaguuacacccugggaguua | 1 | 1 | 1 | 0,08 |

FIG. 10A (Cont.)

| | | | | | | |
|---|---|---|---|---|---|---|
| SEQ ID NO: 892 | 218 | hsa-let-7f-1* | cuauacaaucuauugccuuccc | | 1 | 0,08 |
| SEQ ID NO: 891 | 219 | hsa-let-7f-2* | cuauacaguCuacugucuuucc | | 1 | 0,08 |
| SEQ ID NO: 879 | 220 | hsa-miR-103-as | ucauagcCccuguacaaugcugcu | | 1 | 0,08 |
| SEQ ID NO: 878 | 221 | hsa-miR-105 | ucaaaugcucagacuccugggu | 1 | 1 | 0,08 |
| SEQ ID NO: 871 | 222 | hsa-miR-10a | uacccuguagaUccgaauuugug | 34,22 | 1,12 | 0,08 |
| SEQ ID NO: 860 | 223 | hsa-miR-1185 | agaggauacccuuuguauguu | 1 | 1 | 0,08 |
| SEQ ID NO: 857 | 224 | hsa-miR-1201 | agccugauuaaacacaugcucuga | 37,89 | 2,09 | 0,08 |
| SEQ ID NO: 853 | 225 | hsa-miR-1205 | ucugcaggguuugcuuuag | 1 | 1 | 0,08 |
| SEQ ID NO: 848 | 226 | hsa-miR-122 | uggagugugacaaugguguug | 17,11 | 0,81 | 0,08 |
| SEQ ID NO: 824 | 227 | hsa-miR-1247 | accCguccCguucgucccCgga | 9,56 | 0,59 | 0,08 |
| SEQ ID NO: 820 | 228 | hsa-miR-1251 | acucuagcugccaaaggcgcu | 1 | 1 | 0,08 |
| SEQ ID NO: 801 | 229 | hsa-miR-1262 | auggugaauuuguagaaggau | 11,33 | 0,09 | 0,08 |
| SEQ ID NO: 793 | 230 | hsa-miR-1270 | cuggaguauuggaagagcugugu | 30,44 | 1,04 | 0,08 |
| SEQ ID NO: 791 | 231 | hsa-miR-1277 | gaugaugauggcagcaaauucugaaa | 31,56 | 1 | 0,08 |
| SEQ ID NO: 783 | 232 | hsa-miR-1277 | uacguagaauauauaguauuuuu | | 1 | 0,08 |
| SEQ ID NO: 775 | 233 | hsa-miR-1284 | ucuauacagaccCuggcuuuuc | 11,56 | 0,09 | 0,08 |
| SEQ ID NO: 770 | 234 | hsa-miR-1289 | uggagUccaggaaucacugcauuu | 4,44 | 0,23 | 0,08 |
| SEQ ID NO: 747 | 235 | hsa-miR-130a* | uuuacagugcuacugucugc | 1 | 1 | 0,08 |
| SEQ ID NO: 741 | 236 | hsa-miR-1322 | gaugcugcugaaugcgaugcug | 1,56 | 0,24 | 0,08 |
| SEQ ID NO: 739 | 237 | hsa-miR-1324 | ccagacagaauucuaugcaccuuuc | 6,56 | 1 | 0,08 |
| SEQ ID NO: 738 | 238 | hsa-miR-133a | uuuggucccCuucaaccagcug | 34,22 | 1,62 | 0,08 |
| SEQ ID NO: 732 | 239 | hsa-miR-135b* | augaagggcuaaaagccauggg | 21,11 | 2,83 | 0,08 |
| SEQ ID NO: 729 | 240 | hsa-miR-137 | uuauugcuuaagaauacgcguag | 12,11 | 1 | 0,08 |
| SEQ ID NO: 721 | 241 | hsa-miR-141 | uaacacugucugguaaagaugg | 4 | 4 | 0,08 |
| SEQ ID NO: 718 | 242 | hsa-miR-142-5p | cauaaaguagaaagcacuacu | 29,11 | 2,79 | 0,08 |
| SEQ ID NO: 715 | 243 | hsa-miR-144 | uacaguauagaugauguacu | 40,67 | 0,5 | 0,08 |
| SEQ ID NO: 711 | 244 | hsa-miR-1468 | cuccguuugccuguuucgcug | 82,06 | 0,24 | 0,08 |
| SEQ ID NO: 708 | 245 | hsa-miR-146a* | ccucuguuauucagUuucucag | 4,22 | 1 | 0,08 |
| SEQ ID NO: 707 | 246 | hsa-miR-146b-3p | ugccCuguggacuucaguucugg | 1 | 1 | 0,08 |
| SEQ ID NO: 705 | 247 | hsa-miR-147 | guguggaaaugcuucugc | 1 | 1 | 0,08 |
| SEQ ID NO: 702 | 248 | hsa-miR-147b | gugugcggaaaugcuucugcua | 1 | 1 | 0,08 |
| SEQ ID NO: 697 | 249 | hsa-miR-149 | ucuggcucuguucuucacuccc | 9,56 | 0,84 | 0,08 |
| SEQ ID NO: 690 | 250 | hsa-miR-153 | uugcauaguCacaaaaguqauC | 1 | 1 | 0,08 |
| SEQ ID NO: 687 | 251 | hsa-miR-1539 | uccugcgguccCagaugcC | 5,22 | 0,25 | 0,08 |
| SEQ ID NO: 685 | 252 | hsa-miR-154* | aaucauacacgguuqaccuauu | 21,11 | 1 | 0,08 |
| SEQ ID NO: 677 | 253 | hsa-miR-16-1* | ccaguauuaacugugcugcuga | 1,56 | 0,64 | 0,08 |
| SEQ ID NO: 668 | 254 | hsa-miR-181c* | aaccaucgaccguugagugac | 1 | 1 | 0,08 |

FIG. 10A (Cont.)

| | | | | | | |
|---|---|---|---|---|---|---|
| SEQ ID NO: 662 | 255 | hsa-miR-1827 | ugaggcaguagaugaau | 9,56 | 4,44 | 2,15 | 0,08 |
| SEQ ID NO: 648 | 256 | hsa-miR-18b | uaaggugcaucuagugcaguuag | 137,22 | 234,33 | 0,59 | 0,08 |
| SEQ ID NO: 638 | 257 | hsa-miR-1911 | ugaguaccgccaugucuguuggg | 1 | 1,56 | 0,64 | 0,08 |
| SEQ ID NO: 637 | 258 | hsa-miR-1911* | caccaggcauugugucucc | 1 | 1 | 1 | 0,08 |
| SEQ ID NO: 636 | 259 | hsa-miR-1912 | uacccagagcaugcagugugaa | 1 | 1,56 | 0,64 | 0,08 |
| SEQ ID NO: 629 | 260 | hsa-miR-192* | cugccaauuccauaagucacag | 1 | 1 | 1 | 0,08 |
| SEQ ID NO: 628 | 261 | hsa-miR-193a-3p | aacuggccuacaaagucccagu | 20,83 | 21,11 | 0,99 | 0,08 |
| SEQ ID NO: 626 | 262 | hsa-miR-193b | aacuggcccucaaagucccgcu | 1 | 1,56 | 0,64 | 0,08 |
| SEQ ID NO: 604 | 263 | hsa-miR-199b-3p | acaguagucugcaauuggua | 1 | 11,56 | 0,09 | 0,08 |
| SEQ ID NO: 596 | 264 | hsa-miR-200a* | ceucuuaccggacagugcugga | 1 | 1 | 1 | 0,08 |
| SEQ ID NO: 595 | 265 | hsa-miR-200b | uaauacugccugguaaugaua | 1 | 1 | 1 | 0,08 |
| SEQ ID NO: 593 | 266 | hsa-miR-200c | uaauacugccgguaaugauga | 7,44 | 10,44 | 0,71 | 0,08 |
| SEQ ID NO: 562 | 267 | hsa-miR-212 | uaacagucuccagucacggcc | 7,44 | 4,44 | 1,68 | 0,08 |
| SEQ ID NO: 560 | 268 | hsa-miR-214* | ugccugucuacacucugcugug | 1 | 1 | 1 | 0,08 |
| SEQ ID NO: 557 | 269 | hsa-miR-216b | aaauucucugcaggcaaaugug | 1 | 1 | 1 | 0,08 |
| SEQ ID NO: 503 | 270 | hsa-miR-29b-2* | cugguucaaugguugcuuag | 34,44 | 47,22 | 0,73 | 0,08 |
| SEQ ID NO: 493 | 271 | hsa-miR-302c | uaaguguuccauguuucagugg | 1 | 1 | 1 | 0,08 |
| SEQ ID NO: 489 | 272 | hsa-miR-302e | uaagugcuuccauguuu | 1 | 1 | 1 | 0,08 |
| SEQ ID NO: 488 | 273 | hsa-miR-302f | uaauugcuuccauguuu | 1 | 1 | 1 | 0,08 |
| SEQ ID NO: 479 | 274 | hsa-miR-30d* | cuuucagucagauguuugcugc | 1 | 1 | 0,07 | 0,08 |
| SEQ ID NO: 464 | 275 | hsa-miR-325 | ccuaguagguguccaguaagugu | 1 | 14,89 | 1 | 0,08 |
| SEQ ID NO: 437 | 276 | hsa-miR-34a* | caaucagcaaguauacugcccu | 1 | 1 | 1 | 0,08 |
| SEQ ID NO: 434 | 277 | hsa-miR-34c-3p | aaucacuaaccacacggccagg | 4 | 28,44 | 0,14 | 0,08 |
| SEQ ID NO: 421 | 278 | hsa-miR-369-5p | agaucgaccguguuauuauucgc | 1 | 1 | 1 | 0,08 |
| SEQ ID NO: 413 | 279 | hsa-miR-374a* | cuuaucagauuguuauauucau | 1 | 1 | 1 | 0,08 |
| SEQ ID NO: 411 | 280 | hsa-miR-374b* | ugguugaccauagaacaugcgc | 1 | 1 | 1 | 0,08 |
| SEQ ID NO: 398 | 281 | hsa-miR-380* | auuccuagaaauaguucaua | 1 | 1 | 1 | 0,08 |
| SEQ ID NO: 394 | 282 | hsa-miR-384 | agguuaccegagcaacuuugcau | 53 | 1,56 | 0,64 | 0,08 |
| SEQ ID NO: 392 | 283 | hsa-miR-409-5p | uauguaaacacguccaucuaacc | 1 | 1 | 1 | 0,08 |
| SEQ ID NO: 389 | 284 | hsa-miR-411* | cagcagcaauucauguuuugaa | 1 | 40,78 | 1,3 | 0,08 |
| SEQ ID NO: 383 | 285 | hsa-miR-424 | cagcagcaauucauguuuugaa | 1 | 1 | 1 | 0,08 |
| SEQ ID NO: 371 | 286 | hsa-miR-449b | aggcaguguauuguuagcugge | 1 | 1 | 1 | 0,08 |
| SEQ ID NO: 362 | 287 | hsa-miR-452* | cucauucgaaagaaguaagug | 39,67 | 50,89 | 0,78 | 0,08 |
| SEQ ID NO: 352 | 288 | hsa-miR-485-5p | agagguccgugaugaauuc | 20,56 | 12,11 | 1,7 | 0,08 |
| SEQ ID NO: 348 | 289 | hsa-miR-487b | aaucuacagcaagucacuu | 1 | 1 | 1 | 0,08 |
| SEQ ID NO: 331 | 290 | hsa-miR-499-3p | aacaucagagggcucaagcu | 1 | 1 | 1 | 0,08 |
| SEQ ID NO: 316 | 291 | hsa-miR-508-5p | uacuccagagggcgucacucaug | 22,67 | 31,33 | 0,72 | 0,08 |

FIG. 10A (Cont.)

| | | | | | |
|---|---|---|---|---|---|
| SEQ ID NO: 308 | 292 | hsa-miR-513a-3p | uaaaauuucaccuuucugagaagg | 1 | 1 |
| SEQ ID NO: 304 | 293 | hsa-miR-514 | auugacacuucugugaguaga | 1 | 1 |
| SEQ ID NO: 284 | 294 | hsa-miR-518f | gaaagcgcuucucuuuuagagg | 1 | 1 |
| SEQ ID NO: 278 | 295 | hsa-miR-519c-3p | aaagugcaucucuuuuagaggau | 12 | 0,08 |
| SEQ ID NO: 271 | 296 | hsa-miR-520b | aaagugcuuccuuuuagaggg | 1 | 1 |
| SEQ ID NO: 266 | 297 | hsa-miR-520e | aaagugcuuccuuuuugaggg | 1 | 1 |
| SEQ ID NO: 264 | 298 | hsa-miR-520g | acaaagugcuuccccuuuagagugu | 1 | 1 |
| SEQ ID NO: 262 | 299 | hsa-miR-521 | aacgcacuuccccuuuagagugu | 4,44 | 0,23 |
| SEQ ID NO: 260 | 300 | hsa-miR-522* | cucuagagggaagcgcuuucug | 12,11 | 0,33 |
| SEQ ID NO: 259 | 301 | hsa-miR-523 | gaacgcgcuuccuauagagggu | 4 | 1 |
| SEQ ID NO: 240 | 302 | hsa-miR-545 | ucagcaacacauuuauugugugc | 1 | 1 |
| SEQ ID NO: 236 | 303 | hsa-miR-548b-3p | caagaaccucaguugcuuuugu | 1 | 1 |
| SEQ ID NO: 235 | 304 | hsa-miR-548b-5p | aaaaguaauugugguuuuuggcc | 1 | 1 |
| SEQ ID NO: 225 | 305 | hsa-miR-548j | aaaagaacaauugcgucuuuggu | 1 | 1 |
| SEQ ID NO: 217 | 306 | hsa-miR-549 | ugacaacuauggaugguuuucca | 1 | 1 |
| SEQ ID NO: 214 | 307 | hsa-miR-551a | gcgacccacucuugguuucca | 1 | 1 |
| SEQ ID NO: 208 | 308 | hsa-miR-555 | aggguaagcugcugaaccucugau | 1 | 1 |
| SEQ ID NO: 204 | 309 | hsa-miR-558 | ugagcugcugucuuaccaaaau | 1 | 1 |
| SEQ ID NO: 202 | 310 | hsa-miR-561 | caaaguuuuaagaauccuugaagu | 1 | 1 |
| SEQ ID NO: 196 | 311 | hsa-miR-568 | auguauaaaugaauccuggaaagu | 1 | 1 |
| SEQ ID NO: 195 | 312 | hsa-miR-569 | aguuaaugaauccuggaaagu | 1 | 1 |
| SEQ ID NO: 192 | 313 | hsa-miR-572 | guccgcucgcggugggccca | 6,78 | 1,53 |
| SEQ ID NO: 186 | 314 | hsa-miR-576-5p | auucuaauuucuccaacgucuuu | 1 | 1 |
| SEQ ID NO: 185 | 315 | hsa-miR-577 | uagauaaaauauuggguaccug | 4,22 | 0,24 |
| SEQ ID NO: 181 | 316 | hsa-miR-581 | ucuugguucuuagaacagu | 1 | 1 |
| SEQ ID NO: 180 | 317 | hsa-miR-582-3p | uaacugguugaacaacugaacc | 4,22 | 0,95 |
| SEQ ID NO: 178 | 318 | hsa-miR-583 | caaagaggaaggucccauuac | 49,56 | 0,9 |
| SEQ ID NO: 177 | 319 | hsa-miR-584 | uuaugguuugccugggacugag | 114,67 | 1,05 |
| SEQ ID NO: 174 | 320 | hsa-miR-587 | uuuccauaggugauagagucac | 1,56 | 0,64 |
| SEQ ID NO: 170 | 321 | hsa-miR-590-3p | uaauuuuauguauaagcuagu | 1 | 1 |
| SEQ ID NO: 165 | 322 | hsa-miR-593* | aggcaccagcaggcauugcucagc | 12,11 | 0,08 |
| SEQ ID NO: 153 | 323 | hsa-miR-606 | aaacacugaaaaucaaagau | 1 | 1 |
| SEQ ID NO: 150 | 324 | hsa-miR-609 | aggguuuccccucauucu | 1 | 1 |
| SEQ ID NO: 139 | 325 | hsa-miR-618 | aaacucuacuugucccuucuagu | 1 | 1 |
| SEQ ID NO: 133 | 326 | hsa-miR-624 | cacaagguauuggauauaccu | 1 | 1 |
| SEQ ID NO: 124 | 327 | hsa-miR-629* | guucuccaacguaagcccagc | 31,56 | 33,56 | 0,94 |
| SEQ ID NO: 117 | 328 | hsa-miR-636 | ugugccuugcugucccgcccgca | 46,89 | 49,22 | 0,95 |

FIG. 10A (Cont.)

| | | | | | | |
|---|---|---|---|---|---|---|
| SEQ ID NO: 112 | 329 | hsa-miR-641 | aaagacauaggauagagaguccauc | 34 | 21,56 | 1,58 | 0,08 |
| SEQ ID NO: 109 | 330 | hsa-miR-644 | aguguggcuuucuuagagc | 1 | 1 | 1 | 0,08 |
| SEQ ID NO: 107 | 331 | hsa-miR-646 | aagcagcugccucugaggc | 1 | 1 | 1 | 0,08 |
| SEQ ID NO: 105 | 332 | hsa-miR-648 | aagugugcagggcacuggu | 1 | 1 | 1 | 0,08 |
| SEQ ID NO: 104 | 333 | hsa-miR-649 | aaaccuguguguuucaagaguc | 1 | 1 | 1 | 0,08 |
| SEQ ID NO: 100 | 334 | hsa-miR-653 | guguugaaacaaucuacug | 1 | 1 | 1 | 0,08 |
| SEQ ID NO: 97 | 335 | hsa-miR-655 | auaauacauggguuaaccucuuu | 1 | 1 | 1 | 0,08 |
| SEQ ID NO: 90 | 336 | hsa-miR-662 | ucccacguugguggccagcag | 1 | 3,11 | 0,32 | 0,08 |
| SEQ ID NO: 87 | 337 | hsa-miR-664 | uauucauuuaucccagccuaca | 8,44 | 11,33 | 0,75 | 0,08 |
| SEQ ID NO: 72 | 338 | hsa-miR-7-2* | caacaaaauccaguccauaa | 13 | 12,11 | 1,07 | 0,08 |
| SEQ ID NO: 68 | 339 | hsa-miR-758 | uuugacccuggccacuaaacc | 9,11 | 14,89 | 0,61 | 0,08 |
| SEQ ID NO: 60 | 340 | hsa-miR-767-3p | ucugcucaucccauggsuuucu | 16,78 | 18,72 | 0,9 | 0,08 |
| SEQ ID NO: 51 | 341 | hsa-miR-875-5p | uauaccucaguuuuuaucaggug | 1 | 1 | 1 | 0,08 |
| SEQ ID NO: 45 | 342 | hsa-miR-885-5p | uccauuacacuaccccugcucu | 5,56 | 28 | 0,2 | 0,08 |
| SEQ ID NO: 42 | 343 | hsa-miR-887 | guaacggcgccaucccgagg | 22,67 | 31,33 | 0,72 | 0,08 |
| SEQ ID NO: 16 | 344 | hsa-miR-937 | auccgcgucugacucucugcc | 4 | 10,44 | 0,38 | 0,08 |
| SEQ ID NO: 428 | 345 | hsa-miR-363 | aauugaacgguauccaucugua | 2790,67 | 3303,71 | 0,84 | 0,08 |
| SEQ ID NO: 483 | 346 | hsa-miR-30c | uguaaacauccuacacucucagc | 8969,72 | 4779,31 | 1,88 | 0,08 |
| SEQ ID NO: 701 | 347 | hsa-miR-148a | ucaguugcacauagaacuuugu | 382 | 901,96 | 0,42 | 0,08 |
| SEQ ID NO: 485 | 348 | hsa-miR-30b | uguaaacauccuacacucagcu | 5530,88 | 3303,71 | 1,67 | 0,08 |
| SEQ ID NO: 575 | 349 | hsa-miR-21 | uagcuuaucagacugauguuga | 708,06 | 857,3 | 0,83 | 0,08 |
| SEQ ID NO: 645 | 350 | hsa-miR-1908 | cggcgggacggcgauuggac | 5944,79 | 6597,61 | 0,9 | 0,08 |
| SEQ ID NO: 850 | 351 | hsa-miR-1207-5p | ugggcagggagcuggguggggg | 5382,15 | 4318,58 | 1,25 | 0,08 |
| SEQ ID NO: 766 | 352 | hsa-miR-1292 | ugggaacgguuccggcgagacgag | 252,11 | 158,89 | 1,59 | 0,08 |
| SEQ ID NO: 542 | 353 | hsa-miR-222 | agcuacaucugguagccccauc | 320,78 | 1 | 320,78 | 0,08 |
| SEQ ID NO: 292 | 354 | hsa-miR-518a-5p | cugcaaagggaagcccuuuc | 55,33 | 34 | 1,63 | 0,07 |
| SEQ ID NO: 524 | 355 | hsa-miR-26a | uucaaguaauccaggauaggcu | 8969,72 | 11137,35 | 0,81 | 0,07 |
| SEQ ID NO: 456 | 356 | hsa-miR-335 | ucaagagcaauaacgaaaaaugu | 115,33 | 67,44 | 1,71 | 0,07 |
| SEQ ID NO: 756 | 357 | hsa-miR-1301 | uugcagcugccugggagugacuuc | 22,67 | 18,11 | 1,25 | 0,07 |
| SEQ ID NO: 767 | 358 | hsa-miR-1291 | uggcccugacugaagaccagcagu | 30,44 | 1 | 30,44 | 0,07 |
| SEQ ID NO: 827 | 359 | hsa-miR-1244 | aaguaguuguuuuuugagauggu | 25,56 | 1 | 25,56 | 0,07 |
| SEQ ID NO: 635 | 360 | hsa-miR-1913 | ucucgccccucccgcugcugcca | 34,22 | 51,56 | 0,66 | 0,06 |
| SEQ ID NO: 427 | 361 | hsa-miR-363* | cgguggaucacgaugcaauuu | 2425,74 | 723,61 | 3,35 | 0,06 |
| SEQ ID NO: 14 | 362 | hsa-miR-939 | uggggagcuggaggcucugggug | 203,17 | 58,78 | 3,46 | 0,06 |
| SEQ ID NO: 675 | 363 | hsa-miR-17 | caaagugcuuacagugcagguag | 3976,97 | 5242,15 | 0,76 | 0,06 |
| SEQ ID NO: 765 | 364 | hsa-miR-1293 | uggggugggacgggagauuugc | 50,56 | 21,11 | 2,39 | 0,06 |
| SEQ ID NO: 23 | 365 | hsa-miR-92b* | agguggccgggacgggugcagug | 1344,42 | 2425,74 | 0,55 | 0,06 |

FIG. 10A (Cont.)

| | | | | | | |
|---|---|---|---|---|---|---|
| SEQ ID NO: 794 | 366 | hsa-miR-1269 | cuggacugagccgugcuacugg | 4 | 34,44 | 0,06 |
| SEQ ID NO: 762 | 367 | hsa-miR-1295 | uuaggccgcagaucuggguga | 8,44 | 11,33 | 0,06 |
| SEQ ID NO: 684 | 368 | hsa-miR-155 | uuaaugcuaaucgugauaggggu | 128,44 | 14,89 | 0,06 |
| SEQ ID NO: 342 | 369 | hsa-miR-491-3p | cuuaucaagauuccuucuac | 1 | 1 | 0,06 |
| SEQ ID NO: 280 | 370 | hsa-miR-519b-3p | aaagugcaucccuuuuagagggu | 1 | 1 | 0,06 |
| SEQ ID NO: 265 | 371 | hsa-miR-520f | aagucuuccuuuuagagagguu | 1 | 4,22 | 0,06 |
| SEQ ID NO: 132 | 372 | hsa-miR-624* | uaguaccaguaccuugugugca | 1 | 27,78 | 0,06 |
| SEQ ID NO: 121 | 373 | hsa-miR-632 | gugucugcuuccugugggga | 2,67 | 4,44 | 0,06 |
| SEQ ID NO: 623 | 374 | hsa-miR-194* | ccagugggcugcuguuaucug | 6,78 | 5,11 | 0,06 |
| SEQ ID NO: 532 | 375 | hsa-miR-23a* | ggguucugggggauggguuu | 74 | 122,44 | 0,06 |
| SEQ ID NO: 211 | 376 | hsa-miR-552 | aacaggugacuggaaauagacaa | 1 | 22,22 | 0,06 |
| SEQ ID NO: 187 | 377 | hsa-miR-576-3p | aagugguggaaaaauuggaauc | 4 | 11,33 | 0,06 |
| SEQ ID NO: 480 | 378 | hsa-miR-30d | uguaaacauccccgacuggaag | 6349,31 | 4318,58 | 0,06 |
| SEQ ID NO: 337 | 379 | hsa-miR-494 | ugaaacauacacgggaaaccuc | 20349,58 | 20349,58 | 0,06 |
| SEQ ID NO: 838 | 380 | hsa-miR-1228* | gugggcggggcagguguguq | 5944,79 | 5802,55 | 0,05 |
| SEQ ID NO: 666 | 381 | hsa-miR-182 | uuuggcaauggaagaacucacacu | 7639,53 | 5073,69 | 0,05 |
| SEQ ID NO: 875 | 382 | hsa-miR-106a* | cugcaauguaagcacuuacuu | 1 | 4,44 | 0,05 |
| SEQ ID NO: 859 | 383 | hsa-miR-1197 | uaggacaauggucuacuucu | 1 | 1,56 | 0,05 |
| SEQ ID NO: 847 | 384 | hsa-miR-122* | aacgccauuaucacacuaaaua | 1 | 1 | 0,05 |
| SEQ ID NO: 846 | 385 | hsa-miR-1224-3p | ccccaccucucucucuccucag | 25,56 | 67,44 | 0,05 |
| SEQ ID NO: 829 | 386 | hsa-miR-124* | cguucacagcggaccuugau | 2,67 | 1 | 0,05 |
| SEQ ID NO: 817 | 387 | hsa-miR-1254 | agccuggaagcuggagccugcagu | 245 | 723,61 | 0,05 |
| SEQ ID NO: 809 | 388 | hsa-miR-125a-5p | ucccugagacccuuuaaccuguga | 82,89 | 21,56 | 0,05 |
| SEQ ID NO: 800 | 389 | hsa-miR-1263 | augguacccuggcauacuagu | 1 | 1 | 0,05 |
| SEQ ID NO: 785 | 390 | hsa-miR-127-5p | cugaagcucagagggcucucgau | 5,56 | 21,56 | 0,05 |
| SEQ ID NO: 792 | 391 | hsa-miR-1271 | cuuggcaccuagcaagugacca | 15,78 | 1,56 | 0,05 |
| SEQ ID NO: 774 | 392 | hsa-miR-1285 | ucuggcaacaaagugagaccu | 300,67 | 53 | 5,67 |
| SEQ ID NO: 773 | 393 | hsa-miR-1286 | ugcaggaccaagaugagccu | 12,44 | 12 | 1,04 |
| SEQ ID NO: 772 | 394 | hsa-miR-1287 | ugcuggaucaguggguugagc | 1 | 12,44 | 0,08 |
| SEQ ID NO: 763 | 395 | hsa-miR-1294 | ugugaggguggcaaguuugucu | 29,11 | 18,72 | 1,55 |
| SEQ ID NO: 743 | 396 | hsa-miR-132* | accguggcuuucgauuguuacu | 1 | 1 | 0,05 |
| SEQ ID NO: 726 | 397 | hsa-miR-138-2* | gcuauuucacgacaccagggu | 4,44 | 4,44 | 0,05 |
| SEQ ID NO: 689 | 398 | hsa-miR-1537 | aaaaccgucuaguuuacaguugu | 1 | 1 | 0,05 |
| SEQ ID NO: 681 | 399 | hsa-miR-15a* | caggccauauugugcugccuca | 1 | 1 | 0,05 |
| SEQ ID NO: 676 | 400 | hsa-miR-16-2* | ccaauauuacugugcugcuuua | 40,56 | 30,22 | 1,34 |
| SEQ ID NO: 667 | 401 | hsa-miR-181d | aacauucauuguugucgguggu | 2,67 | 2,67 | 0,05 |
| SEQ ID NO: 665 | 402 | hsa-miR-182* | ugguucuagacuugccaacua | 1 | 1 | 0,05 |

FIG. 10A (Cont.)

| | | | | | | |
|---|---|---|---|---|---|---|
| SEQ ID NO: 618 | 403 | hsa-miR-196b | uagguaguuuccuguuguuggg | 1 | 1 | 0,05 |
| SEQ ID NO: 590 | 404 | hsa-miR-202* | uuccuaugcauauacuucuuug | 1 | 1 | 0,05 |
| SEQ ID NO: 574 | 405 | hsa-miR-21* | caaaccagucgaugggcugu | 1 | 1 | 0,05 |
| SEQ ID NO: 552 | 406 | hsa-miR-219-1-3p | agaguugagucuggacguccg | 1 | 1 | 0,05 |
| SEQ ID NO: 550 | 407 | hsa-miR-219-5p | ugauugcucaaacgcaaucu | 1 | 1 | 0,05 |
| SEQ ID NO: 547 | 408 | hsa-miR-220a | ccacacguaucugacacuuu | 1 | 1 | 0,05 |
| SEQ ID NO: 541 | 409 | hsa-miR-222* | cucaguagccaguguagauccu | 1 | 1 | 0,05 |
| SEQ ID NO: 508 | 410 | hsa-miR-299-5p | ugguuuaccguccacauacau | 1 | 21,56 | 0,05 |
| SEQ ID NO: 500 | 411 | hsa-miR-300 | uauacaagggcagacucucucu | 1 | 1 | 0,05 |
| SEQ ID NO: 498 | 412 | hsa-miR-301b | cagugcaaugauauugucaaagc | 1 | 1 | 0,05 |
| SEQ ID NO: 496 | 413 | hsa-miR-302a* | acuuaaacguggaugguacuugcu | 1 | 1 | 0,05 |
| SEQ ID NO: 491 | 414 | hsa-miR-302d | uaagugcuuccauguuugagugu | 1 | 1 | 0,05 |
| SEQ ID NO: 475 | 415 | hsa-miR-31* | ugcuaugccaacauauugccau | 1 | 1 | 0,05 |
| SEQ ID NO: 474 | 416 | hsa-miR-32 | uauugcacauuacuaaguugca | 1 | 3,67 | 0,27 |
| SEQ ID NO: 473 | 417 | hsa-miR-32* | caauuuagugugaugauaauuu | 1 | 1 | 0,05 |
| SEQ ID NO: 468 | 418 | hsa-miR-323-3p | cacauuacacggucagccucu | 1 | 1 | 0,05 |
| SEQ ID NO: 465 | 419 | hsa-miR-324-5p | cgcaucccuaggcauuggugu | 232,67 | 56,22 | 4,14 |
| SEQ ID NO: 460 | 420 | hsa-miR-330-3p | gcaaagcacacggccugcagaga | 15,33 | 11,11 | 1,38 |
| SEQ ID NO: 454 | 421 | hsa-miR-337-3p | cuccuauaugaugccuuuuuc | 1 | 4,44 | 0,23 |
| SEQ ID NO: 448 | 422 | hsa-miR-33a | gugcauuguaguugcauugca | 1 | 1 | 0,05 |
| SEQ ID NO: 446 | 423 | hsa-miR-33b | gugcauugcuguugcauugc | 1 | 1,56 | 0,64 |
| SEQ ID NO: 445 | 424 | hsa-miR-33b* | cagugcoucgcggcagugccugcccc | 1 | 1 | 0,05 |
| SEQ ID NO: 439 | 425 | hsa-miR-346 | ugucugcccgcaugccugccuugu | 1 | 1 | 0,05 |
| SEQ ID NO: 438 | 426 | hsa-miR-34a | uggcaguguguuagcugguugu | 1 | 1 | 0,05 |
| SEQ ID NO: 433 | 427 | hsa-miR-34c-5p | aggcaguguaguuagcugauugc | 1 | 1 | 0,05 |
| SEQ ID NO: 424 | 428 | hsa-miR-367 | aauugcacuuuagcaauggga | 1 | 1 | 0,05 |
| SEQ ID NO: 422 | 429 | hsa-miR-369-3p | aauaauacaugguugaucuuu | 1 | 1 | 0,05 |
| SEQ ID NO: 417 | 430 | hsa-miR-372 | aaagugcugacauuugagcgu | 1 | 1 | 0,05 |
| SEQ ID NO: 409 | 431 | hsa-miR-376a | aucauagaggaaaauccacgu | 1 | 3,11 | 0,32 |
| SEQ ID NO: 408 | 432 | hsa-miR-376a* | guuauuuccucuauagagua | 1 | 1 | 0,05 |
| SEQ ID NO: 407 | 433 | hsa-miR-376b | aucauagaggaaaauccauguu | 1 | 6,56 | 0,15 |
| SEQ ID NO: 399 | 434 | hsa-miR-380 | uauguaauauggucacaucugu | 1 | 1 | 0,05 |
| SEQ ID NO: 391 | 435 | hsa-miR-410 | aauauaacacagauggccugu | 1 | 1 | 0,05 |
| SEQ ID NO: 386 | 436 | hsa-miR-422a | acuggacuuaggucagaaggc | 166,44 | 1 | 166,44 |
| SEQ ID NO: 379 | 437 | hsa-miR-429 | uaauacugucugguaaaaccgu | 1 | 1 | 0,05 |
| SEQ ID NO: 377 | 438 | hsa-miR-431* | caggucgucuugcagggcuucu | 1 | 1 | 0,05 |
| SEQ ID NO: 375 | 439 | hsa-miR-432* | cuggauggcucuccauguu | 1 | 1 | 0,05 |

FIG. 10A (Cont.)

| | | | | | | | |
|---|---|---|---|---|---|---|---|
| SEQ ID NO: 366 | 440 | hsa-miR-450b-3p | uugggaucauuuugcauccaua | | | | 0,05 |
| SEQ ID NO: 357 | 441 | hsa-miR-455-5p | uaugugccuuuggacuacaucg | | | | 0,05 |
| SEQ ID NO: 347 | 442 | hsa-miR-488 | uugaaaggcuauuucuugguc | | | | 0,05 |
| SEQ ID NO: 346 | 443 | hsa-miR-488* | cccagauaauggcacucucaa | | | | 0,05 |
| SEQ ID NO: 345 | 444 | hsa-miR-489 | gugacaucacauauacggcagc | | | | 0,05 |
| SEQ ID NO: 343 | 445 | hsa-miR-490-5p | ccauggaucuccaggugggu | | 4,22 | | 0,05 |
| SEQ ID NO: 341 | 446 | hsa-miR-491-5p | aguggggaacccuuccaugagg | 101,11 | 96,94 | 1,04 | 0,05 |
| SEQ ID NO: 340 | 447 | hsa-miR-492 | aggaccugcgggacaagauucu | 88,56 | 87,67 | 1,01 | 0,05 |
| SEQ ID NO: 339 | 448 | hsa-miR-493 | ugaagucuacugugugccagg | | 1 | 1 | 0,05 |
| SEQ ID NO: 334 | 449 | hsa-miR-497 | cagcagcacacugugguuugu | 15,78 | 39,44 | 0,4 | 0,05 |
| SEQ ID NO: 333 | 450 | hsa-miR-497* | caaaccacacugugguuuaga | | 1 | 1 | 0,05 |
| SEQ ID NO: 319 | 451 | hsa-miR-506 | uaaggcaccccuucugaguaga | | 1 | 1 | 0,05 |
| SEQ ID NO: 314 | 452 | hsa-miR-509-3p | ugauuggUacgucuguggguag | 1,89 | 1,56 | 1,21 | 0,05 |
| SEQ ID NO: 311 | 453 | hsa-miR-511 | gugucuuuugcucugcagucα | | 1 | 1 | 0,05 |
| SEQ ID NO: 303 | 454 | hsa-miR-515-3p | gaguccuucuuuuugagcguu | | 1 | 1 | 0,05 |
| SEQ ID NO: 301 | 455 | hsa-miR-516a-3p | ugcuuccuuucagaggu | | 1 | 1 | 0,05 |
| SEQ ID NO: 291 | 456 | hsa-miR-518b | caaagcgcuccccuuuuagaggu | 20,56 | 4,44 | 4,63 | 0,05 |
| SEQ ID NO: 282 | 457 | hsa-miR-519a | aaagugcauccuuuuuagagugu | | 1 | 1 | 0,05 |
| SEQ ID NO: 276 | 458 | hsa-miR-519d | caaagugccuccuuuuagagug | | 1 | 1 | 0,05 |
| SEQ ID NO: 273 | 459 | hsa-miR-520a-3p | aaagugcuuccuuuuggacugu | | 1 | 1 | 0,05 |
| SEQ ID NO: 270 | 460 | hsa-miR-520c-3p | aaagugcuuccuuuuagaggu | | 1 | 1 | 0,05 |
| SEQ ID NO: 255 | 461 | hsa-miR-525-3p | gaaggcguccccuuuagagcg | | 1 | 1 | 0,05 |
| SEQ ID NO: 239 | 462 | hsa-miR-545* | ucaguaaaugUUuauuagauga | | 1 | 1 | 0,05 |
| SEQ ID NO: 237 | 463 | hsa-miR-548a-5p | aaaaggaauugcgaguuuuacc | | 1 | 1 | 0,05 |
| SEQ ID NO: 231 | 464 | hsa-miR-548d-5p | aaaaguaauugcggucuuuugcc | | 1 | 1 | 0,05 |
| SEQ ID NO: 228 | 465 | hsa-miR-548g | aaaacuguaauuacuuuuguac | | 1 | 1 | 0,05 |
| SEQ ID NO: 224 | 466 | hsa-miR-548k | aaaagugcggauuuugcu | | 1 | 1 | 0,05 |
| SEQ ID NO: 221 | 467 | hsa-miR-548n | caaaaguaaugugauuuugu | | 1 | 1 | 0,05 |
| SEQ ID NO: 216 | 468 | hsa-miR-550 | agugccugagggaguaagagccc | 136,17 | 90,78 | 1,5 | 0,05 |
| SEQ ID NO: 210 | 469 | hsa-miR-553 | aaaacggugagauuuuguuuu | | 1 | 1 | 0,05 |
| SEQ ID NO: 206 | 470 | hsa-miR-556-5p | gauggcucauugUgaauaugag | | 1 | 1 | 0,05 |
| SEQ ID NO: 198 | 471 | hsa-miR-566 | gggcgccugugaucccaac | | 1 | 1 | 0,05 |
| SEQ ID NO: 197 | 472 | hsa-miR-567 | aguauuucuuccaggacagaac | | 1 | 1 | 0,05 |
| SEQ ID NO: 194 | 473 | hsa-miR-570 | cgaaaacagcaauuaccuuugc- | | 1 | 1 | 0,05 |
| SEQ ID NO: 190 | 474 | hsa-miR-574-3p | cacgcucaugcacacaccaca | 48 | 58,78 | 0,82 | 0,05 |
| SEQ ID NO: 176 | 475 | hsa-miR-585 | ugggcguaucuguaugcua | | 1 | 1 | 0,05 |
| SEQ ID NO: 169 | 476 | hsa-miR-590-5p | gagcuuauuucauaaagugcag | | 1 | 1 | 0,05 |

FIG. 10A (Cont.)

| | | | | | |
|---|---|---|---|---|---|
| SEQ ID NO: 168 | 477 | hsa-miR-591 | agaccauggumcucauugu | 1 | 1 | |
| SEQ ID NO: 154 | 478 | hsa-miR-605 | uaaaucccauggugccuucuccu | 6,78 | 3,67 | 1,85 | 0,05 |
| SEQ ID NO: 147 | 479 | hsa-miR-612 | gcugggcaggccuucugagcuccuu | 24,56 | 33,44 | 0,73 | 0,05 |
| SEQ ID NO: 144 | 480 | hsa-miR-615-3p | uccgagccugggucuccccucu | 1 | 1 | 1 | 0,05 |
| SEQ ID NO: 142 | 481 | hsa-miR-616 | agucauuggagggumuugagcag | 27 | 30,44 | 0,89 | 0,05 |
| SEQ ID NO: 140 | 482 | hsa-miR-617 | agacuuccauuugaaggugc | 2,67 | 4,44 | 0,6 | 0,05 |
| SEQ ID NO: 137 | 483 | hsa-miR-620 | auggagauagauagaaau | 1 | 1,56 | 0,64 | 0,05 |
| SEQ ID NO: 127 | 484 | hsa-miR-628-3p | ucuaguaagaguggcagucga | 49,56 | 34,44 | 1,44 | 0,05 |
| SEQ ID NO: 126 | 485 | hsa-miR-628-5p | augcugacauauuuacuagagg | 1 | 1 | 1 | 0,05 |
| SEQ ID NO: 118 | 486 | hsa-miR-635 | acuugggcacugaaacaaugcc | 1 | 1 | 1 | 0,05 |
| SEQ ID NO: 95 | 487 | hsa-miR-657 | ggcagguuucucacccucucuagg | 130,44 | 1 | 1 | 0,05 |
| SEQ ID NO: 92 | 488 | hsa-miR-660 | uacccauugcauauccggaguug | 1 | 57 | 2,29 | 0,05 |
| SEQ ID NO: 964 | 489 | hsa-miR-675b | cuguaugccccuccgcuca | 4 | 4,44 | 0,9 | 0,05 |
| SEQ ID NO: 77 | 490 | hsa-miR-708 | aaggagcuuacaaucuagccuggg | 1 | 1 | 1 | 0,05 |
| SEQ ID NO: 76 | 491 | hsa-miR-708* | caaucuagacugugagcuucuag | 1 | 1 | 1 | 0,05 |
| SEQ ID NO: 69 | 492 | hsa-miR-744* | cuguugccacuaaccucaaccu | 15,33 | 11,33 | 1,35 | 0,05 |
| SEQ ID NO: 55 | 493 | hsa-miR-802 | caguaacaaagauuucauccuugu | 1 | 1 | 1 | 0,05 |
| SEQ ID NO: 50 | 494 | hsa-miR-876-3p | uggugmuuacaaaguaauuca | 1 | 1 | 1 | 0,05 |
| SEQ ID NO: 49 | 495 | hsa-miR-876-5p | uggauuucuuugugaaucacca | 1 | 1 | 1 | 0,05 |
| SEQ ID NO: 41 | 496 | hsa-miR-888 | uacucaaaagcugucaguca | 1 | 1 | 1 | 0,05 |
| SEQ ID NO: 36 | 497 | hsa-miR-891b | ugcaacuaaccugagaguauuga | 1 | 1 | 1 | 0,05 |
| SEQ ID NO: 34 | 498 | hsa-miR-892b | cacuggcucuuuuuguaga | 1 | 1 | 1 | 0,05 |
| SEQ ID NO: 33 | 499 | hsa-miR-9 | ucuuugguuaucuagcuguauga | 1 | 1 | 1 | 0,05 |
| SEQ ID NO: 32 | 500 | hsa-miR-9* | auaaagcuagauaaccgaaagu | 1 | 1 | 1 | 0,05 |
| SEQ ID NO: 28 | 501 | hsa-miR-924 | agagucuugugaugcuugc | 1 | 1 | 1 | 0,05 |
| SEQ ID NO: 19 | 502 | hsa-miR-934 | ugucuacuacuggagacacugg | 1 | 1 | 1 | 0,05 |
| SEQ ID NO: 10 | 503 | hsa-miR-943 | cugacuguugccgucuccag | 1 | 1 | 1 | 0,05 |
| SEQ ID NO: 6 | 504 | hsa-miR-96* | aaucauugcaguccaauaug | 1 | 1 | 1 | 0,05 |
| SEQ ID NO: 3 | 505 | hsa-miR-99a* | caagcucgcuugucuaugggucg | 1 | 1 | 1 | 0,05 |
| SEQ ID NO: 1 | 506 | hsa-miR-99b* | caagcucgugucuguggguccg | 1 | 1 | 1 | 0,05 |
| SEQ ID NO: 472 | 507 | hsa-miR-320a | aaaagcuggguugagagggcga | 10047,96 | 8310,31 | 1,21 | 0,05 |
| SEQ ID NO: 780 | 508 | hsa-miR-128 | ucacaguggcggucacc | 773,97 | 21,56 | 35,91 | 0,05 |
| SEQ ID NO: 779 | 509 | hsa-miR-1280 | ucccaccgcugccaccc | 237,33 | 158,89 | 1,49 | 0,05 |
| SEQ ID NO: 506 | 510 | hsa-miR-29a* | acugauuucuuuugguucag | 2,22 | 1 | 2,22 | 0,05 |
| SEQ ID NO: 447 | 511 | hsa-miR-33a* | caauguuccacagugcaucac | 1 | 1 | 1 | 0,05 |
| SEQ ID NO: 429 | 512 | hsa-miR-362-5p | aauccuugaaccuaggugugagu | 260,22 | 14,89 | 17,48 | 0,05 |
| SEQ ID NO: 420 | 513 | hsa-miR-370 | gccugcuggggugaaccugagu | 194 | 156,56 | 1,24 | 0,05 |

FIG. 10A (Cont.)

| | | | | | |
|---|---|---|---|---|---|
| SEQ ID NO: 325 | 514 | hsa-miR-502-3p | aaugcaccucuggcaaggauuca | 364,22 | 14,89 | 24,46 | 0,05 |
| SEQ ID NO: 215 | 515 | hsa-miR-550* | ugucuuaacucccucaggcacau | 331,06 | 5,11 | 64,77 | 0,05 |
| SEQ ID NO: 175 | 516 | hsa-miR-586 | uaugcauugualuuuuaggucc | 1 | 1 | 1 | 0,05 |
| SEQ ID NO: 102 | 517 | hsa-miR-651 | uuuaggauaagcuugacuuuug | 1 | 1 | 1 | 0,05 |
| SEQ ID NO: 62 | 518 | hsa-miR-765 | uggaggagaggaaggugaug | 1085,22 | 1101,78 | 0,98 | 0,05 |
| SEQ ID NO: 11 | 519 | hsa-miR-942 | ucuucucuguuuggccaugug | 52 | 18,11 | 2,87 | 0,05 |
| SEQ ID NO: 807 | 520 | hsa-miR-125b-1* | acgguuaggcucuugggagcu | 49,56 | 56,22 | 0,88 | 0,05 |
| SEQ ID NO: 663 | 521 | hsa-miR-1826 | auugaucaacgcacacuucgaacgcaau | 35853,42 | 35853,42 | 1 | 0,05 |
| SEQ ID NO: 442 | 522 | hsa-miR-342-3p | ucucacacagaaaauugcaaccgu | 3428,42 | 2319,9 | 1,48 | 0,05 |
| SEQ ID NO: 305 | 523 | hsa-miR-513c | uucucaaggaggugucguuuau | 68,67 | 45,11 | 1,52 | 0,04 |
| SEQ ID NO: 786 | 524 | hsa-miR-1275 | gugggggaggcuguc | 1146,69 | 901,96 | 1,27 | 0,04 |
| SEQ ID NO: 243 | 525 | hsa-miR-542-5p | ucggggaucaucugugugagga | 6,78 | 1 | 6,78 | 0,04 |
| SEQ ID NO: 300 | 526 | hsa-miR-516a-5p | uucucgaggaagaagcacuuuc | 39,67 | 58,78 | 0,67 | 0,04 |
| SEQ ID NO: 256 | 527 | hsa-miR-524-5p | cuacaaggaggugucguuuuc | 31,11 | 29,44 | 1,06 | 0,04 |
| SEQ ID NO: 965 | 528 | hsa-miR-923 | gucagcggaggaaagaaacu | 24783,94 | 20349,58 | 1,22 | 0,04 |
| SEQ ID NO: 24 | 529 | hsa-miR-92b | uauugcacucguccgcccc | 4260,36 | 5530,88 | 0,77 | 0,04 |
| SEQ ID NO: 757 | 530 | hsa-miR-1299 | uucuggaaucucugugaggga | 1 | 29,94 | 0,03 | 0,04 |
| SEQ ID NO: 708 | 531 | hsa-miR-146b-5p | ugagaacugaauuccauaggcu | 92,56 | 67,44 | 1,37 | 0,04 |
| SEQ ID NO: 497 | 532 | hsa-miR-302a | uaagugcuuccauguuuugguga | 1 | 1 | 1 | 0,04 |
| SEQ ID NO: 400 | 533 | hsa-miR-379* | uguaacaugguccacuaacu | 1 | 1,56 | 0,64 | 0,04 |
| SEQ ID NO: 317 | 534 | hsa-miR-508-3p | ugauuguagccuuuuggaguaga | 1 | 1 | 1 | 0,04 |
| SEQ ID NO: 310 | 535 | hsa-miR-512-3p | aagugcugucauagcugaggug | 1 | 1 | 1 | 0,04 |
| SEQ ID NO: 295 | 536 | hsa-miR-517b | ucgugcaucccuuuagaguguu | 1 | 1 | 1 | 0,04 |
| SEQ ID NO: 263 | 537 | hsa-miR-520h | acaaagugcuuccuuuagagu | 1 | 1 | 1 | 0,04 |
| SEQ ID NO: 238 | 538 | hsa-miR-548a-3p | caaaacuggcaauucccuuuagc | 1 | 1 | 1 | 0,04 |
| SEQ ID NO: 183 | 539 | hsa-miR-579 | uucauuuggualauaaaccgcgauu | 1 | 1 | 1 | 0,04 |
| SEQ ID NO: 47 | 540 | hsa-miR-877* | uccucuucucccucccag | 20,83 | 21,11 | 0,99 | 0,04 |
| SEQ ID NO: 40 | 541 | hsa-miR-888* | gacugacccucuuugggugaa | 1 | 6,56 | 0,15 | 0,04 |
| SEQ ID NO: 752 | 542 | hsa-miR-1305 | uuuucaacuauggggagaga | 1 | 3,67 | 0,27 | 0,04 |
| SEQ ID NO: 415 | 543 | hsa-miR-373* | acucaaaaugggcgcuuuc | 79,67 | 116,33 | 0,68 | 0,04 |
| SEQ ID NO: 401 | 544 | hsa-miR-379 | ugguagacuaugguaacguagg | 25,56 | 39,22 | 0,65 | 0,04 |
| SEQ ID NO: 376 | 545 | hsa-miR-432 | ucuuggagauaggucauugggugg | 41,89 | 39,22 | 1,07 | 0,04 |
| SEQ ID NO: 312 | 546 | hsa-miR-510 | uacucaggagagguggcaaucac | 26,78 | 8,33 | 3,21 | 0,04 |
| SEQ ID NO: 285 | 547 | hsa-miR-518e* | cucuagagggaagcgcuuucug | 2,22 | 2,67 | 0,83 | 0,04 |
| SEQ ID NO: 277 | 548 | hsa-miR-519c-5p | cucuagagggaagcgcuuucug | 1,56 | 13,72 | 0,11 | 0,04 |
| SEQ ID NO: 267 | 549 | hsa-miR-520d-5p | cuacaaggaagcccuuuc | 37,67 | 44,89 | 0,84 | 0,04 |
| SEQ ID NO: 149 | 550 | hsa-miR-610 | ugagcuaaaugugugcugga | 24 | 36,11 | 0,66 | 0,04 |

FIG. 10A (Cont.)

| | | | | | | |
|---|---|---|---|---|---|---|
| SEQ ID NO: 31 | 551 | hsa-miR-920 | gggagcugugaagcagua | 50,56 | 80,11 | 0,63 | 0,04 |
| SEQ ID NO: 548 | 552 | hsa-miR-22* | aguucuucaguggcaagcuuua | 69,67 | 36,11 | 1,93 | 0,03 |
| SEQ ID NO: 27 | 553 | hsa-miR-92a | uauugcacuuguccggccugu | 22685,5 | 18004,17 | 1,26 | 0,03 |
| SEQ ID NO: 856 | 554 | hsa-miR-1202 | gugccagcugcagugggggag | 71,56 | 86,67 | 0,83 | 0,03 |
| SEQ ID NO: 307 | 555 | hsa-miR-513a-5p | uucacagggaggugucau | 450,61 | 348,22 | 1,29 | 0,03 |
| SEQ ID NO: 749 | 556 | hsa-miR-1308 | gcauggguggguucagugg | 15421,86 | 9312,5 | 1,66 | 0,03 |
| SEQ ID NO: 862 | 557 | hsa-miR-1183 | cacuguaggugugguguagagugggca | 120,44 | 82,89 | 1,45 | 0,03 |
| SEQ ID NO: 843 | 558 | hsa-miR-1225-5p | gugguacgcccaguggggg | 142,83 | 194 | 0,74 | 0,03 |
| SEQ ID NO: 963 | 559 | hsa-miR-1300 | uugagaaggaggcugcg | 327,33 | 192,67 | 1,7 | 0,03 |
| SEQ ID NO: 725 | 560 | hsa-miR-139-3p | ggagacgcggccuguuggagu | 43,11 | 33,78 | 1,28 | 0,03 |
| SEQ ID NO: 525 | 561 | hsa-miR-25* | aggggagacuuugggcaaug | 111,78 | 68,44 | 1,63 | 0,03 |
| SEQ ID NO: 522 | 562 | hsa-miR-26a-2* | ccuauucuugauuacuguuuc | 1 | 1 | 1 | 0,03 |
| SEQ ID NO: 459 | 563 | hsa-miR-330-5p | ucucuggggccugugucuagc | 13,72 | 1 | 13,72 | 0,03 |
| SEQ ID NO: 452 | 564 | hsa-miR-338-3p | uccagcaucagugaugugug | 101,11 | 58,78 | 1,72 | 0,03 |
| SEQ ID NO: 332 | 565 | hsa-miR-498 | uuucaagccagggggcguuuuuc | 254,28 | 8,33 | 30,51 | 0,03 |
| SEQ ID NO: 328 | 566 | hsa-miR-500* | augccacugggcaaggcacuucug | 36,78 | 19,78 | 1,86 | 0,03 |
| SEQ ID NO: 287 | 567 | hsa-miR-518d-5p | cucuagaggaagcacuucug | 31,56 | 30,44 | 1,04 | 0,03 |
| SEQ ID NO: 269 | 568 | hsa-miR-520c-5p | cucuagaggaagcacuucug | 1 | 1 | 1 | 0,03 |
| SEQ ID NO: 222 | 569 | hsa-miR-548m | caaggauuuugguuuug | 97,33 | 87,67 | 1,11 | 0,03 |
| SEQ ID NO: 212 | 570 | hsa-miR-551b* | gaaaucaagcgugggugagacc | 272 | 168,11 | 1,62 | 0,03 |
| SEQ ID NO: 81 | 571 | hsa-miR-671-5p | aggaagcccuggagggcuggag | 189,89 | 61,56 | 3,08 | 0,03 |
| SEQ ID NO: 71 | 572 | hsa-miR-720 | ucucgcugggggccuca | 106,11 | 70,89 | 1,5 | 0,03 |
| SEQ ID NO: 61 | 573 | hsa-miR-766 | acucagcccacacaggccuagc | 364,22 | 450,61 | 0,81 | 0,03 |
| SEQ ID NO: 48 | 574 | hsa-miR-877 | guagaggagaugcgcaggg | 4,78 | 4,22 | 1,13 | 0,03 |
| SEQ ID NO: 903 | 575 | hsa-let-7a* | cuauacaauuacucugcaggg | 1 | 1 | 1 | 0,03 |
| SEQ ID NO: 894 | 576 | hsa-let-7e* | cuauacccaguaguaguuuuc | 1 | 1 | 1 | 0,03 |
| SEQ ID NO: 887 | 577 | hsa-let-7i* | cugcgcaagcuacugccuugcu | 5,22 | 1 | 5,22 | 0,03 |
| SEQ ID NO: 884 | 578 | hsa-miR-100* | caagcuugauucuauagguaug | 1 | 1 | 1 | 0,03 |
| SEQ ID NO: 882 | 579 | hsa-miR-101* | caguuaucecagugcugaugcu | 1 | 1 | 1 | 0,03 |
| SEQ ID NO: 828 | 580 | hsa-miR-1243 | aacuggaucaauuauaggagug | 1 | 1 | 1 | 0,03 |
| SEQ ID NO: 789 | 581 | hsa-miR-127-3p | ucggauccgucugagcuuggcu | 1 | 1 | 1 | 0,03 |
| SEQ ID NO: 737 | 582 | hsa-miR-133b | uuugucccuuuuuaaccagcua | 24 | 19,78 | 1,21 | 0,03 |
| SEQ ID NO: 735 | 583 | hsa-miR-135a | uauggcuuuuuauucccuauguga | 1 | 1 | 1 | 0,03 |
| SEQ ID NO: 730 | 584 | hsa-miR-136* | caucaucguucaaaaugagucu | 1 | 1 | 1 | 0,03 |
| SEQ ID NO: 720 | 585 | hsa-miR-141* | caucuuccaguacaguugga | 1 | 1 | 1 | 0,03 |
| SEQ ID NO: 660 | 586 | hsa-miR-183* | gugaauuacgaagggccauaa | 82,06 | 72,22 | 1,14 | 0,03 |
| SEQ ID NO: 646 | 587 | hsa-miR-190 | ugauauguuugauauauuaggu | 1 | 1 | 1 | 0,03 |

FIG. 10A (Cont.)

| | | | | | | |
|---|---|---|---|---|---|---|
| SEQ ID NO: 597 | 588 | hsa-miR-200a | uaacacugucugguaacgaugu | 1 | 1 | 0,03 |
| SEQ ID NO: 594 | 589 | hsa-miR-200b* | caucuuacugggcagcauugga | 7,44 | 4,22 | 0,03 |
| SEQ ID NO: 581 | 590 | hsa-miR-208a | auaagacgagcaaaaagcuugu | 19,89 | 14,89 | 0,03 |
| SEQ ID NO: 578 | 591 | hsa-miR-20a* | acugcauuaugagcacuaaag | 1 | 1 | 0,03 |
| SEQ ID NO: 556 | 592 | hsa-miR-217 | uacugcaucaggaacugauugga | 1 | 1 | 0,03 |
| SEQ ID NO: 554 | 593 | hsa-miR-218-1* | agguuccgucaagcaccaugg | 1 | 1 | 0,03 |
| SEQ ID NO: 523 | 594 | hsa-miR-26a-1* | ccuauucuugguuacuugcacg | 1 | 1 | 0,03 |
| SEQ ID NO: 518 | 595 | hsa-miR-27a* | agggcuuagcugcuugugagca | 1 | 1 | 0,03 |
| SEQ ID NO: 461 | 596 | hsa-miR-329 | aacacaccugguuaaccucuuu | 1 | 1,56 | 0,03 |
| SEQ ID NO: 457 | 597 | hsa-miR-331-5p | cuagguauggucccaggggauc | 22,22 | 21,11 | 1,05 | 0,03 |
| SEQ ID NO: 453 | 598 | hsa-miR-337-5p | gaacggcuucauacaggaguu | 2,67 | 8,33 | 0,32 | 0,03 |
| SEQ ID NO: 423 | 599 | hsa-miR-367* | acuguugcuaauauugcaacu | 1 | 1 | 1 | 0,03 |
| SEQ ID NO: 416 | 600 | hsa-miR-373 | gaagugcuucgauuuugggcgu | 1 | 1,56 | 0,64 | 0,03 |
| SEQ ID NO: 404 | 601 | hsa-miR-377* | agagguugcccugguguaauc | 1 | 1 | 1 | 0,03 |
| SEQ ID NO: 397 | 602 | hsa-miR-381 | uauacaagggcaagcucucugu | 7,44 | 1 | 7,44 | 0,03 |
| SEQ ID NO: 388 | 603 | hsa-miR-412 | acuucaccuggucccacuagccgu | 4 | 1,56 | 2,57 | 0,03 |
| SEQ ID NO: 373 | 604 | hsa-miR-448 | uugcauauguaggaugucccuagau | 1 | 1 | 1 | 0,03 |
| SEQ ID NO: 367 | 605 | hsa-miR-450a | uuuugcgauguguuccuaauau | 1 | 1 | 1 | 0,03 |
| SEQ ID NO: 363 | 606 | hsa-miR-452 | aacuguuugcagagggaaacuga | 2,67 | 1 | 2,67 | 0,03 |
| SEQ ID NO: 353 | 607 | hsa-miR-485-3p | gucauacacggcucucucucu | 1 | 1,56 | 0,64 | 0,03 |
| SEQ ID NO: 349 | 608 | hsa-miR-487a | aaucauacaggacaucagu | 1,56 | 1,56 | 1 | 0,03 |
| SEQ ID NO: 322 | 609 | hsa-miR-504 | agacccugucugcacucuauc | 1 | 1 | 1 | 0,03 |
| SEQ ID NO: 309 | 610 | hsa-miR-512-5p | cacucagccuugaggcacuuuc | 1 | 4,22 | 0,24 | 0,03 |
| SEQ ID NO: 294 | 611 | hsa-miR-517c | augugcaucuuuaagugug | 1 | 1 | 1 | 0,03 |
| SEQ ID NO: 290 | 612 | hsa-miR-518c | caaagcgcuucucuuuagugugu | 1 | 1 | 1 | 0,03 |
| SEQ ID NO: 286 | 613 | hsa-miR-518e | aaagcgcuuccuuuucagagug | 1 | 1 | 1 | 0,03 |
| SEQ ID NO: 247 | 614 | hsa-miR-539 | ggagaaauuauccuugguguguug | 1 | 1 | 1 | 0,03 |
| SEQ ID NO: 234 | 615 | hsa-miR-548c-3p | caaaaauccaauuuacuuuugc | 1 | 1 | 1 | 0,03 |
| SEQ ID NO: 220 | 616 | hsa-miR-548o | ccaaaacugcaguuacuuugc | 1 | 1 | 1 | 0,03 |
| SEQ ID NO: 207 | 617 | hsa-miR-556-3p | auauuaccauuagcucaucuuu | 1 | 1 | 1 | 0,03 |
| SEQ ID NO: 203 | 618 | hsa-miR-559 | uaaguaaauaugcaccaaaa | 1 | 1 | 1 | 0,03 |
| SEQ ID NO: 191 | 619 | hsa-miR-573 | cugagugaugugauaacugacag | 1 | 1 | 1 | 0,03 |
| SEQ ID NO: 182 | 620 | hsa-miR-580 | uugaguugugaucaguaauagg | 1 | 1 | 1 | 0,03 |
| SEQ ID NO: 179 | 621 | hsa-miR-582-5p | uuacaguugagccegguuaccu | 1 | 3,11 | 0,32 | 0,03 |
| SEQ ID NO: 171 | 622 | hsa-miR-589* | ucagaacaaaugccgguuccaga | 22,67 | 20,56 | 1,1 | 0,03 |
| SEQ ID NO: 146 | 623 | hsa-miR-613 | aggaaguuucuuuugcc | 1 | 1 | 1 | 0,03 |
| SEQ ID NO: 136 | 624 | hsa-miR-621 | ggcuagcaacagcgcuuaccu | 1 | 1 | 1 | 0,03 |

FIG. 10A (Cont.)

| | | | | | | |
|---|---|---|---|---|---|---|
| SEQ ID NO: 129 | 625 | hsa-miR-626 | agcgucugaaaugucuu | 1 | 1 | 0,03 |
| SEQ ID NO: 120 | 626 | hsa-miR-633 | cuaauaguaucuaccacaauaaa | 1 | 1 | 0,03 |
| SEQ ID NO: 103 | 627 | hsa-miR-650 | aggaggcagcgcucucaggac | 14,89 | 12,44 | 1,2 | 0,03 |
| SEQ ID NO: 91 | 628 | hsa-miR-661 | ugccugguccugugucugcgcgu | 4 | 4 | 1 | 0,03 |
| SEQ ID NO: 59 | 629 | hsa-miR-767-5p | ugccaugguuguugucgagcaug | 1 | 1 | 1 | 0,03 |
| SEQ ID NO: 56 | 630 | hsa-miR-770-5p | uccaguaccacguucccguagcca | 9,11 | 11,33 | 0,8 | 0,03 |
| SEQ ID NO: 18 | 631 | hsa-miR-935 | ccaguuaccgcuucccgcuacccgc | 1 | 1 | 1 | 0,03 |
| SEQ ID NO: 12 | 632 | hsa-miR-941 | cacccggcugugugcacaugugc | 39,67 | 4,22 | 9,39 | 0,03 |
| SEQ ID NO: 9 | 633 | hsa-miR-944 | aaauauuguaacaucggaugag | 1 | 1 | 1 | 0,03 |
| SEQ ID NO: 654 | 634 | hsa-miR-187 | ucgugucugugugguugcagccgg | 1 | 4,44 | 0,23 | 0,03 |
| SEQ ID NO: 640 | 635 | hsa-miR-191* | gcucgcuuggauuucguccc | 53 | 47,06 | 1,13 | 0,03 |
| SEQ ID NO: 470 | 636 | hsa-miR-320c | aaaagcuggguugagagggu | 5382,15 | 6141,96 | 0,88 | 0,02 |
| SEQ ID NO: 840 | 637 | hsa-miR-1227 | cgugccacccuuuuccccag | 32 | 29,94 | 1,07 | 0,02 |
| SEQ ID NO: 699 | 638 | hsa-miR-148b | ucagugcaucacagaacuuugu | 364,22 | 1 | 364,22 | 0,02 |
| SEQ ID NO: 656 | 639 | hsa-miR-186 | caaagaauuccuuuugggcu | 39,67 | 18,72 | 2,12 | 0,02 |
| SEQ ID NO: 642 | 640 | hsa-miR-190b | ugauauguuuugauauugggguu | 1 | 1 | 1 | 0,02 |
| SEQ ID NO: 444 | 641 | hsa-miR-340 | uuauaaagcaaugagaacugauu | 79,67 | 21,56 | 3,7 | 0,02 |
| SEQ ID NO: 355 | 642 | hsa-miR-483-5p | aagacgggaggaaagaaggag | 4541,94 | 3572,67 | 1,27 | 0,02 |
| SEQ ID NO: 324 | 643 | hsa-miR-502-5p | auccugcuaucugguguca | 6,78 | 1 | 6,78 | 0,02 |
| SEQ ID NO: 172 | 644 | hsa-miR-589 | ugagaaccagugcucucugag | 6,78 | 1 | 6,78 | 0,02 |
| SEQ ID NO: 471 | 645 | hsa-miR-320b | aaaagcuggguugagagggcaa | 6349,31 | 6349,31 | 1 | 0,02 |
| SEQ ID NO: 688 | 646 | hsa-miR-1538 | cggccggguugcugcuguuccu | 48 | 18,72 | 2,56 | 0,02 |
| SEQ ID NO: 350 | 647 | hsa-miR-486-5p | uccugugggagcugcgccccgag | 42197,28 | 42197,28 | 1 | 0,02 |
| SEQ ID NO: 696 | 648 | hsa-miR-149* | agggaggggacggggcgugc | 18004,17 | 13307,74 | 1,35 | 0,02 |
| SEQ ID NO: 900 | 649 | hsa-let-7b* | cuaaccuacugccuucccc | 22,22 | 13,72 | 1,62 | 0,02 |
| SEQ ID NO: 865 | 650 | hsa-miR-1180 | uuuccggcgcguggugugu | 61,11 | 21,11 | 2,89 | 0,02 |
| SEQ ID NO: 855 | 651 | hsa-miR-1203 | cccggagccaggaugcagcuc | 43,11 | 28 | 1,54 | 0,02 |
| SEQ ID NO: 813 | 652 | hsa-miR-1257 | agugaaugggguucugacc | 2,67 | 1,56 | 1,71 | 0,02 |
| SEQ ID NO: 812 | 653 | hsa-miR-1258 | aguuaggauuagguucgugaa | 15,78 | 12,44 | 1,27 | 0,02 |
| SEQ ID NO: 799 | 654 | hsa-miR-1264 | caagucuauuuugagaccuguu | 1 | 1 | 1 | 0,02 |
| SEQ ID NO: 704 | 655 | hsa-miR-1470 | gcccucccgccggcugcaccccg | 20,56 | 12,11 | 1,7 | 0,02 |
| SEQ ID NO: 647 | 656 | hsa-miR-18b* | ugccuaaaugcccccuucggc | 24,56 | 18,11 | 1,36 | 0,02 |
| SEQ ID NO: 631 | 657 | hsa-miR-1915* | accuugccuugcgccgggcc | 1 | 11,33 | 0,09 | 0,02 |
| SEQ ID NO: 598 | 658 | hsa-miR-19b-2* | aguuuugcagguuugcauuca | 1 | 1 | 1 | 0,02 |
| SEQ ID NO: 589 | 659 | hsa-miR-203 | gugaaugguuuagaccaucuag | 1 | 1 | 1 | 0,02 |
| SEQ ID NO: 582 | 660 | hsa-miR-206 | uggaauguaaggaaguguggg | 15,78 | 28,44 | 0,55 | 0,02 |
| SEQ ID NO: 572 | 661 | hsa-miR-211 | uucccuuugcauccuucccgcu | 1 | 3,67 | 0,27 | 0,02 |

FIG. 10A (Cont.)

| | | | | | | |
|---|---|---|---|---|---|---|
| SEQ ID NO: 551 | 662 | hsa-miR-219-2-3p | agaauuguggcuggacaucugu | 4 | | 4 |
| SEQ ID NO: 545 | 663 | hsa-miR-220c | acacagggcuguuugugaagacu | 1 | 3,11 | 0,32 | 0,02 |
| SEQ ID NO: 539 | 664 | hsa-miR-223* | cguguauuugacaagcugagu | 1 | 4,44 | 0,23 | 0,02 |
| SEQ ID NO: 538 | 665 | hsa-miR-224 | caagucacuagugguucgu | 1 | 1 | 1 | 0,02 |
| SEQ ID NO: 517 | 666 | hsa-miR-27b | uucacaguugcuaaguucgc | 73,33 | 33,78 | 2,17 | 0,02 |
| SEQ ID NO: 512 | 667 | hsa-miR-296-5p | agggccccccacaauccugu | 48 | 58,89 | 0,82 | 0,02 |
| SEQ ID NO: 482 | 668 | hsa-miR-30c-1* | cuggagaggguuguuuacucc | 101,11 | 101,11 | 1 | 0,02 |
| SEQ ID NO: 476 | 669 | hsa-miR-31 | aggcaagaugcuggcauagcu | 8,44 | 3,67 | 2,3 | 0,02 |
| SEQ ID NO: 396 | 670 | hsa-miR-382 | gaaguguuccgugugugaauccg | 9,56 | 1,56 | 6,14 | 0,02 |
| SEQ ID NO: 359 | 671 | hsa-miR-454* | acccuaucaaauaugucucugc | 27 | 21,11 | 1,28 | 0,02 |
| SEQ ID NO: 351 | 672 | hsa-miR-486-3p | cggggcagcugcuggcaaucaggau | 37,89 | 18,72 | 2,02 | 0,02 |
| SEQ ID NO: 315 | 673 | hsa-miR-509-3-5p | uacugcagaggaagcacaucuc | 1 | 1 | 1 | 0,02 |
| SEQ ID NO: 283 | 674 | hsa-miR-518f* | cucuagagggaagcacuuucuc | 25,17 | 58,89 | 0,43 | 0,02 |
| SEQ ID NO: 279 | 675 | hsa-miR-519b-5p | cucuagagggaagcgcuuucug | 1,56 | 4,44 | 0,35 | 0,02 |
| SEQ ID NO: 275 | 676 | hsa-miR-519e | aagugcccuucuuuuagagugu | 1 | 1 | 1 | 0,02 |
| SEQ ID NO: 268 | 677 | hsa-miR-520d-3p | aaagugcuucucuuuggugggu | 1 | 1 | 1 | 0,02 |
| SEQ ID NO: 258 | 678 | hsa-miR-523* | cucuagagggaagcgcuuucug | 6,78 | 18,72 | 0,36 | 0,02 |
| SEQ ID NO: 257 | 679 | hsa-miR-524-3p | gaagcgcuucccuuuggagu | 1 | 1 | 1 | 0,02 |
| SEQ ID NO: 246 | 680 | hsa-miR-541 | uggugggcacagaaucuggacu | 16,78 | 28,44 | 0,59 | 0,02 |
| SEQ ID NO: 242 | 681 | hsa-miR-543 | aaacauucgcggugcacuuuuu | 1 | 1 | 1 | 0,02 |
| SEQ ID NO: 233 | 682 | hsa-miR-548c-5p | aaaaguaauugcgguuuuugcc | 1 | 1 | 1 | 0,02 |
| SEQ ID NO: 230 | 683 | hsa-miR-548e | aaaaacugagacuacuuuugca | 1 | 1 | 1 | 0,02 |
| SEQ ID NO: 226 | 684 | hsa-miR-548i | aaaaguaauugcggauuuugcc | 1 | 1 | 1 | 0,02 |
| SEQ ID NO: 223 | 685 | hsa-miR-548l | aaaaguaauugcgguuuuugcc | 1 | 1 | 1 | 0,02 |
| SEQ ID NO: 219 | 686 | hsa-miR-548p | uagcaaaaacugcaguuacuuu | 1 | 1 | 1 | 0,02 |
| SEQ ID NO: 193 | 687 | hsa-miR-571 | ugaguugggcaucgagugag | 1 | 1 | 1 | 0,02 |
| SEQ ID NO: 163 | 688 | hsa-miR-596 | aagccugcccggcugugucccggg | 12,22 | 3,11 | 0,32 | 0,02 |
| SEQ ID NO: 161 | 689 | hsa-miR-598 | uacgucaucguugucaucguca | 1 | 12,22 | 12,22 | 0,02 |
| SEQ ID NO: 159 | 690 | hsa-miR-600 | acuuacagacaagagccuugcuc | 1 | 1 | 1 | 0,02 |
| SEQ ID NO: 134 | 691 | hsa-miR-623 | auccccuugcaggggcuguuggu | 1 | 1 | 1 | 0,02 |
| SEQ ID NO: 123 | 692 | hsa-miR-630 | aguauucuccaaaugucaugu | 4 | 6,56 | 0,61 | 0,02 |
| SEQ ID NO: 111 | 693 | hsa-miR-642 | gucccucucaaauguacaggu | 1 | 1 | 1 | 0,02 |
| SEQ ID NO: 110 | 694 | hsa-miR-643 | acuuguauugcuagaccucagu | 1 | 1 | 1 | 0,02 |
| SEQ ID NO: 99 | 695 | hsa-miR-654-3p | uauguucugcugaccaaccu | 1 | 1 | 1 | 0,02 |
| SEQ ID NO: 54 | 696 | hsa-miR-873 | gcaggaacuugugagucucu | 1 | 5,11 | 0,2 | 0,02 |
| SEQ ID NO: 38 | 697 | hsa-miR-890 | uacuuggaaggcaucagug | 20,56 | 11,56 | 1,78 | 0,02 |
| SEQ ID NO: 695 | 698 | hsa-miR-150 | ucucccaaccuguaccagug | 600,34 | 839,63 | 0,72 | 0,02 |

FIG. 10A (Cont.)

| | | | | | | |
|---|---|---|---|---|---|---|
| SEQ ID NO: 808 | 698 | hsa-miR-125b | ucccugagacccuuaacuuguga | 65,56 | 38,33 | 1,71 | 0,01 |
| SEQ ID NO: 619 | 700 | hsa-miR-198a* | cggcaacaagaaacugccugag | 15,33 | 18,72 | 0,82 | 0,01 |
| SEQ ID NO: 606 | 701 | hsa-miR-199a-3p | acaguagucugcacauugguua | 1 | 19,78 | 0,05 | 0,01 |
| SEQ ID NO: 387 | 702 | hsa-miR-421 | aucaacagacauuaauuggggc | 217,67 | 1 | 217,67 | 0,01 |
| SEQ ID NO: 356 | 703 | hsa-miR-483-3p | ucacuccucuccucccgucuu | 13 | 30,44 | 0,43 | 0,01 |
| SEQ ID NO: 302 | 704 | hsa-miR-515-5p | uucuccaaaagaaagcacuuucug | 1 | 1 | 1 | 0,01 |
| SEQ ID NO: 245 | 705 | hsa-miR-541* | aaaggauucugcugucggucccacu | 1 | 1 | 1 | 0,01 |
| SEQ ID NO: 784 | 706 | hsa-miR-1276 | uaaagagccugugggagaca | 24,56 | 30,44 | 0,81 | 0,01 |
| SEQ ID NO: 641 | 707 | hsa-miR-191 | caacggaaucccaaaagcagcug | 31577,57 | 27467,24 | 1,15 | 0,01 |
| SEQ ID NO: 492 | 708 | hsa-miR-302c* | uuuaacauggguaccugcug | 68,67 | 18,72 | 3,67 | 0,01 |
| SEQ ID NO: 484 | 709 | hsa-miR-30b* | cugggaggugaugcuuacuuc | 88,56 | 98,56 | 0,9 | 0,01 |
| SEQ ID NO: 544 | 710 | hsa-miR-221 | agcuacauugucugcugguuuc | 382 | 539,56 | 0,71 | 0,01 |
| SEQ ID NO: 632 | 711 | hsa-miR-1915 | ccccaggggcgacggccccc | 2223,89 | 3080,08 | 0,72 | 0,01 |
| SEQ ID NO: 839 | 712 | hsa-miR-1228 | ucacacugccccugccccc | 39,67 | 140,78 | 0,28 | 0,01 |
| SEQ ID NO: 832 | 713 | hsa-miR-1237 | uccuucugcucuguccucag | 37,89 | 30,44 | 1,24 | 0,01 |
| SEQ ID NO: 761 | 714 | hsa-miR-129-5p | cuuuuugcgguucugggccuug | 33,78 | 14,89 | 2,27 | 0,01 |
| SEQ ID NO: 694 | 715 | hsa-miR-150* | cuggauacaggccuggggacag | 101,11 | 101,78 | 0,99 | 0,01 |
| SEQ ID NO: 643 | 716 | hsa-miR-1909* | ugagugcacucugcugccug | 20,56 | 16,33 | 1,26 | 0,01 |
| SEQ ID NO: 639 | 717 | hsa-miR-1910 | ccagucuugccugcugccgccu | 7,44 | 11,56 | 0,64 | 0,01 |
| SEQ ID NO: 591 | 718 | hsa-miR-202 | agaggualaugggcaugggaa | 111,78 | 61,11 | 1,83 | 0,01 |
| SEQ ID NO: 555 | 719 | hsa-miR-218 | uugugcuugaucuaaccaugu | 1 | 1 | 1 | 0,01 |
| SEQ ID NO: 486 | 720 | hsa-miR-30a* | cuuucaguccgaugguuugcagc | 1 | 1 | 1 | 0,01 |
| SEQ ID NO: 463 | 721 | hsa-miR-326 | cccuggcccuucccucag | 20,56 | 19,78 | 1,04 | 0,01 |
| SEQ ID NO: 418 | 722 | hsa-miR-371-5p | acucaaacugugggcacu | 98 | 93,22 | 1,05 | 0,01 |
| SEQ ID NO: 321 | 723 | hsa-miR-505 | cgucaacacugucggguuuccu | 53 | 11,33 | 4,68 | 0,01 |
| SEQ ID NO: 188 | 724 | hsa-miR-575 | gagccaguugqacaqqaqc | 58,78 | 70,67 | 0,83 | 0,01 |
| SEQ ID NO: 78 | 725 | hsa-miR-7 | uggaagacuagugauuuuguugu | 256,44 | 1 | 256,44 | 0,01 |
| SEQ ID NO: 15 | 726 | hsa-miR-938 | ugcccuuaaaggugaaccccagu | 2,22 | 1 | 2,22 | 0,01 |
| SEQ ID NO: 443 | 727 | hsa-miR-340* | uccgucucagguuacuuuuauagc | 4 | 1 | 4 | 0,01 |
| SEQ ID NO: 885 | 728 | hsa-miR-100 | aacccguagauccgaacuugug | 212 | 98,56 | 2,15 | 0,01 |
| SEQ ID NO: 837 | 729 | hsa-miR-1229 | cucuccaccugccccccacag | 27,89 | 33,78 | 0,83 | 0,01 |
| SEQ ID NO: 835 | 730 | hsa-miR-1233 | ugagccugcuccccgag | 8,44 | 12,44 | 0,68 | 0,01 |
| SEQ ID NO: 833 | 731 | hsa-miR-1236 | cccuguccuugucucuccag | 39,67 | 44 | 0,9 | 0,01 |
| SEQ ID NO: 788 | 732 | hsa-miR-1274a | guccugguucaggcgca | 93,89 | 12 | 7,82 | 0,01 |
| SEQ ID NO: 777 | 733 | hsa-miR-1282 | ucguuugccuuuuucugcuu | 29,44 | 1,56 | 18,93 | 0,01 |
| SEQ ID NO: 764 | 734 | hsa-miR-129-3p | aagcccuuacccccaaaaagcau | 4 | 28,33 | 0,14 | 0,01 |
| SEQ ID NO: 769 | 735 | hsa-miR-129* | aagcccuuacccccaaaaaguau | 8,44 | 1 | 8,44 | 0,01 |

FIG. 10A (Cont.)

| | | | | | |
|---|---|---|---|---|---|
| SEQ ID NO: 760 | 736 | hsa-miR-1296 | uuagggcccuggcuccaucucc | 14,56 | 4,22 | 3,45 | 0,01 |
| SEQ ID NO: 119 | 737 | hsa-miR-634 | aaccagcaccccaacuuugac | 36,78 | 49,22 | 0,75 | 0,01 |
| SEQ ID NO: 58 | 738 | hsa-miR-769-3p | cuggaucucgggucuugguu | 25,56 | 15,56 | 1,64 | 0,01 |
| SEQ ID NO: 469 | 739 | hsa-miR-320d | aaaagcugguugagagga | 4318,58 | 4380,58 | 0,98 | 0,01 |
| SEQ ID NO: 22 | 740 | hsa-miR-93 | caaagugcuguucgugugcagguag | 4779,31 | 5660,31 | 0,84 | 0,01 |
| SEQ ID NO: 889 | 741 | hsa-let-7g* | cuguacaggccacugccuugc | 1 | 1 | 1 | 0,01 |
| SEQ ID NO: 796 | 742 | hsa-miR-1267 | ccuguuaagugugccuauccca | 9,56 | 1,56 | 6,14 | 0,01 |
| SEQ ID NO: 745 | 743 | hsa-miR-130b* | acucuuucccuugcacuac | 2,67 | 1 | 2,67 | 0,01 |
| SEQ ID NO: 744 | 744 | hsa-miR-132 | uaacagucuacagccauggucg | 24,56 | 4,22 | 5,82 | 0,01 |
| SEQ ID NO: 727 | 745 | hsa-miR-138-1* | gcuacuucacaacaccagggcc | 19,89 | 4,22 | 4,71 | 0,01 |
| SEQ ID NO: 719 | 746 | hsa-miR-142-3p | uguaguguuuccuacuuuuagga | 1 | 1 | 1 | 0,01 |
| SEQ ID NO: 621 | 747 | hsa-miR-195* | ccaauauggcugugugcgucc | 1 | 1 | 1 | 0,01 |
| SEQ ID NO: 327 | 748 | hsa-miR-501-3p | aaugcaccggggcaaggauucu | 286,11 | 21,56 | 13,27 | 0,01 |
| SEQ ID NO: 734 | 749 | hsa-miR-135a* | uauaggauuggagccguggcg | 644,9 | 480,44 | 1,34 | 0,01 |
| SEQ ID NO: 728 | 750 | hsa-miR-138 | agcuggugguuguugaaucaggccg | 8,44 | 1 | 8,44 | 0,01 |
| SEQ ID NO: 561 | 751 | hsa-miR-214 | acagcaggcacagacaggcagu | 29,11 | 3,11 | 9,36 | 0,01 |
| SEQ ID NO: 513 | 752 | hsa-miR-296-3p | gagguuggugugaggcucuc | 606,46 | 408,44 | 1,48 | 0,01 |
| SEQ ID NO: 151 | 753 | hsa-miR-608 | aggguguggguugggacagcucogu | 106,89 | 96,94 | 1,1 | 0,01 |
| SEQ ID NO: 868 | 754 | hsa-miR-10b* | acagauuucuagggguggaau | 1 | 1 | 1 | 0,01 |
| SEQ ID NO: 861 | 755 | hsa-miR-1184 | ccugcagccacuugaugggcuucc | 1 | 1 | 1 | 0,01 |
| SEQ ID NO: 836 | 756 | hsa-miR-1231 | gugucugggcggacagcugc | 43,11 | 30,44 | 1,42 | 0,01 |
| SEQ ID NO: 778 | 757 | hsa-miR-1281 | ucggccuccucucucuc | 8,44 | 35,83 | 0,24 | 0,01 |
| SEQ ID NO: 768 | 758 | hsa-miR-1290 | uggauuuuugggaucaggga | 39,67 | 28,33 | 1,4 | 0,01 |
| SEQ ID NO: 742 | 759 | hsa-miR-1321 | cagggaggcuggaggugugau | 74,22 | 58,78 | 1,26 | 0,01 |
| SEQ ID NO: 736 | 760 | hsa-miR-134 | ugugacugguugaccagaggg | 55,67 | 34 | 1,64 | 0,01 |
| SEQ ID NO: 700 | 761 | hsa-miR-148a* | aaaguucugagacagacuccgacu | 1 | 1 | 1 | 0,01 |
| SEQ ID NO: 691 | 762 | hsa-miR-152 | ucagugcaugacagaacuugg | 16,78 | 12,11 | 1,39 | 0,01 |
| SEQ ID NO: 664 | 763 | hsa-miR-1825 | uccagugcccucucucc | 21,11 | 30,44 | 0,69 | 0,01 |
| SEQ ID NO: 634 | 764 | hsa-miR-1914 | cccugugcccggccacuucug | 6,78 | 14,89 | 0,46 | 0,01 |
| SEQ ID NO: 588 | 765 | hsa-miR-204 | uucccuuugucauccuaugccu | 1 | 1 | 1 | 0,01 |
| SEQ ID NO: 520 | 766 | hsa-miR-26b* | ccguucccauuacuuccgc | 4,22 | 4,22 | 0,24 | 0,01 |
| SEQ ID NO: 481 | 767 | hsa-miR-30c-2* | cuggagaaggcuguuuacucu | 68,67 | 56,78 | 1,21 | 0,01 |
| SEQ ID NO: 435 | 768 | hsa-miR-34b* | uaggcagugucauuagcugauug | 1 | 1 | 1 | 0,01 |
| SEQ ID NO: 410 | 769 | hsa-miR-375 | uuuguucguucggcucgcguga | 1 | 1 | 1 | 0,01 |
| SEQ ID NO: 395 | 770 | hsa-miR-383 | agaucagaaggugauuguggcu | 15,33 | 18,67 | 0,82 | 0,01 |
| SEQ ID NO: 393 | 771 | hsa-miR-409-3p | gaauuguccggugaaccccu | 97,33 | 68,44 | 1,42 | 0,01 |
| SEQ ID NO: 365 | 772 | hsa-miR-450b-5p | uuuugcaauaugucccugaaua | 1 | 1 | 1 | 0,01 |

FIG. 10A (Cont.)

| SEQ ID NO | # | miRNA | Sequence | V1 | V2 | V3 |
|---|---|---|---|---|---|---|
| SEQ ID NO: 358 | 773 | hsa-miR-455-3p | gcaguccaugggcauauacac | | | 0,01 |
| SEQ ID NO: 344 | 774 | hsa-miR-490-3p | caaccuggaggacuccaugcug | | | 0,01 |
| SEQ ID NO: 336 | 775 | hsa-miR-495 | aaacaaacauggugcacucucu | 2,67 | 3,67 | 0,01 |
| SEQ ID NO: 326 | 776 | hsa-miR-501-5p | aauccuuugucccugguugaga | 4,78 | 3,11 | 0,01 |
| SEQ ID NO: 299 | 777 | hsa-miR-516b | aucuggagguaagaagcacuuu | 52 | 56,22 | 1,54 |
| SEQ ID NO: 272 | 778 | hsa-miR-520a-5p | cuccagagggaaguacuuuuci | 15,33 | 18,72 | 0,92 |
| SEQ ID NO: 166 | 779 | hsa-miR-593 | ugucucugcuggggguuucu | 30,44 | 46,44 | 0,82 |
| SEQ ID NO: 131 | 780 | hsa-miR-625 | aggggaaaguucuauagucc | 182,44 | 109,67 | 0,66 |
| SEQ ID NO: 80 | 781 | hsa-miR-675 | uggugcggagggcccacagug | 185,22 | 172,44 | 1,66 |
| SEQ ID NO: 66 | 782 | hsa-miR-760 | cggcucugggucugggga | 34,89 | 53,33 | 1,07 |
| SEQ ID NO: 57 | 783 | hsa-miR-769-5p | ugagaccucugggguucugagcu | 15,33 | 3,67 | 0,65 |
| SEQ ID NO: 52 | 784 | hsa-miR-875-3p | ccuggaaacacugaggguug | 6,78 | 1 | 4,18 |
| SEQ ID NO: 26 | 785 | hsa-miR-92a-1* | agguuggaucgguugcaaugcu | 20,56 | 21,56 | 6,78 |
| SEQ ID NO: 872 | 786 | hsa-miR-107 | agcagcauuguacagggcuauca | 4106,11 | 4915,83 | 0,95 |
| SEQ ID NO: 842 | 787 | hsa-miR-1226 | ucaccagcccuguguuccuag | 1 | 4,44 | 0,84 |
| SEQ ID NO: 803 | 788 | hsa-miR-1260 | auccaccucugccacca | 84,17 | 51,33 | 0,23 |
| SEQ ID NO: 787 | 789 | hsa-miR-1274b | ucccguuuugccugcca | 176,56 | 63,61 | 1,64 |
| SEQ ID NO: 724 | 790 | hsa-miR-139-5p | ucuacaguguacguguccag | 1,56 | 4,22 | 2,78 |
| SEQ ID NO: 592 | 791 | hsa-miR-200c* | cgucuuaccccagcaguguugg | 1 | 1 | 0,37 |
| SEQ ID NO: 490 | 792 | hsa-miR-302d* | acuuuaacauggaggcacuugc | 1 | 11,33 | 1 |
| SEQ ID NO: 378 | 793 | hsa-miR-431 | ugucuuugcaggcgcucaugca | 1 | 3,67 | 0,09 |
| SEQ ID NO: 330 | 794 | hsa-miR-499-5p | uuaagacuugcaguguguuu | 1 | 1 | 0,27 |
| SEQ ID NO: 251 | 795 | hsa-miR-526b* | gaaagugcuucccuuuuagagc | 1 | 1 | 1 |
| SEQ ID NO: 145 | 796 | hsa-miR-614 | gaacgccuguucugccagugg | 9,11 | 4,22 | 2,16 |
| SEQ ID NO: 39 | 797 | hsa-miR-889 | uuaauacggacaaccaugu | 1 | 1 | 1 |
| SEQ ID NO: 7 | 798 | hsa-miR-96 | uuuggcacuagcacauuugcu | 106,89 | 36,11 | 2,96 |
| SEQ ID NO: 625 | 799 | hsa-miR-193b* | cggguuuuagggcgagauga | 81,11 | 108,56 | 0,75 |
| SEQ ID NO: 289 | 800 | hsa-miR-518c* | ucucuggagggaagcacuucug | 109,67 | 63,61 | 1,72 |
| SEQ ID NO: 281 | 801 | hsa-miR-519a* | cucuagaggagcacuuucug | 1 | 4,44 | 0,23 |
| SEQ ID NO: 253 | 802 | hsa-miR-526a | cucuagagggaagcacuugucu | 27 | 56,22 | 0,48 |
| SEQ ID NO: 164 | 803 | hsa-miR-595 | gaagugccgugugucu | 12 | 11,33 | 1,06 |
| SEQ ID NO: 4 | 804 | hsa-miR-99a | aacccguagauccgaucuugug | 92,56 | 22,22 | 4,17 |
| SEQ ID NO: 25 | 805 | hsa-miR-92a-2* | gggugggauuuguugcauuac | 148,44 | 67,44 | 2,2 |
| SEQ ID NO: 673 | 806 | hsa-miR-181a | aacauucaacgcugucggugagu | 586,78 | 133,11 | 4,41 |
| SEQ ID NO: 709 | 807 | hsa-miR-146a | ugagaacugaauuccauaggguu | 136,17 | 129,44 | 1,05 |
| SEQ ID NO: 877 | 808 | hsa-miR-105* | acgaugguuugagcaugugcua | 2,67 | 1 | 2,67 |
| SEQ ID NO: 781 | 809 | hsa-miR-1279 | ucauauugcucuuucu | 1 | 1 | 1 |

FIG. 10A (Cont.)

| | | | | | | |
|---|---|---|---|---|---|---|
| SEQ ID NO: 686 | 810 | hsa-miR-154 | uagguuauccguguugccuuca | 1 | 1 | |
| SEQ ID NO: 406 | 811 | hsa-miR-376c | aacauagaggaaauuccacgu | 1 | 1 | 0 |
| SEQ ID NO: 306 | 812 | hsa-miR-513b | uucacaaggaggugucauuuau | 91,17 | 72,22 | 0 |
| SEQ ID NO: 167 | 813 | hsa-miR-592 | uugugucaauaugcgaugaugu | 1 | 1 | 0 |
| SEQ ID NO: 815 | 814 | hsa-miR-1255b | cggaugagcaaagaaagugguu | 87,67 | 76,56 | 1,15 |
| SEQ ID NO: 252 | 815 | hsa-miR-526b | cucuugagggaagcacuuucugu | 67,78 | 33,78 | 2,01 |
| SEQ ID NO: 173 | 816 | hsa-miR-588 | uuggccacaauggguuagaac | 1,56 | 1,56 | 1 |
| SEQ ID NO: 866 | 817 | hsa-miR-1179 | aagcauuuuucauugguugg | 1 | 1 | 1 |
| SEQ ID NO: 849 | 818 | hsa-miR-1208 | ucacuguucagacaggcgga | 27 | 18,72 | 1,44 |
| SEQ ID NO: 844 | 819 | hsa-miR-1225-3p | ugagccccugugccgccccag | 39,67 | 42,78 | 0,93 |
| SEQ ID NO: 841 | 820 | hsa-miR-1226* | gugagggcaugcaggccuggauggg | 99,11 | 96,94 | 1,02 |
| SEQ ID NO: 834 | 821 | hsa-miR-1234 | ucggccugaccaccaccccac | 53,67 | 82,06 | 0,65 |
| SEQ ID NO: 822 | 822 | hsa-miR-1249 | acgcccuuccccccuuucuua | 24,56 | 30,22 | 0,81 |
| SEQ ID NO: 717 | 823 | hsa-miR-143 | ugagaugaagcacuguagcuc | 20,56 | 12 | 1,71 |
| SEQ ID NO: 671 | 824 | hsa-miR-181a-2* | accacugaccguugacuguacc | 115,33 | 67,44 | 1,71 |
| SEQ ID NO: 659 | 825 | hsa-miR-184 | uggacggagaacugauaagggu | 94,56 | 56,78 | 1,67 |
| SEQ ID NO: 620 | 826 | hsa-miR-196a | uagguaguuucauguuguugg | 4 | 1 | 4 |
| SEQ ID NO: 603 | 827 | hsa-miR-199b-5p | cccaguguuuagacuaucuguuc | 4 | 1 | 4 |
| SEQ ID NO: 558 | 828 | hsa-miR-216a | uaaucucagcuggcaacuguga | 1 | 1 | 1 |
| SEQ ID NO: 519 | 829 | hsa-miR-27a | uucacaguggcuaaguuccgc | 150,56 | 55,22 | 2,73 |
| SEQ ID NO: 440 | 830 | hsa-miR-345 | gcugacuccuaguccaaggcuc | 168,11 | 34,44 | 4,88 |
| SEQ ID NO: 430 | 831 | hsa-miR-362-3p | aacacucuauucaaggauuca | 16,44 | 14,89 | 1,1 |
| SEQ ID NO: 318 | 832 | hsa-miR-507 | uuuugcaccuuuuggagugaa | 1 | 1 | 1 |
| SEQ ID NO: 297 | 833 | hsa-miR-517* | ccucuagaugggaagcacugucu | 16,78 | 12,11 | 1,39 |
| SEQ ID NO: 293 | 834 | hsa-miR-518a-3p | gaaagcgcuucccuuugcugga | 1 | 1 | 1 |
| SEQ ID NO: 184 | 835 | hsa-miR-578 | cuucuugugcucuuaggaugu | 1 | 1 | 1 |
| SEQ ID NO: 158 | 836 | hsa-miR-601 | uggucuaggauuguuggaggag | 20,56 | 21,89 | 0,94 |
| SEQ ID NO: 143 | 837 | hsa-miR-615-5p | gggguccccggugcuggauc | 34 | 12,11 | 2,81 |
| SEQ ID NO: 135 | 838 | hsa-miR-622 | acagucugcuuaggguugagc | 6,78 | 3,11 | 2,18 |
| SEQ ID NO: 114 | 839 | hsa-miR-639 | aucgcugcgguuucgagcugu | 1 | 1 | 1 |
| SEQ ID NO: 44 | 840 | hsa-miR-886-3p | cgggguguuacugagccuu | 12,33 | 1 | 12,33 |
| SEQ ID NO: 13 | 841 | hsa-miR-940 | aagcagggcccccgcuccc | 112,44 | 67,44 | 1,67 |
| SEQ ID NO: 869 | 842 | hsa-miR-10b | uacccuguagaaccgaauuugug | 22,22 | 8,33 | 2,67 |
| SEQ ID NO: 867 | 843 | hsa-miR-1178 | uugcucacuguccucccuag | 1 | 1 | 1 |
| SEQ ID NO: 864 | 844 | hsa-miR-1181 | ccgucgcgcaccgagccg | 21,11 | 28 | 0,75 |
| SEQ ID NO: 819 | 845 | hsa-miR-1252 | agaaggaaauugaauucauua | 1 | 1 | 1 |
| SEQ ID NO: 758 | 846 | hsa-miR-1298 | uucauucggcuguccagauga | 1 | 1 | 1 |

FIG. 10A (Cont.)

| SEQ ID NO: 698 | 847 | hsa-miR-148b* | aaguucuguuauauacacucaggc | | | 1 | 0 |
|---|---|---|---|---|---|---|---|
| SEQ ID NO: 683 | 848 | hsa-miR-155* | cuccuacauauuagcauuaaca | | | 1 | 0 |
| SEQ ID NO: 528 | 849 | hsa-miR-24-1* | ugccuacugagcugauaucagu | | | 1 | 0 |
| SEQ ID NO: 504 | 850 | hsa-miR-29b-1* | gcugguuucauaugugguuuaga | | | 1 | 0 |
| SEQ ID NO: 335 | 851 | hsa-miR-496 | ugaguauuacauggccaaucuc | 15,33 | 4,44 | 3,45 | 0 |
| SEQ ID NO: 288 | 852 | hsa-miR-518d-3p | caaagcgcuucccuuuggagc | | | 1 | 0 |
| SEQ ID NO: 241 | 853 | hsa-miR-544 | auucugcauuuuagcaaguuc | | | 1 | 0 |
| SEQ ID NO: 141 | 854 | hsa-miR-616* | acucaaaaccucagagacuu | | 1,56 | 0,64 | 0 |
| SEQ ID NO: 113 | 855 | hsa-miR-640 | augauccaggaaccugccucu | 4 | 4,44 | 0,9 | 0 |
| SEQ ID NO: 96 | 856 | hsa-miR-656 | aauauuauacagucaaccucu | | | 1 | 0 |
| SEQ ID NO: 75 | 857 | hsa-miR-7-1* | caacaaaucacaguccugccaua | 15,78 | 28,33 | 0,56 | 0 |
| SEQ ID NO: 35 | 858 | hsa-miR-892a | cacuguccuuucugcguag | 7,89 | 14,89 | 0,53 | 0 |
| SEQ ID NO: 8 | 859 | hsa-miR-95 | uucaacgguauuuauugagca | | | 1 | 0 |
| SEQ ID NO: 821 | 860 | hsa-miR-1250 | acggugcuggaugugccuuu | 37,67 | 40,78 | 0,92 | 0 |
| SEQ ID NO: 798 | 861 | hsa-miR-1265 | caggaugguggucaaguguguu | 6,78 | 1,56 | 4,36 | 0 |
| SEQ ID NO: 751 | 862 | hsa-miR-1308 | acguugcucugguguug | 6,78 | 4,22 | 1,61 | 0 |
| SEQ ID NO: 651 | 863 | hsa-miR-188-5p | caucccuugcauggugaggg | 21,44 | 22,22 | 0,97 | 0 |
| SEQ ID NO: 274 | 864 | hsa-miR-519e* | uucuccaaaaggagcacuuuc | 17,11 | 19,78 | 0,87 | 0 |
| SEQ ID NO: 128 | 865 | hsa-miR-627 | gugagucucuaagaaaagagga | | | 1 | 0 |

FIG. 10B

| SEQ ID No | No | microRNA | Sequence | Median Cancer | Median Normal | Fold Quotient | t-test significance |
|---|---|---|---|---|---|---|---|
| SEQ ID NO: 805 | 1 | hsa-miR-126 | ucuaccguagaguaauaaugcg | 606,46 | 3428,42 | 0,18 | 3,43E-05 |
| SEQ ID NO: 384 | 2 | hsa-miR-423-5p | ugaggggcagagagcgagacuuu | 6795,89 | 3976,97 | 1,71 | 0 |
| SEQ ID NO: 888 | 3 | hsa-let-7i | ugagguaguaguuugugcuguu | 4106,11 | 6349,31 | 0,65 | 0 |
| SEQ ID NO: 897 | 4 | hsa-let-7d | agagguaguaguugcauaguu | 6795,89 | 13307,74 | 0,51 | 0 |
| SEQ ID NO: 549 | 5 | hsa-miR-22 | aagcugccaguugaagaacugu | 7978,5 | 3868,5 | 2,06 | 0,01 |
| SEQ ID NO: 682 | 6 | hsa-miR-15a | uagcagcacauaauggguuugug | 3428,42 | 5944,79 | 0,58 | 0,01 |
| SEQ ID NO: 5 | 7 | hsa-miR-98 | ugagguaguaaguuguauuguu | 322,44 | 1440,75 | 0,22 | 0,01 |
| SEQ ID NO: 602 | 8 | hsa-miR-19a | ugugcaaaucuaugcaaaacuga | 420,06 | 1 | 420,06 | 0,02 |
| SEQ ID NO: 189 | 9 | hsa-miR-574-5p | ugagugugugugugugugagugu | 108,56 | 30,22 | 3,59 | 0,02 |
| SEQ ID NO: 466 | 10 | hsa-miR-324-3p | acugcccaggugcugcugg | 1221,94 | 700,5 | 1,74 | 0,02 |
| SEQ ID NO: 577 | 11 | hsa-miR-20b | caaagugcuuauagugcagguag | 1118,35 | 2947,83 | 0,38 | 0,02 |
| SEQ ID NO: 526 | 12 | hsa-miR-25 | cauugcacuugucucggucuga | 12517,64 | 7639,53 | 1,64 | 0,02 |
| SEQ ID NO: 622 | 13 | hsa-miR-195 | uagcagcacagaaauauuggc | 2575,72 | 4462,58 | 0,58 | 0,02 |
| SEQ ID NO: 895 | 14 | hsa-let-7e | ugagguaggagguuguauaguu | 1297,51 | 2947,83 | 0,44 | 0,02 |
| SEQ ID NO: 899 | 15 | hsa-let-7c | ugagguaguaguuuguauaguu | 5660,31 | 8969,72 | 0,63 | 0,02 |
| SEQ ID NO: 893 | 16 | hsa-let-7f | ugagguaguaguuguauaguu | 5382,15 | 9746,17 | 0,55 | 0,02 |
| SEQ ID NO: 904 | 17 | hsa-let-7a | ugagguaguaguuuguacaguu | 6795,89 | 12517,64 | 0,54 | 0,02 |
| SEQ ID NO: 890 | 18 | hsa-let-7g | ugagguaguaguuuguacaggu | 3428,42 | 6795,89 | 0,5 | 0,02 |
| SEQ ID NO: 723 | 19 | hsa-miR-140-3p | uaccacagggguagaaccacg | 9312,5 | 4621,29 | 2,02 | 0,02 |
| SEQ ID NO: 449 | 20 | hsa-miR-339-5p | uccccugucuccaggagcucacg | 312,11 | 12,44 | 25,08 | 0,03 |
| SEQ ID NO: 431 | 21 | hsa-miR-361-5p | uuaucagaaucuccaggguac | 53 | 4,44 | 11,44 | 0,03 |
| SEQ ID NO: 776 | 22 | hsa-miR-1283 | ucuacaaaggaaagcguuucu | 2,33 | 22,22 | 0,11 | 0,04 |
| SEQ ID NO: 649 | 23 | hsa-miR-18a* | acugcccuaagugcuccuucugg | 1040,44 | 119,89 | 8,68 | 0,04 |
| SEQ ID NO: 521 | 24 | hsa-miR-26b | uucaaguauuccaggauagu | 1085,22 | 2058,85 | 0,53 | 0,04 |
| SEQ ID NO: 155 | 25 | hsa-miR-604 | aggcugcggaaucaggac | 245 | 90,78 | 2,7 | 0,05 |
| SEQ ID NO: 385 | 26 | hsa-miR-423-3p | agcucggucugaggccccucagu | 1797,04 | 463,22 | 3,88 | 0,05 |
| SEQ ID NO: 21 | 27 | hsa-miR-93* | acugcugagcuagcacuccccg | 480,44 | 30,44 | 15,78 | 0,05 |
| SEQ ID NO: 507 | 28 | hsa-miR-29a | uagcaccaucugaaaucgguua | 447 | 108,56 | 4,12 | 0,07 |
| SEQ ID NO: 823 | 29 | hsa-miR-1248 | accuucuuguauaagcacugugcuaaa | 154,22 | 31,33 | 4,92 | 0,08 |
| SEQ ID NO: 573 | 30 | hsa-miR-210 | ougugcguguugacagcgcuga | 412,67 | 58,89 | 7,01 | 0,08 |
| SEQ ID NO: 600 | 31 | hsa-miR-19b | ugugcaaauccaugcaaaacuga | 3428,42 | 1853,1 | 1,85 | 0,08 |
| SEQ ID NO: 361 | 32 | hsa-miR-453 | agguaguccguggugaguucgca | 6,78 | 57 | 0,12 | 0,09 |
| SEQ ID NO: 804 | 33 | hsa-miR-126* | cauuauuacuuuugguacgcg | 1 | 33,78 | 0,03 | 0,09 |
| SEQ ID NO: 652 | 34 | hsa-miR-188-3p | oucccacaugcagguuugca | 1 | 4,44 | 0,23 | 0,09 |
| SEQ ID NO: 132 | 35 | hsa-miR-624* | uaguaccaguaccuuguauagu | 1 | 27,78 | 0,04 | 0,09 |
| SEQ ID NO: 320 | 36 | hsa-miR-505* | gggagccaggaaguauuagaugu | 280,11 | 90,78 | 3,09 | 0,1 |

FIG. 10B (Cont.)

| | | | | | | |
|---|---|---|---|---|---|---|
| SEQ ID NO: 381 | 37 | hsa-miR-425 | aaugacacgaucacucccguuga | 11838,82 | 7392,17 | 0,1 |
| SEQ ID NO: 450 | 38 | hsa-miR-339-3p | ugagcgccucgacgacagagccg | 209,67 | 109,67 | 0,1 |
| SEQ ID NO: 84 | 39 | hsa-miR-668 | ugucacucggcucggcccacuac | 276,44 | 92,56 | 0,1 |
| SEQ ID NO: 427 | 40 | hsa-miR-363* | cgggugaucacagaugcaauu | 2425,74 | 723,61 | 0,1 |
| SEQ ID NO: 679 | 41 | hsa-miR-15b* | cgaaucauuauuugcugucua | 46,89 | 1 | 0,1 |
| SEQ ID NO: 501 | 42 | hsa-miR-29c* | ugaccgauuuccuugugucc | 61,11 | 46,89 | 0,1 |
| SEQ ID NO: 215 | 43 | hsa-miR-550* | ugucuuacuccccucaggcacau | 331,06 | 61,11 | 0,11 |
| SEQ ID NO: 434 | 44 | hsa-miR-34c-3p | aaucacuaaccacacagccagg | 4 | 5,11 | 0,13 |
| SEQ ID NO: 579 | 45 | hsa-miR-20a | uaaagugcuuauagugcagguag | 2319,9 | 28,44 | 0,13 |
| SEQ ID NO: 414 | 46 | hsa-miR-374a | uuauaacaaccuguauaagug | 225,11 | 4202,14 | 0,14 |
| SEQ ID NO: 712 | 47 | hsa-miR-145* | ggauuccuggaaauacuguucu | 1 | 692,94 | 0,14 |
| SEQ ID NO: 495 | 48 | hsa-miR-302b | uaagugcuuccauguuuuaguag | 1 | 1 | 0,14 |
| SEQ ID NO: 876 | 49 | hsa-miR-106a | aaaagugcuuacagugcagguag | 4462,58 | 6349,31 | 0,15 |
| SEQ ID NO: 478 | 50 | hsa-miR-30e | uguaaacauccuugacuggaag | 369,89 | 129,44 | 0,17 |
| SEQ ID NO: 540 | 51 | hsa-miR-223 | ugucaguuugucaaauacccca | 3080,08 | 5660,31 | 0,17 |
| SEQ ID NO: 794 | 52 | hsa-miR-1269 | cuggacugagccgugcuacugg | 4 | 34,44 | 0,17 |
| SEQ ID NO: 901 | 53 | hsa-let-7b | ugagguaguagguugugugguu | 6349,31 | 9746,17 | 0,17 |
| SEQ ID NO: 244 | 54 | hsa-miR-542-3p | ugugacagauugauaacugaaa | 1 | 18,72 | 0,17 |
| SEQ ID NO: 298 | 55 | hsa-miR-516b* | ugcuuccuuucagagggu | 9,56 | 31,33 | 0,17 |
| SEQ ID NO: 364 | 56 | hsa-miR-451 | aaaccguuaccauuacugaguu | 1118,35 | 4106,11 | 0,17 |
| SEQ ID NO: 278 | 57 | hsa-miR-519c-3p | aaagugcaucuuuuuagaggau | 12 | 12 | 0,17 |
| SEQ ID NO: 827 | 58 | hsa-miR-1244 | aaguaguugguuguauagaugguu | 25,56 | 1 | 0,19 |
| SEQ ID NO: 157 | 59 | hsa-miR-602 | gacacgggacacagucggcc | 20,56 | 44 | 0,19 |
| SEQ ID NO: 432 | 60 | hsa-miR-361-3p | uccccagugguugauucugauuu | 367,06 | 256,44 | 0,19 |
| SEQ ID NO: 601 | 61 | hsa-miR-19a* | aguuuugcauaguuugcacuaca | 1 | 1 | 0,19 |
| SEQ ID NO: 374 | 62 | hsa-miR-433 | aucaugaugggcuccucgugu | 1 | 1 | 0,19 |
| SEQ ID NO: 858 | 63 | hsa-miR-1200 | cucuaggcauuucugagccuc | 1 | 5,11 | 0,2 |
| SEQ ID NO: 261 | 64 | hsa-miR-522 | aaaaugguucccuuuagaggu | 1 | 8,33 | 0,2 |
| SEQ ID NO: 265 | 65 | hsa-miR-520f | aaguguucuucuuuugggguu | 1 | 4,22 | 0,2 |
| SEQ ID NO: 277 | 66 | hsa-miR-519c-5p | cucuagagggaagcgcuuucug | 1 | 13,72 | 0,2 |
| SEQ ID NO: 630 | 67 | hsa-miR-192 | cugaccuaugaauugacagcc | 3080,08 | 1675,67 | 0,21 |
| SEQ ID NO: 826 | 68 | hsa-miR-1245 | aagucuaaaggccuuacau | 1 | 1 | 0,21 |
| SEQ ID NO: 692 | 69 | hsa-miR-151-5p | ucgagggagcucacucuagu | 1732,86 | 1024,56 | 0,21 |
| SEQ ID NO: 771 | 70 | hsa-miR-1288 | uggagucccugaucugaga | 1 | 1 | 0,21 |
| SEQ ID NO: 323 | 71 | hsa-miR-503 | uagcagcgggaacaguucugcag | 68,67 | 73,33 | 0,21 |
| SEQ ID NO: 200 | 72 | hsa-miR-563 | agguugacauacguuucc | 1 | 1 | 0,21 |
| SEQ ID NO: 88 | 73 | hsa-miR-663b | gguggcccgccgugcugagg | 5,56 | 4,44 | 0,21 |

FIG. 10B (Cont.)

| SEQ ID NO | # | miRNA | Sequence | | | |
|---|---|---|---|---|---|---|
| SEQ ID NO: 896 | 74 | hsa-let-7d* | cuauacgaccugcugccuuucu | 39,44 | 6 | 6,57 | 0,21 |
| SEQ ID NO: 605 | 75 | hsa-miR-199a-5p | cccaguguuucagacuaccuguuc | 145,33 | 36,11 | 4,02 | 0,21 |
| SEQ ID NO: 71 | 76 | hsa-miR-720 | ucucgcuggggcuuca | 189,89 | 61,56 | 3,08 | 0,21 |
| SEQ ID NO: 825 | 77 | hsa-miR-1246 | aauggauuuuuggagcagg | 4915,83 | 3572,67 | 1,38 | 0,21 |
| SEQ ID NO: 451 | 78 | hsa-miR-338-5p | aacaauauccuggugcugaguq | 1 | 1 | 1 | 0,21 |
| SEQ ID NO: 511 | 79 | hsa-miR-297 | auguaugugugcauguqcauq | 1 | 12,11 | 0,08 | 0,21 |
| SEQ ID NO: 802 | 80 | hsa-miR-1261 | auggauaaggcuuuggcuu | 1 | 10,44 | 0,1 | 0,21 |
| SEQ ID NO: 29 | 81 | hsa-miR-922 | gcagagaauaggacuacguc | 1 | 18,72 | 0,05 | 0,21 |
| SEQ ID NO: 658 | 82 | hsa-miR-185 | uggagagaaaggcaguuccuga | 15421,86 | 13307,74 | 1,16 | 0,21 |
| SEQ ID NO: 148 | 83 | hsa-miR-611 | gcgaggaccccucgggucugac | 30,44 | 18,11 | 1,68 | 0,21 |
| SEQ ID NO: 791 | 84 | hsa-miR-1272 | gaugaugcagcagcaaauucugaaa | 1 | 1 | 1 | 0,21 |
| SEQ ID NO: 757 | 85 | hsa-miR-1299 | uucuggaaucugugugagga | 1 | 29,94 | 0,03 | 0,21 |
| SEQ ID NO: 455 | 86 | hsa-miR-335* | uuuucauuaugccuccugacc | 1 | 1,56 | 0,64 | 0,21 |
| SEQ ID NO: 334 | 87 | hsa-miR-497 | cagcagcacacugguuugu | 15,78 | 39,44 | 0,4 | 0,22 |
| SEQ ID NO: 851 | 88 | hsa-miR-1207-3p | ucagcuggcccucauuuc | 1 | 18,11 | 0,06 | 0,22 |
| SEQ ID NO: 678 | 89 | hsa-miR-16 | uagcagcacguaaauauugqcq | 20349,58 | 24783,94 | 0,82 | 0,22 |
| SEQ ID NO: 886 | 90 | hsa-miR-1 | uggaauguaaagaaguauguau | 1 | 1 | 1 | 0,22 |
| SEQ ID NO: 767 | 91 | hsa-miR-1291 | uggcccugacugaagaccagcagu | 30,44 | 1 | 30,44 | 0,22 |
| SEQ ID NO: 726 | 92 | hsa-miR-138-2* | gcuauuucacgugaucaccagggu | 1 | 4,44 | 0,23 | 0,22 |
| SEQ ID NO: 731 | 93 | hsa-miR-136 | acuccauuuguuuugaugauqga | 1 | 1,56 | 0,64 | 0,22 |
| SEQ ID NO: 232 | 94 | hsa-miR-548d-3p | caaaaaccacagugguuucuugc | 1 | 1 | 1 | 0,22 |
| SEQ ID NO: 202 | 95 | hsa-miR-561 | caaaguuuaagauccuugagu | 1 | 1 | 1 | 0,22 |
| SEQ ID NO: 227 | 96 | hsa-miR-548h | aaaguaaucgcgguuuuuguc | 1 | 1 | 1 | 0,22 |
| SEQ ID NO: 458 | 97 | hsa-miR-331-3p | gccccugggccuauccuagaa | 723,61 | 403,89 | 1,79 | 0,22 |
| SEQ ID NO: 655 | 98 | hsa-miR-186* | gccccaaaggugaauuuuuuggg | 1 | 1 | 1 | 0,23 |
| SEQ ID NO: 713 | 99 | hsa-miR-145 | guccaguuuuccaggaauccu | 577,78 | 101,11 | 5,66 | 0,23 |
| SEQ ID NO: 675 | 100 | hsa-miR-17 | caaagugcuuaacagugcagguag | 3976,97 | 5242,15 | 0,76 | 0,23 |
| SEQ ID NO: 485 | 101 | hsa-miR-30b | uguaaacauccuacacucagcu | 5530,88 | 3303,71 | 1,67 | 0,24 |
| SEQ ID NO: 892 | 102 | hsa-let-7f-1* | cuauacaaucuauugccuuccc | 1 | 1 | 1 | 0,25 |
| SEQ ID NO: 752 | 103 | hsa-miR-1305 | uuuucaaucucuaauggaqaqa | 3,67 | 1 | 0,27 | 0,26 |
| SEQ ID NO: 761 | 104 | hsa-miR-129-5p | cuuuugcggucugggcuugc | 33,78 | 14,89 | 2,27 | 0,26 |
| SEQ ID NO: 854 | 105 | hsa-miR-1204 | ucguggccuggucuccauuau | 1 | 4,44 | 0,23 | 0,27 |
| SEQ ID NO: 873 | 106 | hsa-miR-106b* | ccgacugugguacuugcagc | 901,96 | 137,56 | 6,56 | 0,27 |
| SEQ ID NO: 138 | 107 | hsa-miR-619 | gaccuggacauguuugugccagu | 1 | 1 | 1 | 0,27 |
| SEQ ID NO: 437 | 108 | hsa-miR-34a* | caaucagcaaguauacugcccu | 1 | 1 | 1 | 0,27 |
| SEQ ID NO: 101 | 109 | hsa-miR-652 | aauggcgccacuucuucacuagcu | 1388,26 | 961,58 | 1,44 | 0,28 |
| SEQ ID NO: 814 | 110 | hsa-miR-1256 | aggcauuuacucucacuagcu | 1 | 1 | 1 | 0,28 |

FIG. 10B (Cont.)

| | | | | | | |
|---|---|---|---|---|---|---|
| SEQ ID NO: 576 | 111 | hsa-miR-20b* | acuguaguaugggcacuuccag | | | 0,28 |
| SEQ ID NO: 382 | 112 | hsa-miR-424* | caaaacgugaggcgcugcuau | 34 | 46,11 | 0,74 | 0,28 |
| SEQ ID NO: 296 | 113 | hsa-miR-517a | aucgugcauccuuuagagugu | 1 | 1 | 1 | 0,28 |
| SEQ ID NO: 775 | 114 | hsa-miR-1284 | ucuauacagaccccuggcuuuuc | 1 | 11,56 | 0,09 | 0,28 |
| SEQ ID NO: 604 | 115 | hsa-miR-199b-3p | acaguagucgcacauugguua | 1 | 11,56 | 0,09 | 0,28 |
| SEQ ID NO: 160 | 116 | hsa-miR-599 | guugugucaguuuaucaaac | 1 | 1 | 1 | 0,29 |
| SEQ ID NO: 390 | 117 | hsa-miR-411 | uaguagaccguauagcguacg | 1 | 1 | 1 | 0,29 |
| SEQ ID NO: 531 | 118 | hsa-miR-23b | aucacauugccagggauuacc | 3976,97 | 2099,43 | 1,89 | 0,29 |
| SEQ ID NO: 755 | 119 | hsa-miR-1302 | uugggacauacuuuaugcuaaa | 1 | 1 | 1 | 0,29 |
| SEQ ID NO: 372 | 120 | hsa-miR-449a | uggcaguguauugcuguggu | 1 | 1 | 1 | 0,29 |
| SEQ ID NO: 229 | 121 | hsa-miR-548f | aaaaacguaauuacuuuu | 1 | 1 | 1 | 0,29 |
| SEQ ID NO: 162 | 122 | hsa-miR-597 | ugugucacucgaugaccacugu | 1 | 1,56 | 0,64 | 0,29 |
| SEQ ID NO: 156 | 123 | hsa-miR-603 | cacacacuuugacaauagcuuge | 1 | 16,33 | 0,59 | 0,29 |
| SEQ ID NO: 824 | 124 | hsa-miR-1247 | acccguccguuuguccggga | 9,56 | 21,11 | 0,25 | 0,29 |
| SEQ ID NO: 687 | 125 | hsa-miR-1539 | uccugcgcguccagaugccc | 5,22 | 1,56 | 0,64 | 0,29 |
| SEQ ID NO: 638 | 126 | hsa-miR-1911 | ugaguacgccaugucagugugg | 1 | 14,89 | 0,07 | 0,29 |
| SEQ ID NO: 464 | 127 | hsa-miR-325 | ccuaguaguguccaguaagugu | 1 | 1 | 1 | 0,3 |
| SEQ ID NO: 392 | 128 | hsa-miR-409-5p | agguuaccgagcaacuuugcau | 1 | 5073,69 | 1,51 | 0,3 |
| SEQ ID NO: 666 | 129 | hsa-miR-182 | uuuggcaauggaguaguaacucacacu | 7639,53 | 1118,35 | 2,17 | 0,3 |
| SEQ ID NO: 94 | 130 | hsa-miR-658 | ggcgaggaaguaggucguuggu | 2425,74 | 463,22 | 2,34 | 0,3 |
| SEQ ID NO: 559 | 131 | hsa-miR-215 | augccuauagaaugcuucugacagaac | 1085,22 | 1 | 1 | 0,3 |
| SEQ ID NO: 702 | 132 | hsa-miR-147b | gugugcggaaaugcuucugcua | 1 | 4318,58 | 1,47 | 0,3 |
| SEQ ID NO: 480 | 133 | hsa-miR-30d | uguaaacauccccgacuggaag | 6349,31 | 28 | 3,99 | 0,3 |
| SEQ ID NO: 402 | 134 | hsa-miR-378* | cuccugaccuccagguccugugu | 111,78 | 1 | 1 | 0,3 |
| SEQ ID NO: 543 | 135 | hsa-miR-221* | accuggcauacaaugaguagauuu | 1 | 19,78 | 0,13 | 0,3 |
| SEQ ID NO: 436 | 136 | hsa-miR-34b | caaucacuaacuccacugccau | 2,67 | 12,11 | 0,08 | 0,3 |
| SEQ ID NO: 165 | 137 | hsa-miR-593* | aggcaccagcaggcauugcucage | 1 | 22,22 | 0,18 | 0,3 |
| SEQ ID NO: 211 | 138 | hsa-miR-552 | aacaggugacuuggagucagacaa | 4 | 21,56 | 13,19 | 0,3 |
| SEQ ID NO: 403 | 139 | hsa-miR-378 | acuggacuuggagucucuggagg | 284,22 | 1 | 1 | 0,3 |
| SEQ ID NO: 716 | 140 | hsa-miR-143* | ggucagugcugcaucucuggu | 1 | 29,94 | 0,57 | 0,3 |
| SEQ ID NO: 797 | 141 | hsa-miR-1266 | ccucaggucucuagaacagggcu | 17,11 | 1 | 1 | 0,3 |
| SEQ ID NO: 209 | 142 | hsa-miR-554 | gcuaguccugugacucagccagu | 1 | 1 | 1 | 0,3 |
| SEQ ID NO: 122 | 143 | hsa-miR-631 | agaccuggccugaccucagc | 2,67 | 13,72 | 0,19 | 0,3 |
| SEQ ID NO: 150 | 144 | hsa-miR-609 | agggguuuuucuucucucu | 1 | 1 | 1 | 0,3 |
| SEQ ID NO: 483 | 145 | hsa-miR-30c | uguaaacauccuacacucucagc | 8969,72 | 4779,31 | 1,88 | 0,3 |
| SEQ ID NO: 514 | 146 | hsa-miR-28-5p | aaggagcucacagucuauugag | 454,22 | 108,56 | 4,18 | 0,3 |
| SEQ ID NO: 533 | 147 | hsa-miR-23a | aucacauugccagggauuuucc | 3428,42 | 1797,04 | 1,91 | 0,3 |

FIG. 10B (Cont.)

| | | | | | |
|---|---|---|---|---|---|
| SEQ ID NO: 108 | 148 | hsa-miR-645 | ucuaggcuguacugcuga | 1 | 1 |
| SEQ ID NO: 106 | 149 | hsa-miR-647 | guggcugcacacuucccuc | 1 | 1 |
| SEQ ID NO: 494 | 150 | hsa-miR-302b* | acuuuaacauggaagugcuuuc | | 0,3 |
| SEQ ID NO: 152 | 151 | hsa-miR-607 | guucaaaucagaaucuauaac | 1 | 0,3 |
| SEQ ID NO: 770 | 152 | hsa-miR-1289 | uggaguccaggaaucugcauuuu | 4,44 | 0,23 |
| SEQ ID NO: 739 | 153 | hsa-miR-1324 | ccagacagaauucuaugcacuuuc | 1 | 1 |
| SEQ ID NO: 308 | 154 | hsa-miR-513a-3p | uaaauuucaccuuucugagaagg | 1 | 1 |
| SEQ ID NO: 14 | 155 | hsa-miR-939 | uggggagcugaggcucuggggug | 203,17 | 3,46 |
| SEQ ID NO: 505 | 156 | hsa-miR-29b | uagcaccauuugaaaucagugu | 337,83 | 4,12 |
| SEQ ID NO: 85 | 157 | hsa-miR-665 | accaggaggcugaggcccu | 212 | 1,11 |
| SEQ ID NO: 650 | 158 | hsa-miR-18a | uaaggugcaucuagugcagauag | 143,78 | 2,44 |
| SEQ ID NO: 845 | 159 | hsa-miR-1224-5p | gugaggacucggggugggug | 586,78 | 1,51 |
| SEQ ID NO: 870 | 160 | hsa-miR-10a* | caaauucguaucaggggaaua | 1 | 0,23 |
| SEQ ID NO: 672 | 161 | hsa-miR-181a* | accaucgaccguugauuguacc | 1 | 1 |
| SEQ ID NO: 553 | 162 | hsa-miR-218-2* | cauguucugucaagcaccgcg | 1 | 1 |
| SEQ ID NO: 419 | 163 | hsa-miR-371-3p | aagugccgccaucuuuuugagugu | 1 | 1 |
| SEQ ID NO: 405 | 164 | hsa-miR-377 | aucacacaaaggcaacuuuugu | 1 | 1 |
| SEQ ID NO: 722 | 165 | hsa-miR-140-5p | cagugguuuuacccuauggag | 1 | 1 |
| SEQ ID NO: 499 | 166 | hsa-miR-301a | cagugcaauaguauugucaaagc | 16,78 | 0,78 |
| SEQ ID NO: 783 | 167 | hsa-miR-1277 | uacguagauauauauguauuuu | 1 | 1 |
| SEQ ID NO: 747 | 168 | hsa-miR-130a* | uucacauugugcuacugucugc | 1 | 1 |
| SEQ ID NO: 636 | 169 | hsa-miR-1912 | uaccagagcaugcagugugaa | 1,56 | 0,64 |
| SEQ ID NO: 626 | 170 | hsa-miR-193b | aacuggcccucuacaaguccccgcu | 1,56 | 0,64 |
| SEQ ID NO: 560 | 171 | hsa-miR-214* | ugccugucucugccuuggcugc | 1 | 1 |
| SEQ ID NO: 557 | 172 | hsa-miR-216b | aaaucucugcaggcaaaugug | 1 | 1 |
| SEQ ID NO: 488 | 173 | hsa-miR-302f | uaauugcuuccauguuu | 1 | 1 |
| SEQ ID NO: 260 | 174 | hsa-miR-522* | cucuagagggaagcgcuuucug | 4 | 12,11 |
| SEQ ID NO: 225 | 175 | hsa-miR-548j | aaaaguaaauugcgguucuuuggu | 1 | 1 |
| SEQ ID NO: 196 | 176 | hsa-miR-568 | auguauaaauguauuacacac | 1 | 1 |
| SEQ ID NO: 105 | 177 | hsa-miR-648 | aagugugcagggcacuggu | 1 | 1 |
| SEQ ID NO: 90 | 178 | hsa-miR-662 | uccccaguuuggcccagcag | 3,11 | 0,32 |
| SEQ ID NO: 542 | 179 | hsa-miR-222 | agcuacaucuggcuacugggu | 320,78 | 320,78 |
| SEQ ID NO: 772 | 180 | hsa-miR-1287 | ugcuggaucaggguucgagac | 1 | 0,08 |
| SEQ ID NO: 36 | 181 | hsa-miR-891b | ugcaacuuaccugaguucauuga | 12,44 | 1 |
| SEQ ID NO: 442 | 182 | hsa-miR-342-3p | ucucacacagaaaucgcacccgu | 2319,9 | 1,48 |
| SEQ ID NO: 310 | 183 | hsa-miR-512-3p | aagugcucuuauagcugagguc | 1 | 1 |
| SEQ ID NO: 134 | 184 | hsa-miR-623 | auccccuugcaggggcuguggggu | 1 | 1 |

FIG. 10B (Cont.)

| | | | | | | |
|---|---|---|---|---|---|---|
| SEQ ID NO: 580 | 185 | hsa-miR-208b | auaagacgaacaaaagguuugu | 6,78 | 6,78 | 0,3 |
| SEQ ID NO: 677 | 186 | hsa-miR-16-1* | ccaguauuaacugugcugcuga | 1 | 1,56 | 0,31 |
| SEQ ID NO: 213 | 187 | hsa-miR-551b | gcgaccccauuacuuggucag | 1 | 1 | 0,31 |
| SEQ ID NO: 707 | 188 | hsa-miR-146b-3p | ugcccugggacucaguucugg | 1 | 1 | 0,31 |
| SEQ ID NO: 271 | 189 | hsa-miR-520b | aaagugcuuccuuuuagagg | 1 | 1 | 0,31 |
| SEQ ID NO: 371 | 190 | hsa-miR-449b | aggcaguguauuguuagcugg | 1 | 1 | 0,31 |
| SEQ ID NO: 264 | 191 | hsa-miR-520g | acaaagugcuucccuuuagagugu | 1 | 1 | 0,31 |
| SEQ ID NO: 527 | 192 | hsa-miR-24-2* | ugccuacugagcugaaacacag | 1 | 1 | 0,31 |
| SEQ ID NO: 284 | 193 | hsa-miR-518f | gaaagcgcuucucuuuuagagg | 1 | 1 | 0,32 |
| SEQ ID NO: 104 | 194 | hsa-miR-649 | aaaccugugguuccaagagc | 1 | 1 | 0,32 |
| SEQ ID NO: 474 | 195 | hsa-miR-32 | uauugcacauuacuaaguugca | 1 | 3,67 | 0,32 |
| SEQ ID NO: 693 | 196 | hsa-miR-151-3p | cuagacugaagcuccuugagg | 344,56 | 90,78 | 0,32 |
| SEQ ID NO: 360 | 197 | hsa-miR-454 | uagugcaauauugcuuauagggu | 90,44 | 26,56 | 0,32 |
| SEQ ID NO: 883 | 198 | hsa-miR-101 | uacaguacugauaacugaa | 94,56 | 138,61 | 0,32 |
| SEQ ID NO: 599 | 199 | hsa-miR-19b-1* | aguuuugcaggguuugcauccagc | 1 | 1 | 0,32 |
| SEQ ID NO: 313 | 200 | hsa-miR-509-5p | uacugcagacaguggcaauca | 1 | 1 | 0,32 |
| SEQ ID NO: 715 | 201 | hsa-miR-144 | uacaguauagaugauguacu | 40,67 | 82,06 | 0,32 |
| SEQ ID NO: 316 | 202 | hsa-miR-508-5p | uacucagagggcgucacucaug | 22,67 | 31,33 | 0,32 |
| SEQ ID NO: 195 | 203 | hsa-miR-569 | aguuaaugaauccuggaaagu | 1 | 1 | 0,32 |
| SEQ ID NO: 117 | 204 | hsa-miR-636 | ugugcuuugcucugucccgcgca | 46,89 | 49,22 | 0,32 |
| SEQ ID NO: 16 | 205 | hsa-miR-937 | auccgcucugcucugacucucugc | 4 | 10,44 | 0,38 |
| SEQ ID NO: 439 | 206 | hsa-miR-346 | ugucugcccgcauggccugcucu | 1 | 1 | 0,32 |
| SEQ ID NO: 319 | 207 | hsa-miR-506 | uaaggcaccuucugaguaga | 1 | 1 | 0,32 |
| SEQ ID NO: 400 | 208 | hsa-miR-379* | uauguaacauggucacuaaacu | 1 | 1,56 | 0,64 |
| SEQ ID NO: 861 | 209 | hsa-miR-1184 | ccugcagcugacuugauggcuucc | 1 | 1 | 0,32 |
| SEQ ID NO: 183 | 210 | hsa-miR-579 | uucauuuggauauaaaccgcgauuu | 1 | 1 | 0,32 |
| SEQ ID NO: 530 | 211 | hsa-miR-23b* | uggguuccuggcaugcugauu | 1 | 1 | 0,32 |
| SEQ ID NO: 801 | 212 | hsa-miR-1262 | auggugaauuugugaaggau | 1 | 11,33 | 0,09 |
| SEQ ID NO: 690 | 213 | hsa-miR-153 | uugcauaguccaaaagugauc | 1 | 1 | 0,32 |
| SEQ ID NO: 266 | 214 | hsa-miR-520e | aaagugcuuccuuuuagggg | 1 | 1 | 0,32 |
| SEQ ID NO: 121 | 215 | hsa-miR-632 | gugucaauuccuguggga | 2,67 | 4,44 | 0,6 |
| SEQ ID NO: 875 | 216 | hsa-miR-106a* | cugcaaguaagcacuucauc | 1 | 4,44 | 0,23 |
| SEQ ID NO: 475 | 217 | hsa-miR-31* | ugcuagcaacauauugccau | 1 | 1 | 0,32 |
| SEQ ID NO: 445 | 218 | hsa-miR-33b* | cagugccucggcagugcagcc | 1 | 1 | 0,32 |
| SEQ ID NO: 99 | 219 | hsa-miR-654-3p | uauugucucugcugacauccccu | 1 | 1 | 0,32 |
| SEQ ID NO: 1 | 220 | hsa-miR-99b* | caagcucgugucuguggguccg | 1 | 1 | 0,32 |
| SEQ ID NO: 782 | 221 | hsa-miR-1278 | uaguacugugcauaucuau | 1 | 1 | 0,32 |

FIG. 10B (Cont.)

| | | | | | |
|---|---|---|---|---|---|
| SEQ ID NO: 733 | 222 | hsa-miR-135b | uauggcuuuucauuccuaugaga | 1 | 1 | 0,32 |
| SEQ ID NO: 898 | 223 | hsa-let-7c* | uagaguuacacccugguuaguua | 1 | 1 | 0,32 |
| SEQ ID NO: 711 | 224 | hsa-miR-1468 | cuccguuugccuguuuucgcug | 4,22 | 0,24 | 0,32 |
| SEQ ID NO: 411 | 225 | hsa-miR-374b* | cuuagcagguguauuaucauu | 1 | 1 | 0,32 |
| SEQ ID NO: 304 | 226 | hsa-miR-514 | auugacacuucgugagaguaga | 1 | 1 | 0,32 |
| SEQ ID NO: 170 | 227 | hsa-miR-590-3p | uaauuuauguauaagcuagu | 1 | 1 | 0,32 |
| SEQ ID NO: 153 | 228 | hsa-miR-606 | aaacacugaaaaucaaagau | 1 | 1 | 0,32 |
| SEQ ID NO: 422 | 229 | hsa-miR-369-3p | aauaauacaugguugaucuuu | 1 | 1 | 0,32 |
| SEQ ID NO: 347 | 230 | hsa-miR-488 | uugaaggcuauuucuugguc | 1 | 1 | 0,32 |
| SEQ ID NO: 780 | 231 | hsa-miR-128 | ucacagugaaccggucucuuu | 773,97 | 21,56 | 35,91 | 0,32 |
| SEQ ID NO: 429 | 232 | hsa-miR-362-5p | aauccuugaaccuaggugugagu | 260,22 | 14,89 | 17,48 | 0,32 |
| SEQ ID NO: 81 | 233 | hsa-miR-671-5p | aggaagcccuggaggggcuggag | 272 | 168,11 | 1,62 | 0,32 |
| SEQ ID NO: 53 | 234 | hsa-miR-874 | cugcccugccgagggaccga | 34 | 35,83 | 0,95 | 0,33 |
| SEQ ID NO: 637 | 235 | hsa-miR-1911* | caccaggcauugugucucc | 1 | 1 | 1 | 0,33 |
| SEQ ID NO: 766 | 236 | hsa-miR-1292 | ugggaacgguuccggcagacgcug | 252,11 | 158,89 | 1,59 | 0,33 |
| SEQ ID NO: 624 | 237 | hsa-miR-194 | uguaacagcaaccauugugaa | 1853,1 | 1440,75 | 1,29 | 0,33 |
| SEQ ID NO: 680 | 238 | hsa-miR-15b | uagcagcacaucauggguuuaca | 20349,58 | 23734,72 | 0,86 | 0,33 |
| SEQ ID NO: 441 | 239 | hsa-miR-342-5p | aggggcuaucucugugauuga | 82,44 | 73,33 | 1,12 | 0,33 |
| SEQ ID NO: 806 | 240 | hsa-miR-125b-2* | ucaagucaggcucuuggac | 1 | 3,67 | 0,27 | 0,33 |
| SEQ ID NO: 759 | 241 | hsa-miR-1297 | uucaaguauauucaggug | 1 | 1 | 1 | 0,33 |
| SEQ ID NO: 20 | 242 | hsa-miR-933 | ugugcgcagggagaccucucc | 18,11 | 28,44 | 0,64 | 0,33 |
| SEQ ID NO: 338 | 243 | hsa-miR-493* | uguacauguuaggcuuucauu | 1,56 | 3,11 | 0,5 | 0,33 |
| SEQ ID NO: 878 | 244 | hsa-miR-105 | ucaaaugcucagacucugugu | 1 | 1 | 1 | 0,33 |
| SEQ ID NO: 721 | 245 | hsa-miR-141 | uaacacugucugguaaagaugg | 1 | 1 | 1 | 0,33 |
| SEQ ID NO: 668 | 246 | hsa-miR-181c* | aaccaucgaccguugagugac | 1 | 1 | 1 | 0,33 |
| SEQ ID NO: 628 | 247 | hsa-miR-193a-3p | aacuggccuacaaagucccagu | 20,83 | 21,11 | 0,99 | 0,33 |
| SEQ ID NO: 493 | 248 | hsa-miR-302c | agagugcuuccgugaucagg | 1 | 1 | 1 | 0,33 |
| SEQ ID NO: 352 | 249 | hsa-miR-485-5p | agaggcuggccgugaugaauuc | 39,67 | 50,89 | 0,78 | 0,33 |
| SEQ ID NO: 331 | 250 | hsa-miR-499-3p | aacaucacagcaagucugugcu | 1 | 1 | 1 | 0,33 |
| SEQ ID NO: 240 | 251 | hsa-miR-545 | ucagcaacaauuuauugugugc | 1 | 1 | 1 | 0,33 |
| SEQ ID NO: 235 | 252 | hsa-miR-548b-5p | aaaguaauugugguuuuggcc | 1 | 1 | 1 | 0,33 |
| SEQ ID NO: 217 | 253 | hsa-miR-549 | ugacaaccuuuccuagagcucu | 1 | 1 | 1 | 0,33 |
| SEQ ID NO: 186 | 254 | hsa-miR-576-5p | auucuauuuccacgucuuu | 1 | 4,22 | 0,24 | 0,33 |
| SEQ ID NO: 185 | 255 | hsa-miR-577 | uagauaaaauauugguaccug | 1 | 1 | 1 | 0,33 |
| SEQ ID NO: 178 | 256 | hsa-miR-583 | caaagaggaaguccauuac | 49,56 | 55,22 | 0,9 | 0,33 |
| SEQ ID NO: 174 | 257 | hsa-miR-587 | uuucauaggugaugaucac | 1 | 1,56 | 0,64 | 0,33 |
| SEQ ID NO: 133 | 258 | hsa-miR-624 | cacaaggauuggauauaccu | 1 | 1 | 1 | 0,33 |

FIG. 10B (Cont.)

| | | | | | | |
|---|---|---|---|---|---|---|
| SEQ ID NO: 107 | 259 | hsa-miR-646 | aagcagcugcucugaggc | 1 | 1 | 0,33 |
| SEQ ID NO: 97 | 260 | hsa-miR-655 | auaauacauggucuaaccucuuu | 1 | 1 | 0,33 |
| SEQ ID NO: 45 | 261 | hsa-miR-885-5p | uccauuacacuaccugcucu | 5,56 | 0,2 | 0,33 |
| SEQ ID NO: 623 | 262 | hsa-miR-194* | ccaguggggcugcuguuaucg | 6,78 | 1,33 | 0,33 |
| SEQ ID NO: 508 | 263 | hsa-miR-299-5p | ugguuuaccgucccacauacau | 1 | 1 | 0,33 |
| SEQ ID NO: 454 | 264 | hsa-miR-337-3p | cuccuauaugaugccuuucuc | 4,44 | 0,23 | 0,33 |
| SEQ ID NO: 339 | 265 | hsa-miR-493 | ugaaggucuacugugugccagg | 1 | 1 | 0,33 |
| SEQ ID NO: 333 | 266 | hsa-miR-497* | caaaccacacugggguuaga | 1 | 1 | 0,33 |
| SEQ ID NO: 282 | 267 | hsa-miR-519a | aaagugcaucccuuuuagagugu | 1 | 1 | 0,33 |
| SEQ ID NO: 3 | 268 | hsa-miR-99a* | caagcucgcuucuauggguag | 1 | 1 | 0,33 |
| SEQ ID NO: 779 | 269 | hsa-miR-1280 | ucccaccgcugccaccc | 237,33 | 1,49 | 0,33 |
| SEQ ID NO: 258 | 270 | hsa-miR-523* | cucuagagggaagcgcuuucug | 6,78 | 0,36 | 0,33 |
| SEQ ID NO: 607 | 271 | hsa-miR-198 | ggucagaggggagaauaggucc | 428,39 | 1,12 | 0,33 |
| SEQ ID NO: 19 | 272 | hsa-miR-934 | ugucuacuacuggagacacaugg | 1 | 1 | 0,33 |
| SEQ ID NO: 479 | 273 | hsa-miR-30d* | cuuucagucagauuguuugcugc | 1 | 1 | 0,33 |
| SEQ ID NO: 362 | 274 | hsa-miR-452* | ccaucugcaaagaaguuugug | 1 | 1 | 0,33 |
| SEQ ID NO: 236 | 275 | hsa-miR-548b-3p | caagacucuuguugcuuuugu | 1 | 1 | 0,33 |
| SEQ ID NO: 175 | 276 | hsa-miR-586 | uauugcacucguccccggcaccc | 1 | 1 | 0,33 |
| SEQ ID NO: 24 | 277 | hsa-miR-92b | uauugcacucgucccggcccuguguguu | 4260,36 | 1 | 0,33 |
| SEQ ID NO: 295 | 278 | hsa-miR-517b | ucgugcauccccuuuagagugu | 1 | 0,77 | 0,33 |
| SEQ ID NO: 238 | 279 | hsa-miR-548a-3p | caaaacuggcaauuuuuugguu | 1 | 1 | 0,33 |
| SEQ ID NO: 51 | 280 | hsa-miR-875-5p | uauacucaguuuuauucaggug | 1 | 1 | 0,34 |
| SEQ ID NO: 377 | 281 | hsa-miR-431* | caggucguuugagaaaugucau | 1 | 1 | 0,34 |
| SEQ ID NO: 394 | 282 | hsa-miR-384 | auuccuagaaauugucaua | 1 | 1 | 0,34 |
| SEQ ID NO: 109 | 283 | hsa-miR-644 | aguguggcuuuucugagc | 1 | 1 | 0,34 |
| SEQ ID NO: 860 | 284 | hsa-miR-1185 | agagauacccuuuguaugu | 1 | 1 | 0,34 |
| SEQ ID NO: 503 | 285 | hsa-miR-29b-2* | cugguuucaugguggcuuag | 34,44 | 0,73 | 0,34 |
| SEQ ID NO: 345 | 286 | hsa-miR-489 | gugacaucacauaacggcagc | 1 | 1 | 0,34 |
| SEQ ID NO: 198 | 287 | hsa-miR-566 | gggcgccugugauccccaac | 1 | 1 | 0,34 |
| SEQ ID NO: 688 | 288 | hsa-miR-1538 | cggccggggcugcugcuguuccu | 48 | 2,56 | 0,34 |
| SEQ ID NO: 515 | 289 | hsa-miR-28-3p | cacuagauugugagcuccugga | 29,11 | 1,38 | 0,34 |
| SEQ ID NO: 891 | 290 | hsa-let-7f-2* | cuauacaguccugucuuuucc | 1 | 1 | 0,34 |
| SEQ ID NO: 741 | 291 | hsa-miR-1322 | gaugaugcugcugaugcug | 1,56 | 6,56 | 0,34 |
| SEQ ID NO: 662 | 292 | hsa-miR-1827 | ugagcuaguagauugaau | 9,56 | 0,24 | 0,34 |
| SEQ ID NO: 629 | 293 | hsa-miR-192* | cugcaauuccauaggucacag | 4,44 | 2,15 | 0,34 |
| SEQ ID NO: 489 | 294 | hsa-miR-302e | uaagugcuuccauguuu | 1 | 1 | 0,34 |
| SEQ ID NO: 389 | 295 | hsa-miR-411* | uauguaacacguccacuaacc | 1,56 | 0,64 | 0,34 |

FIG. 10B (Cont.)

| | | | | | |
|---|---|---|---|---|---|
| SEQ ID NO: 383 | 296 | hsa-miR-424 | cagcagcaauucauguuuugaa | 53 | 40,78 | 1,3 | 0,34 |
| SEQ ID NO: 180 | 297 | hsa-miR-582-3p | uaacugguugaacaacugaacc | 4 | 4,22 | 0,95 | 0,34 |
| SEQ ID NO: 124 | 298 | hsa-miR-629* | guucuccaacguaaccccuucuac | 31,56 | 33,56 | 0,94 | 0,34 |
| SEQ ID NO: 342 | 299 | hsa-miR-491-3p | cuuaugcaagauuccuuuucuac | 1 | 1 | 1 | 0,34 |
| SEQ ID NO: 280 | 300 | hsa-miR-519b-3p | aaagugcauccuuuuagagguu | 1 | 1 | 1 | 0,34 |
| SEQ ID NO: 859 | 301 | hsa-miR-1197 | uaggacacaugguucuacuucu | 1 | 1,56 | 0,64 | 0,34 |
| SEQ ID NO: 785 | 302 | hsa-miR-127-5p | cugaagcucagagggcucugau | 5,56 | 21,56 | 0,26 | 0,34 |
| SEQ ID NO: 773 | 303 | hsa-miR-1286 | ugcaggaccaagaugagcccu | 12,44 | 12 | 1,04 | 0,34 |
| SEQ ID NO: 743 | 304 | hsa-miR-132* | accguggcuuucgauuguuacu | 1 | 1 | 1 | 0,34 |
| SEQ ID NO: 446 | 305 | hsa-miR-33b | gugcauugcuguugcauugc | 1 | 1,56 | 0,64 | 0,34 |
| SEQ ID NO: 210 | 306 | hsa-miR-553 | aaaacgugagauuuuguuuu | 1 | 1 | 1 | 0,34 |
| SEQ ID NO: 137 | 307 | hsa-miR-620 | auggagauagauaagaaau | 1 | 1,56 | 0,64 | 0,34 |
| SEQ ID NO: 77 | 308 | hsa-miR-708 | aaggagcuuacaaucuagcuggg | 1 | 1 | 1 | 0,34 |
| SEQ ID NO: 34 | 309 | hsa-miR-892b | cacggcucccuuuucuggguaga | 1 | 1 | 1 | 0,34 |
| SEQ ID NO: 263 | 310 | hsa-miR-520h | acaaaugcuuccccuuuagagu | 1 | 1 | 1 | 0,34 |
| SEQ ID NO: 328 | 311 | hsa-miR-500* | augcaccuggcaaggauucug | 254,28 | 8,33 | 30,51 | 0,34 |
| SEQ ID NO: 212 | 312 | hsa-miR-551b* | gaaaucaagcguggugagacc | 97,33 | 87,67 | 1,11 | 0,34 |
| SEQ ID NO: 656 | 313 | hsa-miR-186 | caaagaaauucuccuuuuggggcu | 39,67 | 18,72 | 2,12 | 0,34 |
| SEQ ID NO: 204 | 314 | hsa-miR-558 | ugagcugcuguaccaaaau | 1 | 1 | 1 | 0,34 |
| SEQ ID NO: 524 | 315 | hsa-miR-26a | uucaaguaaccaggauaggcu | 8969,72 | 11137,35 | 0,81 | 0,34 |
| SEQ ID NO: 800 | 316 | hsa-miR-1263 | augguaccuggcauacugagu | 1 | 1 | 1 | 0,34 |
| SEQ ID NO: 572 | 317 | hsa-miR-211 | uucccuuugucauccuucgccu | 3,67 | 3,67 | 1 | 0,34 |
| SEQ ID NO: 753 | 318 | hsa-miR-1304 | uuugagcuacgugucugagugug | 20,56 | 28 | 0,73 | 0,35 |
| SEQ ID NO: 546 | 319 | hsa-miR-220b | ccaccacgacgucugacacu | 2,67 | 1 | 2,67 | 0,35 |
| SEQ ID NO: 37 | 320 | hsa-miR-891a | ugcaaccgaaucagagcacuga | 6,78 | 6,56 | 1,03 | 0,35 |
| SEQ ID NO: 818 | 321 | hsa-miR-1253 | agagaagaagaucagcugca | 1 | 1 | 1 | 0,35 |
| SEQ ID NO: 853 | 322 | hsa-miR-1205 | ucugcagguuugcuuugag | 1 | 1 | 1 | 0,35 |
| SEQ ID NO: 729 | 323 | hsa-miR-137 | uuauugcuuaagaauacgcguag | 1 | 1 | 1 | 0,35 |
| SEQ ID NO: 685 | 324 | hsa-miR-154* | aaucauacacgguugaccuauu | 1 | 1 | 1 | 0,35 |
| SEQ ID NO: 208 | 325 | hsa-miR-555 | agguaagcugaaccucugau | 1 | 1 | 1 | 0,35 |
| SEQ ID NO: 42 | 326 | hsa-miR-887 | gugaagggcgccauccgagg | 22,67 | 31,33 | 0,72 | 0,35 |
| SEQ ID NO: 428 | 327 | hsa-miR-363 | aauugcacgguaccaucugua | 2790,67 | 3303,71 | 0,84 | 0,35 |
| SEQ ID NO: 689 | 328 | hsa-miR-1537 | aaaaccgucuaguucaguugu | 1 | 1 | 1 | 0,35 |
| SEQ ID NO: 552 | 329 | hsa-miR-219-1-3p | agagauugaguucgacacuuu | 1 | 1 | 1 | 0,35 |
| SEQ ID NO: 547 | 330 | hsa-miR-220a | ccacacgcuauccugacacuuu | 1 | 1 | 1 | 0,35 |
| SEQ ID NO: 541 | 331 | hsa-miR-222* | cucaguagccaguguagauccu | 1 | 1 | 1 | 0,35 |
| SEQ ID NO: 468 | 332 | hsa-miR-323-3p | cacauuacacgguccgaccucu | 1 | 1 | 1 | 0,35 |

FIG. 10B (Cont.)

| | | | | | | |
|---|---|---|---|---|---|---|
| SEQ ID NO: 407 | 333 | hsa-miR-376b | aucauagaggaaaauccauguu | | 6,56 | 0,15 | 0,35 |
| SEQ ID NO: 343 | 334 | hsa-miR-490-5p | ccauggaucuccaggugggu | 1 | 4,22 | 0,24 | 0,35 |
| SEQ ID NO: 259 | 335 | hsa-miR-523 | gaacgcgcuccccuauagagggu | 1 | 1 | 1 | 0,35 |
| SEQ ID NO: 496 | 336 | hsa-miR-302a* | acuuaaacguggaugguacuugcu | | 1 | 1 | 0,35 |
| SEQ ID NO: 516 | 337 | hsa-miR-27b* | agagcuuagcugauuggugaac | 8,44 | 4,22 | 2 | 0,35 |
| SEQ ID NO: 168 | 338 | hsa-miR-591 | agaccauugggurucuaugu | 1 | 1 | 1 | 0,35 |
| SEQ ID NO: 41 | 339 | hsa-miR-888 | uacucaaaaagcugcaguca | | 1 | 1 | 0,35 |
| SEQ ID NO: 408 | 340 | hsa-miR-376a* | guagauuccuccuauagagua | | 1 | 1 | 0,35 |
| SEQ ID NO: 139 | 341 | hsa-miR-618 | aaacuuacuugucccuucugagu | | 1 | 1 | 0,35 |
| SEQ ID NO: 863 | 342 | hsa-miR-1182 | gaggucuuggaggaugaugugac | 708,06 | 674,69 | 1,05 | 0,35 |
| SEQ ID NO: 249 | 343 | hsa-miR-532-3p | ccuccacaccccaagcuugca | 88,11 | 114,67 | 0,77 | 0,35 |
| SEQ ID NO: 670 | 344 | hsa-miR-181b | aacauucauugcugucgguggu | 61,11 | 27,78 | 2,2 | 0,35 |
| SEQ ID NO: 262 | 345 | hsa-miR-521 | aacgcauucccuuuagagugu | | 4,44 | 0,23 | 0,35 |
| SEQ ID NO: 239 | 346 | hsa-miR-545* | ucaguaaauguuuuauuagauga | | 1 | 1 | 0,35 |
| SEQ ID NO: 32 | 347 | hsa-miR-9* | auaaagcuagauaaccgaaagu | | 1 | 1 | 0,35 |
| SEQ ID NO: 31 | 348 | hsa-miR-920 | ggggagcuguguggaagcagua | 50,56 | 80,11 | 0,63 | 0,35 |
| SEQ ID NO: 193 | 349 | hsa-miR-571 | ugaguuggccaucugagugag | | 1 | 1 | 0,35 |
| SEQ ID NO: 118 | 350 | hsa-miR-635 | acuuggcacugaaacaaugucc | | 1 | 1 | 0,35 |
| SEQ ID NO: 595 | 351 | hsa-miR-200b | uaauacugccuggwaaugauga | | 1 | 1 | 0,35 |
| SEQ ID NO: 357 | 352 | hsa-miR-455-5p | uaugccuuugugacuacaucg | | 1 | 1 | 0,35 |
| SEQ ID NO: 50 | 353 | hsa-miR-876-3p | uggurguuuacaaaguaauuca | | 1 | 1 | 0,35 |
| SEQ ID NO: 415 | 354 | hsa-miR-373* | acucaaaaugggcgcuuucc | 79,67 | 116,33 | 0,68 | 0,35 |
| SEQ ID NO: 708 | 355 | hsa-miR-146a* | ccucugaaauucaguucucag | | 1 | 1 | 0,35 |
| SEQ ID NO: 847 | 356 | hsa-miR-122* | aacgccauuaucacacuaaaua | | 1 | 1 | 0,35 |
| SEQ ID NO: 366 | 357 | hsa-miR-450b-3p | uugggaucaguuugcauccaua | | 1 | 1 | 0,35 |
| SEQ ID NO: 529 | 358 | hsa-miR-24 | uggcucaguucaggaacag | 511,89 | 331,06 | 1,55 | 0,35 |
| SEQ ID NO: 354 | 359 | hsa-miR-484 | ucaggcucaguccccuccgau | 3778,89 | 2575,72 | 1,47 | 0,35 |
| SEQ ID NO: 879 | 360 | hsa-miR-103-as | ucauagcccuguacaaugcugcu | | 1 | 1 | 0,35 |
| SEQ ID NO: 399 | 361 | hsa-miR-380 | uauguaaueuggeccacauuu | | 1 | 1 | 0,35 |
| SEQ ID NO: 307 | 362 | hsa-miR-513a-5p | uucacagggaggugucau | 450,61 | 348,22 | 1,29 | 0,35 |
| SEQ ID NO: 315 | 363 | hsa-miR-509-3-5p | uacugcagacguggaaucaug | | 1 | 1 | 0,35 |
| SEQ ID NO: 54 | 364 | hsa-miR-873 | gcaggaacgcguggagucuccu | | 1 | 1 | 0,35 |
| SEQ ID NO: 206 | 365 | hsa-miR-556-5p | gauagcucauugguaaaugag | 5,11 | 1 | 0,2 | 0,35 |
| SEQ ID NO: 421 | 366 | hsa-miR-369-5p | agaucgaccguguuauauucgc | | 1 | 1 | 0,35 |
| SEQ ID NO: 100 | 367 | hsa-miR-653 | guguugaaacaaucucuacug | | 1 | 1 | 0,35 |
| SEQ ID NO: 60 | 368 | hsa-miR-767-3p | ucugcucauaccccaugguuucu | 16,78 | 18,72 | 0,9 | 0,35 |
| SEQ ID NO: 301 | 369 | hsa-miR-516a-3p | ugcuuccuuuuagagggu | | 1 | 1 | 0,35 |

FIG. 10B (Cont.)

| | | | | | |
|---|---|---|---|---|---|
| SEQ ID NO: 270 | 370 | hsa-miR-520c-3p | aaagugcuuccuuuuagagggu | 1 | 1 | 0,35 |
| SEQ ID NO: 76 | 371 | hsa-miR-708* | caacuagacugugaguucuag | 1 | 1 | 0,35 |
| SEQ ID NO: 28 | 372 | hsa-miR-924 | agagucuugaugucuugc | 1 | 1 | 0,35 |
| SEQ ID NO: 267 | 373 | hsa-miR-520d-5p | cuacaaagggaagcccuuuc | 37,67 | 44,89 | 0,84 | 0,35 |
| SEQ ID NO: 309 | 374 | hsa-miR-512-5p | cacucagccuugaggcacuuuc | 1 | 4,22 | 0,24 | 0,35 |
| SEQ ID NO: 413 | 375 | hsa-miR-374a* | cuuaucagauuguauuguaauu | 1 | 1 | 1 | 0,35 |
| SEQ ID NO: 30 | 376 | hsa-miR-921 | cuagugaggaacagaaccaggauuc | 260,22 | 207,33 | 1,26 | 0,36 |
| SEQ ID NO: 852 | 377 | hsa-miR-1206 | uguucauguagaugcuuuaagc | 1 | 10,44 | 0,1 | 0,36 |
| SEQ ID NO: 811 | 378 | hsa-miR-1259 | auauauaugaugcauuagcuuuu | 112,44 | 106,11 | 1,06 | 0,36 |
| SEQ ID NO: 254 | 379 | hsa-miR-525-5p | cuccagagggaugcacuuuc | 1,89 | 4,22 | 0,45 | 0,36 |
| SEQ ID NO: 596 | 380 | hsa-miR-200a* | caauuaccggacagugauugga | 1 | 1 | 1 | 0,36 |
| SEQ ID NO: 765 | 381 | hsa-miR-1293 | ugggugucuggagauuugugc | 50,56 | 21,11 | 2,39 | 0,36 |
| SEQ ID NO: 417 | 382 | hsa-miR-372 | aaagugcugcgacauuugagcgu | 1 | 1 | 1 | 0,36 |
| SEQ ID NO: 237 | 383 | hsa-miR-548a-5p | aaaaguaaaugccgcguuuuacc | 1 | 1 | 1 | 0,36 |
| SEQ ID NO: 224 | 384 | hsa-miR-548k | aaaagcacguugcggauuuugcu | 1 | 1 | 1 | 0,36 |
| SEQ ID NO: 963 | 385 | hsa-miR-1300 | uugagaggaggcugcug | 327,33 | 192,67 | 1,7 | 0,36 |
| SEQ ID NO: 799 | 386 | hsa-miR-1264 | caagucuuauuuugagccacuguu | 1 | 1 | 1 | 0,36 |
| SEQ ID NO: 214 | 387 | hsa-miR-551a | gcgaccacuaguucca | 1 | 1 | 1 | 0,36 |
| SEQ ID NO: 618 | 388 | hsa-miR-196b | uaggaguuucugguugugg | 1 | 21,56 | 0,05 | 0,36 |
| SEQ ID NO: 473 | 389 | hsa-miR-32* | caauuaaguguguguganuauuu | 1 | 1 | 1 | 0,36 |
| SEQ ID NO: 448 | 390 | hsa-miR-33a | gugcauuguaguugcauugca | 1 | 1 | 1 | 0,36 |
| SEQ ID NO: 231 | 391 | hsa-miR-548d-5p | aaaaguaauuguugguuuugcc | 1 | 1 | 1 | 0,36 |
| SEQ ID NO: 142 | 392 | hsa-miR-616 | aguccauuggaggguuugagcag | 27 | 30,44 | 0,89 | 0,36 |
| SEQ ID NO: 49 | 393 | hsa-miR-876-5p | uggauuucuuugugaaucacca | 1 | 1 | 1 | 0,36 |
| SEQ ID NO: 317 | 394 | hsa-miR-505-3p | ugauuugcccuuuuggaguaga | 1 | 1 | 1 | 0,36 |
| SEQ ID NO: 522 | 395 | hsa-miR-26a-2* | ccuauucuugauuuacuguuc | 1 | 1 | 1 | 0,36 |
| SEQ ID NO: 654 | 396 | hsa-miR-187 | ucgugucuuguuguugcagccgg | 1,89 | 4,44 | 0,23 | 0,36 |
| SEQ ID NO: 606 | 397 | hsa-miR-199a-3p | acaguaguucugcacaugguua | 120,44 | 19,78 | 0,05 | 0,36 |
| SEQ ID NO: 6 | 398 | hsa-miR-96* | aaucaugugcagugccaauaug | 1 | 1 | 1 | 0,36 |
| SEQ ID NO: 648 | 399 | hsa-miR-18b | uaaggugcaucuagugcaguuag | 137,22 | 234,33 | 0,59 | 0,36 |
| SEQ ID NO: 375 | 400 | hsa-miR-432* | cuggauggcucccauguu | 1 | 1 | 1 | 0,36 |
| SEQ ID NO: 314 | 401 | hsa-miR-509-3p | ugauuguaguucucugugguag | 1,89 | 1,56 | 1,21 | 0,36 |
| SEQ ID NO: 862 | 402 | hsa-miR-1183 | cacguagguguagagaugggca | 120,44 | 82,89 | 1,45 | 0,36 |
| SEQ ID NO: 129 | 403 | hsa-miR-626 | agcugcuuguugaaaugucuu | 1 | 1 | 1 | 0,36 |
| SEQ ID NO: 306 | 404 | hsa-miR-513b | uucacaaggaggugucauuuau | 91,17 | 72,22 | 1,26 | 0,36 |
| SEQ ID NO: 140 | 405 | hsa-miR-617 | agacuccccauuugaaggugc | 2,67 | 4,44 | 0,6 | 0,36 |
| SEQ ID NO: 33 | 406 | hsa-miR-9 | ucuuuggtuuaucuagcuguauga | 1 | 1 | 1 | 0,36 |

FIG. 10B (Cont.)

| | | | | | | |
|---|---|---|---|---|---|---|
| SEQ ID NO: 275 | 407 | hsa-miR-519e | aagugcccuuuuagagugu | | 1 | 0,36 |
| SEQ ID NO: 588 | 408 | hsa-miR-204 | uucccuuugucauccuaugccu | | 1 | 0,36 |
| SEQ ID NO: 502 | 409 | hsa-miR-29c | uagcaccauuugaaaucgguua | 340,89 | 9,44 | 0,36 |
| SEQ ID NO: 795 | 410 | hsa-miR-1268 | cgggcgugguggggg | 901,96 | 1056,33 | 0,36 |
| SEQ ID NO: 848 | 411 | hsa-miR-122 | uggagugugacaaugguguuug | 17,11 | 0,85 | 0,36 |
| SEQ ID NO: 72 | 412 | hsa-miR-7-2* | caacaaauccagucucaccua | 13 | 0,81 | 0,36 |
| SEQ ID NO: 681 | 413 | hsa-miR-15a* | caggccauauugugcugccuca | 1 | 1,07 | 0,36 |
| SEQ ID NO: 667 | 414 | hsa-miR-181d | aacauucauuguugucggugggu | 2,67 | 1 | 0,36 |
| SEQ ID NO: 550 | 415 | hsa-miR-219-5p | ugauguccaaacgcaauucu | 1 | 1 | 0,36 |
| SEQ ID NO: 491 | 416 | hsa-miR-302d | uaagugcuuccauguuugaguguu | 1 | 1 | 0,36 |
| SEQ ID NO: 438 | 417 | hsa-miR-34a | uggcagugucuuagcugguugu | 1 | 1 | 0,36 |
| SEQ ID NO: 391 | 418 | hsa-miR-410 | aauauaacacagauggccugu | 1 | 1 | 0,36 |
| SEQ ID NO: 447 | 419 | hsa-miR-33a* | caauguuccacagugcaucac | 1 | 1 | 0,36 |
| SEQ ID NO: 325 | 420 | hsa-miR-502-3p | aaugcaccuggcaaggauuca | 364,22 | 14,89 | 0,36 |
| SEQ ID NO: 401 | 421 | hsa-miR-379 | ugguagcauauugguaacguagg | 25,56 | 39,22 | 0,36 |
| SEQ ID NO: 332 | 422 | hsa-miR-498 | uuucaaggccagggguugcacuuuuuc | 101,11 | 58,78 | 0,36 |
| SEQ ID NO: 287 | 423 | hsa-miR-518d-5p | cucuagaggaagcacucucuuu | 36,78 | 19,78 | 0,36 |
| SEQ ID NO: 207 | 424 | hsa-miR-558-3p | aueuuaccauuagcucaucuuu | 1 | 1 | 0,36 |
| SEQ ID NO: 324 | 425 | hsa-miR-502-5p | auccuuguaucuggcauagcu | 6,78 | 6,78 | 0,36 |
| SEQ ID NO: 476 | 426 | hsa-miR-31 | aggcaagaugcuggcauagcu | 8,44 | 2,3 | 0,36 |
| SEQ ID NO: 885 | 427 | hsa-miR-100 | aacccguagaucccgaacuug | 212 | 2,15 | 0,36 |
| SEQ ID NO: 513 | 428 | hsa-miR-296-3p | gagguugguggaggcucucc | 606,46 | 1,48 | 0,36 |
| SEQ ID NO: 143 | 429 | hsa-miR-615-5p | ggggugucccggugcugggauc | 34 | 2,81 | 0,36 |
| SEQ ID NO: 574 | 430 | hsa-miR-21* | caacaccagucgauggcugu | 1 | 1 | 0,36 |
| SEQ ID NO: 95 | 431 | hsa-miR-657 | ggcagguucucacccucucuuugg | 1 | 1 | 0,36 |
| SEQ ID NO: 102 | 432 | hsa-miR-651 | uuuaggauaagcuuugacauug | 1085,22 | 1 | 0,36 |
| SEQ ID NO: 62 | 433 | hsa-miR-765 | uggaggaggaaguuuugaug | 1 | 0,98 | 0,36 |
| SEQ ID NO: 222 | 434 | hsa-miR-548m | caaaguauuuuguguuuug | 1 | 1 | 0,36 |
| SEQ ID NO: 551 | 435 | hsa-miR-219-2-3p | agaauuggcuggacaucugu | 4 | 4 | 0,36 |
| SEQ ID NO: 327 | 436 | hsa-miR-501-3p | aaugcaccugggcaaggauucu | 286,11 | 21,56 | 13,27 | 0,36 |
| SEQ ID NO: 497 | 437 | hsa-miR-302a | uaagugcuuccauguuuugguga | 1 | 1 | 0,36 |
| SEQ ID NO: 590 | 438 | hsa-miR-202* | uuccuugccauauacuucuuug | 1 | 1 | 0,37 |
| SEQ ID NO: 582 | 439 | hsa-miR-206 | uggaauguaaggaagugugugg | 15,78 | 28,44 | 0,55 | 0,37 |
| SEQ ID NO: 268 | 440 | hsa-miR-520d-3p | aaagugcuucucuuugguuggu | 1 | 1 | 0,37 |
| SEQ ID NO: 226 | 441 | hsa-miR-548i | aaaaguaauugcggauuuugcc | 1 | 1 | 0,37 |
| SEQ ID NO: 311 | 442 | hsa-miR-511 | gugucuuuugcucaguca | 1 | 1 | 0,37 |
| SEQ ID NO: 487 | 443 | hsa-miR-30a | uguaaacauccucgacuggaag | 1175,03 | 1056,33 | 1,11 | 0,37 |

FIG. 10B (Cont.)

| | | | | | | |
|---|---|---|---|---|---|---|
| SEQ ID NO: 846 | 444 | hsa-miR-1224-3p | ccccaccucucucucucucag | 25,56 | 67,44 | 0,38 |
| SEQ ID NO: 255 | 445 | hsa-miR-525-3p | gaaggcgcuuccuuuagagcg | 1 | 1 | 0,37 |
| SEQ ID NO: 843 | 446 | hsa-miR-1225-5p | gugguacggcccagugggggg | 142,83 | 194 | 0,37 |
| SEQ ID NO: 539 | 447 | hsa-miR-223* | cguguauuugacaagcugaguu | 1 | 4,44 | 0,37 |
| SEQ ID NO: 144 | 448 | hsa-miR-615-3p | uccgagccugguuccccucuu | 1 | 1 | 0,37 |
| SEQ ID NO: 194 | 449 | hsa-miR-570 | cgaaaacagcaauuacccuugc | 1 | 1 | 0,37 |
| SEQ ID NO: 472 | 450 | hsa-miR-320a | aaaagcuggguugagagggcga | 10047,96 | 8310,31 | 0,37 |
| SEQ ID NO: 56 | 451 | hsa-miR-770-5p | uccaguaccacguucagggcca | 9,11 | 11,33 | 1,21 | 0,37 |
| SEQ ID NO: 179 | 452 | hsa-miR-582-5p | uuacaguguuaaccaguuacu | 1 | 3,11 | 0,8 | 0,38 |
| SEQ ID NO: 169 | 453 | hsa-miR-590-5p | gagcuuuauucauaaagugcag | 1 | 1 | 0,32 | 0,38 |
| SEQ ID NO: 93 | 454 | hsa-miR-659 | cuugguucagggaggguccca | 150,56 | 133,11 | 1,13 | 0,38 |
| SEQ ID NO: 820 | 455 | hsa-miR-1251 | acucuagcugccaaaggcgcu | 1 | 1 | 1 | 0,38 |
| SEQ ID NO: 87 | 456 | hsa-miR-664 | uauucauuuauccccagccuaca | 8,44 | 11,33 | 0,75 | 0,38 |
| SEQ ID NO: 346 | 457 | hsa-miR-488* | cccagauaauggcacucucaa | 1 | 1 | 1 | 0,38 |
| SEQ ID NO: 228 | 458 | hsa-miR-548g | aaaacguaauuacuuuguuguac | 1 | 1 | 1 | 0,38 |
| SEQ ID NO: 55 | 459 | hsa-miR-802 | caguaacaaagauucaucacugu | 1 | 1 | 1 | 0,38 |
| SEQ ID NO: 243 | 460 | hsa-miR-542-5p | ucgggaucaucaugucacgaga | 6,78 | 1 | 6,78 | 0,38 |
| SEQ ID NO: 646 | 461 | hsa-miR-190 | ugauauguuugauauauuaggu | 1 | 1 | 1 | 0,38 |
| SEQ ID NO: 554 | 462 | hsa-miR-218-1* | agguuccgucaagauugcaaucu | 1 | 1 | 1 | 0,38 |
| SEQ ID NO: 423 | 463 | hsa-miR-367* | acuguugcuaauaugcaacucu | 1 | 1 | 1 | 0,38 |
| SEQ ID NO: 367 | 464 | hsa-miR-450a | uuuuugcgaugauguuccaaauau | 1 | 1 | 1 | 0,38 |
| SEQ ID NO: 424 | 465 | hsa-miR-367 | aauugcaccuuuagcaagguga | 20,56 | 11,33 | 1,81 | 0,38 |
| SEQ ID NO: 830 | 466 | hsa-miR-124 | uaaggcacgcggugaaugcc | 1 | 1 | 1 | 0,38 |
| SEQ ID NO: 59 | 467 | hsa-miR-767-5p | ugcaccaugguugucugagcaug | 1 | 1 | 1 | 0,38 |
| SEQ ID NO: 593 | 468 | hsa-miR-200c | uaauacugccggguaaugaauga | 7,44 | 10,44 | 0,71 | 0,38 |
| SEQ ID NO: 192 | 469 | hsa-miR-572 | gucccucggcgcguugccca | 6,78 | 4,44 | 1,53 | 0,38 |
| SEQ ID NO: 253 | 470 | hsa-miR-526a | cucuagagggaagcacuuucg | 27 | 56,22 | 0,48 | 0,39 |
| SEQ ID NO: 17 | 471 | hsa-miR-936 | acaagagggaggaaucgcag | 683,82 | 660,47 | 1,04 | 0,39 |
| SEQ ID NO: 221 | 472 | hsa-miR-548n | caaaaguaauuguggauuuugu | 1 | 1 | 1 | 0,39 |
| SEQ ID NO: 575 | 473 | hsa-miR-21 | uagcuuaucagacugauguuga | 708,06 | 857,3 | 0,83 | 0,39 |
| SEQ ID NO: 685 | 474 | hsa-miR-182* | ugguucuagacuugccaacua | 1 | 1 | 1 | 0,39 |
| SEQ ID NO: 433 | 475 | hsa-miR-34c-5p | aggcaguguaguuagcugauugc | 1 | 1 | 1 | 0,39 |
| SEQ ID NO: 379 | 476 | hsa-miR-429 | uaauacugucugguaaaaccgu | 1 | 1 | 1 | 0,39 |
| SEQ ID NO: 126 | 477 | hsa-miR-628-5p | augcugacauauuuacuagagg | 1 | 1 | 1 | 0,39 |
| SEQ ID NO: 506 | 478 | hsa-miR-29a* | acugauuucuuuugguguucag | 2,22 | 1 | 2,22 | 0,39 |
| SEQ ID NO: 420 | 479 | hsa-miR-370 | gccugcuggguggaaccuggu | 194 | 156,56 | 1,24 | 0,39 |
| SEQ ID NO: 903 | 480 | hsa-let-7a* | cuauacaaucuacuguciuuc | 4,78 | 4,22 | 1,13 | 0,39 |

FIG. 10B (Cont.)

| | | | | | | |
|---|---|---|---|---|---|---|
| SEQ ID NO: 882 | 481 | hsa-miR-101* | caguuuaucacagugcugaugcu | | 1 | 0,39 |
| SEQ ID NO: 203 | 482 | hsa-miR-559 | uaaaguaaauaugcaccaaaa | | 1 | 0,39 |
| SEQ ID NO: 556 | 483 | hsa-miR-217 | uacugcaucaggaacugauugga | | 1 | 0,39 |
| SEQ ID NO: 279 | 484 | hsa-miR-519b-5p | cucuagagguaagcguuucug | 1,56 | 4,44 | 0,39 |
| SEQ ID NO: 477 | 485 | hsa-miR-30e* | cuuucagucggauguuuacagc | 20,56 | 8,33 | 2,47 |
| SEQ ID NO: 705 | 486 | hsa-miR-147 | gugugugaaaugcuucugc | 4 | 4 | 4 |
| SEQ ID NO: 348 | 487 | hsa-miR-487b | aauguacagggucauccacuu | 20,56 | 12,11 | 1,7 |
| SEQ ID NO: 40 | 488 | hsa-miR-888* | gacugaccucucuugggugaa | 1 | 6,56 | 0,15 |
| SEQ ID NO: 587 | 489 | hsa-miR-205 | uccuucauuccaccggagucug | | 1 | 1 |
| SEQ ID NO: 813 | 490 | hsa-miR-1257 | agugaaugauggguucugacc | 2,67 | 1,56 | 1,71 |
| SEQ ID NO: 78 | 491 | hsa-miR-7 | uggaagacuagugauuuuguugu | 256,44 | 1 | 256,44 |
| SEQ ID NO: 512 | 492 | hsa-miR-296-5p | agggccccccucaaucugu | 48 | 58,89 | 0,82 |
| SEQ ID NO: 816 | 493 | hsa-miR-1255a | aggaugagcaaagaaaguagaauu | 46,44 | 28,44 | 1,63 |
| SEQ ID NO: 398 | 494 | hsa-miR-380* | ugguugaccauagaacaugcgc | 1 | 1 | 1 |
| SEQ ID NO: 786 | 495 | hsa-miR-1275 | gugggggagacgcuguc | 1146,69 | 901,96 | 1,27 |
| SEQ ID NO: 459 | 496 | hsa-miR-330-5p | ucucucgggccugugucuuaggc | | 1 | 1 |
| SEQ ID NO: 828 | 497 | hsa-miR-1243 | aacugaucaauuauauagagagug | | 1 | 1 |
| SEQ ID NO: 730 | 498 | hsa-miR-136* | caucaucucagacuagugucu | | 1 | 1 |
| SEQ ID NO: 720 | 499 | hsa-miR-141* | caucuucagauacagugucuu | | 1 | 1 |
| SEQ ID NO: 294 | 500 | hsa-miR-517c | aucgugcauccuuuagagugu | | 1 | 1 |
| SEQ ID NO: 136 | 501 | hsa-miR-621 | ggcuagcaacagcgcuuaccu | | 1 | 1 |
| SEQ ID NO: 631 | 502 | hsa-miR-1915* | accuugccuugcugucccgggcc | 1 | 11,33 | 0,09 |
| SEQ ID NO: 246 | 503 | hsa-miR-541 | uggugggcacagaaucuggacu | 16,78 | 28,44 | 0,59 |
| SEQ ID NO: 242 | 504 | hsa-miR-543 | aaacauucggugcacuucuu | | 1 | 1 |
| SEQ ID NO: 11 | 505 | hsa-miR-942 | ucuucucuguuuuggccaugug | 52 | 18,11 | 2,87 |
| SEQ ID NO: 523 | 506 | hsa-miR-26a-1* | ccuauucuuggauuacucugcacg | | 1 | 1 |
| SEQ ID NO: 197 | 507 | hsa-miR-567 | aguauguucuucaggacagaac | | 1 | 1 |
| SEQ ID NO: 659 | 508 | hsa-miR-184 | uggacggagaacugauaagggu | 94,56 | 56,78 | 1,67 |
| SEQ ID NO: 409 | 509 | hsa-miR-376a | aucauagaggaaaauccacgu | 1 | 3,11 | 0,32 |
| SEQ ID NO: 829 | 510 | hsa-miR-124* | cguguucacagcggaccuugau | 2,67 | 1 | 2,67 |
| SEQ ID NO: 817 | 511 | hsa-miR-1254 | agccuggaagcggagccugcagu | 245 | 723,61 | 0,34 |
| SEQ ID NO: 850 | 512 | hsa-miR-1207-5p | uggcaggugggcuggggg | 5382,15 | 4318,58 | 1,25 |
| SEQ ID NO: 182 | 513 | hsa-miR-580 | uugagaaugaugaaucauuagg | 1 | 1 | 1 |
| SEQ ID NO: 900 | 514 | hsa-let-7b* | cuauacaaccuacugccuucc | 22,22 | 13,72 | 1,62 |
| SEQ ID NO: 247 | 515 | hsa-miR-539 | ggagaauuauccuuggugugu | | 1 | 1 |
| SEQ ID NO: 273 | 516 | hsa-miR-520a-3p | aaagugcuucccuuuggacugu | | 1 | 1 |
| SEQ ID NO: 176 | 517 | hsa-miR-585 | ugggcguaucuguauugcua | | 1 | 1 |

FIG. 10B (Cont.)

| | | | | | | |
|---|---|---|---|---|---|---|
| SEQ ID NO: 964 | 518 | hsa-miR-875b | cuguaugcccucaccgcuca | 4 | 0,9 | 0,41 |
| SEQ ID NO: 10 | 519 | hsa-miR-943 | cugacuguuugcccguccccag | 1 | 1 | 0,41 |
| SEQ ID NO: 191 | 520 | hsa-miR-573 | cugaagugaugugugugaacugaucag | 1 | 1 | 0,41 |
| SEQ ID NO: 22 | 521 | hsa-miR-93 | caaagugcugguucugugcagguag | 4779,31 | 0,84 | 0,41 |
| SEQ ID NO: 518 | 522 | hsa-miR-27a* | agggcuuagcugcuugugagca | 1 | 1 | 0,41 |
| SEQ ID NO: 146 | 523 | hsa-miR-613 | aggaaugguuccuucuuugcc | 1 | 1 | 0,41 |
| SEQ ID NO: 545 | 524 | hsa-miR-220c | acacagggcuguugugaagacu | 3,11 | 0,32 | 0,41 |
| SEQ ID NO: 257 | 525 | hsa-miR-524-3p | gaaggcguuccuuuggagu | 1 | 1 | 0,42 |
| SEQ ID NO: 329 | 526 | hsa-miR-500 | uaauccuugcuaccuggugaga | 136,17 | 2,32 | 0,42 |
| SEQ ID NO: 857 | 527 | hsa-miR-1201 | agccugauuaaacacaugcucuga | 37,89 | 2,09 | 0,42 |
| SEQ ID NO: 578 | 528 | hsa-miR-20a* | acugcauuauagagcacuaaag | 1 | 1 | 0,42 |
| SEQ ID NO: 633 | 529 | hsa-miR-1914* | ggaggggguccccgcacuggagg | 249,39 | 1,63 | 0,42 |
| SEQ ID NO: 380 | 530 | hsa-miR-425* | aucggaaugucgugucccgcc | 98 | 2,9 | 0,42 |
| SEQ ID NO: 303 | 531 | hsa-miR-515-3p | gagucccuucuuuuggagcguu | 33,78 | 1 | 0,42 |
| SEQ ID NO: 404 | 532 | hsa-miR-377* | aggguugcccuugugcauuc | 1 | 1 | 0,42 |
| SEQ ID NO: 322 | 533 | hsa-miR-504 | agacccuguucugcacucuauc | 1 | 1 | 0,42 |
| SEQ ID NO: 234 | 534 | hsa-miR-548c-3p | caaaaaucuaauacauuugc | 1 | 1 | 0,42 |
| SEQ ID NO: 784 | 535 | hsa-miR-1276 | uaaagagcccuguggagaca | 24,56 | 0,81 | 0,42 |
| SEQ ID NO: 728 | 536 | hsa-miR-138 | agcugguguuguguaaucaggccg | 8,44 | 8,44 | 0,42 |
| SEQ ID NO: 378 | 537 | hsa-miR-431 | ugucuuugcaggccgucaugca | 3,67 | 0,27 | 0,42 |
| SEQ ID NO: 337 | 538 | hsa-miR-484 | ugaaacauuacacggaaccuc | 20349,58 | 1 | 0,42 |
| SEQ ID NO: 373 | 539 | hsa-miR-448 | uugcauaguauucuccaauaaa | 1 | 1 | 0,42 |
| SEQ ID NO: 120 | 540 | hsa-miR-633 | cuaauacagggacaucagu | 1,56 | 1,56 | 0,42 |
| SEQ ID NO: 349 | 541 | hsa-miR-487a | aauacauacagggacaucaggu | 1 | 1 | 0,42 |
| SEQ ID NO: 697 | 542 | hsa-miR-149 | ucuggcuccgugucuuucacuccc | 9,56 | 11,33 | 0,42 |
| SEQ ID NO: 500 | 543 | hsa-miR-300 | uauacaagggcagacucucucu | 1 | 0,84 | 0,42 |
| SEQ ID NO: 663 | 544 | hsa-miR-1826 | auugaucauucgcacucgaacgcaau | 35853,42 | 1 | 0,42 |
| SEQ ID NO: 789 | 545 | hsa-miR-127-3p | ucgauccgucugagcuuggcu | 1 | 1 | 0,42 |
| SEQ ID NO: 350 | 546 | hsa-miR-486-5p | uccugacugagcugcccgag | 42197,28 | 1 | 0,42 |
| SEQ ID NO: 701 | 547 | hsa-miR-1148a | ucaggcacuacagaacuuugu | 382 | 901,96 | 0,42 |
| SEQ ID NO: 763 | 548 | hsa-miR-1294 | ugugaggguugcauuguuugucu | 29,11 | 18,72 | 0,42 |
| SEQ ID NO: 223 | 549 | hsa-miR-548l | aaaaguauuuugggguuuugc | 1 | 1,55 | 0,42 |
| SEQ ID NO: 718 | 550 | hsa-miR-142-5p | cauaaaucugcagaaaagcacuacu | 29,11 | 2,79 | 0,42 |
| SEQ ID NO: 39 | 551 | hsa-miR-889 | uuaaauccuggauagaccauugu | 1 | 1 | 0,43 |
| SEQ ID NO: 426 | 552 | hsa-miR-365 | uaauugcccuaaaaauccuuau | 24 | 0,56 | 0,43 |
| SEQ ID NO: 2 | 553 | hsa-miR-99b | cacccguagaaccgaccuugcg | 73,33 | 2,19 | 0,44 |
| SEQ ID NO: 594 | 554 | hsa-miR-200b* | caucuuacugggcagcauugga | 7,44 | 1,76 | 0,44 |

FIG. 10B (Cont.)

| SEQ ID NO | # | miRNA | sequence | | | |
|---|---|---|---|---|---|---|
| SEQ ID NO: 597 | 555 | hsa-miR-200a | uaacacugucugguaacgaugu | | 1 | 0,44 |
| SEQ ID NO: 286 | 556 | hsa-miR-518e | aaagcgcuucccuucugagcuag | | 1 | 0,44 |
| SEQ ID NO: 147 | 557 | hsa-miR-612 | gcugggcagggcuucugagccuu | 24,56 | 0,73 | 0,44 |
| SEQ ID NO: 660 | 558 | hsa-miR-183* | gugaauuacagaagggccauaa | 82,06 | 1,14 | 0,44 |
| SEQ ID NO: 699 | 559 | hsa-miR-148b | ucagugcaucagaaacuuugu | 364,22 | 364,22 | 0,44 |
| SEQ ID NO: 881 | 560 | hsa-miR-103 | agcagcauuguacagggcuauga | 3868,5 | 5382,15 | 0,44 |
| SEQ ID NO: 220 | 561 | hsa-miR-548o | ccaaaacugcaguuacuuuugc | 1 | 0,72 | 0,44 |
| SEQ ID NO: 855 | 562 | hsa-miR-1203 | cccgagccaggaugccagcuc | 43,11 | 1 | 0,44 |
| SEQ ID NO: 734 | 563 | hsa-miR-135a* | uauagggauuggagccguggcg | 644,9 | 1,54 | 0,44 |
| SEQ ID NO: 395 | 564 | hsa-miR-383 | agaucagaaggugauguggggcu | 15,33 | 480,44 | 0,44 |
| SEQ ID NO: 635 | 565 | hsa-miR-1913 | ucugccccucgcucugccca | 34,22 | 18,67 | 0,44 |
| SEQ ID NO: 416 | 566 | hsa-miR-373 | gaagugcuucgauuuugggugu | 1 | 51,56 | 0,44 |
| SEQ ID NO: 418 | 567 | hsa-miR-371-5p | acucaaacuguggggcacu | 98 | 1,56 | 0,44 |
| SEQ ID NO: 510 | 568 | hsa-miR-298 | agcagaagcagggagguuucucca | 71,56 | 93,22 | 0,44 |
| SEQ ID NO: 68 | 569 | hsa-miR-758 | uuugcaccugggucacuaacc | 9,11 | 53,33 | 0,45 |
| SEQ ID NO: 388 | 570 | hsa-miR-412 | acuucaaccugguccacuagccgu | 4 | 14,89 | 0,45 |
| SEQ ID NO: 290 | 571 | hsa-miR-518c | caaagcguucuucccuuuagagugu | 1 | 1,56 | 0,45 |
| SEQ ID NO: 171 | 572 | hsa-miR-589* | ucagaacaaaugccgguccccaga | 22,67 | 1,05 | 0,45 |
| SEQ ID NO: 110 | 573 | hsa-miR-643 | acuugaugcuagcuacagguag | 1 | 1,34 | 0,45 |
| SEQ ID NO: 167 | 574 | hsa-miR-592 | uugugucaauaugcgaugaugu | 1 | 0,61 | 0,45 |
| SEQ ID NO: 35 | 575 | hsa-miR-892a | cacugugucccuuucugugag | 7,89 | 2,57 | 0,45 |
| SEQ ID NO: 9 | 576 | hsa-miR-944 | aaauuauguacaucggauag | 1 | 1 | 0,45 |
| SEQ ID NO: 187 | 577 | hsa-miR-576-3p | aagauguggaaaaauuggaauc | 11,33 | 0,53 | 0,45 |
| SEQ ID NO: 181 | 578 | hsa-miR-581 | ucuugugucuuucuagaucagu | 1 | 1 | 0,45 |
| SEQ ID NO: 130 | 579 | hsa-miR-625* | gacuauagaacuuuccccuca | 52 | 0,09 | 0,45 |
| SEQ ID NO: 803 | 580 | hsa-miR-1260 | aucccaccucugccacca | 21,89 | 2,38 | 0,45 |
| SEQ ID NO: 778 | 581 | hsa-miR-1281 | ucgccucccucucccc | 84,17 | 1,64 | 0,45 |
| SEQ ID NO: 453 | 582 | hsa-miR-337-5p | gaacggcuucauacaggagu | 8,44 | 0,24 | 0,45 |
| SEQ ID NO: 737 | 583 | hsa-miR-133b | uuuggucccuucaaccagcua | 2,67 | 0,32 | 0,46 |
| SEQ ID NO: 25 | 584 | hsa-miR-92a-2* | ggguggguauuugugcauuac | 24 | 1,21 | 0,46 |
| SEQ ID NO: 884 | 585 | hsa-miR-100* | caagcugauuacuauaagguag | 148,44 | 2,2 | 0,46 |
| SEQ ID NO: 172 | 586 | hsa-miR-589 | ugagaaccacgucucucugag | 1 | 1 | 0,46 |
| SEQ ID NO: 555 | 587 | hsa-miR-218 | uugugcuugaucuaaccaugu | 6,78 | 6,78 | 0,46 |
| SEQ ID NO: 538 | 588 | hsa-miR-224 | caagucacuaguuccagu | 1 | 1 | 0,46 |
| SEQ ID NO: 676 | 589 | hsa-miR-16-2* | ccaauauuacugugcugcuuua | 40,56 | 1,34 | 0,47 |
| SEQ ID NO: 498 | 590 | hsa-miR-301b | cagugcaaugguuuugauucaaagc | 1 | 1 | 0,47 |
| SEQ ID NO: 642 | 591 | hsa-miR-190b | ugauaugguuugauauggggu | 1 | 1 | 0,47 |

FIG. 10B (Cont.)

| SEQ ID NO: | | | | | | |
|---|---|---|---|---|---|---|
| SEQ ID NO: 410 | 592 | hsa-miR-375 | uuuguucguucgcucgcguga | 1 | 1 | 0,47 |
| SEQ ID NO: 219 | 593 | hsa-miR-548p | uagcaaaaacugcaguuacuuu | 1 | 1 | 0,47 |
| SEQ ID NO: 657 | 594 | hsa-miR-185* | agggcuggcuuuccucugguc | 55,56 | 47,06 | 0,47 |
| SEQ ID NO: 276 | 595 | hsa-miR-519d | caaagugcaucccuuuagagug | 1 | 1 | 0,48 |
| SEQ ID NO: 154 | 596 | hsa-miR-605 | uaaauccccauggugccuucuccu | 6,78 | 3,67 | 0,48 |
| SEQ ID NO: 48 | 597 | hsa-miR-877 | guagaggagaucggcgaggg | 364,22 | 450,61 | 0,48 |
| SEQ ID NO: 810 | 598 | hsa-miR-125a-3p | acagggguucuuggagcc | 56,33 | 39,22 | 0,48 |
| SEQ ID NO: 69 | 599 | hsa-miR-744* | cuguugccacuaaccucaaccu | 15,33 | 11,33 | 0,48 |
| SEQ ID NO: 269 | 600 | hsa-miR-520c-5p | cucuagaggaagcacuuuucug | 31,56 | 30,44 | 0,48 |
| SEQ ID NO: 700 | 601 | hsa-miR-148a* | aaaguucugagacaucccgacu | 1 | 1 | 0,49 |
| SEQ ID NO: 562 | 602 | hsa-miR-212 | uaacagucucagucacggcc | 7,44 | 4,44 | 0,49 |
| SEQ ID NO: 321 | 603 | hsa-miR-505 | cgucaacacugccaaucuc | 53 | 11,33 | 0,49 |
| SEQ ID NO: 335 | 604 | hsa-miR-496 | ugauuuacauggccaaucuc | 15,33 | 4,44 | 0,49 |
| SEQ ID NO: 740 | 605 | hsa-miR-1323 | ucaaaacugagggcauuuucu | 68,22 | 44 | 0,49 |
| SEQ ID NO: 230 | 606 | hsa-miR-548e | aaaaaacugagacuacuuugca | 1 | 1 | 0,5 |
| SEQ ID NO: 127 | 607 | hsa-miR-628-3p | ucuaguaagagauggcagucga | 49,56 | 34,44 | 0,5 |
| SEQ ID NO: 634 | 608 | hsa-miR-1914 | ccccugucccugggacucgag | 6,78 | 14,89 | 0,5 |
| SEQ ID NO: 177 | 609 | hsa-miR-584 | uuauuggucucccuggacugag | 119,89 | 114,67 | 0,5 |
| SEQ ID NO: 732 | 610 | hsa-miR-135b* | auguagggcuaaaagccauggg | 34,22 | 12,11 | 0,5 |
| SEQ ID NO: 762 | 611 | hsa-miR-1295 | uuaggccgcagaucuggguga | 8,44 | 11,33 | 0,5 |
| SEQ ID NO: 8 | 612 | hsa-miR-95 | uucaacggguauuauuugagca | 1 | 1 | 0,5 |
| SEQ ID NO: 738 | 613 | hsa-miR-133a | uuugguccccuucaaccagcug | 34,22 | 21,11 | 0,5 |
| SEQ ID NO: 353 | 614 | hsa-miR-485-3p | gucauacacggucucucuccu | 1 | 1,56 | 0,51 |
| SEQ ID NO: 245 | 615 | hsa-miR-541* | aaagauucucgucugguccacu | 1 | 1 | 0,51 |
| SEQ ID NO: 412 | 616 | hsa-miR-374b | auauauacaaccuguuaaccucuuu | 126,44 | 21,56 | 0,51 |
| SEQ ID NO: 461 | 617 | hsa-miR-329 | aacacaccuggguuaaccucuuu | 1 | 1,56 | 0,51 |
| SEQ ID NO: 355 | 618 | hsa-miR-483-5p | aagacgggaggaaagaggag | 4541,94 | 3572,67 | 0,51 |
| SEQ ID NO: 46 | 619 | hsa-miR-885-3p | aggcagcgguguaguggaua | 463,22 | 1040,44 | 0,52 |
| SEQ ID NO: 887 | 620 | hsa-let-7i* | cugcgcaagcuacugcuu | 5,22 | 1 | 0,52 |
| SEQ ID NO: 18 | 621 | hsa-miR-935 | ccaguuaccgcuuccgcuaccgc | 1 | 1 | 0,52 |
| SEQ ID NO: 746 | 622 | hsa-miR-130b | caguucaaugaaaagggcau | 388 | 185,22 | 0,52 |
| SEQ ID NO: 788 | 623 | hsa-miR-1274a | guccccuguucaggcgcca | 93,89 | 12 | 0,52 |
| SEQ ID NO: 842 | 624 | hsa-miR-1226 | ucaccagcccuguguuccccag | 1 | 4,44 | 0,53 |
| SEQ ID NO: 285 | 625 | hsa-miR-518e* | cucuagaggagcgcuuuucug | 2,22 | 2,67 | 0,53 |
| SEQ ID NO: 844 | 626 | hsa-miR-1225-3p | ugagccccugucgcgccccca | 39,67 | 42,78 | 0,53 |
| SEQ ID NO: 965 | 627 | hsa-miR-923 | gucagcgggagaaagaaacu | 24783,94 | 20349,58 | 0,53 |
| SEQ ID NO: 619 | 628 | hsa-miR-196a* | cggcaacaagaaacugcugag | 15,33 | 18,72 | 0,53 |

FIG. 10B (Cont.)

| | | | | | | |
|---|---|---|---|---|---|---|
| SEQ ID NO: 793 | 629 | hsa-miR-1270 | cuggagauaugguaagagcucugugu | 31,56 | 1,04 | 0,53 |
| SEQ ID NO: 792 | 630 | hsa-miR-1271 | cuuggccuuagcaagcaagcugga | 15,78 | 10,14 | 0,53 |
| SEQ ID NO: 149 | 631 | hsa-miR-610 | ugagcuaaaugugugcugga | 24 | 0,66 | 0,53 |
| SEQ ID NO: 190 | 632 | hsa-miR-574-3p | cacgcucaugcacacaccaca | 48 | 0,82 | 0,53 |
| SEQ ID NO: 777 | 633 | hsa-miR-1282 | ucguuugccuuuuuucugcuu | 29,44 | 18,93 | 0,53 |
| SEQ ID NO: 868 | 634 | hsa-miR-10b* | acagauucgauucuaggggaau | 1 | 1 | 0,53 |
| SEQ ID NO: 558 | 635 | hsa-miR-216a | uaaucucagcuggcaaucuguga | 1 | 1 | 0,53 |
| SEQ ID NO: 714 | 636 | hsa-miR-144* | ggauaucacauauacuguaag | 340,89 | 0,76 | 0,53 |
| SEQ ID NO: 532 | 637 | hsa-miR-23a* | gggguuccuggggaugggauuu | 74 | 0,6 | 0,54 |
| SEQ ID NO: 330 | 638 | hsa-miR-499-5p | uuaagacuugcaguguguu | 1 | 1 | 0,54 |
| SEQ ID NO: 661 | 639 | hsa-miR-183 | uauggcacuguagaaucacu | 90,11 | 3,39 | 0,54 |
| SEQ ID NO: 344 | 640 | hsa-miR-490-3p | caaccugaggacuccaugcug | 1 | 1 | 0,55 |
| SEQ ID NO: 460 | 641 | hsa-miR-330-3p | gcaaagcacacggccugagaga | 15,33 | 1,38 | 0,55 |
| SEQ ID NO: 889 | 642 | hsa-let-7g* | cuguacaggccacugccuugc | 1 | 1 | 0,55 |
| SEQ ID NO: 356 | 643 | hsa-miR-483-3p | ucacucucucuccgcucu | 13 | 0,43 | 0,55 |
| SEQ ID NO: 561 | 644 | hsa-miR-214 | acagcaggcacagagacagcagu | 29,11 | 9,36 | 0,55 |
| SEQ ID NO: 435 | 645 | hsa-miR-34b* | uaggcagugucauuagcugauug | 1 | 1 | 0,56 |
| SEQ ID NO: 490 | 646 | hsa-miR-302d* | acuuuaacauggaggcacuug | 11,33 | 0,09 | 0,56 |
| SEQ ID NO: 396 | 647 | hsa-miR-382 | gaaguuguguggguugauucg | 1,56 | 6,14 | 0,56 |
| SEQ ID NO: 359 | 648 | hsa-miR-454* | acccuauaauauugucucucgc | 27 | 1,28 | 0,56 |
| SEQ ID NO: 856 | 649 | hsa-miR-1202 | gugccagcugugcagugggag | 71,56 | 0,83 | 0,56 |
| SEQ ID NO: 591 | 650 | hsa-miR-202 | agagguauagggcauggga | 86,67 | 1,83 | 0,56 |
| SEQ ID NO: 241 | 651 | hsa-miR-544 | auucugcauuuuuagcaaguc | 111,78 | 1 | 0,56 |
| SEQ ID NO: 166 | 652 | hsa-miR-593 | ugucucugcuggguucu | 30,44 | 0,66 | 0,56 |
| SEQ ID NO: 66 | 653 | hsa-miR-760 | cggcucugggucugugga | 34,89 | 0,65 | 0,57 |
| SEQ ID NO: 13 | 654 | hsa-miR-940 | aaggcagggccccgucccc | 112,44 | 1,67 | 0,57 |
| SEQ ID NO: 894 | 655 | hsa-let-7e* | cuauacggccuccuuagccuuucc | 1 | 1 | 0,57 |
| SEQ ID NO: 832 | 656 | hsa-miR-1237 | uccuucugcuccgucccccag | 37,89 | 1,24 | 0,57 |
| SEQ ID NO: 647 | 657 | hsa-miR-18b* | ugccccuaaaugcccuuucugc | 24,56 | 1,36 | 0,58 |
| SEQ ID NO: 123 | 658 | hsa-miR-630 | aguauucucuaccagggaagu | 4 | 0,61 | 0,58 |
| SEQ ID NO: 274 | 659 | hsa-miR-519e* | uuccuccaaagggagcacuuuc | 6,56 | 0,87 | 0,58 |
| SEQ ID NO: 363 | 660 | hsa-miR-452 | aacugugguuuccagagaaacuga | 19,78 | 2,67 | 0,58 |
| SEQ ID NO: 520 | 661 | hsa-miR-26b* | ccuguuccauuacuuggcuc | 17,11 | 0,24 | 0,58 |
| SEQ ID NO: 299 | 662 | hsa-miR-516b | aucugguaagaagcacuuuu | 4,22 | 0,92 | 0,58 |
| SEQ ID NO: 509 | 663 | hsa-miR-299-3p | uaugugggauguaaaccgcuu | 52 | 1,06 | 0,58 |
| SEQ ID NO: 397 | 664 | hsa-miR-381 | uauacaagggcaagcucucugu | 58,78 | 7,44 | 0,58 |
| SEQ ID NO: 444 | 665 | hsa-miR-340 | uuauaaagcaaugagacugauu | 7,44 | 3,7 | 0,58 |

FIG. 10B (Cont.)

| | | | | | |
|---|---|---|---|---|---|
| SEQ ID NO: 744 | 666 | hsa-miR-132 | uaacagucuacagccauggucg | 24,56 | 5,82 | 0,58 |
| SEQ ID NO: 719 | 667 | hsa-miR-142-3p | uguaguguuuccuacuuuaugga | 1 | 1 | 0,58 |
| SEQ ID NO: 807 | 668 | hsa-miR-125b-1* | acgggUuagcucuuggagcu | 49,56 | 0,88 | 0,59 |
| SEQ ID NO: 481 | 669 | hsa-miR-30c-2* | cuggagaaggcuguuuuaucucu | 68,67 | 1,21 | 0,59 |
| SEQ ID NO: 128 | 670 | hsa-miR-627 | gugagucucuaagaaaagagga | 1 | 1 | 0,59 |
| SEQ ID NO: 645 | 671 | hsa-miR-1908 | cggcagggacggcgauuggguc | 5944,79 | 6597,81 | 0,59 |
| SEQ ID NO: 796 | 672 | hsa-miR-1267 | ccuguuigaaguguaauccca | 9,56 | 1,56 | 0,59 |
| SEQ ID NO: 318 | 673 | hsa-miR-507 | uuuugccaccuuuuggagugaa | 1 | 6,14 | 0,59 |
| SEQ ID NO: 651 | 674 | hsa-miR-188-5p | caucccuugcauguuggaggg | 21,44 | 0,97 | 0,59 |
| SEQ ID NO: 351 | 675 | hsa-miR-486-3p | cgggcagcucaguacaggau | 37,89 | 2,02 | 0,59 |
| SEQ ID NO: 163 | 676 | hsa-miR-596 | aagccugccggucuccucggg | 1 | 0,32 | 0,6 |
| SEQ ID NO: 627 | 677 | hsa-miR-193a-5p | uggggucuuugcgggcgagauga | 46,89 | 1,54 | 0,6 |
| SEQ ID NO: 82 | 678 | hsa-miR-671-3p | uccggtuucagggggcuccacc | 21,11 | 1,54 | 0,6 |
| SEQ ID NO: 528 | 679 | hsa-miR-24-1* | ugccuacugagcugauuugcagu | 1 | 1 | 0,6 |
| SEQ ID NO: 598 | 680 | hsa-miR-19b-2* | aguuuugcaggguuugcauuca | 1 | 1 | 0,61 |
| SEQ ID NO: 749 | 681 | hsa-miR-1308 | gcauggugguucagugu | 15421,86 | 1,66 | 0,61 |
| SEQ ID NO: 581 | 682 | hsa-miR-208a | auaagacgagcaaaaagcuugu | 19,89 | 1,34 | 0,61 |
| SEQ ID NO: 735 | 683 | hsa-miR-135a | uauggcuuuuuauuccuaugga | 1 | 1 | 0,61 |
| SEQ ID NO: 457 | 684 | hsa-miR-331-5p | cuagguauggucccagggaucc | 22,22 | 1,05 | 0,61 |
| SEQ ID NO: 669 | 685 | hsa-miR-181c | aacauucaaccugucggugagu | 130,44 | 5,99 | 0,62 |
| SEQ ID NO: 113 | 686 | hsa-miR-640 | auguccaggaaccugccucu | 4 | 0,9 | 0,62 |
| SEQ ID NO: 644 | 687 | hsa-miR-1909 | cgcaggggcgggguguccaccg | 154,22 | 1,16 | 0,63 |
| SEQ ID NO: 125 | 688 | hsa-miR-629 | uggguuuacguuggggagaacu | 106,11 | 1,68 | 0,63 |
| SEQ ID NO: 871 | 689 | hsa-miR-10a | uacccuguagauccgaauuugug | 34,22 | 1,12 | 0,63 |
| SEQ ID NO: 341 | 690 | hsa-miR-491-5p | aguggggaaccuuccaugagg | 101,11 | 1,04 | 0,63 |
| SEQ ID NO: 340 | 691 | hsa-miR-492 | aggacccgggggacaagaauuccu | 88,56 | 1,01 | 0,63 |
| SEQ ID NO: 300 | 692 | hsa-miR-516a-5p | uucucgaggaaagaagcacuuuc | 39,67 | 0,67 | 0,63 |
| SEQ ID NO: 312 | 693 | hsa-miR-510 | uacucaggagauggcaaucac | 26,78 | 3,21 | 0,63 |
| SEQ ID NO: 632 | 694 | hsa-miR-1915 | ccccaggggcgacgcggcggg | 2223,89 | 3080,08 | 0,63 |
| SEQ ID NO: 289 | 695 | hsa-miR-518c* | ucucuggagggaagcacuuucug | 109,67 | 0,72 | 0,63 |
| SEQ ID NO: 790 | 696 | hsa-miR-1273 | gggcgacaagcaagacucuuucu | 26,44 | 1,72 | 0,63 |
| SEQ ID NO: 525 | 697 | hsa-miR-25* | aggcgagacuggccaaug | 111,78 | 0,84 | 0,63 |
| SEQ ID NO: 70 | 698 | hsa-miR-744 | ugcggguucuagggcuaacagca | 364,22 | 1,63 | 0,63 |
| SEQ ID NO: 216 | 699 | hsa-miR-550 | agugccugagggagaagagccc | 136,17 | 0,94 | 0,63 |
| SEQ ID NO: 38 | 700 | hsa-miR-890 | uacuugggaaagcaucagguug | 20,56 | 1,5 | 0,63 |
| SEQ ID NO: 754 | 701 | hsa-miR-1303 | uuagagacgggucuugcucu | 41,89 | 1,78 | 0,63 |
| SEQ ID NO: 103 | 702 | hsa-miR-650 | agggaggcaggcucucucaggac | 14,89 | 1,34 | 0,63 |
| | | | | 12,44 | 1,2 | 0,63 |

FIG. 10B (Cont.)

| | | | | | |
|---|---|---|---|---|---|
| SEQ ID NO: 840 | 703 | hsa-miR-1227 | cguguccaccuuuuucccag | 32 | 29,94 | 1,07 | 0,63 |
| SEQ ID NO: 164 | 704 | hsa-miR-595 | gaagugccguggugugucu | 12 | 11,33 | 1,06 | 0,63 |
| SEQ ID NO: 815 | 705 | hsa-miR-1255b | cggaugagcaaagaaaguggu | 87,67 | 76,56 | 1,15 | 0,63 |
| SEQ ID NO: 819 | 706 | hsa-miR-1252 | agaaggaaaaugaauucauuua | 1 | 1 | 1 | 0,63 |
| SEQ ID NO: 358 | 707 | hsa-miR-455-3p | gcaguccauggcauauacac | 1 | 1 | 1 | 0,63 |
| SEQ ID NO: 440 | 708 | hsa-miR-345 | gcugacuccuagucccagggcuc | 168,11 | 34,44 | 4,88 | 0,63 |
| SEQ ID NO: 7 | 709 | hsa-miR-96 | uuuggcacuagcacauuuuugcu | 106,89 | 36,11 | 2,96 | 0,63 |
| SEQ ID NO: 742 | 710 | hsa-miR-1321 | cagggaggugaaugugau | 74,22 | 58,78 | 1,26 | 0,64 |
| SEQ ID NO: 305 | 711 | hsa-miR-513c | uucucaaggaggugucguuuau | 68,67 | 45,11 | 1,52 | 0,64 |
| SEQ ID NO: 233 | 712 | hsa-miR-548c-5p | aaaaguaauugcgguuuuugcc | 1 | 1 | 1 | 0,64 |
| SEQ ID NO: 89 | 713 | hsa-miR-663 | aggcggggcgccgcggaccgc | 715,83 | 1175,03 | 0,61 | 0,64 |
| SEQ ID NO: 470 | 714 | hsa-miR-320c | aaaagcuggguugagaggu | 5382,15 | 6141,96 | 0,88 | 0,64 |
| SEQ ID NO: 471 | 715 | hsa-miR-320b | aaaagcuggguugagggcaa | 6349,31 | 6349,31 | 1 | 0,64 |
| SEQ ID NO: 98 | 716 | hsa-miR-654-5p | uggugggccgcagaacaugugc | 124,11 | 98,56 | 1,26 | 0,65 |
| SEQ ID NO: 463 | 717 | hsa-miR-326 | ccucuggcccucucucuc | 20,56 | 19,78 | 1,04 | 0,65 |
| SEQ ID NO: 664 | 718 | hsa-miR-1825 | uccagugcccucucucc | 21,11 | 30,44 | 0,69 | 0,65 |
| SEQ ID NO: 462 | 719 | hsa-miR-328 | cuggcccucucugcccuuccgu | 72,22 | 68,44 | 1,06 | 0,65 |
| SEQ ID NO: 706 | 720 | hsa-miR-146b-5p | ugagaacugaauuccauaggcu | 92,56 | 67,44 | 1,37 | 0,66 |
| SEQ ID NO: 44 | 721 | hsa-miR-886-3p | cgcggguucuugacugaccuu | 12,33 | 1 | 12,33 | 0,66 |
| SEQ ID NO: 643 | 722 | hsa-miR-1909* | ugagugccuggcugccugcug | 20,56 | 16,33 | 1,26 | 0,67 |
| SEQ ID NO: 710 | 723 | hsa-miR-1469 | cucggcggggcgggagcuc | 961,58 | 1297,51 | 0,74 | 0,67 |
| SEQ ID NO: 452 | 724 | hsa-miR-338-3p | uccagcaucagugauuuguug | 13,72 | 1 | 13,72 | 0,68 |
| SEQ ID NO: 43 | 725 | hsa-miR-886-5p | cgggucggaguagcucaagcgg | 126,44 | 87,67 | 1,44 | 0,68 |
| SEQ ID NO: 158 | 726 | hsa-miR-601 | uggucuaggauuguuggaggag | 20,56 | 21,89 | 0,94 | 0,68 |
| SEQ ID NO: 758 | 727 | hsa-miR-1298 | uucauucgcuguccagaugua | 1 | 1 | 1 | 0,68 |
| SEQ ID NO: 639 | 728 | hsa-miR-1910 | ccagucccugugugccugcgccu | 7,44 | 11,56 | 0,64 | 0,69 |
| SEQ ID NO: 841 | 729 | hsa-miR-1226* | gugagggcagcaggccuggauggg | 99,11 | 96,94 | 1,02 | 0,69 |
| SEQ ID NO: 387 | 730 | hsa-miR-421 | aucaacagacaauuagggccgc | 217,67 | 1 | 217,67 | 0,69 |
| SEQ ID NO: 703 | 731 | hsa-miR-1471 | gcccgcguguggagccaggugu | 37,89 | 33,78 | 1,12 | 0,69 |
| SEQ ID NO: 694 | 732 | hsa-miR-150* | cuggugcaggccuggggacag | 101,11 | 101,78 | 0,99 | 0,7 |
| SEQ ID NO: 837 | 733 | hsa-miR-1229 | cucucaccacucgcccacag | 27,89 | 33,78 | 0,83 | 0,7 |
| SEQ ID NO: 674 | 734 | hsa-miR-17* | acucaguaaggcacugugag | 194 | 90,78 | 2,14 | 0,7 |
| SEQ ID NO: 469 | 735 | hsa-miR-320d | aaaagcugggutugagaga | 4318,58 | 4390,58 | 0,98 | 0,7 |
| SEQ ID NO: 869 | 736 | hsa-miR-10b | uacccuguagaaccgaauuugug | 22,22 | 8,33 | 2,67 | 0,71 |
| SEQ ID NO: 61 | 737 | hsa-miR-766 | acucuagcccacaguccccagc | 106,11 | 70,89 | 1,5 | 0,72 |
| SEQ ID NO: 159 | 738 | hsa-miR-600 | acuuacagacaagagccuugcuc | 1 | 1 | 1 | 0,72 |
| SEQ ID NO: 112 | 739 | hsa-miR-641 | aaagacauaggauagagucaccuc | 34 | 21,56 | 1,58 | 0,73 |

FIG. 10B (Cont.)

| | | | | | |
|---|---|---|---|---|---|
| SEQ ID NO: 443 | 740 | hsa-miR-340* | uccgucucaguuacuuuauagc | 4 | 4 | 0,73 |
| SEQ ID NO: 141 | 741 | hsa-miR-616* | acucaaaaacccuucagugacuu | 1 | 0,64 | 0,73 |
| SEQ ID NO: 272 | 742 | hsa-miR-520a-5p | cuccagagggaaguacuuucu | 15,33 | 18,72 | 0,73 |
| SEQ ID NO: 866 | 743 | hsa-miR-1179 | aagcaauucuucauugguugg | 1 | 1 | 0,73 |
| SEQ ID NO: 867 | 744 | hsa-miR-1178 | uugcucacuguucuuucccuag | 1 | 1 | 0,73 |
| SEQ ID NO: 484 | 745 | hsa-miR-30b* | cugggagguggauguuuacuuc | 88,56 | 98,56 | 0,9 | 0,73 |
| SEQ ID NO: 683 | 746 | hsa-miR-155* | cuccuacauauuagcauuaaca | 1 | 1 | 0,73 |
| SEQ ID NO: 727 | 747 | hsa-miR-138-1* | gcuacuucacaacaccagggc | 19,89 | 4,22 | 4,71 | 0,74 |
| SEQ ID NO: 326 | 748 | hsa-miR-501-5p | aauccuuugucccuggguga | 4,78 | 3,11 | 1,54 | 0,74 |
| SEQ ID NO: 641 | 749 | hsa-miR-191 | caacggaaucccaaaagcagcug | 31577,57 | 27467,24 | 1,15 | 0,74 |
| SEQ ID NO: 872 | 750 | hsa-miR-107 | agcagcauuguacagggcuauca | 4106,11 | 4915,83 | 0,84 | 0,74 |
| SEQ ID NO: 114 | 751 | hsa-miR-639 | auogcugcgguugcgagcgcugu | 1 | 1 | 1 | 0,74 |
| SEQ ID NO: 288 | 752 | hsa-miR-518c-3p | caaaagcgcuucccuuuggagc | 1 | 1 | 1 | 0,75 |
| SEQ ID NO: 874 | 753 | hsa-miR-106b | uaaaagugcugacagugcagau | 3080,08 | 2319,9 | 1,33 | 0,75 |
| SEQ ID NO: 764 | 754 | hsa-miR-129-3p | aagcccuuaccccaaaaagcau | 4 | 28,33 | 0,14 | 0,75 |
| SEQ ID NO: 751 | 755 | hsa-miR-1306 | acguugcucugguggug | 6,78 | 4,22 | 1,61 | 0,75 |
| SEQ ID NO: 653 | 756 | hsa-miR-187* | ggcuacaacacagaccccggc | 88,56 | 68,44 | 1,29 | 0,76 |
| SEQ ID NO: 808 | 757 | hsa-miR-125b | ucccugagacccuaacuguga | 65,56 | 38,33 | 1,71 | 0,77 |
| SEQ ID NO: 111 | 758 | hsa-miR-642 | gucccucucaaaugugucuug | 1 | 1 | 1 | 0,77 |
| SEQ ID NO: 486 | 759 | hsa-miR-30a* | cuuucagucggaugauugcagc | 1 | 1 | 1 | 0,77 |
| SEQ ID NO: 724 | 760 | hsa-miR-139-5p | ucuacagugcacgugucucag | 1,56 | 4,22 | 0,37 | 0,77 |
| SEQ ID NO: 750 | 761 | hsa-miR-1307 | acucgccguggcguggucgug | 82,06 | 70,67 | 1,16 | 0,77 |
| SEQ ID NO: 58 | 762 | hsa-miR-769-3p | cuggaauccgggucuaugguu | 25,56 | 15,56 | 1,64 | 0,78 |
| SEQ ID NO: 248 | 763 | hsa-miR-532-5p | caugccuugagugugggaccgu | 121,44 | 92,56 | 1,31 | 0,78 |
| SEQ ID NO: 75 | 764 | hsa-miR-7-1* | caacaaaucacagucugccaua | 15,78 | 28,33 | 0,56 | 0,78 |
| SEQ ID NO: 620 | 765 | hsa-miR-196a | uagguaguuucauguuuggg | 4 | 1 | 4 | 0,78 |
| SEQ ID NO: 760 | 766 | hsa-miR-1296 | uuaaggcccuggcuccauccc | 14,56 | 4,22 | 3,45 | 0,78 |
| SEQ ID NO: 640 | 767 | hsa-miR-191* | gcugcgcuuggauuucgucc | 53 | 47,06 | 1,13 | 0,79 |
| SEQ ID NO: 544 | 768 | hsa-miR-221 | agcuacauugucugcuggguuc | 382 | 539,56 | 0,71 | 0,79 |
| SEQ ID NO: 26 | 769 | hsa-miR-92a-1* | agguuggauggguugcaaugcu | 20,56 | 21,56 | 0,95 | 0,79 |
| SEQ ID NO: 774 | 770 | hsa-miR-1285 | ucugggcaacaaagugagauga | 300,67 | 53 | 5,67 | 0,8 |
| SEQ ID NO: 283 | 771 | hsa-miR-518f* | cucuagagcgagcacuuucuc | 25,17 | 58,89 | 0,43 | 0,8 |
| SEQ ID NO: 835 | 772 | hsa-miR-1233 | ugagcccugcucccgcag | 8,44 | 12,44 | 0,68 | 0,8 |
| SEQ ID NO: 768 | 773 | hsa-miR-1290 | uggauuuuuggaucagga | 39,67 | 28,33 | 1,4 | 0,8 |
| SEQ ID NO: 161 | 774 | hsa-miR-598 | uacgucguugacuguca | 12,22 | 1 | 12,22 | 0,8 |
| SEQ ID NO: 57 | 775 | hsa-miR-769-5p | ugagaccucuggguucugagcu | 15,33 | 3,67 | 4,18 | 0,8 |
| SEQ ID NO: 145 | 776 | hsa-miR-614 | gaacgccuguucucuugccaggug | 9,11 | 4,22 | 2,16 | 0,8 |

FIG. 10B (Cont.)

| | | | | | |
|---|---|---|---|---|---|
| SEQ ID NO: 184 | 777 | hsa-miR-578 | cuucugugcucuaggauugu | 1 | 1 | 0,8 |
| SEQ ID NO: 756 | 778 | hsa-miR-1301 | uugcagcugccugggagugacuuc | 22,67 | 18,11 | 1,25 | 0,8 |
| SEQ ID NO: 302 | 779 | hsa-miR-515-5p | uucuccaaaagaaagcacuucug | 1 | 1 | 1 | 0,81 |
| SEQ ID NO: 199 | 780 | hsa-miR-564 | aggcacggugucagcaggc | 56,78 | 47,06 | 1,21 | 0,81 |
| SEQ ID NO: 119 | 781 | hsa-miR-634 | aacagcacccaacuuuggac | 36,78 | 49,22 | 0,75 | 0,81 |
| SEQ ID NO: 291 | 782 | hsa-miR-518b | caaagcgcuccccuuuagaggu | 20,56 | 4,44 | 4,63 | 0,81 |
| SEQ ID NO: 12 | 783 | hsa-miR-941 | cacccggcugugugcacaugugc | 39,67 | 4,22 | 9,39 | 0,82 |
| SEQ ID NO: 406 | 784 | hsa-miR-376c | aacauagaggaaauuccacgu | 1 | 1 | 1 | 0,83 |
| SEQ ID NO: 821 | 785 | hsa-miR-195* | ccaauauuggcugugcugcucc | 1 | 1 | 1 | 0,83 |
| SEQ ID NO: 292 | 786 | hsa-miR-518a-5p | cugcaaagggaagcccuuuc | 55,33 | 34 | 1,63 | 0,83 |
| SEQ ID NO: 205 | 787 | hsa-miR-557 | guuugcacggugugggccuugucu | 114,67 | 132 | 0,87 | 0,83 |
| SEQ ID NO: 838 | 788 | hsa-miR-1228* | guggggcggggcaggugugug | 5944,79 | 5802,55 | 1,02 | 0,83 |
| SEQ ID NO: 548 | 789 | hsa-miR-22* | aguucuucaguggcaagcuuua | 69,67 | 36,11 | 1,93 | 0,83 |
| SEQ ID NO: 834 | 790 | hsa-miR-1234 | ucggccugaccaccccaccc | 53,67 | 82,06 | 0,65 | 0,83 |
| SEQ ID NO: 696 | 791 | hsa-miR-149* | agggagacgggggcugguc | 18004,17 | 13307,74 | 1,35 | 0,84 |
| SEQ ID NO: 482 | 792 | hsa-miR-30c-1* | cugggagagcaguuguuuaacucc | 101,11 | 101,11 | 1 | 0,84 |
| SEQ ID NO: 592 | 793 | hsa-miR-200c* | cguuuaccgcagugguugg | 1 | 1 | 1 | 0,84 |
| SEQ ID NO: 864 | 794 | hsa-miR-1181 | ccguccgcgccaccggccg | 21,11 | 28 | 0,75 | 0,84 |
| SEQ ID NO: 467 | 795 | hsa-miR-323-5p | aggugucccuguggcgucguugc | 58,33 | 67,44 | 0,86 | 0,84 |
| SEQ ID NO: 836 | 796 | hsa-miR-1231 | gugucuggcggaagcagcug | 43,11 | 30,44 | 1,42 | 0,84 |
| SEQ ID NO: 589 | 797 | hsa-miR-203 | gugaaauguuuuaggaccacuag | 1 | 1 | 1 | 0,84 |
| SEQ ID NO: 492 | 798 | hsa-miR-302c* | uuuaacaugggggauaccugcug | 88,67 | 18,72 | 3,67 | 0,84 |
| SEQ ID NO: 4 | 799 | hsa-miR-99a | aacccguagauccgaucuugug | 92,56 | 22,22 | 4,17 | 0,84 |
| SEQ ID NO: 709 | 800 | hsa-miR-146a | ugagaacugaauuccauggguu | 136,17 | 129,44 | 1,05 | 0,84 |
| SEQ ID NO: 96 | 801 | hsa-miR-656 | aauauuauacaguccaauccucu | 1 | 1 | 1 | 0,84 |
| SEQ ID NO: 251 | 802 | hsa-miR-526b* | gaaagugcuuccuuuuagaggc | 1 | 1 | 1 | 0,84 |
| SEQ ID NO: 698 | 803 | hsa-miR-148b* | aagucugguuuuecacucaggc | 1 | 1 | 1 | 0,85 |
| SEQ ID NO: 673 | 804 | hsa-miR-181a | aacauucaacgcuguucgugagu | 586,78 | 133,11 | 4,41 | 0,85 |
| SEQ ID NO: 135 | 805 | hsa-miR-622 | acagucugaggguuggagc | 6,78 | 3,11 | 2,18 | 0,85 |
| SEQ ID NO: 809 | 806 | hsa-miR-125a-5p | ucccugagacccuuuaaccuguga | 82,89 | 21,56 | 3,85 | 0,86 |
| SEQ ID NO: 691 | 807 | hsa-miR-152 | ucagugcaugacagaacuugg | 16,78 | 12,11 | 1,39 | 0,86 |
| SEQ ID NO: 616 | 808 | hsa-miR-197 | uucaccaccuuccaccagc | 143,78 | 111,78 | 1,28 | 0,87 |
| SEQ ID NO: 517 | 809 | hsa-miR-27b | uucacaguggcuaaguucugc | 73,33 | 33,78 | 2,17 | 0,87 |
| SEQ ID NO: 833 | 810 | hsa-miR-1236 | ccucucccuugucuccag | 39,67 | 44 | 0,9 | 0,87 |
| SEQ ID NO: 336 | 811 | hsa-miR-495 | aaacaaacauggugcacuucuu | 2,67 | 3,67 | 0,73 | 0,87 |
| SEQ ID NO: 717 | 812 | hsa-miR-143 | ugagaugaagcacuguagcuc | 20,56 | 12 | 1,71 | 0,87 |
| SEQ ID NO: 430 | 813 | hsa-miR-362-3p | aacaccuauucaaggauuca | 16,44 | 14,89 | 1,1 | 0,88 |

FIG. 10B (Cont.)

| | | | | | | |
|---|---|---|---|---|---|---|
| SEQ ID NO: 80 | 814 | hsa-miR-675 | uggugggagagggcccacagug | 185,22 | 172,44 | 0,88 |
| SEQ ID NO: 787 | 815 | hsa-miR-1274b | ucccuguucgggcgcca | 176,56 | 63,61 | 0,88 |
| SEQ ID NO: 725 | 816 | hsa-miR-139-3p | ggagacgcggcccuguuggagu | 43,11 | 33,78 | 0,89 |
| SEQ ID NO: 745 | 817 | hsa-miR-130b* | acucuuuccauugcacuac | 2,67 | 1 | 0,89 |
| SEQ ID NO: 839 | 818 | hsa-miR-1228 | ucacacugccucgcccccc | 39,67 | 140,78 | 0,89 |
| SEQ ID NO: 865 | 819 | hsa-miR-1180 | uuuccggcucgcguggugugu | 61,11 | 21,11 | 0,89 |
| SEQ ID NO: 188 | 820 | hsa-miR-575 | gagccaguuggacgagc | 58,78 | 70,67 | 0,89 |
| SEQ ID NO: 736 | 821 | hsa-miR-134 | ugugacugguugaccagagggg | 55,67 | 34 | 0,89 |
| SEQ ID NO: 52 | 822 | hsa-miR-875-3p | ccuggaaacacugggguugu | 6,78 | 1 | 0,89 |
| SEQ ID NO: 23 | 823 | hsa-miR-92b* | agggacgggacgcggugcagug | 1344,42 | 2425,74 | 0,9 |
| SEQ ID NO: 92 | 824 | hsa-miR-660 | uaccaaugcauaucggagaug | 130,44 | 57 | 0,9 |
| SEQ ID NO: 252 | 825 | hsa-miR-526b | cucuuagggaagcacuuuucgu | 67,78 | 33,78 | 0,9 |
| SEQ ID NO: 386 | 826 | hsa-miR-422a | acugaccuggguucagaaggc | 166,44 | 1 | 0,9 |
| SEQ ID NO: 821 | 827 | hsa-miR-1250 | acgguccaauggaugugguggc | 37,67 | 40,78 | 0,9 |
| SEQ ID NO: 15 | 828 | hsa-miR-938 | ugcccuuaaaagugaaccccagu | 2,22 | 1 | 0,91 |
| SEQ ID NO: 151 | 829 | hsa-miR-608 | aggguguguuggacagcucgu | 106,89 | 96,94 | 0,91 |
| SEQ ID NO: 781 | 830 | hsa-miR-1279 | ucauauugcuucuuucu | 1 | 1 | 0,91 |
| SEQ ID NO: 822 | 831 | hsa-miR-1249 | acgcccuuccccccccuucuuca | 24,56 | 30,22 | 0,91 |
| SEQ ID NO: 91 | 832 | hsa-miR-661 | ugccuggucucuggccugcgu | 4 | 1 | 0,92 |
| SEQ ID NO: 849 | 833 | hsa-miR-1208 | ucacguucagacaggcgga | 27 | 18,72 | 0,92 |
| SEQ ID NO: 748 | 834 | hsa-miR-130a | cagugcaauguuaaaagggcau | 746,29 | 874,97 | 0,92 |
| SEQ ID NO: 365 | 835 | hsa-miR-450b-5p | uuuugcaauauguuccugaaua | 1 | 1 | 0,92 |
| SEQ ID NO: 376 | 836 | hsa-miR-432 | ucuugggaguaggucauugggg | 41,89 | 39,22 | 0,93 |
| SEQ ID NO: 393 | 837 | hsa-miR-409-3p | gaaugugcucggugaacccuuc | 97,33 | 68,44 | 0,93 |
| SEQ ID NO: 250 | 838 | hsa-miR-527 | cugcaaagggaagcccuc | 74,78 | 68,44 | 0,94 |
| SEQ ID NO: 47 | 839 | hsa-miR-877* | uccucucuccuccucugccag | 20,83 | 21,11 | 0,95 |
| SEQ ID NO: 831 | 840 | hsa-miR-1238 | cuuccucagauggaagcacugucc | 52 | 58,89 | 0,95 |
| SEQ ID NO: 297 | 841 | hsa-miR-517* | ccucuagaugagcagucucc | 16,78 | 12,11 | 0,96 |
| SEQ ID NO: 625 | 842 | hsa-miR-193b* | cggguuuugagggcgagauga | 81,11 | 108,56 | 0,97 |
| SEQ ID NO: 256 | 843 | hsa-miR-524-5p | cuacaagggaagcacuuuucuc | 31,11 | 29,44 | 0,97 |
| SEQ ID NO: 812 | 844 | hsa-miR-1258 | aguuaggauuagucuggaa | 15,78 | 12,44 | 0,97 |
| SEQ ID NO: 686 | 845 | hsa-miR-154 | uagguuauccguguugccuug | 1 | 1 | 0,97 |
| SEQ ID NO: 116 | 846 | hsa-miR-637 | acuggggcuuuucggcucucgcgu | 90,11 | 70,89 | 0,97 |
| SEQ ID NO: 173 | 847 | hsa-miR-588 | uuggcccaauggguuagaac | 1,56 | 1 | 0,98 |
| SEQ ID NO: 684 | 848 | hsa-miR-155 | uuaaugcuaaucgugauaggggu | 128,44 | 14,89 | 0,98 |
| SEQ ID NO: 86 | 849 | hsa-miR-664* | acuggcuaggaaaaugauuggau | 61,56 | 39,44 | 0,99 |
| SEQ ID NO: 704 | 850 | hsa-miR-1470 | gccucgcgcggaaucccgugcacccg | 20,56 | 12,11 | 0,99 |

FIG. 10B (Cont.)

| | | | | | | |
|---|---|---|---|---|---|---|
| SEQ ID NO: 877 | 851 | hsa-miR-105* | acggauguuugagcaugugcua | 2,67 | 1 | 2,67 | 0,99 |
| SEQ ID NO: 465 | 852 | hsa-miR-324-5p | cgcauccccuagggcauugugu | 232,67 | 56,22 | 4,14 | 0,99 |
| SEQ ID NO: 769 | 853 | hsa-miR-129* | aagcccuuacccaaaaaguau | 8,44 | 1 | 8,44 | 0,99 |
| SEQ ID NO: 131 | 854 | hsa-miR-625 | aggggaaaguucuauagucc | 182,44 | 109,67 | 1,66 | 0,99 |
| SEQ ID NO: 281 | 855 | hsa-miR-519a* | cucuagaggaagcguugacuuucug | 1 | 4,44 | 0,23 | 0,99 |
| SEQ ID NO: 671 | 856 | hsa-miR-181a-2* | accacugaccguugacuauacc | 115,33 | 67,44 | 1,71 | 0,99 |
| SEQ ID NO: 603 | 857 | hsa-miR-199b-5p | cccaguguuuagacuauacuguuc | 4 | 1 | 4 | 0,99 |
| SEQ ID NO: 519 | 858 | hsa-miR-27a | uucacaguggcuaaguuccgc | 150,56 | 55,22 | 2,73 | 0,99 |
| SEQ ID NO: 293 | 859 | hsa-miR-518a-3p | gaaagcgcuuccccuuugcugga | 1 | 1 | 1 | 0,99 |
| SEQ ID NO: 798 | 860 | hsa-miR-1265 | caggaugugucaaguugugu | 6,78 | 1,56 | 4,36 | 0,99 |
| SEQ ID NO: 27 | 861 | hsa-miR-92a | uauugcacuuguccoggccugu | 22685,5 | 18004,17 | 1,26 | 0,99 |
| SEQ ID NO: 504 | 862 | hsa-miR-29b-1* | gcugguuucauauggugguuuaga | 1 | 1 | 1 | 0,99 |
| SEQ ID NO: 695 | 863 | hsa-miR-150 | ucucccaaccccuuguaccagug | 600,34 | 839,63 | 0,72 | 1 |
| SEQ ID NO: 456 | 864 | hsa-miR-335 | ucaagagcaauaacgaaaaaugu | 115,33 | 67,44 | 1,71 | 1 |
| SEQ ID NO: 115 | 865 | hsa-miR-638 | agggaucgcggggcgggugggccu | 4915,83 | 5944,79 | 0,83 | 1 |

FIG. 11A

| SEQ ID NO: | microRNA | sequence | median g1 | median g2 | g1/median g2 | Log2 median | t-test raw p | t-test adj p | AUC | limma raw p | limma adj p |
|---|---|---|---|---|---|---|---|---|---|---|---|
| SEQ ID NO: 329 | hsa-miR-500 | uaauccuugcuaccugguaga | 213 | 445 | 0,478 | -0,739 | 2,02E-03 | 5,62E-02 | 0,294 | 1,13E-03 | 4,89E-02 |
| SEQ ID NO: 469 | hsa-miR-320d | aaaagcugggguugagaga | 908 | 466 | 1,947 | 0,666 | 4,44E-05 | 1,28E-02 | 0,694 | 8,05E-04 | 4,13E-02 |
| SEQ ID NO: 216 | hsa-miR-550 | agugccugaggaguaagagccc | 114 | 169 | 0,673 | -0,396 | 1,55E-04 | 1,67E-02 | 0,260 | 2,93E-03 | 8,24E-02 |
| SEQ ID NO: 470 | hsa-miR-320c | aaaagcugggguugaggggu | 783 | 466 | 1,679 | 0,518 | 3,07E-04 | 2,25E-02 | 0,677 | 1,40E-03 | 5,26E-02 |
| SEQ ID NO: 788 | hsa-miR-1274a | guccguucaggcgca | 142 | 275 | 0,518 | -0,659 | 1,08E-03 | 4,24E-02 | 0,295 | 3,78E-03 | 8,58E-02 |
| SEQ ID NO: 635 | hsa-miR-1913 | ucugccccucgcucugcca | 359 | 258 | 1,391 | 0,330 | 1,79E-03 | 5,62E-02 | 0,649 | 2,62E-02 | 2,15E-01 |
| SEQ ID NO: 199 | hsa-miR-564 | aggcacgugucagcagg | 157 | 126 | 1,246 | 0,220 | 3,92E-03 | 6,27E-02 | 0,638 | 7,28E-02 | 3,48E-01 |
| SEQ ID NO: 787 | hsa-miR-1274b | ucccuguucgggcgcca | 770 | 1244 | 0,619 | -0,480 | 6,78E-03 | 8,73E-02 | 0,338 | 2,05E-02 | 1,86E-01 |
| SEQ ID NO: 663 | hsa-miR-1826 | auugaucaccaacuugaacgcaau | 195 | 139 | 1,406 | 0,341 | 7,29E-03 | 8,80E-02 | 0,670 | 1,97E-01 | 5,35E-01 |
| SEQ ID NO: 896 | hsa-let-7d* | cuauacgaccugcugccuuucu | 59 | 166 | 0,353 | -1,042 | 7,04E-04 | 3,51E-02 | 0,264 | 6,30E-04 | 4,13E-02 |
| SEQ ID NO: 131 | hsa-miR-625 | agggggaaaguucuauagccc | 59 | 165 | 0,356 | -1,032 | 8,59E-04 | 3,90E-02 | 0,289 | 4,32E-03 | 9,10E-02 |
| SEQ ID NO: 402 | hsa-miR-378* | cuccugacuccagguccugugu | 51 | 123 | 0,417 | -0,876 | 7,84E-03 | 9,14E-02 | 0,365 | 2,16E-01 | 5,64E-01 |
| SEQ ID NO: 660 | hsa-miR-183* | gugaauuaccgaagggccauaa | 85 | 146 | 0,577 | -0,549 | 1,25E-04 | 1,54E-02 | 0,233 | 7,70E-04 | 4,13E-02 |
| SEQ ID NO: 574 | hsa-miR-21* | caacaccaguggcauggggcugu | 102 | 79 | 1,300 | 0,263 | 4,45E-04 | 2,40E-02 | 0,690 | 2,83E-02 | 2,24E-01 |
| SEQ ID NO: 48 | hsa-miR-877 | guagaggagauggcgaggg | 60 | 102 | 0,587 | -0,532 | 2,50E-03 | 5,64E-02 | 0,299 | 5,71E-03 | 9,77E-02 |
| SEQ ID NO: 776 | hsa-miR-1283 | ucuacaaaggaaaggcuuucu | 109 | 71 | 1,548 | 0,437 | 2,68E-03 | 5,64E-02 | 0,685 | 3,02E-04 | 2,74E-02 |
| SEQ ID NO: 773 | hsa-miR-1286 | ugcaggaccaagaugagccu | 120 | 92 | 1,296 | 0,259 | 2,81E-03 | 5,64E-02 | 0,661 | 3,13E-01 | 6,60E-01 |
| SEQ ID NO: 283 | hsa-miR-518f* | cucuagagggaagcacuuucuc | 123 | 83 | 1,476 | 0,390 | 3,78E-03 | 6,19E-02 | 0,671 | 8,61E-04 | 4,13E-02 |
| SEQ ID NO: 93 | hsa-miR-659 | cuugguucagggaggguccca | 65 | 109 | 0,597 | -0,515 | 5,40E-03 | 8,02E-02 | 0,320 | 3,35E-02 | 2,43E-01 |
| SEQ ID NO: 29 | hsa-miR-922 | gcagcagagaauaggaacuacguc | 126 | 83 | 1,521 | 0,419 | 5,58E-03 | 8,02E-02 | 0,629 | 1,42E-02 | 1,61E-01 |
| SEQ ID NO: 316 | hsa-miR-508-5p | uacuccagagggcucaaucaug | 114 | 94 | 1,207 | 0,188 | 6,26E-03 | 8,58E-02 | 0,631 | 6,29E-03 | 1,01E-01 |
| SEQ ID NO: 665 | hsa-miR-182* | uggucuagacugccaacua | 47 | 20 | 2,311 | 0,838 | 8,53E-05 | 1,28E-02 | 0,723 | 1,64E-03 | 5,42E-02 |
| SEQ ID NO: 501 | hsa-miR-29c* | ugacgauuucucgguguc | 1 | 24 | 0,052 | -2,955 | 1,61E-03 | 5,57E-02 | 0,361 | 2,68E-02 | 2,18E-01 |
| SEQ ID NO: 11 | hsa-miR-942 | ucuucucguuuuggccauguug | 16 | 73 | 0,219 | -1,520 | 1,85E-03 | 5,62E-02 | 0,305 | 5,64E-03 | 9,77E-02 |
| SEQ ID NO: 60 | hsa-miR-767-3p | ucugcucuauacccauggguuucu | 44 | 18 | 2,502 | 0,917 | 2,60E-03 | 5,64E-02 | 0,683 | 1,97E-02 | 1,83E-01 |
| SEQ ID NO: 814 | hsa-miR-1256 | aggcaugacuucucacuagcu | 67 | 26 | 2,582 | 0,949 | 2,72E-03 | 5,64E-02 | 0,678 | 3,29E-04 | 2,74E-02 |
| SEQ ID NO: 421 | hsa-miR-369-5p | agaucgaccuguuauauucgc | 31 | 14 | 2,160 | 0,770 | 3,55E-03 | 6,12E-02 | 0,628 | 1,79E-01 | 5,15E-01 |
| SEQ ID NO: 664 | hsa-miR-1825 | uccaguccuccucucc | 46 | 93 | 0,498 | -0,698 | 3,67E-03 | 6,19E-02 | 0,300 | 1,39E-02 | 1,61E-01 |
| SEQ ID NO: 274 | hsa-miR-519e* | uucuccaaaaggagcacuuuc | 60 | 20 | 2,981 | 1,092 | 4,73E-03 | 7,29E-02 | 0,711 | 5,65E-05 | 9,76E-03 |
| SEQ ID NO: 852 | hsa-miR-1206 | uguuacauguagaugguuaagc | 59 | 22 | 2,616 | 0,962 | 5,72E-03 | 8,10E-02 | 0,674 | 3,09E-03 | 8,24E-02 |
| SEQ ID NO: 356 | hsa-miR-483-3p | ucacuccucuccuccgucucu | 21 | 51 | 0,415 | -0,879 | 7,35E-03 | 8,80E-02 | 0,344 | 2,48E-02 | 2,12E-01 |
| SEQ ID NO: 560 | hsa-miR-214* | ugccugucuacacuugcugugc | 58 | 34 | 1,736 | 0,551 | 3,90E-05 | 1,28E-02 | 0,744 | 4,99E-05 | 9,76E-03 |
| SEQ ID NO: 754 | hsa-miR-1303 | uuuagacgggguucuugcucu | 29 | 56 | 0,522 | -0,650 | 3,51E-04 | 2,25E-02 | 0,258 | 8,27E-04 | 4,13E-02 |
| SEQ ID NO: 36 | hsa-miR-891b | ugcaacuuaccugagucauuga | 95 | 68 | 1,409 | 0,343 | 7,32E-04 | 3,51E-02 | 0,693 | 3,25E-03 | 8,24E-02 |
| SEQ ID NO: 477 | hsa-miR-30e* | cuuucagucggauguuuacagc | 39 | 63 | 0,621 | -0,476 | 9,23E-04 | 3,98E-02 | 0,290 | 1,70E-03 | 5,42E-02 |

FIG. 11A (Cont.)

| | | | | | | | | | | |
|---|---|---|---|---|---|---|---|---|---|---|
| SEQ ID NO: 683 | hsa-miR-155* | cuccuacauauuagcauuaaca | 59 | 39 | 1,490 | 0,399 | 1,49E-03 | 5,36E-02 | 0,677 | 1,79E-02 | 1,80E-01 |
| SEQ ID NO: 84 | hsa-miR-668 | ugucacucggcucggcccacuac | 38 | 59 | 0,647 | -0,436 | 1,93E-03 | 5,62E-02 | 0,280 | 1,35E-03 | 5,26E-02 |
| SEQ ID NO: 842 | hsa-miR-1226 | ucaccagcccugugugucccuag | 49 | 85 | 0,584 | -0,538 | 1,70E-03 | 5,62E-02 | 0,261 | 1,90E-02 | 1,80E-01 |
| SEQ ID NO: 437 | hsa-miR-34a* | caaucagcaaguauacugcccu | 90 | 68 | 1,327 | 0,283 | 2,35E-03 | 5,64E-02 | 0,687 | 3,75E-03 | 8,58E-02 |
| SEQ ID NO: 105 | hsa-miR-647 | guggcugcacucacuuccuuc | 68 | 41 | 1,673 | 0,515 | 2,78E-03 | 5,64E-02 | 0,704 | 4,91E-06 | 2,12E-03 |
| SEQ ID NO: 149 | hsa-miR-610 | ugagcuaaauguguguguggaa | 50 | 33 | 1,521 | 0,419 | 3,03E-03 | 5,73E-02 | 0,640 | 8,59E-02 | 3,80E-01 |
| SEQ ID NO: 720 | hsa-miR-141* | caucuuccaguacaguguugga | 88 | 68 | 1,288 | 0,253 | 4,10E-03 | 6,43E-02 | 0,690 | 3,49E-04 | 2,74E-02 |
| SEQ ID NO: 511 | hsa-miR-297 | auguaugugcaugugcaug | 50 | 74 | 0,682 | -0,382 | 5,52E-03 | 8,02E-02 | 0,295 | 8,24E-03 | 1,23E-01 |
| SEQ ID NO: 18 | hsa-miR-935 | ccaguuaccguuccgcuaccgc | 29 | 15 | 1,872 | 0,627 | 5,95E-03 | 8,28E-02 | 0,627 | 9,63E-02 | 3,90E-01 |
| SEQ ID NO: 95 | hsa-miR-657 | ggcagguucucaccccucuagg | 59 | 37 | 1,570 | 0,451 | 6,77E-03 | 8,73E-02 | 0,660 | 7,04E-02 | 3,43E-01 |
| SEQ ID NO: 238 | hsa-miR-548a-3p | caaaacuggcaauuacuuuugc | 70 | 60 | 1,151 | 0,140 | 6,58E-03 | 8,73E-02 | 0,615 | 1,63E-01 | 4,96E-01 |
| SEQ ID NO: 55 | hsa-miR-802 | caguaacaaagauucauccuugu | 60 | 39 | 1,544 | 0,434 | 7,24E-03 | 8,80E-02 | 0,647 | 7,96E-02 | 3,65E-01 |
| SEQ ID NO: 580 | hsa-miR-208b | auaagacgaacaaaaaggauugu | 60 | 33 | 1,830 | 0,604 | 7,26E-03 | 8,80E-02 | 0,687 | 5,73E-03 | 9,77E-02 |
| SEQ ID NO: 707 | hsa-miR-146b-3p | ugccuguggacucagagguucgg | 55 | 34 | 1,611 | 0,477 | 8,01E-03 | 9,22E-02 | 0,656 | 1,12E-02 | 1,45E-01 |
| SEQ ID NO: 605 | hsa-miR-199a-5p | cccaguuuagcagacaccuguuc | 236 | 573 | 0,411 | -0,889 | 5,30E-06 | 4,57E-03 | 0,188 | 2,45E-07 | 2,12E-04 |
| SEQ ID NO: 809 | hsa-miR-125a-5p | uccccugagacccuuuaaccuguga | 151 | 418 | 0,362 | -1,017 | 3,65E-04 | 2,25E-02 | 0,277 | 2,87E-04 | 2,74E-02 |
| SEQ ID NO: 746 | hsa-miR-130b | cagugcaaugaugaaagggcau | 1463 | 946 | 1,547 | 0,436 | 1,78E-04 | 1,70E-02 | 0,708 | 1,33E-02 | 1,61E-01 |
| SEQ ID NO: 385 | hsa-miR-423-3p | agcucggucugaggccccucagu | 1105 | 1587 | 0,696 | -0,362 | 3,23E-04 | 2,25E-02 | 0,253 | 2,72E-04 | 2,74E-02 |
| SEQ ID NO: 465 | hsa-miR-324-5p | cgcauccccuaggggcauuggugu | 332 | 496 | 0,669 | -0,402 | 1,01E-03 | 4,15E-02 | 0,286 | 1,48E-03 | 5,31E-02 |
| SEQ ID NO: 431 | hsa-miR-361-5p | uuaucagaaucuccagggguac | 418 | 629 | 0,664 | -0,410 | 2,52E-03 | 5,64E-02 | 0,320 | 2,59E-03 | 7,70E-02 |
| SEQ ID NO: 325 | hsa-miR-502-3p | aaugcacuggauagcuuauca | 662 | 926 | 0,714 | -0,336 | 2,36E-03 | 5,64E-02 | 0,317 | 4,96E-03 | 9,73E-02 |
| SEQ ID NO: 600 | hsa-miR-19b | ugugcaaauccaugcaaaacuga | 10422 | 12496 | 0,834 | -0,181 | 3,06E-03 | 5,73E-02 | 0,338 | 1,86E-02 | 1,80E-01 |
| SEQ ID NO: 458 | hsa-miR-331-3p | gcccugguaacuacucacuagcu | 970 | 1621 | 0,598 | -0,513 | 3,43E-03 | 6,05E-02 | 0,299 | 3,09E-03 | 8,24E-02 |
| SEQ ID NO: 485 | hsa-miR-30b | uguaacaucuuacuacacacuc | 7318 | 6233 | 1,174 | 0,160 | 3,37E-03 | 6,05E-02 | 0,639 | 2,89E-02 | 2,25E-01 |
| SEQ ID NO: 718 | hsa-miR-142-5p | cauaaagauagaaagcacuau | 752 | 520 | 1,446 | 0,369 | 3,80E-03 | 6,19E-02 | 0,640 | 1,32E-02 | 4,40E-01 |
| SEQ ID NO: 462 | hsa-miR-328 | cuggcccucucugcccuucgu | 57 | 123 | 0,466 | -0,764 | 4,39E-04 | 2,40E-02 | 0,268 | 1,57E-03 | 5,41E-02 |
| SEQ ID NO: 627 | hsa-miR-193a-5p | uggguucuuugcgggcgagauga | 55 | 125 | 0,441 | -0,819 | 1,35E-03 | 5,08E-02 | 0,250 | 6,11E-04 | 4,13E-02 |
| SEQ ID NO: 353 | hsa-miR-485-3p | gucauaacacggucucucucuc | 52 | 103 | 0,509 | -0,675 | 1,96E-03 | 5,62E-02 | 0,273 | 1,40E-03 | 5,26E-02 |
| SEQ ID NO: 719 | hsa-miR-142-3p | uguaguguuuucuacuuuuaugga | 18 | 93 | 0,195 | -1,632 | 2,13E-03 | 5,64E-02 | 0,300 | 2,59E-03 | 7,70E-02 |
| SEQ ID NO: 306 | hsa-miR-513b | uucaaggaggugucauuuau | 46 | 18 | 2,480 | 0,908 | 2,99E-03 | 5,73E-02 | 0,654 | 3,76E-02 | 2,54E-01 |
| SEQ ID NO: 547 | hsa-miR-220a | ccaaccguaucugacacuuu | 61 | 29 | 2,064 | 0,725 | 3,17E-03 | 5,83E-02 | 0,685 | 4,87E-03 | 9,73E-02 |
| SEQ ID NO: 656 | hsa-miR-186 | caaagaauucuccuuuugggcu | 34 | 99 | 0,340 | -1,078 | 6,67E-03 | 8,73E-02 | 0,298 | 3,50E-03 | 8,58E-02 |
| SEQ ID NO: 597 | hsa-miR-200a | uaacacugucugguaacgaugu | 90 | 74 | 1,218 | 0,197 | 7,67E-03 | 9,07E-02 | 0,636 | 8,84E-02 | 3,84E-01 |
| SEQ ID NO: 713 | hsa-miR-145 | guccaguuuuccaggaauccccu | 131 | 268 | 0,488 | -0,717 | 2,34E-03 | 5,64E-02 | 0,310 | 7,15E-03 | 1,10E-01 |
| SEQ ID NO: 881 | hsa-miR-103 | agcagcauuguacagggcuaugga | 6845 | 3626 | 1,887 | 0,635 | 8,87E-05 | 1,28E-02 | 0,711 | 1,65E-02 | 1,76E-01 |
| SEQ ID NO: 701 | hsa-miR-148a | ucagugcacuacagaacuuugu | 950 | 682 | 1,393 | 0,331 | 6,12E-05 | 1,28E-02 | 0,685 | 6,43E-02 | 3,32E-01 |
| SEQ ID NO: 872 | hsa-miR-107 | agcagcauuguacagggcuauca | 1305 | 774 | 1,686 | 0,523 | 2,19E-04 | 1,89E-02 | 0,685 | 1,93E-02 | 1,81E-01 |

FIG. 11A (Cont.)

| SEQ ID NO: 714 | hsa-miR-144* | ggauaucaucauauacuguaag | 636 | 386 | 1,648 | 0,499 | 2,17E-03 | 5,64E-02 | 0,626 | 4,31E-01 | 7,56E-01 |
| --- | --- | --- | --- | --- | --- | --- | --- | --- | --- | --- | --- |
| SEQ ID NO: 577 | hsa-miR-20b | caaagugcucauagugcagguag | 2820 | 2010 | 1,403 | 0,339 | 7,08E-03 | 8,80E-02 | 0,636 | 6,40E-01 | 8,75E-01 |
| SEQ ID NO: 343 | hsa-miR-490-5p | ccauggaucuccaggugggu | 130 | 94 | 1,381 | 0,323 | 5,55E-03 | 8,02E-02 | 0,657 | 8,83E-03 | 1,25E-01 |

FIG. 11B

| Signature | SEQ ID Nos. | miRNA identifiers | Acc | Spec | Sens |
|---|---|---|---|---|---|
| L-1 | SEQ ID NO: 469, SEQ ID NO: 216, SEQ ID NO: 470 | hsa-miR-320d, hsa-miR-550, hsa-miR-320c | 60% | 60% | 60% |
| L-2 | SEQ ID NO: 470, SEQ ID NO: 788, SEQ ID NO: 896 | hsa-miR-320c, hsa-miR-1274a, hsa-let-7d* | 70% | 82% | 59% |
| L-3 | SEQ ID NO: 896, SEQ ID NO: 131, SEQ ID NO: 660 | hsa-let-7d*, hsa-miR-625, hsa-miR-183* | 74% | 86% | 63% |
| L-4 | SEQ ID NO: 660, SEQ ID NO: 574, SEQ ID NO: 665 | hsa-miR-183*, hsa-miR-21*, hsa-miR-182* | 73% | 78% | 68% |
| L-5 | SEQ ID NO: 665, SEQ ID NO: 560, SEQ ID NO: 754 | hsa-miR-182*, hsa-miR-214*, hsa-miR-1303 | 72% | 76% | 68% |
| L-6 | SEQ ID NO: 754, SEQ ID NO: 36, SEQ ID NO: 477 | hsa-miR-1303, hsa-miR-891b, hsa-miR-30e* | 67% | 75% | 58% |
| L-7 | SEQ ID NO: 477, SEQ ID NO: 605, SEQ ID NO: 809 | hsa-miR-30e*, hsa-miR-199a-5p, hsa-miR-125a-5p | 80% | 92% | 68% |
| L-8 | SEQ ID NO: 809, SEQ ID NO: 746, SEQ ID NO: 385 | hsa-miR-125a-5p, hsa-miR-130b, hsa-miR-423-3p | 76% | 84% | 68% |
| L-9 | SEQ ID NO: 385, SEQ ID NO: 465, SEQ ID NO: 462 | hsa-miR-423-3p, hsa-miR-324-5p, hsa-miR-328 | 75% | 83% | 67% |
| L-10 | SEQ ID NO: 462, SEQ ID NO: 881, SEQ ID NO: 701 | hsa-miR-328, hsa-miR-103, hsa-miR-148a | 77% | 84% | 71% |
| L-11 | SEQ ID NO: 701, SEQ ID NO: 872 | hsa-miR-148a, hsa-miR-107 | 76% | 82% | 69% |
| L-12 | SEQ ID NO: 469, SEQ ID NO: 216, SEQ ID NO: 470, SEQ ID NO: 788, SEQ ID NO: 896 | hsa-miR-320d, hsa-miR-550, hsa-miR-320c, hsa-miR-1274a, hsa-let-7d* | 71% | 88% | 54% |
| L-13 | SEQ ID NO: 470, SEQ ID NO: 788, SEQ ID NO: 896, SEQ ID NO: 131, SEQ ID NO: 660 | hsa-miR-320c, hsa-miR-1274a, hsa-let-7d*, hsa-miR-625, hsa-miR-183* | 76% | 86% | 65% |
| L-14 | SEQ ID NO: 896, SEQ ID NO: 131, SEQ ID NO: 660, SEQ ID NO: 574, SEQ ID NO: 665 | hsa-let-7d*, hsa-miR-625, hsa-miR-183*, hsa-miR-21*, hsa-miR-182* | 77% | 75% | 78% |
| L-15 | SEQ ID NO: 131, SEQ ID NO: 660, SEQ ID NO: 574, SEQ ID NO: 665, SEQ ID NO: 560 | hsa-miR-625, hsa-miR-183*, hsa-miR-21*, hsa-miR-182*, hsa-miR-214* | 72% | 72% | 72% |
| L-16 | SEQ ID NO: 574, SEQ ID NO: 665, SEQ ID NO: 560, SEQ ID NO: 754, SEQ ID NO: 36 | hsa-miR-21*, hsa-miR-182*, hsa-miR-214*, hsa-miR-1303, hsa-miR-891b | 76% | 78% | 75% |
| L-17 | SEQ ID NO: 560, SEQ ID NO: 754, SEQ ID NO: 36, SEQ ID NO: 477, SEQ ID NO: 605 | hsa-miR-214*, hsa-miR-1303, hsa-miR-891b, hsa-miR-30e*, hsa-miR-199a-5p | 78% | 85% | 72% |

FIG. 11B (Cont.)

| | SEQ IDs | miRNAs | | | |
|---|---|---|---|---|---|
| L-18 | SEQ ID NO: 754, SEQ ID NO: 36, SEQ ID NO: 477, SEQ ID NO: 605, SEQ ID NO: 809, SEQ ID NO: 746 | hsa-miR-1303, hsa-miR-891b, hsa-miR-30e*, hsa-miR-199a-5p, hsa-miR-125a-5p, hsa-miR-130b | 81% | 88% | 74% |
| L-19 | SEQ ID NO: 605, SEQ ID NO: 809, SEQ ID NO: 746, SEQ ID NO: 385, SEQ ID NO: 465, SEQ ID NO: 462 | hsa-miR-199a-5p, hsa-miR-125a-5p, hsa-miR-130b, hsa-miR-423-3p, hsa-miR-324-5p, hsa-miR-328 | 78% | 88% | 69% |
| L-20 | SEQ ID NO: 385, SEQ ID NO: 465, SEQ ID NO: 462, SEQ ID NO: 881, SEQ ID NO: 701, SEQ ID NO: 872 | hsa-miR-423-3p, hsa-miR-324-5p, hsa-miR-328, hsa-miR-103, hsa-miR-148a, hsa-miR-107 | 80% | 84% | 75% |
| L-21 | SEQ ID NO: 469, SEQ ID NO: 216, SEQ ID NO: 470, SEQ ID NO: 788, SEQ ID NO: 896, SEQ ID NO: 131, SEQ ID NO: 660, SEQ ID NO: 574, SEQ ID NO: 665, SEQ ID NO: 560 | hsa-miR-320d, hsa-miR-550, hsa-miR-320c, hsa-miR-1274a, hsa-let-7d*, hsa-miR-625, hsa-miR-183*, hsa-miR-21*, hsa-miR-182*, hsa-miR-214* | 75% | 78% | 72% |
| L-22 | SEQ ID NO: 131, SEQ ID NO: 660, SEQ ID NO: 574, SEQ ID NO: 665, SEQ ID NO: 560, SEQ ID NO: 754, SEQ ID NO: 36, SEQ ID NO: 477, SEQ ID NO: 605, SEQ ID NO: 809, SEQ ID NO: 746 | hsa-miR-625, hsa-miR-183*, hsa-miR-21*, hsa-miR-182*, hsa-miR-214*, hsa-miR-1303, hsa-miR-891b, hsa-miR-30e*, hsa-miR-199a-5p, hsa-miR-125a-5p, hsa-miR-130b | 81% | 84% | 78% |
| L-23 | SEQ ID NO: 36, SEQ ID NO: 477, SEQ ID NO: 605, SEQ ID NO: 809, SEQ ID NO: 746, SEQ ID NO: 385, SEQ ID NO: 465, SEQ ID NO: 462, SEQ ID NO: 881, SEQ ID NO: 701 | hsa-miR-891b, hsa-miR-30e*, hsa-miR-199a-5p, hsa-miR-125a-5p, hsa-miR-130b, hsa-miR-423-3p, hsa-miR-324-5p, hsa-miR-328, hsa-miR-148a | 79% | 84% | 75% |
| L-24 | SEQ ID NO: 385, SEQ ID NO: 465, SEQ ID NO: 462, SEQ ID NO: 881, SEQ ID NO: 701, SEQ ID NO: 872 | hsa-miR-423-3p, hsa-miR-324-5p, hsa-miR-328, hsa-miR-103, hsa-miR-148a, hsa-miR-107 | 81% | 85% | 76% |
| L-25 | SEQ ID NO: 469, SEQ ID NO: 470, SEQ ID NO: 896, SEQ ID NO: 660, SEQ ID NO: 665 | hsa-miR-320d, hsa-miR-320c, hsa-let-7d*, hsa-miR-183*, hsa-miR-182* | 72% | 83% | 60% |
| L-26 | SEQ ID NO: 788, SEQ ID NO: 131, SEQ ID NO: 560, SEQ ID NO: 36 | hsa-miR-1274a, hsa-miR-625, hsa-miR-21*, hsa-miR-891b | 78% | 74% | 82% |
| L-27 | SEQ ID NO: 574, SEQ ID NO: 560, SEQ ID NO: 605, SEQ ID NO: 746 | hsa-miR-21*, hsa-miR-214*, hsa-miR-891b, hsa-miR-199a-5p, hsa-miR-130b | 74% | 81% | 68% |
| L-28 | SEQ ID NO: 469, SEQ ID NO: 216, SEQ ID NO: 470 | hsa-miR-320d, hsa-miR-550, hsa-miR-320c | 61% | 61% | 60% |
| L-29 | SEQ ID NO: 470, SEQ ID NO: 788, SEQ ID NO: 896 | hsa-miR-320c, hsa-miR-1274a, hsa-let-7d* | 72% | 83% | 61% |
| L-30 | SEQ ID NO: 896, SEQ ID NO: 131, SEQ ID NO: 660 | hsa-let-7d*, hsa-miR-625, hsa-miR-183* | 73% | 83% | 62% |

FIG. 11B (Cont.)

|  | | | | |
|---|---|---|---|---|
| L-31 | SEQ ID NO: 660, SEQ ID NO: 574, SEQ ID NO: 665 | hsa-miR-183*, hsa-miR-21*, hsa-miR-182* | 73% | 76% | 70% |
| L-32 | SEQ ID NO: 665, SEQ ID NO: 560, SEQ ID NO: 754 | hsa-miR-182*, hsa-miR-214**, hsa-miR-1303 | 70% | 75% | 65% |
| L-33 | SEQ ID NO: 754, SEQ ID NO: 36, SEQ ID NO: 477 | hsa-miR-1303, hsa-miR-891b, hsa-miR-30e* | 67% | 76% | 58% |
| L-34 | SEQ ID NO: 477, SEQ ID NO: 605, SEQ ID NO: 809 | hsa-miR-30e*, hsa-miR-199a-5p, hsa-miR-125a-5p | 79% | 91% | 68% |
| L-35 | SEQ ID NO: 809, SEQ ID NO: 881, SEQ ID NO: 701 | hsa-miR-125a-5p, hsa-miR-103, hsa-miR-148a | 76% | 77% | 75% |
| L-36 | SEQ ID NO: 701, SEQ ID NO: 746, SEQ ID NO: 872 | hsa-miR-148a, hsa-miR-130b, hsa-miR-107 | 78% | 83% | 72% |
| L-37 | SEQ ID NO: 872, SEQ ID NO: 385, SEQ ID NO: 465 | hsa-miR-107, hsa-miR-423-3p, hsa-miR-324-5p | 74% | 81% | 67% |
| L-38 | SEQ ID NO: 465, SEQ ID NO: 462 | hsa-miR-324-5p, hsa-miR-328 | 74% | 88% | 60% |
| L-39 | SEQ ID NO: 469, SEQ ID NO: 216, SEQ ID NO: 788, SEQ ID NO: 896 | hsa-miR-320d, hsa-miR-550, hsa-miR-320c, hsa-miR-1274a, hsa-let-7d* | 71% | 87% | 55% |
| L-40 | SEQ ID NO: 470, SEQ ID NO: 788, SEQ ID NO: 896, SEQ ID NO: 131, SEQ ID NO: 660 | hsa-miR-320c, hsa-miR-1274a, hsa-let-7d*, hsa-miR-625, hsa-miR-183* | 77% | 86% | 67% |
| L-41 | SEQ ID NO: 896, SEQ ID NO: 131, SEQ ID NO: 660, SEQ ID NO: 574, SEQ ID NO: 665 | hsa-let-7d*, hsa-miR-625, hsa-miR-183*, hsa-miR-21*, hsa-miR-182* | 77% | 75% | 78% |
| L-42 | SEQ ID NO: 131, SEQ ID NO: 660, SEQ ID NO: 665, SEQ ID NO: 560 | hsa-miR-625, hsa-miR-183*, hsa-miR-21*, hsa-miR-182*, hsa-miR-214* | 72% | 72% | 72% |
| L-43 | SEQ ID NO: 574, SEQ ID NO: 665, SEQ ID NO: 560, SEQ ID NO: 754, SEQ ID NO: 36 | hsa-miR-21*, hsa-miR-182*, hsa-miR-214*, hsa-miR-1303, hsa-miR-891b | 74% | 75% | 73% |
| L-44 | SEQ ID NO: 560, SEQ ID NO: 754, SEQ ID NO: 36, SEQ ID NO: 477, SEQ ID NO: 605 | hsa-miR-214*, hsa-miR-1303, hsa-miR-891b, hsa-miR-30e*, hsa-miR-199a-5p | 80% | 87% | 73% |
| L-45 | SEQ ID NO: 754, SEQ ID NO: 36, SEQ ID NO: 477, SEQ ID NO: 605, SEQ ID NO: 809, SEQ ID NO: 881 | hsa-miR-1303, hsa-miR-891b, hsa-miR-30e*, hsa-miR-199a-5p, hsa-miR-125a-5p, hsa-miR-103 | 81% | 87% | 74% |
| L-46 | SEQ ID NO: 605, SEQ ID NO: 809, SEQ ID NO: 881, SEQ ID NO: 701, SEQ ID NO: 746, SEQ ID NO: 872 | hsa-miR-199a-5p, hsa-miR-125a-5p, hsa-miR-103, hsa-miR-148a, hsa-miR-130b, hsa-miR-107 | 81% | 90% | 72% |
| L-47 | SEQ ID NO: 701, SEQ ID NO: 746, SEQ ID NO: 872, SEQ ID NO: 385, SEQ ID NO: 465, SEQ ID NO: 462 | hsa-miR-148a, hsa-miR-130b, hsa-miR-107, hsa-miR-423-3p, hsa-miR-324-5p, hsa-miR-328 | 81% | 85% | 78% |

FIG. 11B (Cont.)

| | | | | |
|---|---|---|---|---|
| L-48 | SEQ ID NO: 469, SEQ ID NO: 216, SEQ ID NO: 470, SEQ ID NO: 788, SEQ ID NO: 896, SEQ ID NO: 131, SEQ ID NO: 660, SEQ ID NO: 574, SEQ ID NO: 665, SEQ ID NO: 560 | hsa-miR-320d, hsa-miR-550, hsa-miR-320c, hsa-miR-1274a, hsa-let-7d*, hsa-miR-625, hsa-miR-183*, hsa-miR-21*, hsa-miR-182*, hsa-miR-214* | 73% | 77% | 69% |
| L-49 | SEQ ID NO: 131, SEQ ID NO: 660, SEQ ID NO: 574, SEQ ID NO: 665, SEQ ID NO: 560, SEQ ID NO: 754, SEQ ID NO: 36, SEQ ID NO: 477, SEQ ID NO: 605, SEQ ID NO: 809, SEQ ID NO: 881 | hsa-miR-625, hsa-miR-183*, hsa-miR-21*, hsa-miR-182*, hsa-miR-214*, hsa-miR-1303, hsa-miR-891b, hsa-miR-30e*, hsa-miR-199a-5p, hsa-miR-125a-5p, hsa-miR-103 | 85% | 84% | 87% |
| L-50 | SEQ ID NO: 36, SEQ ID NO: 477, SEQ ID NO: 605, SEQ ID NO: 809, SEQ ID NO: 881, SEQ ID NO: 701, SEQ ID NO: 746, SEQ ID NO: 872, SEQ ID NO: 385, SEQ ID NO: 465 | hsa-miR-891b, hsa-miR-30e*, hsa-miR-199a-5p, hsa-miR-125a-5p, hsa-miR-103, hsa-miR-148a, hsa-miR-130b, hsa-miR-107, hsa-miR-423-3p, hsa-miR-324-5p | 79% | 84% | 74% |
| L-51 | SEQ ID NO: 701, SEQ ID NO: 746, SEQ ID NO: 872, SEQ ID NO: 385, SEQ ID NO: 465, SEQ ID NO: 462 | hsa-miR-148a, hsa-miR-130b, hsa-miR-107, hsa-miR-423-3p, hsa-miR-324-5p, hsa-miR-328 | 81% | 86% | 77% |
| L-52 | SEQ ID NO: 469, SEQ ID NO: 470, SEQ ID NO: 896, SEQ ID NO: 660, SEQ ID NO: 665 | hsa-miR-320d, hsa-miR-320c, hsa-let-7d*, hsa-miR-183*, hsa-miR-182* | 71% | 82% | 60% |
| L-53 | SEQ ID NO: 788, SEQ ID NO: 131, SEQ ID NO: 560, SEQ ID NO: 36 | hsa-miR-1274a, hsa-miR-625, hsa-miR-21*, hsa-miR-214*, hsa-miR-891b | 75% | 71% | 80% |
| L-54 | SEQ ID NO: 574, SEQ ID NO: 560, SEQ ID NO: 36, SEQ ID NO: 605, SEQ ID NO: 881 | hsa-miR-21*, hsa-miR-214*, hsa-miR-891b, hsa-miR-199a-5p, hsa-miR-103 | 75% | 78% | 72% |
| L-55 | SEQ ID NO: 605, SEQ ID NO: 809, SEQ ID NO: 469 | hsa-miR-199a-5p, hsa-miR-125a-5p, hsa-miR-320d | 80% | 93% | 67% |
| L-56 | SEQ ID NO: 469, SEQ ID NO: 216, SEQ ID NO: 470 | hsa-miR-320d, hsa-miR-550, hsa-miR-320c | 60% | 61% | 59% |
| L-57 | SEQ ID NO: 470, SEQ ID NO: 788, SEQ ID NO: 746 | hsa-miR-320c, hsa-miR-1274a, hsa-miR-130b | 69% | 72% | 65% |
| L-58 | SEQ ID NO: 746, SEQ ID NO: 385, SEQ ID NO: 465 | hsa-miR-130b, hsa-miR-324-5p, hsa-miR-423-3p, hsa-miR-324-5p | 67% | 66% | 68% |
| L-59 | SEQ ID NO: 465, SEQ ID NO: 131 | hsa-miR-324-5p, hsa-let-7d*, hsa-miR-625 | 75% | 86% | 64% |
| L-60 | SEQ ID NO: 131, SEQ ID NO: 462, SEQ ID NO: 660 | hsa-miR-625, hsa-miR-328, hsa-miR-183* | 71% | 82% | 60% |
| L-61 | SEQ ID NO: 660, SEQ ID NO: 574, SEQ ID NO: 665 | hsa-miR-183*, hsa-miR-21*, hsa-miR-182* | 73% | 76% | 70% |

FIG. 11B (Cont.)

| | | | | | |
|---|---|---|---|---|---|
| L-62 | SEQ ID NO: 665, SEQ ID NO: 560, SEQ ID NO: 754 | hsa-miR-182*, hsa-miR-214*, hsa-miR-1303 | 71% | 76% | 67% |
| L-63 | SEQ ID NO: 754, SEQ ID NO: 36, SEQ ID NO: 477 | hsa-miR-1303, hsa-miR-891b, hsa-miR-30e* | 65% | 73% | 56% |
| L-64 | SEQ ID NO: 477, SEQ ID NO: 881, SEQ ID NO: 701 | hsa-miR-30e*, hsa-miR-103, hsa-miR-148a | 79% | 78% | 80% |
| L-65 | SEQ ID NO: 701, SEQ ID NO: 872 | hsa-miR-148a, hsa-miR-107 | 75% | 81% | 68% |
| L-66 | SEQ ID NO: 605, SEQ ID NO: 809, SEQ ID NO: 469, SEQ ID NO: 216, SEQ ID NO: 470 | hsa-miR-199a-5p, hsa-miR-125a-5p, hsa-miR-320d, hsa-miR-550, hsa-miR-320c | 77% | 92% | 61% |
| L-67 | SEQ ID NO: 469, SEQ ID NO: 216, SEQ ID NO: 470, SEQ ID NO: 788, SEQ ID NO: 746 | hsa-miR-320d, hsa-miR-550, hsa-miR-320c, hsa-miR-1274a, hsa-miR-130b | 68% | 72% | 64% |
| L-68 | SEQ ID NO: 470, SEQ ID NO: 788, SEQ ID NO: 746, SEQ ID NO: 385, SEQ ID NO: 465 | hsa-miR-320c, hsa-miR-1274a, hsa-miR-130b, hsa-miR-423-3p, hsa-miR-324-5p | 78% | 78% | 79% |
| L-69 | SEQ ID NO: 788, SEQ ID NO: 746, SEQ ID NO: 385, SEQ ID NO: 465, SEQ ID NO: 896 | hsa-miR-1274a, hsa-miR-130b, hsa-miR-423-3p, hsa-miR-324-5p, hsa-let-7d* | 76% | 82% | 70% |
| L-70 | SEQ ID NO: 385, SEQ ID NO: 465, SEQ ID NO: 896, SEQ ID NO: 131, SEQ ID NO: 462 | hsa-miR-423-3p, hsa-miR-324-5p, hsa-let-7d*, hsa-miR-625, hsa-miR-328 | 78% | 85% | 72% |
| L-71 | SEQ ID NO: 896, SEQ ID NO: 131, SEQ ID NO: 462, SEQ ID NO: 660, SEQ ID NO: 574 | hsa-let-7d*, hsa-miR-625, hsa-miR-328, hsa-miR-183*, hsa-miR-21* | 71% | 80% | 63% |
| L-72 | SEQ ID NO: 131, SEQ ID NO: 462, SEQ ID NO: 660, SEQ ID NO: 574, SEQ ID NO: 665, SEQ ID NO: 560 | hsa-miR-625, hsa-miR-328, hsa-miR-183*, hsa-miR-21*, hsa-miR-182*, hsa-miR-214* | 70% | 72% | 69% |
| L-73 | SEQ ID NO: 574, SEQ ID NO: 660, SEQ ID NO: 574, SEQ ID NO: 754, SEQ ID NO: 36, SEQ ID NO: 477 | hsa-miR-21*, hsa-miR-182*, hsa-miR-214*, hsa-miR-1303, hsa-miR-891b, hsa-miR-30e* | 75% | 74% | 76% |
| L-74 | SEQ ID NO: 754, SEQ ID NO: 36, SEQ ID NO: 477, SEQ ID NO: 881, SEQ ID NO: 701, SEQ ID NO: 872 | hsa-miR-1303, hsa-miR-891b, hsa-miR-30e*, hsa-miR-103, hsa-miR-148a, hsa-miR-107 | 82% | 77% | 87% |
| L-75 | SEQ ID NO: 605, SEQ ID NO: 809, SEQ ID NO: 469, SEQ ID NO: 216, SEQ ID NO: 470, SEQ ID NO: 788, SEQ ID NO: 746, SEQ ID NO: 385, SEQ ID NO: 465, SEQ ID NO: 896 | hsa-miR-199a-5p, hsa-miR-125a-5p, hsa-miR-320d, hsa-miR-550, hsa-miR-320c, hsa-miR-1274a, hsa-miR-130b, hsa-miR-423-3p, hsa-miR-324-5p, hsa-let-7d* | 77% | 88% | 66% |
| L-76 | SEQ ID NO: 788, SEQ ID NO: 746, SEQ ID NO: 385, SEQ ID NO: 465, SEQ ID NO: 896, SEQ ID NO: 131, SEQ ID NO: 462, SEQ ID NO: 660, SEQ ID NO: 574, SEQ ID NO: 665, SEQ ID NO: 560 | hsa-miR-1274a, hsa-miR-130b, hsa-miR-423-3p, hsa-miR-324-5p, hsa-let-7d*, hsa-miR-625, hsa-miR-328, hsa-miR-183*, hsa-miR-21*, hsa-miR-182*, hsa-miR-214* | 79% | 80% | 79% |

FIG. 11B (Cont.)

| | SEQ ID NOs | miRNAs | | | |
|---|---|---|---|---|---|
| L-77 | SEQ ID NO: 462, SEQ ID NO: 660, SEQ ID NO: 574, SEQ ID NO: 665, SEQ ID NO: 560, SEQ ID NO: 754, SEQ ID NO: 36, SEQ ID NO: 477, SEQ ID NO: 881, SEQ ID NO: 701 | hsa-miR-328, hsa-miR-183*, hsa-miR-21*, hsa-miR-182*, hsa-miR-214*, hsa-miR-1303, hsa-miR-891b, hsa-miR-30e*, hsa-miR-103, hsa-miR-148a | 88% | 87% | 89% |
| L-78 | SEQ ID NO: 754, SEQ ID NO: 36, SEQ ID NO: 477, SEQ ID NO: 881, SEQ ID NO: 701, SEQ ID NO: 872 | hsa-miR-1303, hsa-miR-891b, hsa-miR-30e*, hsa-miR-103, hsa-miR-148a, hsa-miR-107 | 80% | 76% | 84% |
| L-79 | SEQ ID NO: 605, SEQ ID NO: 469, SEQ ID NO: 470, SEQ ID NO: 746, SEQ ID NO: 465 | hsa-miR-199a-5p, hsa-miR-320d, hsa-miR-320c, hsa-miR-130b, hsa-miR-324-5p | 72% | 80% | 63% |
| L-80 | SEQ ID NO: 216, SEQ ID NO: 788, SEQ ID NO: 385, SEQ ID NO: 896, SEQ ID NO: 462 | hsa-miR-550, hsa-miR-1274a, hsa-miR-423-3p, hsa-let-7d*, hsa-miR-328 | 74% | 77% | 71% |
| L-81 | SEQ ID NO: 385, SEQ ID NO: 896, SEQ ID NO: 462, SEQ ID NO: 574, SEQ ID NO: 560 | hsa-miR-423-3p, hsa-let-7d*, hsa-miR-328, hsa-miR-21*, hsa-miR-214* | 75% | 79% | 71% |
| L-82 | SEQ ID NO: 605, SEQ ID NO: 809, SEQ ID NO: 329 | hsa-miR-199a-5p, hsa-miR-125a-5p, hsa-miR-500 | 78% | 92% | 64% |
| L-83 | SEQ ID NO: 329, SEQ ID NO: 469, SEQ ID NO: 216 | hsa-miR-500, hsa-miR-320d, hsa-miR-550 | 65% | 72% | 58% |
| L-84 | SEQ ID NO: 216, SEQ ID NO: 746, SEQ ID NO: 470 | hsa-miR-550, hsa-miR-130b, hsa-miR-320c | 65% | 66% | 63% |
| L-85 | SEQ ID NO: 470, SEQ ID NO: 385, SEQ ID NO: 465 | hsa-miR-320c, hsa-miR-423-3p, hsa-miR-324-5p | 65% | 67% | 62% |
| L-86 | SEQ ID NO: 465, SEQ ID NO: 788, SEQ ID NO: 635 | hsa-miR-324-5p, hsa-miR-1274a, hsa-miR-1913 | 76% | 83% | 70% |
| L-87 | SEQ ID NO: 635, SEQ ID NO: 431, SEQ ID NO: 325 | hsa-miR-1913, hsa-miR-361-5p, hsa-miR-502-3p | 67% | 77% | 57% |
| L-88 | SEQ ID NO: 325, SEQ ID NO: 600, SEQ ID NO: 458 | hsa-miR-502-3p, hsa-miR-19b, hsa-miR-331-3p | 74% | 76% | 73% |
| L-89 | SEQ ID NO: 458, SEQ ID NO: 485, SEQ ID NO: 718 | hsa-miR-331-3p, hsa-miR-30b, hsa-miR-142-5p | 77% | 86% | 69% |
| L-90 | SEQ ID NO: 718, SEQ ID NO: 199, SEQ ID NO: 787 | hsa-miR-142-5p, hsa-miR-1274b, hsa-miR-1826 | 71% | 74% | 68% |
| L-91 | SEQ ID NO: 787, SEQ ID NO: 663, SEQ ID NO: 462 | hsa-miR-1274b, hsa-miR-1826, hsa-miR-328 | 72% | 83% | 61% |
| L-92 | SEQ ID NO: 462, SEQ ID NO: 896, SEQ ID NO: 131 | hsa-miR-328, hsa-let-7d*, hsa-miR-625 | 73% | 84% | 62% |
| L-93 | SEQ ID NO: 131, SEQ ID NO: 627, SEQ ID NO: 402 | hsa-miR-625, hsa-miR-193a-5p, hsa-miR-378* | 72% | 90% | 53% |

FIG. 11B (Cont.)

| | | | | |
|---|---|---|---|---|
| L-94 | SEQ ID NO: 402, SEQ ID NO: 574, SEQ ID NO: 48 | hsa-miR-378*, hsa-miR-21*, hsa-miR-877 | 70% | 79% | 60% |
| L-95 | SEQ ID NO: 574, SEQ ID NO: 353, SEQ ID NO: 48 | hsa-miR-21*, hsa-miR-485-3p, hsa-miR-877 | 73% | 78% | 68% |
| L-96 | SEQ ID NO: 48, SEQ ID NO: 776, SEQ ID NO: 773 | hsa-miR-877, hsa-miR-1283, hsa-miR-1286 | 70% | 74% | 66% |
| L-97 | SEQ ID NO: 605, SEQ ID NO: 809, SEQ ID NO: 329, SEQ ID NO: 469, SEQ ID NO: 216 | hsa-miR-199a-5p, hsa-miR-125a-5p, hsa-miR-500, hsa-miR-320d, hsa-miR-550 | 78% | 89% | 67% |
| L-98 | SEQ ID NO: 329, SEQ ID NO: 469, SEQ ID NO: 216, SEQ ID NO: 746, SEQ ID NO: 470 | hsa-miR-500, hsa-miR-320d, hsa-miR-550, hsa-miR-130b, hsa-miR-320c | 67% | 72% | 63% |
| L-99 | SEQ ID NO: 216, SEQ ID NO: 746, SEQ ID NO: 470, SEQ ID NO: 385, SEQ ID NO: 465 | hsa-miR-550, hsa-miR-130b, hsa-miR-320c, hsa-miR-423-3p, hsa-miR-324-5p | 70% | 76% | 63% |
| L-100 | SEQ ID NO: 746, SEQ ID NO: 470, SEQ ID NO: 385, SEQ ID NO: 465, SEQ ID NO: 788 | hsa-miR-130b, hsa-miR-320c, hsa-miR-423-3p, hsa-miR-324-5p, hsa-miR-1274a | 78% | 77% | 78% |
| L-101 | SEQ ID NO: 385, SEQ ID NO: 465, SEQ ID NO: 788, SEQ ID NO: 635, SEQ ID NO: 431 | hsa-miR-423-3p, hsa-miR-324-5p, hsa-miR-1274a, hsa-miR-1913, hsa-miR-361-5p | 84% | 87% | 82% |
| L-102 | SEQ ID NO: 788, SEQ ID NO: 635, SEQ ID NO: 431, SEQ ID NO: 325, SEQ ID NO: 600 | hsa-miR-1274a, hsa-miR-1913, hsa-miR-361-5p, hsa-miR-502-3p, hsa-miR-19b | 81% | 81% | 81% |
| L-103 | SEQ ID NO: 635, SEQ ID NO: 431, SEQ ID NO: 325, SEQ ID NO: 600, SEQ ID NO: 458, SEQ ID NO: 485 | hsa-miR-1913, hsa-miR-361-5p, hsa-miR-502-3p, hsa-miR-19b, hsa-miR-331-3p, hsa-miR-30b | 75% | 77% | 73% |
| L-104 | SEQ ID NO: 600, SEQ ID NO: 458, SEQ ID NO: 485, SEQ ID NO: 718, SEQ ID NO: 199, SEQ ID NO: 787 | hsa-miR-19b, hsa-miR-331-3p, hsa-miR-30b, hsa-miR-142-5p, hsa-miR-564, hsa-miR-1274b | 82% | 88% | 76% |
| L-105 | SEQ ID NO: 718, SEQ ID NO: 199, SEQ ID NO: 787, SEQ ID NO: 663, SEQ ID NO: 462, SEQ ID NO: 896 | hsa-miR-142-5p, hsa-miR-564, hsa-miR-1274b, hsa-miR-1826, hsa-miR-328, hsa-let-7d* | 78% | 81% | 75% |
| L-106 | SEQ ID NO: 663, SEQ ID NO: 462, SEQ ID NO: 896, SEQ ID NO: 131, SEQ ID NO: 627, SEQ ID NO: 402 | hsa-miR-1826, hsa-miR-328, hsa-let-7d*, hsa-miR-625, hsa-miR-193a-5p, hsa-miR-378* | 69% | 84% | 54% |
| L-107 | SEQ ID NO: 131, SEQ ID NO: 627, SEQ ID NO: 402, SEQ ID NO: 660, SEQ ID NO: 574, SEQ ID NO: 353 | hsa-miR-625, hsa-miR-193a-5p, hsa-miR-378*, hsa-miR-183*, hsa-miR-21*, hsa-miR-485-3p | 77% | 84% | 71% |
| L-108 | SEQ ID NO: 660, SEQ ID NO: 574, SEQ ID NO: 353, SEQ ID NO: 48, SEQ ID NO: 776, SEQ ID NO: 773 | hsa-miR-183*, hsa-miR-21*, hsa-miR-485-3p, hsa-miR-877, hsa-miR-1283, hsa-miR-1286 | 73% | 75% | 71% |

FIG. 11B (Cont.)

| | | | | |
|---|---|---|---|---|
| L-109 | SEQ ID NO: 48, SEQ ID NO: 776, SEQ ID NO: 773, SEQ ID NO: 283, SEQ ID NO: 93, SEQ ID NO: 29 | hsa-miR-877, hsa-miR-1283, hsa-miR-1286, hsa-miR-518f*, hsa-miR-659, hsa-miR-922 | 69% | 77% | 61% |
| L-110 | SEQ ID NO: 283, SEQ ID NO: 93, SEQ ID NO: 29, SEQ ID NO: 316, SEQ ID NO: 665, SEQ ID NO: 501 | hsa-miR-518f*, hsa-miR-659, hsa-miR-922, hsa-miR-508-5p, hsa-miR-182*, hsa-miR-29c* | 73% | 83% | 62% |
| L-111 | SEQ ID NO: 316, SEQ ID NO: 665, SEQ ID NO: 501, SEQ ID NO: 11, SEQ ID NO: 60, SEQ ID NO: 719 | hsa-miR-508-5p, hsa-miR-182*, hsa-miR-29c*, hsa-miR-942, hsa-miR-767-3p, hsa-miR-142-3p | 71% | 80% | 62% |
| L-112 | SEQ ID NO: 605, SEQ ID NO: 809, SEQ ID NO: 329, SEQ ID NO: 469, SEQ ID NO: 216, SEQ ID NO: 746, SEQ ID NO: 470, SEQ ID NO: 385, SEQ ID NO: 465, SEQ ID NO: 788 | hsa-miR-199a-5p, hsa-miR-125a-5p, hsa-miR-500, hsa-miR-320d, hsa-miR-550, hsa-miR-130b, hsa-miR-320c, hsa-miR-423-3p, hsa-miR-324-5p, hsa-miR-1274a | 75% | 81% | 68% |
| L-113 | SEQ ID NO: 746, SEQ ID NO: 470, SEQ ID NO: 385, SEQ ID NO: 465, SEQ ID NO: 788, SEQ ID NO: 635, SEQ ID NO: 431, SEQ ID NO: 325, SEQ ID NO: 600, SEQ ID NO: 458, SEQ ID NO: 485 | hsa-miR-130b, hsa-miR-320c, hsa-miR-423-3p, hsa-miR-324-5p, hsa-miR-1274a, hsa-miR-1913, hsa-miR-361-5p, hsa-miR-502-3p, hsa-miR-19b, hsa-miR-331-3p, hsa-miR-30b | 81% | 80% | 83% |
| L-114 | SEQ ID NO: 431, SEQ ID NO: 325, SEQ ID NO: 600, SEQ ID NO: 458, SEQ ID NO: 485, SEQ ID NO: 718, SEQ ID NO: 199, SEQ ID NO: 787, SEQ ID NO: 663, SEQ ID NO: 462 | hsa-miR-361-5p, hsa-miR-502-3p, hsa-miR-19b, hsa-miR-331-3p, hsa-miR-30b, hsa-miR-142-5p, hsa-miR-1826, hsa-miR-564, hsa-miR-1274b, hsa-miR-328 | 80% | 82% | 79% |
| L-115 | SEQ ID NO: 718, SEQ ID NO: 199, SEQ ID NO: 787, SEQ ID NO: 663, SEQ ID NO: 462, SEQ ID NO: 896, SEQ ID NO: 131, SEQ ID NO: 627, SEQ ID NO: 402, SEQ ID NO: 660 | hsa-miR-142-5p, hsa-miR-1826, hsa-miR-564, hsa-miR-328, hsa-let-7d*, hsa-miR-625, hsa-miR-193a-5p, hsa-miR-378*, hsa-miR-877, hsa-miR-183* | 76% | 84% | 67% |
| L-116 | SEQ ID NO: 896, SEQ ID NO: 131, SEQ ID NO: 627, SEQ ID NO: 402, SEQ ID NO: 660, SEQ ID NO: 574, SEQ ID NO: 353, SEQ ID NO: 48, SEQ ID NO: 776, SEQ ID NO: 773 | hsa-let-7d*, hsa-miR-625, hsa-miR-193a-5p, hsa-miR-378*, hsa-miR-183*, hsa-miR-21*, hsa-miR-485-3p, hsa-miR-877, hsa-miR-1283, hsa-miR-1286 | 74% | 77% | 70% |
| L-117 | SEQ ID NO: 574, SEQ ID NO: 353, SEQ ID NO: 48, SEQ ID NO: 776, SEQ ID NO: 773, SEQ ID NO: 283, SEQ ID NO: 93, SEQ ID NO: 29, SEQ ID NO: 316, SEQ ID NO: 665 | hsa-miR-21*, hsa-miR-485-3p, hsa-miR-877, hsa-miR-1283, hsa-miR-1286, hsa-miR-518f*, hsa-miR-659, hsa-miR-922, hsa-miR-508-5p, hsa-miR-182* | 69% | 76% | 62% |

FIG. 11B (Cont.)

| | | | | |
|---|---|---|---|---|
| L-118 | SEQ ID NO: 283, SEQ ID NO: 93, SEQ ID NO: 29, SEQ ID NO: 316, SEQ ID NO: 665, SEQ ID NO: 501, SEQ ID NO: 11, SEQ ID NO: 60, SEQ ID NO: 719, SEQ ID NO: 814 | hsa-miR-518f*, hsa-miR-659, hsa-miR-922, hsa-miR-508-5p, hsa-miR-182*, hsa-miR-29c*, hsa-miR-942, hsa-miR-767-3p, hsa-miR-142-3p, hsa-miR-1256 | 70% | 80% | 61% |
| L-119 | SEQ ID NO: 501, SEQ ID NO: 11, SEQ ID NO: 60, SEQ ID NO: 719, SEQ ID NO: 814, SEQ ID NO: 306, SEQ ID NO: 547, SEQ ID NO: 421, SEQ ID NO: 664, SEQ ID NO: 274 | hsa-miR-29c*, hsa-miR-942, hsa-miR-767-3p, hsa-miR-142-3p, hsa-miR-1256, hsa-miR-513b, hsa-miR-220a, hsa-miR-369-5p, hsa-miR-1825, hsa-miR-519e* | 69% | 84% | 53% |
| L-120 | SEQ ID NO: 306, SEQ ID NO: 547, SEQ ID NO: 421, SEQ ID NO: 664, SEQ ID NO: 274, SEQ ID NO: 852, SEQ ID NO: 656, SEQ ID NO: 356, SEQ ID NO: 560, SEQ ID NO: 754 | hsa-miR-513b, hsa-miR-220a, hsa-miR-369-5p, hsa-miR-1825, hsa-miR-519e*, hsa-miR-1206, hsa-miR-186, hsa-miR-483-3p, hsa-miR-214*, hsa-miR-1303 | 67% | 76% | 57% |
| L-121 | SEQ ID NO: 605, SEQ ID NO: 329, SEQ ID NO: 216, SEQ ID NO: 470, SEQ ID NO: 465 | hsa-miR-199a-5p, hsa-miR-500, hsa-miR-550, hsa-miR-320c, hsa-miR-324-5p | 76% | 84% | 69% |
| L-122 | SEQ ID NO: 469, SEQ ID NO: 746, SEQ ID NO: 385, SEQ ID NO: 788, SEQ ID NO: 431 | hsa-miR-320d, hsa-miR-130b, hsa-miR-423-3p, hsa-miR-1274a, hsa-miR-361-5p | 76% | 76% | 76% |
| L-123 | SEQ ID NO: 385, SEQ ID NO: 788, SEQ ID NO: 431, SEQ ID NO: 600, SEQ ID NO: 485 | hsa-miR-423-3p, hsa-miR-1274a, hsa-miR-361-5p, hsa-miR-19b, hsa-miR-30b | 78% | 75% | 80% |
| L-124 | SEQ ID NO: 329, SEQ ID NO: 469, SEQ ID NO: 216 | hsa-miR-500, hsa-miR-320d, hsa-miR-550 | 65% | 73% | 57% |
| L-125 | SEQ ID NO: 216, SEQ ID NO: 470, SEQ ID NO: 788 | hsa-miR-550, hsa-miR-1274a, hsa-miR-1274a | 66% | 71% | 61% |
| L-126 | SEQ ID NO: 788, SEQ ID NO: 635, SEQ ID NO: 199 | hsa-miR-1274a, hsa-miR-1913, hsa-miR-564 | 69% | 79% | 59% |
| L-127 | SEQ ID NO: 199, SEQ ID NO: 787, SEQ ID NO: 663 | hsa-miR-564, hsa-miR-1274b, hsa-miR-1826 | 68% | 75% | 60% |
| L-128 | SEQ ID NO: 663, SEQ ID NO: 896, SEQ ID NO: 131 | hsa-miR-1826, hsa-let-7d*, hsa-miR-625 | 71% | 85% | 58% |
| L-129 | SEQ ID NO: 131, SEQ ID NO: 402, SEQ ID NO: 660 | hsa-miR-625, hsa-miR-378*, hsa-miR-183* | 74% | 90% | 59% |
| L-130 | SEQ ID NO: 660, SEQ ID NO: 574, SEQ ID NO: 48 | hsa-miR-183*, hsa-miR-877 | 68% | 65% | 70% |
| L-131 | SEQ ID NO: 48, SEQ ID NO: 776, SEQ ID NO: 773 | hsa-miR-877, hsa-miR-1283, hsa-miR-1286 | 69% | 75% | 63% |
| L-132 | SEQ ID NO: 773, SEQ ID NO: 283, SEQ ID NO: 93 | hsa-miR-1286, hsa-miR-518f*, hsa-miR-659 | 64% | 61% | 67% |

FIG. 11B (Cont.)

| | | | | | |
|---|---|---|---|---|---|
| L-133 | SEQ ID NO: 93, SEQ ID NO: 29, SEQ ID NO: 316 | hsa-miR-659, hsa-miR-922, hsa-miR-508-5p | 59% | 61% | 57% |
| L-134 | SEQ ID NO: 316, SEQ ID NO: 665, SEQ ID NO: 501 | hsa-miR-508-5p, hsa-miR-182*, hsa-miR-29c* | 72% | 84% | 59% |
| L-135 | SEQ ID NO: 501, SEQ ID NO: 11, SEQ ID NO: 60 | hsa-miR-29c*, hsa-miR-942, hsa-miR-767-3p | 69% | 74% | 63% |
| L-136 | SEQ ID NO: 60, SEQ ID NO: 421, SEQ ID NO: 274 | hsa-miR-767-3p, hsa-miR-369-5p, hsa-miR-519e* | 66% | 80% | 52% |
| L-137 | SEQ ID NO: 421, SEQ ID NO: 664, SEQ ID NO: 274 | hsa-miR-369-5p, hsa-miR-1825, hsa-miR-519e* | 64% | 78% | 51% |
| L-138 | SEQ ID NO: 274, SEQ ID NO: 852, SEQ ID NO: 356 | hsa-miR-519e*, hsa-miR-1206, hsa-miR-483-3p | 63% | 74% | 51% |
| L-139 | SEQ ID NO: 329, SEQ ID NO: 469, SEQ ID NO: 216, SEQ ID NO: 470, SEQ ID NO: 788 | hsa-miR-500, hsa-miR-320d, hsa-miR-550, hsa-miR-320c, hsa-miR-1274a | 71% | 76% | 66% |
| L-140 | SEQ ID NO: 216, SEQ ID NO: 470, SEQ ID NO: 788, SEQ ID NO: 635, SEQ ID NO: 199 | hsa-miR-550, hsa-miR-320c, hsa-miR-1274a, hsa-miR-1913, hsa-miR-564 | 67% | 72% | 62% |
| L-141 | SEQ ID NO: 788, SEQ ID NO: 635, SEQ ID NO: 199, SEQ ID NO: 787, SEQ ID NO: 663 | hsa-miR-1274a, hsa-miR-1913, hsa-miR-564, hsa-miR-1274b, hsa-miR-1826 | 71% | 76% | 67% |
| L-142 | SEQ ID NO: 635, SEQ ID NO: 199, SEQ ID NO: 787, SEQ ID NO: 663, SEQ ID NO: 896 | hsa-miR-1913, hsa-miR-564, hsa-miR-1274b, hsa-miR-1826, hsa-let-7d* | 73% | 81% | 65% |
| L-143 | SEQ ID NO: 787, SEQ ID NO: 663, SEQ ID NO: 896, SEQ ID NO: 131, SEQ ID NO: 402 | hsa-miR-1274b, hsa-miR-1826, hsa-let-7d*, hsa-miR-625, hsa-miR-378* | 75% | 88% | 63% |
| L-144 | SEQ ID NO: 896, SEQ ID NO: 131, SEQ ID NO: 402, SEQ ID NO: 660, SEQ ID NO: 574 | hsa-let-7d*, hsa-miR-625, hsa-miR-378*, hsa-miR-183*, hsa-miR-21* | 75% | 80% | 71% |
| L-145 | SEQ ID NO: 131, SEQ ID NO: 402, SEQ ID NO: 660, SEQ ID NO: 574, SEQ ID NO: 48, SEQ ID NO: 776 | hsa-miR-625, hsa-miR-378*, hsa-miR-183*, hsa-miR-21*, hsa-miR-877, hsa-miR-1283 | 71% | 76% | 67% |
| L-146 | SEQ ID NO: 574, SEQ ID NO: 48, SEQ ID NO: 776, SEQ ID NO: 773, SEQ ID NO: 283, SEQ ID NO: 93 | hsa-miR-21*, hsa-miR-877, hsa-miR-1283, hsa-miR-1286, hsa-miR-518f*, hsa-miR-659 | 68% | 73% | 63% |
| L-147 | SEQ ID NO: 773, SEQ ID NO: 283, SEQ ID NO: 93, SEQ ID NO: 29, SEQ ID NO: 316, SEQ ID NO: 665 | hsa-miR-1286, hsa-miR-518f*, hsa-miR-659, hsa-miR-922, hsa-miR-508-5p, hsa-miR-182* | 67% | 74% | 61% |
| L-148 | SEQ ID NO: 29, SEQ ID NO: 316, SEQ ID NO: 665, SEQ ID NO: 501, SEQ ID NO: 11, SEQ ID NO: 60 | hsa-miR-922, hsa-miR-508-5p, hsa-miR-182*, hsa-miR-29c*, hsa-miR-942, hsa-miR-767-3p | 71% | 80% | 63% |

FIG. 11B (Cont.)

| | | | | |
|---|---|---|---|---|
| L-149 | SEQ ID NO: 501, SEQ ID NO: 11, SEQ ID NO: 60, SEQ ID NO: 814, SEQ ID NO: 421, SEQ ID NO: 664 | hsa-miR-29c*, hsa-miR-942, hsa-miR-767-3p, hsa-miR-1256, hsa-miR-369-5p, hsa-miR-1825 | 67% | 81% | 53% |
| L-150 | SEQ ID NO: 814, SEQ ID NO: 421, SEQ ID NO: 664, SEQ ID NO: 274, SEQ ID NO: 852, SEQ ID NO: 356 | hsa-miR-1256, hsa-miR-369-5p, hsa-miR-1825, hsa-miR-519e*, hsa-miR-1206, hsa-miR-483-3p | 65% | 79% | 52% |
| L-151 | SEQ ID NO: 274, SEQ ID NO: 852, SEQ ID NO: 356, SEQ ID NO: 560, SEQ ID NO: 754, SEQ ID NO: 36 | hsa-miR-519e*, hsa-miR-1206, hsa-miR-483-3p, hsa-miR-214*, hsa-miR-1303, hsa-miR-891b | 70% | 79% | 62% |
| L-152 | SEQ ID NO: 560, SEQ ID NO: 754, SEQ ID NO: 36, SEQ ID NO: 477, SEQ ID NO: 683, SEQ ID NO: 84 | hsa-miR-214*, hsa-miR-1303, hsa-miR-891b, hsa-miR-30e*, hsa-miR-155*, hsa-miR-668 | 74% | 75% | 74% |
| L-153 | SEQ ID NO: 477, SEQ ID NO: 683, SEQ ID NO: 84, SEQ ID NO: 842, SEQ ID NO: 437, SEQ ID NO: 106 | hsa-miR-30e*, hsa-miR-155*, hsa-miR-668, hsa-miR-1226, hsa-miR-34a*, hsa-miR-647 | 72% | 70% | 73% |
| L-154 | SEQ ID NO: 329, SEQ ID NO: 469, SEQ ID NO: 216, SEQ ID NO: 470, SEQ ID NO: 788, SEQ ID NO: 635, SEQ ID NO: 199, SEQ ID NO: 787, SEQ ID NO: 663, SEQ ID NO: 896 | hsa-miR-500, hsa-miR-320d, hsa-miR-550, hsa-miR-320c, hsa-miR-1274a, hsa-miR-1913, hsa-miR-564, hsa-miR-1274b, hsa-miR-1826, hsa-let-7d* | 75% | 85% | 64% |
| L-155 | SEQ ID NO: 635, SEQ ID NO: 199, SEQ ID NO: 787, SEQ ID NO: 663, SEQ ID NO: 896, SEQ ID NO: 131, SEQ ID NO: 402, SEQ ID NO: 660, SEQ ID NO: 574, SEQ ID NO: 48, SEQ ID NO: 776 | hsa-miR-1913, hsa-miR-564, hsa-miR-1274b, hsa-miR-1826, hsa-let-7d*, hsa-miR-625, hsa-miR-378*, hsa-miR-183*, hsa-miR-877, hsa-miR-1283 | 75% | 83% | 67% |
| L-156 | SEQ ID NO: 402, SEQ ID NO: 660, SEQ ID NO: 574, SEQ ID NO: 48, SEQ ID NO: 776, SEQ ID NO: 773, SEQ ID NO: 283, SEQ ID NO: 93, SEQ ID NO: 29, SEQ ID NO: 316 | hsa-miR-378*, hsa-miR-183*, hsa-miR-21*, hsa-miR-877, hsa-miR-1283, hsa-miR-1286, hsa-miR-518f*, hsa-miR-659, hsa-miR-922, hsa-miR-508-5p | 72% | 75% | 68% |
| L-157 | SEQ ID NO: 773, SEQ ID NO: 283, SEQ ID NO: 93, SEQ ID NO: 29, SEQ ID NO: 316, SEQ ID NO: 665, SEQ ID NO: 501, SEQ ID NO: 11, SEQ ID NO: 60, SEQ ID NO: 814 | hsa-miR-1286, hsa-miR-518f*, hsa-miR-659, hsa-miR-922, hsa-miR-508-5p, hsa-miR-182*, hsa-miR-29c*, hsa-miR-942, hsa-miR-767-3p, hsa-miR-1256 | 71% | 80% | 62% |
| L-158 | SEQ ID NO: 665, SEQ ID NO: 501, SEQ ID NO: 11, SEQ ID NO: 60, SEQ ID NO: 814, SEQ ID NO: 421, SEQ ID NO: 664, SEQ ID NO: 274, SEQ ID NO: 852, SEQ ID NO: 356 | hsa-miR-182*, hsa-miR-29c*, hsa-miR-942, hsa-miR-767-3p, hsa-miR-1256, hsa-miR-369-5p, hsa-miR-1825, hsa-miR-519e*, hsa-miR-1206, hsa-miR-483-3p | 76% | 88% | 64% |

FIG. 11B (Cont.)

| | | | | |
|---|---|---|---|---|
| L-159 | SEQ ID NO: 421, SEQ ID NO: 664, SEQ ID NO: 274, SEQ ID NO: 852, SEQ ID NO: 366, SEQ ID NO: 560, SEQ ID NO: 754, SEQ ID NO: 36, SEQ ID NO: 477, SEQ ID NO: 683 | hsa-miR-369-5p, hsa-miR-1825, hsa-miR-519e*, hsa-miR-1206, hsa-miR-483-3p, hsa-miR-214*, hsa-miR-1303, hsa-miR-891b, hsa-miR-30e*, hsa-miR-155* | 69% | 77% | 60% |
| L-160 | SEQ ID NO: 560, SEQ ID NO: 754, SEQ ID NO: 36, SEQ ID NO: 477, SEQ ID NO: 683, SEQ ID NO: 84, SEQ ID NO: 842, SEQ ID NO: 437, SEQ ID NO: 106, SEQ ID NO: 149 | hsa-miR-214*, hsa-miR-1303, hsa-miR-891b, hsa-miR-30e*, hsa-miR-155*, hsa-miR-668, hsa-miR-1226, hsa-miR-34a*, hsa-miR-647, hsa-miR-610 | 72% | 75% | 68% |
| L-161 | SEQ ID NO: 84, SEQ ID NO: 842, SEQ ID NO: 437, SEQ ID NO: 106, SEQ ID NO: 149, SEQ ID NO: 720, SEQ ID NO: 511, SEQ ID NO: 18, SEQ ID NO: 95, SEQ ID NO: 238 | hsa-miR-668, hsa-miR-1226, hsa-miR-34a*, hsa-miR-647, hsa-miR-610, hsa-miR-141*, hsa-miR-297, hsa-miR-935, hsa-miR-657, hsa-miR-548a-3p | 65% | 73% | 58% |
| L-162 | SEQ ID NO: 720, SEQ ID NO: 511, SEQ ID NO: 18, SEQ ID NO: 95, SEQ ID NO: 238, SEQ ID NO: 55, SEQ ID NO: 580, SEQ ID NO: 707, SEQ ID NO: 605, SEQ ID NO: 809 | hsa-miR-141*, hsa-miR-297, hsa-miR-935, hsa-miR-657, hsa-miR-548a-3p, hsa-miR-802, hsa-miR-208b, hsa-miR-146b-3p, hsa-miR-199a-5p, hsa-miR-125a-5p | 72% | 81% | 63% |
| L-163 | SEQ ID NO: 329, SEQ ID NO: 216, SEQ ID NO: 788, SEQ ID NO: 199, SEQ ID NO: 663 | hsa-miR-500, hsa-miR-1274a, hsa-miR-564, hsa-miR-1826 | 66% | 73% | 59% |
| L-164 | SEQ ID NO: 470, SEQ ID NO: 635, SEQ ID NO: 787, SEQ ID NO: 896, SEQ ID NO: 402 | hsa-miR-320c, hsa-miR-1913, hsa-miR-1274b, hsa-let-7d*, hsa-miR-378* | 69% | 83% | 55% |
| L-165 | SEQ ID NO: 787, SEQ ID NO: 896, SEQ ID NO: 402, SEQ ID NO: 574, SEQ ID NO: 776 | hsa-miR-1274b, hsa-let-7d*, hsa-miR-378*, hsa-miR-21*, hsa-miR-1283 | 73% | 77% | 68% |
| L-166 | SEQ ID NO: 805, SEQ ID NO: 384, SEQ ID NO: 888 | hsa-miR-126, hsa-miR-423-5p, hsa-let-7i | 78% | 74% | 82% |
| L-167 | SEQ ID NO: 888, SEQ ID NO: 897, SEQ ID NO: 549 | hsa-let-7i, hsa-let-7d, hsa-miR-22 | 48% | 44% | 53% |
| L-168 | SEQ ID NO: 549, SEQ ID NO: 682, SEQ ID NO: 5 | hsa-miR-22, hsa-let-7d, hsa-miR-15a, hsa-miR-98 | 54% | 56% | 52% |
| L-169 | SEQ ID NO: 5, SEQ ID NO: 602, SEQ ID NO: 189 | hsa-miR-98, hsa-miR-19a, hsa-miR-574-5p | 65% | 78% | 52% |
| L-170 | SEQ ID NO: 189, SEQ ID NO: 466, SEQ ID NO: 577 | hsa-miR-574-5p, hsa-miR-324-3p, hsa-miR-20b | 73% | 72% | 74% |
| L-171 | SEQ ID NO: 577, SEQ ID NO: 526, SEQ ID NO: 622 | hsa-miR-20b, hsa-miR-25, hsa-miR-195 | 74% | 76% | 71% |
| L-172 | SEQ ID NO: 622, SEQ ID NO: 895, SEQ ID NO: 899 | hsa-miR-195, hsa-let-7e, hsa-let-7c | 58% | 55% | 61% |

FIG. 11B (Cont.)

| | | | | | |
|---|---|---|---|---|---|
| L-173 | SEQ ID NO: 899, SEQ ID NO: 893, SEQ ID NO: 904 | hsa-let-7c, hsa-let-7f, hsa-let-7a | 50% | 41% | 59% |
| L-174 | SEQ ID NO: 904, SEQ ID NO: 890, SEQ ID NO: 723 | hsa-let-7a, hsa-let-7g, hsa-miR-140-3p | 40% | 41% | 38% |
| L-175 | SEQ ID NO: 723, SEQ ID NO: 449, SEQ ID NO: 431 | hsa-miR-140-3p, hsa-miR-339-5p, hsa-miR-361-5p | 68% | 73% | 63% |
| L-176 | SEQ ID NO: 431, SEQ ID NO: 776, SEQ ID NO: 649 | hsa-miR-361-5p, hsa-miR-1283, hsa-miR-18a* | 74% | 79% | 69% |
| L-177 | SEQ ID NO: 649, SEQ ID NO: 521, SEQ ID NO: 155 | hsa-miR-18a*, hsa-miR-26b, hsa-miR-604 | 69% | 67% | 71% |
| L-178 | SEQ ID NO: 155, SEQ ID NO: 21, SEQ ID NO: 823 | hsa-miR-604, hsa-miR-93*, hsa-miR-1248 | 62% | 69% | 55% |
| L-179 | SEQ ID NO: 21, SEQ ID NO: 507, SEQ ID NO: 823 | hsa-miR-93*, hsa-miR-1248, hsa-miR-1248 | 65% | 76% | 54% |
| L-180 | SEQ ID NO: 823, SEQ ID NO: 573, SEQ ID NO: 600 | hsa-miR-1248, hsa-miR-210, hsa-miR-19b | 62% | 75% | 49% |
| L-181 | SEQ ID NO: 805, SEQ ID NO: 384, SEQ ID NO: 888, SEQ ID NO: 897, SEQ ID NO: 549 | hsa-miR-126, hsa-miR-423-5p, hsa-let-7i, hsa-let-7d, hsa-miR-22 | 74% | 70% | 78% |
| L-182 | SEQ ID NO: 888, SEQ ID NO: 897, SEQ ID NO: 549, SEQ ID NO: 682, SEQ ID NO: 5 | hsa-let-7i, hsa-let-7d, hsa-miR-22, hsa-miR-15a, hsa-miR-98 | 52% | 47% | 58% |
| L-183 | SEQ ID NO: 549, SEQ ID NO: 682, SEQ ID NO: 5, SEQ ID NO: 602, SEQ ID NO: 189 | hsa-miR-22, hsa-miR-15a, hsa-miR-98, hsa-miR-19a, hsa-miR-574-5p | 62% | 69% | 56% |
| L-184 | SEQ ID NO: 682, SEQ ID NO: 5, SEQ ID NO: 602, SEQ ID NO: 189, SEQ ID NO: 466 | hsa-miR-15a, hsa-miR-98, hsa-miR-19a, hsa-miR-574-5p, hsa-miR-324-3p | 67% | 72% | 63% |
| L-185 | SEQ ID NO: 602, SEQ ID NO: 189, SEQ ID NO: 466, SEQ ID NO: 577, SEQ ID NO: 526 | hsa-miR-19a, hsa-miR-574-5p, hsa-miR-324-3p, hsa-miR-20b, hsa-miR-25 | 75% | 73% | 78% |
| L-186 | SEQ ID NO: 466, SEQ ID NO: 577, SEQ ID NO: 526, SEQ ID NO: 622, SEQ ID NO: 895 | hsa-miR-324-3p, hsa-miR-20b, hsa-miR-25, hsa-miR-195, hsa-let-7e | 76% | 78% | 75% |
| L-187 | SEQ ID NO: 577, SEQ ID NO: 526, SEQ ID NO: 622, SEQ ID NO: 895, SEQ ID NO: 899, SEQ ID NO: 893 | hsa-miR-20b, hsa-miR-25, hsa-let-7e, hsa-let-7c, hsa-let-7f | 73% | 75% | 71% |
| L-188 | SEQ ID NO: 895, SEQ ID NO: 899, SEQ ID NO: 893, SEQ ID NO: 904, SEQ ID NO: 890, SEQ ID NO: 723 | hsa-let-7e, hsa-let-7c, hsa-let-7f, hsa-let-7a, hsa-let-7g, hsa-miR-140-3p | 49% | 49% | 49% |
| L-189 | SEQ ID NO: 904, SEQ ID NO: 890, SEQ ID NO: 723, SEQ ID NO: 449, SEQ ID NO: 431, SEQ ID NO: 776 | hsa-let-7a, hsa-let-7g, hsa-miR-140-3p, hsa-miR-339-5p, hsa-miR-361-5p, hsa-miR-1283 | 73% | 80% | 67% |

FIG. 11B (Cont.)

| | | | | | |
|---|---|---|---|---|---|
| L-190 | SEQ ID NO: 449, SEQ ID NO: 431, SEQ ID NO: 776, SEQ ID NO: 649, SEQ ID NO: 521, SEQ ID NO: 155 | hsa-miR-339-5p, hsa-miR-361-5p, hsa-miR-1283, hsa-miR-18a*, hsa-miR-26b, hsa-miR-604 | 72% | 70% | 74% |
| L-191 | SEQ ID NO: 649, SEQ ID NO: 521, SEQ ID NO: 155, SEQ ID NO: 385, SEQ ID NO: 21, SEQ ID NO: 507 | hsa-miR-18a*, hsa-miR-26b, hsa-miR-604, hsa-miR-423-3p, hsa-miR-93*, hsa-miR-29a | 69% | 67% | 72% |
| L-192 | SEQ ID NO: 385, SEQ ID NO: 21, SEQ ID NO: 507, SEQ ID NO: 823, SEQ ID NO: 573, SEQ ID NO: 600 | hsa-miR-423-3p, hsa-miR-93*, hsa-miR-29a, hsa-miR-1248, hsa-miR-210, hsa-miR-19b | 77% | 78% | 75% |
| L-193 | SEQ ID NO: 823, SEQ ID NO: 573, SEQ ID NO: 600, SEQ ID NO: 361, SEQ ID NO: 804, SEQ ID NO: 652 | hsa-miR-1248, hsa-miR-210, hsa-miR-19b, hsa-miR-453, hsa-miR-126*, hsa-miR-188-3p | 64% | 74% | 54% |
| L-194 | SEQ ID NO: 361, SEQ ID NO: 804, SEQ ID NO: 652, SEQ ID NO: 132, SEQ ID NO: 320, SEQ ID NO: 381 | hsa-miR-453, hsa-miR-126*, hsa-miR-188-3p, hsa-miR-624*, hsa-miR-505*, hsa-miR-425 | 69% | 78% | 60% |
| L-195 | SEQ ID NO: 132, SEQ ID NO: 320, SEQ ID NO: 381, SEQ ID NO: 450, SEQ ID NO: 84, SEQ ID NO: 427 | hsa-miR-624*, hsa-miR-505*, hsa-miR-425, hsa-miR-339-3p, hsa-miR-668, hsa-miR-363* | 72% | 77% | 68% |
| L-196 | SEQ ID NO: 805, SEQ ID NO: 384, SEQ ID NO: 888, SEQ ID NO: 897, SEQ ID NO: 549, SEQ ID NO: 682, SEQ ID NO: 5, SEQ ID NO: 602, SEQ ID NO: 189, SEQ ID NO: 466 | hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p | 77% | 74% | 79% |
| L-197 | SEQ ID NO: 682, SEQ ID NO: 5, SEQ ID NO: 602, SEQ ID NO: 189, SEQ ID NO: 466, SEQ ID NO: 577, SEQ ID NO: 526, SEQ ID NO: 622, SEQ ID NO: 895, SEQ ID NO: 899, SEQ ID NO: 893 | hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f | 79% | 80% | 77% |
| L-198 | SEQ ID NO: 526, SEQ ID NO: 622, SEQ ID NO: 895, SEQ ID NO: 899, SEQ ID NO: 893, SEQ ID NO: 904, SEQ ID NO: 890, SEQ ID NO: 723, SEQ ID NO: 449, SEQ ID NO: 431 | hsa-miR-25, hsa-let-7f, hsa-let-7a, hsa-let-7g, hsa-miR-140-3p, hsa-miR-339-5p, hsa-miR-361-5p | 73% | 77% | 69% |
| L-199 | SEQ ID NO: 904, SEQ ID NO: 890, SEQ ID NO: 431, SEQ ID NO: 723, SEQ ID NO: 449, SEQ ID NO: 776, SEQ ID NO: 649, SEQ ID NO: 521, SEQ ID NO: 155, SEQ ID NO: 385 | hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p | 76% | 73% | 80% |

FIG. 11B (Cont.)

| | | | | | |
|---|---|---|---|---|---|
| L-200 | SEQ ID NO: 776, SEQ ID NO: 649, SEQ ID NO: 521, SEQ ID NO: 155, SEQ ID NO: 385, SEQ ID NO: 21, SEQ ID NO: 507, SEQ ID NO: 823, SEQ ID NO: 573, SEQ ID NO: 600 | hsa-miR-1283, hsa-miR-18a*, hsa-miR-26b, hsa-miR-604, hsa-miR-423-3p, hsa-miR-93*, hsa-miR-29a, hsa-miR-1248, hsa-miR-210, hsa-miR-19b | 77% | 73% | 82% |
| L-201 | SEQ ID NO: 21, SEQ ID NO: 507, SEQ ID NO: 823, SEQ ID NO: 573, SEQ ID NO: 600, SEQ ID NO: 361, SEQ ID NO: 804, SEQ ID NO: 652, SEQ ID NO: 132, SEQ ID NO: 320 | hsa-miR-93*, hsa-miR-29a, hsa-miR-1248, hsa-miR-210, hsa-miR-19b, hsa-miR-453, hsa-miR-126*, hsa-miR-188-3p, hsa-miR-624*, hsa-miR-505* | 80% | 83% | 77% |
| L-202 | SEQ ID NO: 361, SEQ ID NO: 804, SEQ ID NO: 652, SEQ ID NO: 132, SEQ ID NO: 320, SEQ ID NO: 381, SEQ ID NO: 450, SEQ ID NO: 84, SEQ ID NO: 427, SEQ ID NO: 679 | hsa-miR-453, hsa-miR-126*, hsa-miR-188-3p, hsa-miR-624*, hsa-miR-505*, hsa-miR-425, hsa-miR-339-3p, hsa-miR-668, hsa-miR-363*, hsa-miR-15b* | 73% | 81% | 65% |
| L-203 | SEQ ID NO: 381, SEQ ID NO: 450, SEQ ID NO: 84, SEQ ID NO: 427, SEQ ID NO: 679, SEQ ID NO: 501, SEQ ID NO: 215, SEQ ID NO: 434, SEQ ID NO: 579, SEQ ID NO: 414 | hsa-miR-425, hsa-miR-339-3p, hsa-miR-668, hsa-miR-363*, hsa-miR-15b*, hsa-miR-29c*, hsa-miR-550*, hsa-miR-34c-3p, hsa-miR-374a | 73% | 76% | 69% |
| L-204 | SEQ ID NO: 501, SEQ ID NO: 215, SEQ ID NO: 434, SEQ ID NO: 579, SEQ ID NO: 414, SEQ ID NO: 712, SEQ ID NO: 495, SEQ ID NO: 876, SEQ ID NO: 478, SEQ ID NO: 540 | hsa-miR-29c*, hsa-miR-550*, hsa-miR-34c-3p, hsa-miR-20a, hsa-miR-374a, hsa-miR-145*, hsa-miR-302b, hsa-miR-106a, hsa-miR-30e, hsa-miR-223 | 70% | 73% | 68% |
| L-205 | SEQ ID NO: 805, SEQ ID NO: 888, SEQ ID NO: 549, SEQ ID NO: 5, SEQ ID NO: 189 | hsa-miR-126, hsa-let-7i, hsa-miR-22, hsa-miR-98, hsa-miR-574-5p | 72% | 68% | 76% |
| L-206 | SEQ ID NO: 897, SEQ ID NO: 682, SEQ ID NO: 602, SEQ ID NO: 466, SEQ ID NO: 526 | hsa-let-7d, hsa-miR-15a, hsa-miR-19a, hsa-miR-324-3p, hsa-miR-25 | 64% | 69% | 60% |
| L-207 | SEQ ID NO: 602, SEQ ID NO: 466, SEQ ID NO: 526, SEQ ID NO: 895, SEQ ID NO: 893 | hsa-miR-19a, hsa-miR-324-3p, hsa-miR-25, hsa-let-7e, hsa-let-7f | 68% | 74% | 62% |
| L-208 | SEQ ID NO: 431, SEQ ID NO: 531, SEQ ID NO: 805 | hsa-miR-361-5p, hsa-miR-23b, hsa-miR-126 | 72% | 79% | 65% |
| L-209 | SEQ ID NO: 805, SEQ ID NO: 250, SEQ ID NO: 507 | hsa-miR-126, hsa-miR-527, hsa-miR-29a | 77% | 73% | 82% |
| L-210 | SEQ ID NO: 507, SEQ ID NO: 888, SEQ ID NO: 602 | hsa-miR-29a, hsa-let-7i, hsa-miR-19a | 56% | 72% | 39% |
| L-211 | SEQ ID NO: 602, SEQ ID NO: 514, SEQ ID NO: 657 | hsa-miR-19a, hsa-miR-28-5p, hsa-miR-185* | 51% | 64% | 39% |
| L-212 | SEQ ID NO: 657, SEQ ID NO: 533, SEQ ID NO: 633 | hsa-miR-185*, hsa-miR-23a, hsa-miR-1914* | 52% | 54% | 51% |

FIG. 11B (Cont.)

| | | | | | |
|---|---|---|---|---|---|
| L-213 | SEQ ID NO: 633, SEQ ID NO: 502, SEQ ID NO: 320 | hsa-miR-1914*, hsa-miR-29c, hsa-miR-505* | 51% | 49% | 53% |
| L-214 | SEQ ID NO: 320, SEQ ID NO: 897, SEQ ID NO: 403 | hsa-miR-505*, hsa-let-7d, hsa-miR-378 | 49% | 40% | 58% |
| L-215 | SEQ ID NO: 403, SEQ ID NO: 505, SEQ ID NO: 155 | hsa-miR-378, hsa-miR-29b, hsa-miR-604 | 42% | 37% | 48% |
| L-216 | SEQ ID NO: 155, SEQ ID NO: 549, SEQ ID NO: 901 | hsa-miR-604, hsa-miR-22, hsa-let-7b | 44% | 44% | 43% |
| L-217 | SEQ ID NO: 901, SEQ ID NO: 509, SEQ ID NO: 385 | hsa-let-7b, hsa-miR-299-3p, hsa-miR-423-3p | 67% | 68% | 65% |
| L-218 | SEQ ID NO: 385, SEQ ID NO: 649, SEQ ID NO: 644 | hsa-miR-423-3p, hsa-miR-18a*, hsa-miR-1909 | 74% | 75% | 72% |
| L-219 | SEQ ID NO: 644, SEQ ID NO: 899, SEQ ID NO: 682 | hsa-miR-1909, hsa-let-7c, hsa-miR-15a | 59% | 57% | 61% |
| L-220 | SEQ ID NO: 682, SEQ ID NO: 21, SEQ ID NO: 478 | hsa-miR-15a, hsa-miR-93*, hsa-miR-30e | 61% | 69% | 52% |
| L-221 | SEQ ID NO: 21, SEQ ID NO: 85, SEQ ID NO: 478 | hsa-miR-93*, hsa-miR-665, hsa-miR-30e | 63% | 75% | 52% |
| L-222 | SEQ ID NO: 478, SEQ ID NO: 450, SEQ ID NO: 750 | hsa-miR-30e, hsa-miR-339-3p, hsa-miR-1307 | 49% | 54% | 44% |
| L-223 | SEQ ID NO: 431, SEQ ID NO: 531, SEQ ID NO: 805, SEQ ID NO: 250, SEQ ID NO: 507 | hsa-miR-361-5p, hsa-miR-23b, hsa-miR-126, hsa-miR-527, hsa-miR-29a | 76% | 76% | 76% |
| L-224 | SEQ ID NO: 805, SEQ ID NO: 250, SEQ ID NO: 507, SEQ ID NO: 888, SEQ ID NO: 602 | hsa-miR-126, hsa-miR-527, hsa-miR-29a, hsa-let-7i, hsa-miR-19a | 75% | 69% | 80% |
| L-225 | SEQ ID NO: 507, SEQ ID NO: 888, SEQ ID NO: 602, SEQ ID NO: 514, SEQ ID NO: 657 | hsa-miR-29a, hsa-let-7i, hsa-miR-19a, hsa-miR-28-5p, hsa-miR-185* | 46% | 52% | 40% |
| L-226 | SEQ ID NO: 888, SEQ ID NO: 602, SEQ ID NO: 514, SEQ ID NO: 657, SEQ ID NO: 533 | hsa-let-7i, hsa-miR-19a, hsa-miR-28-5p, hsa-miR-185*, hsa-miR-23a | 58% | 69% | 47% |
| L-227 | SEQ ID NO: 514, SEQ ID NO: 657, SEQ ID NO: 533, SEQ ID NO: 502 | hsa-miR-28-5p, hsa-miR-185*, hsa-miR-23a, hsa-miR-1914*, hsa-miR-29c | 54% | 60% | 47% |
| L-228 | SEQ ID NO: 533, SEQ ID NO: 633, SEQ ID NO: 502, SEQ ID NO: 320, SEQ ID NO: 897 | hsa-miR-23a, hsa-miR-1914*, hsa-miR-29c, hsa-miR-505*, hsa-let-7d | 55% | 62% | 49% |
| L-229 | SEQ ID NO: 633, SEQ ID NO: 502, SEQ ID NO: 320, SEQ ID NO: 897, SEQ ID NO: 403, SEQ ID NO: 505 | hsa-miR-1914*, hsa-miR-29c, hsa-miR-505*, hsa-let-7d, hsa-miR-378, hsa-miR-29b | 49% | 45% | 53% |

FIG. 11B (Cont.)

| | | | | | |
|---|---|---|---|---|---|
| L-230 | SEQ ID NO: 897, SEQ ID NO: 403, SEQ ID NO: 505, SEQ ID NO: 155, SEQ ID NO: 549, SEQ ID NO: 901 | hsa-let-7d, hsa-miR-378, hsa-miR-29b, hsa-miR-604, hsa-miR-22, hsa-let-7b | 51% | 46% | 55% |
| L-231 | SEQ ID NO: 155, SEQ ID NO: 549, SEQ ID NO: 901, SEQ ID NO: 509, SEQ ID NO: 385, SEQ ID NO: 649 | hsa-miR-604, hsa-miR-22, hsa-let-7b, hsa-miR-299-3p, hsa-miR-423-3p, hsa-miR-18a* | 68% | 73% | 63% |
| L-232 | SEQ ID NO: 509, SEQ ID NO: 385, SEQ ID NO: 649, SEQ ID NO: 644, SEQ ID NO: 899, SEQ ID NO: 682 | hsa-miR-299-3p, hsa-miR-423-3p, hsa-miR-18a*, hsa-miR-1909, hsa-let-7c, hsa-miR-15a | 73% | 75% | 71% |
| L-233 | SEQ ID NO: 644, SEQ ID NO: 899, SEQ ID NO: 682, SEQ ID NO: 381, SEQ ID NO: 21, SEQ ID NO: 85 | hsa-miR-1909, hsa-let-7c, hsa-miR-15a, hsa-miR-425, hsa-miR-93*, hsa-miR-665 | 69% | 75% | 62% |
| L-234 | SEQ ID NO: 381, SEQ ID NO: 21, SEQ ID NO: 85, SEQ ID NO: 478, SEQ ID NO: 450, SEQ ID NO: 750 | hsa-miR-425, hsa-miR-93*, hsa-miR-665, hsa-miR-30e, hsa-miR-339-3p, hsa-miR-1307 | 60% | 63% | 56% |
| L-235 | SEQ ID NO: 478, SEQ ID NO: 450, SEQ ID NO: 750, SEQ ID NO: 130, SEQ ID NO: 627, SEQ ID NO: 746 | hsa-miR-30e, hsa-miR-339-3p, hsa-miR-1307, hsa-miR-625*, hsa-miR-193a-5p, hsa-miR-130b | 62% | 67% | 57% |
| L-236 | SEQ ID NO: 130, SEQ ID NO: 627, SEQ ID NO: 746, SEQ ID NO: 674, SEQ ID NO: 189, SEQ ID NO: 466 | hsa-miR-625*, hsa-miR-193a-5p, hsa-miR-130b, hsa-miR-17*, hsa-miR-574-5p, hsa-miR-324-3p | 77% | 81% | 73% |
| L-237 | SEQ ID NO: 674, SEQ ID NO: 189, SEQ ID NO: 466, SEQ ID NO: 529, SEQ ID NO: 125, SEQ ID NO: 740 | hsa-miR-17*, hsa-miR-574-5p, hsa-miR-324-3p, hsa-miR-24, hsa-miR-629, hsa-miR-1323 | 70% | 76% | 63% |
| L-238 | SEQ ID NO: 431, SEQ ID NO: 531, SEQ ID NO: 805, SEQ ID NO: 250, SEQ ID NO: 507, SEQ ID NO: 888, SEQ ID NO: 602, SEQ ID NO: 514, SEQ ID NO: 657, SEQ ID NO: 533 | hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a | 77% | 82% | 72% |
| L-239 | SEQ ID NO: 888, SEQ ID NO: 602, SEQ ID NO: 514, SEQ ID NO: 657, SEQ ID NO: 533, SEQ ID NO: 633, SEQ ID NO: 502, SEQ ID NO: 320, SEQ ID NO: 897, SEQ ID NO: 403, SEQ ID NO: 505 | hsa-let-7i, hsa-miR-19a, hsa-miR-28-5p, hsa-miR-23a, hsa-miR-1914*, hsa-miR-29c, hsa-miR-185*, hsa-miR-505*, hsa-let-7d, hsa-miR-378, hsa-miR-29b | 55% | 55% | 54% |
| L-240 | SEQ ID NO: 502, SEQ ID NO: 320, SEQ ID NO: 897, SEQ ID NO: 403, SEQ ID NO: 505, SEQ ID NO: 155, SEQ ID NO: 549, SEQ ID NO: 901, SEQ ID NO: 509, SEQ ID NO: 385 | hsa-miR-29c, hsa-miR-505*, hsa-let-7d, hsa-miR-378, hsa-miR-29b, hsa-miR-604, hsa-miR-22, hsa-let-7b, hsa-miR-299-3p, hsa-miR-423-3p | 60% | 64% | 56% |

FIG. 11B (Cont.)

| | | | | |
|---|---|---|---|---|
| L-241 | SEQ ID NO: 155, SEQ ID NO: 549, SEQ ID NO: 901, SEQ ID NO: 509, SEQ ID NO: 385, SEQ ID NO: 649, SEQ ID NO: 644, SEQ ID NO: 899, SEQ ID NO: 682, SEQ ID NO: 381 | hsa-miR-604, hsa-miR-22, hsa-let-7b, hsa-miR-299-3p, hsa-miR-423-3p, hsa-miR-18a*, hsa-miR-1909, hsa-let-7c, hsa-miR-15a, hsa-miR-425 | 71% | 71% | 71% |
| L-242 | SEQ ID NO: 649, SEQ ID NO: 644, SEQ ID NO: 899, SEQ ID NO: 682, SEQ ID NO: 381, SEQ ID NO: 21, SEQ ID NO: 85, SEQ ID NO: 478, SEQ ID NO: 450, SEQ ID NO: 750 | hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307 | 75% | 80% | 70% |
| L-243 | SEQ ID NO: 21, SEQ ID NO: 85, SEQ ID NO: 478, SEQ ID NO: 450, SEQ ID NO: 750, SEQ ID NO: 130, SEQ ID NO: 627, SEQ ID NO: 746, SEQ ID NO: 674, SEQ ID NO: 189 | hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p | 75% | 78% | 72% |
| L-244 | SEQ ID NO: 130, SEQ ID NO: 627, SEQ ID NO: 746, SEQ ID NO: 674, SEQ ID NO: 529, SEQ ID NO: 466, SEQ ID NO: 529, SEQ ID NO: 125, SEQ ID NO: 740, SEQ ID NO: 890 | hsa-miR-625*, hsa-miR-17*, hsa-miR-574-5p, hsa-miR-193a-5p, hsa-miR-130b, hsa-miR-24, hsa-miR-629, hsa-miR-1323, hsa-let-7g | 76% | 83% | 70% |
| L-245 | SEQ ID NO: 466, SEQ ID NO: 529, SEQ ID NO: 125, SEQ ID NO: 740, SEQ ID NO: 890, SEQ ID NO: 825, SEQ ID NO: 559, SEQ ID NO: 693, SEQ ID NO: 703, SEQ ID NO: 101 | hsa-miR-324-3p, hsa-miR-24, hsa-miR-629, hsa-miR-1323, hsa-let-7g, hsa-miR-1246, hsa-miR-215, hsa-miR-151-3p, hsa-miR-1471, hsa-miR-652 | 69% | 74% | 64% |
| L-246 | SEQ ID NO: 825, SEQ ID NO: 559, SEQ ID NO: 693, SEQ ID NO: 703, SEQ ID NO: 101, SEQ ID NO: 679, SEQ ID NO: 573, SEQ ID NO: 449, SEQ ID NO: 577, SEQ ID NO: 98 | hsa-miR-1246, hsa-miR-215, hsa-miR-151-3p, hsa-miR-1471, hsa-miR-652, hsa-miR-15b*, hsa-miR-210, hsa-miR-339-5p, hsa-miR-20b, hsa-miR-654-5p | 69% | 72% | 65% |
| L-247 | SEQ ID NO: 431, SEQ ID NO: 805, SEQ ID NO: 507, SEQ ID NO: 602, SEQ ID NO: 657 | hsa-miR-361-5p, hsa-miR-126, hsa-miR-29a, hsa-miR-19a, hsa-miR-185* | 72% | 67% | 76% |
| L-248 | SEQ ID NO: 250, SEQ ID NO: 888, SEQ ID NO: 533, SEQ ID NO: 502 | hsa-miR-527, hsa-let-7i, hsa-miR-28-5p, hsa-miR-23a, hsa-miR-29c | 53% | 65% | 42% |
| L-249 | SEQ ID NO: 514, SEQ ID NO: 533, SEQ ID NO: 502, SEQ ID NO: 897, SEQ ID NO: 505 | hsa-miR-28-5p, hsa-miR-23a, hsa-miR-29c, hsa-let-7d, hsa-miR-29b | 54% | 58% | 50% |
| L-250 | SEQ ID NO: 605, SEQ ID NO: 385, SEQ ID NO: 600, SEQ ID NO: 458, SEQ ID NO: 896 | hsa-miR-199a-5p, hsa-miR-423-3p, hsa-miR-361-5p, hsa-miR-361-5p, hsa-miR-19b, hsa-miR-331-3p, hsa-let-7d* | 77% | 81% | 73% |
| L-251 | SEQ ID NO: 431, SEQ ID NO: 385, SEQ ID NO: 627, SEQ ID NO: 462, SEQ ID NO: 402 | hsa-miR-130b, hsa-miR-423-3p, hsa-miR-361-5p, hsa-miR-193a-5p, hsa-miR-328, hsa-miR-378* | 77% | 81% | 72% |

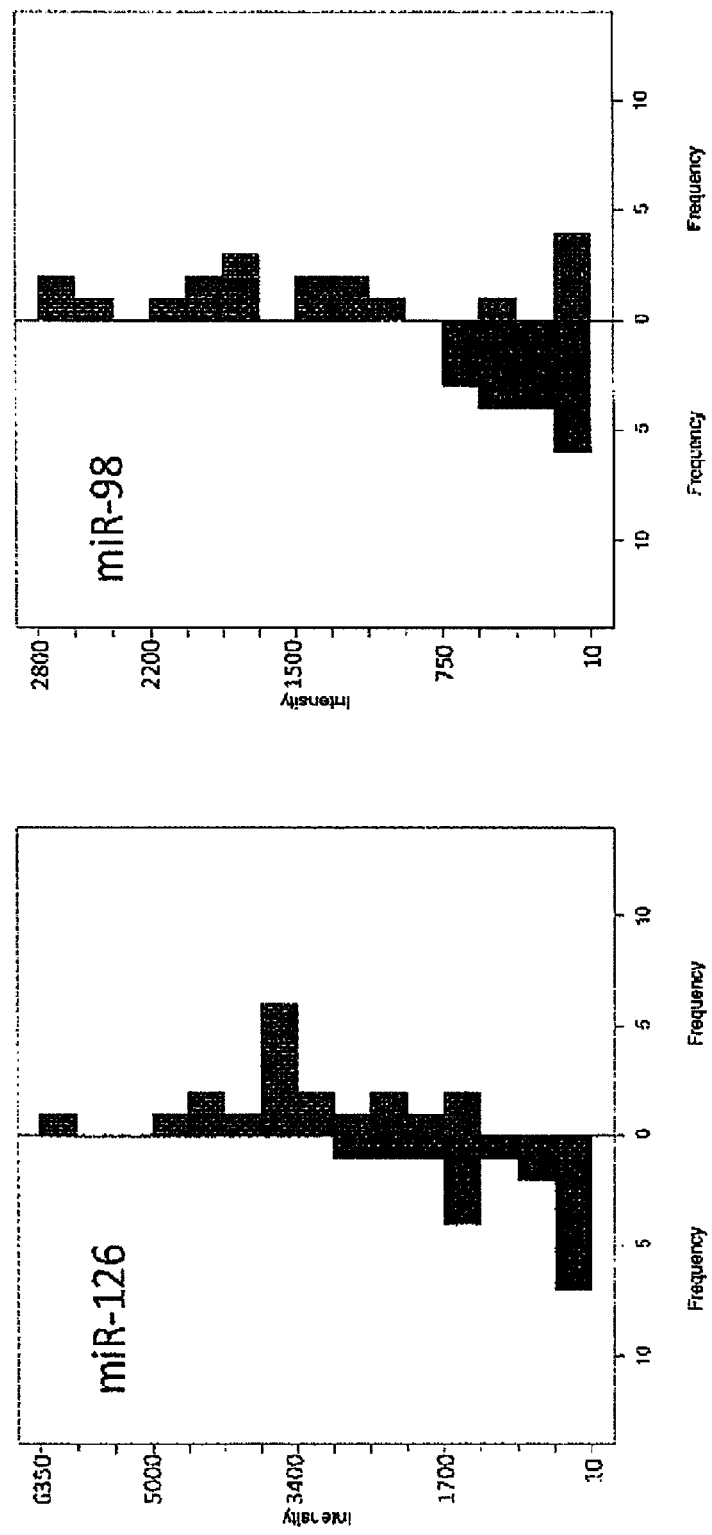

FIG. 18A

| SEQ ID NO | miRNA | Sequence | median g1 | median g2 | qmean | logqmedian | rawPval | adjPval | AUC |
|---|---|---|---|---|---|---|---|---|---|
| SEQ ID NO: 713 | hsa-miR-145 | guccaguuuuccaggaauccu | 602,719 | 174,344 | 3,457 | 1,240 | 6,08E-12 | 5,25E-09 | 0,962 |
| SEQ ID NO: 656 | hsa-miR-186 | caaagaauucucccuuugggcu | 265,295 | 77,719 | 3,414 | 1,228 | 7,91E-10 | 3,42E-07 | 0,961 |
| SEQ ID NO: 87 | hsa-miR-664 | uauucauuuaucccagccuaca | 707,168 | 285,703 | 2,475 | 0,906 | 4,17E-08 | 1,20E-05 | 0,916 |
| SEQ ID NO: 177 | hsa-miR-584 | uuauugguuugcccuggacugag | 332,922 | 106,969 | 3,112 | 1,135 | 1,15E-07 | 1,98E-05 | 0,897 |
| SEQ ID NO: 577 | hsa-miR-20b | caaagugcucauagugcagguag | 2689,207 | 5810,586 | 0,463 | -0,770 | 9,83E-08 | 1,98E-05 | 0,056 |
| SEQ ID NO: 540 | hsa-miR-223 | ugucaguuugucaaauaccca | 5118,574 | 2579,250 | 1,985 | 0,685 | 1,49E-07 | 2,14E-05 | 0,964 |
| SEQ ID NO: 386 | hsa-miR-422a | acuggacuuagggucagaagc | 373,953 | 189,219 | 1,976 | 0,681 | 2,32E-07 | 2,87E-05 | 0,870 |
| SEQ ID NO: 719 | hsa-miR-142-3p | uguauguuuccuacucuuuagga | 215,375 | 40,516 | 5,316 | 1,671 | 2,79E-07 | 3,01E-05 | 0,934 |
| SEQ ID NO: 899 | hsa-let-7c | ugagguaguaguuguguagguu | 1948,098 | 950,223 | 2,050 | 0,718 | 8,00E-07 | 7,68E-05 | 0,889 |
| SEQ ID NO: 693 | hsa-miR-151-3p | cuagacugaagcuccuugagg | 1021,363 | 571,344 | 1,788 | 0,581 | 1,81E-06 | 0 | 0,883 |
| SEQ ID NO: 341 | hsa-miR-491-5p | aguggggaacccuucccaugag | 241,000 | 153,563 | 1,569 | 0,451 | 2,05E-06 | 0 | 0,876 |
| SEQ ID NO: 11 | hsa-miR-942 | ucuucucguuuuugccaugu | 112,969 | 38,094 | 2,966 | 1,087 | 5,09E-06 | 0 | 0,882 |
| SEQ ID NO: 432 | hsa-miR-361-3p | uccccagguguggauucugauuu | 325,766 | 181,375 | 1,796 | 0,586 | 5,77E-06 | 0 | 0,852 |
| SEQ ID NO: 548 | hsa-miR-22* | aguucucagugcaaagcuuua | 178,938 | 103,844 | 1,723 | 0,544 | 6,24E-06 | 0 | 0,868 |
| SEQ ID NO: 722 | hsa-miR-140-5p | caguguuuuaccuauggag | 105,063 | 48,250 | 2,177 | 0,778 | 7,99E-06 | 0 | 0,874 |
| SEQ ID NO: 558 | hsa-miR-216a | uaaucucagcugccaacuga | 202,219 | 315,828 | 0,640 | -0,446 | 8,24E-06 | 0 | 0,060 |
| SEQ ID NO: 786 | hsa-miR-1275 | gugggagaggcugc | 210,203 | 116,969 | 1,797 | 0,586 | 7,04E-06 | 0 | 0,907 |
| SEQ ID NO: 424 | hsa-miR-367 | aauugcacuuuagacaaugga | 92,500 | 160,375 | 0,577 | -0,550 | 8,32E-06 | 0 | 0,138 |
| SEQ ID NO: 709 | hsa-miR-146a | ugagaacugaauuccauggau | 470,359 | 271,342 | 1,733 | 0,550 | 9,61E-06 | 0 | 0,862 |
| SEQ ID NO: 161 | hsa-miR-598 | uacgucaucguugucaucguca | 140,531 | 91,000 | 1,544 | 0,435 | 1,29E-05 | 0 | 0,841 |
| SEQ ID NO: 146 | hsa-miR-613 | aggaauguuccuucuugcc | 60,781 | 19,000 | 3,199 | 1,163 | 1,67E-05 | 0 | 0,862 |
| SEQ ID NO: 649 | hsa-miR-18a* | acugcccuaagugccuuucug | 490,891 | 233,672 | 2,101 | 0,742 | 2,02E-05 | 0 | 0,876 |
| SEQ ID NO: 495 | hsa-miR-302b | uaagugcuuccauguuuuagag | 54,469 | 21,406 | 2,545 | 0,934 | 2,23E-05 | 0 | 0,855 |
| SEQ ID NO: 326 | hsa-miR-501-5p | aauccuuugcccuggagugaga | 139,938 | 79,563 | 1,759 | 0,565 | 2,60E-05 | 0 | 0,866 |
| SEQ ID NO: 478 | hsa-miR-30e | uguaaacauccuugacugaag | 687,488 | 383,609 | 1,792 | 0,583 | 3,66E-05 | 0 | 0,836 |
| SEQ ID NO: 37 | hsa-miR-891a | ugcaacgaaccugagccacuga | 134,250 | 177,000 | 0,758 | -0,276 | 4,27E-05 | 0 | 0,153 |
| SEQ ID NO: 23 | hsa-miR-92b* | agggacgggacgcgugcagug | 400,766 | 179,266 | 2,236 | 0,805 | 4,65E-05 | 0 | 0,926 |
| SEQ ID NO: 429 | hsa-miR-362-5p | aaucuuggaaccuaggugugagu | 353,859 | 211,313 | 1,675 | 0,516 | 5,35E-05 | 0 | 0,830 |
| SEQ ID NO: 756 | hsa-miR-1301 | uugcagugcucuggagugacuuc | 240,098 | 340,063 | 0,706 | -0,348 | 5,65E-05 | 0 | 0,149 |
| SEQ ID NO: 562 | hsa-miR-212 | uaacagucuuguagcugucaagcc | 62,594 | 93,656 | 0,668 | -0,403 | 6,35E-05 | 0 | 0,166 |
| SEQ ID NO: 543 | hsa-miR-221* | accuggcauacaaugagcuagauuu | 127,688 | 203,438 | 0,628 | -0,466 | 7,85E-05 | 0 | 0,162 |
| SEQ ID NO: 203 | hsa-miR-559 | uaaagugauuaugcaccaaaa | 81,875 | 128,203 | 0,639 | -0,448 | 7,87E-05 | 0 | 0,151 |
| SEQ ID NO: 657 | hsa-miR-185* | agggcuuccuucucuccuug | 70,391 | 28,922 | 2,434 | 0,889 | 8,45E-05 | 0 | 0,866 |
| SEQ ID NO: 791 | hsa-miR-1272 | gauaugaugcagcaaauucugaaa | 163,438 | 234,672 | 0,696 | -0,362 | 8,43E-05 | 0 | 0,131 |
| SEQ ID NO: 487 | hsa-miR-30a | uguaaacauccucgacugaag | 747,559 | 472,016 | 1,584 | 0,460 | 9,38E-05 | 0 | 0,778 |
| SEQ ID NO: 644 | hsa-miR-1909 | cgcaggggccggguggucaccg | 238,063 | 181,375 | 1,313 | 0,272 | 9,16E-05 | 0 | 0,843 |

FIG. 18A (Cont.)

| | | | | | | |
|---|---|---|---|---|---|---|
| SEQ ID NO: 306 | hsa-miR-513b | uucacaaggagugucauuuau | 60,063 | 95,219 | 0,631 | -0,461 | 0 | 0,155 |
| SEQ ID NO: 206 | hsa-miR-556-5p | gaugagcucauuguaauaugag | 163,469 | 242,703 | 0,674 | -0,395 | 0 | 0,165 |
| SEQ ID NO: 426 | hsa-miR-365 | uaaugcccuaaaaauccuuau | 231,453 | 132,344 | 1,749 | 0,559 | 0 | 0,841 |
| SEQ ID NO: 254 | hsa-miR-525-5p | cuccagaggaugcacuuucu | 139,281 | 172,344 | 0,808 | -0,213 | 0 | 0,178 |
| SEQ ID NO: 80 | hsa-miR-675 | uggugcggagagggcccacagug | 372,719 | 257,121 | 1,450 | 0,371 | 0 | 0,785 |
| SEQ ID NO: 820 | hsa-miR-1251 | acucuagcugcaaggcgcu | 189,469 | 250,242 | 0,757 | -0,278 | 0 | 0,192 |
| SEQ ID NO: 190 | hsa-miR-574-3p | cacgcucaugcacacaccaca | 1063,672 | 2186,746 | 0,486 | -0,721 | 0 | 0,163 |
| SEQ ID NO: 331 | hsa-miR-499-3p | aacaucacagcaagucugugcu | 135,750 | 187,219 | 0,725 | -0,321 | 0 | 0,138 |
| SEQ ID NO: 865 | hsa-miR-1180 | uuuccggcucgcguggugu | 186,969 | 99,344 | 1,882 | 0,632 | 0 | 0,820 |
| SEQ ID NO: 605 | hsa-miR-199a-5p | cccaguguucagcuaccuguuc | 655,146 | 394,469 | 1,661 | 0,507 | 0 | 0,809 |
| SEQ ID NO: 342 | hsa-miR-491-3p | cuuagcaagauuccuucac | 126,578 | 172,438 | 0,734 | -0,309 | 0 | 0,175 |
| SEQ ID NO: 502 | hsa-miR-29c | uagcaccauuugaaaucgguua | 953,881 | 628,578 | 1,518 | 0,417 | 0 | 0,782 |
| SEQ ID NO: 460 | hsa-miR-330-3p | gcaaagcacacgccugcagaga | 344,703 | 594,125 | 0,580 | -0,544 | 0 | 0,120 |
| SEQ ID NO: 131 | hsa-miR-625 | agggggaaaguucuauagucc | 293,266 | 129,938 | 2,257 | 0,814 | 0 | 0,804 |
| SEQ ID NO: 674 | hsa-miR-17* | acuacgcagaaggcacuuguag | 877,000 | 1154,039 | 0,760 | -0,275 | 0 | 0,169 |
| SEQ ID NO: 896 | hsa-let-7d* | cuauacgacccugcuuucu | 148,656 | 93,813 | 1,585 | 0,460 | 0 | 0,801 |
| SEQ ID NO: 6 | hsa-miR-96* | aauuacgugcagugccaauaug | 239,391 | 340,422 | 0,703 | -0,352 | 0 | 0,188 |
| SEQ ID NO: 809 | hsa-miR-125a-5p | ucccugagacccuuuaaccuguga | 523,871 | 251,680 | 2,081 | 0,733 | 0 | 0,808 |
| SEQ ID NO: 745 | hsa-miR-130b* | acucuuuccugguugcacuac | 84,156 | 35,969 | 2,340 | 0,850 | 0 | 0,850 |
| SEQ ID NO: 561 | hsa-miR-214 | acagcaggcacagacaggcagu | 337,141 | 526,555 | 0,640 | -0,446 | 0,01 | 0,213 |
| SEQ ID NO: 600 | hsa-miR-19b | ugugcaaauccaugcaaaacuga | 12385,297 | 10067,539 | 1,230 | 0,207 | 0,01 | 0,817 |
| SEQ ID NO: 125 | hsa-miR-629 | uggguuuacguuggagaacu | 333,625 | 60,813 | 5,486 | 1,702 | 0,01 | 0,824 |
| SEQ ID NO: 51 | hsa-miR-875-5p | uauaccucaguuuuaucaggug | 45,844 | 85,094 | 0,539 | -0,619 | 0,01 | 0,198 |
| SEQ ID NO: 872 | hsa-miR-107 | agcagcauuguacagggcuauca | 1014,779 | 2342,613 | 0,433 | -0,837 | 0,01 | 0,148 |
| SEQ ID NO: 580 | hsa-miR-208b | auaagacgaacaaaaggguuugu | 106,625 | 155,875 | 0,684 | -0,380 | 0,01 | 0,205 |
| SEQ ID NO: 578 | hsa-miR-20a* | acugcauuaugagcacuuaaag | 203,156 | 264,654 | 0,768 | -0,264 | 0,01 | 0,134 |
| SEQ ID NO: 670 | hsa-miR-181b | aacauucauugcugucgguggu | 131,875 | 77,641 | 1,699 | 0,530 | 0,01 | 0,807 |
| SEQ ID NO: 78 | hsa-miR-7 | uggaagacuagugauuuuguugu | 221,484 | 80,875 | 2,739 | 1,007 | 0,01 | 0,851 |
| SEQ ID NO: 645 | hsa-miR-1908 | cggcggggacggcgauugguc | 2635,699 | 1175,980 | 2,241 | 0,807 | 0,01 | 0,815 |
| SEQ ID NO: 25 | hsa-miR-92a-2* | gggugggggauuuguugcauuac | 52,438 | 28,000 | 1,873 | 0,627 | 0,01 | 0,786 |
| SEQ ID NO: 874 | hsa-miR-106b | uaaagugcugacagugcagau | 13747,000 | 18271,367 | 0,752 | -0,285 | 0,01 | 0,207 |
| SEQ ID NO: 62 | hsa-miR-765 | uggagaagcugaggugaug | 144,219 | 90,422 | 1,595 | 0,467 | 0,01 | 0,784 |
| SEQ ID NO: 701 | hsa-miR-148a | ucagugcacuacagaacuuugu | 845,109 | 1094,980 | 0,772 | -0,259 | 0,01 | 0,188 |
| SEQ ID NO: 423 | hsa-miR-367* | acuguugcaauaugcaauucu | 99,219 | 160,594 | 0,618 | -0,482 | 0,01 | 0,194 |
| SEQ ID NO: 182 | hsa-miR-580 | uuagaauugaugaaucauuagg | 79,594 | 160,594 | 0,788 | -0,238 | 0,01 | 0,201 |
| SEQ ID NO: 362 | hsa-miR-452* | cucaucucaaauggaagugg | 402,109 | 803,891 | 0,500 | -0,693 | 0,01 | 0,104 |
| SEQ ID NO: 881 | hsa-miR-103 | agcagcauuguacagggcuauga | 4825,438 | 9424,113 | 0,512 | -0,669 | 0,01 | 0,201 |

FIG. 18A (Cont.)

| | | | | | | | | |
|---|---|---|---|---|---|---|---|---|
| SEQ ID NO: 152 | hsa-miR-607 | guucaaauccagaucuauaac | 128,625 | 179,688 | 0,716 | -0,334 | 0 | 0,01 | 0,211 |
| SEQ ID NO: 652 | hsa-miR-188-3p | cucccacaugcaggcagguuugca | 206,469 | 259,949 | 0,794 | -0,230 | 0 | 0,01 | 0,217 |
| SEQ ID NO: 136 | hsa-miR-621 | ggcuaguaacagcgucccuuaccu | 371,266 | 644,535 | 0,576 | -0,552 | 0 | 0,01 | 0,178 |
| SEQ ID NO: 24 | hsa-miR-92b | uauugcacugucucaaaugagcuccc | 492,328 | 353,859 | 1,391 | 0,330 | 0 | 0,01 | 0,789 |
| SEQ ID NO: 730 | hsa-miR-136* | caucaucgucucaaaugagucu | 100,875 | 145,625 | 0,693 | -0,367 | 0 | 0,01 | 0,190 |
| SEQ ID NO: 153 | hsa-miR-606 | aaaacuacugaaaaucaaagau | 121,578 | 182,750 | 0,665 | -0,408 | 0 | 0,01 | 0,197 |
| SEQ ID NO: 402 | hsa-miR-378* | cuccugacuccaggucccugugu | 133,844 | 81,859 | 1,635 | 0,492 | 0 | 0,01 | 0,772 |
| SEQ ID NO: 622 | hsa-miR-195 | uagcagcacagaaauauuggc | 665,008 | 917,941 | 0,724 | -0,322 | 0 | 0,01 | 0,211 |
| SEQ ID NO: 398 | hsa-miR-380* | ugguugaccauagaacaugcc | 139,844 | 180,094 | 0,777 | -0,253 | 0 | 0,01 | 0,227 |
| SEQ ID NO: 660 | hsa-miR-183* | gugaauuaccgagggccauaa | 237,781 | 164,250 | 1,448 | 0,370 | 0 | 0,01 | 0,787 |
| SEQ ID NO: 529 | hsa-miR-24 | uggcucaguucagcaggaacag | 1714,877 | 2633,414 | 0,651 | -0,429 | 0 | 0,01 | 0,106 |
| SEQ ID NO: 165 | hsa-miR-593* | aggcaccagcaggcaugcucagc | 338,547 | 495,953 | 0,683 | -0,382 | 0 | 0,01 | 0,208 |
| SEQ ID NO: 32 | hsa-miR-9* | auaaagcuagauaaccgaaagu | 140,594 | 182,406 | 0,771 | -0,260 | 0 | 0,01 | 0,219 |
| SEQ ID NO: 107 | hsa-miR-646 | aagcagcugcccuuucccag | 316,328 | 489,273 | 0,647 | -0,436 | 0 | 0,01 | 0,176 |
| SEQ ID NO: 840 | hsa-miR-1227 | cgugccaccuuuuuccccag | 157,438 | 105,266 | 1,496 | 0,403 | 0 | 0,01 | 0,752 |
| SEQ ID NO: 492 | hsa-miR-302c* | uuuaacaugggguaccugcug | 50,688 | 69,000 | 0,735 | -0,308 | 0 | 0,01 | 0,259 |
| SEQ ID NO: 346 | hsa-miR-488* | cccagauaaugguacacucuca | 126,141 | 151,813 | 0,831 | -0,185 | 0 | 0,01 | 0,248 |
| SEQ ID NO: 135 | hsa-miR-622 | acagucugagguugagc | 120,484 | 159,359 | 0,756 | -0,280 | 0 | 0,01 | 0,229 |
| SEQ ID NO: 97 | hsa-miR-655 | auauaacaaguuaaccucuuu | 71,547 | 116,313 | 0,615 | -0,486 | 0 | 0,01 | 0,231 |
| SEQ ID NO: 876 | hsa-miR-106a | aaaagugcuuacaguguccagguag | 9424,113 | 12784,891 | 0,737 | -0,305 | 0 | 0,01 | 0,179 |
| SEQ ID NO: 127 | hsa-miR-628-3p | ucuaguaagaguggcaguga | 313,141 | 198,219 | 1,580 | 0,457 | 0 | 0,01 | 0,777 |
| SEQ ID NO: 329 | hsa-miR-500 | uaaucccuugcuaccuggugaga | 619,078 | 427,422 | 1,448 | 0,370 | 0 | 0,01 | 0,760 |
| SEQ ID NO: 189 | hsa-miR-574-5p | ugagugugugugugugagugugu | 787,578 | 1535,777 | 0,513 | -0,668 | 0 | 0,01 | 0,145 |
| SEQ ID NO: 196 | hsa-miR-568 | auguauaaaaugugauauacac | 140,906 | 201,219 | 0,700 | -0,356 | 0 | 0,01 | 0,264 |
| SEQ ID NO: 817 | hsa-miR-1254 | agccuggaagcugagcugccagu | 197,250 | 227,516 | 0,867 | -0,143 | 0 | 0,01 | 0,231 |
| SEQ ID NO: 315 | hsa-miR-509-3-5p | uacugcagacaguggcaaucaug | 310,703 | 512,930 | 0,606 | -0,501 | 0 | 0,01 | 0,211 |
| SEQ ID NO: 274 | hsa-miR-519e* | uucuccaaaaggagcucuucauu | 76,375 | 122,406 | 0,624 | -0,472 | 0 | 0,01 | 0,244 |
| SEQ ID NO: 338 | hsa-miR-493* | uuguacauggugccuuuucauu | 63,047 | 96,094 | 0,656 | -0,421 | 0 | 0,01 | 0,217 |
| SEQ ID NO: 834 | hsa-miR-1234 | ucggccugaccacccaccccac | 367,734 | 558,242 | 0,659 | -0,417 | 0 | 0,01 | 0,248 |
| SEQ ID NO: 505 | hsa-miR-29b | uagcaccauuugaaaucaguguu | 632,156 | 416,641 | 1,517 | 0,417 | 0 | 0,02 | 0,815 |
| SEQ ID NO: 779 | hsa-miR-1280 | ucccacccgcugccaccc | 5556,648 | 3055,430 | 1,819 | 0,598 | 0 | 0,02 | 0,763 |
| SEQ ID NO: 334 | hsa-miR-497 | cagcagcacacuguguuugu | 225,906 | 277,840 | 0,813 | -0,207 | 0 | 0,02 | 0,196 |
| SEQ ID NO: 557 | hsa-miR-216b | aaaucucugcaggcaaauguga | 198,953 | 303,781 | 0,655 | -0,423 | 0 | 0,02 | 0,217 |
| SEQ ID NO: 901 | hsa-let-7b | ugagguaguaggugugugguu | 3354,297 | 1788,242 | 1,876 | 0,629 | 0 | 0,02 | 0,787 |
| SEQ ID NO: 666 | hsa-miR-182 | uuuggcaaugguagaacucacacu | 2951,227 | 4465,605 | 0,661 | -0,414 | 0 | 0,02 | 0,237 |
| SEQ ID NO: 544 | hsa-miR-221 | agcuacauugucugcuggguuuc | 272,467 | 170,750 | 1,596 | 0,467 | 0 | 0,02 | 0,777 |
| SEQ ID NO: 792 | hsa-miR-1271 | cuugcaccuagcaagcacuca | 321,375 | 392,281 | 0,819 | -0,199 | 0 | 0,02 | 0,286 |

FIG. 18A (Cont.)

| | | | | | | | |
|---|---|---|---|---|---|---|---|
| SEQ ID NO: 886 | hsa-miR-1 | uggaauguaaagaaguauguau | 45,531 | 75,875 | 0,600 | -0,511 | 0 | 0,02 | 0,247 |
| SEQ ID NO: 158 | hsa-miR-601 | ugguccuaggauugcuuggaggag | 75,625 | 28,781 | 2,628 | 0,966 | 0 | 0,02 | 0,770 |
| SEQ ID NO: 671 | hsa-miR-181a-2* | accacugaccguugacugacc | 196,656 | 131,906 | 1,491 | 0,399 | 0 | 0,02 | 0,776 |
| SEQ ID NO: 963 | hsa-miR-1300 | uugagaaggaggcugug | 65,344 | 99,547 | 0,656 | -0,421 | 0 | 0,02 | 0,273 |
| SEQ ID NO: 518 | hsa-miR-27a* | agggcuuagcugcuugugagca | 81,188 | 104,938 | 0,774 | -0,257 | 0 | 0,02 | 0,256 |
| SEQ ID NO: 105 | hsa-miR-648 | aagugugcagggcacuggu | 75,516 | 115,859 | 0,652 | -0,428 | 0 | 0,02 | 0,233 |
| SEQ ID NO: 507 | hsa-miR-29a | uagcaccaucugaaaucgguua | 1010,279 | 828,117 | 1,220 | 0,199 | 0 | 0,02 | 0,723 |
| SEQ ID NO: 757 | hsa-miR-1299 | uucuggaauucugugugaggga | 64,531 | 44,328 | 1,456 | 0,376 | 0 | 0,02 | 0,763 |
| SEQ ID NO: 755 | hsa-miR-1302 | uuggacauacuuaugcuaaa | 69,438 | 92,766 | 0,749 | -0,290 | 0 | 0,02 | 0,263 |
| SEQ ID NO: 14 | hsa-miR-939 | uggggagcugaggcucugggguug | 177,156 | 93,703 | 1,891 | 0,637 | 0 | 0,02 | 0,833 |
| SEQ ID NO: 776 | hsa-miR-1283 | ucuacaaggaaagcgcuuucu | 161,094 | 193,188 | 0,834 | -0,182 | 0 | 0,02 | 0,217 |
| SEQ ID NO: 824 | hsa-miR-1247 | acccguccguucgucccgga | 143,000 | 107,500 | 1,330 | 0,285 | 0 | 0,02 | 0,773 |
| SEQ ID NO: 345 | hsa-miR-489 | guacaucacauauacggcagc | 234,453 | 368,422 | 0,636 | -0,452 | 0 | 0,02 | 0,282 |
| SEQ ID NO: 636 | hsa-miR-1912 | uaccagagcaugcagugugaa | 229,156 | 285,344 | 0,803 | -0,219 | 0 | 0,02 | 0,180 |
| SEQ ID NO: 473 | hsa-miR-32* | caauuuaguguguguauauuu | 49,938 | 81,938 | 0,609 | -0,495 | 0 | 0,02 | 0,219 |
| SEQ ID NO: 579 | hsa-miR-20a | uaaagugcuuauagugcagguag | 5322,336 | 7318,813 | 0,727 | -0,319 | 0 | 0,02 | 0,274 |
| SEQ ID NO: 843 | hsa-miR-1225-5p | guugguacggccagugggggg | 172,766 | 117,938 | 1,465 | 0,382 | 0 | 0,02 | 0,762 |
| SEQ ID NO: 441 | hsa-miR-342-5p | aggggugcuaucugugauuga | 249,848 | 170,625 | 1,464 | 0,381 | 0 | 0,02 | 0,740 |
| SEQ ID NO: 804 | hsa-miR-126* | cauuauuacuuuugguacgcg | 78,438 | 40,438 | 1,940 | 0,663 | 0 | 0,02 | 0,723 |
| SEQ ID NO: 477 | hsa-miR-30e* | cuuucagucgaugguuuacagc | 152,438 | 107,422 | 1,419 | 0,350 | 0 | 0,02 | 0,731 |
| SEQ ID NO: 70 | hsa-miR-744 | ugcggggcuagggcuaacagca | 866,453 | 1256,912 | 0,689 | -0,372 | 0 | 0,02 | 0,240 |
| SEQ ID NO: 462 | hsa-miR-328 | cuggcccucucugcccuccgu | 203,172 | 86,063 | 2,361 | 0,859 | 0 | 0,02 | 0,752 |
| SEQ ID NO: 430 | hsa-miR-362-3p | aacacaccuauucaaggauuca | 446,391 | 279,703 | 1,596 | 0,467 | 0 | 0,02 | 0,773 |
| SEQ ID NO: 887 | hsa-let-7i* | cugcgcaaguacugccuugcu | 303,922 | 408,766 | 0,744 | -0,296 | 0 | 0,02 | 0,219 |
| SEQ ID NO: 237 | hsa-miR-548a-5p | aaaaguaaaugcgagauuuuuacc | 49,938 | 68,469 | 0,729 | -0,316 | 0 | 0,02 | 0,286 |
| SEQ ID NO: 448 | hsa-miR-33a | gugcauuguaguugcauuqca | 168,473 | 215,250 | 0,783 | -0,245 | 0 | 0,02 | 0,276 |
| SEQ ID NO: 743 | hsa-miR-132* | accgguccuuugauuguaacu | 34,641 | 18,875 | 1,835 | 0,607 | 0 | 0,02 | 0,739 |
| SEQ ID NO: 556 | hsa-miR-217 | uacugcaucaggaacugauuqga | 217,813 | 299,188 | 0,728 | -0,317 | 0 | 0,02 | 0,244 |
| SEQ ID NO: 850 | hsa-miR-1207-5p | ugggggcaggagggcugggggg | 1108,230 | 462,172 | 2,398 | 0,875 | 0 | 0,02 | 0,816 |
| SEQ ID NO: 194 | hsa-miR-670 | cgaaaacagcaauuaccuugc | 125,156 | 159,594 | 0,784 | -0,243 | 0 | 0,02 | 0,242 |
| SEQ ID NO: 475 | hsa-miR-31* | ugcuaugccaacauauuqccau | 231,188 | 305,781 | 0,756 | -0,280 | 0 | 0,02 | 0,220 |
| SEQ ID NO: 323 | hsa-miR-503 | uagcagcgggaacagüucugcag | 396,297 | 524,176 | 0,756 | -0,280 | 0 | 0,02 | 0,284 |
| SEQ ID NO: 762 | hsa-miR-1295 | uuaggccgcagaucugguga | 141,672 | 177,688 | 0,797 | -0,227 | 0 | 0,02 | 0,787 |
| SEQ ID NO: 94 | hsa-miR-658 | ggcggaggaaguggucgguugu | 123,781 | 71,375 | 1,734 | 0,551 | 0 | 0,02 | 0,290 |
| SEQ ID NO: 699 | hsa-miR-148b | ucagugcaucacagaacuuugu | 765,852 | 953,881 | 0,803 | -0,220 | 0 | 0,02 | 0,759 |
| SEQ ID NO: 842 | hsa-miR-1226 | ugacagccugcugugugccccag | 157,594 | 120,781 | 1,305 | 0,266 | 0 | 0,03 | 0,288 |
| SEQ ID NO: 241 | hsa-miR-544 | auucugcauuuuuagcaaguuc | 76,313 | 100,797 | 0,757 | -0,278 | 0 | 0,03 | 0,288 |

FIG. 18A (Cont.)

| | | | | | | | | |
|---|---|---|---|---|---|---|---|---|
| SEQ ID NO: 46 | hsa-miR-885-3p | aggcagcggggugugaguggaua | 398,484 | 226,844 | 1,757 | 0,563 | 0 | 0,03 | 0,781 |
| SEQ ID NO: 525 | hsa-miR-25* | aggcggagacuugggcaauug | 140,594 | 101,172 | 1,390 | 0,329 | 0 | 0,03 | 0,739 |
| SEQ ID NO: 19 | hsa-miR-934 | ugucuacuacuggagacacugg | 136,563 | 175,625 | 0,778 | -0,252 | 0 | 0,03 | 0,258 |
| SEQ ID NO: 4 | hsa-miR-99a | aaccguagauccgaucugugu | 271,453 | 160,375 | 1,693 | 0,526 | 0 | 0,03 | 0,750 |
| SEQ ID NO: 199 | hsa-miR-564 | aggcacggguucagcaggc | 217,969 | 275,764 | 0,790 | -0,235 | 0 | 0,03 | 0,228 |
| SEQ ID NO: 106 | hsa-miR-647 | guggcugcacucacuuccuuc | 94,328 | 126,563 | 0,745 | -0,294 | 0,01 | 0,03 | 0,264 |
| SEQ ID NO: 501 | hsa-miR-29c* | ugagcgauuucucugguguuc | 67,047 | 30,250 | 2,216 | 0,796 | 0,01 | 0,03 | 0,736 |
| SEQ ID NO: 795 | hsa-miR-1268 | cgggcguggugguggg | 612,344 | 259,070 | 2,364 | 0,860 | 0,01 | 0,03 | 0,802 |
| SEQ ID NO: 391 | hsa-miR-1268 | aauauaacacagaugggccgu | 144,219 | 208,125 | 0,693 | -0,367 | 0,01 | 0,03 | 0,321 |
| SEQ ID NO: 773 | hsa-miR-1286 | ugcaggaccaagagagccccu | 179,094 | 220,125 | 0,814 | -0,206 | 0,01 | 0,03 | 0,260 |
| SEQ ID NO: 434 | hsa-miR-34c-3p | aaucacuaaccacacgcagg | 139,688 | 203,875 | 0,685 | -0,378 | 0,01 | 0,03 | 0,231 |
| SEQ ID NO: 28 | hsa-miR-924 | agagucuugugaugucuugc | 49,156 | 64,219 | 0,765 | -0,267 | 0,01 | 0,03 | 0,275 |
| SEQ ID NO: 852 | hsa-miR-1206 | ugauucauguaugaugaauuaagc | 77,203 | 112,313 | 0,687 | -0,375 | 0,01 | 0,03 | 0,283 |
| SEQ ID NO: 365 | hsa-miR-450b-5p | uuuugcaauauguuccugaaua | 102,906 | 129,094 | 0,797 | -0,227 | 0,01 | 0,03 | 0,293 |
| SEQ ID NO: 458 | hsa-miR-331-3p | gccccugggccuauccagaa | 1699,277 | 1162,813 | 1,461 | 0,379 | 0,01 | 0,03 | 0,742 |
| SEQ ID NO: 890 | hsa-let-7g | ugagguaguaguuuguacaguu | 1372,621 | 629,172 | 2,182 | 0,780 | 0,01 | 0,03 | 0,713 |
| SEQ ID NO: 710 | hsa-miR-1469 | cucggcgcgggggcggggccc | 340,547 | 253,742 | 1,342 | 0,294 | 0,01 | 0,03 | 0,730 |
| SEQ ID NO: 845 | hsa-miR-1224-5p | gugaggacucggggaggug | 90,781 | 63,625 | 1,427 | 0,355 | 0,01 | 0,03 | 0,750 |
| SEQ ID NO: 349 | hsa-miR-487a | aaucauacaggacauccaguu | 121,688 | 149,875 | 0,812 | -0,208 | 0,01 | 0,03 | 0,285 |
| SEQ ID NO: 516 | hsa-miR-27b* | agagcuuagcugauugguugaac | 95,797 | 122,969 | 0,779 | -0,250 | 0,01 | 0,03 | 0,278 |
| SEQ ID NO: 797 | hsa-miR-1266 | ccucagggcuguagaacagggcu | 167,875 | 203,188 | 0,826 | -0,191 | 0,01 | 0,03 | 0,244 |
| SEQ ID NO: 59 | hsa-miR-767-5p | ugcaccauggguucugagcaug | 280,109 | 355,078 | 0,789 | -0,237 | 0,01 | 0,03 | 0,300 |
| SEQ ID NO: 316 | hsa-miR-508-5p | uacuccagagggcgucacucaug | 178,969 | 223,578 | 0,800 | -0,223 | 0,01 | 0,03 | 0,207 |
| SEQ ID NO: 302 | hsa-miR-515-5p | uucuccaaaagaaagcacuuucug | 287,500 | 336,016 | 0,856 | -0,156 | 0,01 | 0,04 | 0,339 |
| SEQ ID NO: 61 | hsa-miR-766 | acucccagcgccacagcccagc | 344,594 | 425,313 | 0,810 | -0,210 | 0,01 | 0,04 | 0,352 |
| SEQ ID NO: 716 | hsa-miR-143* | gggcagugcugcaucucuggu | 175,281 | 219,938 | 0,797 | -0,227 | 0,01 | 0,04 | 0,246 |
| SEQ ID NO: 438 | hsa-miR-34a | ugcagugucuuagcuggugu | 87,906 | 67,344 | 1,305 | 0,266 | 0,01 | 0,04 | 0,714 |
| SEQ ID NO: 81 | hsa-miR-671-5p | aggaagcccuggaggggcuggag | 89,844 | 122,172 | 0,735 | -0,307 | 0,01 | 0,04 | 0,272 |
| SEQ ID NO: 480 | hsa-miR-30d | uguaaacauccccgacuggaag | 7669,605 | 6061,430 | 1,265 | 0,235 | 0,01 | 0,04 | 0,742 |
| SEQ ID NO: 811 | hsa-miR-1259 | auauaugaugcuuaacuagcuuuu | 66,750 | 108,078 | 0,618 | -0,482 | 0,01 | 0,04 | 0,300 |
| SEQ ID NO: 675 | hsa-miR-17 | caaagugcuuacagugcagguag | 7669,605 | 9717,992 | 0,789 | -0,237 | 0,01 | 0,04 | 0,238 |
| SEQ ID NO: 590 | hsa-miR-202* | uucccuaugcauauaccuuug | 149,938 | 184,391 | 0,813 | -0,207 | 0,01 | 0,04 | 0,281 |
| SEQ ID NO: 407 | hsa-miR-376b | aucauagaggaaaauccauguu | 111,844 | 147,391 | 0,759 | -0,276 | 0,01 | 0,04 | 0,281 |
| SEQ ID NO: 858 | hsa-miR-1200 | cucccuagcccauucugagccuc | 109,484 | 137,188 | 0,798 | -0,226 | 0,01 | 0,04 | 0,273 |
| SEQ ID NO: 627 | hsa-miR-193a-5p | uggguucugggcgggagauga | 212,063 | 133,875 | 1,584 | 0,460 | 0,01 | 0,04 | 0,717 |
| SEQ ID NO: 324 | hsa-miR-502-5p | auccuugcuaucuggugua | 74,844 | 61,797 | 1,211 | 0,192 | 0,01 | 0,04 | 0,692 |
| SEQ ID NO: 856 | hsa-miR-1202 | gugcagcugcugugggggag | 302,703 | 341,125 | 0,887 | -0,119 | 0,01 | 0,05 | 0,302 |

FIG. 18A (Cont.)

| | | | | | | | | |
|---|---|---|---|---|---|---|---|---|
| SEQ ID NO: 238 | hsa-miR-548a-3p | caaaacuggcaauuacuuugc | 140,906 | 172,438 | 0,817 | -0,202 | 0,01 | 0,05 | 0,295 |
| SEQ ID NO: 132 | hsa-miR-624* | uaguacaguaccuugugca | 128,406 | 78,219 | 1,642 | 0,496 | 0,01 | 0,05 | 0,727 |
| SEQ ID NO: 837 | hsa-miR-1229 | cucucaccacugcccuccacag | 257,025 | 296,609 | 0,867 | -0,143 | 0,01 | 0,05 | 0,314 |
| SEQ ID NO: 440 | hsa-miR-345 | gcugcucccaguccagggcuc | 236,219 | 170,219 | 1,388 | 0,328 | 0,01 | 0,05 | 0,756 |
| SEQ ID NO: 812 | hsa-miR-1258 | aguuaggauuagucguggaa | 30,281 | 8,844 | 3,424 | 1,231 | 0,01 | 0,05 | 0,764 |
| SEQ ID NO: 835 | hsa-miR-1233 | ugagcccugccuccgcag | 157,844 | 188,094 | 0,839 | -0,175 | 0,01 | 0,05 | 0,284 |
| SEQ ID NO: 447 | hsa-miR-33a* | caauguuucacagugcaucac | 119,406 | 157,250 | 0,759 | -0,275 | 0,01 | 0,05 | 0,260 |
| SEQ ID NO: 724 | hsa-miR-139-5p | ucuacagugcacgugucccag | 264,902 | 292,906 | 0,904 | -0,100 | 0,01 | 0,05 | 0,372 |
| SEQ ID NO: 532 | hsa-miR-23a* | ggggucccuggggauggauuu | 42,266 | 30,781 | 1,373 | 0,317 | 0,01 | 0,05 | 0,696 |
| SEQ ID NO: 727 | hsa-miR-138-1* | gcuacuucacaacaccagggcc | 134,531 | 176,594 | 0,762 | -0,272 | 0,01 | 0,05 | 0,290 |
| SEQ ID NO: 172 | hsa-miR-589 | ugagaaccagugucugcucgag | 169,391 | 138,328 | 1,225 | 0,203 | 0,01 | 0,05 | 0,727 |
| SEQ ID NO: 527 | hsa-miR-24-2* | ugccuacugagcugaaacacag | 257,307 | 353,156 | 0,729 | -0,317 | 0,01 | 0,05 | 0,378 |
| SEQ ID NO: 715 | hsa-miR-144 | uacaguauagaugauguacu | 2998,320 | 4285,270 | 0,700 | -0,357 | 0,01 | 0,05 | 0,274 |
| SEQ ID NO: 629 | hsa-miR-192 | cugccaauuccauaggucacag | 179,625 | 194,063 | 0,926 | -0,077 | 0,01 | 0,05 | 0,329 |
| SEQ ID NO: 653 | hsa-miR-187* | ggcuacaacacaggaccccggc | 213,625 | 276,512 | 0,773 | -0,258 | 0,01 | 0,05 | 0,288 |
| SEQ ID NO: 777 | hsa-miR-1282 | ucguuugccuuuuuucgcuu | 36,625 | 6,625 | 5,528 | 1,710 | 0,01 | 0,06 | 0,721 |
| SEQ ID NO: 445 | hsa-miR-33b* | cagugcccuggcagugccc | 205,678 | 259,232 | 0,793 | -0,232 | 0,01 | 0,06 | 0,254 |
| SEQ ID NO: 156 | hsa-miR-603 | cacacacugcaauuacuuuugc | 207,906 | 288,641 | 0,720 | -0,328 | 0,01 | 0,06 | 0,284 |
| SEQ ID NO: 219 | hsa-miR-548p | uagcaaaaacugcagguacuuu | 214,156 | 263,445 | 0,813 | -0,207 | 0,01 | 0,06 | 0,298 |
| SEQ ID NO: 299 | hsa-miR-516b | aucugagguaagaagcacuuu | 64,172 | 88,531 | 0,725 | -0,322 | 0,01 | 0,06 | 0,303 |
| SEQ ID NO: 35 | hsa-miR-892a | cacugugccuuucugcuag | 74,703 | 51,438 | 1,452 | 0,373 | 0,01 | 0,06 | 0,705 |
| SEQ ID NO: 619 | hsa-miR-196a* | cggcaacaagaaacugccugag | 208,156 | 258,695 | 0,805 | -0,217 | 0,01 | 0,06 | 0,318 |
| SEQ ID NO: 98 | hsa-miR-654-5p | uggugggccgcagaacaugugc | 264,451 | 326,281 | 0,811 | -0,210 | 0,01 | 0,06 | 0,260 |
| SEQ ID NO: 581 | hsa-miR-208a | auaagacgagcaaaaagcugu | 138,313 | 134,906 | 1,025 | 0,025 | 0,02 | 0,06 | 0,362 |
| SEQ ID NO: 857 | hsa-miR-1201 | agccugauuaaacacaugcucuga | 208,313 | 279,592 | 0,873 | -0,136 | 0,02 | 0,06 | 0,300 |
| SEQ ID NO: 373 | hsa-miR-448 | uuacugcaauguagccauca | 322,969 | 463,547 | 0,697 | -0,361 | 0,02 | 0,07 | 0,343 |
| SEQ ID NO: 888 | hsa-let-7i | uugcauaguaggaugaaggcau | 154,031 | 185,734 | 0,829 | -0,187 | 0,02 | 0,07 | 0,313 |
| SEQ ID NO: 412 | hsa-miR-374b | cagugcaauguaagggcua | 984,727 | 1288,578 | 0,764 | -0,269 | 0,02 | 0,07 | 0,666 |
| SEQ ID NO: 297 | hsa-miR-517* | acgaugutugagcaugugcua | 27,625 | 52,906 | 0,522 | -0,650 | 0,02 | 0,07 | 0,296 |
| SEQ ID NO: 879 | hsa-miR-103-as | gcagcagauuaggaccagguc | 510,709 | 744,035 | 0,686 | -0,287 | 0,02 | 0,07 | 0,283 |
| SEQ ID NO: 313 | hsa-miR-509-5p | ucccacgcuguggccagagucu | 282,109 | 353,313 | 0,798 | -0,225 | 0,02 | 0,07 | 0,300 |
| SEQ ID NO: 746 | hsa-miR-130b | ucauagcccguaacaaugcugcu | 2307,945 | 1437,787 | 1,605 | 0,473 | 0,02 | 0,07 | 0,265 |
| SEQ ID NO: 877 | hsa-miR-105* | uacugcaaugauaacuga | 137,219 | 157,250 | 0,873 | -0,294 | 0,02 | 0,07 | 0,280 |
| SEQ ID NO: 29 | hsa-miR-922 | gcagcagauuaggaccagguc | 181,281 | 241,600 | 0,750 | -0,287 | 0,02 | 0,07 | 0,291 |
| SEQ ID NO: 90 | hsa-miR-662 | uccacguguggccagaccagc | 166,299 | 130,438 | 1,275 | 0,243 | 0,02 | 0,07 | 0,304 |
| SEQ ID NO: 122 | hsa-miR-631 | agaccuggcccagaaucugcag | 217,672 | 244,598 | 0,890 | -0,117 | 0,02 | 0,07 | 0,714 |
| SEQ ID NO: 246 | hsa-miR-541 | uggugggcacagaauucuggacu | 159,188 | 190,906 | 0,834 | -0,182 | 0,02 | 0,07 | 0,308 |
| | | | | | | | | | 0,294 |

FIG. 18A (Cont.)

| | | | | | | | |
|---|---|---|---|---|---|---|---|
| SEQ ID NO: 351 | hsa-miR-486-3p | cgggcagucaguacaggau | 253,199 | 365,578 | 0,693 | -0,367 | 0,02 | 0,07 | 0,350 |
| SEQ ID NO: 828 | hsa-miR-1243 | aacuggaucaauuauaggagug | 121,969 | 145,766 | 0,837 | -0,178 | 0,02 | 0,07 | 0,304 |
| SEQ ID NO: 159 | hsa-miR-600 | acuuacagacaaagagccuugcuc | 119,422 | 142,906 | 0,836 | -0,180 | 0,02 | 0,07 | 0,371 |
| SEQ ID NO: 173 | hsa-miR-588 | uuggccacaaauggguuagaac | 181,484 | 213,078 | 0,852 | -0,160 | 0,02 | 0,07 | 0,308 |
| SEQ ID NO: 171 | hsa-miR-589* | ucagaacaaaaugccgguucccaga | 180,125 | 159,172 | 1,132 | 0,124 | 0,02 | 0,07 | 0,687 |
| SEQ ID NO: 378 | hsa-miR-431 | ugucuugcaggccgucaugca | 232,438 | 310,016 | 0,750 | -0,288 | 0,02 | 0,07 | 0,283 |
| SEQ ID NO: 763 | hsa-miR-1294 | ugugaggcauuguugucu | 45,797 | 28,563 | 1,603 | 0,472 | 0,02 | 0,07 | 0,688 |
| SEQ ID NO: 826 | hsa-miR-1245 | aaggaucuaaaggccuacau | 85,875 | 107,313 | 0,800 | -0,223 | 0,02 | 0,07 | 0,312 |
| SEQ ID NO: 500 | hsa-miR-300 | uauacaagggcagacucucucu | 75,406 | 112,766 | 0,669 | -0,402 | 0,02 | 0,07 | 0,271 |
| SEQ ID NO: 754 | hsa-miR-1303 | uuuagagacggggucucugucu | 129,313 | 86,063 | 1,503 | 0,407 | 0,02 | 0,08 | 0,696 |
| SEQ ID NO: 816 | hsa-miR-1255a | agguagcaagaaaguagauu | 75,453 | 111,406 | 0,677 | -0,390 | 0,02 | 0,08 | 0,307 |
| SEQ ID NO: 167 | hsa-miR-592 | uugucaauaugcgaugaugu | 90,969 | 120,969 | 0,752 | -0,285 | 0,02 | 0,08 | 0,244 |
| SEQ ID NO: 364 | hsa-miR-451 | aaaccguuaccauuacugaguu | 3657,398 | 1573,316 | 2,325 | 0,844 | 0,02 | 0,08 | 0,788 |
| SEQ ID NO: 215 | hsa-miR-550* | ugucuuacucccucaggcacau | 672,352 | 446,313 | 1,506 | 0,410 | 0,02 | 0,08 | 0,762 |
| SEQ ID NO: 164 | hsa-miR-595 | gaagugccgugggugucu | 96,922 | 158,063 | 0,613 | -0,489 | 0,02 | 0,08 | 0,304 |
| SEQ ID NO: 700 | hsa-miR-148a* | aaaguucugagacaccugacu | 122,375 | 107,281 | 1,141 | 0,132 | 0,02 | 0,08 | 0,702 |
| SEQ ID NO: 48 | hsa-miR-877 | guagaggagauggcgaggg | 164,422 | 133,297 | 1,234 | 0,210 | 0,02 | 0,08 | 0,707 |
| SEQ ID NO: 428 | hsa-miR-363 | aauugcacgguauccauccugua | 2894,117 | 3780,426 | 0,766 | -0,267 | 0,02 | 0,08 | 0,286 |
| SEQ ID NO: 767 | hsa-miR-1291 | uggcccugacugaagaccagagu | 199,047 | 249,492 | 0,798 | -0,226 | 0,02 | 0,08 | 0,295 |
| SEQ ID NO: 891 | hsa-let-7f-2* | cuauacagucuacugucuuucc | 40,938 | 50,250 | 0,815 | -0,205 | 0,02 | 0,08 | 0,338 |
| SEQ ID NO: 802 | hsa-miR-1261 | auggauaaggcuuugggu | 40,766 | 29,563 | 1,379 | 0,321 | 0,02 | 0,08 | 0,688 |
| SEQ ID NO: 115 | hsa-miR-638 | agggaucgcgggcgggguggggcu | 606,984 | 394,188 | 1,540 | 0,432 | 0,02 | 0,09 | 0,688 |
| SEQ ID NO: 71 | hsa-miR-720 | ucucgcugggggccucca | 7180,215 | 4541,121 | 1,581 | 0,458 | 0,02 | 0,09 | 0,664 |
| SEQ ID NO: 201 | hsa-miR-562 | aaaguagcgggguaccauugc | 79,234 | 88,391 | 0,896 | -0,109 | 0,02 | 0,09 | 0,343 |
| SEQ ID NO: 664 | hsa-miR-1825 | uccagugccucucucua | 117,484 | 79,547 | 1,477 | 0,390 | 0,03 | 0,09 | 0,680 |
| SEQ ID NO: 892 | hsa-let-7f-1* | cuauacaaucuauugccuucc | 41,203 | 58,703 | 0,702 | -0,354 | 0,03 | 0,09 | 0,318 |
| SEQ ID NO: 328 | hsa-miR-500* | auggcacgggcaaggauucug | 336,797 | 382,953 | 0,879 | -0,128 | 0,03 | 0,09 | 0,314 |
| SEQ ID NO: 358 | hsa-miR-455-3p | gcaugucaaugggcauauaac | 216,219 | 248,695 | 0,869 | -0,140 | 0,03 | 0,09 | 0,309 |
| SEQ ID NO: 503 | hsa-miR-29b-2* | cuggugauuucacaugguuag | 153,719 | 106,750 | 1,440 | 0,365 | 0,03 | 0,09 | 0,738 |
| SEQ ID NO: 325 | hsa-miR-502-3p | aaugcaccugggcaagauuca | 756,129 | 835,328 | 0,905 | -0,100 | 0,03 | 0,09 | 0,379 |
| SEQ ID NO: 443 | hsa-miR-340* | uccgucucaguuaccuuuaagc | 65,688 | 46,813 | 1,403 | 0,339 | 0,03 | 0,09 | 0,663 |
| SEQ ID NO: 847 | hsa-miR-122* | aacgccauuaucacacuaaaua | 111,938 | 142,000 | 0,788 | -0,238 | 0,03 | 0,09 | 0,304 |
| SEQ ID NO: 198 | hsa-miR-566 | ggggcgccgugauccaac | 145,797 | 160,656 | 0,908 | -0,097 | 0,03 | 0,09 | 0,330 |
| SEQ ID NO: 866 | hsa-miR-1179 | aagcauucuuuucauuguugg | 49,750 | 78,594 | 0,633 | -0,457 | 0,03 | 0,1 | 0,302 |
| SEQ ID NO: 855 | hsa-miR-1203 | cccggaccaagaugcagcuc | 272,811 | 323,891 | 0,842 | -0,172 | 0,03 | 0,1 | 0,322 |
| SEQ ID NO: 815 | hsa-miR-1255b | cggaugagcaaagaagugguu | 130,063 | 142,313 | 0,914 | -0,090 | 0,03 | 0,1 | 0,351 |
| SEQ ID NO: 838 | hsa-miR-1228* | gugggcggggcaggugugug | 2186,746 | 1612,961 | 1,356 | 0,304 | 0,03 | 0,1 | 0,670 |

FIG. 18A (Cont.)

| | | | | | | | | |
|---|---|---|---|---|---|---|---|---|
| SEQ ID NO: 685 | hsa-miR-154* | aaucauacacguugaccuauu | 92,672 | 105,031 | 0,882 | -0,125 | 0,03 | 0,1 | 0,320 |
| SEQ ID NO: 446 | hsa-miR-33b | gugcauugcuguugcauugc | 232,094 | 270,588 | 0,858 | -0,153 | 0,03 | 0,1 | 0,365 |
| SEQ ID NO: 741 | hsa-miR-1322 | gaugaugcugauugcug | 119,313 | 181,422 | 0,658 | -0,419 | 0,03 | 0,1 | 0,289 |
| SEQ ID NO: 134 | hsa-miR-623 | aucccuugcaggggcuguugggu | 115,547 | 93,000 | 1,242 | 0,217 | 0,03 | 0,1 | 0,715 |
| SEQ ID NO: 729 | hsa-miR-137 | uuauugcuuaagaauaacgcguag | 149,234 | 178,281 | 0,837 | -0,178 | 0,03 | 0,11 | 0,337 |
| SEQ ID NO: 244 | hsa-miR-542-3p | ugugacagauugauaaocugaaa | 144,969 | 166,813 | 0,869 | -0,140 | 0,03 | 0,11 | 0,317 |
| SEQ ID NO: 683 | hsa-miR-155* | cuccuacauauuagcauuaaca | 119,000 | 156,063 | 0,763 | -0,271 | 0,03 | 0,11 | 0,362 |
| SEQ ID NO: 474 | hsa-miR-32 | uauugcacauacuaaguuga | 250,160 | 248,332 | 1,007 | 0,007 | 0,03 | 0,11 | 0,442 |
| SEQ ID NO: 433 | hsa-miR-34c-5p | aggcaguguaguuagcugauugc | 108,531 | 130,313 | 0,833 | -0,183 | 0,03 | 0,11 | 0,299 |
| SEQ ID NO: 15 | hsa-miR-938 | ugcccuuaaaggugaaccgcagu | 208,953 | 165,375 | 1,264 | 0,234 | 0,04 | 0,11 | 0,683 |
| SEQ ID NO: 137 | hsa-miR-620 | augagauagauauagaaau | 37,391 | 51,281 | 0,729 | -0,316 | 0,04 | 0,12 | 0,330 |
| SEQ ID NO: 204 | hsa-miR-558 | ugagcugcuguaccacaau | 152,438 | 182,391 | 0,836 | -0,179 | 0,04 | 0,12 | 0,357 |
| SEQ ID NO: 437 | hsa-miR-34a* | caaucagcaaguauauacugcccu | 162,594 | 181,688 | 0,895 | -0,111 | 0,04 | 0,12 | 0,353 |
| SEQ ID NO: 748 | hsa-miR-130a | cagugcaauguuaaaagggcau | 2267,848 | 1859,602 | 1,220 | 0,198 | 0,04 | 0,12 | 0,696 |
| SEQ ID NO: 759 | hsa-miR-1297 | uucaaguaaucaggug | 77,328 | 103,219 | 0,749 | -0,289 | 0,04 | 0,12 | 0,303 |
| SEQ ID NO: 625 | hsa-miR-193b* | cggguuuugagggcgagauga | 106,625 | 66,813 | 1,596 | 0,467 | 0,04 | 0,13 | 0,692 |
| SEQ ID NO: 180 | hsa-miR-582-3p | uaacugguugaacaacugaacc | 167,156 | 188,109 | 0,889 | -0,118 | 0,04 | 0,13 | 0,329 |
| SEQ ID NO: 663 | hsa-miR-1826 | auugaucaucgacacuagaacgcaau | 259,668 | 264,654 | 0,981 | -0,019 | 0,04 | 0,13 | 0,405 |
| SEQ ID NO: 47 | hsa-miR-877* | uccucucuccccucccccaggu | 167,031 | 105,297 | 1,586 | 0,461 | 0,04 | 0,13 | 0,628 |
| SEQ ID NO: 723 | hsa-miR-140-3p | uaccacagguagaaccacgg | 24650,828 | 20868,719 | 1,181 | 0,167 | 0,04 | 0,13 | 0,708 |
| SEQ ID NO: 126 | hsa-miR-628-5p | augcugacauauuuacuagagg | 109,781 | 121,875 | 0,901 | -0,105 | 0,04 | 0,14 | 0,348 |
| SEQ ID NO: 903 | hsa-let-7a* | cuauacaaucuacugucuuuc | 28,500 | 39,469 | 0,722 | -0,326 | 0,04 | 0,14 | 0,367 |
| SEQ ID NO: 43 | hsa-miR-886-5p | cggucggaguuagcucaagcgg | 150,969 | 124,031 | 1,217 | 0,197 | 0,04 | 0,14 | 0,669 |
| SEQ ID NO: 422 | hsa-miR-369-3p | aauaauacaagguugauucuuu | 48,719 | 58,484 | 0,833 | -0,183 | 0,04 | 0,14 | 0,345 |
| SEQ ID NO: 118 | hsa-miR-635 | acuuggcacugaaacaaugucc | 187,375 | 226,094 | 0,829 | -0,188 | 0,04 | 0,14 | 0,326 |
| SEQ ID NO: 89 | hsa-miR-663 | aggcgggcgccgcgggaccgc | 582,203 | 575,703 | 1,011 | 0,011 | 0,05 | 0,14 | 0,605 |
| SEQ ID NO: 355 | hsa-miR-483-5p | aagacgggaggaaagaaggag | 281,328 | 220,516 | 1,276 | 0,244 | 0,05 | 0,14 | 0,683 |
| SEQ ID NO: 463 | hsa-miR-326 | ccucuggcccuucuccag | 188,781 | 147,469 | 1,280 | 0,247 | 0,05 | 0,14 | 0,685 |
| SEQ ID NO: 734 | hsa-miR-135a* | uauaggauuggagccguggcg | 68,156 | 47,031 | 1,449 | 0,371 | 0,05 | 0,14 | 0,649 |
| SEQ ID NO: 330 | hsa-miR-499-5p | uuaagacuugcagugauguuu | 56,406 | 70,531 | 0,800 | -0,223 | 0,05 | 0,14 | 0,343 |
| SEQ ID NO: 882 | hsa-miR-101* | caguuaucacagugugaugau | 234,750 | 185,172 | 1,268 | 0,237 | 0,05 | 0,15 | 0,707 |
| SEQ ID NO: 143 | hsa-miR-615-5p | ggggguccccggugucggagu | 125,625 | 110,219 | 1,140 | 0,131 | 0,05 | 0,15 | 0,653 |
| SEQ ID NO: 9 | hsa-miR-944 | aaauuauuguacaucgdaugag | 79,594 | 93,125 | 0,855 | -0,157 | 0,05 | 0,15 | 0,366 |
| SEQ ID NO: 266 | hsa-miR-520e | aaagugcuucuuuuugaggg | 51,563 | 38,094 | 1,354 | 0,303 | 0,05 | 0,15 | 0,711 |
| SEQ ID NO: 436 | hsa-miR-34b | caaucuaaccuccauugcau | 82,375 | 97,672 | 0,843 | -0,170 | 0,05 | 0,15 | 0,336 |
| SEQ ID NO: 830 | hsa-miR-124 | uaaggcacgcgguguaugc | 188,906 | 230,016 | 0,821 | -0,197 | 0,05 | 0,15 | 0,339 |
| SEQ ID NO: 354 | hsa-miR-484 | ucaggcucagucccccccgau | 8893,313 | 7318,813 | 1,215 | 0,195 | 0,05 | 0,16 | 0,708 |

FIG. 18A (Cont.)

| | | | | | | | |
|---|---|---|---|---|---|---|---|
| SEQ ID NO: 714 | hsa-miR-144* | ggauucaucauauacuguaag | 889,078 | | 0,824 | | 0,05 | 0,16 | 0,324 |
| SEQ ID NO: 259 | hsa-miR-523 | gaacgcgcuucccuauagagggu | 148,531 | 1078,615 | 0,847 | -0,193 | 0,06 | 0,16 | 0,334 |
| SEQ ID NO: 841 | hsa-miR-1226* | gugggcaugcaggccugauggg | 265,391 | 175,328 | 0,858 | -0,166 | 0,06 | 0,16 | 0,372 |
| SEQ ID NO: 821 | hsa-miR-1250 | acgguccuggaugggcugccuuu | 88,078 | 309,375 | 1,203 | -0,153 | 0,06 | 0,16 | 0,673 |
| SEQ ID NO: 801 | hsa-miR-1262 | auggguagauuuguagaaggau | 30,281 | 73,188 | 1,415 | 0,185 | 0,06 | 0,16 | 0,649 |
| SEQ ID NO: 310 | hsa-miR-512-3p | aagugugucauagcugaggguc | 37,828 | 21,406 | 0,597 | 0,347 | 0,06 | 0,16 | 0,347 |
| SEQ ID NO: 449 | hsa-miR-339-5p | uccgucccaggagcugacacg | 734,359 | 63,375 | 0,802 | -0,516 | 0,06 | 0,16 | 0,360 |
| SEQ ID NO: 255 | hsa-miR-525-3p | gaaggcguccuuuagagcg | 132,688 | 915,141 | 0,868 | -0,220 | 0,06 | 0,16 | 0,355 |
| SEQ ID NO: 120 | hsa-miR-633 | cuaauaguaucuaccacaauaaa | 191,594 | 152,875 | 1,053 | -0,142 | 0,06 | 0,17 | 0,465 |
| SEQ ID NO: 768 | hsa-miR-1290 | uggauuuuggaucaggga | 25,828 | 182,031 | 0,707 | 0,051 | 0,06 | 0,17 | 0,329 |
| SEQ ID NO: 752 | hsa-miR-1305 | uuuucaaccuaauggagaga | 158,500 | 36,531 | 0,874 | -0,347 | 0,06 | 0,17 | 0,317 |
| SEQ ID NO: 539 | hsa-miR-223* | cguguauuugacaagcugaguu | 59,938 | 181,375 | 0,853 | -0,135 | 0,06 | 0,17 | 0,340 |
| SEQ ID NO: 661 | hsa-miR-183 | uaugcacuggauaauucacu | 594,391 | 70,266 | 1,182 | -0,159 | 0,06 | 0,17 | 0,652 |
| SEQ ID NO: 188 | hsa-miR-575 | gagccaguugaccagagc | 192,359 | 502,766 | 0,904 | 0,167 | 0,06 | 0,17 | 0,355 |
| SEQ ID NO: 591 | hsa-miR-202 | agaguauaggcauggaa | 35,719 | 212,844 | 0,809 | -0,101 | 0,06 | 0,17 | 0,382 |
| SEQ ID NO: 884 | hsa-miR-100* | caagcuauucuauaguaag | 114,797 | 44,125 | 0,807 | -0,211 | 0,06 | 0,17 | 0,347 |
| SEQ ID NO: 875 | hsa-miR-106a* | cugcaauguaagcacucuuuag | 226,109 | 142,172 | 0,931 | -0,214 | 0,06 | 0,17 | 0,335 |
| SEQ ID NO: 545 | hsa-miR-220c | acacaggcugugugaagacu | 188,656 | 242,766 | 0,906 | -0,071 | 0,06 | 0,17 | 0,406 |
| SEQ ID NO: 187 | hsa-miR-576-3p | aagauguggaaaaauuggaauc | 38,984 | 208,219 | 0,845 | -0,099 | 0,06 | 0,17 | 0,341 |
| SEQ ID NO: 839 | hsa-miR-1228 | ucacacacugccucgccccc | 261,240 | 46,156 | 0,863 | -0,169 | 0,06 | 0,17 | 0,373 |
| SEQ ID NO: 764 | hsa-miR-129-3p | aagcccuuaccccaaaagcau | 135,063 | 302,828 | 0,987 | -0,148 | 0,06 | 0,17 | 0,378 |
| SEQ ID NO: 220 | hsa-miR-548o | ccaaaacugcaguuacuuuugc | 174,656 | 136,828 | 0,819 | -0,013 | 0,06 | 0,17 | 0,341 |
| SEQ ID NO: 380 | hsa-miR-425* | aucggaaugugcauaucaucau | 143,688 | 213,281 | 1,419 | -0,200 | 0,06 | 0,17 | 0,650 |
| SEQ ID NO: 782 | hsa-miR-1278 | uaguacugcaggagaccucuccc | 108,094 | 101,281 | 0,865 | 0,350 | 0,06 | 0,17 | 0,366 |
| SEQ ID NO: 20 | hsa-miR-933 | ugugcgcaggggagaccaauugu | 293,516 | 125,000 | 0,815 | -0,145 | 0,06 | 0,17 | 0,363 |
| SEQ ID NO: 405 | hsa-miR-377 | aucacacaaggcuugcuuuccu | 214,031 | 360,047 | 0,769 | -0,204 | 0,06 | 0,17 | 0,331 |
| SEQ ID NO: 321 | hsa-miR-505 | cggaugcacucuccaugccu | 87,344 | 278,391 | 1,322 | -0,263 | 0,06 | 0,17 | 0,657 |
| SEQ ID NO: 375 | hsa-miR-432* | cuggauggcucuccaugucu | 109,625 | 66,063 | 1,072 | 0,279 | 0,06 | 0,17 | 0,632 |
| SEQ ID NO: 490 | hsa-miR-302d* | acuuuaacauggaggcacuug | 104,438 | 102,250 | 0,844 | 0,070 | 0,06 | 0,17 | 0,325 |
| SEQ ID NO: 895 | hsa-let-7e | ugagguaggagguuguauaguu | 537,031 | 123,781 | 2,359 | -0,170 | 0,06 | 0,17 | 0,682 |
| SEQ ID NO: 178 | hsa-miR-583 | caaagaagaaggcuaccauuac | 93,000 | 227,672 | 0,846 | 0,858 | 0,07 | 0,17 | 0,337 |
| SEQ ID NO: 785 | hsa-miR-127-5p | cugaagcucagaggggcucgau | 216,125 | 109,953 | 0,895 | -0,167 | 0,07 | 0,18 | 0,356 |
| SEQ ID NO: 750 | hsa-miR-1307 | acucugcgggucgucgucgug | 188,469 | 241,391 | 1,330 | -0,111 | 0,07 | 0,18 | 0,669 |
| SEQ ID NO: 814 | hsa-miR-1256 | agccauugacuucacuacgcu | 66,281 | 141,750 | 0,587 | 0,285 | 0,07 | 0,18 | 0,351 |
| SEQ ID NO: 93 | hsa-miR-659 | cuugguuccagggguuauaggu | 207,313 | 112,969 | 1,348 | -0,533 | 0,07 | 0,18 | 0,681 |
| SEQ ID NO: 521 | hsa-miR-26b | uucaaguaauucaggauaggu | 756,129 | 153,844 | 1,255 | 0,298 | 0,07 | 0,18 | 0,647 |
| SEQ ID NO: 176 | hsa-miR-585 | ugggcguaucuguaugcua | 45,219 | 602,609 | 0,900 | 0,227 | 0,07 | 0,18 | 0,363 |
| | | | | 50,250 | | -0,105 | | | |

FIG. 18A (Cont.)

| | | | | | | | | |
|---|---|---|---|---|---|---|---|---|
| SEQ ID NO: 575 | hsa-miR-21 | uagcuuaucagacugauguuga | 1570,813 | 1114,814 | 1,409 | 0,343 | 0,07 | 0,18 | 0,634 |
| SEQ ID NO: 515 | hsa-miR-28-3p | cacuagauugugagcucugu | 250,008 | 204,813 | 1,221 | 0,199 | 0,07 | 0,18 | 0,663 |
| SEQ ID NO: 420 | hsa-miR-370 | gccugcuggguggaaccuggu | 90,094 | 105,094 | 0,857 | -0,154 | 0,07 | 0,18 | 0,339 |
| SEQ ID NO: 5 | hsa-miR-98 | ugagguaguaaguuguauuu | 162,125 | 73,375 | 2,210 | 0,793 | 0,07 | 0,19 | 0,696 |
| SEQ ID NO: 16 | hsa-miR-937 | auccgcgcucugacucucugcc | 89,656 | 109,281 | 0,820 | -0,198 | 0,07 | 0,19 | 0,313 |
| SEQ ID NO: 36 | hsa-miR-891b | ugcaacuuaccugaguccauuga | 151,594 | 180,188 | 0,841 | -0,173 | 0,08 | 0,19 | 0,386 |
| SEQ ID NO: 343 | hsa-miR-490-5p | ccaaggaucuccaggugggu | 191,813 | 225,719 | 0,850 | -0,163 | 0,08 | 0,19 | 0,335 |
| SEQ ID NO: 519 | hsa-miR-27a | uucacaguggcuaaguccgc | 596,141 | 405,328 | 1,471 | 0,386 | 0,08 | 0,19 | 0,691 |
| SEQ ID NO: 790 | hsa-miR-1273 | gggcgacaaagcaagacucuuuucuu | 146,406 | 162,125 | 0,903 | -0,102 | 0,08 | 0,19 | 0,357 |
| SEQ ID NO: 704 | hsa-miR-1470 | gcccucgcccgugcaccccg | 234,250 | 266,260 | 0,880 | -0,128 | 0,08 | 0,2 | 0,329 |
| SEQ ID NO: 771 | hsa-miR-1288 | uggacugccugaucuggaga | 162,156 | 181,375 | 0,894 | -0,112 | 0,08 | 0,2 | 0,331 |
| SEQ ID NO: 154 | hsa-miR-605 | uaaauccauggugccuucccu | 64,688 | 84,313 | 0,767 | -0,265 | 0,08 | 0,2 | 0,366 |
| SEQ ID NO: 160 | hsa-miR-599 | guugucaguuuaucaaac | 65,078 | 77,375 | 0,841 | -0,173 | 0,08 | 0,2 | 0,346 |
| SEQ ID NO: 275 | hsa-miR-519e | aagugccucuuuuagugugu | 24,719 | 19,375 | 1,276 | 0,244 | 0,08 | 0,2 | 0,572 |
| SEQ ID NO: 45 | hsa-miR-885-5p | uccauuacacuaccclugccucu | 81,641 | 65,734 | 1,242 | 0,217 | 0,08 | 0,2 | 0,653 |
| SEQ ID NO: 818 | hsa-miR-1253 | agagaagaaugaucagcaclgca | 131,453 | 147,391 | 0,892 | -0,114 | 0,08 | 0,2 | 0,349 |
| SEQ ID NO: 138 | hsa-miR-619 | gaaccuggacauguuugugcccagu | 158,781 | 145,688 | 1,090 | 0,086 | 0,08 | 0,2 | 0,661 |
| SEQ ID NO: 76 | hsa-miR-708* | caacuagacugugagcucugc | 125,031 | 135,828 | 0,921 | -0,083 | 0,08 | 0,2 | 0,390 |
| SEQ ID NO: 511 | hsa-miR-297 | auguauguguagcaugugcaug | 101,531 | 118,844 | 0,854 | -0,157 | 0,08 | 0,2 | 0,387 |
| SEQ ID NO: 320 | hsa-miR-505* | gggagcuggaagguauugaugu | 257,480 | 220,938 | 1,165 | 0,153 | 0,08 | 0,21 | 0,630 |
| SEQ ID NO: 257 | hsa-miR-524-3p | gaaggcgcuucccuuuggagu | 51,500 | 67,563 | 0,762 | -0,271 | 0,08 | 0,21 | 0,368 |
| SEQ ID NO: 327 | hsa-miR-501-3p | aaugcaccgcggcaaggauucu | 384,297 | 445,109 | 0,863 | -0,147 | 0,08 | 0,21 | 0,348 |
| SEQ ID NO: 293 | hsa-miR-518a-3p | gaaagcgcuucccuuugcugga | 118,906 | 135,063 | 0,880 | -0,127 | 0,08 | 0,21 | 0,351 |
| SEQ ID NO: 836 | hsa-miR-1231 | gugucugggacaguggagacagc | 120,750 | 177,469 | 0,680 | -0,385 | 0,09 | 0,21 | 0,333 |
| SEQ ID NO: 687 | hsa-miR-1539 | uccugcgcuagaugccc | 132,641 | 159,844 | 0,830 | -0,187 | 0,09 | 0,21 | 0,338 |
| SEQ ID NO: 399 | hsa-miR-380 | uauguaauaugguccaacaugauc | 61,484 | 80,531 | 0,763 | -0,270 | 0,09 | 0,21 | 0,326 |
| SEQ ID NO: 690 | hsa-miR-153 | uugcauagucacaaaagugauc | 177,750 | 198,859 | 0,894 | -0,112 | 0,09 | 0,21 | 0,365 |
| SEQ ID NO: 822 | hsa-miR-1249 | acgcccuuccccccuucuuca | 78,516 | 105,344 | 0,745 | -0,294 | 0,09 | 0,21 | 0,353 |
| SEQ ID NO: 772 | hsa-miR-1287 | ugcuggaucaguggcucgagguc | 139,094 | 120,828 | 1,151 | 0,141 | 0,09 | 0,21 | 0,696 |
| SEQ ID NO: 99 | hsa-miR-654-3p | uauguucugcuggaccauccccu | 67,703 | 81,953 | 0,826 | -0,191 | 0,09 | 0,21 | 0,367 |
| SEQ ID NO: 603 | hsa-miR-199b-5p | cccaguuuagacuaucccuu | 56,500 | 49,938 | 1,131 | 0,123 | 0,09 | 0,21 | 0,620 |
| SEQ ID NO: 270 | hsa-miR-520c-3p | aaagugcuucuuuuagagggu | 33,797 | 26,359 | 1,282 | 0,249 | 0,09 | 0,21 | 0,665 |
| SEQ ID NO: 298 | hsa-miR-516b* | ugcuuccuuucagagggu | 93,781 | 69,281 | 1,354 | 0,303 | 0,09 | 0,21 | 0,643 |
| SEQ ID NO: 861 | hsa-miR-1184 | ccugcagcgacuuggauggcuucc | 266,092 | 240,914 | 1,105 | 0,099 | 0,09 | 0,21 | 0,502 |
| SEQ ID NO: 808 | hsa-miR-125b | uccclugagacccuaacuuguga | 984,727 | 780,203 | 1,262 | 0,233 | 0,09 | 0,22 | 0,630 |
| SEQ ID NO: 593 | hsa-miR-200c | uaauacugccggguaaugaugga | 182,156 | 142,531 | 1,278 | 0,245 | 0,09 | 0,22 | 0,646 |
| SEQ ID NO: 643 | hsa-miR-1909* | ugagugccggugccugcccug | 86,188 | 110,125 | 0,783 | -0,245 | 0,09 | 0,22 | 0,380 |

FIG. 18A (Cont.)

| | | | | | | | | |
|---|---|---|---|---|---|---|---|---|
| SEQ ID NO: 686 | hsa-miR-154 | uagguuaucgguguugccuucg | 26,188 | 11,281 | 2,321 | 0,842 | 0,09 | 0,22 | 0,638 |
| SEQ ID NO: 242 | hsa-miR-543 | aaacauucggugcacuucu | 94,125 | 105,031 | 0,896 | -0,110 | 0,1 | 0,22 | 0,349 |
| SEQ ID NO: 718 | hsa-miR-142-5p | cauaaaguagaaagcacuacu | 1372,621 | 972,602 | 1,411 | 0,345 | 0,1 | 0,22 | 0,626 |
| SEQ ID NO: 216 | hsa-miR-650 | agugccugaggaguaagagccc | 198,266 | 232,531 | 0,853 | -0,159 | 0,1 | 0,22 | 0,358 |
| SEQ ID NO: 681 | hsa-miR-15a* | caggccauauugugcugccuca | 228,266 | 200,031 | 1,141 | 0,132 | 0,1 | 0,22 | 0,670 |
| SEQ ID NO: 58 | hsa-miR-769-3p | cugggaucucgggugucuuggu | 47,500 | 38,438 | 1,236 | 0,212 | 0,1 | 0,23 | 0,633 |
| SEQ ID NO: 395 | hsa-miR-383 | agaucagaaggugauuguugcu | 88,109 | 121,188 | 0,727 | -0,319 | 0,1 | 0,23 | 0,364 |
| SEQ ID NO: 669 | hsa-miR-181c | aacauucaaccugucgguagu | 249,816 | 181,375 | 1,377 | 0,320 | 0,1 | 0,23 | 0,700 |
| SEQ ID NO: 410 | hsa-miR-375 | uuuguucgucggcucgcguga | 50,688 | 41,375 | 1,225 | 0,203 | 0,1 | 0,23 | 0,653 |
| SEQ ID NO: 601 | hsa-miR-19a* | aguuuugcauaguugcacuaca | 93,172 | 127,063 | 0,733 | -0,310 | 0,1 | 0,23 | 0,348 |
| SEQ ID NO: 788 | hsa-miR-1274a | guccuguucaggcgca | 271,266 | 234,672 | 1,156 | 0,145 | 0,1 | 0,24 | 0,661 |
| SEQ ID NO: 499 | hsa-miR-301a | cagugcaauaguauugucaaagc | 467,047 | 594,125 | 0,786 | -0,241 | 0,1 | 0,24 | 0,357 |
| SEQ ID NO: 170 | hsa-miR-590-3p | uaauuuuauguaaagcuagu | 40,594 | 56,375 | 0,720 | -0,328 | 0,11 | 0,24 | 0,345 |
| SEQ ID NO: 95 | hsa-miR-657 | ggcagguucaccccucucuagg | 93,984 | 106,359 | 0,884 | -0,124 | 0,11 | 0,24 | 0,341 |
| SEQ ID NO: 226 | hsa-miR-548i | aaaaguaaugcgggauuugcc | 59,625 | 45,156 | 1,320 | 0,278 | 0,11 | 0,24 | 0,643 |
| SEQ ID NO: 531 | hsa-miR-23b | aucacauugccagggauuacc | 4027,828 | 3935,324 | 1,024 | 0,023 | 0,11 | 0,24 | 0,598 |
| SEQ ID NO: 379 | hsa-miR-429 | uaauacugucuguaaaaaccgu | 117,875 | 134,438 | 0,877 | -0,131 | 0,11 | 0,25 | 0,337 |
| SEQ ID NO: 678 | hsa-miR-16 | uagcagcacguaaauauuggcg | 18271,367 | 13747,000 | 1,329 | 0,285 | 0,11 | 0,25 | 0,628 |
| SEQ ID NO: 282 | hsa-miR-519a | aaagugcaucuuuuagagugu | 72,469 | 87,828 | 0,825 | -0,192 | 0,11 | 0,25 | 0,327 |
| SEQ ID NO: 360 | hsa-miR-454 | uagugcaauauugcuuauagggu | 414,703 | 321,016 | 1,292 | 0,256 | 0,11 | 0,25 | 0,648 |
| SEQ ID NO: 124 | hsa-miR-548i | guucuccaacguaagcccagc | 212,250 | 146,766 | 1,446 | 0,369 | 0,12 | 0,26 | 0,744 |
| SEQ ID NO: 541 | hsa-miR-629* | cucacuaagcagugcuagacuu | 118,672 | 128,750 | 0,922 | -0,082 | 0,12 | 0,26 | 0,351 |
| SEQ ID NO: 696 | hsa-miR-222* | agggagggacgggguucuugc | 1078,615 | 664,469 | 1,623 | 0,484 | 0,12 | 0,26 | 0,697 |
| SEQ ID NO: 408 | hsa-miR-149* | guagauucucuucguauagua | 53,719 | 37,875 | 1,418 | 0,349 | 0,12 | 0,26 | 0,670 |
| SEQ ID NO: 711 | hsa-miR-1468 | cucguuugccuguuuucgug | 37,203 | 29,125 | 1,277 | 0,245 | 0,12 | 0,26 | 0,643 |
| SEQ ID NO: 366 | hsa-miR-450b-3p | uuggaucauuugcauccaua | 77,344 | 95,188 | 0,813 | -0,208 | 0,12 | 0,26 | 0,360 |
| SEQ ID NO: 775 | hsa-miR-1284 | ucuauacagaccccuggcuuuuc | 60,484 | 72,203 | 0,838 | -0,177 | 0,12 | 0,26 | 0,366 |
| SEQ ID NO: 300 | hsa-miR-516a-5p | uucucgaggagcucucuggagc | 269,203 | 327,063 | 0,823 | -0,195 | 0,12 | 0,27 | 0,314 |
| SEQ ID NO: 103 | hsa-miR-650 | aggaggcaggguccuaggac | 195,156 | 212,688 | 0,918 | -0,086 | 0,12 | 0,27 | 0,374 |
| SEQ ID NO: 344 | hsa-miR-490-3p | caaccuggaggacuccaugcug | 140,125 | 150,313 | 0,932 | -0,070 | 0,12 | 0,27 | 0,366 |
| SEQ ID NO: 96 | hsa-miR-656 | aauauauacaguaaccucu | 68,359 | 98,750 | 0,692 | -0,368 | 0,12 | 0,27 | 0,385 |
| SEQ ID NO: 431 | hsa-miR-361-5p | uuaucagaauccccaggguac | 727,172 | 606,656 | 1,199 | 0,181 | 0,12 | 0,27 | 0,685 |
| SEQ ID NO: 376 | hsa-miR-432 | ucuggagaggucauuggugg | 28,141 | 19,938 | 1,411 | 0,345 | 0,13 | 0,27 | 0,619 |
| SEQ ID NO: 528 | hsa-miR-24-1* | ugccuacugagugaucuauagu | 184,344 | 214,344 | 0,860 | -0,151 | 0,13 | 0,27 | 0,403 |
| SEQ ID NO: 454 | hsa-miR-337-3p | cuccuauauagcccuuuuc | 72,156 | 87,219 | 0,827 | -0,190 | 0,13 | 0,27 | 0,355 |
| SEQ ID NO: 169 | hsa-miR-590-5p | gagcuuaauucauaaagugcag | 318,109 | 290,625 | 1,095 | 0,090 | 0,13 | 0,27 | 0,620 |
| SEQ ID NO: 800 | hsa-miR-1263 | augguacccuggcauacugagu | 123,672 | 154,578 | 0,800 | -0,223 | 0,13 | 0,27 | 0,372 |

FIG. 18A (Cont.)

| | | | | | | | | |
|---|---|---|---|---|---|---|---|---|
| SEQ ID NO: 39 | hsa-miR-889 | uuaauaucggacaaccauugu | 83,563 | 85,391 | 0,979 | -0,022 | 0,13 | 0,27 | 0,417 |
| SEQ ID NO: 142 | hsa-miR-616 | agucauuggagguuuugagcag | 57,531 | 68,219 | 0,843 | -0,170 | 0,13 | 0,28 | 0,381 |
| SEQ ID NO: 766 | hsa-miR-1292 | ugggaacggguuccggcagacgcug | 150,250 | 132,875 | 1,131 | 0,123 | 0,13 | 0,28 | 0,630 |
| SEQ ID NO: 864 | hsa-miR-1181 | ccgucgcgccaccgagccg | 260,195 | 288,328 | 0,902 | -0,103 | 0,13 | 0,28 | 0,301 |
| SEQ ID NO: 356 | hsa-miR-483-3p | ucacucucucccucccguculu | 97,219 | 53,109 | 1,831 | 0,605 | 0,13 | 0,28 | 0,636 |
| SEQ ID NO: 179 | hsa-miR-582-5p | uacaguuguucaaccaguuacu | 67,047 | 77,094 | 0,870 | -0,140 | 0,13 | 0,28 | 0,394 |
| SEQ ID NO: 650 | hsa-miR-18a | uaaggugcaucuagugcagauag | 2342,613 | 2951,227 | 0,794 | -0,231 | 0,13 | 0,28 | 0,402 |
| SEQ ID NO: 1 | hsa-miR-99b* | caagcucgugucugugggucccg | 111,250 | 99,547 | 1,118 | 0,111 | 0,14 | 0,29 | 0,610 |
| SEQ ID NO: 742 | hsa-miR-1321 | cagggaggugaaugugau | 37,281 | 30,391 | 1,227 | 0,204 | 0,14 | 0,29 | 0,599 |
| SEQ ID NO: 758 | hsa-miR-1298 | uucauuccgcugucagaugua | 88,141 | 115,859 | 0,761 | -0,273 | 0,14 | 0,29 | 0,353 |
| SEQ ID NO: 249 | hsa-miR-532-3p | ccucccacaccaaggcuuga | 3596,766 | 3412,176 | 1,054 | 0,053 | 0,14 | 0,29 | 0,433 |
| SEQ ID NO: 285 | hsa-miR-518e* | cucuagaggaagcguuucug | 281,047 | 314,609 | 0,893 | -0,113 | 0,14 | 0,29 | 0,401 |
| SEQ ID NO: 130 | hsa-miR-625* | gacuauagaacuuuccccuca | 393,625 | 308,203 | 1,277 | 0,245 | 0,14 | 0,29 | 0,670 |
| SEQ ID NO: 885 | hsa-miR-100 | aacccguagauccgaacuugug | 208,375 | 159,797 | 1,304 | 0,265 | 0,15 | 0,29 | 0,538 |
| SEQ ID NO: 640 | hsa-miR-191* | gcucgcgugauuucgucccc | 87,719 | 110,094 | 0,797 | -0,227 | 0,14 | 0,3 | 0,390 |
| SEQ ID NO: 483 | hsa-miR-30c | uguaaacauccuacacucucagc | 2267,848 | 1917,672 | 1,183 | 0,168 | 0,14 | 0,3 | 0,638 |
| SEQ ID NO: 484 | hsa-miR-30b* | cuggagguggauguuuaacuuc | 58,453 | 42,000 | 1,392 | 0,331 | 0,15 | 0,3 | 0,616 |
| SEQ ID NO: 618 | hsa-miR-196b | uagguaguuuccuguuguuggg | 28,078 | 21,844 | 1,285 | 0,251 | 0,14 | 0,3 | 0,610 |
| SEQ ID NO: 292 | hsa-miR-518a-5p | cugcaaagggaagcccuuuc | 301,641 | 294,422 | 1,025 | 0,024 | 0,15 | 0,3 | 0,478 |
| SEQ ID NO: 280 | hsa-miR-519b-3p | aaagugcaucculuugagaguu | 65,688 | 80,156 | 0,819 | -0,199 | 0,15 | 0,3 | 0,354 |
| SEQ ID NO: 819 | hsa-miR-1252 | agaaggaaauugaaucauuua | 61,141 | 84,563 | 0,723 | -0,324 | 0,15 | 0,3 | 0,380 |
| SEQ ID NO: 774 | hsa-miR-1285 | ucugggcaacaaagagagacu | 298,891 | 307,953 | 0,971 | -0,030 | 0,15 | 0,3 | 0,416 |
| SEQ ID NO: 442 | hsa-miR-342-3p | ucucacacagaaaucgcacccgu | 3596,766 | 4186,395 | 0,859 | -0,152 | 0,15 | 0,31 | 0,378 |
| SEQ ID NO: 510 | hsa-miR-298 | agcagaagcagggagguucuccca | 242,285 | 249,037 | 0,973 | -0,027 | 0,15 | 0,31 | 0,487 |
| SEQ ID NO: 825 | hsa-miR-1246 | aaggauuuuuggagcag | 27,625 | 19,125 | 1,444 | 0,368 | 0,15 | 0,31 | 0,567 |
| SEQ ID NO: 374 | hsa-miR-433 | aucaugaugggcucucugugu | 147,547 | 159,531 | 0,925 | -0,078 | 0,15 | 0,31 | 0,438 |
| SEQ ID NO: 250 | hsa-miR-527 | cugcaagggcccucaauccug | 252,535 | 276,516 | 0,913 | -0,091 | 0,16 | 0,32 | 0,374 |
| SEQ ID NO: 512 | hsa-miR-296-5p | agggcccccucaauccgu | 343,078 | 265,949 | 1,290 | 0,255 | 0,16 | 0,32 | 0,643 |
| SEQ ID NO: 223 | hsa-miR-548l | aaaaguauuugcgguuuuguc | 14,344 | 27,656 | 0,519 | -0,657 | 0,16 | 0,32 | 0,376 |
| SEQ ID NO: 522 | hsa-miR-26a-2* | ccuauucugauuacuaggguuu | 10,484 | 33,344 | 0,314 | -1,157 | 0,16 | 0,32 | 0,360 |
| SEQ ID NO: 630 | hsa-miR-192 | cugaccuaugaauugacagcc | 4443,836 | 5205,789 | 0,854 | -0,158 | 0,16 | 0,32 | 0,353 |
| SEQ ID NO: 261 | hsa-miR-522 | aaaaugguuccuuuagagagugu | 54,938 | 44,250 | 1,242 | 0,216 | 0,16 | 0,32 | 0,603 |
| SEQ ID NO: 793 | hsa-miR-1270 | cuggagauauggaagagcugugu | 60,375 | 73,344 | 0,823 | -0,195 | 0,16 | 0,32 | 0,367 |
| SEQ ID NO: 726 | hsa-miR-138-2* | gcuauuucacgacaucagguu | 83,359 | 107,469 | 0,776 | -0,254 | 0,16 | 0,32 | 0,384 |
| SEQ ID NO: 707 | hsa-miR-146b-3p | ugcccuguggacucaguucgg | 101,422 | 87,438 | 1,160 | 0,148 | 0,16 | 0,32 | 0,607 |
| SEQ ID NO: 642 | hsa-miR-190b | ugauauuuguugauaaugguu | 18,938 | 6,000 | 3,156 | 1,149 | 0,17 | 0,32 | 0,621 |
| SEQ ID NO: 13 | hsa-miR-940 | aaggcagggccccgcucccc | 239,344 | 271,906 | 0,880 | -0,128 | 0,17 | 0,32 | 0,377 |

FIG. 18A (Cont.)

| | | | | | | | | |
|---|---|---|---|---|---|---|---|---|
| SEQ ID NO: 697 | hsa-miR-149 | ucuggcucgugucuucacuccc | 82,875 | 63,938 | 1,296 | 0,259 | 0,17 | 0,32 | 0,600 |
| SEQ ID NO: 227 | hsa-miR-548h | aaaaguaaucgcgguuuugc | 35,500 | 39,281 | 0,904 | -0,101 | 0,17 | 0,32 | 0,415 |
| SEQ ID NO: 53 | hsa-miR-874 | cugcccuggccgagggaccga | 294,891 | 267,203 | 1,104 | 0,099 | 0,17 | 0,32 | 0,684 |
| SEQ ID NO: 472 | hsa-miR-320a | aaaagcugggguugagaggcga | 20868,719 | 18271,367 | 1,142 | 0,133 | 0,17 | 0,32 | 0,619 |
| SEQ ID NO: 119 | hsa-miR-634 | aaccagcaccccaacuuuggac | 184,500 | 217,375 | 0,849 | -0,164 | 0,17 | 0,33 | 0,390 |
| SEQ ID NO: 174 | hsa-miR-587 | uuuccauagggugauagucac | 93,688 | 102,344 | 0,915 | -0,088 | 0,17 | 0,33 | 0,431 |
| SEQ ID NO: 400 | hsa-miR-379* | uauguaacauguuccacuaacu | 88,891 | 106,891 | 0,832 | -0,184 | 0,17 | 0,33 | 0,385 |
| SEQ ID NO: 350 | hsa-miR-486-5p | uccugacugagcugccccgag | 38923,641 | 38923,641 | 1,000 | 0,000 | 0,18 | 0,34 | 0,431 |
| SEQ ID NO: 102 | hsa-miR-651 | uuuagqauaagcuugacuuug | 32,719 | 19,375 | 1,689 | 0,524 | 0,18 | 0,34 | 0,620 |
| SEQ ID NO: 290 | hsa-miR-518c | caaagcgcuucucucuuuagagugu | 170,094 | 155,375 | 1,095 | 0,091 | 0,18 | 0,34 | 0,607 |
| SEQ ID NO: 863 | hsa-miR-1182 | gagqucuuggqgaggagugac | 59,516 | 43,625 | 1,364 | 0,311 | 0,18 | 0,34 | 0,612 |
| SEQ ID NO: 739 | hsa-miR-1324 | ccagacagaauucuaugcacuuuc | 184,875 | 200,656 | 0,921 | -0,082 | 0,18 | 0,34 | 0,419 |
| SEQ ID NO: 632 | hsa-miR-1915 | ccccaggggcgacgcggcggg | 923,578 | 910,625 | 1,014 | 0,014 | 0,18 | 0,34 | 0,588 |
| SEQ ID NO: 559 | hsa-miR-215 | augaccuaugaauugaacagac | 508,645 | 442,156 | 1,150 | 0,140 | 0,18 | 0,34 | 0,602 |
| SEQ ID NO: 573 | hsa-miR-210 | cugugcgugacagcggcuga | 1035,832 | 1247,510 | 0,830 | -0,186 | 0,18 | 0,34 | 0,384 |
| SEQ ID NO: 635 | hsa-miR-1913 | ucugccucccgacugcgcca | 340,891 | 364,984 | 0,934 | -0,068 | 0,18 | 0,35 | 0,458 |
| SEQ ID NO: 256 | hsa-miR-524-5p | cuacaaagggaagcacuucucu | 102,531 | 106,219 | 0,965 | -0,035 | 0,18 | 0,35 | 0,427 |
| SEQ ID NO: 109 | hsa-miR-644 | aguugcuuucuuagc | 51,563 | 43,438 | 1,187 | 0,171 | 0,18 | 0,35 | 0,619 |
| SEQ ID NO: 637 | hsa-miR-1911* | caccaggcauugugucucc | 142,891 | 160,313 | 0,891 | -0,115 | 0,19 | 0,35 | 0,428 |
| SEQ ID NO: 401 | hsa-miR-379 | uggaagacuaggaacguagg | 52,531 | 53,156 | 0,988 | -0,012 | 0,19 | 0,35 | 0,424 |
| SEQ ID NO: 588 | hsa-miR-204 | uuccuuugucaucuauugccu | 28,500 | 24,609 | 1,158 | 0,147 | 0,19 | 0,35 | 0,589 |
| SEQ ID NO: 634 | hsa-miR-1914 | cccugugccggccacuucug | 60,875 | 57,875 | 1,052 | 0,051 | 0,19 | 0,36 | 0,584 |
| SEQ ID NO: 452 | hsa-miR-338-3p | uccagcaucaguguauuuguug | 256,100 | 216,203 | 1,185 | 0,169 | 0,19 | 0,36 | 0,665 |
| SEQ ID NO: 66 | hsa-miR-760 | cggcucugggucucugaggu | 79,750 | 59,188 | 1,347 | 0,298 | 0,19 | 0,36 | 0,626 |
| SEQ ID NO: 301 | hsa-miR-516a-3p | ugcuguuucuguguccugcca | 43,125 | 52,469 | 0,822 | -0,196 | 0,19 | 0,36 | 0,350 |
| SEQ ID NO: 114 | hsa-miR-639 | aucugcuguugcgagcgcugug | 109,563 | 118,172 | 0,927 | -0,076 | 0,2 | 0,36 | 0,397 |
| SEQ ID NO: 451 | hsa-miR-338-5p | aacaauauccuggugcugagug | 81,313 | 87,828 | 0,926 | -0,077 | 0,2 | 0,36 | 0,426 |
| SEQ ID NO: 192 | hsa-miR-572 | gucgcucggcgguugccca | 171,094 | 139,281 | 1,228 | 0,206 | 0,2 | 0,36 | 0,616 |
| SEQ ID NO: 648 | hsa-miR-18b | uaaggugcaucuagugcaguag | 563,453 | 647,594 | 0,870 | -0,139 | 0,2 | 0,36 | 0,372 |
| SEQ ID NO: 867 | hsa-miR-1178 | uugcucacaugguuccccag | 59,516 | 70,938 | 0,839 | -0,176 | 0,2 | 0,37 | 0,443 |
| SEQ ID NO: 191 | hsa-miR-573 | cugaaguguaguguccccuag | 88,078 | 102,750 | 0,857 | -0,154 | 0,2 | 0,37 | 0,367 |
| SEQ ID NO: 538 | hsa-miR-224 | caagucacuagugguuccguu | 77,875 | 55,875 | 1,394 | 0,332 | 0,21 | 0,37 | 0,627 |
| SEQ ID NO: 576 | hsa-miR-20b* | acuguaguauggguacuuccag | 142,406 | 149,141 | 0,955 | -0,046 | 0,21 | 0,37 | 0,386 |
| SEQ ID NO: 554 | hsa-miR-218-1 | auguugcucaagcaccaugg | 163,234 | 171,109 | 0,954 | -0,047 | 0,21 | 0,37 | 0,420 |
| SEQ ID NO: 684 | hsa-miR-155 | uuaaugcuaaucgugauagggu | 162,938 | 143,781 | 1,133 | 0,125 | 0,21 | 0,38 | 0,661 |
| SEQ ID NO: 692 | hsa-miR-151-5p | ucgaggagcugcacacaguagu | 5683,617 | 6825,539 | 0,833 | -0,183 | 0,21 | 0,38 | 0,393 |
| SEQ ID NO: 439 | hsa-miR-346 | ugucugcccgcaugccugccucu | 116,250 | 130,656 | 0,890 | -0,117 | 0,21 | 0,38 | 0,383 |

FIG. 18A (Cont.)

| | | | | | | | |
|---|---|---|---|---|---|---|---|
| SEQ ID NO: 765 | hsa-miR-1293 | ugguggucuggagauuugugc | 63,484 | 58,188 | 1,091 | 0,087 | 0,21 | 0,39 | 0,612 |
| SEQ ID NO: 803 | hsa-miR-1260 | aucccacucucugccacca | 2027,289 | 2522,371 | 0,804 | -0,218 | 0,22 | 0,39 | 0,377 |
| SEQ ID NO: 309 | hsa-miR-512-5p | cacucagccuugagggcacuuuc | 125,750 | 120,438 | 1,044 | 0,043 | 0,22 | 0,39 | 0,589 |
| SEQ ID NO: 688 | hsa-miR-1538 | cggcccgggccugcugcuguuccu | 133,328 | 131,188 | 1,016 | 0,016 | 0,22 | 0,39 | 0,579 |
| SEQ ID NO: 384 | hsa-miR-423-5p | ugaggggcagagcuggagacuuu | 5000,809 | 3412,176 | 1,466 | 0,382 | 0,22 | 0,39 | 0,620 |
| SEQ ID NO: 116 | hsa-miR-637 | acugggggcuuucgggcucugu | 63,938 | 53,719 | 1,190 | 0,174 | 0,22 | 0,39 | 0,601 |
| SEQ ID NO: 703 | hsa-miR-1471 | gcccgcgugugggagccaggugu | 179,625 | 202,219 | 0,888 | -0,118 | 0,22 | 0,39 | 0,381 |
| SEQ ID NO: 810 | hsa-miR-125a-3p | acagguggagguucuugggagcc | 60,938 | 73,109 | 0,834 | -0,182 | 0,22 | 0,39 | 0,383 |
| SEQ ID NO: 7 | hsa-miR-96 | uuuggcacuaguacaauuugcu | 388,156 | 322,922 | 1,202 | 0,184 | 0,22 | 0,39 | 0,684 |
| SEQ ID NO: 359 | hsa-miR-454* | acccuaucaauaugucugc | 81,875 | 51,031 | 1,604 | 0,473 | 0,22 | 0,39 | 0,643 |
| SEQ ID NO: 157 | hsa-miR-602 | gacagggcgacagcugugcggcc | 175,281 | 223,578 | 0,784 | -0,243 | 0,23 | 0,4 | 0,376 |
| SEQ ID NO: 466 | hsa-miR-324-3p | acugcccaggugugcugcug | 873,297 | 911,125 | 0,958 | -0,042 | 0,23 | 0,4 | 0,450 |
| SEQ ID NO: 108 | hsa-miR-645 | ucuaggcuggauucaguga | 100,875 | 120,156 | 0,840 | -0,175 | 0,23 | 0,4 | 0,411 |
| SEQ ID NO: 155 | hsa-miR-604 | aggcugcggaauucaggac | 126,750 | 135,813 | 0,933 | -0,069 | 0,23 | 0,4 | 0,434 |
| SEQ ID NO: 560 | hsa-miR-214* | ugccucuguacacugcugugc | 104,438 | 119,922 | 0,871 | -0,138 | 0,23 | 0,4 | 0,418 |
| SEQ ID NO: 388 | hsa-miR-412 | acuucaccccugguccacuagccgu | 99,703 | 105,031 | 0,949 | -0,052 | 0,23 | 0,4 | 0,413 |
| SEQ ID NO: 798 | hsa-miR-1265 | caggaugugucaagugugu | 42,469 | 37,375 | 1,136 | 0,128 | 0,24 | 0,41 | 0,554 |
| SEQ ID NO: 427 | hsa-miR-363* | cggguguaucacgaugaucaauuu | 156,781 | 126,813 | 1,236 | 0,212 | 0,23 | 0,41 | 0,599 |
| SEQ ID NO: 86 | hsa-miR-664* | acuggcuaggaaaaugauuggau | 103,047 | 128,313 | 0,803 | -0,219 | 0,24 | 0,41 | 0,375 |
| SEQ ID NO: 209 | hsa-miR-554 | gcuagucuggacucagcagu | 167,799 | 204,109 | 0,822 | -0,196 | 0,24 | 0,41 | 0,380 |
| SEQ ID NO: 389 | hsa-miR-411* | uauguaacacgguccacuaacc | 102,938 | 114,469 | 0,899 | -0,106 | 0,24 | 0,41 | 0,401 |
| SEQ ID NO: 552 | hsa-miR-219-1-3p | agaguugagucuggacguccg | 79,438 | 93,281 | 0,852 | -0,161 | 0,24 | 0,41 | 0,396 |
| SEQ ID NO: 82 | hsa-miR-671-3p | uccggucucaggggcuccacc | 81,156 | 75,656 | 1,073 | 0,070 | 0,24 | 0,41 | 0,634 |
| SEQ ID NO: 598 | hsa-miR-19b-2* | aguuuugcaggguuugcauuca | 27,875 | 38,906 | 0,716 | -0,333 | 0,24 | 0,41 | 0,416 |
| SEQ ID NO: 486 | hsa-miR-30a* | cuuucagucgauguuugcagc | 78,516 | 91,156 | 0,861 | -0,149 | 0,24 | 0,41 | 0,395 |
| SEQ ID NO: 869 | hsa-miR-10b | uacccuguagaaccgaauuugug | 105,375 | 114,391 | 0,921 | -0,082 | 0,24 | 0,42 | 0,417 |
| SEQ ID NO: 268 | hsa-miR-520d-3p | aaagugcuucucuuugguggg | 18,094 | 15,547 | 1,164 | 0,152 | 0,24 | 0,42 | 0,585 |
| SEQ ID NO: 506 | hsa-miR-29a* | acugauuucuuuugguucag | 42,266 | 46,188 | 0,915 | -0,089 | 0,25 | 0,42 | 0,377 |
| SEQ ID NO: 732 | hsa-miR-135b* | auguaggccuaaaagccauugg | 90,969 | 98,391 | 0,925 | -0,078 | 0,25 | 0,42 | 0,394 |
| SEQ ID NO: 694 | hsa-miR-150* | cuggagcaggccugguggaag | 167,844 | 135,609 | 1,238 | 0,213 | 0,25 | 0,42 | 0,603 |
| SEQ ID NO: 195 | hsa-miR-569 | aguuaaugaauccuggaaagu | 60,938 | 63,109 | 0,966 | -0,035 | 0,25 | 0,42 | 0,415 |
| SEQ ID NO: 450 | hsa-miR-339-3p | ugagcgccucgacgacagaggcg | 409,547 | 375,109 | 1,092 | 0,088 | 0,25 | 0,42 | 0,539 |
| SEQ ID NO: 849 | hsa-miR-1208 | ucacugucagguuuagacaggcga | 158,344 | 169,891 | 0,932 | -0,070 | 0,25 | 0,42 | 0,392 |
| SEQ ID NO: 589 | hsa-miR-203 | gugaaauguuuaggaccacuag | 52,719 | 60,438 | 0,872 | -0,137 | 0,25 | 0,43 | 0,365 |
| SEQ ID NO: 145 | hsa-miR-614 | gaacgccuguuucugcaggugg | 82,719 | 98,422 | 0,840 | -0,174 | 0,25 | 0,43 | 0,413 |
| SEQ ID NO: 397 | hsa-miR-381 | uauacaagggcaagcugcucucugu | 169,063 | 171,109 | 0,988 | -0,012 | 0,25 | 0,43 | 0,419 |
| SEQ ID NO: 476 | hsa-miR-31 | aggcaagaugcuggcauagcu | 238,875 | 240,156 | 0,995 | -0,005 | 0,26 | 0,43 | 0,413 |

FIG. 18A (Cont.)

| | | | | | | | | |
|---|---|---|---|---|---|---|---|---|
| SEQ ID NO: 728 | hsa-miR-138 | agcugugugguugaaucaggccg | 99,000 | 89,000 | 1,112 | 0,106 | 0,26 | 0,43 | 0,597 |
| SEQ ID NO: 44 | hsa-miR-886-3p | cgcggguguuacugacccuu | 66,438 | 53,719 | 1,237 | 0,212 | 0,26 | 0,43 | 0,558 |
| SEQ ID NO: 469 | hsa-miR-320d | aaaagcugggguugagga | 923,578 | 845,186 | 1,093 | 0,089 | 0,26 | 0,43 | 0,495 |
| SEQ ID NO: 271 | hsa-miR-520b | aaagugcuuccuuuuagagg | 61,297 | 57,219 | 1,071 | 0,069 | 0,26 | 0,43 | 0,583 |
| SEQ ID NO: 823 | hsa-miR-1248 | accucuuguauaagcacugucuaaa | 106,594 | 88,094 | 1,210 | 0,191 | 0,26 | 0,43 | 0,626 |
| SEQ ID NO: 898 | hsa-let-7c* | uagaguacacccugggaguua | 82,875 | 67,438 | 1,229 | 0,206 | 0,26 | 0,43 | 0,595 |
| SEQ ID NO: 151 | hsa-miR-608 | aggguguguugggacagcuccgu | 120,422 | 102,344 | 1,177 | 0,163 | 0,26 | 0,43 | 0,620 |
| SEQ ID NO: 523 | hsa-miR-26a-1* | ccuauucugguuacugcacg | 40,094 | 53,563 | 0,749 | -0,290 | 0,27 | 0,44 | 0,382 |
| SEQ ID NO: 49 | hsa-miR-876-5p | uggauucuuugugaaucacca | 66,438 | 80,156 | 0,829 | -0,188 | 0,27 | 0,45 | 0,398 |
| SEQ ID NO: 263 | hsa-miR-520h | acaaagugcuccccuuuagagu | 88,031 | 76,375 | 1,153 | 0,142 | 0,27 | 0,45 | 0,613 |
| SEQ ID NO: 239 | hsa-miR-545* | ucaguaaauguuauuagauga | 61,844 | 76,625 | 0,807 | -0,214 | 0,28 | 0,45 | 0,387 |
| SEQ ID NO: 602 | hsa-miR-19a | ugugcaaaucuaugcaaaacuga | 3109,006 | 2951,227 | 1,053 | 0,052 | 0,28 | 0,45 | 0,607 |
| SEQ ID NO: 784 | hsa-miR-1276 | uaaagagcccugagaca | 84,625 | 95,781 | 0,884 | -0,124 | 0,28 | 0,45 | 0,411 |
| SEQ ID NO: 680 | hsa-miR-15b | uagcagcacaucaugguuuaca | 13747,000 | 14869,586 | 0,925 | -0,078 | 0,28 | 0,45 | 0,387 |
| SEQ ID NO: 304 | hsa-miR-514 | auugacacucucugugagaga | 87,891 | 100,813 | 0,872 | -0,137 | 0,28 | 0,45 | 0,364 |
| SEQ ID NO: 267 | hsa-miR-520d-5p | cuacaaaggaagcccuuuc | 120,156 | 123,688 | 0,971 | -0,029 | 0,28 | 0,45 | 0,400 |
| SEQ ID NO: 546 | hsa-miR-220b | ccacacggugucugacacu | 96,828 | 75,875 | 1,276 | 0,244 | 0,28 | 0,45 | 0,622 |
| SEQ ID NO: 212 | hsa-miR-551b* | gaaucaagcuggguggagac | 118,969 | 108,250 | 1,099 | 0,094 | 0,28 | 0,46 | 0,572 |
| SEQ ID NO: 417 | hsa-miR-372 | aaagugcugcgacauuugagcgu | 70,859 | 84,141 | 0,842 | -0,172 | 0,28 | 0,46 | 0,384 |
| SEQ ID NO: 735 | hsa-miR-135a | uauugcuuuuuauuccuuagguga | 18,469 | 24,953 | 0,740 | -0,301 | 0,29 | 0,46 | 0,474 |
| SEQ ID NO: 383 | hsa-miR-424 | cagcaguuccauguuuugaa | 366,547 | 329,953 | 1,111 | 0,105 | 0,29 | 0,46 | 0,589 |
| SEQ ID NO: 296 | hsa-miR-517a | aucgugcauccuuuuagagugu | 78,188 | 94,375 | 0,828 | -0,188 | 0,29 | 0,46 | 0,366 |
| SEQ ID NO: 17 | hsa-miR-936 | acaguagagggaaucgcag | 97,406 | 92,250 | 1,056 | 0,054 | 0,29 | 0,46 | 0,430 |
| SEQ ID NO: 572 | hsa-miR-211 | uucccuugucauccuucgccu | 13,375 | 23,500 | 0,569 | -0,564 | 0,29 | 0,46 | 0,411 |
| SEQ ID NO: 251 | hsa-miR-526b* | gaaagugcuuccuuuuagagc | 41,078 | 51,281 | 0,801 | -0,222 | 0,29 | 0,46 | 0,411 |
| SEQ ID NO: 12 | hsa-miR-941 | caccccggcuguguccuugcaugug | 173,906 | 181,688 | 0,957 | -0,044 | 0,29 | 0,47 | 0,559 |
| SEQ ID NO: 695 | hsa-miR-150 | ucuccaacccuguacagug | 2736,684 | 2186,016 | 1,252 | 0,225 | 0,29 | 0,47 | 0,632 |
| SEQ ID NO: 414 | hsa-miR-374a | uuauaauacaaccugauaaug | 472,641 | 533,855 | 0,885 | -0,122 | 0,29 | 0,47 | 0,429 |
| SEQ ID NO: 751 | hsa-miR-1306 | acguuggcucguuggug | 39,844 | 47,844 | 0,833 | -0,183 | 0,3 | 0,47 | 0,454 |
| SEQ ID NO: 100 | hsa-miR-653 | gugugugaaacaaucucuacug | 71,391 | 88,594 | 0,806 | -0,216 | 0,3 | 0,47 | 0,362 |
| SEQ ID NO: 672 | hsa-miR-181a* | accaucgaccguugauugauacc | 146,813 | 127,813 | 1,149 | 0,139 | 0,3 | 0,47 | 0,579 |
| SEQ ID NO: 235 | hsa-miR-548b-5p | aaaaguaauugguuuuggcc | 20,172 | 37,625 | 0,536 | -0,623 | 0,3 | 0,47 | 0,346 |
| SEQ ID NO: 623 | hsa-miR-194* | ccagugggcugcaacugccucug | 115,422 | 100,297 | 1,151 | 0,140 | 0,3 | 0,48 | 0,605 |
| SEQ ID NO: 52 | hsa-miR-875-3p | ccuggaaacacugagguugu | 81,500 | 87,750 | 0,929 | -0,074 | 0,31 | 0,48 | 0,430 |
| SEQ ID NO: 279 | hsa-miR-519b-5p | cucuagagggaagcgcuuucug | 253,035 | 262,354 | 0,964 | -0,036 | 0,31 | 0,48 | 0,432 |
| SEQ ID NO: 393 | hsa-miR-409-3p | gaauugcucggguugaaccciu | 140,125 | 93,656 | 1,496 | 0,403 | 0,31 | 0,49 | 0,638 |
| SEQ ID NO: 497 | hsa-miR-302a | uaagugcuuccaugguuuuggga | 29,328 | 30,313 | 0,968 | -0,033 | 0,31 | 0,49 | 0,447 |

FIG. 18A (Cont.)

| | | | | | | | | |
|---|---|---|---|---|---|---|---|---|
| SEQ ID NO: 2 | hsa-miR-99b | cacccguagaaccgacuugcg | 230,953 | | 1,184 | 0,169 | 0,32 | 0,49 | 0,615 |
| SEQ ID NO: 50 | hsa-miR-876-3p | ugguguuuacaaguaauuca | 49,856 | 195,078 | 0,992 | -0,008 | 0,32 | 0,49 | 0,553 |
| SEQ ID NO: 357 | hsa-miR-455-5p | uaugugccuuuggacuacaucg | 47,344 | 50,063 | 0,827 | -0,191 | 0,32 | 0,49 | 0,392 |
| SEQ ID NO: 787 | hsa-miR-1274b | ucccuguucgggcgcca | 1288,578 | 57,281 | 1,001 | 0,001 | 0,32 | 0,49 | 0,561 |
| SEQ ID NO: 339 | hsa-miR-493 | ugaagguacucgugugccagg | 82,719 | 1287,377 | 1,256 | 0,228 | 0,32 | 0,49 | 0,647 |
| SEQ ID NO: 778 | hsa-miR-1281 | ucgccucucucucucc | 247,281 | 65,875 | 1,960 | 0,673 | 0,32 | 0,49 | 0,700 |
| SEQ ID NO: 30 | hsa-miR-921 | cuagugggacagaaccaggauuc | 133,031 | 126,188 | 1,103 | 0,098 | 0,32 | 0,49 | 0,551 |
| SEQ ID NO: 706 | hsa-miR-146b-5p | ugagaacuggaauuccauaggcu | 257,480 | 120,641 | 1,297 | 0,260 | 0,32 | 0,49 | 0,601 |
| SEQ ID NO: 361 | hsa-miR-453 | agguugucguggugaguucgca | 47,438 | 198,500 | 0,819 | -0,200 | 0,32 | 0,49 | 0,425 |
| SEQ ID NO: 112 | hsa-miR-641 | aaagacauagaaugagucaccuc | 90,969 | 57,938 | 0,866 | -0,144 | 0,32 | 0,49 | 0,372 |
| SEQ ID NO: 415 | hsa-miR-373* | acucaaaaugggggcuuucc | 59,891 | 105,031 | 0,929 | -0,073 | 0,32 | 0,49 | 0,403 |
| SEQ ID NO: 597 | hsa-miR-200a | uaacacugucugguaacgaugu | 164,094 | 64,438 | 0,888 | -0,118 | 0,32 | 0,5 | 0,364 |
| SEQ ID NO: 468 | hsa-miR-323-3p | cacauuacacgucgaccucu | 105,031 | 184,703 | 0,852 | -0,160 | 0,33 | 0,5 | 0,446 |
| SEQ ID NO: 129 | hsa-miR-626 | agcugucugaaaugucuu | 67,047 | 123,219 | 0,907 | -0,097 | 0,33 | 0,5 | 0,436 |
| SEQ ID NO: 281 | hsa-miR-519a* | cucuagaggaagcgcuuucug | 260,965 | 73,906 | 0,966 | -0,035 | 0,33 | 0,5 | 0,419 |
| SEQ ID NO: 733 | hsa-miR-135b | uauggcuuuucauuccuauguga | 62,500 | 270,137 | 1,355 | 0,304 | 0,33 | 0,5 | 0,622 |
| SEQ ID NO: 57 | hsa-miR-769-5p | ugagaccucugggguucagagcu | 61,266 | 46,125 | 1,438 | 0,364 | 0,34 | 0,51 | 0,589 |
| SEQ ID NO: 385 | hsa-miR-423-3p | agcucggucugaggcccccucagu | 1582,602 | 42,594 | 0,944 | -0,058 | 0,34 | 0,51 | 0,427 |
| SEQ ID NO: 133 | hsa-miR-624 | cacaagguauugguauaccu | 129,813 | 1677,063 | 1,044 | 0,043 | 0,34 | 0,52 | 0,555 |
| SEQ ID NO: 163 | hsa-miR-596 | aagccugccgguccucuggg | 155,469 | 124,344 | 1,075 | 0,072 | 0,35 | 0,52 | 0,566 |
| SEQ ID NO: 509 | hsa-miR-299-3p | uauguggaugguaaaccgcuu | 34,266 | 144,609 | 0,904 | -0,101 | 0,35 | 0,52 | 0,407 |
| SEQ ID NO: 753 | hsa-miR-1304 | uuuugaggcuacagugagaugug | 101,609 | 37,906 | 0,831 | -0,185 | 0,35 | 0,52 | 0,311 |
| SEQ ID NO: 247 | hsa-miR-539 | ggagaaauuaucccugugugu | 41,000 | 122,313 | 0,929 | -0,073 | 0,35 | 0,52 | 0,527 |
| SEQ ID NO: 781 | hsa-miR-1279 | ucauauugcuucuu | 39,391 | 44,125 | 0,972 | -0,029 | 0,35 | 0,53 | 0,437 |
| SEQ ID NO: 547 | hsa-miR-220a | ccacacgauccguacgacuu | 111,391 | 40,531 | 1,055 | 0,053 | 0,35 | 0,53 | 0,580 |
| SEQ ID NO: 33 | hsa-miR-9 | ucuuuggutuaucuagcuguauga | 54,844 | 105,625 | 0,919 | -0,084 | 0,35 | 0,53 | 0,416 |
| SEQ ID NO: 520 | hsa-miR-26b* | ccguguuuccauuacuuggcuc | 60,422 | 59,672 | 1,282 | 0,249 | 0,36 | 0,53 | 0,565 |
| SEQ ID NO: 620 | hsa-miR-196a | uagguaguuucauguuguuggg | 9,750 | 47,125 | 0,448 | -0,804 | 0,36 | 0,54 | 0,354 |
| SEQ ID NO: 307 | hsa-miR-513a-5p | uucacaggagugucau | 66,422 | 21,781 | 0,811 | -0,210 | 0,36 | 0,54 | 0,420 |
| SEQ ID NO: 628 | hsa-miR-193a-3p | aacuggccuacaaaguccaguu | 275,766 | 81,906 | 1,136 | 0,127 | 0,37 | 0,55 | 0,612 |
| SEQ ID NO: 390 | hsa-miR-411 | uagtagaccguauagguacg | 111,719 | 242,801 | 0,943 | -0,058 | 0,37 | 0,55 | 0,430 |
| SEQ ID NO: 553 | hsa-miR-218-2* | cauguggucuagucagcaccgcg | 121,156 | 118,422 | 0,938 | -0,064 | 0,38 | 0,55 | 0,417 |
| SEQ ID NO: 871 | hsa-miR-10a | uaccctugugugauccgaauuugug | 70,734 | 129,188 | 0,792 | -0,234 | 0,38 | 0,56 | 0,399 |
| SEQ ID NO: 607 | hsa-miR-198 | gguccagguggagauuggttuc | 104,781 | 89,344 | 1,150 | 0,140 | 0,38 | 0,56 | 0,614 |
| SEQ ID NO: 101 | hsa-miR-652 | aauggcgccacaagauugguguu | 2146,648 | 91,094 | 0,895 | -0,111 | 0,39 | 0,57 | 0,411 |
| SEQ ID NO: 55 | hsa-miR-802 | caguaacaaagauucauccuugu | 131,906 | 2399,334 | 0,801 | -0,221 | 0,39 | 0,57 | 0,383 |
| SEQ ID NO: 273 | hsa-miR-520a-3p | aaagugcuucccuuuggacugu | 34,813 | 164,594 | 1,143 | 0,133 | 0,39 | 0,57 | 0,570 |

FIG. 18A (Cont.)

| | | | | | | | | |
|---|---|---|---|---|---|---|---|---|
| SEQ ID NO: 769 | hsa-miR-129* | aagcccuuaccccaaaaguau | 96,828 | 114,969 | 0,842 | -0,172 | 0,39 | 0,57 | 0,409 |
| SEQ ID NO: 459 | hsa-miR-330-5p | ucucugggccuguguucuuagg | 82,219 | 60,500 | 1,359 | 0,307 | 0,4 | 0,58 | 0,585 |
| SEQ ID NO: 403 | hsa-miR-378 | acuggacuuggagucagaagg | 524,176 | 410,141 | 1,278 | 0,245 | 0,4 | 0,58 | 0,605 |
| SEQ ID NO: 498 | hsa-miR-301b | cagugcaaugauauugucaaagc | 229,281 | 261,775 | 0,876 | -0,133 | 0,4 | 0,58 | 0,405 |
| SEQ ID NO: 41 | hsa-miR-888 | uacucaaaaagcugucaguca | 108,719 | 131,438 | 0,827 | -0,190 | 0,4 | 0,58 | 0,427 |
| SEQ ID NO: 60 | hsa-miR-767-3p | ucugcuccuaccccauggguucu | 69,781 | 86,625 | 0,806 | -0,216 | 0,4 | 0,58 | 0,394 |
| SEQ ID NO: 148 | hsa-miR-611 | gccgaggaccccucgggggucugac | 154,656 | 139,344 | 1,110 | 0,104 | 0,4 | 0,58 | 0,566 |
| SEQ ID NO: 21 | hsa-miR-93* | acugcgagcuagcacuuccg | 1645,012 | 1322,637 | 1,244 | 0,218 | 0,4 | 0,58 | 0,532 |
| SEQ ID NO: 599 | hsa-miR-19b-1* | aguuuugcagguuugcauccagc | 110,469 | 128,453 | 0,860 | -0,151 | 0,41 | 0,59 | 0,417 |
| SEQ ID NO: 606 | hsa-miR-199a-3p | acaguagucugcacauugguua | 180,750 | 165,688 | 1,091 | 0,087 | 0,41 | 0,59 | 0,587 |
| SEQ ID NO: 312 | hsa-miR-510 | uacucaggagagugcaaucac | 124,328 | 135,859 | 0,915 | -0,089 | 0,41 | 0,59 | 0,469 |
| SEQ ID NO: 595 | hsa-miR-200b | uaauacugccuguaaugauga | 100,688 | 106,547 | 0,945 | -0,057 | 0,41 | 0,59 | 0,430 |
| SEQ ID NO: 549 | hsa-miR-22 | aagcugccaguugaagaacugu | 5683,617 | 6505,273 | 0,874 | -0,135 | 0,41 | 0,59 | 0,413 |
| SEQ ID NO: 457 | hsa-miR-331-5p | cuagguauggucccagggaucc | 107,016 | 93,813 | 1,141 | 0,132 | 0,41 | 0,59 | 0,552 |
| SEQ ID NO: 319 | hsa-miR-506 | uaaggcaccuuucugaguaga | 109,719 | 115,969 | 0,946 | -0,055 | 0,42 | 0,59 | 0,436 |
| SEQ ID NO: 413 | hsa-miR-374a* | cuuaucagauuguauuguaauu | 100,281 | 107,609 | 0,932 | -0,071 | 0,42 | 0,59 | 0,413 |
| SEQ ID NO: 662 | hsa-miR-1827 | ugagcaguagaugaau | 73,094 | 74,734 | 0,978 | -0,022 | 0,42 | 0,59 | 0,430 |
| SEQ ID NO: 166 | hsa-miR-593 | uguccucgcuggguuucu | 20,875 | 25,391 | 0,822 | -0,196 | 0,42 | 0,6 | 0,423 |
| SEQ ID NO: 833 | hsa-miR-1236 | ccuuucccccuugcucucucag | 65,969 | 53,594 | 1,231 | 0,208 | 0,42 | 0,6 | 0,585 |
| SEQ ID NO: 783 | hsa-miR-1277 | uacuagauauauaaugcauuuu | 114,969 | 108,719 | 1,057 | 0,056 | 0,42 | 0,6 | 0,587 |
| SEQ ID NO: 760 | hsa-miR-1296 | uuagggcccuggcuccaucuc | 126,453 | 104,219 | 1,213 | 0,193 | 0,42 | 0,6 | 0,649 |
| SEQ ID NO: 75 | hsa-miR-7-1* | caacaaaucacagugcccaua | 417,656 | 398,828 | 1,047 | 0,046 | 0,43 | 0,6 | 0,509 |
| SEQ ID NO: 38 | hsa-miR-890 | uacuugaaagcaucaguug | 77,688 | 71,063 | 1,093 | 0,089 | 0,43 | 0,6 | 0,452 |
| SEQ ID NO: 336 | hsa-miR-495 | aaacaaacaugguugcacuucuu | 145,938 | 167,500 | 0,871 | -0,138 | 0,43 | 0,6 | 0,421 |
| SEQ ID NO: 264 | hsa-miR-520g | acaaagugcuuccccuuuagagugu | 103,781 | 115,969 | 0,895 | -0,111 | 0,43 | 0,6 | 0,415 |
| SEQ ID NO: 668 | hsa-miR-181c* | aaccaugacccuuguguggac | 136,016 | 125,281 | 1,086 | 0,082 | 0,43 | 0,6 | 0,595 |
| SEQ ID NO: 494 | hsa-miR-302b* | acuuuaaacauggaagugcuuuc | 84,797 | 84,453 | 1,004 | 0,004 | 0,43 | 0,6 | 0,497 |
| SEQ ID NO: 702 | hsa-miR-147b | gugugcggaaaugcuucugua | 104,125 | 96,328 | 1,081 | 0,078 | 0,43 | 0,6 | 0,455 |
| SEQ ID NO: 854 | hsa-miR-1204 | ucguggccugguccauuau | 36,875 | 40,047 | 0,921 | -0,083 | 0,43 | 0,6 | 0,519 |
| SEQ ID NO: 665 | hsa-miR-182* | ugguucuagacuugccaacua | 127,938 | 108,219 | 1,182 | 0,167 | 0,44 | 0,6 | 0,594 |
| SEQ ID NO: 394 | hsa-miR-384 | auuccuagaaauuguacaua | 182,375 | 154,563 | 1,180 | 0,165 | 0,44 | 0,6 | 0,566 |
| SEQ ID NO: 113 | hsa-miR-640 | augauccaggaaccugcccu | 188,531 | 200,547 | 0,940 | -0,062 | 0,44 | 0,6 | 0,431 |
| SEQ ID NO: 288 | hsa-miR-518d-3p | caaagcgcuucccccuuuuggagc | 138,328 | 146,813 | 0,942 | -0,060 | 0,44 | 0,61 | 0,471 |
| SEQ ID NO: 175 | hsa-miR-586 | uaugcauuguauuuuuaggucc | 54,000 | 77,375 | 0,698 | -0,360 | 0,45 | 0,61 | 0,330 |
| SEQ ID NO: 258 | hsa-miR-523* | cucuagagggaagcguuucug | 235,594 | 250,195 | 0,942 | -0,060 | 0,45 | 0,61 | 0,419 |
| SEQ ID NO: 421 | hsa-miR-369-5p | auaucgaccguguauauccgc | 55,438 | 64,578 | 0,858 | -0,153 | 0,45 | 0,61 | 0,435 |
| SEQ ID NO: 121 | hsa-miR-632 | gugucugcuucugga | 72,813 | 74,813 | 0,973 | -0,027 | 0,45 | 0,62 | 0,494 |

FIG. 18A (Cont.)

| | | | | | | | |
|---|---|---|---|---|---|---|---|
| SEQ ID NO: 419 | hsa-miR-371-3p | aagugccgccaucuuuugagugu | 84,453 | 88,078 | 0,959 | -0,042 | 0,45 | 0,62 | 0,435 |
| SEQ ID NO: 335 | hsa-miR-496 | ugaguauuacauggccaaucuc | 176,703 | 174,781 | 1,011 | 0,011 | 0,45 | 0,62 | 0,468 |
| SEQ ID NO: 72 | hsa-miR-7-2* | caacaaauccagucuaccuaa | 70,953 | 63,500 | 1,117 | 0,111 | 0,45 | 0,62 | 0,580 |
| SEQ ID NO: 85 | hsa-miR-665 | accaggaggcugaggcccu | 199,156 | 195,625 | 1,018 | 0,018 | 0,46 | 0,62 | 0,562 |
| SEQ ID NO: 796 | hsa-miR-1267 | ccuguugaaguguaauccca | 72,281 | 80,141 | 0,902 | -0,103 | 0,47 | 0,64 | 0,438 |
| SEQ ID NO: 128 | hsa-miR-627 | gugagucucuaagaaaagaga | 370,391 | 288,438 | 1,284 | 0,250 | 0,47 | 0,64 | 0,774 |
| SEQ ID NO: 526 | hsa-miR-25 | cauugcacuuguucucgucuga | 8255,773 | 6994,664 | 1,180 | 0,166 | 0,48 | 0,65 | 0,631 |
| SEQ ID NO: 353 | hsa-miR-485-3p | gucauacacggcucucucucu | 111,844 | 130,438 | 0,857 | -0,154 | 0,48 | 0,65 | 0,531 |
| SEQ ID NO: 231 | hsa-miR-548d-5p | aaaaguaauuguggguuuugcc | 20,438 | 20,438 | 1,000 | 0,000 | 0,48 | 0,65 | 0,543 |
| SEQ ID NO: 418 | hsa-miR-371-5p | acucaaacugugggagcacu | 81,156 | 75,547 | 1,074 | 0,072 | 0,48 | 0,65 | 0,539 |
| SEQ ID NO: 233 | hsa-miR-548c-5p | aaaaguaauugcgguuuuugcc | 39,391 | 43,719 | 0,901 | -0,104 | 0,48 | 0,65 | 0,441 |
| SEQ ID NO: 897 | hsa-let-7d | agagguaguagguugcauaguu | 4027,828 | 4193,930 | 0,960 | -0,040 | 0,49 | 0,65 | 0,459 |
| SEQ ID NO: 42 | hsa-miR-887 | gugaacgggcgccauccgagg | 213,625 | 186,953 | 1,143 | 0,133 | 0,49 | 0,65 | 0,574 |
| SEQ ID NO: 689 | hsa-miR-1537 | aaaaccgcucaguuacaguugu | 94,281 | 79,688 | 1,183 | 0,168 | 0,49 | 0,66 | 0,592 |
| SEQ ID NO: 371 | hsa-miR-449b | aggcagugcauuguuagcugc | 92,656 | 95,188 | 0,973 | -0,027 | 0,5 | 0,67 | 0,534 |
| SEQ ID NO: 260 | hsa-miR-522* | cucuagaggaagcguuucug | 239,188 | 249,070 | 0,960 | -0,040 | 0,5 | 0,67 | 0,480 |
| SEQ ID NO: 287 | hsa-miR-518d-5p | cucuagaggaagcacuuucug | 261,387 | 292,324 | 0,894 | -0,112 | 0,5 | 0,67 | 0,462 |
| SEQ ID NO: 295 | hsa-miR-517b | ucgugcauccuuuagagugu | 70,906 | 62,797 | 1,129 | 0,121 | 0,5 | 0,67 | 0,576 |
| SEQ ID NO: 806 | hsa-miR-1255b-2* | ucaaguacaggcucuugggac | 60,484 | 80,906 | 0,748 | -0,291 | 0,5 | 0,67 | 0,388 |
| SEQ ID NO: 488 | hsa-miR-302f | uaauugcuuccaguuu | 24,813 | 24,281 | 1,022 | 0,022 | 0,5 | 0,67 | 0,436 |
| SEQ ID NO: 240 | hsa-miR-545 | ucagcaaacauuuauugugc | 177,250 | 195,344 | 0,907 | -0,097 | 0,51 | 0,67 | 0,413 |
| SEQ ID NO: 616 | hsa-miR-197 | uucaccaccuucuccaccagc | 761,898 | 644,236 | 1,183 | 0,168 | 0,51 | 0,67 | 0,581 |
| SEQ ID NO: 555 | hsa-miR-218 | uugugcuugaucuaaccaugu | 61,297 | 74,625 | 0,821 | -0,197 | 0,51 | 0,68 | 0,395 |
| SEQ ID NO: 243 | hsa-miR-542-5p | ucgggaucaucaugucacgaga | 183,719 | 190,500 | 0,964 | -0,036 | 0,51 | 0,68 | 0,442 |
| SEQ ID NO: 676 | hsa-miR-16-2* | ccaauauuacugcugcuuua | 195,906 | 176,594 | 1,109 | 0,104 | 0,51 | 0,68 | 0,574 |
| SEQ ID NO: 894 | hsa-let-7e* | cuauacgccucucuagcuuuc | 60,063 | 51,547 | 1,165 | 0,153 | 0,51 | 0,68 | 0,460 |
| SEQ ID NO: 18 | hsa-miR-935 | ccaguaccgcuucccguaccgc | 72,031 | 84,094 | 0,857 | -0,155 | 0,52 | 0,68 | 0,436 |
| SEQ ID NO: 633 | hsa-miR-1914* | ggagggcugguccgcacuggagg | 290,328 | 283,406 | 1,024 | 0,024 | 0,52 | 0,68 | 0,533 |
| SEQ ID NO: 149 | hsa-miR-610 | ugagcuaaaugugucuggga | 77,875 | 85,391 | 0,912 | -0,092 | 0,53 | 0,7 | 0,428 |
| SEQ ID NO: 110 | hsa-miR-643 | acuuguaugcuagcucagauag | 123,500 | 134,594 | 0,918 | -0,086 | 0,53 | 0,7 | 0,408 |
| SEQ ID NO: 278 | hsa-miR-519c-3p | aaagugcaucuuuuagaggau | 95,859 | 101,688 | 0,943 | -0,059 | 0,54 | 0,7 | 0,439 |
| SEQ ID NO: 262 | hsa-miR-521 | aacgcacuuccuuuagagugu | 87,813 | 88,375 | 0,994 | -0,006 | 0,54 | 0,71 | 0,459 |
| SEQ ID NO: 860 | hsa-miR-1185 | agaggauaccuuuguauguu | 45,844 | 48,172 | 0,952 | -0,050 | 0,54 | 0,71 | 0,417 |
| SEQ ID NO: 91 | hsa-miR-661 | ugccuggguccucggccugcgcgu | 79,750 | 71,719 | 1,112 | 0,106 | 0,54 | 0,71 | 0,479 |
| SEQ ID NO: 740 | hsa-miR-1323 | ucaaaacgugagggcauuucu | 93,656 | 96,188 | 0,974 | -0,027 | 0,55 | 0,72 | 0,452 |
| SEQ ID NO: 404 | hsa-miR-377* | agagguugcccuuggugaauuc | 26,328 | 33,391 | 0,788 | -0,238 | 0,55 | 0,72 | 0,498 |
| SEQ ID NO: 68 | hsa-miR-758 | uuugugaccuggguccacuaacc | 105,031 | 110,719 | 0,949 | -0,053 | 0,56 | 0,72 | 0,438 |

FIG. 18A (Cont.)

| | | | | | | | | |
|---|---|---|---|---|---|---|---|---|
| SEQ ID NO: 873 | hsa-miR-106b* | ccgcacugugguacuugcugc | 281,828 | 286,531 | 0,984 | -0,017 | 0,55 | 0,72 | 0,556 |
| SEQ ID NO: 217 | hsa-miR-549 | ugacaacuauggaugagcucu | 119,469 | 117,297 | 1,019 | 0,018 | 0,55 | 0,72 | 0,490 |
| SEQ ID NO: 582 | hsa-miR-206 | uggaauguaaggaagugugugg | 38,219 | 31,719 | 1,205 | 0,186 | 0,56 | 0,72 | 0,558 |
| SEQ ID NO: 508 | hsa-miR-299-5p | uggucuuuaccgucccacauacau | 75,625 | 78,969 | 0,958 | -0,043 | 0,56 | 0,73 | 0,413 |
| SEQ ID NO: 332 | hsa-miR-498 | uuucaagccaggggcguuuuuc | 83,047 | 78,125 | 1,063 | 0,061 | 0,56 | 0,73 | 0,536 |
| SEQ ID NO: 682 | hsa-miR-15a | uagcagcacauaauggutuugug | 3475,531 | 3470,055 | 1,002 | 0,002 | 0,56 | 0,73 | 0,518 |
| SEQ ID NO: 770 | hsa-miR-1289 | uggaguccaggaaucugcauuuu | 182,813 | 175,219 | 1,043 | 0,042 | 0,57 | 0,73 | 0,562 |
| SEQ ID NO: 140 | hsa-miR-617 | agacuccsauuugaaggugc | 70,734 | 73,297 | 0,965 | -0,036 | 0,57 | 0,73 | 0,539 |
| SEQ ID NO: 883 | hsa-miR-101 | uacaguacugugauaacugaa | 987,070 | 1008,195 | 0,979 | -0,021 | 0,57 | 0,73 | 0,526 |
| SEQ ID NO: 205 | hsa-miR-557 | guuugcacggugggccuugucu | 66,406 | 75,047 | 0,885 | -0,122 | 0,57 | 0,73 | 0,467 |
| SEQ ID NO: 807 | hsa-miR-125b-1* | acgggtuaggcucuuggggagcu | 36,125 | 39,938 | 0,905 | -0,100 | 0,57 | 0,73 | 0,499 |
| SEQ ID NO: 453 | hsa-miR-337-5p | gaacggcuucaucacaggaguu | 98,500 | 93,656 | 1,052 | 0,050 | 0,57 | 0,73 | 0,477 |
| SEQ ID NO: 904 | hsa-let-7a | ugagguaguagguugauauaguu | 2421,387 | 1845,953 | 1,312 | 0,271 | 0,58 | 0,74 | 0,617 |
| SEQ ID NO: 485 | hsa-miR-30b | uguaaacauccuacacucagcu | 8969,791 | 6561,965 | 1,367 | 0,313 | 0,58 | 0,74 | 0,561 |
| SEQ ID NO: 363 | hsa-miR-452 | aacuguuugcagaggaaacuga | 116,047 | 106,406 | 1,091 | 0,087 | 0,58 | 0,74 | 0,507 |
| SEQ ID NO: 232 | hsa-miR-548d-3p | caaaaaccacaguuucuuuugc | 95,219 | 99,172 | 0,960 | -0,041 | 0,59 | 0,74 | 0,502 |
| SEQ ID NO: 26 | hsa-miR-92a-1* | agguugggaucgggucaaugc | 57,813 | 58,313 | 0,991 | -0,009 | 0,59 | 0,75 | 0,463 |
| SEQ ID NO: 594 | hsa-miR-200b* | caucuacugggucagcauugga | 109,797 | 135,281 | 0,812 | -0,209 | 0,59 | 0,75 | 0,421 |
| SEQ ID NO: 737 | hsa-miR-133b | uuugguccccuucaaccagcua | 74,703 | 66,719 | 1,120 | 0,113 | 0,59 | 0,75 | 0,558 |
| SEQ ID NO: 654 | hsa-miR-187 | ucgugucuuguguuggcagcgg | 61,297 | 53,859 | 1,138 | 0,129 | 0,59 | 0,75 | 0,572 |
| SEQ ID NO: 382 | hsa-miR-424 | caaaacgugaggcgcugcuau | 237,781 | 213,875 | 1,112 | 0,106 | 0,6 | 0,75 | 0,584 |
| SEQ ID NO: 367 | hsa-miR-450a | uuuugcgauguuggcuuaauau | 53,156 | 43,438 | 1,224 | 0,202 | 0,6 | 0,75 | 0,560 |
| SEQ ID NO: 277 | hsa-miR-519c-5p | cucuagagggaagcgcuuucug | 249,180 | 220,500 | 1,130 | 0,122 | 0,6 | 0,76 | 0,570 |
| SEQ ID NO: 352 | hsa-miR-485-5p | agaggcuggccgugaugauuc | 77,750 | 78,813 | 0,987 | -0,014 | 0,6 | 0,76 | 0,463 |
| SEQ ID NO: 193 | hsa-miR-571 | ugaguuggccaucugagugag | 111,844 | 107,656 | 1,039 | 0,038 | 0,6 | 0,76 | 0,504 |
| SEQ ID NO: 862 | hsa-miR-1183 | cacuguaggugauggugagugggca | 136,063 | 141,219 | 0,963 | -0,037 | 0,61 | 0,76 | 0,456 |
| SEQ ID NO: 780 | hsa-miR-128 | ucacagugaaccggucagcua | 753,641 | 803,486 | 0,938 | -0,064 | 0,61 | 0,76 | 0,473 |
| SEQ ID NO: 27 | hsa-miR-92a | uauugcacuuguccoggcccugu | 18271,367 | 15553,496 | 1,175 | 0,161 | 0,61 | 0,76 | 0,647 |
| SEQ ID NO: 631 | hsa-miR-1915* | accugccugcugcccgggc | 63,938 | 64,859 | 0,986 | -0,014 | 0,61 | 0,76 | 0,539 |
| SEQ ID NO: 225 | hsa-miR-548j | aaaaguaaaugcggucuuuggu | 31,438 | 29,219 | 1,076 | 0,073 | 0,61 | 0,76 | 0,512 |
| SEQ ID NO: 305 | hsa-miR-513c | uucucaaggaggugcacuccgguua | 42,859 | 45,969 | 0,932 | -0,070 | 0,62 | 0,77 | 0,420 |
| SEQ ID NO: 381 | hsa-miR-425 | aaugacacgaucacauuacguuga | 12784,891 | 11122,227 | 1,149 | 0,139 | 0,62 | 0,77 | 0,563 |
| SEQ ID NO: 234 | hsa-miR-548c-3p | caaaaaucuaauuacuuugc | 98,813 | 97,859 | 1,010 | 0,010 | 0,62 | 0,77 | 0,491 |
| SEQ ID NO: 229 | hsa-miR-548f | aaaaacuguaauuacuacuu | 77,219 | 95,406 | 0,809 | -0,212 | 0,62 | 0,77 | 0,405 |
| SEQ ID NO: 647 | hsa-miR-18b* | ugcccuaaauugcccucuggc | 147,813 | 143,000 | 1,034 | 0,033 | 0,62 | 0,77 | 0,562 |
| SEQ ID NO: 530 | hsa-miR-23b* | uggguuccuggcaugcugauuu | 85,969 | 84,906 | 1,013 | 0,012 | 0,62 | 0,77 | 0,508 |
| SEQ ID NO: 641 | hsa-miR-191 | caacggaaucccaaagcagcug | 11122,227 | 10769,656 | 1,033 | 0,032 | 0,63 | 0,77 | 0,541 |

FIG. 18A (Cont.)

| | | | | | | | | |
|---|---|---|---|---|---|---|---|---|
| SEQ ID NO: 185 | hsa-miR-577 | uagauaaaauauuggugaccug | 50,875 | 57,266 | 0,888 | -0,118 | 0,63 | 0,78 | 0,443 |
| SEQ ID NO: 893 | hsa-let-7f | ugagguaguagauuguauaguu | 1170,113 | 827,930 | 1,413 | 0,346 | 0,63 | 0,78 | 0,569 |
| SEQ ID NO: 144 | hsa-miR-615-3p | uccgagccugggucuccccucu | 70,422 | 72,938 | 0,966 | -0,035 | 0,63 | 0,78 | 0,479 |
| SEQ ID NO: 311 | hsa-miR-511 | gugcuuuugcucugcaguca | 84,125 | 89,156 | 0,944 | -0,058 | 0,64 | 0,78 | 0,471 |
| SEQ ID NO: 736 | hsa-miR-134 | ugugacuggguugaccagaggg | 83,563 | 89,344 | 0,935 | -0,067 | 0,64 | 0,78 | 0,450 |
| SEQ ID NO: 805 | hsa-miR-126 | ucguaccgugaguaauaaugcg | 2576,535 | 2966,773 | 0,868 | -0,141 | 0,64 | 0,78 | 0,460 |
| SEQ ID NO: 747 | hsa-miR-130a* | uucacauugugcuacugucugc | 146,938 | 172,391 | 0,852 | -0,160 | 0,64 | 0,79 | 0,478 |
| SEQ ID NO: 347 | hsa-miR-488 | uugaaagcuauuucugguc | 32,203 | 25,500 | 1,263 | 0,233 | 0,65 | 0,79 | 0,593 |
| SEQ ID NO: 721 | hsa-miR-141 | uaacacugucugguaaagaugg | 113,266 | 116,875 | 0,969 | -0,031 | 0,65 | 0,79 | 0,440 |
| SEQ ID NO: 848 | hsa-miR-122 | uggagugugacaauggugung | 54,094 | 51,063 | 1,059 | 0,058 | 0,65 | 0,79 | 0,540 |
| SEQ ID NO: 482 | hsa-miR-30c-1* | cuggagagguugunuacucc | 120,422 | 100,875 | 1,194 | 0,177 | 0,66 | 0,8 | 0,502 |
| SEQ ID NO: 411 | hsa-miR-374b* | cuuacagguugunauuaucau | 76,875 | 79,313 | 0,969 | -0,031 | 0,66 | 0,8 | 0,472 |
| SEQ ID NO: 181 | hsa-miR-581 | ucuuguucucuagaucagu | 44,578 | 51,438 | 0,867 | -0,143 | 0,66 | 0,8 | 0,381 |
| SEQ ID NO: 69 | hsa-miR-744* | cuguugccacuaaccucaaccu | 123,438 | 109,906 | 1,123 | 0,116 | 0,66 | 0,8 | 0,483 |
| SEQ ID NO: 84 | hsa-miR-668 | ugucacucggcgucggccacuac | 106,031 | 96,313 | 1,101 | 0,096 | 0,67 | 0,8 | 0,569 |
| SEQ ID NO: 859 | hsa-miR-1197 | uaggacucggucuauucucu | 90,625 | 95,000 | 0,954 | -0,047 | 0,67 | 0,8 | 0,520 |
| SEQ ID NO: 667 | hsa-miR-181d | aacauucaugugugugugug | 52,438 | 58,484 | 0,897 | -0,109 | 0,67 | 0,81 | 0,447 |
| SEQ ID NO: 372 | hsa-miR-449a | uggcaguguauuguugcuggu | 22,688 | 32,969 | 0,688 | -0,374 | 0,67 | 0,81 | 0,417 |
| SEQ ID NO: 481 | hsa-miR-30c-2* | cuggagaaggcugunuuacucu | 59,578 | 53,938 | 1,105 | 0,099 | 0,68 | 0,81 | 0,513 |
| SEQ ID NO: 604 | hsa-miR-199b-3p | acaguagucugcacauuggua | 212,641 | 212,672 | 1,000 | 0,000 | 0,68 | 0,81 | 0,455 |
| SEQ ID NO: 493 | hsa-miR-302c | uaagugcuuccauguuuagugg | 61,141 | 66,281 | 0,922 | -0,081 | 0,68 | 0,81 | 0,439 |
| SEQ ID NO: 870 | hsa-miR-10a* | caaauucguauccuguagggaaua | 102,531 | 96,594 | 1,061 | 0,060 | 0,68 | 0,81 | 0,543 |
| SEQ ID NO: 56 | hsa-miR-770-5p | uccaguaccacgugucagggcca | 100,016 | 92,406 | 1,082 | 0,079 | 0,68 | 0,81 | 0,561 |
| SEQ ID NO: 749 | hsa-miR-1308 | gcauggugguucagugg | 79,625 | 92,281 | 0,863 | -0,148 | 0,68 | 0,81 | 0,448 |
| SEQ ID NO: 514 | hsa-miR-28-5p | aaggagcucacagucuauugag | 426,203 | 422,703 | 1,008 | 0,008 | 0,69 | 0,81 | 0,549 |
| SEQ ID NO: 236 | hsa-miR-548b-3p | caagaaccucaguugcuuuugu | 97,234 | 95,000 | 1,024 | 0,023 | 0,69 | 0,82 | 0,537 |
| SEQ ID NO: 479 | hsa-miR-30d* | cuuucagucagauguuugcugc | 126,203 | 132,375 | 0,953 | -0,048 | 0,69 | 0,82 | 0,507 |
| SEQ ID NO: 284 | hsa-miR-518f | gaaaggcuucucuuuagg | 118,281 | 118,438 | 0,999 | -0,001 | 0,69 | 0,82 | 0,510 |
| SEQ ID NO: 162 | hsa-miR-597 | ugugcacucgugaccacugu | 143,000 | 149,500 | 0,957 | -0,044 | 0,7 | 0,82 | 0,498 |
| SEQ ID NO: 387 | hsa-miR-421 | aucacauugacauuggugcgc | 272,063 | 215,926 | 1,260 | 0,231 | 0,7 | 0,82 | 0,587 |
| SEQ ID NO: 333 | hsa-miR-497* | caaaccacacugugguuaga | 181,563 | 195,156 | 0,930 | -0,072 | 0,7 | 0,82 | 0,446 |
| SEQ ID NO: 183 | hsa-miR-579 | ucauuugguauaaaccgcgau | 88,891 | 90,125 | 0,986 | -0,014 | 0,7 | 0,82 | 0,471 |
| SEQ ID NO: 230 | hsa-miR-548e | aaaaacugagacucuuuugca | 93,203 | 90,969 | 1,025 | 0,024 | 0,7 | 0,82 | 0,564 |
| SEQ ID NO: 377 | hsa-miR-431* | cagguguucugcaggggcucu | 60,781 | 65,359 | 0,930 | -0,073 | 0,7 | 0,83 | 0,471 |
| SEQ ID NO: 272 | hsa-miR-520a-5p | cuccagggaaguacuuucu | 188,531 | 172,438 | 1,093 | 0,089 | 0,7 | 0,83 | 0,537 |
| SEQ ID NO: 524 | hsa-miR-26a | uucaaguaaucaggauaaggcu | 6989,555 | 7855,156 | 0,890 | -0,117 | 0,7 | 0,83 | 0,388 |
| SEQ ID NO: 314 | hsa-miR-509-3p | ugauuggauacgucugugggug | 33,484 | 32,453 | 1,032 | 0,031 | 0,71 | 0,83 | 0,515 |

FIG. 18A (Cont.)

| | | | | | | | | |
|---|---|---|---|---|---|---|---|---|
| SEQ ID NO: 551 | hsa-miR-219-2-3p | agaauugugcuggacaucugu | 44,578 | 37,375 | 1,193 | 0,176 | 0,71 | 0,83 | 0,530 |
| SEQ ID NO: 517 | hsa-miR-27b | uucacaguggcuaaguucugc | 281,047 | 277,281 | 1,014 | 0,013 | 0,72 | 0,84 | 0,539 |
| SEQ ID NO: 467 | hsa-miR-323-5p | aggugguccguggcgcugcgc | 63,313 | 58,922 | 1,075 | 0,072 | 0,72 | 0,84 | 0,541 |
| SEQ ID NO: 889 | hsa-let-7g* | cuguacaggccacugccugc | 233,219 | 234,938 | 0,993 | -0,007 | 0,72 | 0,84 | 0,538 |
| SEQ ID NO: 8 | hsa-miR-95 | uucaacgguauuuauugagca | 50,500 | 55,375 | 0,912 | -0,092 | 0,72 | 0,84 | 0,466 |
| SEQ ID NO: 10 | hsa-miR-943 | cugacuguugccgucuccag | 97,234 | 91,438 | 1,063 | 0,061 | 0,73 | 0,84 | 0,565 |
| SEQ ID NO: 141 | hsa-miR-616* | acucaaaaccuucagugacuu | 101,906 | 90,297 | 1,129 | 0,121 | 0,73 | 0,85 | 0,537 |
| SEQ ID NO: 679 | hsa-miR-15b* | cgaaucauuauuugcugcucua | 130,250 | 121,516 | 1,072 | 0,069 | 0,73 | 0,85 | 0,534 |
| SEQ ID NO: 592 | hsa-miR-200c* | cguuuaccagcaguguuugg | 99,281 | 100,688 | 0,986 | -0,014 | 0,74 | 0,85 | 0,452 |
| SEQ ID NO: 40 | hsa-miR-888* | gacugacacucuuugggugaa | 69,766 | 79,438 | 0,878 | -0,130 | 0,74 | 0,85 | 0,471 |
| SEQ ID NO: 291 | hsa-miR-518b | caaagcgcuccuuuagaggu | 198,984 | 190,797 | 1,043 | 0,042 | 0,74 | 0,85 | 0,552 |
| SEQ ID NO: 587 | hsa-miR-205 | uccuucauuccaccgagucug | 139,656 | 125,547 | 1,112 | 0,107 | 0,74 | 0,85 | 0,541 |
| SEQ ID NO: 303 | hsa-miR-515-3p | gagugccuucuuuuggagugaa | 37,391 | 29,875 | 1,252 | 0,224 | 0,74 | 0,85 | 0,535 |
| SEQ ID NO: 318 | hsa-miR-507 | uuuugcacuuuuggagugaa | 72,813 | 80,125 | 0,909 | -0,096 | 0,74 | 0,85 | 0,465 |
| SEQ ID NO: 286 | hsa-miR-518e | aaagcgcuuccuucagagug | 146,813 | 139,500 | 1,052 | 0,051 | 0,74 | 0,85 | 0,554 |
| SEQ ID NO: 844 | hsa-miR-1225-3p | ugagccccugucgcccccag | 234,969 | 213,891 | 1,099 | 0,094 | 0,75 | 0,85 | 0,553 |
| SEQ ID NO: 456 | hsa-miR-335 | ucaagagcaauaacgaaaaaugu | 573,906 | 667,367 | 0,860 | -0,151 | 0,75 | 0,85 | 0,435 |
| SEQ ID NO: 435 | hsa-miR-34b* | uaggcagugucauuagcugauug | 97,922 | 99,625 | 0,983 | -0,017 | 0,74 | 0,85 | 0,500 |
| SEQ ID NO: 31 | hsa-miR-920 | ggggagcugggaagcagua | 77,219 | 71,375 | 1,082 | 0,079 | 0,75 | 0,85 | 0,546 |
| SEQ ID NO: 92 | hsa-miR-660 | uacccauugcauaucggaguug | 668,680 | 665,008 | 1,006 | 0,006 | 0,75 | 0,86 | 0,503 |
| SEQ ID NO: 186 | hsa-miR-576-5p | auucuaauucuccacgucuuu | 40,938 | 40,359 | 1,014 | 0,014 | 0,75 | 0,86 | 0,526 |
| SEQ ID NO: 621 | hsa-miR-195* | ccaauauggcugugaauuuuuggg | 101,719 | 105,563 | 0,964 | -0,037 | 0,76 | 0,86 | 0,476 |
| SEQ ID NO: 655 | hsa-miR-186* | gcccaaggugaauuuuuggg | 169,344 | 197,266 | 0,858 | -0,153 | 0,76 | 0,86 | 0,477 |
| SEQ ID NO: 794 | hsa-miR-1269 | cuggacugagccgugcuacugg | 100,219 | 97,969 | 1,023 | 0,023 | 0,76 | 0,86 | 0,528 |
| SEQ ID NO: 197 | hsa-miR-567 | aguaguucuucaggacagaac | 138,609 | 139,563 | 0,993 | -0,007 | 0,77 | 0,87 | 0,482 |
| SEQ ID NO: 868 | hsa-miR-10b* | acagauucgauucuaggggaau | 161,094 | 151,563 | 1,063 | 0,061 | 0,77 | 0,87 | 0,560 |
| SEQ ID NO: 222 | hsa-miR-548m | caaaguauuuguguguuuug | 22,719 | 27,453 | 0,828 | -0,189 | 0,77 | 0,87 | 0,500 |
| SEQ ID NO: 461 | hsa-miR-329 | aacacaccugguuaaccucuuu | 158,438 | 145,000 | 1,093 | 0,089 | 0,78 | 0,87 | 0,493 |
| SEQ ID NO: 705 | hsa-miR-147 | gugugugaaaugcuucug | 86,172 | 77,375 | 1,114 | 0,108 | 0,78 | 0,87 | 0,579 |
| SEQ ID NO: 624 | hsa-miR-194 | uguaacagcaacuccaugugga | 5810,586 | 6505,273 | 0,893 | -0,113 | 0,78 | 0,87 | 0,412 |
| SEQ ID NO: 853 | hsa-miR-1205 | ucugcaggguuugcguugg | 142,141 | 131,469 | 1,081 | 0,078 | 0,78 | 0,88 | 0,500 |
| SEQ ID NO: 789 | hsa-miR-127-3p | ucggauccgucugagcuuggcu | 115,969 | 130,375 | 0,890 | -0,117 | 0,79 | 0,88 | 0,475 |
| SEQ ID NO: 213 | hsa-miR-551b | gcgaccauaacuuggguuucag | 118,547 | 88,031 | 1,347 | 0,298 | 0,79 | 0,89 | 0,499 |
| SEQ ID NO: 491 | hsa-miR-302d | uaagugcuuccauguuugagugu | 32,719 | 40,875 | 0,800 | -0,223 | 0,79 | 0,89 | 0,444 |
| SEQ ID NO: 827 | hsa-miR-1244 | aaggaguauugguuugagauggu | 6,500 | 3,875 | 1,677 | 0,517 | 0,8 | 0,89 | 0,529 |
| SEQ ID NO: 574 | hsa-miR-21* | caacaccaguccugguuaaccucuu | 167,625 | 184,641 | 0,908 | -0,097 | 0,8 | 0,89 | 0,458 |
| SEQ ID NO: 245 | hsa-miR-541* | aaaggauucugcugucggucccacu | 40,906 | 40,203 | 1,017 | 0,017 | 0,8 | 0,89 | 0,462 |

FIG. 18A (Cont.)

| | | | | | | | | |
|---|---|---|---|---|---|---|---|---|
| SEQ ID NO: 659 | hsa-miR-184 | uggacgagaacugauaagggu | 47,219 | 51,281 | 0,921 | -0,083 | 0,8 | 0,89 | 0,489 |
| SEQ ID NO: 208 | hsa-miR-555 | agguaagcugaaccucugau | 95,219 | 87,406 | 1,089 | 0,086 | 0,8 | 0,89 | 0,540 |
| SEQ ID NO: 168 | hsa-miR-591 | agaccaugguuucauugu | 122,844 | 116,844 | 1,051 | 0,050 | 0,8 | 0,89 | 0,542 |
| SEQ ID NO: 104 | hsa-miR-649 | aaaccugguuguucaagaguc | 54,281 | 60,813 | 0,893 | -0,114 | 0,8 | 0,89 | 0,442 |
| SEQ ID NO: 832 | hsa-miR-1237 | uccuucugcucgucccccag | 152,094 | 152,156 | 1,000 | 0,000 | 0,81 | 0,89 | 0,483 |
| SEQ ID NO: 269 | hsa-miR-520c-5p | cucuagagggaagcacuuucug | 235,219 | 218,563 | 1,076 | 0,073 | 0,81 | 0,89 | 0,531 |
| SEQ ID NO: 464 | hsa-miR-325 | ccuaguagguguccaguaagugu | 117,188 | 108,906 | 1,076 | 0,073 | 0,81 | 0,89 | 0,519 |
| SEQ ID NO: 265 | hsa-miR-520f | aagugcuuccuuuuagagggu | 28,906 | 29,219 | 0,989 | -0,011 | 0,82 | 0,9 | 0,502 |
| SEQ ID NO: 731 | hsa-miR-520f | acuccauuuguuuugaugauga | 94,625 | 85,422 | 1,108 | 0,102 | 0,82 | 0,9 | 0,527 |
| SEQ ID NO: 744 | hsa-miR-136 | uaacagucuacagccaugucg | 174,750 | 168,688 | 1,036 | 0,035 | 0,82 | 0,9 | 0,579 |
| SEQ ID NO: 132 | hsa-miR-132 | cgcaucccuaggcauuggugu | 588,781 | 613,781 | 0,959 | -0,042 | 0,82 | 0,9 | 0,491 |
| SEQ ID NO: 465 | hsa-miR-324-5p | gcuggcagggcuucugagcuccuu | 144,719 | 133,859 | 1,081 | 0,078 | 0,83 | 0,9 | 0,564 |
| SEQ ID NO: 147 | hsa-miR-612 | aguauucuguaccaggaaggu | 91,500 | 89,938 | 1,017 | 0,017 | 0,83 | 0,9 | 0,539 |
| SEQ ID NO: 123 | hsa-miR-630 | aaaacuguaauuacuuuuguac | 99,094 | 96,875 | 1,023 | 0,023 | 0,83 | 0,9 | 0,492 |
| SEQ ID NO: 228 | hsa-miR-548g | ugauuagccuuuuggagaga | 33,484 | 36,625 | 0,914 | -0,090 | 0,83 | 0,91 | 0,474 |
| SEQ ID NO: 317 | hsa-miR-508-3p | gagguugggggaggcuccc | 127,000 | 121,594 | 1,044 | 0,044 | 0,83 | 0,91 | 0,512 |
| SEQ ID NO: 513 | hsa-miR-296-3p | caucccuucaugguggaggg | 215,844 | 212,844 | 1,014 | 0,014 | 0,83 | 0,91 | 0,500 |
| SEQ ID NO: 651 | hsa-miR-188-5p | aacaucucuggcuacugggu | 655,146 | 661,336 | 0,991 | -0,009 | 0,84 | 0,91 | 0,521 |
| SEQ ID NO: 542 | hsa-miR-222 | aacaucaacgcugucgugagu | 1197,650 | 855,281 | 1,400 | 0,337 | 0,84 | 0,91 | 0,634 |
| SEQ ID NO: 673 | hsa-miR-181a | cguguucagcagcggccugau | 180,563 | 183,594 | 0,983 | -0,017 | 0,84 | 0,91 | 0,461 |
| SEQ ID NO: 829 | hsa-miR-124* | caugccugaguguaggaccgu | 437,328 | 347,672 | 1,258 | 0,229 | 0,84 | 0,91 | 0,574 |
| SEQ ID NO: 248 | hsa-miR-532-5p | agguugacauacguuucc | 63,953 | 61,344 | 1,043 | 0,042 | 0,84 | 0,91 | 0,487 |
| SEQ ID NO: 200 | hsa-miR-563 | agguuaccggacaacuuugcau | 158,750 | 149,625 | 1,061 | 0,059 | 0,84 | 0,91 | 0,556 |
| SEQ ID NO: 392 | hsa-miR-409-5p | auauuaccauuuagcucaucuuu | 29,672 | 25,563 | 1,161 | 0,149 | 0,84 | 0,91 | 0,519 |
| SEQ ID NO: 207 | hsa-miR-556-3p | cucuagagggaagcacuuucug | 221,047 | 255,043 | 0,867 | -0,143 | 0,84 | 0,91 | 0,393 |
| SEQ ID NO: 253 | hsa-miR-526a | uuugguccccuucaaccagcug | 126,813 | 118,578 | 1,069 | 0,067 | 0,85 | 0,91 | 0,549 |
| SEQ ID NO: 738 | hsa-miR-133a | gcaggaacugugaguccu | 121,094 | 126,813 | 0,955 | -0,046 | 0,85 | 0,91 | 0,443 |
| SEQ ID NO: 54 | hsa-miR-873 | aaaagcugggguugagagggu | 886,344 | 790,391 | 1,121 | 0,115 | 0,85 | 0,91 | 0,549 |
| SEQ ID NO: 470 | hsa-miR-320c | caucuuccaguacagugugga | 166,281 | 168,531 | 0,987 | -0,013 | 0,85 | 0,91 | 0,504 |
| SEQ ID NO: 720 | hsa-miR-141* | caucuuaccggacagugcugga | 171,348 | 159,844 | 1,072 | 0,069 | 0,85 | 0,91 | 0,466 |
| SEQ ID NO: 596 | hsa-miR-200a* | ucagugcaugacagaacugg | 334,141 | 306,234 | 1,091 | 0,087 | 0,86 | 0,92 | 0,531 |
| SEQ ID NO: 691 | hsa-miR-152 | ccucugaaauucaguucucag | 189,938 | 185,766 | 1,022 | 0,022 | 0,86 | 0,92 | 0,527 |
| SEQ ID NO: 708 | hsa-miR-146a* | gcuguucauuguggauuuugu | 33,797 | 37,906 | 0,892 | -0,115 | 0,86 | 0,92 | 0,485 |
| SEQ ID NO: 504 | hsa-miR-29b-1* | ceaaagaauugguggauuuugu | 82,906 | 88,375 | 0,938 | -0,064 | 0,87 | 0,93 | 0,469 |
| SEQ ID NO: 221 | hsa-miR-548n | ccaguauuaacugucccgcuga | 168,393 | 158,484 | 1,063 | 0,061 | 0,87 | 0,93 | 0,558 |
| SEQ ID NO: 677 | hsa-miR-16-1* | ugugcuugcucgucccccgca | 306,016 | 300,641 | 1,018 | 0,018 | 0,87 | 0,93 | 0,567 |
| SEQ ID NO: 489 | hsa-miR-302e | uaagugcuuccaugcuu | 59,938 | 53,719 | 1,116 | 0,110 | 0,87 | 0,93 | 0,543 |

FIG. 18A (Cont.)

| | | | | | | | | |
|---|---|---|---|---|---|---|---|---|
| SEQ ID NO: 799 | hsa-miR-1264 | caagucuuauuugagcaccuguu | 68,313 | 74,563 | 0,916 | -0,088 | 0,88 | 0,93 | 0,482 |
| SEQ ID NO: 550 | hsa-miR-219-5p | ugauugguccaaacgcaauucu | 106,281 | 91,719 | 1,159 | 0,147 | 0,88 | 0,93 | 0,587 |
| SEQ ID NO: 646 | hsa-miR-190 | ugauauguuuugauauuaggu | 27,969 | 37,375 | 0,748 | -0,290 | 0,88 | 0,93 | 0,467 |
| SEQ ID NO: 337 | hsa-miR-494 | ugaaacauacacgggaaccuc | 126,813 | 122,313 | 1,037 | 0,036 | 0,89 | 0,94 | 0,506 |
| SEQ ID NO: 22 | hsa-miR-93 | caaagugcuguuguugcagguag | 6179,910 | 6647,320 | 0,930 | -0,073 | 0,89 | 0,94 | 0,510 |
| SEQ ID NO: 416 | hsa-miR-373 | gaagugccucgauuuuggggugu | 18,844 | 14,688 | 1,283 | 0,249 | 0,89 | 0,94 | 0,586 |
| SEQ ID NO: 224 | hsa-miR-548k | aaaaguacuugcggauuugcu | 55,500 | 68,688 | 0,808 | -0,213 | 0,9 | 0,94 | 0,464 |
| SEQ ID NO: 658 | hsa-miR-185 | uggagagaaaggcaguccuga | 30296,156 | 27473,492 | 1,103 | 0,098 | 0,9 | 0,95 | 0,509 |
| SEQ ID NO: 150 | hsa-miR-609 | aggguguuucucucaucau | 12,625 | 16,703 | 0,756 | -0,280 | 0,9 | 0,95 | 0,476 |
| SEQ ID NO: 761 | hsa-miR-129-5p | cuuuugcggucugggcugc | 100,000 | 97,156 | 1,029 | 0,029 | 0,91 | 0,95 | 0,514 |
| SEQ ID NO: 626 | hsa-miR-193b | aacugccucaaagucccgcu | 146,969 | 139,719 | 1,052 | 0,051 | 0,91 | 0,95 | 0,540 |
| SEQ ID NO: 851 | hsa-miR-1207-3p | ucagcuggcccucauuc | 69,250 | 75,547 | 0,917 | -0,087 | 0,91 | 0,95 | 0,479 |
| SEQ ID NO: 406 | hsa-miR-376c | aacauagagaaauccacgu | 155,625 | 161,250 | 0,965 | -0,036 | 0,91 | 0,95 | 0,502 |
| SEQ ID NO: 496 | hsa-miR-302a* | acuuaaacguggauacuugcu | 96,828 | 99,844 | 0,970 | -0,031 | 0,91 | 0,95 | 0,485 |
| SEQ ID NO: 639 | hsa-miR-1910 | ccaguccugcugccgcgccu | 68,000 | 88,828 | 0,766 | -0,267 | 0,91 | 0,95 | 0,419 |
| SEQ ID NO: 900 | hsa-let-7b* | cuauacaaccuacugccauccc | 45,688 | 38,625 | 1,183 | 0,168 | 0,92 | 0,95 | 0,520 |
| SEQ ID NO: 455 | hsa-miR-335* | uuuuucauuaugccuccugacc | 35,141 | 42,563 | 0,826 | -0,192 | 0,92 | 0,96 | 0,469 |
| SEQ ID NO: 322 | hsa-miR-504 | agaccuugucucacucauc | 76,453 | 73,031 | 1,047 | 0,046 | 0,92 | 0,96 | 0,498 |
| SEQ ID NO: 202 | hsa-miR-561 | caaguuuaagauccuugaagu | 96,828 | 104,891 | 0,923 | -0,080 | 0,92 | 0,96 | 0,487 |
| SEQ ID NO: 139 | hsa-miR-618 | aaacucuacuugcccuucgagu | 70,344 | 68,625 | 1,025 | 0,025 | 0,93 | 0,96 | 0,523 |
| SEQ ID NO: 111 | hsa-miR-642 | gucccuccaaaugugucuug | 84,500 | 77,844 | 1,086 | 0,082 | 0,93 | 0,96 | 0,500 |
| SEQ ID NO: 3 | hsa-miR-99a* | caagcucguuucuauggguucu | 72,328 | 73,375 | 0,986 | -0,014 | 0,93 | 0,96 | 0,487 |
| SEQ ID NO: 184 | hsa-miR-578 | cuucugugcucuaggauugu | 38,781 | 38,094 | 1,018 | 0,018 | 0,93 | 0,96 | 0,496 |
| SEQ ID NO: 340 | hsa-miR-492 | aggaccugcggacaagauucuu | 159,969 | 155,484 | 1,029 | 0,028 | 0,94 | 0,97 | 0,491 |
| SEQ ID NO: 471 | hsa-miR-320b | aaaagcuggguugagagggcaa | 3376,021 | 2522,371 | 1,338 | 0,291 | 0,94 | 0,97 | 0,544 |
| SEQ ID NO: 878 | hsa-miR-105 | ucaaaugcucagacuccuguggu | 89,656 | 96,563 | 0,928 | -0,074 | 0,94 | 0,97 | 0,476 |
| SEQ ID NO: 1257 | hsa-miR-1257 | agugaaugaugggguucugac | 36,297 | 42,156 | 0,861 | -0,150 | 0,94 | 0,97 | 0,464 |
| SEQ ID NO: 211 | hsa-miR-552 | aacagugacugccgguuagacaa | 70,719 | 61,797 | 1,144 | 0,135 | 0,95 | 0,97 | 0,525 |
| SEQ ID NO: 638 | hsa-miR-1911 | ugaguaccgccauguucuuggg | 96,641 | 98,453 | 0,982 | -0,019 | 0,95 | 0,98 | 0,512 |
| SEQ ID NO: 214 | hsa-miR-551a | gcgaccacucucuggguuca | 88,938 | 94,719 | 0,939 | -0,063 | 0,95 | 0,98 | 0,496 |
| SEQ ID NO: 77 | hsa-miR-708 | aaggagcuuacaaucagcugg | 102,313 | 108,063 | 0,947 | -0,055 | 0,96 | 0,98 | 0,495 |
| SEQ ID NO: 252 | hsa-miR-526b | cuuugaggaagcacuuucugu | 89,766 | 85,891 | 1,045 | 0,044 | 0,96 | 0,98 | 0,487 |
| SEQ ID NO: 276 | hsa-miR-519d | caaagugccucccuuuagagu | 106,438 | 116,688 | 0,912 | -0,092 | 0,96 | 0,98 | 0,492 |
| SEQ ID NO: 712 | hsa-miR-145* | ggauuccuggaaauacguucc | 151,969 | 160,000 | 0,950 | -0,051 | 0,97 | 0,99 | 0,565 |
| SEQ ID NO: 283 | hsa-miR-518f* | cucuagugaagcacuuuccc | 227,875 | 190,703 | 1,195 | 0,178 | 0,97 | 0,99 | 0,565 |
| SEQ ID NO: 533 | hsa-miR-23a | aucacauugccagggauuuccc | 4776,795 | 4344,961 | 1,099 | 0,095 | 0,97 | 0,99 | 0,565 |
| SEQ ID NO: 289 | hsa-miR-518c* | ucucuggagggaagcacuuucug | 119,125 | 123,906 | 0,961 | -0,039 | 0,97 | 0,99 | 0,462 |

FIG. 18A (Cont.)

| | | | | | | | |
|---|---|---|---|---|---|---|---|
| SEQ ID NO: 725 | hsa-miR-139-3p | ggagacgcggccugmuggagu | 140,125 | 128,500 | 1,090 | 0,087 | 0,97 | 0,99 | 0,572 |
| SEQ ID NO: 210 | hsa-miR-553 | aaaacggugagagattuuuguuuu | 49,469 | 40,938 | 1,208 | 0,189 | 0,97 | 0,99 | 0,529 |
| SEQ ID NO: 409 | hsa-miR-376a | aucauagaggaaaauccacgu | 172,391 | 162,938 | 1,058 | 0,056 | 0,98 | 0,99 | 0,503 |
| SEQ ID NO: 698 | hsa-miR-148b* | aaguucuguuauacacucaggc | 84,625 | 82,125 | 1,030 | 0,030 | 0,98 | 0,99 | 0,525 |
| SEQ ID NO: 717 | hsa-miR-143 | ugagaugaagcacuguagcuc | 361,125 | 304,734 | 1,185 | 0,170 | 0,98 | 0,99 | 0,602 |
| SEQ ID NO: 34 | hsa-miR-892b | cacuggcuccuuucuggguaga | 84,125 | 76,625 | 1,098 | 0,093 | 0,98 | 0,99 | 0,534 |
| SEQ ID NO: 846 | hsa-miR-1224-3p | ccccaccccucucucucucag | 243,566 | 159,594 | 1,526 | 0,423 | 0,99 | 1 | 0,614 |
| SEQ ID NO: 831 | hsa-miR-1238 | cuuccucgucugucugcccc | 54,766 | 51,781 | 1,058 | 0,056 | 0,99 | 1 | 0,563 |
| SEQ ID NO: 308 | hsa-miR-513a-3p | uaaauuucaccucuuuugagaagg | 119,828 | 111,813 | 1,072 | 0,069 | 0,99 | 1 | 0,551 |
| SEQ ID NO: 294 | hsa-miR-517c | aucugcaucccuuuuagagugu | 50,875 | 44,969 | 1,131 | 0,123 | 0,99 | 1 | 0,509 |
| SEQ ID NO: 88 | hsa-miR-663b | gguggcccggccgugccugagg | 141,750 | 143,000 | 0,991 | -0,009 | 1 | 1 | 0,498 |
| SEQ ID NO: 396 | hsa-miR-382 | gaaguuguucgugguggauucg | 43,688 | 50,750 | 0,861 | -0,150 | 1 | 1 | 0,502 |
| SEQ ID NO: 444 | hsa-miR-340 | uuauaaagcaaugagacugauu | 286,125 | 289,609 | 0,988 | -0,012 | 1 | 1 | 0,498 |
| SEQ ID NO: 348 | hsa-miR-487b | aaucguacaggugucauccacuu | 134,344 | 124,344 | 1,080 | 0,077 | 1 | 1 | 0,512 |

FIG. 18B

| SEQ ID NO: | Seq Id | Name (mature miRNA) miRBase | Sequence | level significance |
|---|---|---|---|---|
| SEQ ID NO: 713 | Tab1-1 | hsa-miR-145 | GUCCAGUUUUCCCAGGAAUCCCU | 1,48E-07 |
| SEQ ID NO: 656 | Tab1-2 | hsa-miR-186 | CAAAGAAUUCUCCUUUUGGGCU | 2,89E-07 |
| SEQ ID NO: 87 | Tab1-3 | hsa-miR-664 | UAUUCAUUUAUCCCCAGCCUACA | 5,25E-05 |
| SEQ ID NO: 577 | Tab1-4 | hsa-miR-20b | CAAAGUGCUCAUAGUGCAGGUAG | 0,000148065 |
| SEQ ID NO: 386 | Tab1-5 | hsa-miR-422a | ACUGGACUUAGGGUCAGAAAGC | 0,000148065 |
| SEQ ID NO: 719 | Tab1-6 | hsa-miR-142-3p | UGUAGUGUUUCCUACUUUAUGGA | 0,000154481 |
| SEQ ID NO: 177 | Tab1-7 | hsa-miR-584 | UUAUGGUUUGCCUGGGACUGAG | 0,000156481 |
| SEQ ID NO: 540 | Tab1-8 | hsa-miR-223 | UGUCAGUUUGUCAAAUACCCCA | 0,00016217 |
| SEQ ID NO: 786 | Tab1-9 | hsa-miR-1275 | GUGGGGGAGAGGCUGUC | 0,000163285 |
| SEQ ID NO: 341 | Tab1-10 | hsa-miR-491-5p | AGUGGGGAACCCUUCCAUGAGG | 0,000283444 |
| SEQ ID NO: 693 | Tab1-11 | hsa-miR-151-3p | CUAGACUGAAGCUCCUUGAGG | 0,000461766 |
| SEQ ID NO: 23 | Tab1-12 | hsa-miR-92b* | AGGGACGGGACGCGGUUGUAUGGUU | 0,000499915 |
| SEQ ID NO: 899 | Tab1-13 | hsa-let-7c | UGAGGUAGUAGGUUGUAUGGUU | 0,000626377 |
| SEQ ID NO: 558 | Tab1-14 | hsa-miR-216a | UAAUCUCAGCUGGCAACUGUGA | 0,000697573 |
| SEQ ID NO: 424 | Tab1-15 | hsa-miR-367 | AAUUGCACUUUAGCAAUGGUGA | 0,000736487 |
| SEQ ID NO: 11 | Tab1-16 | hsa-miR-942 | UCUUCUGUUUUGGCCAUGUG | 0,000736487 |
| SEQ ID NO: 876 | Tab1-17 | hsa-miR-106a | AAAAGUGCUUACAGUGCAGGUAG | 0,000843844 |
| SEQ ID NO: 495 | Tab1-18 | hsa-miR-302b | UAAGUGCUUCCAUGUUUUAGUAG | 0,001057227 |
| SEQ ID NO: 426 | Tab1-19 | hsa-miR-365 | UAAUGCCCCUAAAAAUCCUUAU | 0,001057227 |
| SEQ ID NO: 722 | Tab1-20 | hsa-miR-140-5p | CAGUGGUUUUACCCUAUGGUAG | 0,001139983 |
| SEQ ID NO: 478 | Tab1-21 | hsa-miR-30e | UGUAAACAUCCUUGACUGGAAG | 0,01187881 |
| SEQ ID NO: 548 | Tab1-22 | hsa-miR-22* | AGUUCUUCAGUGGCAAGCUUUA | 0,001302256 |
| SEQ ID NO: 657 | Tab1-23 | hsa-miR-185* | AGGGGCUGGCUUUCCUCUGGUC | 0,001302256 |
| SEQ ID NO: 432 | Tab1-24 | hsa-miR-361-3p | UCCCCCAGGUGUGAUUCUGAUUU | 0,001372655 |
| SEQ ID NO: 756 | Tab1-25 | hsa-miR-1301 | UUGCAGCUGCCUGGGAGUGACUUC | 0,001391723 |
| SEQ ID NO: 644 | Tab1-26 | hsa-miR-1909 | CGCAGGGGCCGGGUGCUCACCG | 0,001553322 |
| SEQ ID NO: 872 | Tab1-27 | hsa-miR-107 | AGCAGCAUUGUACAGGGCUAUCA | 0,002210862 |
| SEQ ID NO: 649 | Tab1-28 | hsa-miR-18a* | ACUGCCCUAAGUGCUCCUUCUGG | 0,00263885 |
| SEQ ID NO: 709 | Tab1-29 | hsa-miR-146a | UGAGAACUGAAUUCCAUGGGUU | 0,00263885 |
| SEQ ID NO: 326 | Tab1-30 | hsa-miR-501-5p | AAUCCUUUGUCCCUGGGUGAGA | 0,00273563 |
| SEQ ID NO: 37 | Tab1-31 | hsa-miR-891a | UGCAACGAACCUGAGCCACUGA | 0,00282418 |
| SEQ ID NO: 161 | Tab1-32 | hsa-miR-598 | UACGUCAUCGUUGUCAUCGUCA | 0,002982077 |
| SEQ ID NO: 791 | Tab1-33 | hsa-miR-1272 | GAUGAUGAUGGCAGCAAAUUCUGAAA | 0,00298827 |
| SEQ ID NO: 131 | Tab1-34 | hsa-miR-625 | AGGGGGAAAGUUCUAUAGUCC | 0,003045666 |

FIG. 18B (Cont.)

| SEQ ID NO | Tab1 | miRNA | Sequence | Value |
|---|---|---|---|---|
| SEQ ID NO: 423 | Tab1-35 | hsa-miR-367* | ACUGUUGCUAAUAUGCAACUCU | 0.0030045666 |
| SEQ ID NO: 146 | Tab1-36 | hsa-miR-613 | AGGAAUGUUCCUUCUUUGCC | 0.0030045666 |
| SEQ ID NO: 881 | Tab1-37 | hsa-miR-103 | AGCAGCAUUGUACAGGGCUAUGA | 0.00348231 |
| SEQ ID NO: 605 | Tab1-38 | hsa-miR-199a-5p | CCCAGUGUUCAGACUACCUGUUC | 0.003507036 |
| SEQ ID NO: 306 | Tab1-39 | hsa-miR-513b | UUCACAAGGAGGUGUCAUUUAU | 0.003974635 |
| SEQ ID NO: 487 | Tab1-40 | hsa-miR-30a | UGUAAACAUCCUCGACUGGAAG | 0.003974635 |
| SEQ ID NO: 809 | Tab1-41 | hsa-miR-125a-5p | UCCCUGAGACCCUUUAACCUGUGA | 0.003974635 |
| SEQ ID NO: 562 | Tab1-42 | hsa-miR-212 | UAACAGUCUCCAGUCACGGCC | 0.004251563 |
| SEQ ID NO: 429 | Tab1-43 | hsa-miR-362-5p | AAUCCUUGGAACCUAGGUGUGAGU | 0.00477326 |
| SEQ ID NO: 502 | Tab1-44 | hsa-miR-29c | UAGCACCAUUUGAAAUCGGUUA | 0.00492113 |
| SEQ ID NO: 331 | Tab1-45 | hsa-miR-499-3p | AACAUCACAGCAAGUCUGUGCU | 0.00492113 |
| SEQ ID NO: 6 | Tab1-46 | hsa-miR-96* | AAUCAUGUGCAGUGCCAAUAUG | 0.005326734 |
| SEQ ID NO: 820 | Tab1-47 | hsa-miR-1251 | ACUCUAGCUGCCAAAGCGCU | 0.005693262 |
| SEQ ID NO: 364 | Tab1-48 | hsa-miR-451 | AAACCGUUACCAUUACUGAGUU | 0.006594945 |
| SEQ ID NO: 674 | Tab1-49 | hsa-miR-17* | ACUGCAGUGAAGGCACUUGUAG | 0.006594945 |
| SEQ ID NO: 80 | Tab1-50 | hsa-miR-675 | UGGUGCGGAGAGGGCCCACAGUG | 0.006594945 |
| SEQ ID NO: 206 | Tab1-51 | hsa-miR-556-5p | GAUGAGCUCAUGUGAAUAUGAG | 0.006594945 |
| SEQ ID NO: 896 | Tab1-52 | hsa-let-7d* | CUAUACGACCCUGCUCCUUUCU | 0.006594945 |
| SEQ ID NO: 203 | Tab1-53 | hsa-miR-559 | UAAAGUAAAUAUGCACCAAAA | 0.006594945 |
| SEQ ID NO: 865 | Tab1-54 | hsa-miR-1180 | UUCCGGCUCGCGUGGGUGUGU | 0.006594945 |
| SEQ ID NO: 254 | Tab1-55 | hsa-miR-525-5p | CUCCAGAGGGAUGCACUUUCU | 0.006594945 |
| SEQ ID NO: 152 | Tab1-56 | hsa-miR-607 | GUUCAAAUCCAGAUCAAUGUAAAC | 0.006594945 |
| SEQ ID NO: 543 | Tab1-57 | hsa-miR-221* | ACCUGGCAUACAAUGUAGAUUU | 0.006878721 |
| SEQ ID NO: 153 | Tab1-58 | hsa-miR-606 | AAACUAUCCUACAAAAUCAAAGAU | 0.007108129 |
| SEQ ID NO: 14 | Tab1-59 | hsa-miR-939 | UGGGGAGCUGAGGCUCUGGGGGUG | 0.007227517 |
| SEQ ID NO: 190 | Tab1-60 | hsa-miR-574-3p | CACGCUCAUGCACACACACACA | 0.007227517 |
| SEQ ID NO: 561 | Tab1-61 | hsa-miR-214 | ACAGCAGGCACAGACAGGCAGU | 0.00766807 |
| SEQ ID NO: 580 | Tab1-62 | hsa-miR-208b | AUAAGACGAACAAAAGGUUUGU | 0.00766807 |
| SEQ ID NO: 652 | Tab1-63 | hsa-miR-188-3p | CUCCCAGAUGCAAGGGUUUGCA | 0.00766807 |
| SEQ ID NO: 342 | Tab1-64 | hsa-miR-491-3p | CUUAUGCAAGAUUCCCUUCUAC | 0.00766807 |
| SEQ ID NO: 215 | Tab1-65 | hsa-miR-550* | UGUCUUACUCCCUCAGGCACAU | 0.007676623 |
| SEQ ID NO: 840 | Tab1-66 | hsa-miR-1227 | CGUGCCACCCUUUUCCCAG | 0.008145006 |
| SEQ ID NO: 24 | Tab1-67 | hsa-miR-92b | UAUUGCACUCGUCCCGGCCUCC | 0.008146137 |
| SEQ ID NO: 460 | Tab1-68 | hsa-miR-330-3p | GCAAAGCACACGGCCUGCAGAGA | 0.008687984 |
| SEQ ID NO: 745 | Tab1-69 | hsa-miR-130b* | ACUCUUCCCUGUUGCACUAC | 0.008846701 |
| SEQ ID NO: 97 | Tab1-70 | hsa-miR-655 | AUAAUACAUGGUUAACCUCUUU | 0.008894239 |
| SEQ ID NO: 182 | Tab1-71 | hsa-miR-580 | UUGAGAAUGAUGAAUCAUUAGG | 0.010153347 |

FIG. 18B (Cont.)

| | | | |
|---|---|---|---|
| SEQ ID NO: 402 | Tab1-72 | hsa-miR-378* | CUCCUGACUCCAGGUCCUGUGU | 0.01028601 |
| SEQ ID NO: 125 | Tab1-73 | hsa-miR-629 | UGGGUUUACGUUGGGAGAACU | 0.01028601 |
| SEQ ID NO: 579 | Tab1-74 | hsa-miR-20a | UAAAGUGCUUAUAGUGCAGGUAG | 0.01028601 |
| SEQ ID NO: 730 | Tab1-75 | hsa-miR-136* | CAUCAUCGUCUCAAAUGAGUCU | 0.010690643 |
| SEQ ID NO: 458 | Tab1-76 | hsa-miR-331-3p | GCCCUGGGCCUAUCCUAGAA | 0.011065082 |
| SEQ ID NO: 25 | Tab1-77 | hsa-miR-92a-2* | GGGUGGGGAUUUGUUGCAUUAC | 0.011648579 |
| SEQ ID NO: 622 | Tab1-78 | hsa-miR-195 | UAGCAGCACAGAAAUAUUGGC | 0.012487876 |
| SEQ ID NO: 398 | Tab1-79 | hsa-miR-380* | UGGUUGACCAUAGAACAUGCGC | 0.012565569 |
| SEQ ID NO: 62 | Tab1-80 | hsa-miR-765 | UGGAGGAGAAGGAAGGUGAUG | 0.013190076 |
| SEQ ID NO: 334 | Tab1-81 | hsa-miR-497 | CAGCAGCACACUGUGGUUUGU | 0.013799137 |
| SEQ ID NO: 701 | Tab1-82 | hsa-miR-148a | UCAGUGCACUACAGAACUUUGU | 0.014433595 |
| SEQ ID NO: 578 | Tab1-83 | hsa-miR-20a* | ACUGCAUUAUGAGCACUUAAAG | 0.014433595 |
| SEQ ID NO: 645 | Tab1-84 | hsa-miR-1908 | CGGCGGGGACGCGAUUGGUC | 0.014489428 |
| SEQ ID NO: 51 | Tab1-85 | hsa-miR-875-5p | UAUACCUCAGUUUUAUCAGGUG | 0.015447027 |
| SEQ ID NO: 94 | Tab1-86 | hsa-miR-658 | GGCGGAGGGAAGUAGGUCGUUGGU | 0.015501759 |
| SEQ ID NO: 78 | Tab1-87 | hsa-miR-7 | UGGAAGACUAGUGAUUUGUUGU | 0.015927763 |
| SEQ ID NO: 165 | Tab1-88 | hsa-miR-593* | AGGCACCAGCCAGGCAUUGCUCAGC | 0.016362518 |
| SEQ ID NO: 670 | Tab1-89 | hsa-miR-181b | AACAUUCAUUGCUGUCGGUGGGU | 0.016362518 |
| SEQ ID NO: 4 | Tab1-90 | hsa-miR-99a | AACCCGUAGAUCCGAUCUGUG | 0.016953767 |
| SEQ ID NO: 776 | Tab1-91 | hsa-miR-1283 | UCUACAAAGGAAAGCGCUUUCU | 0.016953767 |
| SEQ ID NO: 430 | Tab1-92 | hsa-miR-362-3p | AACACACCUAUUCAAGGAUUCA | 0.016953767 |
| SEQ ID NO: 158 | Tab1-93 | hsa-miR-601 | UGGUCUAGGAUUGUUGGAGAG | 0.016953767 |
| SEQ ID NO: 362 | Tab1-94 | hsa-miR-452* | CUCAUCUGCAAAGAAGUAAGUG | 0.01746741 |
| SEQ ID NO: 600 | Tab1-95 | hsa-miR-19b | UGUGCAAAUCCAUGCAAAACUGA | 0.017528239 |
| SEQ ID NO: 529 | Tab1-96 | hsa-miR-24 | UGGCUCAGUUCAGCAGGAACAG | 0.017530497 |
| SEQ ID NO: 557 | Tab1-97 | hsa-miR-216b | AAAUCUCUGCAGGCAAAUGUGA | 0.017530497 |
| SEQ ID NO: 817 | Tab1-98 | hsa-miR-1254 | AGCCUGGAAGCUGGAGCCUGCAGU | 0.017530497 |
| SEQ ID NO: 196 | Tab1-99 | hsa-miR-568 | AUGUAUAAAAUGUAUACAC | 0.018441588 |
| SEQ ID NO: 274 | Tab1-100 | hsa-miR-519e* | UUCUCCAAAAGGGAGCACUUUC | 0.018759484 |
| SEQ ID NO: 136 | Tab1-101 | hsa-miR-621 | GGCUAGCAACAGCGCUUACCU | 0.018759484 |
| SEQ ID NO: 329 | Tab1-102 | hsa-miR-500 | UAAUCCUUGCUACCUGGGUGAGA | 0.019371611 |
| SEQ ID NO: 507 | Tab1-103 | hsa-miR-29a | UAGCACCAUCUGAAAUCGGUUA | 0.019371611 |
| SEQ ID NO: 70 | Tab1-104 | hsa-miR-744 | UGCGGGGCUAGGGCUAACAGCA | 0.019881348 |
| SEQ ID NO: 874 | Tab1-105 | hsa-miR-106b | UAAAGUGCUGACAGUGCAGAU | 0.020439781 |
| SEQ ID NO: 850 | Tab1-106 | hsa-miR-1207-5p | UGGCAGGGAGGCUGGGAGGGG | 0.020549704 |
| SEQ ID NO: 671 | Tab1-107 | hsa-miR-181a-2* | ACCACUGACCGUUGACUGUACC | 0.020549704 |
| SEQ ID NO: 795 | Tab1-108 | hsa-miR-1268 | CGGGCGUGGUGGUGGGG | 0.020810512 |

FIG. 18B (Cont.)

| | | | |
|---|---|---|---|
| SEQ ID NO: 834 | Tab1-109 | hsa-miR-1234 | UCGGCCUGACCACCGACCCCAC | 0.021434867 |
| SEQ ID NO: 852 | Tab1-110 | hsa-miR-1206 | UGUUCAUGUAGUGUGUAUUAAGC | 0.023397664 |
| SEQ ID NO: 189 | Tab1-111 | hsa-miR-574-5p | UGAGUGUGUGUGUGUGAGUGUGU | 0.023404017 |
| SEQ ID NO: 448 | Tab1-112 | hsa-miR-33a | GUGCAUUGUAGUUGCAUUGCA | 0.023541941 |
| SEQ ID NO: 473 | Tab1-113 | hsa-miR-32* | CAAUUAGUGUGUGUGUGAUAUUU | 0.023572686 |
| SEQ ID NO: 32 | Tab1-114 | hsa-miR-9* | AUAAAGCUAGAUAACCGAAAGU | 0.023572686 |
| SEQ ID NO: 241 | Tab1-115 | hsa-miR-544 | AUUCUGCAUUUUAGCAAGUUC | 0.023858088 |
| SEQ ID NO: 127 | Tab1-116 | hsa-miR-628-3p | UCUAGUAAGAGUGGCAGUCGA | 0.023858088 |
| SEQ ID NO: 556 | Tab1-117 | hsa-miR-217 | UACUGCAUCAGGAACUGAUUGGA | 0.023858088 |
| SEQ ID NO: 636 | Tab1-118 | hsa-miR-1912 | UACCCAGAGCAUCAGUGUGAA | 0.023858088 |
| SEQ ID NO: 107 | Tab1-119 | hsa-miR-646 | AAGCAGCUGCCUCUGAGGC | 0.023858088 |
| SEQ ID NO: 886 | Tab1-120 | hsa-miR-1 | UGGAAUGUAAAGAAGUAUGUAU | 0.025157317 |
| SEQ ID NO: 797 | Tab1-121 | hsa-miR-1266 | CCUCAGGGCUGUAGAACAGGGCU | 0.025157317 |
| SEQ ID NO: 346 | Tab1-122 | hsa-miR-488* | CCCAGAUAAUGGCACUCUCAA | 0.025320273 |
| SEQ ID NO: 699 | Tab1-123 | hsa-miR-148b | UCAGUGCAUCACAGAACUUUGU | 0.02642468 |
| SEQ ID NO: 315 | Tab1-124 | hsa-miR-509-3-5p | UACUGCAGACGUGGCAAUCAUG | 0.02642468 |
| SEQ ID NO: 323 | Tab1-125 | hsa-miR-503 | UAGCAGCGGGAACAGUUCUGCAG | 0.027387368 |
| SEQ ID NO: 501 | Tab1-126 | hsa-miR-29c* | UGACCGAUUUCUCCUGGUGUUC | 0.027434153 |
| SEQ ID NO: 963 | Tab1-127 | hsa-miR-1300 | | 0.028179038 |
| SEQ ID NO: 845 | Tab1-128 | hsa-miR-1224-5p | GUGAGGACUCGGGAGGUGG | 0.028544926 |
| SEQ ID NO: 843 | Tab1-129 | hsa-miR-1225-5p | GUGGGUACGGCCCAGUGGGGGG | 0.029255392 |
| SEQ ID NO: 660 | Tab1-130 | hsa-miR-183* | GUGAAUUACCGAAGGGCACUGG | 0.029478737 |
| SEQ ID NO: 105 | Tab1-131 | hsa-miR-648 | AAGUGUGCAGGGCACUGGU | 0.029600689 |
| SEQ ID NO: 675 | Tab1-132 | hsa-miR-17 | CAAAGUGCUUACAGUGCAGGUAG | 0.029636086 |
| SEQ ID NO: 666 | Tab1-133 | hsa-miR-182 | UUUGGCAAUGGUAGAACUCACACU | 0.029636086 |
| SEQ ID NO: 447 | Tab1-134 | hsa-miR-33a* | CAAUGUUUCCACAGUGCAUCAC | 0.031805111 |
| SEQ ID NO: 518 | Tab1-135 | hsa-miR-27a* | AGGGCUUAGCUGCUUGUGAGCA | 0.032378715 |
| SEQ ID NO: 237 | Tab1-136 | hsa-miR-548a-5p | AAAAGUAAUUGCGAGUUUUACC | 0.033678224 |
| SEQ ID NO: 792 | Tab1-137 | hsa-miR-1271 | CUUGGCACCUAGCAAGCACUCA | 0.033894671 |
| SEQ ID NO: 812 | Tab1-138 | hsa-miR-1258 | AGUUAGGACAUUAGGUGUGGAA | 0.034205811 |
| SEQ ID NO: 755 | Tab1-139 | hsa-miR-1302 | UUGGGACAUACUUACUGCUAA | 0.034708746 |
| SEQ ID NO: 887 | Tab1-140 | hsa-let-7i* | CUGCGCAAGCUACUGCCUUGCU | 0.036510983 |
| SEQ ID NO: 391 | Tab1-141 | hsa-miR-410 | AAUAUAACACAGAUGGCCUGU | 0.036612975 |
| SEQ ID NO: 779 | Tab1-142 | hsa-miR-1280 | UCCCACCGCUGCCACCC | 0.037250015 |
| SEQ ID NO: 715 | Tab1-143 | hsa-miR-144 | UACAGUAUAGAUGAUGUACU | 0.037250015 |
| SEQ ID NO: 462 | Tab1-144 | hsa-miR-328 | CUGGCCCUCUCUGCCCUUCCGU | 0.038220527 |
| SEQ ID NO: 842 | Tab1-145 | hsa-miR-1226 | UCACCAGCCCUGUGUUCCCUAG | 0.039816047 |

FIG. 18B (Cont.)

| | | | | |
|---|---|---|---|---|
| SEQ ID NO: 194 | Tab1-146 | hsa-miR-570 | CGAAAACAGCAAUUACCUUUGC | 0,040473359 |
| SEQ ID NO: 349 | Tab1-147 | hsa-miR-487a | AAUCAUACAGGGACAUCCAGUU | 0,041006357 |
| SEQ ID NO: 743 | Tab1-148 | hsa-miR-132* | ACCGUGGCUUUCGAUUGUUACU | 0,041006357 |
| SEQ ID NO: 135 | Tab1-149 | hsa-miR-622 | ACAGUCUGCUGAGGUUGGAGC | 0,041006357 |
| SEQ ID NO: 412 | Tab1-150 | hsa-miR-374b | AUAUAAUACAACCUGCUAAGUG | 0,041006357 |
| SEQ ID NO: 544 | Tab1-151 | hsa-miR-221 | AGCUACAUUGUCUGCUGGGUUUC | 0,041971145 |
| SEQ ID NO: 516 | Tab1-152 | hsa-miR-27b* | AGAGCUUAGCUGAUUGGUGAAC | 0,04237911 |
| SEQ ID NO: 757 | Tab1-153 | hsa-miR-1299 | UUCUGGAAUUCUGUGUGAGGGA | 0,04237911 |
| SEQ ID NO: 46 | Tab1-154 | hsa-miR-885-3p | AGGCAGCGGGGUGUAGUGGAUA | 0,043261584 |
| SEQ ID NO: 238 | Tab1-155 | hsa-miR-548a-3p | CAAAACUGGCAAUUACUUUUGC | 0,043953954 |
| SEQ ID NO: 901 | Tab1-156 | hsa-let-7b | UGAGGUAGUAGGUUGUGUGGUU | 0,045126664 |
| SEQ ID NO: 590 | Tab1-157 | hsa-miR-202* | UUCCUAUGCAUAUACUUCUUUG | 0,045544732 |
| SEQ ID NO: 122 | Tab1-158 | hsa-miR-631 | AGACCUGGCCCAGACCUCAGC | 0,046793089 |
| SEQ ID NO: 434 | Tab1-159 | hsa-miR-34c-3p | AAUCACUAACCACACGGCCAGG | 0,046921038 |
| SEQ ID NO: 475 | Tab1-160 | hsa-miR-31* | UGCUAUGCCAACAUAUUGCCAU | 0,047209787 |
| SEQ ID NO: 824 | Tab1-161 | hsa-miR-1247 | ACCCGUCCCGUUCGUCCCCGGA | 0,048608753 |
| SEQ ID NO: 826 | Tab1-162 | hsa-miR-1245 | AAGUGAUCUAAAGGCCUACAU | 0,048831114 |
| SEQ ID NO: 302 | Tab1-163 | hsa-miR-515-5p | UUCUCCAAAAGAAAGCACUUUCUG | 0,048930534 |
| SEQ ID NO: 407 | Tab1-164 | hsa-miR-376b | AUCAUAGAGGAAAAUCCAUGUU | 0,049319483 |
| SEQ ID NO: 629 | Tab1-165 | hsa-miR-192* | CUGCCAAUUCCAUAGGUCACAG | 0,050350013 |
| SEQ ID NO: 28 | Tab1-166 | hsa-miR-924 | AGAGCUUGUGUGAUGUUUGC | 0,050591776 |
| SEQ ID NO: 480 | Tab1-167 | hsa-miR-30d | UGUAAACAUCCCCGACUGGAAG | 0,050591776 |
| SEQ ID NO: 890 | Tab1-168 | hsa-let-7g | UGAGGUAGUAGUUUGUACAGUU | 0,050591778 |
| SEQ ID NO: 316 | Tab1-169 | hsa-miR-508-5p | UACUCCAGAGGGCGUCACUCAUG | 0,051169589 |
| SEQ ID NO: 505 | Tab1-170 | hsa-miR-29b | UAGCACCAUUUGAAAUCAGUGUU | 0,052910562 |
| SEQ ID NO: 438 | Tab1-171 | hsa-miR-34a | UGGCAGUGUCUUAGCUGGUUGU | 0,05376323 |
| SEQ ID NO: 477 | Tab1-172 | hsa-miR-30e* | CUUUCAGUCGGAUGUUUACAGC | 0,053923696 |
| SEQ ID NO: 199 | Tab1-173 | hsa-miR-564 | AGGCACGGUGUCAGCAGGC | 0,053923696 |
| SEQ ID NO: 345 | Tab1-174 | hsa-miR-489 | GUGACAUCACAUAUACGGCAGC | 0,053923696 |
| SEQ ID NO: 724 | Tab1-175 | hsa-miR-139-5p | UCUACAGUGCACGUGUCUCCAG | 0,053923696 |
| SEQ ID NO: 53 | Tab1-176 | hsa-miR-874 | CUGCCCUGGCCCGAGGGACCGA | 0,053923696 |
| SEQ ID NO: 98 | Tab1-177 | hsa-miR-654-5p | UGGUGGGCCGCAGAACCAUGUA | 0,053923696 |
| SEQ ID NO: 428 | Tab1-178 | hsa-miR-363 | AAUUGCACGGUAUCCAUCUGUA | 0,054156699 |
| SEQ ID NO: 338 | Tab1-179 | hsa-miR-493* | UUGUACAUGGUAGGCUUUCAUU | 0,054156699 |
| SEQ ID NO: 440 | Tab1-180 | hsa-miR-345 | GCUGACUCCUAGUCCAGGGCUC | 0,054314773 |
| SEQ ID NO: 500 | Tab1-181 | hsa-miR-300 | UAUACAAGGGCAGACUCUCUCU | 0,054314773 |
| SEQ ID NO: 729 | Tab1-182 | hsa-miR-137 | UUAUUGCUUAAGAAUACGCGUAG | 0,054314773 |

FIG. 18B (Cont.)

| SEQ ID NO: | | | | |
|---|---|---|---|---|
| SEQ ID NO: 837 | Tab1-183 | hsa-miR-1229 | CUCUCACCACUGCCCUCCCACAG | 0.05448776 |
| SEQ ID NO: 811 | Tab1-184 | hsa-miR-1259 | AUAUAUGAUGACUUAGCUUUU | 0.05485668 |
| SEQ ID NO: 59 | Tab1-185 | hsa-miR-767-5p | UGCACCAUGGUUGUCUGAGCAUG | 0.05485668 |
| SEQ ID NO: 445 | Tab1-186 | hsa-miR-33b* | CAGUGCCUCGCAGUGCAGCCC | 0.056466966 |
| SEQ ID NO: 804 | Tab1-187 | hsa-miR-126* | CAUUAUUACUUUUGGUACGCG | 0.056466966 |
| SEQ ID NO: 525 | Tab1-188 | hsa-miR-25* | AGGCGGAGACUUGGGCAAUUG | 0.057237751 |
| SEQ ID NO: 527 | Tab1-189 | hsa-miR-24-2* | UGCCUACUGAGCUGAAACACAG | 0.059014671 |
| SEQ ID NO: 219 | Tab1-190 | hsa-miR-548p | UAGCAAAAACUGCAGUUACUUU | 0.060600928 |
| SEQ ID NO: 463 | Tab1-191 | hsa-miR-326 | CCUCUGGGCCCUUCCUCCAG | 0.06228617 |
| SEQ ID NO: 762 | Tab1-192 | hsa-miR-1295 | UUAGGCCGCAGAUCUGUCUGAG | 0.063344113 |
| SEQ ID NO: 172 | Tab1-193 | hsa-miR-589 | UGAGAACCACGUCUGGAGACACUGG | 0.065346969 |
| SEQ ID NO: 19 | Tab1-194 | hsa-miR-934 | UGUCUACUACGCCCACAGCCUCAGC | 0.065346969 |
| SEQ ID NO: 156 | Tab1-195 | hsa-miR-766 | ACUCCAGCCACUGCAAUUACUUUUGC | 0.065674214 |
| SEQ ID NO: 61 | Tab1-196 | hsa-miR-603 | CACACACUGCAAUUAUUUCCUGAAUA | 0.067215048 |
| SEQ ID NO: 365 | Tab1-197 | hsa-miR-450b-5p | UUUUGCAAUAUGUUCCUGAAUA | 0.068231645 |
| SEQ ID NO: 324 | Tab1-198 | hsa-miR-502-5p | AUCCUUGCUAUCUGGGUGCUA | 0.06879968 |
| SEQ ID NO: 835 | Tab1-199 | hsa-miR-1233 | UGAGCCCUGUCCUCCCGACUA | 0.072408565 |
| SEQ ID NO: 877 | Tab1-200 | hsa-miR-105* | ACGGAUGUUUGAGCAUGUGCUA | 0.072566994 |
| SEQ ID NO: 118 | Tab1-201 | hsa-miR-635 | ACUUGGGCACUGAAACAAUGUCC | 0.073440463 |
| SEQ ID NO: 773 | Tab1-202 | hsa-miR-1286 | UGCAGGACCAAGAUGAGCCCU | 0.073440463 |
| SEQ ID NO: 330 | Tab1-203 | hsa-miR-499-5p | UUAAGACUUGCAGUGAUGUUU | 0.074311961 |
| SEQ ID NO: 492 | Tab1-204 | hsa-miR-302c* | UUUAACAUGGGGGUACCUGCUG | 0.075099522 |
| SEQ ID NO: 891 | Tab1-205 | hsa-let-7f-2* | CUAUACAGUCCCUUUUCUGCU | 0.075395505 |
| SEQ ID NO: 777 | Tab1-206 | hsa-miR-1282 | UCGUUUGCCUUUGGCGCGGCC | 0.083275792 |
| SEQ ID NO: 710 | Tab1-207 | hsa-miR-1469 | CUCGGCGGCCAUUCUGAGCCUC | 0.083930302 |
| SEQ ID NO: 858 | Tab1-208 | hsa-miR-1200 | CUCCUGAGCCAUUCUGAGCCUC | 0.086375453 |
| SEQ ID NO: 132 | Tab1-209 | hsa-miR-624* | UAGUACCAGUAGUACCUUGUUCA | 0.086375453 |
| SEQ ID NO: 767 | Tab1-210 | hsa-miR-1291 | UGGCCCUGAGUCAAGAGACCAGU | 0.086375453 |
| SEQ ID NO: 441 | Tab1-211 | hsa-miR-342-5p | AGGGGUGCUAUCUGUGAUUGA | 0.088548673 |
| SEQ ID NO: 313 | Tab1-212 | hsa-miR-509-5p | UACUGCAGACAGUGGCAAUCA | 0.089271772 |
| SEQ ID NO: 771 | Tab1-213 | hsa-miR-1288 | UGGACUGCCUGAUCUGGAGA | 0.094543349 |
| SEQ ID NO: 619 | Tab1-214 | hsa-miR-196a* | CGGCAACAAGAAACUGCCUGAG | 0.095837993 |
| SEQ ID NO: 716 | Tab1-215 | hsa-miR-143* | GGUGCAGUGCUGCAUCUCUGU | 0.096157896 |
| SEQ ID NO: 856 | Tab1-216 | hsa-miR-1202 | GUGCCAGCUGCAGUGGGGAG | 0.098703462 |
| SEQ ID NO: 627 | Tab1-217 | hsa-miR-193a-5p | UGGGUCUUUGCGGGCGAGAUGA | 0.098703462 |
| SEQ ID NO: 171 | Tab1-218 | hsa-miR-589* | UCAGAACAAAUGCCGGUUCCCAGA | 0.098703462 |
| SEQ ID NO: 81 | Tab1-219 | hsa-miR-671-5p | AGGAAGCCCUGGAGGGGCUGGAG | 0.099228864 |

FIG. 18B (Cont.)

| | | | | |
|---|---|---|---|---|
| SEQ ID NO: 173 | Tab1-220 | hsa-miR-588 | UUGGCCACAAUGGGUUAGAAC | 0.09947915 |
| SEQ ID NO: 816 | Tab1-221 | hsa-miR-1255a | AGGAUGAGCAAAGAAAGUAGAUU | 0.103097462 |
| SEQ ID NO: 727 | Tab1-222 | hsa-miR-138-1* | GCUACUUCACAACACCAGGGCC | 0.104240406 |
| SEQ ID NO: 857 | Tab1-223 | hsa-miR-1201 | AGCCUGAUUAAACACAUGCCUGCUGA | 0.108839833 |
| SEQ ID NO: 159 | Tab1-224 | hsa-miR-600 | ACUUACAGACAAUAGAGCCUUGCUC | 0.111467992 |
| SEQ ID NO: 828 | Tab1-225 | hsa-miR-1243 | AACUGGAUCAAUUACUAAGGAGUG | 0.113572086 |
| SEQ ID NO: 474 | Tab1-226 | hsa-miR-32 | UAUUGCACAUUACUAAGUUGCA | 0.113572086 |
| SEQ ID NO: 354 | Tab1-227 | hsa-miR-484 | UCAGGCUCAGUCCCCUCCGAU | 0.113991637 |
| SEQ ID NO: 746 | Tab1-228 | hsa-miR-130b | CAGUGCAAUGAUGAAAGGGCAU | 0.114412538 |
| SEQ ID NO: 437 | Tab1-229 | hsa-miR-34a* | CAAUCAGCAAGUAUACUGCCCU | 0.11971985 |
| SEQ ID NO: 167 | Tab1-230 | hsa-miR-592 | UUGUGUCAAUAUGCGAUGAUGU | 0.120627634 |
| SEQ ID NO: 351 | Tab1-231 | hsa-miR-486-3p | CGGGGCAGCUCAGUACAGGAU | 0.120627634 |
| SEQ ID NO: 446 | Tab1-232 | hsa-miR-33b | GUGCAUUGCUGUUGCAUUGC | 0.120627634 |
| SEQ ID NO: 373 | Tab1-233 | hsa-miR-448 | UUGCAUAUGUAGGAUGUCCCAU | 0.120627634 |
| SEQ ID NO: 187 | Tab1-234 | hsa-miR-576-3p | AAGAUGUGGAAAAAUUGGAAUC | 0.120627634 |
| SEQ ID NO: 29 | Tab1-235 | hsa-miR-922 | GCAGCAGAGAAUAGGACUACGUC | 0.120627634 |
| SEQ ID NO: 201 | Tab1-236 | hsa-miR-562 | AAAGUAGCUGGUUGACAUUGC | 0.120627634 |
| SEQ ID NO: 244 | Tab1-237 | hsa-miR-542-3p | UGUGACAGAUUGAUAACUGAAA | 0.120627634 |
| SEQ ID NO: 683 | Tab1-238 | hsa-miR-155* | CUCCUACAUAUUAGCAUUAACA | 0.123726223 |
| SEQ ID NO: 106 | Tab1-239 | hsa-miR-647 | GUGGCUGCACUCACUUCCUUC | 0.124342172 |
| SEQ ID NO: 39 | Tab1-240 | hsa-miR-889 | UUAAUAUCGGACAACCAAUGU | 0.124454817 |
| SEQ ID NO: 328 | Tab1-241 | hsa-miR-500* | AUGCACCUGGGCAAGGAUUCUG | 0.125602142 |
| SEQ ID NO: 838 | Tab1-242 | hsa-miR-1228* | GUGGGGCGGGGGCCAGGUGUGUG | 0.125602142 |
| SEQ ID NO: 15 | Tab1-243 | hsa-miR-938 | UGCCCUUAAAGGUGAACCAGU | 0.125602142 |
| SEQ ID NO: 879 | Tab1-245 | hsa-miR-103-as | UCAUAGCCCUGUACAAUGCUGCU | 0.125746226 |
| SEQ ID NO: 723 | Tab1-246 | hsa-miR-140-3p | UACCACAGGGUAGAACCACGG | 0.127736191 |
| SEQ ID NO: 847 | Tab1-247 | hsa-miR-122* | AACGCCAUUAUCACACUAAAUA | 0.127736191 |
| SEQ ID NO: 164 | Tab1-248 | hsa-miR-595 | GAAGUGUGCCGUGGUGUGUCU | 0.131738431 |
| SEQ ID NO: 754 | Tab1-249 | hsa-miR-1303 | UUUAGAGACGGGGUCUUGCUCU | 0.133160819 |
| SEQ ID NO: 532 | Tab1-250 | hsa-miR-23a* | GGGGUUCCUGGGGAUGGGAUUU | 0.133247268 |
| SEQ ID NO: 399 | Tab1-251 | hsa-miR-380 | UAUGUAAUAUGGUCCACACUUU | 0.13436639 |
| SEQ ID NO: 246 | Tab1-252 | hsa-miR-541 | UGGUGGGCACAGAAUCUGGACU | 0.140533368 |
| SEQ ID NO: 422 | Tab1-253 | hsa-miR-369-3p | AAUAAUACAUGGUUGAUCUUU | 0.141905308 |
| SEQ ID NO: 47 | Tab1-254 | hsa-miR-877* | UCCUCUUCUCCCUCCUCCCAG | 0.141905308 |
| SEQ ID NO: 650 | Tab1-255 | hsa-miR-18a | UAAGGUGCAUCUAGUGCAGAUAG | 0.144823637 |
| SEQ ID NO: 885 | Tab1-256 | hsa-miR-100 | AACCCGUAGAUCCGAACUUGUG | 0.145916876 |
| SEQ ID NO: 198 | Tab1-256 | hsa-miR-566 | GGGCGCCUGUGAUCCCAAC | 0.14716172 |

FIG. 18B (Cont.)

| | | | | |
|---|---|---|---|---|
| SEQ ID NO: 653 | Tab1-257 | hsa-miR-187* | GGCUACAACACAGGACCCGGGC | 0,149917174 |
| SEQ ID NO: 815 | Tab1-258 | hsa-miR-1255b | CGGAUGAGCAAAGAAAGUGGUU | 0,150146074 |
| SEQ ID NO: 581 | Tab1-259 | hsa-miR-208a | AUAAGACGAGCAAAAAGCUUGU | 0,153053938 |
| SEQ ID NO: 888 | Tab1-260 | hsa-let-7i | UGAGGUAGUAGUUUGUGCUGUU | 0,155584098 |
| SEQ ID NO: 115 | Tab1-261 | hsa-miR-638 | AGGGAUCGCGGGCGGGUGGCGGCCU | 0,155685705 |
| SEQ ID NO: 539 | Tab1-262 | hsa-miR-223* | CGUGUAUUUGACAAGCUGAGUU | 0,158227157 |
| SEQ ID NO: 752 | Tab1-263 | hsa-miR-1305 | UUUUCAACUCUAAUGGGAGAGA | 0,158277678 |
| SEQ ID NO: 120 | Tab1-264 | hsa-miR-633 | CUAAUAGUAUCUACCACAAUAAA | 0,158861635 |
| SEQ ID NO: 393 | Tab1-265 | hsa-miR-409-3p | GAAUGUUGCUCGGUGAACCCCU | 0,158861635 |
| SEQ ID NO: 143 | Tab1-266 | hsa-miR-615-5p | GGGGGUCCCCGGUGCUCGGAUC | 0,159074635 |
| SEQ ID NO: 310 | Tab1-267 | hsa-miR-512-3p | AAGUGCUGUCAUAGCUGAGGUC | 0,159074635 |
| SEQ ID NO: 176 | Tab1-268 | hsa-miR-585 | UGGGCGUAUCUGCUAUGCUA | 0,159838843 |
| SEQ ID NO: 741 | Tab1-269 | hsa-miR-1322 | GAUGAUCUGCUGAUGCUG | 0,159838843 |
| SEQ ID NO: 714 | Tab1-270 | hsa-miR-144* | GGAUAUCAUCAUAUACUGUAAG | 0,161061186 |
| SEQ ID NO: 242 | Tab1-271 | hsa-miR-543 | AAACAUUCGCGGUGCACUCUU | 0,161061186 |
| SEQ ID NO: 90 | Tab1-272 | hsa-miR-662 | UCCCACGUUGUGGCCCAGCAG | 0,161061186 |
| SEQ ID NO: 380 | Tab1-273 | hsa-miR-425* | AUCGGGAAUGUACAUCGGAUGAG | 0,161436981 |
| SEQ ID NO: 9 | Tab1-274 | hsa-miR-944 | AAAUUAUUGUACAUCGGAUGAG | 0,161436981 |
| SEQ ID NO: 366 | Tab1-275 | hsa-miR-450b-3p | UUGGGAUCAUUUUGCAUCCAUA | 0,16360492 |
| SEQ ID NO: 36 | Tab1-276 | hsa-miR-891b | UGCAACUUACCUGAGUCAUUGA | 0,16360492 |
| SEQ ID NO: 545 | Tab1-277 | hsa-miR-220c | ACACAGGGCUGUUUGUGAAGACU | 0,16360492 |
| SEQ ID NO: 358 | Tab1-278 | hsa-miR-455-3p | GCAGUCCAUGGGCAUAUACAC | 0,16360492 |
| SEQ ID NO: 483 | Tab1-279 | hsa-miR-30c | UGUAAACAUCCUACACUCUCAGC | 0,16360492 |
| SEQ ID NO: 763 | Tab1-280 | hsa-miR-1294 | UGUGAGGUUGGCAUUGUUGUCU | 0,164265257 |
| SEQ ID NO: 758 | Tab1-281 | hsa-miR-1298 | UUCAUUCGGCUGUCCAGAUGUA | 0,16708942 |
| SEQ ID NO: 603 | Tab1-282 | hsa-miR-199b-5p | CCCAGUGUUUAGACUAUCUGUUC | 0,1671671 |
| SEQ ID NO: 266 | Tab1-283 | hsa-miR-520e | AAAGUGCUUCCUUUUUGAGGG | 0,1671671 |
| SEQ ID NO: 839 | Tab1-284 | hsa-miR-1228 | UCACACCUGCCUCGCCCCC | 0,169045179 |
| SEQ ID NO: 48 | Tab1-285 | hsa-miR-877 | GUAGAGGAGAUGGCGCAGGG | 0,169045179 |
| SEQ ID NO: 378 | Tab1-286 | hsa-miR-431 | UGUCUUGCAGGCCGUCAUGCA | 0,171256018 |
| SEQ ID NO: 299 | Tab1-287 | hsa-miR-516b | AUCUGGAGGUAAGAAGCACUUU | 0,171330477 |
| SEQ ID NO: 855 | Tab1-288 | hsa-miR-1203 | CCCGGAGCCAGGACCUAACUGUGA | 0,174507788 |
| SEQ ID NO: 808 | Tab1-289 | hsa-miR-125b | UCCCUGAGACCCUAACUUGUGA | 0,1765915 |
| SEQ ID NO: 704 | Tab1-290 | hsa-miR-1470 | GCCCUCCGCCCGUGCACCCG | 0,177102193 |
| SEQ ID NO: 35 | Tab1-291 | hsa-miR-892a | CACUGUGGCCUUUUCUGGGUAG | 0,177102193 |
| SEQ ID NO: 154 | Tab1-292 | hsa-miR-605 | UAAAUCCCAUGGUGCCUUCUCCU | 0,177440007 |
| SEQ ID NO: 180 | Tab1-293 | hsa-miR-582-3p | UAACUGGUUGAACAACUGAACC | 0,177440007 |

FIG. 18B (Cont.)

| SEQ ID NO | Tab1 | miRNA | Sequence | Value |
|---|---|---|---|---|
| SEQ ID NO: 503 | Tab1-294 | hsa-miR-29b-2* | CUGGUUUCACAUGGUGGCUUAG | 0.177440007 |
| SEQ ID NO: 204 | Tab1-295 | hsa-miR-558 | UGAGCUGCUGUACCAAAAU | 0.177440007 |
| SEQ ID NO: 43 | Tab1-296 | hsa-miR-886-5p | CGGGUCGGAGUUAGCUCAAGCGG | 0.178116551 |
| SEQ ID NO: 86 | Tab1-297 | hsa-miR-664* | ACUGGCUAGGGAAAAUGAUUGGAU | 0.188436337 |
| SEQ ID NO: 696 | Tab1-298 | hsa-miR-149* | AGGGAGGGACGGGGCUGUGC | 0.188436337 |
| SEQ ID NO: 718 | Tab1-299 | hsa-miR-142-5p | CAUAAAGUAGAAAGCACUACU | 0.193859516 |
| SEQ ID NO: 325 | Tab1-300 | hsa-miR-502-3p | AAUGCACCUGGGCAAGGAUUCA | 0.193859516 |
| SEQ ID NO: 707 | Tab1-301 | hsa-miR-146b-3p | UGCCCUGUGGACUCAGUUCUGG | 0.193859516 |
| SEQ ID NO: 321 | Tab1-302 | hsa-miR-505 | CGUCAACACUUGCUGGUUUCCU | 0.193859516 |
| SEQ ID NO: 375 | Tab1-303 | hsa-miR-432* | CUGGAUGGCUCCUCCAUGUCU | 0.194166922 |
| SEQ ID NO: 126 | Tab1-304 | hsa-miR-628-5p | AUGCUGACAUAUUACUAGAGG | 0.196879788 |
| SEQ ID NO: 490 | Tab1-305 | hsa-miR-302d* | ACUUUAACAUGGAGGCACUUGC | 0.196879788 |
| SEQ ID NO: 137 | Tab1-306 | hsa-miR-620 | AUGGAGAUAAGGCAUUAGAAAU | 0.198281114 |
| SEQ ID NO: 802 | Tab1-307 | hsa-miR-1261 | ACUUGAUGCUAGCUCAGGUAG | 0.19909011 |
| SEQ ID NO: 110 | Tab1-308 | hsa-miR-843 | UAAUACUGCUGGUAAAACCGU | 0.200122644 |
| SEQ ID NO: 379 | Tab1-309 | hsa-miR-429 | GGGCAGCCAGGAAGUAUUGAUGU | 0.200164698 |
| SEQ ID NO: 320 | Tab1-310 | hsa-miR-505* | CGCAAUGUAAGCACUUCUUAC | 0.201432258 |
| SEQ ID NO: 875 | Tab1-311 | hsa-miR-106a* | CCUCUAGAUGGAAGCACUGUCU | 0.206009053 |
| SEQ ID NO: 297 | Tab1-312 | hsa-miR-517* | AAAGUUCUGAGACACUCCGACU | 0.206009053 |
| SEQ ID NO: 700 | Tab1-313 | hsa-miR-148a* | CUAUACAAUCUAAUGCCUUCCC | 0.20830304 |
| SEQ ID NO: 892 | Tab1-314 | hsa-let-7f-1* | CACCCGUAGAACCGACCUUGCG | 0.20830304 |
| SEQ ID NO: 2 | Tab1-315 | hsa-miR-99b | AGAGGUAGAUAAGGGCAUGGGAA | 0.20830304 |
| SEQ ID NO: 591 | Tab1-316 | hsa-miR-202 | UCUCGCUGGGGCCCUCCA | 0.20830304 |
| SEQ ID NO: 71 | Tab1-317 | hsa-miR-720 | AGAUCAGAAGGUGAUUGUGGCU | 0.20830304 |
| SEQ ID NO: 395 | Tab1-318 | hsa-miR-383 | UAAUUUAGGUAUAAGCUAGU | 0.20830304 |
| SEQ ID NO: 170 | Tab1-319 | hsa-miR-590-3p | GUGAGCAUGCAGGCCUGGAUGGGG | 0.210087753 |
| SEQ ID NO: 841 | Tab1-320 | hsa-miR-1226* | CGGGGUUUUGAGGGCGAGAUGA | 0.210087753 |
| SEQ ID NO: 625 | Tab1-321 | hsa-miR-193b* | UCCAGUGCCCUCCUCUCC | 0.211111594 |
| SEQ ID NO: 664 | Tab1-322 | hsa-miR-1825 | AAAGUGCUUCCUUUUAGAGGGU | 0.211111594 |
| SEQ ID NO: 270 | Tab1-323 | hsa-miR-520c-3p | UCCGUCUCAGUUACUUUAUAGC | 0.211111594 |
| SEQ ID NO: 443 | Tab1-324 | hsa-miR-340* | AGGCAGUGUAGUUAGCUGAUUGC | 0.211386507 |
| SEQ ID NO: 433 | Tab1-325 | hsa-miR-34c-5p | AUCACACAAAGGCAACUUUUGU | 0.211896525 |
| SEQ ID NO: 405 | Tab1-326 | hsa-miR-377 | GUAGAUCUCCCUUUCUAUGAGUA | 0.211896525 |
| SEQ ID NO: 408 | Tab1-327 | hsa-miR-376a* | GUAGAUUCUCCUUCUAUGAGUA | 0.211896525 |
| SEQ ID NO: 220 | Tab1-328 | hsa-miR-548o | CCAAAACUGCAGUUACUUUUGC | 0.212680979 |
| SEQ ID NO: 255 | Tab1-329 | hsa-miR-525-3p | GAAGGCGCUUCCCUUUAGAGCG | 0.213227096 |
| SEQ ID NO: 801 | Tab1-330 | hsa-miR-1262 | AUGGGUGAAUUUGUAGAAGGAU | 0.21721339 |

FIG. 18B (Cont.)

| | | | |
|---|---|---|---|
| SEQ ID NO: 830 | Tab1-331 | hsa-miR-124 | UAAGGCACGCGGUGAAUGCC | 0.2202220099 |
| SEQ ID NO: 355 | Tab1-332 | hsa-miR-483-5p | AAGACGGGAGGAAAGAAGGGAG | 0.2209910651 |
| SEQ ID NO: 95 | Tab1-333 | hsa-miR-657 | GGCAGGUUCUCACCCUCUCUAGG | 0.221053377 |
| SEQ ID NO: 259 | Tab1-334 | hsa-miR-523 | GAACGCGCUUCCCUAUAGAGGGU | 0.221053377 |
| SEQ ID NO: 5 | Tab1-335 | hsa-miR-98 | UGAGGUAGUAAGUUGUAUUGUU | 0.22261375 |
| SEQ ID NO: 454 | Tab1-336 | hsa-miR-337-3p | CUCCUAUAUGAUGCCUUUCUUC | 0.22261375 |
| SEQ ID NO: 20 | Tab1-337 | hsa-miR-933 | UGUGCGCAGGGAGACCUCUCCC | 0.226590856 |
| SEQ ID NO: 179 | Tab1-338 | hsa-miR-582-5p | UUACAGUUGUUCAACCAGUUACU | 0.227821919 |
| SEQ ID NO: 538 | Tab1-339 | hsa-miR-224 | CAAGUCACUAGUGGUUCCGUU | 0.229624448 |
| SEQ ID NO: 226 | Tab1-340 | hsa-miR-548i | AAAAGUAAUUGCGGAUUUUGCC | 0.234720663 |
| SEQ ID NO: 669 | Tab1-341 | hsa-miR-181c | AACAUUCAACCUGUCGGUGAGU | 0.234720663 |
| SEQ ID NO: 782 | Tab1-342 | hsa-miR-1278 | UAGUACUGUGCAUAUCAUCUAU | 0.238939335 |
| SEQ ID NO: 882 | Tab1-343 | hsa-miR-101* | CAGUUAUCACAGUGCUGAUGCU | 0.239144648 |
| SEQ ID NO: 748 | Tab1-344 | hsa-miR-130a | CAGUGCAAUGUUAAAAGGGCAU | 0.239144648 |
| SEQ ID NO: 515 | Tab1-345 | hsa-miR-28-3p | CACUAGAUUGUGAGCUCCUGGA | 0.239144648 |
| SEQ ID NO: 903 | Tab1-346 | hsa-let-7a* | CUAUACAAUCUACUGUCUUUC | 0.239144648 |
| SEQ ID NO: 593 | Tab1-347 | hsa-miR-200c | UAAUACUGCCGGGUAAUGAUGGA | 0.239144648 |
| SEQ ID NO: 686 | Tab1-348 | hsa-miR-154 | UAGGUUAUCCGUGUUGCCUUCG | 0.239144648 |
| SEQ ID NO: 519 | Tab1-349 | hsa-miR-27a | UUCACAGUGGCUAAGUUCCGC | 0.239144648 |
| SEQ ID NO: 1 | Tab1-350 | hsa-miR-99b* | CAAGCUCGUGUCUGUGGGUCCG | 0.239236378 |
| SEQ ID NO: 257 | Tab1-351 | hsa-miR-524-3p | GAAGGCGCUUCCCUUUGGAGU | 0.239236378 |
| SEQ ID NO: 531 | Tab1-352 | hsa-miR-23b | AUCACAUUGCCAGGGAUUACC | 0.239236378 |
| SEQ ID NO: 759 | Tab1-353 | hsa-miR-1297 | UUCAAGUAAAUGUCAGGGUG | 0.242177174 |
| SEQ ID NO: 866 | Tab1-354 | hsa-miR-1179 | AAGCAUUCUUUCAUUGGUUGG | 0.242259609 |
| SEQ ID NO: 45 | Tab1-355 | hsa-miR-885-5p | UCCAUUACACUACCCUGCCUCU | 0.245878592 |
| SEQ ID NO: 89 | Tab1-356 | hsa-miR-663 | AGGCGGGGCGCCGCGGGACGGC | 0.24900771 |
| SEQ ID NO: 575 | Tab1-357 | hsa-miR-21 | UAGCUUAUCAGACUGAUGUUGA | 0.251460511 |
| SEQ ID NO: 732 | Tab1-358 | hsa-miR-135b* | AUGUAGGGCUAAAAGCCAUGGG | 0.253113558 |
| SEQ ID NO: 16 | Tab1-359 | hsa-miR-937 | AUCCGCGUCUGACUCCACUGCC | 0.253997054 |
| SEQ ID NO: 436 | Tab1-360 | hsa-miR-34b | CAAUCACUAACUACCACAAUGGAGG | 0.254258845 |
| SEQ ID NO: 678 | Tab1-361 | hsa-miR-16 | UAGCAGCACGUAAAUAUUGGCG | 0.25438781 |
| SEQ ID NO: 663 | Tab1-362 | hsa-miR-1826 | AUUGAUCAUCACACUUCGAACGCAAU | 0.256862278 |
| SEQ ID NO: 685 | Tab1-363 | hsa-miR-154* | AAUCAUACACGGUUGACCUAUU | 0.257604511 |
| SEQ ID NO: 13 | Tab1-364 | hsa-miR-940 | AAGGCAGGGCCCCCGCUCCCC | 0.258972955 |
| SEQ ID NO: 93 | Tab1-365 | hsa-miR-659 | CUUGGUUCAGGGAGGGUCCCA | 0.258972955 |
| SEQ ID NO: 124 | Tab1-366 | hsa-miR-629* | GUUCUCCCAAGUAAGCCAGC | 0.259713934 |
| SEQ ID NO: 486 | Tab1-367 | hsa-miR-30a* | CUUUCAGUCGGAUGUUUGCAGC | 0.259713934 |

FIG. 18B (Cont.)

| | | | | |
|---|---|---|---|---|
| SEQ ID NO: 506 | Tab1-368 | hsa-miR-29a* | ACUGAUUUCUUUUGGUGUUCAG | 0.260164521 |
| SEQ ID NO: 119 | Tab1-369 | hsa-miR-634 | AACCAGCACCCCAACUUUGGAC | 0.260164521 |
| SEQ ID NO: 344 | Tab1-370 | hsa-miR-490-3p | CAACCUGGAGGACUCCAUGCUG | 0.260164521 |
| SEQ ID NO: 521 | Tab1-371 | hsa-miR-26b | UUCAAGUAAUUCAGGAUAGGU | 0.264400976 |
| SEQ ID NO: 601 | Tab1-372 | hsa-miR-19a* | AGUUUUGCAUAGUUGCACUACA | 0.264567923 |
| SEQ ID NO: 442 | Tab1-373 | hsa-miR-342-3p | UCUCACACAGAAAUCGCACCCGU | 0.264567923 |
| SEQ ID NO: 528 | Tab1-374 | hsa-miR-24-1* | UGCCUACUGAGCUGAUAUCAGU | 0.264890121 |
| SEQ ID NO: 449 | Tab1-375 | hsa-miR-339-5p | UCCCUGUCCUCCAGGAGCUCACG | 0.266489431 |
| SEQ ID NO: 216 | Tab1-376 | hsa-miR-550 | AGUGCCUGAGGGAGUAAGAGCCC | 0.266995739 |
| SEQ ID NO: 895 | Tab1-377 | hsa-let-7e | UGAGGUAGGAGGUUGUAUAGUU | 0.268841801 |
| SEQ ID NO: 431 | Tab1-378 | hsa-miR-361-5p | UUAUCAGAAUCUCCAGGGGUAC | 0.268841801 |
| SEQ ID NO: 742 | Tab1-379 | hsa-miR-1321 | CAGGGAGGUGAAUGUGAU | 0.273455554 |
| SEQ ID NO: 499 | Tab1-380 | hsa-miR-301a | CAGUGCAAUAGUAUUGUCAAAGC | 0.273455554 |
| SEQ ID NO: 635 | Tab1-381 | hsa-miR-1913 | UCUGCCCCCUCCGCUGCUGCCA | 0.274833654 |
| SEQ ID NO: 99 | Tab1-382 | hsa-miR-654-3p | UAUGUCUGCUGACCAUCACCUU | 0.275703435 |
| SEQ ID NO: 282 | Tab1-383 | hsa-miR-519a | AAAGUGCAUCCUUUUAGAGUGU | 0.277196408 |
| SEQ ID NO: 130 | Tab1-384 | hsa-miR-625* | GACUAUAGAACUUUCCCCCUCA | 0.277196408 |
| SEQ ID NO: 788 | Tab1-385 | hsa-miR-1274a | GUCCCUGUUCAGGCGCCA | 0.277196408 |
| SEQ ID NO: 768 | Tab1-386 | hsa-miR-1290 | UGGAUUUUUGGAUCAGGGA | 0.279227266 |
| SEQ ID NO: 523 | Tab1-387 | hsa-miR-26a-1* | CCUAUUCUUGGUUACUUGCACG | 0.283847021 |
| SEQ ID NO: 541 | Tab1-388 | hsa-miR-222* | CUCAGUAGCCAGUGUAGAUCCU | 0.286671943 |
| SEQ ID NO: 420 | Tab1-389 | hsa-miR-370 | GCCUGCUGGGGUGGAACCUGGU | 0.291662183 |
| SEQ ID NO: 169 | Tab1-390 | hsa-miR-590-5p | GAGCUUAUUCAUAAAAGUGCAG | 0.298436524 |
| SEQ ID NO: 82 | Tab1-391 | hsa-miR-671-3p | UCCGGUUCUCAGGGAAGCACC | 0.298436524 |
| SEQ ID NO: 256 | Tab1-392 | hsa-miR-524-5p | CUACAAAGGGAAGCACUUUCUC | 0.308517636 |
| SEQ ID NO: 897 | Tab1-393 | hsa-let-7d | AGAGGUAGUAGGUUGCAUAGUU | 0.308759989 |
| SEQ ID NO: 174 | Tab1-394 | hsa-miR-587 | UUUCCAUAGGUGAUGAGUCAC | 0.311658225 |
| SEQ ID NO: 661 | Tab1-395 | hsa-miR-183 | UAUGGCACUGGUAGAAUUCACU | 0.311762874 |
| SEQ ID NO: 785 | Tab1-396 | hsa-miR-127-5p | CUGAAGCUCAGAGGGCUCUGAU | 0.311762874 |
| SEQ ID NO: 573 | Tab1-397 | hsa-miR-210 | CUGUGCGUGUGACAGCGGCUGA | 0.312879774 |
| SEQ ID NO: 138 | Tab1-398 | hsa-miR-619 | GACCUGGACAUUUGUGCCCAGU | 0.315454067 |
| SEQ ID NO: 697 | Tab1-399 | hsa-miR-149 | UCUGGCUCCGUGUCUUCACUCCC | 0.315454067 |
| SEQ ID NO: 290 | Tab1-400 | hsa-miR-518c | CAAAGCGCUUCUCUUUAGAGUGU | 0.315454067 |
| SEQ ID NO: 775 | Tab1-401 | hsa-miR-1284 | UCUAUACAGACCCUGGCUUUUC | 0.315591256 |
| SEQ ID NO: 134 | Tab1-402 | hsa-miR-623 | AUCCCUUGCAGGGGCUGUUGGGU | 0.319657836 |
| SEQ ID NO: 275 | Tab1-403 | hsa-miR-519e | AAGUGCCUCCUUUUAGAGUGUU | 0.32006095 |
| SEQ ID NO: 690 | Tab1-404 | hsa-miR-153 | UUGCAUAGUCACAAAAGUGAUC | |

FIG. 18B (Cont.)

| | | | |
|---|---|---|---|
| SEQ ID NO: 160 | Tab1-405 | hsa-miR-599 | GUUGUGUCAGUUUAUCAAAC | 0.320979054 |
| SEQ ID NO: 389 | Tab1-406 | hsa-miR-411* | UAUGUAACACGGUCCACUAACC | 0.320979054 |
| SEQ ID NO: 293 | Tab1-407 | hsa-miR-518a-3p | GAAAGCGCUUCCCUUUGCUGGA | 0.324308422 |
| SEQ ID NO: 298 | Tab1-408 | hsa-miR-516b* | UGCUUCCUUUCAGAGGGU | 0.324372505 |
| SEQ ID NO: 142 | Tab1-409 | hsa-miR-616 | AGUCAUUGAGGGUUUGAGCAG | 0.324748713 |
| SEQ ID NO: 634 | Tab1-410 | hsa-miR-1914 | CCCUGUGCCGGCCCACUCUG | 0.326381759 |
| SEQ ID NO: 628 | Tab1-411 | hsa-miR-193a-3p | AACUGGCCUACAAAGUCCCAGU | 0.326381759 |
| SEQ ID NO: 711 | Tab1-412 | hsa-miR-1468 | CUCCGUUUGCCUGUUUCGCUG | 0.326594517 |
| SEQ ID NO: 356 | Tab1-413 | hsa-miR-483-3p | UCACUCCUCUCCUCCGUCUU | 0.328858287 |
| SEQ ID NO: 261 | Tab1-414 | hsa-miR-522 | AAAAUGGUUCCCUUUAGAGUGU | 0.330220519 |
| SEQ ID NO: 825 | Tab1-415 | hsa-miR-1246 | AAUGGAUUUUUGGAGCAGG | 0.330414212 |
| SEQ ID NO: 864 | Tab1-416 | hsa-miR-1181 | CCGUCGCCGCCACCCGAGCCG | 0.330414212 |
| SEQ ID NO: 884 | Tab1-417 | hsa-miR-100* | CAAGCUUGAUCUAUAGGUAUG | 0.330836904 |
| SEQ ID NO: 793 | Tab1-418 | hsa-miR-1270 | CUGGAGAAUAUGGAAGAGCUGUGU | 0.331309957 |
| SEQ ID NO: 821 | Tab1-419 | hsa-miR-1250 | ACGUGCUGGAUGGGCCC | 0.331309957 |
| SEQ ID NO: 687 | Tab1-420 | hsa-miR-1539 | UCCGCGCGUCCAGAUGCCC | 0.331309957 |
| SEQ ID NO: 681 | Tab1-421 | hsa-miR-15a* | CAGGCCAUAUUGUGCUGCCUCA | 0.331309957 |
| SEQ ID NO: 301 | Tab1-422 | hsa-miR-516a-3p | UGCUUCCUUUCAGAGGGU | 0.331945413 |
| SEQ ID NO: 618 | Tab1-423 | hsa-miR-196b | UAGGUAGUUUCCUGUUGUUGGG | 0.331945413 |
| SEQ ID NO: 163 | Tab1-424 | hsa-miR-596 | AAGCCUGCCCGGCCUCUCGGG | 0.332241443 |
| SEQ ID NO: 417 | Tab1-425 | hsa-miR-372 | AAAGUGCUGCGACAUUUGAGCGU | 0.338337546 |
| SEQ ID NO: 790 | Tab1-426 | hsa-miR-1273 | GGGCAGUGGACAAAGCAAGACUCUUUCUU | 0.34131865 |
| SEQ ID NO: 734 | Tab1-427 | hsa-miR-135a* | UAUAGGGAUUGGAGCCGUGGCG | 0.341540665 |
| SEQ ID NO: 114 | Tab1-428 | hsa-miR-639 | AUCGCUGCGGUUGCGAGCGCUGU | 0.341540665 |
| SEQ ID NO: 643 | Tab1-429 | hsa-miR-1909* | UGAGUGCCGGUGCCUGCCCUG | 0.341540665 |
| SEQ ID NO: 512 | Tab1-430 | hsa-miR-296-5p | AGGGCCCCCCUCACAGUCAACCUGU | 0.341540665 |
| SEQ ID NO: 96 | Tab1-431 | hsa-miR-658 | AAUAUUAUACAGUCAACCUCU | 0.343325022 |
| SEQ ID NO: 630 | Tab1-432 | hsa-miR-192 | CUGACCUAUGAAUUGACAGCC | 0.354100965 |
| SEQ ID NO: 223 | Tab1-433 | hsa-miR-548l | AAAAGUAUUUGCGGGUUUUGUC | 0.354487159 |
| SEQ ID NO: 100 | Tab1-434 | hsa-miR-653 | GUGUAGAAACAAUCUCUACUG | 0.354642247 |
| SEQ ID NO: 383 | Tab1-435 | hsa-miR-424 | CAGCAGCAAUUCAUGUUUUGAA | 0.355052546 |
| SEQ ID NO: 818 | Tab1-436 | hsa-miR-1253 | AGAGAAGAAGAUCAGCCUGCA | 0.357014754 |
| SEQ ID NO: 285 | Tab1-437 | hsa-miR-518e* | CUCUAGAGGGAAGCGCUUUCUG | 0.362045451 |
| SEQ ID NO: 642 | Tab1-438 | hsa-miR-190b | UGAUAUGUUUGAUAUUGGGUU | 0.362820484 |
| SEQ ID NO: 145 | Tab1-439 | hsa-miR-614 | GAACGCCUGUUUCUUGCCAGGUGG | 0.362820484 |
| SEQ ID NO: 810 | Tab1-440 | hsa-miR-125a-3p | ACAGGUGAGGUUCUUGGGAGCC | 0.362820484 |
| SEQ ID NO: 102 | Tab1-441 | hsa-miR-651 | UUUAGGAUAAGCUUGACUUUUG | 0.363753509 |

FIG. 18B (Cont.)

| | | | |
|---|---|---|---|
| SEQ ID NO: 360 | Tab1-442 | hsa-miR-454 | UAGUGCAAUAUUGCUUAUAGGGU | 0.366097513 |
| SEQ ID NO: 109 | Tab1-443 | hsa-miR-644 | AGUGUGGCUUUCUUGGAGC | 0.368756685 |
| SEQ ID NO: 484 | Tab1-444 | hsa-miR-30b* | CUGGAGGUGGAUGUUUACUUC | 0.369278576 |
| SEQ ID NO: 861 | Tab1-445 | hsa-miR-1184 | CCUGCAGCGACUUGAUGGCUUCC | 0.369769198 |
| SEQ ID NO: 263 | Tab1-446 | hsa-miR-520h | ACAAAGUGCUUCCCUUUAGAGU | 0.37157953 |
| SEQ ID NO: 511 | Tab1-447 | hsa-miR-297 | AUGUAUGUGUGCAUGUGCAUG | 0.37157953 |
| SEQ ID NO: 798 | Tab1-448 | hsa-miR-1265 | CAGGAUGUGGUCAAGUGUUGUU | 0.372890385 |
| SEQ ID NO: 178 | Tab1-449 | hsa-miR-583 | CAAAGAGGAAGGUCCCAUUAC | 0.375142139 |
| SEQ ID NO: 648 | Tab1-450 | hsa-miR-18b | UAAGGUGCAUCUAGUGCAGUUAG | 0.375142139 |
| SEQ ID NO: 17 | Tab1-451 | hsa-miR-936 | ACAGUAGAGGGAGGAAUCGCAG | 0.375142139 |
| SEQ ID NO: 800 | Tab1-452 | hsa-miR-1263 | AUGGUACCCUGGCAUACUGAGU | 0.375142139 |
| SEQ ID NO: 192 | Tab1-453 | hsa-miR-572 | GUCCGCUCGGCGGUGGGCCCA | 0.375265231 |
| SEQ ID NO: 472 | Tab1-454 | hsa-miR-320a | AAAAGCUGGGUUGAGAGGGCGA | 0.377013669 |
| SEQ ID NO: 822 | Tab1-455 | hsa-miR-1249 | ACGCCCUUCCCCCCUUCUUCA | 0.378689797 |
| SEQ ID NO: 750 | Tab1-456 | hsa-miR-1307 | ACUCGGCGUGGCGUCGGUGUG | 0.378689797 |
| SEQ ID NO: 350 | Tab1-457 | hsa-miR-486-5p | UCCUGUACUGAGCUGCCCCGAG | 0.378689797 |
| SEQ ID NO: 343 | Tab1-458 | hsa-miR-490-5p | CCAUGGAUCUCCAGGUGGGU | 0.378689797 |
| SEQ ID NO: 589 | Tab1-459 | hsa-miR-203 | GUGAAAUGUUUAGGACCACUAG | 0.378689797 |
| SEQ ID NO: 764 | Tab1-460 | hsa-miR-129-3p | AAGCCCUUACCCCAAAAGCAU | 0.378689797 |
| SEQ ID NO: 188 | Tab1-461 | hsa-miR-575 | GAGCCAGUUGGACAGGAGC | 0.378689797 |
| SEQ ID NO: 522 | Tab1-462 | hsa-miR-268-2* | CCUAUUCUUGAUUACUGUUUC | 0.378689797 |
| SEQ ID NO: 510 | Tab1-463 | hsa-miR-298 | AGCAGAAGCAGGGAGGUUCUCCCA | 0.378689797 |
| SEQ ID NO: 327 | Tab1-464 | hsa-miR-501-3p | AAUGCACCCGGGCAAGGAUUCU | 0.382606427 |
| SEQ ID NO: 427 | Tab1-465 | hsa-miR-363* | CGGGUGGAUCAGGCCUGGGGACAG | 0.387972126 |
| SEQ ID NO: 694 | Tab1-466 | hsa-miR-150* | CUGGUACAGGCCUGGGGACAG | 0.38963321 |
| SEQ ID NO: 66 | Tab1-467 | hsa-miR-760 | CGGCUCUGGGCUGUGUGGGA | 0.389646374 |
| SEQ ID NO: 49 | Tab1-468 | hsa-miR-876-5p | UGGAUUCUUGUGUGAAUCACCA | 0.391926575 |
| SEQ ID NO: 129 | Tab1-469 | hsa-miR-626 | AGCUGUCUGAAAAUGUCUU | 0.395413561 |
| SEQ ID NO: 157 | Tab1-470 | hsa-miR-602 | GACACGGGCGACAGCUGCGGCCC | 0.396803101 |
| SEQ ID NO: 76 | Tab1-471 | hsa-miR-708* | CAACUAGACUGUGAGCUUCUAG | 0.397410101 |
| SEQ ID NO: 765 | Tab1-472 | hsa-miR-1293 | UGGGUGGUCGGGAGAUUUGUGA | 0.397410101 |
| SEQ ID NO: 735 | Tab1-473 | hsa-miR-135a | UAUGGCUUUUUAUUCCUAUGUGA | 0.397852695 |
| SEQ ID NO: 572 | Tab1-474 | hsa-miR-211 | UUCCCUUUGUCAUCCUUCGCCU | 0.399198327 |
| SEQ ID NO: 739 | Tab1-475 | hsa-miR-1324 | CCAGACAGAAUUCUAUGCACUUUC | 0.399198327 |
| SEQ ID NO: 58 | Tab1-476 | hsa-miR-769-3p | CUGGAGUCUAUGGGUCUUGGUU | 0.400864102 |
| SEQ ID NO: 401 | Tab1-477 | hsa-miR-379 | UGGUAGACUAUGGAACGUAGG | 0.401906727 |
| SEQ ID NO: 268 | Tab1-478 | hsa-miR-520d-3p | AAAGUGCUUCUCUUUGGUGGGU | 0.401906727 |

FIG. 18B (Cont.)

| | | | | |
|---|---|---|---|---|
| SEQ ID NO: 292 | Tab1-479 | hsa-miR-518a-5p | CUGCAAAGGGAAGCCCUUUC | 0.402813063 |
| SEQ ID NO: 166 | Tab1-480 | hsa-miR-593 | UGUCUCGCAAGGGAAGCCCGGUUUCU | 0.410733773 |
| SEQ ID NO: 250 | Tab1-481 | hsa-miR-527 | CUGCAAAGGGAAGCCCUUUC | 0.411425252 |
| SEQ ID NO: 300 | Tab1-482 | hsa-miR-518a-5p | UUCUCGAGAGAAAGAAGCACUUUC | 0.412047849 |
| SEQ ID NO: 103 | Tab1-483 | hsa-miR-650 | AGGAGGCAGGCAGCGCUCUCAGGAC | 0.412792045 |
| SEQ ID NO: 867 | Tab1-484 | hsa-miR-1178 | UUGGCUCACUGUUCUUCCCUAG | 0.413823037 |
| SEQ ID NO: 836 | Tab1-485 | hsa-miR-1231 | GUGUCUGGGGACAGCUGC | 0.414294389 |
| SEQ ID NO: 414 | Tab1-486 | hsa-miR-374a | UUAUAAUACAACCUGAUAAGUG | 0.417875814 |
| SEQ ID NO: 814 | Tab1-487 | hsa-miR-1256 | AGGCAUUGACUUCUCACUAGCU | 0.422404938 |
| SEQ ID NO: 12 | Tab1-488 | hsa-miR-941 | CACCCGCGUGUGUGCACAUGUGC | 0.423233999 |
| SEQ ID NO: 637 | Tab1-489 | hsa-miR-1911* | CACCAGGCAUUGUGUCUCC | 0.424076618 |
| SEQ ID NO: 778 | Tab1-490 | hsa-miR-1281 | UCGCCUCUCCUCCCCUCUCCC | 0.426525923 |
| SEQ ID NO: 819 | Tab1-491 | hsa-miR-1252 | AGAAGGAAAUUGAAUUCAUUUA | 0.42807231 |
| SEQ ID NO: 148 | Tab1-492 | hsa-miR-611 | GCGAGGACCCUCGGGGUCUGAC | 0.434004119 |
| SEQ ID NO: 410 | Tab1-493 | hsa-miR-375 | UUUGUUCGUUCGGCUCGCGUGA | 0.434020339 |
| SEQ ID NO: 604 | Tab1-494 | hsa-miR-199b-3p | ACAGUAGUCUGCACAUUGGUUA | 0.437090287 |
| SEQ ID NO: 559 | Tab1-495 | hsa-miR-215 | AUGACCUAUGCCCGCAUGCCUGCCUCU | 0.439973637 |
| SEQ ID NO: 439 | Tab1-496 | hsa-miR-346 | UGUCUGCCCGCAUGCCUGCCUCU | 0.440177538 |
| SEQ ID NO: 607 | Tab1-497 | hsa-miR-198 | GGUCCAGAGGGGAGAUGAGUGGAC | 0.44024154 |
| SEQ ID NO: 668 | Tab1-498 | hsa-miR-181c* | AACCAUCGACCGUGAGUGAGCU | 0.44024154 |
| SEQ ID NO: 57 | Tab1-499 | hsa-miR-769-5p | UGAGACCUCUGGGUUCUGAGCU | 0.446525942 |
| SEQ ID NO: 640 | Tab1-500 | hsa-miR-191* | GCUGCGCUUGGAUUUGUCCCC | 0.446573004 |
| SEQ ID NO: 309 | Tab1-501 | hsa-miR-512-5p | CACUCAGCCUUGAGGGCACUUUC | 0.446601179 |
| SEQ ID NO: 546 | Tab1-502 | hsa-miR-220b | CCACCACCGUGCUGUCUGACACUU | 0.446608937 |
| SEQ ID NO: 336 | Tab1-503 | hsa-miR-886-3p | CGCGGGUGCUUACUGACCCU | 0.4500346 |
| SEQ ID NO: 576 | Tab1-504 | hsa-miR-20b* | ACUGUAGUAUGGGCACUUCCAG | 0.452108102 |
| SEQ ID NO: 497 | Tab1-505 | hsa-miR-302a | UAAGUGCUUCCAUGUUUUGGUGA | 0.454000804 |
| SEQ ID NO: 873 | Tab1-506 | hsa-miR-106b* | CCGCACUGUGGGUACUUGCUGC | 0.459710333 |
| SEQ ID NO: 75 | Tab1-507 | hsa-miR-7-1* | CAACAAAUCACAGUCUGCCAUA | 0.460376321 |
| SEQ ID NO: 155 | Tab1-508 | hsa-miR-604 | AGGCUGCGGAAUUCAGGAC | 0.460376321 |
| SEQ ID NO: 726 | Tab1-509 | hsa-miR-138-2* | GCUAUUUCACGACACCAGGGUU | 0.461435075 |
| SEQ ID NO: 335 | Tab1-510 | hsa-miR-496 | UGAGUAUUACAUGGCCAAUCUC | 0.461695951 |
| SEQ ID NO: 469 | Tab1-511 | hsa-miR-320d | AAAAGCUGGGUUGAGAGGA | 0.468379686 |
| SEQ ID NO: 336 | Tab1-512 | hsa-miR-495 | AAACAAACAUGGUAGCACUUCUU | 0.468379686 |
| SEQ ID NO: 376 | Tab1-513 | hsa-miR-432 | UCUUGGAGUAGGUCAUUGGGUGG | 0.468802712 |
| SEQ ID NO: 251 | Tab1-514 | hsa-miR-526b* | GAAAGUGCUUCCUUUUAGAGGC | 0.474699836 |
| SEQ ID NO: 728 | Tab1-515 | hsa-miR-138 | AGCUGGUGUUGUGAAUCAGGCCG | 0.475071987 |

FIG. 18B (Cont.)

| SEQ ID NO | Tab1 | miRNA | Sequence | Value |
|---|---|---|---|---|
| SEQ ID NO: 554 | Tab1-516 | hsa-miR-218-1* | AUGGUUCCGUCAAGCACCAUGG | 0.475596861 |
| SEQ ID NO: 319 | Tab1-517 | hsa-miR-506 | UAAGGCACCCUUCUGAGUAGA | 0.483842553 |
| SEQ ID NO: 766 | Tab1-518 | hsa-miR-1292 | UGGGAACGGGUUCCGGCAGACGCUG | 0.483842553 |
| SEQ ID NO: 595 | Tab1-519 | hsa-miR-200b | UAAUACUGCCUGGUAAUGAUGA | 0.488956479 |
| SEQ ID NO: 421 | Tab1-520 | hsa-miR-369-5p | AGAUCGACCGUGUUAUAUUCGC | 0.491381288 |
| SEQ ID NO: 703 | Tab1-521 | hsa-miR-1471 | GCCCGCGUGUGGAGCCAGGUGU | 0.493639719 |
| SEQ ID NO: 598 | Tab1-522 | hsa-miR-19b-2* | AGUUUUGCAGGUUUGCAUUUCA | 0.496570991 |
| SEQ ID NO: 33 | Tab1-523 | hsa-miR-9 | UCUUUGGUUAUCUAGCUGUAUGA | 0.500011514 |
| SEQ ID NO: 371 | Tab1-524 | hsa-miR-449b | AGGCAGUGUAUUGUUAGCUGGC | 0.502446002 |
| SEQ ID NO: 526 | Tab1-525 | hsa-miR-25 | CAUUGCACUUGUCUCGGUCUGA | 0.505665104 |
| SEQ ID NO: 796 | Tab1-526 | hsa-miR-1267 | CCUGUUGAAGUGUAAUCCCA | 0.509629962 |
| SEQ ID NO: 271 | Tab1-527 | hsa-miR-520b | AAAGUGCUUCCUUUUAGAGGG | 0.509979611 |
| SEQ ID NO: 520 | Tab1-528 | hsa-miR-26b* | CCUGUUCUCCAUUACUUGGCUC | 0.512172529 |
| SEQ ID NO: 209 | Tab1-529 | hsa-miR-554 | GCUAGUCCUGACUCAGCCAGU | 0.515829635 |
| SEQ ID NO: 384 | Tab1-530 | hsa-miR-423-5p | UGAGGGGCAGAGAGCGAGACUUU | 0.519402593 |
| SEQ ID NO: 374 | Tab1-531 | hsa-miR-433 | AUCAUGAUGGGCUCCUCGGGUG | 0.519402593 |
| SEQ ID NO: 751 | Tab1-532 | hsa-miR-1306 | ACGUUGGCUCUGGUGCUG | 0.519402593 |
| SEQ ID NO: 108 | Tab1-533 | hsa-miR-645 | UCUAGGCUGGUACUGCUGA | 0.5194025933 |
| SEQ ID NO: 234 | Tab1-534 | hsa-miR-548c-3p | CAAAAAUCUCAAUUACUUUUUGC | 0.521228772 |
| SEQ ID NO: 227 | Tab1-535 | hsa-miR-548h | AAAAGUAAUCGCGGUUUUUGUC | 0.525614604 |
| SEQ ID NO: 233 | Tab1-536 | hsa-miR-548c-5p | AAAAGUAAUUGCGGUUUUUGCC | 0.531224088 |
| SEQ ID NO: 772 | Tab1-537 | hsa-miR-1287 | UGCUGGAUCAGUGGUUCGAGUC | 0.531854468 |
| SEQ ID NO: 388 | Tab1-538 | hsa-miR-412 | ACUUCACCUGGUCCACAGCCGU | 0.534911351 |
| SEQ ID NO: 753 | Tab1-539 | hsa-miR-1304 | UUUGAGGCUACAGUGAGAUGUG | 0.541471772 |
| SEQ ID NO: 560 | Tab1-540 | hsa-miR-214* | UGCCUGUCUACACUUGCUGUGC | 0.544892491 |
| SEQ ID NO: 514 | Tab1-541 | hsa-miR-28-5p | AAGGAGCUCACAGUCUAUUGAG | 0.545336294 |
| SEQ ID NO: 823 | Tab1-542 | hsa-miR-1248 | ACCUUCUUGUAUAAGCACUGUCUAAA | 0.547251927 |
| SEQ ID NO: 468 | Tab1-543 | hsa-miR-323-3p | CACAUUACACGGUCGAUGCU | 0.547251927 |
| SEQ ID NO: 249 | Tab1-544 | hsa-miR-532-3p | CCUCCCACACACCAAGGCUUGCA | 0.548448982 |
| SEQ ID NO: 552 | Tab1-545 | hsa-miR-219-1-3p | AGAGUUGAGUCUGGACGUCCCG | 0.549136112 |
| SEQ ID NO: 116 | Tab1-546 | hsa-miR-637 | ACUGGGGGCAUCCUUUAGAGGUU | 0.552482272 |
| SEQ ID NO: 280 | Tab1-547 | hsa-miR-519b-3p | AAAGUGCAUCCUUUAGAGGUUU | 0.554013697 |
| SEQ ID NO: 871 | Tab1-548 | hsa-miR-10a | UACCCUGUAGAUCCGAAUUUGUG | 0.554013697 |
| SEQ ID NO: 733 | Tab1-549 | hsa-miR-135b | UAUGGCUUUUCAUUCCUAUGUGA | 0.554013697 |
| SEQ ID NO: 488 | Tab1-550 | hsa-miR-302f | UAAUUGCUUCCAUGUUU | 0.556112545 |
| SEQ ID NO: 101 | Tab1-551 | hsa-miR-652 | AAUUGCGCCACUAGGGUUGUG | 0.556112545 |
| SEQ ID NO: 623 | Tab1-552 | hsa-miR-194* | CCAGUGGGGCUGCUGUUAUCUG | 0.556112545 |

FIG. 18B (Cont.)

| | | | | |
|---|---|---|---|---|
| SEQ ID NO: 620 | Tab1-553 | hsa-miR-196a | UAGGUAGUUUCAUGUUGUUGGG | 0,556112545 |
| SEQ ID NO: 898 | Tab1-554 | hsa-let-7c* | UAGAGUUACACCCUGGGAGUUA | 0,556112545 |
| SEQ ID NO: 582 | Tab1-555 | hsa-miR-206 | UGGAAUGUAAGGAAGUGUGUGG | 0,556112545 |
| SEQ ID NO: 894 | Tab1-556 | hsa-let-7e* | CUAUACGGCCUCCUAGCUUUCC | 0,556112545 |
| SEQ ID NO: 702 | Tab1-557 | hsa-miR-147b | GUGUGCGGAAAUGCUUCUGCUA | 0,556112545 |
| SEQ ID NO: 286 | Tab1-558 | hsa-miR-518e | AAAGCGCUUCCCUUCAGAGUG | 0,556112545 |
| SEQ ID NO: 770 | Tab1-559 | hsa-miR-1289 | UGGAGUCCAGGAAUCUGCAUUU | 0,561548903 |
| SEQ ID NO: 849 | Tab1-560 | hsa-miR-1208 | UCACUGUUCAGACAGGCGGA | 0,563707633 |
| SEQ ID NO: 419 | Tab1-561 | hsa-miR-371-3p | AAGUGCCGCCAUCUUUUGAGUGU | 0,564921522 |
| SEQ ID NO: 361 | Tab1-562 | hsa-miR-453 | AGGUUGCCGUGUGAGUUCGCA | 0,567377405 |
| SEQ ID NO: 476 | Tab1-563 | hsa-miR-31 | AGGCAAGAUGCUGGCAUAGCU | 0,567377405 |
| SEQ ID NO: 632 | Tab1-564 | hsa-miR-1915 | CCCCAGGGCGACGCGGCGGG | 0,567503712 |
| SEQ ID NO: 781 | Tab1-565 | hsa-miR-1279 | UCAUAUUGCUUCUUUCU | 0,571092246 |
| SEQ ID NO: 397 | Tab1-566 | hsa-miR-381 | UAUACAAGGGCAAGCUCUCUGU | 0,571523437 |
| SEQ ID NO: 774 | Tab1-567 | hsa-miR-1285 | UCUGGGCAACAAAGUGAGACCU | 0,571523437 |
| SEQ ID NO: 692 | Tab1-568 | hsa-miR-151-5p | UCGAGGAGCUCACAGUCUAGU | 0,573198276 |
| SEQ ID NO: 679 | Tab1-569 | hsa-miR-15b* | CGAAUCAUUAUUGCUCCUCUA | 0,573359824 |
| SEQ ID NO: 361 | Tab1-570 | hsa-miR-425 | AAUGACACGAUGACUCCCGUUGA | 0,577510466 |
| SEQ ID NO: 452 | Tab1-571 | hsa-miR-338-3p | UCCAGCAUCAGUGAUUUACAAAGUAAUUCA | 0,580169863 |
| SEQ ID NO: 50 | Tab1-572 | hsa-miR-876-3p | UGGGUUUACAAAGUAAUUCA | 0,580169863 |
| SEQ ID NO: 807 | Tab1-573 | hsa-miR-125b-1* | ACGGGUUAGGCUCUUGGGAGCU | 0,580169863 |
| SEQ ID NO: 22 | Tab1-574 | hsa-miR-93 | CAAAGUGCUGUUCGUGCAGGUAG | 0,580169863 |
| SEQ ID NO: 339 | Tab1-575 | hsa-miR-493 | UGAAGGUCUACUGGUGUCCAGG | 0,581097836 |
| SEQ ID NO: 353 | Tab1-576 | hsa-miR-485-3p | GUCAUACACGGCUCUCCUCUCU | 0,585714021 |
| SEQ ID NO: 672 | Tab1-577 | hsa-miR-181a* | ACCAUCGACCGUUGAUUGUACC | 0,591370567 |
| SEQ ID NO: 740 | Tab1-578 | hsa-miR-1323 | UCAAAACUGAGGGGCAUUUUCU | 0,591370567 |
| SEQ ID NO: 647 | Tab1-579 | hsa-miR-18b* | UGCCCUAAAUGCCCCUCACAUCAU | 0,592146368 |
| SEQ ID NO: 508 | Tab1-580 | hsa-miR-299-5p | UGGUUUACCGUCCCACAUACAU | 0,592146368 |
| SEQ ID NO: 783 | Tab1-581 | hsa-miR-1277 | UACGUAGAUAUAUAUGUAUUU | 0,592146368 |
| SEQ ID NO: 695 | Tab1-582 | hsa-miR-150 | UCUCCCAACCCUUGUACCAGUG | 0,592146368 |
| SEQ ID NO: 415 | Tab1-583 | hsa-miR-373* | ACUCAAAAUGGGGGCGCUUUCC | 0,592146368 |
| SEQ ID NO: 281 | Tab1-584 | hsa-miR-519a* | CUCUAGAGGGAAGCGCUUUCUG | 0,592146368 |
| SEQ ID NO: 18 | Tab1-585 | hsa-miR-935 | CCAAUUAUACCGCUUCCGCUUACCGC | 0,595432308 |
| SEQ ID NO: 676 | Tab1-586 | hsa-miR-16-2* | CCAAUAUUACUGUGCUGCUUUA | 0,595432308 |
| SEQ ID NO: 357 | Tab1-587 | hsa-miR-455-5p | UAUGUGCCUUUGGACUACAUCG | 0,595432308 |
| SEQ ID NO: 744 | Tab1-588 | hsa-miR-132 | UAACAGUCUACAGCCAUGGUCG | 0,595432308 |
| SEQ ID NO: 359 | Tab1-589 | hsa-miR-454* | ACCCUAUCAAUAUUGUCUCUGC | 0,595432308 |

FIG. 18B (Cont.)

| | | | |
|---|---|---|---|
| SEQ ID NO: 239 | Tab1-590 | hsa-miR-545* | UCAGUAAAUGUUUAUUAGAUGA | 0.595543256 |
| SEQ ID NO: 588 | Tab1-591 | hsa-miR-204 | UUCCUUUGUCAUCCUUAUGCCU | 0.598928408 |
| SEQ ID NO: 235 | Tab1-592 | hsa-miR-548b-5p | AAAAGUAAUUGUGGUUUUGGCC | 0.601885514 |
| SEQ ID NO: 56 | Tab1-593 | hsa-miR-770-5p | UCCAGUACCACGUGUCAGGGCCA | 0.605158716 |
| SEQ ID NO: 706 | Tab1-594 | hsa-miR-146b-5p | UGAGAACUGAAUUCCAUAGGCU | 0.605158716 |
| SEQ ID NO: 287 | Tab1-595 | hsa-miR-518d-5p | CUCUAGAGGGAAGCACUUUCUG | 0.607320615 |
| SEQ ID NO: 680 | Tab1-596 | hsa-miR-15b | UAGCAGCACAUCAAUGGUUUACA | 0.611319842 |
| SEQ ID NO: 599 | Tab1-597 | hsa-miR-19b-1* | AGUUUUGCAGGUUUGCAUCCAGC | 0.611319842 |
| SEQ ID NO: 403 | Tab1-598 | hsa-miR-378 | ACUGGACUUGGAGUCAGAAGG | 0.612379274 |
| SEQ ID NO: 761 | Tab1-599 | hsa-miR-129-5p | CUUUUGGGUCUGGGCUUGC | 0.612998945 |
| SEQ ID NO: 312 | Tab1-600 | hsa-miR-510 | UACUCAGGAGAGUGGCAAUCAC | 0.612998945 |
| SEQ ID NO: 451 | Tab1-601 | hsa-miR-338-5p | AACAAUAUCCUGGUGCUGAGUG | 0.614264927 |
| SEQ ID NO: 267 | Tab1-602 | hsa-miR-520d-5p | CUACAAAGGGAAGCCCUUUC | 0.619628052 |
| SEQ ID NO: 305 | Tab1-603 | hsa-miR-513c | UUCUCAAGGAGGAGUGUCGUUUAU | 0.619598756 |
| SEQ ID NO: 247 | Tab1-604 | hsa-miR-539 | GGAGAAAUUAUCCUUGGUGUGU | 0.620252569 |
| SEQ ID NO: 602 | Tab1-605 | hsa-miR-19a | UGUGCAAAUCUAUGCAAAACUGA | 0.620252569 |
| SEQ ID NO: 597 | Tab1-606 | hsa-miR-200a | UAACACUGUCUGGUAACGAUGU | 0.620252569 |
| SEQ ID NO: 594 | Tab1-607 | hsa-miR-200b* | CAUCUUACUGGGCAGCAUUGGA | 0.620252569 |
| SEQ ID NO: 456 | Tab1-608 | hsa-miR-335 | UCAAGAGCAAUAACGAAAAAUGU | 0.620252569 |
| SEQ ID NO: 195 | Tab1-609 | hsa-miR-569 | AGUAAUGAAUCCUGGAAAGU | 0.620252569 |
| SEQ ID NO: 633 | Tab1-610 | hsa-miR-1914* | GGAGGGGUCCCGCACUGGGAGG | 0.621973183 |
| SEQ ID NO: 279 | Tab1-611 | hsa-miR-519b-5p | CUCUAGAGGGAAGCGCUUUCUG | 0.627550294 |
| SEQ ID NO: 283 | Tab1-612 | hsa-miR-518f* | CUCUAGAGGGAAGCACUUUCUC | 0.628289927 |
| SEQ ID NO: 191 | Tab1-613 | hsa-miR-573 | CUGAAGUGAUGGCUGCUGUAACUGAUCAG | 0.628289927 |
| SEQ ID NO: 212 | Tab1-614 | hsa-miR-551b* | GAAAUCAAGCGUGGGUGAGACC | 0.628289927 |
| SEQ ID NO: 52 | Tab1-615 | hsa-miR-875-3p | CCUGGAAACACUGAGGUUGUG | 0.629452457 |
| SEQ ID NO: 688 | Tab1-616 | hsa-miR-1538 | CGGCCCGGGCUGCUGCUGUUCCU | 0.631620045 |
| SEQ ID NO: 264 | Tab1-617 | hsa-miR-520g | ACAAAGUGCUUCCUUUAGAGUGU | 0.638581862 |
| SEQ ID NO: 117 | Tab1-618 | hsa-miR-636 | UGUGCUUGCUCGUCCCGCCCGCA | 0.639310876 |
| SEQ ID NO: 682 | Tab1-619 | hsa-miR-15a | UAGCAGCACAUAAUGGUUUGUG | 0.643794056 |
| SEQ ID NO: 128 | Tab1-620 | hsa-miR-627 | GUGAGUCUCUAAGAAAAGAGGA | 0.643794056 |
| SEQ ID NO: 411 | Tab1-621 | hsa-miR-374b* | CUUAGCAGGUUGUAUUAUCAUU | 0.645024259 |
| SEQ ID NO: 7 | Tab1-622 | hsa-miR-96 | UUUGGCACUAGCACAUUUUUGCU | 0.651179502 |
| SEQ ID NO: 390 | Tab1-623 | hsa-miR-411 | UAGUAGACCGUAUAGCGUACG | 0.652371304 |
| SEQ ID NO: 193 | Tab1-624 | hsa-miR-571 | UGAGUUGGCCAUCUGAGUGAG | 0.652815994 |
| SEQ ID NO: 863 | Tab1-625 | hsa-miR-1182 | GAGGGUCUUGGGAGGGAUGUGAC | 0.652815994 |
| SEQ ID NO: 494 | Tab1-626 | hsa-miR-302b* | ACUUUAACAUGGAAGUGCUUUC | 0.652815994 |

FIG. 18B (Cont.)

| | | | | |
|---|---|---|---|---|
| SEQ ID NO: 400 | Tab1-627 | hsa-miR-379* | UAUGUAACAUGGUCCACUAACU | 0.652815994 |
| SEQ ID NO: 547 | Tab1-628 | hsa-miR-220a | CCACACCGUAUCGUGACACUUU | 0.657009528 |
| SEQ ID NO: 805 | Tab1-629 | hsa-miR-126 | UCGUACCGUGAGUAAUAAUGCG | 0.657009528 |
| SEQ ID NO: 304 | Tab1-630 | hsa-miR-514 | AUUGACACUCUGUGCCACCA | 0.657844854 |
| SEQ ID NO: 803 | Tab1-631 | hsa-miR-1260 | AUCCCACCUCUGCCACCA | 0.657844854 |
| SEQ ID NO: 592 | Tab1-632 | hsa-miR-200c* | CGUCUUACCCAGAGUGUGUUGG | 0.66185069 |
| SEQ ID NO: 466 | Tab1-633 | hsa-miR-324-3p | ACUGCCCAGGUGCUGCUGG | 0.661950447 |
| SEQ ID NO: 240 | Tab1-634 | hsa-miR-545 | UCAGCAAACAUUAUUGUGUGC | 0.664274223 |
| SEQ ID NO: 307 | Tab1-635 | hsa-miR-513a-5p | UUCACAGGGAGGUGUCAU | 0.664274223 |
| SEQ ID NO: 631 | Tab1-636 | hsa-miR-1915* | ACCUUGCCUUGCUGCCCGGGCC | 0.665742723 |
| SEQ ID NO: 112 | Tab1-637 | hsa-miR-641 | AAAGACAUAGGAUAGAGUCACCUC | 0.668569181 |
| SEQ ID NO: 41 | Tab1-638 | hsa-miR-888 | UACUCAAAAAGCUGCAGUCA | 0.672838942 |
| SEQ ID NO: 553 | Tab1-639 | hsa-miR-218-2* | CAUGGUUCUGUCAAGCACCGCG | 0.672838942 |
| SEQ ID NO: 318 | Tab1-640 | hsa-miR-507 | UUUUGCACCUUUUGGAGUGAA | 0.681686382 |
| SEQ ID NO: 394 | Tab1-641 | hsa-miR-384 | AUUCCUAGAAAUUGUUCAUA | 0.687308342 |
| SEQ ID NO: 555 | Tab1-642 | hsa-miR-218 | UUGUGCUUGAUCGUGAUAGGGGU | 0.687308342 |
| SEQ ID NO: 684 | Tab1-643 | hsa-miR-155 | UUAAUGCUAAUCGUGAUAGGGGU | 0.688911345 |
| SEQ ID NO: 654 | Tab1-644 | hsa-miR-187 | UCGUGUCUUGUGUUGCAGCCGG | 0.891825163 |
| SEQ ID NO: 332 | Tab1-645 | hsa-miR-498 | UUUCAAGCCAGGGGGCGUUUUUC | 0.699502459 |
| SEQ ID NO: 27 | Tab1-646 | hsa-miR-92a | UAUUGCACUUGUCCCGGCCUGU | 0.699502459 |
| SEQ ID NO: 288 | Tab1-647 | hsa-miR-518d-3p | CAAAGCGCUUCCCUUUGGAGC | 0.701120366 |
| SEQ ID NO: 413 | Tab1-648 | hsa-miR-374a* | CUUAUCAGAUUGUAUGUAAUU | 0.704329351 |
| SEQ ID NO: 662 | Tab1-649 | hsa-miR-1827 | UGAGGCAGUAGAUUGAAU | 0.709330539 |
| SEQ ID NO: 868 | Tab1-650 | hsa-miR-10b* | ACAGAUUCGAUUCUAGGGGAAU | 0.709330539 |
| SEQ ID NO: 387 | Tab1-651 | hsa-miR-421 | AUCAACAGACAUUAAUUGGGCGC | 0.709330539 |
| SEQ ID NO: 245 | Tab1-652 | hsa-miR-541* | AAAGGAUUCUGCUGUCGGUCCCACU | 0.710634011 |
| SEQ ID NO: 721 | Tab1-653 | hsa-miR-141 | UAACACUGUCUGGUAAAGAUGG | 0.711881595 |
| SEQ ID NO: 295 | Tab1-654 | hsa-miR-517b | UCGUGCAUCCCUUUAGAGUGUU | 0.718740147 |
| SEQ ID NO: 485 | Tab1-655 | hsa-miR-30b | UGUAAACAUCCUACACUCAGCU | 0.720045031 |
| SEQ ID NO: 225 | Tab1-656 | hsa-miR-548j | AAAAGUAAAUGCGGGUCUUUGGU | 0.720045031 |
| SEQ ID NO: 133 | Tab1-657 | hsa-miR-624 | CACAAGGUAUUGGUAUUACCU | 0.721718233 |
| SEQ ID NO: 641 | Tab1-658 | hsa-miR-191 | CAACGGAAUCCCAAAAGCAGCUG | 0.721759568 |
| SEQ ID NO: 55 | Tab1-659 | hsa-miR-802 | CAGUAACAAAGAUUCAUCCUUGU | 0.721759568 |
| SEQ ID NO: 243 | Tab1-660 | hsa-miR-542-5p | UCGGGGAUCAUCAUGUCACGAGA | 0.722960963 |
| SEQ ID NO: 308 | Tab1-661 | hsa-miR-513a-3p | UAAAUUCACCUUUCUGAGAAGG | 0.728749257 |
| SEQ ID NO: 151 | Tab1-662 | hsa-miR-608 | AGGGGUGGUGUUGGGACAGCUCCGU | 0.731671228 |
| SEQ ID NO: 392 | Tab1-663 | hsa-miR-409-5p | AGGUUACCCGAGCAACUUUGCAU | 0.731671228 |

FIG. 18B (Cont.)

| SEQ ID NO: | Tab1- | miRNA | Sequence | Value |
|---|---|---|---|---|
| SEQ ID NO: 296 | Tab1-664 | hsa-miR-517a | AUCGUGCAUCCCUUUAGAGUGU | 0.73479974 |
| SEQ ID NO: 21 | Tab1-665 | hsa-miR-93* | ACUGCUGAGCUAGCACUUCCCG | 0.742283122 |
| SEQ ID NO: 904 | Tab1-666 | hsa-let-7a | UGAGGUAGUAGGUUGUAUAGUU | 0.742283122 |
| SEQ ID NO: 659 | Tab1-667 | hsa-miR-184 | UGGACGGAGAACUGAUAAGGGU | 0.74447289 |
| SEQ ID NO: 606 | Tab1-668 | hsa-miR-199a-3p | ACAGUAGUCUGCACAUUGGUUA | 0.748072189 |
| SEQ ID NO: 221 | Tab1-669 | hsa-miR-548n | CAAAAGUAAUGUGGAUUUUGU | 0.750397294 |
| SEQ ID NO: 689 | Tab1-670 | hsa-miR-1537 | AAAACGUCAGUAGUACAGUUGU | 0.750397294 |
| SEQ ID NO: 667 | Tab1-671 | hsa-miR-181d | AACAUUCAUUGUUGUCGGUGGGU | 0.757344712 |
| SEQ ID NO: 453 | Tab1-672 | hsa-miR-337-5p | GAACGGCUUCAUACAGGAGUU | 0.758994236 |
| SEQ ID NO: 747 | Tab1-673 | hsa-miR-130a* | UUCACAUUGUGCUACUGUCUGC | 0.761640489 |
| SEQ ID NO: 498 | Tab1-674 | hsa-miR-301b | CAGUGCAAUGAUAUUGUCAAAGC | 0.767436325 |
| SEQ ID NO: 418 | Tab1-675 | hsa-miR-371-5p | ACUCAAAACUGUGGGGCACU | 0.769306239 |
| SEQ ID NO: 232 | Tab1-676 | hsa-miR-548d-3p | CAAAAACCACAGUUUCUUUUGC | 0.769306239 |
| SEQ ID NO: 787 | Tab1-677 | hsa-miR-1274b | UCCCUGUUCGGGCGCCA | 0.773050164 |
| SEQ ID NO: 183 | Tab1-678 | hsa-miR-579 | UUCAUUUGGUAUAAACCGCGAUU | 0.774794391 |
| SEQ ID NO: 121 | Tab1-679 | hsa-miR-632 | GUGUCUGCUUCCUGUGGGA | 0.775709011 |
| SEQ ID NO: 72 | Tab1-680 | hsa-miR-7-2* | CAACAAAUCCCAGUCUACCUAA | 0.775709011 |
| SEQ ID NO: 854 | Tab1-681 | hsa-miR-1204 | UCGUGGCCUGGGUCUCCAUAU | 0.775709011 |
| SEQ ID NO: 30 | Tab1-682 | hsa-miR-921 | CUAGUGAGGGAACAGAACCAGGAUUC | 0.775709011 |
| SEQ ID NO: 272 | Tab1-683 | hsa-miR-520a-5p | CUCCAGAGGGAAGACUUUCU | 0.775709011 |
| SEQ ID NO: 84 | Tab1-684 | hsa-miR-668 | UGUCACUCGGCUCGGCCACUAC | 0.775709011 |
| SEQ ID NO: 705 | Tab1-685 | hsa-miR-147 | GUGUGUGGAAAUGCUUCUGC | 0.775709011 |
| SEQ ID NO: 416 | Tab1-686 | hsa-miR-373 | GAAGUGCUUCGAUUUUGGGGUGU | 0.775709011 |
| SEQ ID NO: 760 | Tab1-687 | hsa-miR-1296 | UUAGGGCCCUGGCUCCAUCUCC | 0.775709011 |
| SEQ ID NO: 509 | Tab1-688 | hsa-miR-299-3p | UAUGUGGGUGGGUAAACCGCUU | 0.775709011 |
| SEQ ID NO: 197 | Tab1-689 | hsa-miR-567 | AGUAUGUUCUUCCAGGACAGAAC | 0.785026312 |
| SEQ ID NO: 149 | Tab1-690 | hsa-miR-610 | UGAGCUAAAUGUGUGCUGGGA | 0.786493938 |
| SEQ ID NO: 258 | Tab1-691 | hsa-miR-523* | CUCUAGAGGGAAGCGCUUUCUG | 0.788520251 |
| SEQ ID NO: 144 | Tab1-692 | hsa-miR-615-3p | UCCGAGCCUGGGUCUCCCUCUU | 0.788783622 |
| SEQ ID NO: 780 | Tab1-693 | hsa-miR-128 | UCACAGUGAACCGGUCUCUUU | 0.788783622 |
| SEQ ID NO: 889 | Tab1-694 | hsa-let-7g* | CUGUACAGGCCACUGCCUUGC | 0.78975234 |
| SEQ ID NO: 229 | Tab1-695 | hsa-miR-548f | AAAAACUGUAAUUACUUUU | 0.792669588 |
| SEQ ID NO: 587 | Tab1-696 | hsa-miR-205 | UCCUUCAUUCCACCGGAGUCUG | 0.792669588 |
| SEQ ID NO: 459 | Tab1-697 | hsa-miR-330-5p | UCUCUGGGCCUGUGUCUUAGGC | 0.792669588 |
| SEQ ID NO: 846 | Tab1-698 | hsa-miR-1224-3p | CCCCACCUCCUCUCUCCUCAG | 0.792669588 |
| SEQ ID NO: 352 | Tab1-699 | hsa-miR-485-5p | AGAGGCUGGCCGUGAUGAAUUC | 0.792669588 |
| SEQ ID NO: 691 | Tab1-700 | hsa-miR-152 | UCAGUGCAUGACAGAACUUGG | 0.792669588 |

FIG. 18B (Cont.)

| SEQ ID NO | Tab ID | miRNA | Sequence | Value |
|---|---|---|---|---|
| SEQ ID NO: 665 | Tab1-701 | hsa-miR-182* | UGGUUCUAGACUUGCCAACUA | 0.792669588 |
| SEQ ID NO: 277 | Tab1-702 | hsa-miR-519c-5p | CUCUAGAGGGAAGCGCUUUCUG | 0.797511408 |
| SEQ ID NO: 217 | Tab1-703 | hsa-miR-549 | UGACAACUAUGGAUGAGCUCU | 0.797511408 |
| SEQ ID NO: 202 | Tab1-704 | hsa-miR-561 | CAAAGUUUAAGAUCCUUGAAGU | 0.7984642 |
| SEQ ID NO: 377 | Tab1-705 | hsa-miR-431* | CAGGUCGUCUUGCAGGGCUUCU | 0.799246708 |
| SEQ ID NO: 833 | Tab1-706 | hsa-miR-1236 | CCUCUUCCCGUUGUCUCUCCAG | 0.799246708 |
| SEQ ID NO: 749 | Tab1-707 | hsa-miR-1308 | GCAUGGGUGGUUCAGUGG | 0.799246708 |
| SEQ ID NO: 175 | Tab1-708 | hsa-miR-586 | UAUGCAUUGUAUUUUUAGGUCC | 0.800314761 |
| SEQ ID NO: 68 | Tab1-709 | hsa-miR-758 | UUUGUGACCUGGUCCACUAACC | 0.80582552 |
| SEQ ID NO: 457 | Tab1-710 | hsa-miR-331-5p | CUAGGUAUGGUCCCAGGGAUCC | 0.806071461 |
| SEQ ID NO: 382 | Tab1-711 | hsa-miR-424* | CAAAACGUGAGGCGCUGCUAU | 0.807375071 |
| SEQ ID NO: 533 | Tab1-712 | hsa-miR-23a | AUCACAUUGCCAGGGAUUUCC | 0.807448834 |
| SEQ ID NO: 859 | Tab1-713 | hsa-miR-1197 | UAGGACACAUGGUCUACUUCU | 0.810196672 |
| SEQ ID NO: 139 | Tab1-714 | hsa-miR-618 | AAACUCUACUGUCCUUCUGAGU | 0.813971435 |
| SEQ ID NO: 91 | Tab1-715 | hsa-miR-661 | UGCCUGGGUCUCUGGCCUGCGCGU | 0.813971435 |
| SEQ ID NO: 799 | Tab1-716 | hsa-miR-1264 | CAAGUCUUAUUGAGAGGAAACUGA | 0.815546928 |
| SEQ ID NO: 363 | Tab1-717 | hsa-miR-452 | AACUGUUUGCAGAGGAAACUGA | 0.815546928 |
| SEQ ID NO: 92 | Tab1-718 | hsa-miR-660 | UACCCAUUGCAUAUCGGAGUUG | 0.815546928 |
| SEQ ID NO: 883 | Tab1-719 | hsa-miR-101 | UACAGUACUGUGAUAACUGAA | 0.818290788 |
| SEQ ID NO: 273 | Tab1-720 | hsa-miR-520a-3p | AAAGUGCUUCCCUUUGGACUGU | 0.818290788 |
| SEQ ID NO: 655 | Tab1-721 | hsa-miR-186* | GCCCAAAGGUGAAUUUUUUGGG | 0.822137456 |
| SEQ ID NO: 147 | Tab1-722 | hsa-miR-612 | GCUGGGCAGGGCUUCUGAGCUCCUU | 0.824341004 |
| SEQ ID NO: 200 | Tab1-723 | hsa-miR-563 | AGGUUGACAUACGUUCC | 0.824494104 |
| SEQ ID NO: 893 | Tab1-724 | hsa-let-7f | UGAGGUAGUAGAUUGUAUAGUU | 0.825308686 |
| SEQ ID NO: 725 | Tab1-725 | hsa-miR-139-3p | GGAGACGCGGCCCUGUUGGAGU | 0.825989592 |
| SEQ ID NO: 150 | Tab1-726 | hsa-miR-609 | AGGGUGUUUCUCUCAUCUCU | 0.828936411 |
| SEQ ID NO: 450 | Tab1-727 | hsa-miR-339-3p | UGAGCGCCUCGACGACAGAGCCG | 0.829563183 |
| SEQ ID NO: 784 | Tab1-728 | hsa-miR-1276 | UAAAGAGCCCUGUGGAGACA | 0.831337059 |
| SEQ ID NO: 224 | Tab1-729 | hsa-miR-548k | AAAAGUACUUGCGGAUUUGCU | 0.831337059 |
| SEQ ID NO: 284 | Tab1-730 | hsa-miR-518f | GAAAGCGCUUCUCUUUAGAGG | 0.831337059 |
| SEQ ID NO: 85 | Tab1-731 | hsa-miR-665 | ACCAGGAGGCUGAGGCCCU | 0.831337059 |
| SEQ ID NO: 184 | Tab1-732 | hsa-miR-578 | CUUCUUGUGCUCUAGGAUUGU | 0.831337059 |
| SEQ ID NO: 794 | Tab1-733 | hsa-miR-1269 | CUGGACUGAGCCGUGCUACUGG | 0.831337059 |
| SEQ ID NO: 461 | Tab1-734 | hsa-miR-329 | AACACAUCCUUUAAGUU | 0.832130588 |
| SEQ ID NO: 262 | Tab1-735 | hsa-miR-521 | AACGCACUGUCCUUUAAGUU | 0.832130588 |
| SEQ ID NO: 530 | Tab1-736 | hsa-miR-23b* | UGGGUUCCUGGCAUGCUGAUUU | 0.832130588 |
| SEQ ID NO: 493 | Tab1-737 | hsa-miR-302c | UAAGUGCUUCCAUGUUUCAGUGG | 0.834010232 |

FIG. 18B (Cont.)

| | | | | |
|---|---|---|---|---|
| SEQ ID NO: 720 | Tab1-738 | hsa-miR-141* | CAUCUUCCAGUACAGUGUUGGA | 0.834010232 |
| SEQ ID NO: 252 | Tab1-739 | hsa-miR-526b | CUCUUGAGGGAAGCACUUUCUGU | 0.83442217 |
| SEQ ID NO: 205 | Tab1-740 | hsa-miR-557 | GUUUGCACGGGUGGGCCUUGUCU | 0.83442217 |
| SEQ ID NO: 409 | Tab1-741 | hsa-miR-376a | AUCAUAGAGGAAAAUCCACGU | 0.835148073 |
| SEQ ID NO: 806 | Tab1-742 | hsa-miR-125b-2* | UCACAAGUCAGGCUCUUGGGAC | 0.837311353 |
| SEQ ID NO: 60 | Tab1-743 | hsa-miR-767-3p | UCUGCUCAUAUCCCAUGGUUUCU | 0.84316404 |
| SEQ ID NO: 479 | Tab1-744 | hsa-miR-30d* | CUUUCAGUCAGAUGUUUGCUGC | 0.84316404 |
| SEQ ID NO: 10 | Tab1-745 | hsa-miR-943 | CUGACUGUUGCCGUCCUCCAG | 0.860000686 |
| SEQ ID NO: 294 | Tab1-746 | hsa-miR-517c | AUCGUGCAUCCUUUUAGAGUGU | 0.861406109 |
| SEQ ID NO: 491 | Tab1-747 | hsa-miR-302d | UAAGUGCUUCCAUGUUUGAGUGU | 0.86160008 |
| SEQ ID NO: 736 | Tab1-748 | hsa-miR-134 | UGUGACUGGUUGACCAGAGGGG | 0.862347398 |
| SEQ ID NO: 367 | Tab1-749 | hsa-miR-450a | UUUUGCGAUGUGUUCCUAAUAU | 0.862492671 |
| SEQ ID NO: 465 | Tab1-750 | hsa-miR-324-5p | CGCAUCCCCUAGGGCAUUGGUGU | 0.865866588 |
| SEQ ID NO: 347 | Tab1-751 | hsa-miR-488 | UUGAAAGGCUAUUUCUUGGUC | 0.865866588 |
| SEQ ID NO: 289 | Tab1-752 | hsa-miR-518c* | UCUCUGGAGGGAAGCACUUUCUG | 0.865866588 |
| SEQ ID NO: 207 | Tab1-753 | hsa-miR-556-3p | AUAUUACCAUUAGCUCAUCUUU | 0.86721168 |
| SEQ ID NO: 489 | Tab1-754 | hsa-miR-302e | UAAGUGCUUCCAUGCUU | 0.86880513 |
| SEQ ID NO: 769 | Tab1-755 | hsa-miR-129* | AAGCCCUUACCCCAAAAAGUAU | 0.86880513 |
| SEQ ID NO: 712 | Tab1-756 | hsa-miR-145* | GGAUUCCUGGAAAUACUGUUCU | 0.870825969 |
| SEQ ID NO: 596 | Tab1-757 | hsa-miR-200a* | CAUCUUACCGGACAGUGCUGGA | 0.8719536 38 |
| SEQ ID NO: 869 | Tab1-758 | hsa-miR-10b | UACCCUGUAGAACCGAAUUUGUG | 0.8719536 38 |
| SEQ ID NO: 870 | Tab1-759 | hsa-miR-10a* | CAAAUUCGUAUCUAGGGGAAUA | 0.872075585 |
| SEQ ID NO: 31 | Tab1-760 | hsa-miR-920 | GGGAGCUGUGGAAGCAGUA | 0.872156739 |
| SEQ ID NO: 646 | Tab1-761 | hsa-miR-190 | UGAUAUGUUUGAUAUUAGGU | 0.875624581 |
| SEQ ID NO: 482 | Tab1-762 | hsa-miR-30c-1* | CUGGGAGAGGGUUGUUUACUCC | 0.876832201 |
| SEQ ID NO: 737 | Tab1-763 | hsa-miR-1183 | CACUGUAGGUGAGGUGAGUGGGCA | 0.87724303 |
| SEQ ID NO: 616 | Tab1-764 | hsa-miR-133b | UUUGGUCCCCUUCAACCAGCUA | 0.87977382 |
| SEQ ID NO: 278 | Tab1-765 | hsa-miR-197 | UUCACCACCUUCUCCACCCAGC | 0.87977382 |
| SEQ ID NO: 181 | Tab1-766 | hsa-miR-519c-3p | AAAGUGCAUCUUUUUAGAGGAU | 0.87977382 |
| SEQ ID NO: 851 | Tab1-767 | hsa-miR-581 | UCUUUGUGUUCUCUAGAUCAGU | 0.881969477 |
| SEQ ID NO: 481 | Tab1-768 | hsa-miR-1207-3p | UCAGCUGGCCCUCAUUUC | 0.882006154 |
| SEQ ID NO: 372 | Tab1-769 | hsa-miR-30c-2* | CUGGGAGAAGGCUGUUUACUCU | 0.88738286 |
| SEQ ID NO: 322 | Tab1-770 | hsa-miR-449a | UGGCAGUGUAUUGUUAGCUGGU | 0.887654613 |
| SEQ ID NO: 813 | Tab1-771 | hsa-miR-504 | AGACCCUGGUCUGCACUCUAUC | 0.888605891 |
| SEQ ID NO: 186 | Tab1-772 | hsa-miR-1257 | AGUGAAUGAUGGGUUCUGACC | 0.889196695 |
| SEQ ID NO: 186 | Tab1-773 | hsa-miR-576-5p | AUUCUAAUUUCUCCACGUCUUU | 0.889196695 |
| SEQ ID NO: 42 | Tab1-774 | hsa-miR-887 | GUGAACGGGCGCCAUCCCGAGG | 0.892039618 |

FIG. 18B (Cont.)

| | | | | |
|---|---|---|---|---|
| SEQ ID NO: 140 | Tab1-775 | hsa-miR-617 | AGACUUCCCAUUUGAAGGUGGC | 0.892039618 |
| SEQ ID NO: 34 | Tab1-776 | hsa-miR-892b | CACUGGCUCCUUUCUGGGUAGA | 0.89282672 |
| SEQ ID NO: 717 | Tab1-777 | hsa-miR-143 | UGAGAUGAAGCACUGUAGCUC | 0.89282672 |
| SEQ ID NO: 265 | Tab1-778 | hsa-miR-520f | AAGUGCUUCCUUUUAGAGGGUU | 0.89282672 |
| SEQ ID NO: 504 | Tab1-779 | hsa-miR-29b-1* | GCUGGUUUCAUAUGGUGGUUUAGA | 0.89282672 |
| SEQ ID NO: 213 | Tab1-780 | hsa-miR-551b | GCGACCCAUACUUGGUUUCAG | 0.907405606 |
| SEQ ID NO: 269 | Tab1-781 | hsa-miR-520c-5p | CUCUAGAGGGAAGCACUUUCUG | 0.907598391 |
| SEQ ID NO: 168 | Tab1-782 | hsa-miR-591 | AGACCAUGGGUUCUCAUUGU | 0.907598391 |
| SEQ ID NO: 471 | Tab1-783 | hsa-miR-320b | AAAAGCUGGGUUGAGAGGGCAA | 0.909262403 |
| SEQ ID NO: 337 | Tab1-784 | hsa-miR-494 | UGAAACAUACACGGGAAACCUC | 0.909862556 |
| SEQ ID NO: 26 | Tab1-785 | hsa-miR-92a-1* | AGGUUGGGAUCGGUUGCAAUGCU | 0.911189217 |
| SEQ ID NO: 677 | Tab1-786 | hsa-miR-16-1* | CCAGUAUUAACUGUGCUGCUGA | 0.913014432 |
| SEQ ID NO: 385 | Tab1-787 | hsa-miR-423-3p | AGCUCGGUCUGAGGCCCCUCAGU | 0.920112393 |
| SEQ ID NO: 673 | Tab1-788 | hsa-miR-181a | AACAUUCAACGCUGUCGGUGAGU | 0.920112393 |
| SEQ ID NO: 104 | Tab1-789 | hsa-miR-649 | AAACCUGUGUUGUUCAAGAGUC | 0.920112393 |
| SEQ ID NO: 260 | Tab1-790 | hsa-miR-522* | CUCUAGAGGGAAGCGCUUUCUG | 0.9264405 |
| SEQ ID NO: 853 | Tab1-791 | hsa-miR-1205 | UCUGCAGGGUUUGCUUUGAG | 0.928532034 |
| SEQ ID NO: 551 | Tab1-792 | hsa-miR-219-2-3p | AGAAUUGUGGCUGGACAUCUGU | 0.928532034 |
| SEQ ID NO: 231 | Tab1-793 | hsa-miR-548d-5p | AAAAGUAAUUGUGGUUUUUGCC | 0.928532034 |
| SEQ ID NO: 185 | Tab1-794 | hsa-miR-577 | UAGAUAAAAUAUUGGUACCUG | 0.928532034 |
| SEQ ID NO: 549 | Tab1-795 | hsa-miR-22 | AAGCUGCCAGUUGAAGAACUGU | 0.932423244 |
| SEQ ID NO: 639 | Tab1-796 | hsa-miR-1910 | CCAGUCCUGUGCCUGCCGCCU | 0.938411573 |
| SEQ ID NO: 550 | Tab1-797 | hsa-miR-219-5p | UGAUUGUCCAAACGCAAUUCU | 0.940996824 |
| SEQ ID NO: 253 | Tab1-798 | hsa-miR-526a | CUCUAGAGGGAAGCACUUUCUG | 0.943387843 |
| SEQ ID NO: 829 | Tab1-799 | hsa-miR-124* | CGUGUUCACAGCGGACCUUGAU | 0.943387843 |
| SEQ ID NO: 8 | Tab1-800 | hsa-miR-95 | UUCAACGGGUAUUUAUUGAGCA | 0.943387843 |
| SEQ ID NO: 113 | Tab1-801 | hsa-miR-640 | AUGAACCAGGAGUCCAACCCUCU | 0.946088391 |
| SEQ ID NO: 276 | Tab1-802 | hsa-miR-519d | CAAAGUGCCUCCCUUUAGAGUG | 0.94617422 |
| SEQ ID NO: 731 | Tab1-803 | hsa-miR-136 | ACUCCAUUUGUUUUGAUGAUGGA | 0.946781524 |
| SEQ ID NO: 40 | Tab1-804 | hsa-miR-888* | GACUUGACACCUCUUUGGGAA | 0.946781524 |
| SEQ ID NO: 123 | Tab1-805 | hsa-miR-630 | AGUAUUCUGUACCAGGGAAGGU | 0.947028321 |
| SEQ ID NO: 832 | Tab1-806 | hsa-miR-1237 | UCCUUCUGCUCCGUCCCCAG | 0.949368934 |
| SEQ ID NO: 524 | Tab1-807 | hsa-miR-26a | UUCAAGUAAUCCAGGAUAGGCU | 0.949368934 |
| SEQ ID NO: 464 | Tab1-808 | hsa-miR-325 | CCUAGUAGGUGUCCAGUAAGUGU | 0.949368934 |
| SEQ ID NO: 626 | Tab1-809 | hsa-miR-193b | AACUGGCCCUCAAAGUCCCGCU | 0.951430819 |
| SEQ ID NO: 396 | Tab1-810 | hsa-miR-382 | GAAGUUGUUCGUGGUGGAUUCG | 0.953697694 |
| SEQ ID NO: 404 | Tab1-811 | hsa-miR-377* | AGAGGUUGCCCUUGGUGAAUUC | 0.954382372 |

FIG. 18B (Cont.)

| | | | |
|---|---|---|---|
| SEQ ID NO: 542 | Tab1-812 | hsa-miR-222 | AGCUACAUCUGGCUACUGGGU | 0.954382372 |
| SEQ ID NO: 77 | Tab1-813 | hsa-miR-708 | AAGGAGCUUACAAUCUAGCUGGG | 0.954382372 |
| SEQ ID NO: 848 | Tab1-814 | hsa-miR-122 | UGGAGUGUGACAAUGGUGUUUG | 0.954382372 |
| SEQ ID NO: 624 | Tab1-815 | hsa-miR-194 | UGUAACAGCAACUCCAUGUGGA | 0.954382372 |
| SEQ ID NO: 248 | Tab1-816 | hsa-miR-532-5p | CAUGCCUUGAGUGUAGGACCGU | 0.954382372 |
| SEQ ID NO: 455 | Tab1-817 | hsa-miR-335* | UUUUCAUUAUUGCUCCUGACC | 0.954382372 |
| SEQ ID NO: 513 | Tab1-818 | hsa-miR-296-3p | GAGGGUUGGGUGGAGGCUCUCC | 0.954382372 |
| SEQ ID NO: 574 | Tab1-819 | hsa-miR-21* | CAACACCAGUCGAUGGGCUGU | 0.958924949 |
| SEQ ID NO: 230 | Tab1-820 | hsa-miR-548e | AAAAACUGAGACUACUUUUGCA | 0.958924949 |
| SEQ ID NO: 69 | Tab1-821 | hsa-miR-744* | CUGUUGCCACUAACCUCAACCU | 0.959289953 |
| SEQ ID NO: 214 | Tab1-822 | hsa-miR-551a | GCGACCCACUCUUGGUUUCCA | 0.959289953 |
| SEQ ID NO: 303 | Tab1-823 | hsa-miR-515-3p | GAGUGCCUUCUUUUGGAGCGUU | 0.963053434 |
| SEQ ID NO: 435 | Tab1-824 | hsa-miR-34b* | UAGGCAGUGUCAUUAGCUGAUUG | 0.963053434 |
| SEQ ID NO: 111 | Tab1-825 | hsa-miR-642 | GUCCCUCUCCAAAUGUGUCUUG | 0.96606999 |
| SEQ ID NO: 860 | Tab1-826 | hsa-miR-1185 | AGAGGAUACCCUUUGUAUGUU | 0.96606999 |
| SEQ ID NO: 340 | Tab1-827 | hsa-miR-492 | AGGACCUGCGGGACAAGAUUCUU | 0.96606999 |
| SEQ ID NO: 467 | Tab1-828 | hsa-miR-323-5p | AGGUGGUCCGUGGCGCGUUGC | 0.96606999 |
| SEQ ID NO: 470 | Tab1-829 | hsa-miR-320c | AAAAGCUGGGUUGAGAGGGU | 0.96606999 |
| SEQ ID NO: 222 | Tab1-830 | hsa-miR-548m | CAAAGGUAUUGUGGCUCCUGUGGU | 0.96606999 |
| SEQ ID NO: 878 | Tab1-831 | hsa-miR-105 | UCAAAUGCUCAGACUCCUGUGGU | 0.966704103 |
| SEQ ID NO: 162 | Tab1-832 | hsa-miR-597 | UGUGUCACUCGAUGACCACUGU | 0.966704103 |
| SEQ ID NO: 827 | Tab1-833 | hsa-miR-1244 | AAGUAGUUGGUUUGUAGAGAUGGUU | 0.969921147 |
| SEQ ID NO: 236 | Tab1-834 | hsa-miR-548b-3p | CAAGAACCUCAGUUGCUUUUGU | 0.972999091 |
| SEQ ID NO: 38 | Tab1-835 | hsa-miR-890 | UACUUGGAAAGGCAUCAGUUG | 0.972999091 |
| SEQ ID NO: 698 | Tab1-836 | hsa-miR-148b* | AAGUUCUGUUAUACACUCAGGC | 0.972999091 |
| SEQ ID NO: 738 | Tab1-837 | hsa-miR-133a | UUUGGUCCCCUUCAACCAGCUG | 0.975482077 |
| SEQ ID NO: 88 | Tab1-838 | hsa-miR-663b | GGUGGCCCGGCCGUGCCUGAGG | 0.975482077 |
| SEQ ID NO: 621 | Tab1-839 | hsa-miR-195* | CCAAUAUGGCUGUGCUGCUCC | 0.975482077 |
| SEQ ID NO: 314 | Tab1-840 | hsa-miR-509-3p | UGAUUGGUACGUCUGUGGGUAG | 0.975482077 |
| SEQ ID NO: 54 | Tab1-841 | hsa-miR-873 | GCAGGAACUUGUGAGUCUCCU | 0.975482077 |
| SEQ ID NO: 900 | Tab1-842 | hsa-let-7b* | CUAUACAACCUACUGCCUUCCC | 0.977944702 |
| SEQ ID NO: 210 | Tab1-843 | hsa-miR-553 | AAAAACGGUGAGAUUUGUUU | 0.981049422 |
| SEQ ID NO: 291 | Tab1-844 | hsa-miR-518b | CAAAGCGCUCCCUUUAGAGGU | 0.982703187 |
| SEQ ID NO: 638 | Tab1-845 | hsa-miR-1911 | UGAGUACCGCCAUGUCGUUGGG | 0.982703187 |
| SEQ ID NO: 789 | Tab1-846 | hsa-miR-127-3p | UCGGAUCCGUCUGAGCUUGGCU | 0.982703187 |
| SEQ ID NO: 444 | Tab1-847 | hsa-miR-340 | UUAUAAAGCAAUGAGACUGAUU | 0.984739991 |
| SEQ ID NO: 708 | Tab1-848 | hsa-miR-146a* | CCUCUGAAAUUCAGUUCUUCAG | 0.984772697 |

FIG. 18B (Cont.)

| SEQ ID NO: | | | Sequence | |
|---|---|---|---|---|
| SEQ ID NO: 228 | Tab1-849 | hsa-miR-548g | AAAACUGUAAUUACUUUUGUAC | 0.984772697 |
| SEQ ID NO: 651 | Tab1-850 | hsa-miR-188-5p | CAUCCCUUGCAUGGUGGAGGG | 0.984772697 |
| SEQ ID NO: 208 | Tab1-851 | hsa-miR-555 | AGGGUAAGCUGAACCUCUGAU | 0.984772697 |
| SEQ ID NO: 844 | Tab1-852 | hsa-miR-1225-3p | UGAGCCCUGUGCCGCCCCAG | 0.988620756 |
| SEQ ID NO: 658 | Tab1-853 | hsa-miR-185 | UGGAGAGAAAGGCAGUUCCUGA | 0.988620756 |
| SEQ ID NO: 3 | Tab1-854 | hsa-miR-99a* | CAAGCUCGCUUCUAUGGGUCUG | 0.988620756 |
| SEQ ID NO: 517 | Tab1-855 | hsa-miR-27b | UUCACAGUGGCUAAGUUCUGC | 0.988620756 |
| SEQ ID NO: 333 | Tab1-856 | hsa-miR-497* | CAAACCACACUGUGGUGUUAGA | 0.988620756 |
| SEQ ID NO: 496 | Tab1-857 | hsa-miR-302a* | ACUUAAACGUGGAUGUACUUGCU | 0.988620756 |
| SEQ ID NO: 317 | Tab1-858 | hsa-miR-508-3p | UGAUUGUAGCCUUUUGGAGUAGA | 0.988620756 |
| SEQ ID NO: 211 | Tab1-859 | hsa-miR-552 | AACAGGUGACUGGUUAGACAA | 0.996239894 |
| SEQ ID NO: 831 | Tab1-860 | hsa-miR-1238 | CUUCCUCGUCGUCUGCCCC | 0.99849342 |
| SEQ ID NO: 348 | Tab1-861 | hsa-miR-487b | AAUCGUACAGGGUCAUCCACUU | 0.99849342 |
| SEQ ID NO: 311 | Tab1-862 | hsa-miR-511 | GUGUCUUUUGCUCUGCAGUCA | 0.99849342 |
| SEQ ID NO: 141 | Tab1-863 | hsa-miR-616* | ACUCAAAACCCUUCAGUGACUU | 0.99849342 |
| SEQ ID NO: 406 | Tab1-864 | hsa-miR-376c | AACAUAGAGGAAAUUCCACGU | 0.999732203 |

FIG. 18C

| SEQ ID NO. | miRNA | median g1 | median g2 | median ratio | logmedian | test_rawp | test_adjp | AUC | intra_rawp | intra_adjp |
|---|---|---|---|---|---|---|---|---|---|---|
| SEQ ID NO: 901 | hsa-let-7b | 902 | 2634 | 0,34 | -1,072 | 1,345E-10 | 1,161E-07 | 0,097 | 1,751E-06 | 1,374E-04 |
| SEQ ID NO: 190 | hsa-miR-574-3p | 2061 | 811 | 2,54 | 0,933 | 2,154E-09 | 5,115E-07 | 0,882 | 2,891E-09 | 1,247E-06 |
| SEQ ID NO: 360 | hsa-miR-454 | 114 | 282 | 0,41 | -0,903 | 1,181E-08 | 1,133E-06 | 0,139 | 3,879E-05 | 1,240E-03 |
| SEQ ID NO: 329 | hsa-miR-500 | 213 | 438 | 0,49 | -0,722 | 2,866E-07 | 1,546E-05 | 0,214 | 1,943E-04 | 4,091E-03 |
| SEQ ID NO: 61 | hsa-miR-766 | 491 | 227 | 2,16 | 0,770 | 1,633E-05 | 3,131E-04 | 0,788 | 3,545E-05 | 1,224E-03 |
| SEQ ID NO: 895 | hsa-let-7e | 141 | 372 | 0,38 | -0,971 | 2,766E-05 | 5,078E-04 | 0,216 | 2,865E-04 | 5,420E-03 |
| SEQ ID NO: 834 | hsa-miR-1234 | 699 | 254 | 2,75 | 1,011 | 7,186E-05 | 8,761E-04 | 0,873 | 2,931E-07 | 4,007E-05 |
| SEQ ID NO: 809 | hsa-miR-125a-5p | 151 | 354 | 0,43 | -0,852 | 1,398E-04 | 1,471E-03 | 0,237 | 2,572E-04 | 5,045E-03 |
| SEQ ID NO: 893 | hsa-let-7f | 418 | 873 | 0,48 | -0,736 | 4,540E-04 | 3,349E-03 | 0,257 | 5,594E-04 | 8,323E-03 |
| SEQ ID NO: 23 | hsa-miR-92b* | 132 | 268 | 0,49 | -0,709 | 2,027E-03 | 9,976E-03 | 0,216 | 7,738E-05 | 1,908E-03 |
| SEQ ID NO: 899 | hsa-let-7c | 423 | 1377 | 0,31 | -1,180 | 2,774E-10 | 1,197E-07 | 0,043 | 1,306E-07 | 2,818E-05 |
| SEQ ID NO: 890 | hsa-let-7g | 294 | 970 | 0,30 | -1,194 | 3,138E-09 | 5,115E-07 | 0,162 | 4,302E-05 | 1,316E-03 |
| SEQ ID NO: 713 | hsa-miR-145 | 131 | 423 | 0,31 | -1,175 | 3,557E-09 | 5,115E-07 | 0,115 | 3,250E-07 | 4,007E-05 |
| SEQ ID NO: 888 | hsa-let-7i | 513 | 1689 | 0,30 | -1,192 | 2,317E-08 | 1,818E-06 | 0,133 | 9,333E-06 | 5,072E-04 |
| SEQ ID NO: 746 | hsa-miR-130b | 1463 | 748 | 1,96 | 0,671 | 2,968E-09 | 5,115E-07 | 0,819 | 4,944E-03 | 3,411E-02 |
| SEQ ID NO: 803 | hsa-miR-1260 | 2587 | 1494 | 1,73 | 0,549 | 5,532E-07 | 2,387E-05 | 0,756 | 2,518E-03 | 2,312E-02 |
| SEQ ID NO: 460 | hsa-miR-330-3p | 377 | 234 | 1,61 | 0,477 | 1,056E-06 | 3,647E-05 | 0,786 | 8,055E-04 | 1,103E-02 |
| SEQ ID NO: 478 | hsa-miR-30e | 241 | 482 | 0,50 | -0,691 | 1,290E-06 | 4,122E-05 | 0,162 | 1,826E-05 | 7,168E-04 |
| SEQ ID NO: 897 | hsa-let-7d | 1987 | 3301 | 0,60 | -0,508 | 4,387E-06 | 1,113E-04 | 0,208 | 4,019E-03 | 3,002E-02 |
| SEQ ID NO: 327 | hsa-miR-501-3p | 372 | 263 | 1,42 | 0,349 | 6,010E-06 | 1,441E-04 | 0,760 | 3,025E-02 | 1,097E-01 |
| SEQ ID NO: 635 | hsa-miR-1913 | 359 | 210 | 1,71 | 0,535 | 8,523E-06 | 1,936E-04 | 0,678 | 5,251E-02 | 1,584E-01 |
| SEQ ID NO: 605 | hsa-miR-199a-5p | 236 | 464 | 0,51 | -0,677 | 1,032E-05 | 2,121E-04 | 0,182 | 1,827E-05 | 7,168E-04 |
| SEQ ID NO: 549 | hsa-miR-22 | 7722 | 5135 | 1,50 | 0,408 | 3,175E-05 | 5,434E-04 | 0,767 | 1,017E-04 | 2,310E-03 |
| SEQ ID NO: 540 | hsa-miR-223 | 2257 | 4200 | 0,54 | -0,621 | 3,135E-05 | 5,434E-04 | 0,163 | 1,117E-05 | 5,072E-04 |
| SEQ ID NO: 622 | hsa-miR-195 | 620 | 477 | 1,30 | 0,262 | 3,211E-05 | 5,434E-04 | 0,720 | 8,910E-02 | 2,231E-01 |
| SEQ ID NO: 249 | hsa-miR-532-3p | 4406 | 2881 | 1,53 | 0,425 | 6,494E-05 | 8,365E-04 | 0,735 | 1,690E-03 | 1,779E-02 |
| SEQ ID NO: 666 | hsa-miR-182 | 4200 | 2208 | 1,90 | 0,643 | 8,322E-05 | 9,839E-04 | 0,769 | 8,014E-03 | 4,770E-02 |
| SEQ ID NO: 630 | hsa-miR-192 | 5652 | 3793 | 1,49 | 0,399 | 2,142E-04 | 1,969E-03 | 0,770 | 1,188E-01 | 2,728E-01 |
| SEQ ID NO: 483 | hsa-miR-30c | 2233 | 1621 | 1,38 | 0,320 | 2,113E-04 | 1,969E-03 | 0,675 | 4,195E-02 | 1,346E-01 |
| SEQ ID NO: 428 | hsa-miR-363 | 3453 | 2208 | 1,56 | 0,447 | 2,674E-04 | 2,267E-03 | 0,697 | 4,408E-01 | 6,257E-01 |
| SEQ ID NO: 872 | hsa-miR-107 | 1305 | 783 | 1,67 | 0,512 | 2,679E-04 | 2,267E-03 | 0,694 | 1,390E-01 | 2,955E-01 |
| SEQ ID NO: 351 | hsa-miR-486-3p | 223 | 158 | 1,41 | 0,343 | 2,806E-04 | 2,351E-03 | 0,660 | 1,249E-01 | 2,794E-01 |
| SEQ ID NO: 334 | hsa-miR-497 | 167 | 138 | 1,20 | 0,186 | 3,052E-04 | 2,508E-03 | 0,665 | 5,713E-02 | 1,650E-01 |
| SEQ ID NO: 449 | hsa-miR-339-5p | 693 | 533 | 1,30 | 0,262 | 3,281E-04 | 2,610E-03 | 0,665 | 2,402E-01 | 4,160E-01 |
| SEQ ID NO: 165 | hsa-miR-593* | 288 | 224 | 1,29 | 0,253 | 3,326E-04 | 2,610E-03 | 0,668 | 1,024E-01 | 2,442E-01 |

FIG. 18C (Cont.)

| | | | | | | | | | |
|---|---|---|---|---|---|---|---|---|---|
| SEQ ID NO: 624 | hsa-miR-194 | 6578 | 5135 | 1.28 | 0.248 | 3.723E-04 | 2.840E-03 | 0.737 | 3.328E-01 | 5.147E-01 |
| SEQ ID NO: 128 | hsa-miR-627 | 155 | 243 | 0.64 | -0.450 | 4.709E-04 | 3.444E-03 | 0.166 | 5.482E-04 | 8.301E-03 |
| SEQ ID NO: 22 | hsa-miR-93 | 3453 | 5652 | 0.61 | -0.493 | 5.069E-04 | 3.646E-03 | 0.239 | 2.265E-03 | 2.148E-02 |
| SEQ ID NO: 616 | hsa-miR-197 | 662 | 559 | 1.18 | 0.168 | 5.395E-04 | 3.755E-03 | 0.589 | 1.839E-01 | 3.574E-01 |
| SEQ ID NO: 883 | hsa-miR-101 | 576 | 723 | 0.80 | -0.226 | 5.588E-04 | 3.827E-03 | 0.295 | 1.355E-02 | 6.465E-02 |
| SEQ ID NO: 27 | hsa-miR-92a | 11992 | 17656 | 0.68 | -0.387 | 5.787E-04 | 3.932E-03 | 0.222 | 4.633E-03 | 3.360E-02 |
| SEQ ID NO: 386 | hsa-miR-422a | 139 | 241 | 0.58 | -0.548 | 5.882E-04 | 3.935E-03 | 0.260 | 1.302E-03 | 1.540E-02 |
| SEQ ID NO: 704 | hsa-miR-1470 | 164 | 143 | 1.15 | 0.136 | 6.257E-04 | 4.122E-03 | 0.612 | 2.368E-01 | 4.143E-01 |
| SEQ ID NO: 756 | hsa-miR-1301 | 202 | 149 | 1.35 | 0.302 | 7.201E-04 | 4.536E-03 | 0.712 | 5.832E-01 | 7.401E-01 |
| SEQ ID NO: 215 | hsa-miR-550* | 697 | 477 | 1.46 | 0.380 | 7.265E-04 | 4.543E-03 | 0.600 | 4.806E-01 | 6.594E-01 |
| SEQ ID NO: 429 | hsa-miR-362-5p | 126 | 220 | 0.57 | -0.556 | 8.225E-04 | 5.034E-03 | 0.270 | 1.405E-03 | 1.555E-02 |
| SEQ ID NO: 561 | hsa-miR-214 | 296 | 218 | 1.35 | 0.303 | 8.750E-04 | 5.280E-03 | 0.660 | 1.287E-01 | 2.836E-01 |
| SEQ ID NO: 629 | hsa-miR-192* | 113 | 102 | 1.11 | 0.109 | 9.224E-04 | 5.528E-03 | 0.680 | 2.289E-02 | 8.806E-02 |
| SEQ ID NO: 475 | hsa-miR-31* | 171 | 139 | 1.23 | 0.206 | 9.631E-04 | 5.693E-03 | 0.661 | 2.125E-01 | 3.902E-01 |
| SEQ ID NO: 706 | hsa-miR-146b-5p | 101 | 157 | 0.64 | -0.439 | 1.130E-03 | 6.466E-03 | 0.270 | 5.794E-03 | 3.720E-02 |
| SEQ ID NO: 529 | hsa-miR-24 | 1762 | 1184 | 1.49 | 0.397 | 1.160E-03 | 6.581E-03 | 0.655 | 7.168E-01 | 8.355E-01 |
| SEQ ID NO: 889 | hsa-let-7g* | 109 | 140 | 0.78 | -0.252 | 1.254E-03 | 6.821E-03 | 0.293 | 2.427E-02 | 9.147E-02 |
| SEQ ID NO: 29 | hsa-miR-922 | 126 | 101 | 1.25 | 0.221 | 1.397E-03 | 7.535E-03 | 0.616 | 3.766E-01 | 5.662E-01 |
| SEQ ID NO: 709 | hsa-miR-146a | 193 | 321 | 0.60 | -0.510 | 1.511E-03 | 7.950E-03 | 0.245 | 1.364E-03 | 1.549E-02 |
| SEQ ID NO: 101 | hsa-miR-652 | 1113 | 1621 | 0.69 | -0.376 | 1.742E-03 | 9.041E-03 | 0.302 | 1.508E-02 | 6.922E-02 |
| SEQ ID NO: 442 | hsa-miR-342-3p | 4525 | 2881 | 1.57 | 0.452 | 1.841E-03 | 9.345E-03 | 0.718 | 8.636E-04 | 1.147E-02 |
| SEQ ID NO: 748 | hsa-miR-130a | 1369 | 1621 | 0.84 | -0.169 | 1.951E-03 | 9.731E-03 | 0.287 | 7.842E-03 | 4.709E-02 |
| SEQ ID NO: 663 | hsa-miR-1826 | 195 | 156 | 1.25 | 0.223 | 2.378E-03 | 1.151E-02 | 0.644 | 6.756E-01 | 8.054E-01 |
| SEQ ID NO: 645 | hsa-miR-1908 | 1071 | 1762 | 0.61 | -0.498 | 2.464E-03 | 1.175E-02 | 0.261 | 5.888E-04 | 8.469E-03 |
| SEQ ID NO: 519 | hsa-miR-27a | 259 | 413 | 0.63 | -0.468 | 2.866E-03 | 1.316E-02 | 0.261 | 1.335E-03 | 1.549E-02 |
| SEQ ID NO: 521 | hsa-miR-1184 | 316 | 543 | 0.58 | -0.542 | 2.883E-03 | 1.316E-02 | 0.277 | 3.925E-03 | 3.002E-02 |
| SEQ ID NO: 861 | hsa-miR-296-5p | 176 | 164 | 1.08 | 0.075 | 3.384E-03 | 1.505E-02 | 0.549 | 4.878E-01 | 6.522E-01 |
| SEQ ID NO: 512 | hsa-miR-378 | 237 | 226 | 1.05 | 0.046 | 3.520E-03 | 1.534E-02 | 0.556 | 2.904E-01 | 4.667E-01 |
| SEQ ID NO: 403 | hsa-miR-675 | 259 | 366 | 0.71 | -0.347 | 3.617E-03 | 1.568E-02 | 0.315 | 1.719E-02 | 7.471E-02 |
| SEQ ID NO: 80 | hsa-miR-103 | 138 | 239 | 0.58 | -0.546 | 4.333E-03 | 1.824E-02 | 0.248 | 3.176E-03 | 2.661E-02 |
| SEQ ID NO: 881 | hsa-miR-452* | 6845 | 4200 | 1.63 | 0.488 | 4.883E-03 | 2.007E-02 | 0.673 | 1.477E-01 | 3.095E-01 |
| SEQ ID NO: 362 | hsa-miR-1203 | 291 | 269 | 1.08 | 0.077 | 4.919E-03 | 2.012E-02 | 0.552 | 6.562E-01 | 7.920E-01 |
| SEQ ID NO: 855 | hsa-miR-874 | 198 | 167 | 1.19 | 0.171 | 4.949E-03 | 2.015E-02 | 0.606 | 5.153E-01 | 6.927E-01 |
| SEQ ID NO: 53 | hsa-miR-588 | 155 | 188 | 0.83 | -0.191 | 5.037E-03 | 2.041E-02 | 0.287 | 6.531E-01 | 4.026E-02 |
| SEQ ID NO: 173 | hsa-miR-106a | 5928 | 8665 | 0.68 | -0.380 | 5.682E-03 | 2.202E-02 | 0.636 | 5.066E-01 | 6.852E-01 |
| SEQ ID NO: 876 | hsa-miR-1202 | 208 | 194 | 1.07 | 0.072 | 5.858E-03 | 2.224E-02 | 0.330 | 1.779E-02 | 7.600E-02 |
| SEQ ID NO: 856 | | | | | | 6.019E-03 | 2.234E-02 | 0.582 | 6.022E-01 | 7.529E-01 |

FIG. 18C (Cont.)

| | | | | | | | | | |
|---|---|---|---|---|---|---|---|---|---|
| SEQ ID NO: 446 | hsa-miR-33b | 172 | 139 | 1.24 | 0.217 | 5.989E-03 | 2.234E-02 | 0.608 | 7.537E-01 | 8.558E-01 |
| SEQ ID NO: 904 | hsa-let-7a | 1025 | 1762 | 0.58 | -0.542 | 6.576E-03 | 2.384E-02 | 0.243 | 2.441E-03 | 2.265E-02 |
| SEQ ID NO: 839 | hsa-miR-1228 | 236 | 164 | 1.43 | 0.361 | 6.514E-03 | 2.384E-02 | 0.678 | 1.862E-01 | 3.612E-01 |
| SEQ ID NO: 136 | hsa-miR-621 | 332 | 251 | 1.32 | 0.278 | 6.624E-03 | 2.392E-02 | 0.639 | 3.959E-01 | 5.870E-01 |
| SEQ ID NO: 358 | hsa-miR-455-3p | 169 | 130 | 1.29 | 0.258 | 7.163E-03 | 2.544E-02 | 0.666 | 4.842E-01 | 6.632E-01 |
| SEQ ID NO: 2 | hsa-miR-99b | 167 | 133 | 1.25 | 0.225 | 7.238E-03 | 2.560E-02 | 0.598 | 4.896E-01 | 6.696E-01 |
| SEQ ID NO: 470 | hsa-miR-320c | 783 | 675 | 1.16 | 0.148 | 7.758E-03 | 2.700E-02 | 0.593 | 2.990E-01 | 4.743E-01 |
| SEQ ID NO: 820 | hsa-miR-1251 | 128 | 109 | 1.17 | 0.157 | 7.813E-03 | 2.708E-02 | 0.648 | 2.473E-01 | 4.208E-01 |
| SEQ ID NO: 628 | hsa-miR-193a-3p | 123 | 173 | 0.71 | -0.339 | 7.950E-03 | 2.735E-02 | 0.292 | 1.922E-02 | 7.976E-02 |
| SEQ ID NO: 364 | hsa-miR-451 | 1604 | 2881 | 0.56 | -0.585 | 8.476E-03 | 2.871E-02 | 0.288 | 1.197E-03 | 1.454E-02 |
| SEQ ID NO: 578 | hsa-miR-20a* | 139 | 118 | 1.19 | 0.170 | 8.548E-03 | 2.876E-02 | 0.612 | 7.580E-01 | 8.562E-01 |
| SEQ ID NO: 469 | hsa-miR-320d | 908 | 697 | 1.30 | 0.263 | 8.735E-03 | 2.922E-02 | 0.593 | 2.809E-01 | 4.591E-01 |
| SEQ ID NO: 345 | hsa-miR-489 | 155 | 145 | 1.07 | 0.066 | 8.938E-03 | 2.955E-02 | 0.612 | 2.187E-01 | 3.991E-01 |
| SEQ ID NO: 313 | hsa-miR-509-5p | 213 | 210 | 1.01 | 0.013 | 9.055E-03 | 2.980E-02 | 0.526 | 8.125E-01 | 8.955E-01 |
| SEQ ID NO: 619 | hsa-miR-196a* | 139 | 122 | 1.14 | 0.128 | 9.082E-03 | 2.980E-02 | 0.570 | 4.546E-01 | 6.411E-01 |
| SEQ ID NO: 412 | hsa-miR-374b | 493 | 352 | 1.40 | 0.338 | 9.159E-03 | 2.994E-02 | 0.594 | 8.125E-01 | 8.955E-01 |
| SEQ ID NO: 199 | hsa-miR-564 | 157 | 129 | 1.21 | 0.195 | 9.547E-03 | 3.074E-02 | 0.619 | 6.265E-01 | 7.746E-01 |
| SEQ ID NO: 681 | hsa-miR-15a* | 112 | 135 | 0.83 | -0.182 | 1.051E-02 | 3.322E-02 | 0.290 | 3.593E-02 | 1.207E-01 |
| SEQ ID NO: 107 | hsa-miR-646 | 206 | 203 | 1.02 | 0.018 | 1.073E-02 | 3.380E-02 | 0.535 | 8.306E-01 | 9.085E-01 |
| SEQ ID NO: 46 | hsa-miR-885-3p | 177 | 268 | 0.66 | -0.412 | 1.139E-02 | 3.561E-02 | 0.292 | 3.297E-03 | 2.736E-02 |
| SEQ ID NO: 328 | hsa-miR-500* | 250 | 222 | 1.13 | 0.119 | 1.143E-02 | 3.561E-02 | 0.612 | 4.720E-01 | 6.539E-01 |
| SEQ ID NO: 774 | hsa-miR-1285 | 264 | 189 | 1.39 | 0.331 | 1.138E-02 | 3.561E-02 | 0.689 | 7.878E-02 | 2.042E-01 |
| SEQ ID NO: 315 | hsa-miR-509-3-5p | 212 | 194 | 1.09 | 0.089 | 1.182E-02 | 3.668E-02 | 0.540 | 7.614E-01 | 8.587E-01 |
| SEQ ID NO: 636 | hsa-miR-1912 | 152 | 138 | 1.11 | 0.100 | 1.198E-02 | 3.705E-02 | 0.606 | 5.817E-01 | 7.401E-01 |
| SEQ ID NO: 240 | hsa-miR-545 | 116 | 102 | 1.14 | 0.130 | 1.210E-02 | 3.728E-02 | 0.621 | 7.126E-01 | 8.343E-01 |
| SEQ ID NO: 466 | hsa-miR-324-3p | 825 | 655 | 1.26 | 0.231 | 1.268E-02 | 3.892E-02 | 0.576 | 4.340E-01 | 6.201E-01 |
| SEQ ID NO: 188 | hsa-miR-575 | 127 | 112 | 1.13 | 0.122 | 1.381E-02 | 4.181E-02 | 0.601 | 5.249E-01 | 6.958E-01 |
| SEQ ID NO: 577 | hsa-miR-20b | 2820 | 2112 | 1.34 | 0.289 | 1.433E-02 | 4.254E-02 | 0.623 | 8.502E-01 | 9.171E-01 |
| SEQ ID NO: 780 | hsa-miR-128 | 623 | 553 | 1.13 | 0.118 | 1.551E-02 | 4.518E-02 | 0.627 | 4.654E-01 | 6.499E-01 |
| SEQ ID NO: 650 | hsa-miR-18a | 1205 | 1762 | 0.68 | -0.380 | 1.620E-02 | 4.677E-02 | 0.294 | 3.983E-03 | 3.002E-02 |
| SEQ ID NO: 189 | hsa-miR-574-5p | 840 | 587 | 1.43 | 0.358 | 1.675E-02 | 4.754E-02 | 0.660 | 1.973E-01 | 3.751E-01 |
| SEQ ID NO: 837 | hsa-miR-1229 | 185 | 164 | 1.13 | 0.124 | 1.722E-02 | 4.856E-02 | 0.612 | 8.303E-01 | 9.085E-01 |
| SEQ ID NO: 717 | hsa-miR-143 | 168 | 232 | 0.73 | -0.321 | 1.779E-02 | 4.984E-02 | 0.325 | 3.118E-02 | 1.103E-01 |
| SEQ ID NO: 882 | hsa-miR-101* | 69 | 140 | 0.50 | -0.703 | 2.462E-07 | 1.416E-05 | 0.161 | 5.439E-04 | 8.301E-03 |
| SEQ ID NO: 544 | hsa-miR-221 | 81 | 164 | 0.49 | -0.704 | 7.761E-06 | 1.810E-04 | 0.159 | 2.889E-04 | 5.420E-03 |
| SEQ ID NO: 426 | hsa-miR-365 | 64 | 132 | 0.48 | -0.728 | 3.896E-05 | 5.899E-04 | 0.191 | 1.140E-02 | 5.789E-02 |
| SEQ ID NO: 548 | hsa-miR-22* | 47 | 101 | 0.46 | -0.776 | 6.863E-05 | 8.710E-04 | 0.223 | 5.851E-04 | 8.469E-03 |

FIG. 18C (Cont.)

| | | | | | | | | | |
|---|---|---|---|---|---|---|---|---|---|
| SEQ ID NO: 786 | hsa-miR-1275 | 60 | 125 | 0.48 | -0.731 | 3.751E-04 | 2.840E-03 | 0.194 | 3.183E-04 | 5.723E-03 |
| SEQ ID NO: 131 | hsa-miR-625 | 59 | 178 | 0.33 | -1.110 | 5.165E-04 | 3.684E-03 | 0.244 | 2.748E-03 | 2.464E-02 |
| SEQ ID NO: 177 | hsa-miR-584 | 84 | 211 | 0.40 | -0.918 | 7.733E-04 | 4.801E-03 | 0.252 | 1.134E-03 | 1.398E-02 |
| SEQ ID NO: 164 | hsa-miR-595 | 103 | 41 | 2.51 | 0.922 | 2.387E-03 | 1.151E-02 | 0.689 | 3.924E-02 | 1.278E-01 |
| SEQ ID NO: 627 | hsa-miR-193a-5p | 55 | 124 | 0.44 | -0.813 | 5.246E-03 | 2.079E-02 | 0.250 | 4.333E-03 | 3.169E-02 |
| SEQ ID NO: 462 | hsa-miR-328 | 57 | 124 | 0.46 | -0.773 | 1.439E-02 | 4.254E-02 | 0.293 | 1.720E-02 | 7.471E-02 |
| SEQ ID NO: 125 | hsa-miR-629 | 58 | 210 | 0.27 | -1.292 | 4.148E-07 | 1.941E-05 | 0.156 | 5.162E-05 | 1.392E-03 |
| SEQ ID NO: 656 | hsa-miR-186 | 34 | 162 | 0.21 | -1.571 | 7.793E-07 | 3.193E-05 | 0.138 | 9.540E-06 | 5.072E-04 |
| SEQ ID NO: 719 | hsa-miR-142-3p | 18 | 127 | 0.14 | -1.941 | 9.396E-06 | 1.978E-04 | 0.131 | 1.146E-07 | 2.818E-05 |
| SEQ ID NO: 78 | hsa-miR-7 | 31 | 127 | 0.25 | -1.406 | 6.070E-05 | 8.060E-04 | 0.171 | 2.564E-05 | 9.620E-04 |
| SEQ ID NO: 37 | hsa-miR-891a | 114 | 71 | 1.60 | 0.471 | 4.274E-07 | 1.941E-05 | 0.791 | 5.642E-05 | 1.475E-03 |
| SEQ ID NO: 762 | hsa-miR-1295 | 113 | 73 | 1.54 | 0.429 | 1.294E-05 | 2.589E-04 | 0.719 | 1.888E-02 | 7.909E-02 |
| SEQ ID NO: 791 | hsa-miR-1272 | 129 | 92 | 1.41 | 0.340 | 5.781E-05 | 7.795E-04 | 0.723 | 1.723E-02 | 7.471E-02 |
| SEQ ID NO: 387 | hsa-miR-421 | 87 | 168 | 0.52 | -0.658 | 9.543E-05 | 1.084E-03 | 0.169 | 5.136E-04 | 8.059E-03 |
| SEQ ID NO: 291 | hsa-miR-518b | 96 | 113 | 0.85 | -0.162 | 1.687E-04 | 1.693E-03 | 0.307 | 1.528E-02 | 6.978E-02 |
| SEQ ID NO: 543 | hsa-miR-221* | 104 | 56 | 1.84 | 0.610 | 1.740E-04 | 1.726E-03 | 0.748 | 1.071E-03 | 1.360E-02 |
| SEQ ID NO: 708 | hsa-miR-146a* | 68 | 109 | 0.62 | -0.471 | 5.993E-04 | 3.979E-03 | 0.248 | 4.070E-03 | 3.002E-02 |
| SEQ ID NO: 441 | hsa-miR-342-5p | 85 | 156 | 0.54 | -0.615 | 1.037E-03 | 6.048E-03 | 0.270 | 4.033E-03 | 3.002E-02 |
| SEQ ID NO: 15 | hsa-miR-938 | 86 | 121 | 0.71 | -0.346 | 1.193E-03 | 6.610E-03 | 0.257 | 8.487E-03 | 4.819E-02 |
| SEQ ID NO: 394 | hsa-miR-384 | 59 | 101 | 0.58 | -0.539 | 2.789E-03 | 1.294E-02 | 0.271 | 3.580E-03 | 2.861E-02 |
| SEQ ID NO: 335 | hsa-miR-496 | 69 | 101 | 0.68 | -0.385 | 3.330E-03 | 1.489E-02 | 0.285 | 2.244E-02 | 8.775E-02 |
| SEQ ID NO: 93 | hsa-miR-659 | 65 | 118 | 0.56 | -0.686 | 4.070E-04 | 1.739E-02 | 0.264 | 1.746E-02 | 7.500E-02 |
| SEQ ID NO: 660 | hsa-miR-183* | 85 | 142 | 0.60 | -0.516 | 4.309E-03 | 1.823E-02 | 0.289 | 3.674E-02 | 1.229E-01 |
| SEQ ID NO: 206 | hsa-miR-556-5p | 117 | 86 | 1.37 | 0.313 | 5.143E-03 | 2.055E-02 | 0.628 | 1.128E-01 | 2.624E-01 |
| SEQ ID NO: 341 | hsa-miR-491-5p | 92 | 143 | 0.64 | -0.444 | 5.715E-03 | 2.202E-02 | 0.268 | 8.714E-03 | 4.883E-02 |
| SEQ ID NO: 750 | hsa-miR-1307 | 57 | 106 | 0.54 | -0.618 | 6.543E-03 | 2.384E-02 | 0.300 | 5.737E-02 | 1.650E-01 |
| SEQ ID NO: 246 | hsa-miR-541 | 106 | 85 | 1.25 | 0.221 | 8.288E-03 | 2.827E-02 | 0.621 | 9.286E-01 | 9.656E-01 |
| SEQ ID NO: 171 | hsa-miR-589* | 83 | 102 | 0.82 | -0.197 | 8.769E-03 | 2.922E-02 | 0.330 | 3.183E-02 | 1.112E-01 |
| SEQ ID NO: 604 | hsa-miR-199b-3p | 93 | 118 | 0.79 | -0.236 | 1.467E-02 | 4.322E-02 | 0.338 | 2.247E-02 | 8.775E-02 |
| SEQ ID NO: 463 | hsa-miR-326 | 86 | 107 | 0.80 | -0.224 | 1.555E-02 | 4.518E-02 | 0.332 | 3.491E-02 | 1.181E-01 |
| SEQ ID NO: 424 | hsa-miR-367 | 85 | 37 | 2.32 | 0.842 | 1.556E-08 | 1.343E-06 | 0.856 | 2.093E-07 | 3.612E-05 |
| SEQ ID NO: 852 | hsa-miR-1206 | 59 | 23 | 2.59 | 0.952 | 1.764E-07 | 1.087E-05 | 0.806 | 2.826E-05 | 1.016E-03 |
| SEQ ID NO: 149 | hsa-miR-610 | 50 | 21 | 2.34 | 0.849 | 2.381E-06 | 6.629E-05 | 0.740 | 9.909E-04 | 1.296E-02 |
| SEQ ID NO: 274 | hsa-miR-519e* | 60 | 23 | 2.64 | 0.970 | 2.836E-06 | 7.648E-05 | 0.784 | 1.036E-05 | 5.072E-04 |
| SEQ ID NO: 40 | hsa-miR-888* | 47 | 18 | 2.67 | 0.984 | 9.351E-06 | 1.978E-04 | 0.728 | 5.913E-03 | 3.725E-02 |
| SEQ ID NO: 52 | hsa-miR-875-3p | 52 | 25 | 2.07 | 0.729 | 7.615E-05 | 9.127E-04 | 0.728 | 2.263E-02 | 8.796E-02 |
| SEQ ID NO: 352 | hsa-miR-485-5p | 47 | 21 | 2.29 | 0.828 | 1.288E-04 | 1.372E-03 | 0.715 | 9.724E-03 | 5.278E-02 |

FIG. 18C (Cont.)

| | | | | | | | | | |
|---|---|---|---|---|---|---|---|---|---|
| SEQ ID NO: 700 | hsa-miR-148a* | 25 | 56 | 0,44 | -0,824 | 2,073E-04 | 1,969E-03 | 0,237 | 4,775E-04 | 7,838E-03 |
| SEQ ID NO: 503 | hsa-miR-29b-2* | 36 | 79 | 0,45 | -0,788 | 2,642E-04 | 2,267E-03 | 0,228 | 3,743E-04 | 6,593E-03 |
| SEQ ID NO: 129 | hsa-miR-626 | 33 | 14 | 2,39 | 0,873 | 2,919E-04 | 2,422E-03 | 0,682 | 3,732E-02 | 1,243E-01 |
| SEQ ID NO: 210 | hsa-miR-553 | 3 | 1 | 2,86 | 1,049 | 3,316E-04 | 2,610E-03 | 0,615 | 1,160E-01 | 2,676E-01 |
| SEQ ID NO: 60 | hsa-miR-767-3p | 44 | 21 | 2,06 | 0,721 | 6,828E-04 | 4,398E-03 | 0,715 | 1,533E-03 | 1,669E-02 |
| SEQ ID NO: 49 | hsa-miR-876-5p | 36 | 14 | 2,61 | 0,959 | 9,829E-04 | 5,770E-03 | 0,670 | 2,781E-02 | 1,017E-01 |
| SEQ ID NO: 105 | hsa-miR-648 | 47 | 19 | 2,45 | 0,896 | 1,257E-03 | 6,821E-03 | 0,713 | 1,946E-03 | 1,953E-02 |
| SEQ ID NO: 759 | hsa-miR-1297 | 44 | 21 | 2,07 | 0,729 | 1,552E-03 | 8,120E-03 | 0,692 | 7,558E-02 | 1,989E-01 |
| SEQ ID NO: 726 | hsa-miR-138-2* | 54 | 27 | 2,03 | 0,706 | 2,673E-03 | 1,254E-02 | 0,684 | 1,570E-02 | 7,058E-02 |
| SEQ ID NO: 822 | hsa-miR-1249 | 68 | 27 | 2,47 | 0,905 | 2,810E-03 | 1,297E-02 | 0,693 | 1,368E-02 | 6,465E-02 |
| SEQ ID NO: 538 | hsa-miR-224 | 47 | 21 | 2,23 | 0,801 | 3,027E-03 | 1,361E-02 | 0,678 | 5,690E-02 | 1,650E-01 |
| SEQ ID NO: 500 | hsa-miR-300 | 48 | 19 | 2,57 | 0,942 | 4,872E-03 | 2,007E-02 | 0,668 | 7,587E-02 | 1,990E-01 |
| SEQ ID NO: 146 | hsa-miR-613 | 2 | 7 | 0,33 | -1,107 | 7,271E-03 | 2,561E-02 | 0,541 | 5,782E-01 | 7,401E-01 |
| SEQ ID NO: 754 | hsa-miR-1303 | 29 | 63 | 0,47 | -0,757 | 8,564E-03 | 2,876E-02 | 0,279 | 1,719E-02 | 7,471E-02 |
| SEQ ID NO: 793 | hsa-miR-1270 | 20 | 8 | 2,64 | 0,970 | 1,508E-02 | 4,426E-02 | 0,605 | 2,480E-01 | 4,208E-01 |
| SEQ ID NO: 229 | hsa-miR-548f | 48 | 20 | 2,46 | 0,899 | 1,636E-02 | 4,707E-02 | 0,706 | 9,627E-03 | 5,258E-02 |
| SEQ ID NO: 848 | hsa-miR-122 | 20 | 8 | 2,41 | 0,881 | 1,710E-02 | 4,838E-02 | 0,624 | 8,385E-01 | 2,131E-01 |
| SEQ ID NO: 310 | hsa-miR-512-3p | 36 | 1 | 36,06 | 3,585 | 5,059E-09 | 6,236E-07 | 0,809 | 9,063E-07 | 8,690E-05 |
| SEQ ID NO: 137 | hsa-miR-620 | 13 | 1 | 13,28 | 2,586 | 7,565E-09 | 8,161E-07 | 0,768 | 1,233E-05 | 5,319E-04 |
| SEQ ID NO: 814 | hsa-miR-1256 | 67 | 11 | 5,93 | 1,779 | 9,667E-08 | 6,952E-06 | 0,821 | 7,897E-07 | 8,519E-05 |
| SEQ ID NO: 751 | hsa-miR-1306 | 24 | 1 | 23,64 | 3,163 | 3,794E-07 | 1,926E-05 | 0,773 | 1,058E-05 | 5,072E-04 |
| SEQ ID NO: 892 | hsa-let-7f-1* | 34 | 1 | 33,91 | 3,524 | 8,509E-07 | 3,193E-05 | 0,793 | 4,996E-06 | 3,593E-04 |
| SEQ ID NO: 306 | hsa-miR-513b | 46 | 7 | 6,86 | 1,926 | 9,913E-07 | 3,565E-05 | 0,807 | 5,542E-06 | 3,679E-04 |
| SEQ ID NO: 591 | hsa-miR-202 | 21 | 1 | 21,29 | 3,058 | 1,257E-06 | 4,122E-05 | 0,753 | 4,719E-05 | 1,357E-03 |
| SEQ ID NO: 509 | hsa-miR-299-3p | 14 | 1 | 13,83 | 2,627 | 1,358E-06 | 4,186E-05 | 0,732 | 6,539E-05 | 1,660E-03 |
| SEQ ID NO: 562 | hsa-miR-212 | 55 | 11 | 5,06 | 1,621 | 1,851E-06 | 5,326E-05 | 0,868 | 1,766E-11 | 1,524E-08 |
| SEQ ID NO: 807 | hsa-miR-125b-1* | 10 | 1 | 9,79 | 2,281 | 3,822E-06 | 9,995E-05 | 0,717 | 3,896E-04 | 6,725E-03 |
| SEQ ID NO: 166 | hsa-miR-593 | 14 | 1 | 13,77 | 2,622 | 5,028E-06 | 1,240E-04 | 0,758 | 6,225E-06 | 3,837E-04 |
| SEQ ID NO: 401 | hsa-miR-379 | 8 | 1 | 8,39 | 2,127 | 1,990E-05 | 3,733E-04 | 0,629 | 4,845E-02 | 1,504E-01 |
| SEQ ID NO: 26 | hsa-miR-92a-1* | 15 | 4 | 3,25 | 1,179 | 3,090E-05 | 5,434E-04 | 0,675 | 1,284E-02 | 6,223E-02 |
| SEQ ID NO: 667 | hsa-miR-181d | 30 | 1 | 30,09 | 3,404 | 3,355E-05 | 5,568E-04 | 0,729 | 7,026E-04 | 9,940E-03 |
| SEQ ID NO: 185 | hsa-miR-577 | 20 | 1 | 19,57 | 2,974 | 3,790E-05 | 5,859E-04 | 0,708 | 4,026E-03 | 3,002E-02 |
| SEQ ID NO: 28 | hsa-miR-924 | 18 | 1 | 17,53 | 2,864 | 3,802E-05 | 5,859E-04 | 0,761 | 4,423E-05 | 1,316E-03 |
| SEQ ID NO: 422 | hsa-miR-369-3p | 16 | 1 | 16,17 | 2,783 | 3,684E-05 | 5,859E-04 | 0,736 | 4,814E-04 | 7,838E-03 |
| SEQ ID NO: 763 | hsa-miR-1294 | 9 | 1 | 9,16 | 2,215 | 4,640E-05 | 6,836E-04 | 0,669 | 9,143E-03 | 5,091E-02 |
| SEQ ID NO: 299 | hsa-miR-516b | 35 | 10 | 3,64 | 1,291 | 7,208E-05 | 8,761E-04 | 0,715 | 1,491E-02 | 6,881E-02 |
| SEQ ID NO: 891 | hsa-let-7f-2* | 4 | 1 | 4,42 | 1,486 | 9,227E-05 | 1,062E-03 | 0,689 | 2,835E-03 | 2,471E-02 |

FIG. 18C (Cont.)

| | | | | | | | | |
|---|---|---|---|---|---|---|---|---|
| SEQ ID NO: 251 | hsa-miR-526b* | 13 | 1 | 13,27 | 2,585 | 9,732E-05 | 1,091E-03 | 0,694 | 5,271E-03 | 3,526E-02 |
| SEQ ID NO: 415 | hsa-miR-373* | 29 | 5 | 5,57 | 1,718 | 1,679E-04 | 1,693E-03 | 0,738 | 1,092E-03 | 1,366E-02 |
| SEQ ID NO: 176 | hsa-miR-585 | 13 | 1 | 12,98 | 2,563 | 1,951E-04 | 1,913E-03 | 0,716 | 1,350E-03 | 1,549E-02 |
| SEQ ID NO: 831 | hsa-miR-1238 | 30 | 1 | 29,83 | 3,396 | 2,092E-04 | 1,969E-03 | 0,686 | 1,549E-02 | 7,000E-02 |
| SEQ ID NO: 467 | hsa-miR-323-5p | 48 | 8 | 5,64 | 1,730 | 2,581E-04 | 2,267E-03 | 0,706 | 1,747E-02 | 7,500E-02 |
| SEQ ID NO: 8 | hsa-miR-95 | 16 | 1 | 16,19 | 2,784 | 2,663E-04 | 2,267E-03 | 0,685 | 1,051E-02 | 5,495E-02 |
| SEQ ID NO: 109 | hsa-miR-644 | 25 | 1 | 24,92 | 3,215 | 3,093E-04 | 2,518E-03 | 0,679 | 1,435E-02 | 6,696E-02 |
| SEQ ID NO: 361 | hsa-miR-453 | 21 | 1 | 20,52 | 3,021 | 3,207E-04 | 2,587E-03 | 0,680 | 1,264E-02 | 6,187E-02 |
| SEQ ID NO: 330 | hsa-miR-499-5p | 21 | 2 | 9,52 | 2,253 | 3,501E-04 | 2,722E-03 | 0,693 | 5,798E-03 | 3,720E-02 |
| SEQ ID NO: 866 | hsa-miR-1179 | 27 | 1 | 27,05 | 3,298 | 4,994E-04 | 3,622E-03 | 0,701 | 2,769E-03 | 2,464E-02 |
| SEQ ID NO: 396 | hsa-miR-382 | 15 | 1 | 15,02 | 2,710 | 5,232E-04 | 3,701E-03 | 0,647 | 3,830E-03 | 1,257E-01 |
| SEQ ID NO: 307 | hsa-miR-513a-5p | 48 | 14 | 3,45 | 1,237 | 5,511E-04 | 3,805E-03 | 0,707 | 2,286E-02 | 8,806E-02 |
| SEQ ID NO: 539 | hsa-miR-223* | 28 | 8 | 3,59 | 1,277 | 5,872E-04 | 3,935E-03 | 0,708 | 2,121E-03 | 2,034E-02 |
| SEQ ID NO: 481 | hsa-miR-30c-2* | 22 | 7 | 3,34 | 1,205 | 6,770E-04 | 4,393E-03 | 0,635 | 9,294E-03 | 2,305E-01 |
| SEQ ID NO: 51 | hsa-miR-875-5p | 27 | 1 | 27,14 | 3,301 | 7,030E-04 | 4,488E-03 | 0,725 | 2,180E-04 | 4,376E-03 |
| SEQ ID NO: 877 | hsa-miR-105* | 8 | 1 | 8,28 | 2,114 | 9,331E-04 | 5,554E-03 | 0,757 | 9,455E-05 | 2,205E-03 |
| SEQ ID NO: 421 | hsa-miR-369-5p | 31 | 1 | 31,08 | 3,436 | 1,167E-03 | 6,581E-03 | 0,690 | 6,782E-03 | 4,151E-02 |
| SEQ ID NO: 257 | hsa-miR-524-3p | 19 | 4 | 4,24 | 1,444 | 1,231E-03 | 6,765E-03 | 0,679 | 1,031E-02 | 5,424E-02 |
| SEQ ID NO: 860 | hsa-miR-1185 | 11 | 1 | 10,99 | 2,397 | 1,420E-03 | 7,582E-03 | 0,680 | 4,830E-03 | 3,381E-02 |
| SEQ ID NO: 294 | hsa-miR-517c | 7 | 1 | 6,86 | 1,926 | 1,766E-03 | 9,074E-03 | 0,606 | 1,394E-01 | 2,956E-01 |
| SEQ ID NO: 854 | hsa-miR-1204 | 18 | 1 | 18,30 | 2,907 | 2,035E-03 | 9,976E-03 | 0,661 | 1,002E-02 | 5,373E-02 |
| SEQ ID NO: 886 | hsa-miR-1 | 13 | 1 | 13,05 | 2,569 | 2,713E-03 | 1,266E-02 | 0,646 | 2,919E-02 | 1,063E-01 |
| SEQ ID NO: 301 | hsa-miR-516a-3p | 6 | 1 | 6,13 | 1,813 | 3,514E-03 | 1,534E-02 | 0,651 | 3,151E-02 | 1,105E-01 |
| SEQ ID NO: 634 | hsa-miR-1914 | 52 | 8 | 6,12 | 1,811 | 3,873E-03 | 1,671E-02 | 0,715 | 1,609E-03 | 1,714E-02 |
| SEQ ID NO: 170 | hsa-miR-590-3p | 4 | 1 | 4,18 | 1,431 | 4,754E-03 | 1,973E-02 | 0,670 | 1,689E-02 | 7,471E-02 |
| SEQ ID NO: 408 | hsa-miR-376a* | 1 | 5 | 0,19 | -1,648 | 5,089E-03 | 2,049E-02 | 0,543 | 6,448E-01 | 7,835E-01 |
| SEQ ID NO: 523 | hsa-miR-26a-1* | 9 | 1 | 9,28 | 2,228 | 5,106E-03 | 2,049E-02 | 0,625 | 6,209E-02 | 1,734E-01 |
| SEQ ID NO: 50 | hsa-miR-876-3p | 10 | 1 | 9,84 | 2,287 | 5,693E-03 | 2,202E-02 | 0,658 | 2,130E-02 | 8,432E-02 |
| SEQ ID NO: 88 | hsa-miR-758 | 12 | 46 | 0,27 | -1,304 | 5,985E-03 | 2,234E-02 | 0,293 | 3,751E-05 | 1,240E-03 |
| SEQ ID NO: 806 | hsa-miR-125b-2* | 32 | 8 | 4,10 | 1,412 | 6,032E-03 | 2,234E-02 | 0,650 | 4,547E-02 | 1,432E-01 |
| SEQ ID NO: 357 | hsa-miR-455-5p | 11 | 1 | 11,35 | 2,429 | 6,570E-03 | 2,384E-02 | 0,650 | 2,661E-02 | 9,857E-02 |
| SEQ ID NO: 338 | hsa-miR-493* | 33 | 10 | 3,19 | 1,161 | 8,157E-03 | 2,793E-02 | 0,667 | 5,649E-02 | 1,647E-01 |
| SEQ ID NO: 492 | hsa-miR-302c* | 23 | 1 | 23,49 | 3,157 | 1,038E-02 | 3,293E-02 | 0,732 | 1,021E-03 | 1,315E-02 |
| SEQ ID NO: 142 | hsa-miR-616 | 17 | 2 | 9,48 | 2,250 | 1,403E-02 | 4,232E-02 | 0,634 | 6,019E-02 | 1,708E-01 |
| SEQ ID NO: 523 | hsa-miR-586 | 30 | 2 | 13,50 | 2,603 | 1,516E-02 | 4,436E-02 | 0,713 | 2,339E-03 | 2,194E-02 |
| SEQ ID NO: 175 | hsa-miR-30e* | 39 | 78 | 0,51 | -0,681 | 1,840E-06 | 5,326E-05 | 0,169 | 1,878E-04 | 4,052E-03 |
| SEQ ID NO: 477 | hsa-miR-628-5p | 78 | 48 | 1,61 | 0,479 | 9,046E-06 | 1,978E-04 | 0,751 | 1,936E-03 | 1,953E-02 |

FIG. 18C (Cont.)

| SEQ ID NO | miR | | | | | | | |
|---|---|---|---|---|---|---|---|---|
| SEQ ID NO: 516 | hsa-miR-27b* | 61 | 36 | 1.70 | 0.530 | 1.320E-05 | 2.589E-04 | 0.759 | 2.152E-04 | 4.376E-03 |
| SEQ ID NO: 488 | hsa-miR-302f | 1 | 1 | 1.46 | 0.376 | 3.526E-05 | 5.742E-04 | 0.726 | 3.181E-04 | 5.723E-03 |
| SEQ ID NO: 106 | hsa-miR-647 | 68 | 38 | 1.79 | 0.584 | 3.982E-05 | 5.924E-04 | 0.772 | 1.426E-06 | 1.230E-04 |
| SEQ ID NO: 182 | hsa-miR-580 | 43 | 22 | 1.95 | 0.667 | 4.163E-05 | 6.089E-04 | 0.729 | 5.064E-03 | 3.441E-02 |
| SEQ ID NO: 95 | hsa-miR-657 | 59 | 34 | 1.71 | 0.538 | 4.691E-05 | 6.636E-04 | 0.737 | 5.482E-02 | 1.609E-01 |
| SEQ ID NO: 903 | hsa-let-7a* | 1 | 1 | 1.00 | 0.000 | 5.009E-05 | 6.972E-04 | 0.692 | 8.398E-04 | 1.132E-02 |
| SEQ ID NO: 203 | hsa-miR-559 | 48 | 27 | 1.81 | 0.593 | 5.409E-05 | 7.409E-04 | 0.746 | 2.613E-03 | 2.373E-02 |
| SEQ ID NO: 207 | hsa-miR-556-3p | 1 | 1 | 1.00 | 0.000 | 6.217E-05 | 8.129E-04 | 0.664 | 3.440E-03 | 2.800E-02 |
| SEQ ID NO: 138 | hsa-miR-619 | 54 | 85 | 0.63 | -0.459 | 7.025E-05 | 8.761E-04 | 0.239 | 4.044E-03 | 3.002E-02 |
| SEQ ID NO: 214 | hsa-miR-551a | 51 | 30 | 1.70 | 0.528 | 8.947E-05 | 1.043E-03 | 0.707 | 3.343E-02 | 1.154E-01 |
| SEQ ID NO: 17 | hsa-miR-936 | 64 | 39 | 1.63 | 0.491 | 1.104E-04 | 1.221E-03 | 0.722 | 2.098E-02 | 8.381E-02 |
| SEQ ID NO: 3 | hsa-miR-99a* | 34 | 18 | 1.87 | 0.626 | 1.117E-04 | 1.221E-03 | 0.693 | 2.780E-02 | 1.017E-01 |
| SEQ ID NO: 347 | hsa-miR-488 | 1 | 1 | 1.00 | 0.000 | 1.155E-04 | 1.246E-03 | 0.630 | 1.634E-02 | 7.307E-02 |
| SEQ ID NO: 858 | hsa-miR-1200 | 75 | 48 | 1.56 | 0.446 | 1.514E-04 | 1.575E-03 | 0.740 | 4.919E-04 | 7.861E-03 |
| SEQ ID NO: 642 | hsa-miR-190b | 1 | 1 | 1.00 | 0.000 | 1.547E-04 | 1.590E-03 | 0.657 | 5.902E-03 | 3.725E-02 |
| SEQ ID NO: 81 | hsa-miR-671-5p | 62 | 33 | 1.84 | 0.611 | 2.103E-04 | 1.969E-03 | 0.744 | 3.377E-03 | 2.776E-02 |
| SEQ ID NO: 290 | hsa-miR-518c | 63 | 99 | 0.63 | -0.455 | 2.484E-04 | 2.233E-03 | 0.239 | 3.491E-03 | 2.815E-02 |
| SEQ ID NO: 842 | hsa-miR-1226 | 49 | 80 | 0.62 | -0.485 | 2.469E-04 | 2.233E-03 | 0.220 | 1.794E-03 | 1.843E-02 |
| SEQ ID NO: 868 | hsa-miR-10b* | 51 | 88 | 0.58 | -0.541 | 2.669E-04 | 2.267E-03 | 0.254 | 7.070E-03 | 4.297E-02 |
| SEQ ID NO: 192 | hsa-miR-572 | 57 | 94 | 0.60 | -0.506 | 3.701E-04 | 2.840E-03 | 0.246 | 3.131E-03 | 2.649E-02 |
| SEQ ID NO: 707 | hsa-miR-146b-3p | 55 | 41 | 1.32 | 0.281 | 4.178E-04 | 3.135E-03 | 0.669 | 7.535E-03 | 1.989E-01 |
| SEQ ID NO: 213 | hsa-miR-551b | 73 | 56 | 1.31 | 0.271 | 4.487E-04 | 3.338E-03 | 0.678 | 1.911E-02 | 7.967E-02 |
| SEQ ID NO: 245 | hsa-miR-541* | 1 | 1 | 1.00 | 0.000 | 5.292E-04 | 3.713E-03 | 0.673 | 5.633E-03 | 3.685E-02 |
| SEQ ID NO: 641 | hsa-miR-129-3p | 58 | 35 | 1.68 | 0.517 | 6.420E-04 | 4.197E-03 | 0.752 | 4.813E-04 | 7.838E-03 |
| SEQ ID NO: 112 | hsa-miR-379* | 77 | 69 | 1.13 | 0.118 | 7.072E-04 | 4.488E-03 | 0.667 | 3.966E-03 | 3.002E-02 |
| SEQ ID NO: 400 | hsa-miR-1258 | 54 | 31 | 1.77 | 0.570 | 8.058E-04 | 4.967E-03 | 0.697 | 5.466E-03 | 3.628E-02 |
| SEQ ID NO: 812 | hsa-miR-200a* | 1 | 1 | 1.00 | 0.000 | 8.407E-04 | 5.109E-03 | 0.641 | 1.086E-02 | 5.580E-02 |
| SEQ ID NO: 596 | hsa-miR-134 | 62 | 96 | 0.65 | -0.437 | 1.047E-03 | 6.063E-03 | 0.270 | 4.831E-03 | 3.381E-02 |
| SEQ ID NO: 736 | hsa-miR-890 | 56 | 33 | 1.66 | 0.509 | 1.131E-03 | 6.466E-03 | 0.692 | 1.540E-02 | 6.995E-02 |
| SEQ ID NO: 38 | hsa-miR-1267 | 37 | 20 | 1.82 | 0.597 | 1.177E-03 | 6.595E-03 | 0.666 | 2.334E-01 | 4.143E-01 |
| SEQ ID NO: 796 | hsa-miR-195* | 41 | 21 | 1.98 | 0.684 | 1.195E-03 | 6.610E-03 | 0.671 | 1.280E-01 | 2.833E-01 |
| SEQ ID NO: 621 | hsa-miR-662 | 69 | 43 | 1.58 | 0.458 | 1.423E-03 | 7.582E-03 | 0.664 | 3.321E-01 | 5.146E-01 |
| SEQ ID NO: 90 | hsa-miR-604 | 52 | 88 | 0.58 | -0.538 | 1.436E-03 | 7.601E-03 | 0.256 | 1.123E-02 | 5.733E-02 |
| SEQ ID NO: 155 | hsa-miR-488* | 89 | 63 | 1.42 | 0.350 | 1.750E-03 | 9.041E-03 | 0.669 | 5.027E-02 | 1.544E-01 |
| SEQ ID NO: 346 | hsa-miR-515-3p | 72 | 59 | 1.22 | 0.197 | 1.813E-03 | 9.260E-03 | 0.651 | 9.967E-02 | 2.403E-01 |
| SEQ ID NO: 303 | hsa-miR-30a* | 1 | 1 | 1.00 | 0.000 | 1.852E-03 | 9.345E-03 | 0.617 | 5.114E-02 | 1.565E-01 |
| SEQ ID NO: 486 | hsa-miR-649* | 40 | 25 | 1.59 | 0.465 | 1.923E-03 | 9.649E-03 | 0.673 | 2.016E-02 | 8.240E-02 |

FIG. 18C (Cont.)

| | | | | | | | | | |
|---|---|---|---|---|---|---|---|---|---|
| SEQ ID NO: 376 | hsa-miR-432 | 1 | 1 | 1.00 | 0.000 | 1.971E-03 | 9.776E-03 | 0.617 | 2.200E-02 | 8.668E-02 |
| SEQ ID NO: 741 | hsa-miR-1322 | 77 | 57 | 1.36 | 0.306 | 2.106E-03 | 1.027E-02 | 0.621 | 1.931E-01 | 3.703E-01 |
| SEQ ID NO: 862 | hsa-miR-1183 | 90 | 73 | 1.24 | 0.212 | 2.453E-03 | 1.175E-02 | 0.645 | 4.858E-03 | 3.381E-02 |
| SEQ ID NO: 365 | hsa-miR-450b-5p | 61 | 43 | 1.41 | 0.340 | 2.522E-03 | 1.191E-02 | 0.684 | 7.913E-04 | 1.101E-02 |
| SEQ ID NO: 56 | hsa-miR-770-5p | 54 | 39 | 1.39 | 0.331 | 2.525E-03 | 1.191E-02 | 0.667 | 9.360E-03 | 5.160E-02 |
| SEQ ID NO: 732 | hsa-miR-135b* | 53 | 33 | 1.60 | 0.469 | 2.922E-03 | 1.320E-02 | 0.708 | 1.713E-03 | 1.781E-02 |
| SEQ ID NO: 150 | hsa-miR-609 | 1 | 1 | 1.00 | 0.000 | 2.914E-03 | 1.320E-02 | 0.680 | 4.030E-03 | 3.002E-02 |
| SEQ ID NO: 771 | hsa-miR-1288 | 55 | 91 | 0.60 | -0.506 | 3.408E-03 | 1.508E-02 | 0.323 | 1.002E-02 | 5.373E-02 |
| SEQ ID NO: 388 | hsa-miR-412 | 51 | 42 | 1.19 | 0.175 | 3.993E-03 | 1.714E-02 | 0.667 | 6.196E-03 | 3.847E-02 |
| SEQ ID NO: 227 | hsa-miR-548h | 1 | 1 | 1.00 | 0.000 | 4.189E-03 | 1.781E-02 | 0.643 | 2.096E-02 | 8.381E-02 |
| SEQ ID NO: 159 | hsa-miR-600 | 73 | 56 | 1.29 | 0.257 | 4.588E-03 | 1.922E-02 | 0.600 | 9.602E-01 | 9.806E-01 |
| SEQ ID NO: 161 | hsa-miR-598 | 52 | 71 | 0.72 | -0.326 | 4.652E-03 | 1.940E-02 | 0.315 | 1.010E-02 | 5.381E-02 |
| SEQ ID NO: 241 | hsa-miR-544 | 37 | 22 | 1.65 | 0.502 | 5.251E-03 | 2.079E-02 | 0.646 | 6.853E-02 | 1.866E-01 |
| SEQ ID NO: 184 | hsa-miR-578 | 1 | 1 | 1.00 | 0.000 | 5.379E-03 | 2.120E-02 | 0.586 | 1.495E-01 | 3.116E-01 |
| SEQ ID NO: 141 | hsa-miR-616* | 57 | 42 | 1.36 | 0.306 | 5.413E-03 | 2.123E-02 | 0.642 | 2.698E-01 | 4.477E-01 |
| SEQ ID NO: 833 | hsa-miR-1236 | 23 | 14 | 1.62 | 0.479 | 5.522E-03 | 2.156E-02 | 0.576 | 5.857E-01 | 7.412E-01 |
| SEQ ID NO: 749 | hsa-miR-1308 | 44 | 27 | 1.62 | 0.483 | 5.801E-03 | 2.215E-02 | 0.605 | 4.347E-01 | 6.201E-01 |
| SEQ ID NO: 322 | hsa-miR-504 | 31 | 20 | 1.55 | 0.440 | 5.798E-03 | 2.215E-02 | 0.638 | 7.391E-02 | 1.969E-01 |
| SEQ ID NO: 48 | hsa-miR-877 | 60 | 94 | 0.63 | -0.455 | 5.901E-03 | 2.224E-02 | 0.285 | 1.154E-02 | 5.826E-02 |
| SEQ ID NO: 580 | hsa-miR-208b | 60 | 46 | 1.31 | 0.272 | 5.899E-03 | 2.224E-02 | 0.642 | 6.131E-02 | 1.718E-01 |
| SEQ ID NO: 191 | hsa-miR-573 | 51 | 31 | 1.66 | 0.500 | 6.132E-03 | 2.261E-02 | 0.682 | 2.811E-02 | 1.099E-01 |
| SEQ ID NO: 418 | hsa-miR-371-5p | 43 | 26 | 1.65 | 0.500 | 6.917E-03 | 2.487E-02 | 0.659 | 3.095E-02 | 1.533E-01 |
| SEQ ID NO: 270 | hsa-miR-520c-3p | 1 | 1 | 1.00 | 0.000 | 6.988E-03 | 2.502E-02 | 0.597 | 4.974E-02 | 5.892E-02 |
| SEQ ID NO: 479 | hsa-miR-30d* | 50 | 66 | 0.76 | -0.275 | 7.090E-03 | 2.528E-02 | 0.338 | 1.174E-02 | 4.798E-02 |
| SEQ ID NO: 349 | hsa-miR-487a | 64 | 58 | 1.10 | 0.092 | 7.450E-03 | 2.614E-02 | 0.629 | 8.395E-03 | 4.795E-02 |
| SEQ ID NO: 344 | hsa-miR-490-3p | 87 | 72 | 1.21 | 0.189 | 7.750E-03 | 2.700E-02 | 0.666 | 8.239E-03 | 1.669E-02 |
| SEQ ID NO: 178 | hsa-miR-583 | 47 | 33 | 1.40 | 0.335 | 7.954E-03 | 2.735E-02 | 0.671 | 1.547E-02 | 1.798E-01 |
| SEQ ID NO: 801 | hsa-miR-1262 | 1 | 1 | 1.00 | 0.000 | 8.484E-03 | 2.871E-02 | 0.625 | 6.543E-02 | 1.098E-01 |
| SEQ ID NO: 825 | hsa-miR-1246 | 1 | 1 | 1.00 | 0.000 | 8.893E-03 | 2.952E-02 | 0.639 | 3.076E-02 | 4.883E-02 |
| SEQ ID NO: 497 | hsa-miR-302a | 1 | 1 | 1.00 | 0.000 | 9.315E-03 | 3.033E-02 | 0.649 | 8.674E-03 | 2.434E-01 |
| SEQ ID NO: 395 | hsa-miR-383 | 49 | 31 | 1.61 | 0.474 | 9.456E-03 | 3.068E-02 | 0.658 | 1.016E-01 | 4.208E-01 |
| SEQ ID NO: 755 | hsa-miR-1302 | 30 | 18 | 1.71 | 0.537 | 9.514E-03 | 3.074E-02 | 0.629 | 2.482E-01 | 1.167E-01 |
| SEQ ID NO: 102 | hsa-miR-651 | 1 | 1 | 1.14 | 0.128 | 9.743E-03 | 3.114E-02 | 0.635 | 3.421E-02 | 3.144E-01 |
| SEQ ID NO: 711 | hsa-miR-1468 | 1 | 1 | 1.00 | 0.000 | 9.733E-03 | 3.114E-02 | 0.568 | 1.515E-01 | 7.763E-01 |
| SEQ ID NO: 420 | hsa-miR-370 | 48 | 34 | 1.44 | 0.362 | 9.983E-03 | 3.179E-02 | 0.669 | 6.351E-01 | 5.339E-01 |
| SEQ ID NO: 811 | hsa-miR-1259 | 23 | 14 | 1.62 | 0.482 | 1.272E-02 | 3.892E-02 | 0.579 | 3.490E-01 | 2.847E-01 |
| SEQ ID NO: 99 | hsa-miR-654-3p | 30 | 18 | 1.71 | 0.535 | 1.327E-02 | 4.047E-02 | 0.625 | 1.319E-01 | |

FIG. 18C (Cont.)

| | | | | | | | | | |
|---|---|---|---|---|---|---|---|---|---|
| SEQ ID NO: 727 | hsa-miR-138-1* | 92 | 72 | 1,28 | 0,246 | 1,359E-02 | 4,129E-02 | 0,637 | 5,819E-01 | 7,401E-01 |
| SEQ ID NO: 172 | hsa-miR-589 | 79 | 93 | 0,85 | -0,167 | 1,412E-02 | 4,246E-02 | 0,338 | 4,518E-02 | 1,428E-01 |
| SEQ ID NO: 747 | hsa-miR-130a* | 53 | 78 | 0,68 | -0,392 | 1,439E-02 | 4,254E-02 | 0,352 | 1,269E-02 | 6,187E-02 |
| SEQ ID NO: 518 | hsa-miR-27a* | 34 | 27 | 1,28 | 0,249 | 1,437E-02 | 4,254E-02 | 0,633 | 1,304E-01 | 2,845E-01 |
| SEQ ID NO: 91 | hsa-miR-661 | 44 | 25 | 1,74 | 0,556 | 1,436E-02 | 4,254E-02 | 0,633 | 2,396E-01 | 4,160E-01 |
| SEQ ID NO: 853 | hsa-miR-1205 | 71 | 75 | 0,95 | -0,048 | 1,566E-02 | 4,535E-02 | 0,577 | 7,557E-02 | 1,989E-01 |
| SEQ ID NO: 262 | hsa-miR-521 | 47 | 33 | 1,39 | 0,331 | 1,663E-02 | 4,753E-02 | 0,630 | 9,387E-03 | 5,160E-02 |
| SEQ ID NO: 506 | hsa-miR-29a* | 1 | 1 | 1,00 | 0,000 | 1,662E-02 | 4,753E-02 | 0,667 | 5,820E-03 | 3,720E-02 |
| SEQ ID NO: 894 | hsa-let-7e* | 10 | 7 | 1,50 | 0,404 | 1,669E-02 | 4,754E-02 | 0,590 | 3,123E-01 | 4,900E-01 |
| SEQ ID NO: 372 | hsa-miR-449a | 1 | 1 | 1,00 | 0,000 | 1,753E-02 | 4,929E-02 | 0,658 | 8,278E-03 | 4,795E-02 |
| SEQ ID NO: 648 | hsa-miR-18b | 166 | 413 | 0,40 | -0,911 | 2,145E-04 | 1,969E-03 | 0,196 | 5,078E-05 | 1,392E-03 |
| SEQ ID NO: 701 | hsa-miR-148a | 950 | 629 | 1,51 | 0,412 | 1,227E-07 | 8,144E-06 | 0,758 | 2,072E-02 | 8,381E-02 |
| SEQ ID NO: 7 | hsa-miR-96 | 156 | 254 | 0,61 | -0,490 | 8,273E-07 | 3,193E-05 | 0,183 | 1,266E-04 | 2,801E-03 |
| SEQ ID NO: 160 | hsa-miR-599 | 29 | 11 | 2,65 | 0,976 | 3,442E-03 | 1,516E-02 | 0,651 | 7,819E-02 | 2,040E-01 |

FIG. 18D

| Signature | SEQ ID Nos | miRNA identifiers | Acc | Spec | Sens |
|---|---|---|---|---|---|
| MS1 | SEQ ID NO: 901, SEQ ID NO: 190, SEQ ID NO: 329 | hsa-let-7b, hsa-miR-574-3p, hsa-miR-500 | 91% | 90% | 93% |
| MS2 | SEQ ID NO: 329, SEQ ID NO: 834, SEQ ID NO: 809 | hsa-miR-500, hsa-miR-1234, hsa-miR-125a-5p | 86% | 80% | 91% |
| MS3 | SEQ ID NO: 809, SEQ ID NO: 23, SEQ ID NO: 899 | hsa-miR-125a-5p, hsa-miR-92b*, hsa-let-7c | 89% | 84% | 94% |
| MS4 | SEQ ID NO: 899, SEQ ID NO: 713, SEQ ID NO: 460 | hsa-let-7c, hsa-miR-145, hsa-miR-330-3p | 91% | 91% | 91% |
| MS5 | SEQ ID NO: 460, SEQ ID NO: 478, SEQ ID NO: 605 | hsa-miR-330-3p, hsa-miR-30e, hsa-miR-199a-5p | 75% | 74% | 76% |
| MS6 | SEQ ID NO: 605, SEQ ID NO: 540, SEQ ID NO: 622 | hsa-miR-199a-5p, hsa-miR-223, hsa-miR-195 | 87% | 86% | 87% |
| MS7 | SEQ ID NO: 622, SEQ ID NO: 666, SEQ ID NO: 872 | hsa-miR-195, hsa-miR-182, hsa-miR-107 | 81% | 80% | 81% |
| MS8 | SEQ ID NO: 872, SEQ ID NO: 334, SEQ ID NO: 165 | hsa-miR-107, hsa-miR-497, hsa-miR-593* | 80% | 73% | 86% |
| MS9 | SEQ ID NO: 165, SEQ ID NO: 386, SEQ ID NO: 756 | hsa-miR-593*, hsa-miR-422a, hsa-miR-1301 | 78% | 69% | 87% |
| MS10 | SEQ ID NO: 756, SEQ ID NO: 429, SEQ ID NO: 561 | hsa-miR-1301, hsa-miR-362-5p, hsa-miR-214 | 68% | 58% | 78% |
| MS11 | SEQ ID NO: 561, SEQ ID NO: 475, SEQ ID NO: 529 | hsa-miR-214, hsa-miR-31*, hsa-miR-24 | 79% | 64% | 94% |
| MS12 | SEQ ID NO: 529, SEQ ID NO: 709, SEQ ID NO: 645 | hsa-miR-24, hsa-miR-146a, hsa-miR-1908 | 79% | 75% | 84% |
| MS13 | SEQ ID NO: 645, SEQ ID NO: 881, SEQ ID NO: 876 | hsa-miR-1908, hsa-miR-103, hsa-miR-106a | 86% | 84% | 87% |
| MS14 | SEQ ID NO: 881, SEQ ID NO: 362, SEQ ID NO: 876 | hsa-miR-103, hsa-miR-452*, hsa-miR-106a | 85% | 87% | 82% |
| MS15 | SEQ ID NO: 876, SEQ ID NO: 136, SEQ ID NO: 820 | hsa-miR-106a, hsa-miR-621, hsa-miR-1251 | 77% | 73% | 82% |
| MS16 | SEQ ID NO: 901, SEQ ID NO: 190, SEQ ID NO: 329, SEQ ID NO: 834, SEQ ID NO: 809 | hsa-let-7b, hsa-miR-574-3p, hsa-miR-500, hsa-miR-1234, hsa-miR-125a-5p | 91% | 90% | 91% |
| MS17 | SEQ ID NO: 329, SEQ ID NO: 834, SEQ ID NO: 809, SEQ ID NO: 23, SEQ ID NO: 899 | hsa-miR-500, hsa-miR-1234, hsa-miR-125a-5p, hsa-miR-92b*, hsa-let-7c | 92% | 93% | 91% |

FIG. 18D (Cont.)

| | | | | | |
|---|---|---|---|---|---|
| MS18 | SEQ ID NO: 809, SEQ ID NO: 23, SEQ ID NO: 899, SEQ ID NO: 713, SEQ ID NO: 460 | hsa-miR-125a-5p, hsa-miR-92b*, hsa-let-7c, hsa-miR-145, hsa-miR-330-3p | 91% | 93% | 90% |
| MS19 | SEQ ID NO: 23, SEQ ID NO: 899, SEQ ID NO: 713, SEQ ID NO: 460, SEQ ID NO: 478 | hsa-miR-92b*, hsa-let-7c, hsa-miR-145, hsa-miR-330-3p, hsa-miR-30e | 91% | 92% | 90% |
| MS20 | SEQ ID NO: 713, SEQ ID NO: 460, SEQ ID NO: 478, SEQ ID NO: 605, SEQ ID NO: 540 | hsa-miR-145, hsa-miR-330-3p, hsa-miR-30e, hsa-miR-199a-5p, hsa-miR-223 | 90% | 89% | 92% |
| MS21 | SEQ ID NO: 478, SEQ ID NO: 605, SEQ ID NO: 540, SEQ ID NO: 622, SEQ ID NO: 666 | hsa-miR-30e, hsa-miR-199a-5p, hsa-miR-223, hsa-miR-195, hsa-miR-182 | 89% | 87% | 92% |
| MS22 | SEQ ID NO: 605, SEQ ID NO: 540, SEQ ID NO: 622, SEQ ID NO: 666, SEQ ID NO: 872, SEQ ID NO: 334 | hsa-miR-199a-5p, hsa-miR-223, hsa-miR-195, hsa-miR-182, hsa-miR-107, hsa-miR-497 | 88% | 86% | 90% |
| MS23 | SEQ ID NO: 666, SEQ ID NO: 872, SEQ ID NO: 334, SEQ ID NO: 165, SEQ ID NO: 386, SEQ ID NO: 756 | hsa-miR-182, hsa-miR-107, hsa-miR-497, hsa-miR-593*, hsa-miR-422a, hsa-miR-1301 | 85% | 82% | 89% |
| MS24 | SEQ ID NO: 165, SEQ ID NO: 386, SEQ ID NO: 756, SEQ ID NO: 429, SEQ ID NO: 561, SEQ ID NO: 475 | hsa-miR-593*, hsa-miR-422a, hsa-miR-1301, hsa-miR-362-5p, hsa-miR-214, hsa-miR-31* | 76% | 67% | 86% |
| MS25 | SEQ ID NO: 429, SEQ ID NO: 561, SEQ ID NO: 475, SEQ ID NO: 529, SEQ ID NO: 709, SEQ ID NO: 645 | hsa-miR-362-5p, hsa-miR-214, hsa-miR-31*, hsa-miR-24, hsa-miR-146a, hsa-miR-1908 | 77% | 74% | 79% |
| MS26 | SEQ ID NO: 529, SEQ ID NO: 709, SEQ ID NO: 645, SEQ ID NO: 80, SEQ ID NO: 881, SEQ ID NO: 362 | hsa-miR-24, hsa-miR-146a, hsa-miR-1908, hsa-miR-675, hsa-miR-103, hsa-miR-452* | 78% | 76% | 80% |
| MS27 | SEQ ID NO: 80, SEQ ID NO: 881, SEQ ID NO: 362, SEQ ID NO: 876, SEQ ID NO: 136, SEQ ID NO: 820 | hsa-miR-675, hsa-miR-103, hsa-miR-452*, hsa-miR-106a, hsa-miR-621, hsa-miR-1251 | 77% | 74% | 80% |
| MS28 | SEQ ID NO: 876, SEQ ID NO: 136, SEQ ID NO: 820, SEQ ID NO: 578, SEQ ID NO: 107, SEQ ID NO: 46 | hsa-miR-106a, hsa-miR-621, hsa-miR-1251, hsa-miR-20a*, hsa-miR-646, hsa-miR-885-3p | 74% | 73% | 74% |
| MS29 | SEQ ID NO: 578, SEQ ID NO: 107, SEQ ID NO: 46, SEQ ID NO: 315, SEQ ID NO: 636, SEQ ID NO: 577 | hsa-miR-20a*, hsa-miR-646, hsa-miR-885-3p, hsa-miR-509-3-5p, hsa-miR-1912, hsa-miR-20b | 70% | 65% | 76% |
| MS30 | SEQ ID NO: 315, SEQ ID NO: 636, SEQ ID NO: 577, SEQ ID NO: 189, SEQ ID NO: 544, SEQ ID NO: 426 | hsa-miR-509-3-5p, hsa-miR-1912, hsa-miR-20b, hsa-miR-574-5p, hsa-miR-221, hsa-miR-365 | 84% | 85% | 84% |

FIG. 18D (Cont.)

| | | | | | |
|---|---|---|---|---|---|
| MS31 | SEQ ID NO: 901, SEQ ID NO: 190, SEQ ID NO: 329, SEQ ID NO: 834, SEQ ID NO: 809, SEQ ID NO: 23, SEQ ID NO: 899, SEQ ID NO: 713, SEQ ID NO: 460, SEQ ID NO: 478 | hsa-let-7b, hsa-miR-574-3p, hsa-miR-500, hsa-miR-1234, hsa-miR-125a-5p, hsa-miR-92b*, hsa-let-7c, hsa-miR-145, hsa-miR-330-3p, hsa-miR-30e | 91% | 93% | 89% |
| MS32 | SEQ ID NO: 23, SEQ ID NO: 899, SEQ ID NO: 713, SEQ ID NO: 460, SEQ ID NO: 478, SEQ ID NO: 605, SEQ ID NO: 540, SEQ ID NO: 622, SEQ ID NO: 666, SEQ ID NO: 872, SEQ ID NO: 334 | hsa-miR-92b*, hsa-let-7c, hsa-miR-145, hsa-miR-330-3p, hsa-miR-30e, hsa-miR-199a-5p, hsa-miR-223, hsa-miR-195, hsa-miR-182, hsa-miR-107, hsa-miR-497 | 92% | 92% | 91% |
| MS33 | SEQ ID NO: 540, SEQ ID NO: 622, SEQ ID NO: 666, SEQ ID NO: 872, SEQ ID NO: 334, SEQ ID NO: 165, SEQ ID NO: 386, SEQ ID NO: 756, SEQ ID NO: 429, SEQ ID NO: 561 | hsa-miR-223, hsa-miR-195, hsa-miR-182, hsa-miR-107, hsa-miR-497, hsa-miR-593*, hsa-miR-422a, hsa-miR-1301, hsa-miR-362-5p, hsa-miR-214 | 85% | 84% | 87% |
| MS34 | SEQ ID NO: 165, SEQ ID NO: 386, SEQ ID NO: 756, SEQ ID NO: 429, SEQ ID NO: 561, SEQ ID NO: 475, SEQ ID NO: 529, SEQ ID NO: 709, SEQ ID NO: 645, SEQ ID NO: 80 | hsa-miR-593*, hsa-miR-422a, hsa-miR-1301, hsa-miR-362-5p, hsa-miR-214, hsa-miR-31*, hsa-miR-24, hsa-miR-146a, hsa-miR-1908, hsa-miR-675 | 80% | 76% | 85% |
| MS35 | SEQ ID NO: 475, SEQ ID NO: 529, SEQ ID NO: 709, SEQ ID NO: 645, SEQ ID NO: 80, SEQ ID NO: 881, SEQ ID NO: 362, SEQ ID NO: 876, SEQ ID NO: 136, SEQ ID NO: 820 | hsa-miR-31*, hsa-miR-24, hsa-miR-146a, hsa-miR-1908, hsa-miR-675, hsa-miR-103, hsa-miR-452*, hsa-miR-106a, hsa-miR-621, hsa-miR-1251 | 79% | 78% | 80% |
| MS36 | SEQ ID NO: 881, SEQ ID NO: 362, SEQ ID NO: 876, SEQ ID NO: 136, SEQ ID NO: 820, SEQ ID NO: 578, SEQ ID NO: 107, SEQ ID NO: 46, SEQ ID NO: 315, SEQ ID NO: 636 | hsa-miR-103, hsa-miR-452*, hsa-miR-106a, hsa-miR-621, hsa-miR-1251, hsa-miR-20a*, hsa-miR-646, hsa-miR-885-3p, hsa-miR-509-3-5p, hsa-miR-1912 | 80% | 79% | 80% |
| MS37 | SEQ ID NO: 578, SEQ ID NO: 107, SEQ ID NO: 46, SEQ ID NO: 315, SEQ ID NO: 636, SEQ ID NO: 577, SEQ ID NO: 189, SEQ ID NO: 544, SEQ ID NO: 426, SEQ ID NO: 548 | hsa-miR-20a*, hsa-miR-646, hsa-miR-885-3p, hsa-miR-509-3-5p, hsa-miR-1912, hsa-miR-20b, hsa-miR-574-5p, hsa-miR-221, hsa-miR-365, hsa-miR-22* | 83% | 84% | 83% |
| MS38 | SEQ ID NO: 577, SEQ ID NO: 189, SEQ ID NO: 544, SEQ ID NO: 426, SEQ ID NO: 548, SEQ ID NO: 786, SEQ ID NO: 131, SEQ ID NO: 177, SEQ ID NO: 462, SEQ ID NO: 125 | hsa-miR-20b, hsa-miR-574-5p, hsa-miR-221, hsa-miR-365, hsa-miR-22*, hsa-miR-1275, hsa-miR-625, hsa-miR-584, hsa-miR-328, hsa-miR-629 | 85% | 86% | 83% |

FIG. 18D (Cont.)

| | | | | | |
|---|---|---|---|---|---|
| MS39 | SEQ ID NO: 786, SEQ ID NO: 131, SEQ ID NO: 177, SEQ ID NO: 462, SEQ ID NO: 125, SEQ ID NO: 656, SEQ ID NO: 719, SEQ ID NO: 78, SEQ ID NO: 37, SEQ ID NO: 791 | hsa-miR-1275, hsa-miR-625, hsa-miR-584, hsa-miR-328, hsa-miR-629, hsa-miR-186, hsa-miR-142-3p, hsa-miR-7, hsa-miR-891a, hsa-miR-1272 | 85% | 85% | 85% |
| MS40 | SEQ ID NO: 901, SEQ ID NO: 329, SEQ ID NO: 809, SEQ ID NO: 899, SEQ ID NO: 460 | hsa-let-7b, hsa-miR-500, hsa-miR-125a-5p, hsa-let-7c, hsa-miR-330-3p | 90% | 89% | 91% |
| MS41 | SEQ ID NO: 834, SEQ ID NO: 23, SEQ ID NO: 713, SEQ ID NO: 478, SEQ ID NO: 540 | hsa-miR-1234, hsa-miR-92b*, hsa-miR-145, hsa-miR-30e, hsa-miR-223 | 92% | 93% | 91% |
| MS42 | SEQ ID NO: 713, SEQ ID NO: 478, SEQ ID NO: 540, SEQ ID NO: 666, SEQ ID NO: 334 | hsa-miR-145, hsa-miR-30e, hsa-miR-223, hsa-miR-182, hsa-miR-497 | 92% | 89% | 95% |
| MS43 | SEQ ID NO: 901, SEQ ID NO: 190, SEQ ID NO: 360 | hsa-let-7b, hsa-miR-574-3p, hsa-miR-454 | 88% | 84% | 91% |
| MS44 | SEQ ID NO: 360, SEQ ID NO: 329, SEQ ID NO: 61 | hsa-miR-454, hsa-miR-500, hsa-miR-766 | 87% | 84% | 90% |
| MS45 | SEQ ID NO: 61, SEQ ID NO: 895, SEQ ID NO: 834 | hsa-miR-766, hsa-let-7e, hsa-miR-1234 | 91% | 87% | 95% |
| MS46 | SEQ ID NO: 834, SEQ ID NO: 809, SEQ ID NO: 893 | hsa-miR-1234, hsa-miR-125a-5p, hsa-let-7f | 82% | 79% | 85% |
| MS47 | SEQ ID NO: 893, SEQ ID NO: 23, SEQ ID NO: 899 | hsa-let-7f, hsa-miR-92b*, hsa-let-7c | 92% | 92% | 93% |
| MS48 | SEQ ID NO: 899, SEQ ID NO: 890, SEQ ID NO: 713 | hsa-let-7c, hsa-let-7g, hsa-miR-145 | 93% | 93% | 94% |
| MS49 | SEQ ID NO: 713, SEQ ID NO: 888, SEQ ID NO: 746 | hsa-miR-145, hsa-let-7i, hsa-miR-130b | 88% | 93% | 83% |
| MS50 | SEQ ID NO: 746, SEQ ID NO: 803, SEQ ID NO: 460 | hsa-miR-130b, hsa-miR-1260, hsa-miR-330-3p | 81% | 77% | 86% |
| MS51 | SEQ ID NO: 460, SEQ ID NO: 478, SEQ ID NO: 897 | hsa-miR-330-3p, hsa-miR-30e, hsa-let-7d | 80% | 77% | 83% |
| MS52 | SEQ ID NO: 897, SEQ ID NO: 327, SEQ ID NO: 635 | hsa-let-7d, hsa-miR-501-3p, hsa-miR-1913 | 84% | 73% | 94% |
| MS53 | SEQ ID NO: 635, SEQ ID NO: 605, SEQ ID NO: 549 | hsa-miR-1913, hsa-miR-199a-5p, hsa-miR-22 | 82% | 78% | 85% |
| MS54 | SEQ ID NO: 549, SEQ ID NO: 540, SEQ ID NO: 622 | hsa-miR-22, hsa-miR-223, hsa-miR-195 | 81% | 87% | 74% |
| MS55 | SEQ ID NO: 622, SEQ ID NO: 666, SEQ ID NO: 483 | hsa-miR-195, hsa-miR-182, hsa-miR-30c | 85% | 81% | 88% |

FIG. 18D (Cont.)

| | | | | | |
|---|---|---|---|---|---|
| MS56 | SEQ ID NO: 666, SEQ ID NO: 630, SEQ ID NO: 483 | hsa-miR-182, hsa-miR-192, hsa-miR-30c | 75% | 77% | 73% |
| MS57 | SEQ ID NO: 483, SEQ ID NO: 428, SEQ ID NO: 872 | hsa-miR-30c, hsa-miR-363, hsa-miR-107 | 84% | 85% | 83% |
| MS58 | SEQ ID NO: 901, SEQ ID NO: 190, SEQ ID NO: 360, SEQ ID NO: 329, SEQ ID NO: 61 | hsa-let-7b, hsa-miR-574-3p, hsa-miR-454, hsa-miR-500, hsa-miR-766 | 91% | 87% | 94% |
| MS59 | SEQ ID NO: 360, SEQ ID NO: 329, SEQ ID NO: 61, SEQ ID NO: 895, SEQ ID NO: 834 | hsa-miR-454, hsa-miR-500, hsa-miR-766, hsa-let-7e, hsa-miR-1234 | 92% | 89% | 94% |
| MS60 | SEQ ID NO: 61, SEQ ID NO: 895, SEQ ID NO: 834, SEQ ID NO: 809, SEQ ID NO: 893 | hsa-miR-766, hsa-let-7e, hsa-miR-1234, hsa-miR-125a-5p, hsa-let-7f | 86% | 85% | 88% |
| MS61 | SEQ ID NO: 895, SEQ ID NO: 834, SEQ ID NO: 809, SEQ ID NO: 893, SEQ ID NO: 23 | hsa-let-7e, hsa-miR-1234, hsa-miR-125a-5p, hsa-let-7f, hsa-miR-92b* | 81% | 77% | 84% |
| MS62 | SEQ ID NO: 809, SEQ ID NO: 893, SEQ ID NO: 23, SEQ ID NO: 899, SEQ ID NO: 890 | hsa-miR-125a-5p, hsa-let-7f, hsa-miR-92b*, hsa-let-7c, hsa-let-7g | 91% | 89% | 92% |
| MS63 | SEQ ID NO: 23, SEQ ID NO: 899, SEQ ID NO: 890, SEQ ID NO: 713, SEQ ID NO: 888 | hsa-miR-92b*, hsa-let-7c, hsa-let-7g, hsa-miR-145, hsa-let-7i | 91% | 91% | 91% |
| MS64 | SEQ ID NO: 899, SEQ ID NO: 890, SEQ ID NO: 713, SEQ ID NO: 888, SEQ ID NO: 746, SEQ ID NO: 803 | hsa-let-7c, hsa-let-7g, hsa-miR-145, hsa-let-7i, hsa-miR-130b, hsa-miR-1260 | 91% | 93% | 89% |
| MS65 | SEQ ID NO: 888, SEQ ID NO: 746, SEQ ID NO: 803, SEQ ID NO: 460, SEQ ID NO: 478, SEQ ID NO: 897 | hsa-let-7i, hsa-miR-130b, hsa-miR-1260, hsa-miR-330-3p, hsa-miR-30e, hsa-let-7d | 86% | 82% | 89% |
| MS66 | SEQ ID NO: 460, SEQ ID NO: 478, SEQ ID NO: 897, SEQ ID NO: 327, SEQ ID NO: 635, SEQ ID NO: 605 | hsa-miR-330-3p, hsa-miR-30e, hsa-let-7d, hsa-miR-501-3p, hsa-miR-1913, hsa-miR-199a-5p | 86% | 84% | 87% |
| MS67 | SEQ ID NO: 327, SEQ ID NO: 635, SEQ ID NO: 605, SEQ ID NO: 549, SEQ ID NO: 540, SEQ ID NO: 622 | hsa-miR-501-3p, hsa-miR-1913, hsa-miR-199a-5p, hsa-miR-22, hsa-miR-223, hsa-miR-195 | 90% | 89% | 90% |
| MS68 | SEQ ID NO: 549, SEQ ID NO: 540, SEQ ID NO: 622, SEQ ID NO: 249, SEQ ID NO: 666, SEQ ID NO: 630 | hsa-miR-22, hsa-miR-223, hsa-miR-195, hsa-miR-532-3p, hsa-miR-182, hsa-miR-192 | 90% | 91% | 89% |
| MS69 | SEQ ID NO: 249, SEQ ID NO: 666, SEQ ID NO: 630, SEQ ID NO: 483, SEQ ID NO: 428, SEQ ID NO: 872 | hsa-miR-532-3p, hsa-miR-182, hsa-miR-192, hsa-miR-30c, hsa-miR-363, hsa-miR-107 | 91% | 91% | 90% |

FIG. 18D (Cont.)

| | | | | | |
|---|---|---|---|---|---|
| MS70 | SEQ ID NO: 483, SEQ ID NO: 428, SEQ ID NO: 872, SEQ ID NO: 351, SEQ ID NO: 334, SEQ ID NO: 449 | hsa-miR-30c, hsa-miR-363, hsa-miR-107, hsa-miR-486-3p, hsa-miR-497, hsa-miR-339-5p | 89% | 86% | 91% |
| MS71 | SEQ ID NO: 351, SEQ ID NO: 334, SEQ ID NO: 449, SEQ ID NO: 165, SEQ ID NO: 624, SEQ ID NO: 128 | hsa-miR-486-3p, hsa-miR-497, hsa-miR-339-5p, hsa-miR-593*, hsa-miR-194, hsa-miR-627 | 83% | 83% | 82% |
| MS72 | SEQ ID NO: 165, SEQ ID NO: 624, SEQ ID NO: 128, SEQ ID NO: 22, SEQ ID NO: 616, SEQ ID NO: 883 | hsa-miR-593*, hsa-miR-194, hsa-miR-627, hsa-miR-93, hsa-miR-197, hsa-miR-101 | 72% | 73% | 72% |
| MS73 | SEQ ID NO: 901, SEQ ID NO: 190, SEQ ID NO: 360, SEQ ID NO: 329, SEQ ID NO: 61, SEQ ID NO: 895, SEQ ID NO: 834, SEQ ID NO: 809, SEQ ID NO: 893, SEQ ID NO: 23 | hsa-let-7b, hsa-miR-574-3p, hsa-miR-454, hsa-miR-500, hsa-miR-766, hsa-let-7e, hsa-miR-1234, hsa-miR-125a-5p, hsa-let-7f, hsa-miR-92b* | 90% | 91% | 89% |
| MS74 | SEQ ID NO: 895, SEQ ID NO: 834, SEQ ID NO: 809, SEQ ID NO: 893, SEQ ID NO: 23, SEQ ID NO: 899, SEQ ID NO: 890, SEQ ID NO: 713, SEQ ID NO: 888, SEQ ID NO: 746, SEQ ID NO: 803 | hsa-let-7e, hsa-miR-1234, hsa-miR-125a-5p, hsa-let-7f, hsa-miR-92b*, hsa-let-7c, hsa-let-7g, hsa-miR-145, hsa-let-7i, hsa-miR-130b, hsa-miR-1260 | 93% | 95% | 91% |
| MS75 | SEQ ID NO: 890, SEQ ID NO: 713, SEQ ID NO: 888, SEQ ID NO: 746, SEQ ID NO: 803, SEQ ID NO: 460, SEQ ID NO: 478, SEQ ID NO: 897, SEQ ID NO: 327, SEQ ID NO: 635 | hsa-let-7g, hsa-miR-145, hsa-let-7i, hsa-miR-130b, hsa-miR-1260, hsa-miR-330-3p, hsa-miR-30e, hsa-let-7d, hsa-miR-501-3p, hsa-miR-1913 | 92% | 93% | 91% |
| MS76 | SEQ ID NO: 460, SEQ ID NO: 478, SEQ ID NO: 897, SEQ ID NO: 327, SEQ ID NO: 635, SEQ ID NO: 605, SEQ ID NO: 549, SEQ ID NO: 540, SEQ ID NO: 622, SEQ ID NO: 249 | hsa-miR-330-3p, hsa-miR-30e, hsa-let-7d, hsa-miR-501-3p, hsa-miR-1913, hsa-miR-199a-5p, hsa-miR-22, hsa-miR-223, hsa-miR-195, hsa-miR-532-3p | 92% | 91% | 93% |
| MS77 | SEQ ID NO: 605, SEQ ID NO: 549, SEQ ID NO: 540, SEQ ID NO: 622, SEQ ID NO: 249, SEQ ID NO: 666, SEQ ID NO: 630, SEQ ID NO: 483, SEQ ID NO: 428, SEQ ID NO: 872 | hsa-miR-199a-5p, hsa-miR-22, hsa-miR-223, hsa-miR-195, hsa-miR-532-3p, hsa-miR-182, hsa-miR-192, hsa-miR-30c, hsa-miR-363, hsa-miR-107 | 95% | 95% | 94% |
| MS78 | SEQ ID NO: 666, SEQ ID NO: 630, SEQ ID NO: 483, SEQ ID NO: 428, SEQ ID NO: 872, SEQ ID NO: 351, SEQ ID NO: 334, SEQ ID NO: 449, SEQ ID NO: 165, SEQ ID NO: 624 | hsa-miR-182, hsa-miR-192, hsa-miR-30c, hsa-miR-363, hsa-miR-107, hsa-miR-486-3p, hsa-miR-497, hsa-miR-339-5p, hsa-miR-593*, hsa-miR-194 | 91% | 95% | 88% |

FIG. 18D (Cont.)

| | | | | | |
|---|---|---|---|---|---|
| MS79 | SEQ ID NO: 351, SEQ ID NO: 334, SEQ ID NO: 449, SEQ ID NO: 165, SEQ ID NO: 624, SEQ ID NO: 128, SEQ ID NO: 22, SEQ ID NO: 616, SEQ ID NO: 883, SEQ ID NO: 27 | hsa-miR-486-3p, hsa-miR-497, hsa-miR-339-5p, hsa-miR-593*, hsa-miR-194, hsa-miR-627, hsa-miR-93, hsa-miR-197, hsa-miR-101, hsa-miR-92a | 84% | 89% | 79% |
| MS80 | SEQ ID NO: 128, SEQ ID NO: 22, SEQ ID NO: 616, SEQ ID NO: 883, SEQ ID NO: 27, SEQ ID NO: 386, SEQ ID NO: 704, SEQ ID NO: 756, SEQ ID NO: 215, SEQ ID NO: 429 | hsa-miR-627, hsa-miR-93, hsa-miR-197, hsa-miR-101, hsa-miR-92a, hsa-miR-422a, hsa-miR-1470, hsa-miR-1301, hsa-miR-550*, hsa-miR-362-5p | 89% | 94% | 83% |
| MS81 | SEQ ID NO: 386, SEQ ID NO: 704, SEQ ID NO: 756, SEQ ID NO: 215, SEQ ID NO: 429, SEQ ID NO: 561, SEQ ID NO: 629, SEQ ID NO: 475, SEQ ID NO: 706, SEQ ID NO: 529 | hsa-miR-422a, hsa-miR-1470, hsa-miR-1301, hsa-miR-550*, hsa-miR-362-5p, hsa-miR-214, hsa-miR-192*, hsa-miR-31*, hsa-miR-146b-5p, hsa-miR-24 | 90% | 90% | 91% |
| MS82 | SEQ ID NO: 901, SEQ ID NO: 360, SEQ ID NO: 61, SEQ ID NO: 834, SEQ ID NO: 893 | hsa-let-7b, hsa-miR-454, hsa-miR-766, hsa-miR-1234, hsa-let-7f | 92% | 89% | 96% |
| MS83 | SEQ ID NO: 329, SEQ ID NO: 895, SEQ ID NO: 809, SEQ ID NO: 23, SEQ ID NO: 890 | hsa-miR-500, hsa-let-7e, hsa-miR-125a-5p, hsa-miR-92b*, hsa-let-7g | 85% | 86% | 84% |
| MS84 | SEQ ID NO: 809, SEQ ID NO: 23, SEQ ID NO: 890, SEQ ID NO: 888, SEQ ID NO: 803 | hsa-miR-125a-5p, hsa-miR-92b*, hsa-let-7g, hsa-let-7i, hsa-miR-1260 | 81% | 77% | 86% |

Figure 19
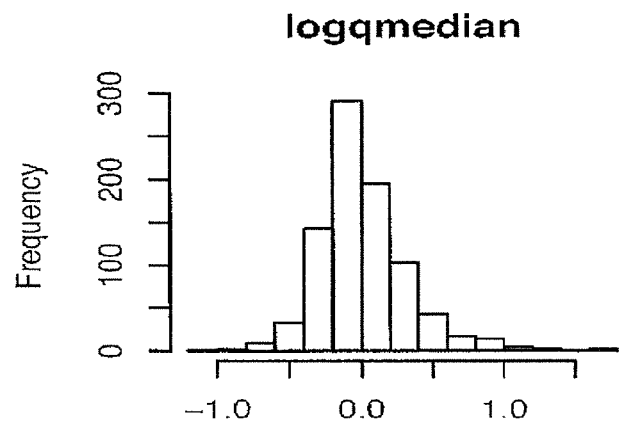
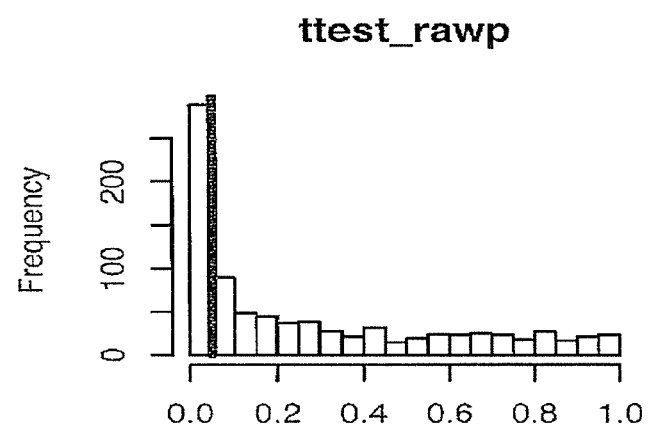
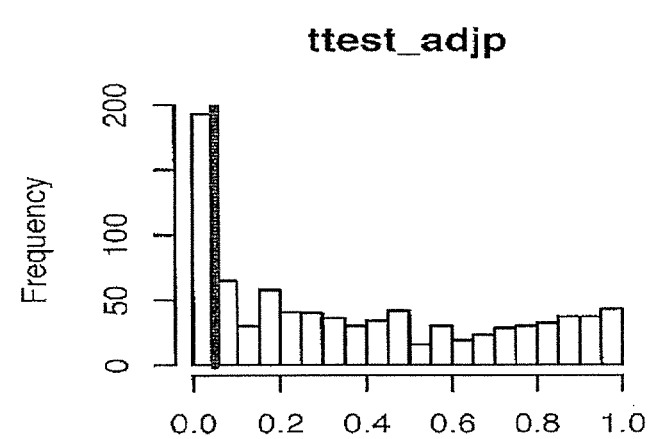

FIG. 30A

| | | | | |
|---|---|---|---|---|
| SEQ ID NO: 656 | Tab3-1 | hsa-miR-186 | CAAAGAAUUCCUUUGGGCU | 1,74E-09 |
| SEQ ID NO: 896 | Tab3-2 | hsa-let-7d* | CUAUACGACCUGCUGCCUUUCU | 1,74E-09 |
| SEQ ID NO: 649 | Tab3-3 | hsa-miR-18a* | ACUGCCCUAAGUGCUCCUUCUGG | 1,72E-08 |
| SEQ ID NO: 713 | Tab3-4 | hsa-miR-145 | GUCCAGUUUUCCCAGGAAUCCCU | 7,98E-08 |
| SEQ ID NO: 4 | Tab3-5 | hsa-miR-99a | AACCCGUAGAUCCGAUCUUGUG | 1,14E-07 |
| SEQ ID NO: 87 | Tab3-6 | hsa-miR-664 | UAUUCAUUUAUCCCCAGCCUACA | 1,26E-07 |
| SEQ ID NO: 326 | Tab3-7 | hsa-miR-501-5p | AAUCCUUUGUCCCUGGGUGAGA | 1,48E-07 |
| SEQ ID NO: 402 | Tab3-8 | hsa-miR-378* | CUCCUGACUCCAGGUCCUGUGU | 1,55E-07 |
| SEQ ID NO: 501 | Tab3-9 | hsa-miR-29c* | UGACCGAUUUCUCCUGGUGUUC | 1,55E-07 |
| SEQ ID NO: 426 | Tab3-10 | hsa-miR-365 | UAAUGCCCCUAAAAAUCCUUAU | 1,78E-07 |
| SEQ ID NO: 779 | Tab3-11 | hsa-miR-1280 | UCCCACCGCUGCCACCC | 1,78E-07 |
| SEQ ID NO: 462 | Tab3-12 | hsa-miR-328 | CUGGCCCUCUCUGCCCUUCCGU | 2,01E-07 |
| SEQ ID NO: 822 | Tab3-13 | hsa-miR-1249 | ACGCCCUUCCCCCCCUUCUCA | 2,01E-07 |
| SEQ ID NO: 386 | Tab3-14 | hsa-miR-422a | ACUGGACUUAGGGUCAGAAGGC | 2,13E-07 |
| SEQ ID NO: 480 | Tab3-15 | hsa-miR-30d | UGUAAACAUCCCCGACUGGAAG | 4,51E-07 |
| SEQ ID NO: 674 | Tab3-16 | hsa-miR-17 | ACUGCAGUGAAGGCACUUGUAG | 4,51E-07 |
| SEQ ID NO: 254 | Tab3-17 | hsa-miR-525-5p | CUCCAGAGGGAUGCACUUUCU | 7,69E-07 |
| SEQ ID NO: 441 | Tab3-18 | hsa-miR-342-5p | AGGGGUGCUAUCUGUGAUUGA | 8,15E-07 |
| SEQ ID NO: 660 | Tab3-19 | hsa-miR-183* | GUGAAUUACCGAAGGGCCAUAA | 8,20E-07 |
| SEQ ID NO: 693 | Tab3-20 | hsa-miR-151-3p | CUAGACUGAAGCUCCUUGAGG | 1,37E-06 |
| SEQ ID NO: 431 | Tab3-21 | hsa-miR-361-5p | UUAUCAGAAUCUCCAGGGGUAC | 1,60E-06 |
| SEQ ID NO: 432 | Tab3-22 | hsa-miR-361-3p | UCCCCCAGGUGUGAUUCUGAUU | 1,60E-06 |
| SEQ ID NO: 577 | Tab3-23 | hsa-miR-20b | CAAAGUGCUCAUAGUGCAGGUAG | 2,45E-06 |
| SEQ ID NO: 487 | Tab3-24 | hsa-miR-30a | UGUAAACAUCCUCGACUGGAAG | 3,76E-06 |
| SEQ ID NO: 26 | Tab3-25 | hsa-miR-92a-1* | AGGUUGGGAUCGGUUGCAAUGCU | 3,76E-06 |
| SEQ ID NO: 671 | Tab3-26 | hsa-miR-181a-2* | ACCACUGACCGUUGACUGUACC | 3,76E-06 |
| SEQ ID NO: 430 | Tab3-27 | hsa-miR-362-3p | AACACACCUAUUCAAGGAUUCA | 3,76E-06 |
| SEQ ID NO: 477 | Tab3-28 | hsa-miR-30e* | CUUUCAGUCGGAUGUUUACAGC | 5,51E-06 |
| SEQ ID NO: 597 | Tab3-29 | hsa-miR-200a | UAACACUGUCUGGUAACGAUGU | 7,43E-06 |
| SEQ ID NO: 840 | Tab3-30 | hsa-miR-1227 | CGUGCCACCCUUUUCCCCAG | 7,43E-06 |
| SEQ ID NO: 786 | Tab3-31 | hsa-miR-1275 | GUGGGGGAGAGGCUGUC | 7,43E-06 |
| SEQ ID NO: 900 | Tab3-32 | hsa-let-7b* | CUAUACAACCUACUGCCUUCCC | 7,43E-06 |
| SEQ ID NO: 429 | Tab3-33 | hsa-miR-362-5p | AAUCCUUGGAACCUAGGUGUGAGU | 7,43E-06 |
| SEQ ID NO: 438 | Tab3-34 | hsa-miR-34a | UGGCAGUGUCUUAGCUGGUUGU | 7,75E-06 |

FIG. 30A (Cont.)

| SEQ ID NO | Tab | miRNA | Sequence | p-value |
|---|---|---|---|---|
| SEQ ID NO: 664 | Tab3-35 | hsa-miR-1825 | UCCAGUGCCCUCCUCUCC | 9,35E-06 |
| SEQ ID NO: 756 | Tab3-36 | hsa-miR-1301 | UUGCAGCUGCCUGGGAGUGACUUC | 1,01E-05 |
| SEQ ID NO: 865 | Tab3-37 | hsa-miR-1180 | UUUCCGGCUCGCGUGGGUGUGU | 1,41E-05 |
| SEQ ID NO: 177 | Tab3-38 | hsa-miR-584 | UUAUGGUUUGCCUGGGACUGAG | 1,46E-05 |
| SEQ ID NO: 600 | Tab3-39 | hsa-miR-19b | UGUGCAAAUCCAUGCAAAACUGA | 1,54E-05 |
| SEQ ID NO: 773 | Tab3-40 | hsa-miR-1286 | UGCAGGACCAAGAUGAGCCCU | 1,69E-05 |
| SEQ ID NO: 559 | Tab3-41 | hsa-miR-215 | AUGACCUAUGAAUUGACAGAC | 1,69E-05 |
| SEQ ID NO: 558 | Tab3-42 | hsa-miR-216a | UAAUCUCAGCUGGCAACUGUGA | 1,69E-05 |
| SEQ ID NO: 131 | Tab3-43 | hsa-miR-625 | AGGGGGAAAGUUCUAUAGUCC | 1,71E-05 |
| SEQ ID NO: 719 | Tab3-44 | hsa-miR-142-3p | UGUAGGUUUCCUACUUUAUGGA | 1,74E-05 |
| SEQ ID NO: 531 | Tab3-45 | hsa-miR-23b | AUCACAUUGCCAGGGAUUACC | 1,86E-05 |
| SEQ ID NO: 515 | Tab3-46 | hsa-miR-28-3p | CACUAGAUUGUGAGCUCCUGGA | 2,16E-05 |
| SEQ ID NO: 803 | Tab3-47 | hsa-miR-1260 | AUCCCACCUCUGCCACCA | 2,16E-05 |
| SEQ ID NO: 341 | Tab3-48 | hsa-miR-491-5p | AGUGGGGAACCCUUCCAUGAGG | 2,28E-05 |
| SEQ ID NO: 281 | Tab3-49 | hsa-miR-519a* | CUCUAGAGGGAAGCGCUUUCUG | 2,32E-05 |
| SEQ ID NO: 11 | Tab3-50 | hsa-miR-942 | UCUUCUCUGUUUUGGCCAUGUG | 2,53E-05 |
| SEQ ID NO: 215 | Tab3-51 | hsa-miR-550* | UGUCUUACUCCCUCAGGCACAU | 2,58E-05 |
| SEQ ID NO: 158 | Tab3-52 | hsa-miR-601 | UGGUCUAGAGGGAUUGUUGGAGGAG | 2,97E-05 |
| SEQ ID NO: 279 | Tab3-53 | hsa-miR-519b-5p | CUCUAGAGGGAAGCGCUUUCUG | 2,97E-05 |
| SEQ ID NO: 820 | Tab3-54 | hsa-miR-1251 | ACUCUAGGCUGCAAAGGCGCU | 3,21E-05 |
| SEQ ID NO: 809 | Tab3-55 | hsa-miR-125a-5p | UCCCUGAGACCCUUUAACCUGUGA | 3,80E-05 |
| SEQ ID NO: 709 | Tab3-56 | hsa-miR-146a | UGAGAACUGAAUUCCAUGGGUU | 3,80E-05 |
| SEQ ID NO: 548 | Tab3-57 | hsa-miR-22* | AGUUCUUCAGUGGCAAGCUUUA | 3,88E-05 |
| SEQ ID NO: 804 | Tab3-58 | hsa-miR-126* | CAUUAUUACUUUUGGUACGCG | 4,44E-05 |
| SEQ ID NO: 788 | Tab3-59 | hsa-miR-1274a | GUCCCUGUUCAGGCGCCA | 4,56E-05 |
| SEQ ID NO: 507 | Tab3-60 | hsa-miR-29a | UAGCACCAUCUGAAAUCGGUUA | 4,86E-05 |
| SEQ ID NO: 356 | Tab3-61 | hsa-miR-483-3p | UCACUCCUCUCCUCCGUCUU | 5,16E-05 |
| SEQ ID NO: 410 | Tab3-62 | hsa-miR-375 | UUUGUUCGUUCGGCUCGCGUGA | 5,16E-05 |
| SEQ ID NO: 309 | Tab3-63 | hsa-miR-512-5p | CACUCAGCCUUGAGGGCACUUUC | 5,94E-05 |
| SEQ ID NO: 206 | Tab3-64 | hsa-miR-556-5p | GAUGAGCUCAUUGUAAUAUGAG | 6,54E-05 |
| SEQ ID NO: 743 | Tab3-65 | hsa-miR-132* | ACCGUGGCUUUCGAUUGCUGUCUA | 6,54E-05 |
| SEQ ID NO: 679 | Tab3-66 | hsa-miR-15b* | CGAAUCAUUAUUUGCUGCUCUA | 6,86E-05 |
| SEQ ID NO: 849 | Tab3-67 | hsa-miR-1208 | UCACUGUUCAGACAGGCGGA | 6,86E-05 |
| SEQ ID NO: 300 | Tab3-68 | hsa-miR-516a-5p | UUCUCGAGGAAAGAAGCACUUUC | 6,94E-05 |
| SEQ ID NO: 520 | Tab3-69 | hsa-miR-26b* | CCUGUUCUCCAUUACUUGGCUC | 8,32E-05 |
| SEQ ID NO: 246 | Tab3-70 | hsa-miR-541 | UGGUGGGCACAGAAUCUGGACU | 8,32E-05 |
| SEQ ID NO: 23 | Tab3-71 | hsa-miR-92b* | AGGGACGGGACGCGGUGCAGUG | 8,99E-05 |

FIG. 30A (Cont.)

| | | | |
|---|---|---|---|
| SEQ ID NO: 670 | Tab3-72 | hsa-miR-181b | AACAUUCAUGCUGUCGGUGGGU | 9.35E-05 |
| SEQ ID NO: 828 | Tab3-73 | hsa-miR-1243 | AACUGGAUCAAUUAUAAGGAGUG | 9.48E-05 |
| SEQ ID NO: 874 | Tab3-74 | hsa-miR-106b | UAAAGUGCUGACAGUGCAGAU | 9.48E-05 |
| SEQ ID NO: 440 | Tab3-75 | hsa-miR-345 | GCUGACUCCUAGUCCAGGGCUC | 9.48E-05 |
| SEQ ID NO: 122 | Tab3-76 | hsa-miR-631 | AGACCUGGCCCAGACCUCAGC | 9.48E-05 |
| SEQ ID NO: 745 | Tab3-77 | hsa-miR-130b* | ACUCUUUCCCUGUUGCACUAC | 9.90E-05 |
| SEQ ID NO: 136 | Tab3-78 | hsa-miR-621 | GGCUAGCAACAGCGCUUACCU | 0.000106177 |
| SEQ ID NO: 543 | Tab3-79 | hsa-miR-221* | ACCUGGCAUACAAUGUAGAUUU | 0.000108099 |
| SEQ ID NO: 358 | Tab3-80 | hsa-miR-455-3p | GCAGUCCAUGGGCAUAUACAC | 0.000108118 |
| SEQ ID NO: 342 | Tab3-81 | hsa-miR-491-3p | CUUAUGCAAGAUUCCCUUCUAC | 0.000108131 |
| SEQ ID NO: 801 | Tab3-82 | hsa-miR-1262 | AUGGGUGAAUUUGUAGAAGGAU | 0.000123646 |
| SEQ ID NO: 705 | Tab3-83 | hsa-miR-147 | GUGUGUGGAAAUGCUUCUGC | 0.000136368 |
| SEQ ID NO: 118 | Tab3-84 | hsa-miR-635 | ACUUGGGCACUGAAACAAUGCC | 0.000146481 |
| SEQ ID NO: 146 | Tab3-85 | hsa-miR-613 | AGGAAUGUUCCUUCUUUGCC | 0.000146481 |
| SEQ ID NO: 127 | Tab3-86 | hsa-miR-628-3p | UCUAGUAAGAGUGGCAGUCGA | 0.000146481 |
| SEQ ID NO: 711 | Tab3-87 | hsa-miR-1468 | CUCCGUUUGCCUGUUUCGCUG | 0.0001502 |
| SEQ ID NO: 45 | Tab3-88 | hsa-miR-885-5p | UCCAUUACACUACCCUGCCUCU | 0.000152216 |
| SEQ ID NO: 182 | Tab3-89 | hsa-miR-580 | UUGAGAAUGAUGAAUCACUUAGG | 0.000155055 |
| SEQ ID NO: 541 | Tab3-90 | hsa-miR-222* | CUCAGUAGCCAGUGUAUAGUGCAGGUAG | 0.000162295 |
| SEQ ID NO: 579 | Tab3-91 | hsa-miR-20a | UAAAGUGCUUAUCGCUCCGGCCUC | 0.000176828 |
| SEQ ID NO: 24 | Tab3-92 | hsa-miR-92b | UAUUGCACUCGUCCCGGCCUCC | 0.000178936 |
| SEQ ID NO: 62 | Tab3-93 | hsa-miR-765 | UGGAGGAGAAGGAAGGUGAUG | 0.000179006 |
| SEQ ID NO: 630 | Tab3-94 | hsa-miR-192 | CUGACCUAUGAAUUGACAGCC | 0.000179006 |
| SEQ ID NO: 255 | Tab3-95 | hsa-miR-525-3p | GAAGGCGCUUCCCUUUAGAGCG | 0.000194745 |
| SEQ ID NO: 66 | Tab3-96 | hsa-miR-760 | CGGCUCUGGGUCUGUGGGGA | 0.000209014 |
| SEQ ID NO: 830 | Tab3-97 | hsa-miR-124 | UAAGGCACGCGGUGAAUGCC | 0.000211903 |
| SEQ ID NO: 297 | Tab3-98 | hsa-miR-517* | CCUCUAGAUGGAAGCACUGUCU | 0.000218124 |
| SEQ ID NO: 59 | Tab3-99 | hsa-miR-767-5p | UGCACCAUGGUUGUCUGAGCAUG | 0.000225313 |
| SEQ ID NO: 264 | Tab3-100 | hsa-miR-520g | ACAAAGUGCUUCCCUUUAGAGUGU | 0.000234546 |
| SEQ ID NO: 172 | Tab3-101 | hsa-miR-589 | UGAGAACCACGUCUGCUCUGAG | 0.000241681 |
| SEQ ID NO: 798 | Tab3-102 | hsa-miR-1265 | CAGGAUGUGGGGAAGCUGUUCUU | 0.000258933 |
| SEQ ID NO: 258 | Tab3-103 | hsa-miR-523* | CUCUAGAGGGAAGCACUUUCUG | 0.000263932 |
| SEQ ID NO: 253 | Tab3-104 | hsa-miR-526a | CUCUAGAGGGAAGCACUUUCUG | 0.000265558 |
| SEQ ID NO: 832 | Tab3-105 | hsa-miR-1237 | UCCUUCUGCUCCGUCCCCCAG | 0.000267379 |
| SEQ ID NO: 165 | Tab3-106 | hsa-miR-593* | AGGCACCAGCCAGGCAUUGCUCAGC | 0.000267379 |
| SEQ ID NO: 6 | Tab3-107 | hsa-miR-96* | AAUCAUGUGCAGUGCCAAUAUG | 0.000267379 |
| SEQ ID NO: 314 | Tab3-108 | hsa-miR-509-3p | UGAUUGGUACGUCUGUGGGUAG | 0.000267379 |

FIG. 30A (Cont.)

| | | | |
|---|---|---|---|
| SEQ ID NO: 407 | Tab3-109 | hsa-miR-376b | AUCAUAGAGGAAAAUCCAUGUU | 0.000271522 |
| SEQ ID NO: 588 | Tab3-110 | hsa-miR-204 | UUCCUUUGUCAUCCUAUGCCU | 0.000274481 |
| SEQ ID NO: 2 | Tab3-111 | hsa-miR-99b | CACCCGUAGAACCGACCUUGCG | 0.000280285 |
| SEQ ID NO: 777 | Tab3-112 | hsa-miR-1282 | UCGUUUGCCUUUUUCUGCUU | 0.000321754 |
| SEQ ID NO: 495 | Tab3-113 | hsa-miR-302b | UAAGUGCUUCCAUGUUUUAGUAG | 0.000336162 |
| SEQ ID NO: 448 | Tab3-114 | hsa-miR-33a | GUGCAUUGUAGUUGCAUUGCA | 0.000336162 |
| SEQ ID NO: 260 | Tab3-115 | hsa-miR-522* | CUCUAGAGGGAAGCGCUUUCUG | 0.000371737 |
| SEQ ID NO: 561 | Tab3-116 | hsa-miR-214 | ACAGCAGGCACAGACAGGCAGU | 0.000377128 |
| SEQ ID NO: 107 | Tab3-117 | hsa-miR-646 | AAGCAGCUGCCUCUGAGGC | 0.000378759 |
| SEQ ID NO: 98 | Tab3-118 | hsa-miR-654-5p | UGGUGGGCCGCAGAACAUGUGC | 0.000383522 |
| SEQ ID NO: 346 | Tab3-119 | hsa-miR-488* | CCCAGAUAAUGGCACUCUCAA | 0.000383522 |
| SEQ ID NO: 152 | Tab3-120 | hsa-miR-607 | GUUCAAAUCCAGAUCUAUAAC | 0.000388921 |
| SEQ ID NO: 225 | Tab3-121 | hsa-miR-548j | AAAAGUAAUUGCGGUCUUUGGU | 0.00039435 |
| SEQ ID NO: 42 | Tab3-122 | hsa-miR-887 | GUGAACGGGCGCCAUCCCGAGG | 0.000410217 |
| SEQ ID NO: 657 | Tab3-123 | hsa-miR-185* | AGGGGCUGGCUUUCCUCUGGUC | 0.000439242 |
| SEQ ID NO: 55 | Tab3-124 | hsa-miR-802 | CAGUAACAAAGAUUCAUCCUUGU | 0.000444479 |
| SEQ ID NO: 712 | Tab3-125 | hsa-miR-145* | GGAUUCCUGGAAAUACUGUUCU | 0.000445059 |
| SEQ ID NO: 887 | Tab3-126 | hsa-let-7i* | CUGCGCAAGCUACUGCCUUGCU | 0.000449525 |
| SEQ ID NO: 355 | Tab3-127 | hsa-miR-483-5p | AAGACGGGAGGAAAGAAGGGAG | 0.000449525 |
| SEQ ID NO: 285 | Tab3-128 | hsa-miR-518e* | CUCUAGAGGGAAGCGCUUUCUG | 0.000449525 |
| SEQ ID NO: 500 | Tab3-129 | hsa-miR-300 | UAUACAAGGGCAGACUCUCUCU | 0.000449525 |
| SEQ ID NO: 315 | Tab3-130 | hsa-miR-509-3-5p | UACUGCAGACAGUGGCAAUCAUG | 0.000457698 |
| SEQ ID NO: 274 | Tab3-131 | hsa-miR-519e* | UUCUCCAAAAGGGAGCACUUUC | 0.000459782 |
| SEQ ID NO: 362 | Tab3-132 | hsa-miR-452* | CUCAUCUGCAAAGAAGUAAGUG | 0.000459782 |
| SEQ ID NO: 578 | Tab3-133 | hsa-miR-20a* | ACUGCAUUAUGAGCACUUAAAG | 0.000459782 |
| SEQ ID NO: 624 | Tab3-134 | hsa-miR-194 | UGUAACAGCAACUCCAUGUGGA | 0.000459782 |
| SEQ ID NO: 199 | Tab3-135 | hsa-miR-564 | AGGCACGGUGUCAGCAGGC | 0.000459782 |
| SEQ ID NO: 876 | Tab3-136 | hsa-miR-106a | AAAAGUGCUUACAGUGCAGGUAG | 0.000459782 |
| SEQ ID NO: 397 | Tab3-137 | hsa-miR-381 | UAUACAAGGGCAAGCUCUCUGU | 0.000483618 |
| SEQ ID NO: 684 | Tab3-138 | hsa-miR-155 | UUAAUGCUAAUCGUGAUAGGGGU | 0.000494181 |
| SEQ ID NO: 721 | Tab3-139 | hsa-miR-141 | UAACACUGUCUGGUAAAGAUGG | 0.00051554 |
| SEQ ID NO: 460 | Tab3-140 | hsa-miR-330-3p | GCAAAGCACACGGCCUGCAGAGA | 0.000518249 |
| SEQ ID NO: 35 | Tab3-141 | hsa-miR-892a | CACUGUGUCCUUUCUGCGUAG | 0.000518249 |
| SEQ ID NO: 113 | Tab3-142 | hsa-miR-640 | AUGAUCCAGGAACCUGUGCUG | 0.000523317 |
| SEQ ID NO: 738 | Tab3-143 | hsa-miR-133a | UUUGGUCCCCUUCAACCAGCUG | 0.000527673 |
| SEQ ID NO: 329 | Tab3-144 | hsa-miR-500 | UAAUCCUUGCUACAGGAACUGA | 0.000527673 |
| SEQ ID NO: 556 | Tab3-145 | hsa-miR-217 | UACUGCAUCAGGAACUGAUUGGA | 0.000545029 |

FIG. 30A (Cont.)

| | | | | |
|---|---|---|---|---|
| SEQ ID NO: 320 | Tab3-146 | hsa-miR-505* | GGGAGCCAGGAAGUAUUGAUGU | 0.000545029 |
| SEQ ID NO: 132 | Tab3-147 | hsa-miR-624* | UAGUACCAGUAGGACUUGUGUUCA | 0.000546077 |
| SEQ ID NO: 791 | Tab3-148 | hsa-miR-1272 | GAUGAUGAUGGCAGCAAAUUCUGAAA | 0.000546077 |
| SEQ ID NO: 842 | Tab3-149 | hsa-miR-1226 | UCACCAGCCCUGUGUUCCUAG | 0.000567222 |
| SEQ ID NO: 627 | Tab3-150 | hsa-miR-193a-5p | UGGGUCUUUGCGGGCGAGAUGA | 0.000557065 |
| SEQ ID NO: 714 | Tab3-151 | hsa-miR-144* | GGAUAUCAUCAUAUACUGUAAG | 0.000593657 |
| SEQ ID NO: 826 | Tab3-152 | hsa-miR-1245 | AAGUUCUAAAGGCCCUACAU | 0.000596824 |
| SEQ ID NO: 553 | Tab3-153 | hsa-miR-218-2* | CAUGGUUCUGUCAAGCACCGCG | 0.000649926 |
| SEQ ID NO: 331 | Tab3-154 | hsa-miR-499-3p | AACAUCACAGCAAGUCUGUGCU | 0.000649926 |
| SEQ ID NO: 605 | Tab3-155 | hsa-miR-199a-5p | CCCAGUGUUCAGACUACCUGUUC | 0.000662728 |
| SEQ ID NO: 94 | Tab3-156 | hsa-miR-658 | GGCGGAGGGAAGUAGGUCCGUUGGU | 0.000680384 |
| SEQ ID NO: 701 | Tab3-157 | hsa-miR-148a | UCAGUGCACUACAGAACUUUGU | 0.000688011 |
| SEQ ID NO: 20 | Tab3-158 | hsa-miR-933 | UGUGCGCAGGGAGACCUCUCCC | 0.000709756 |
| SEQ ID NO: 742 | Tab3-159 | hsa-miR-1321 | CAGGGAGGUGAAUGUGAU | 0.000718543 |
| SEQ ID NO: 382 | Tab3-160 | hsa-miR-424* | CAAAACGUGAGGCGCUGCUAU | 0.000747253 |
| SEQ ID NO: 650 | Tab3-161 | hsa-miR-18a | UAAGGUGCAUCUAGUGCAGAUAG | 0.000790611 |
| SEQ ID NO: 478 | Tab3-162 | hsa-miR-30e | UGUAAACAUCCUUGACUGGAAG | 0.000828808 |
| SEQ ID NO: 167 | Tab3-163 | hsa-miR-592 | UUGUGUCAAUAUGCGAUGAUGU | 0.000882975 |
| SEQ ID NO: 574 | Tab3-164 | hsa-miR-21* | CAACACCAGUCGAUGGGCUGU | 0.000918128 |
| SEQ ID NO: 622 | Tab3-165 | hsa-miR-195 | UAGCAGCACAGAAAUAUUGGC | 0.000972364 |
| SEQ ID NO: 593 | Tab3-166 | hsa-miR-200c | UAAUACUGCCGGGUAAUGAUGGA | 0.000972364 |
| SEQ ID NO: 872 | Tab3-167 | hsa-miR-107 | AGCAGCAUUGUACAGGGCUAUCA | 0.000999099 |
| SEQ ID NO: 881 | Tab3-168 | hsa-miR-103 | AGCAGCAUUGUACAGGGCUAUGA | 0.001014412 |
| SEQ ID NO: 776 | Tab3-169 | hsa-miR-1283 | UCUACAAAGGAAAGCGCUUUCU | 0.001094476 |
| SEQ ID NO: 675 | Tab3-170 | hsa-miR-17 | CAAAGUGCUUACAGUGCAGGUAG | 0.001161942 |
| SEQ ID NO: 47 | Tab3-171 | hsa-miR-877* | UCCUCUUCUCCCUCCUCCCAG | 0.001161942 |
| SEQ ID NO: 324 | Tab3-172 | hsa-miR-502-5p | AUCCUUGCUAUCUGGGUGCUA | 0.001196005 |
| SEQ ID NO: 220 | Tab3-173 | hsa-miR-548o | CCAAAACUGCAGUUACUUUGC | 0.001207378 |
| SEQ ID NO: 378 | Tab3-174 | hsa-miR-431 | UGUCUUGCAGGCCGUCAUGCA | 0.001216841 |
| SEQ ID NO: 393 | Tab3-175 | hsa-miR-409-3p | GAAUGUUGCUCGGUGAACCCCU | 0.001216841 |
| SEQ ID NO: 839 | Tab3-176 | hsa-miR-1228 | UCACACCUGCCUCGCCCCCC | 0.001341108 |
| SEQ ID NO: 557 | Tab3-177 | hsa-miR-216b | AAAUCUCUGCAGGCAAAUGUGA | 0.001341108 |
| SEQ ID NO: 424 | Tab3-178 | hsa-miR-367 | AAUUGCACUUUAGCAAUGGUGA | 0.001410263 |
| SEQ ID NO: 306 | Tab3-179 | hsa-miR-513b | UUCACAAGGAGGUGUCAUUUAU | 0.001415773 |
| SEQ ID NO: 1 | Tab3-180 | hsa-miR-99b* | CAAGCUCGUGUCUGUGGGUCCG | 0.001422059 |
| SEQ ID NO: 374 | Tab3-181 | hsa-miR-433 | AUCAUGAUGGGCUCCUCGGUGU | 0.001422059 |
| SEQ ID NO: 808 | Tab3-182 | hsa-miR-125b | UCCCUGAGACCCUAACUUGUGA | 0.001422059 |

FIG. 30A (Cont.)

| SEQ ID NO: | | | Sequence | |
|---|---|---|---|---|
| SEQ ID NO: 618 | Tab3-183 | hsa-miR-196b | UAGGUAGUUUCCUGUUGUUGGG | 0.001422059 |
| SEQ ID NO: 596 | Tab3-184 | hsa-miR-200a* | CAUCUUACCGGACAGUGCUGGA | 0.001422059 |
| SEQ ID NO: 343 | Tab3-185 | hsa-miR-490-5p | CCAUGGAUCUCCAGGUGGGU | 0.001522874 |
| SEQ ID NO: 512 | Tab3-186 | hsa-miR-296-5p | AGGGCCCCCCUCAAUCCUGU | 0.001528446 |
| SEQ ID NO: 316 | Tab3-187 | hsa-miR-508-5p | UACUCCAGAGGGCGUCACUCAUG | 0.001557578 |
| SEQ ID NO: 171 | Tab3-188 | hsa-miR-589* | UCAGAACAAAUGCGGUUCCCAGA | 0.001557578 |
| SEQ ID NO: 54 | Tab3-189 | hsa-miR-873 | GCAGGAACUUGUGAGUCUCCU | 0.001557578 |
| SEQ ID NO: 323 | Tab3-190 | hsa-miR-503 | UAGCAGCGGGAACAGUUCUGCAG | 0.001600583 |
| SEQ ID NO: 676 | Tab3-191 | hsa-miR-16-2* | CCAAUAUUACUGUGCUGCUUUA | 0.001604921 |
| SEQ ID NO: 737 | Tab3-192 | hsa-miR-133b | UUUGGUCCCCUUCAACCAGCUA | 0.001604921 |
| SEQ ID NO: 44 | Tab3-193 | hsa-miR-886-3p | CGCGGGUGCUUACUGACCCUU | 0.001667106 |
| SEQ ID NO: 483 | Tab3-194 | hsa-miR-30c | UGUAAACAUCCUACACUCUCAGC | 0.001676161 |
| SEQ ID NO: 733 | Tab3-195 | hsa-miR-135b | UAUGGCUUUUCAUUCCUAUGUGA | 0.00169635 |
| SEQ ID NO: 817 | Tab3-196 | hsa-miR-1254 | AGCCUGGAAGCUGGAGCCUGCAGU | 0.00169635 |
| SEQ ID NO: 841 | Tab3-197 | hsa-miR-1226* | GUGAGGGCAUGCAGGCCUGGAUGGGG | 0.00179557 |
| SEQ ID NO: 785 | Tab3-198 | hsa-miR-127-5p | CUGAAGCUCAGAGGGCUCUGAU | 0.001803272 |
| SEQ ID NO: 272 | Tab3-199 | hsa-miR-520a-5p | CUCCAGAGGGAAGUACUUUCU | 0.001811321 |
| SEQ ID NO: 398 | Tab3-200 | hsa-miR-380* | UGGUUGACCAUAGAACAAUGCGC | 0.001818718 |
| SEQ ID NO: 580 | Tab3-201 | hsa-miR-208b | AUAAGACGAACAAAAGGUUUGU | 0.001818718 |
| SEQ ID NO: 186 | Tab3-202 | hsa-miR-576-5p | AUUCUAAUUGCUCCACGUCUUU | 0.001818718 |
| SEQ ID NO: 856 | Tab3-203 | hsa-miR-1202 | GUGCCAGCUGCAGUGGGGAG | 0.002015591 |
| SEQ ID NO: 715 | Tab3-204 | hsa-miR-144 | UACAGUAUAGAUGAUGUACU | 0.002015591 |
| SEQ ID NO: 545 | Tab3-205 | hsa-miR-220c | ACACAGGGCUGUUGUGAAGACU | 0.002136859 |
| SEQ ID NO: 787 | Tab3-206 | hsa-miR-1274b | UCCCUGUGGAGCUGGCGCCA | 0.002157768 |
| SEQ ID NO: 289 | Tab3-207 | hsa-miR-518c* | UCUCUGGAGGGAAGCACUUUCUG | 0.002157768 |
| SEQ ID NO: 282 | Tab3-208 | hsa-miR-519a | AAAGUGCAUCCUUUUAGAGUGU | 0.002174046 |
| SEQ ID NO: 528 | Tab3-209 | hsa-miR-24-1* | UGCCUACUGAGCUGAUAUCAGU | 0.002214127 |
| SEQ ID NO: 124 | Tab3-210 | hsa-miR-629* | GUUCUCCCAACGUGAGCCCAGC | 0.002228151 |
| SEQ ID NO: 135 | Tab3-211 | hsa-miR-622 | ACAGUCUGCUGAGGUUGGAGC | 0.002264447 |
| SEQ ID NO: 173 | Tab3-212 | hsa-miR-588 | UUGGCCACAAUGGGUUAGAAC | 0.002280287 |
| SEQ ID NO: 14 | Tab3-213 | hsa-miR-939 | UGGGGAGCUGAGGCUCUGGGGGUG | 0.002280287 |
| SEQ ID NO: 582 | Tab3-214 | hsa-miR-206 | UGGAAUGUAAGGAAGUGUGUGG | 0.002341549 |
| SEQ ID NO: 821 | Tab3-215 | hsa-miR-1250 | ACGGUGCUGGAUGUGGCCUUU | 0.002375141 |
| SEQ ID NO: 833 | Tab3-216 | hsa-miR-1236 | CCUCAGGGCCCUGUGUCUCUCCAG | 0.002421662 |
| SEQ ID NO: 797 | Tab3-217 | hsa-miR-1266 | UCUCCAAAAGAAAGCACAGGGCU | 0.002482959 |
| SEQ ID NO: 302 | Tab3-218 | hsa-miR-515-5p | UUCUCCAAAAGAAAGCACUUUCUG | 0.002482959 |
| SEQ ID NO: 516 | Tab3-219 | hsa-miR-27b* | AGAGCUUAGCUGAUUGGUGAAC | 0.002506319 |

FIG. 30A (Cont.)

| | | | | |
|---|---|---|---|---|
| SEQ ID NO: 32 | Tab3-220 | hsa-miR-9* | AUAAAGCUAGAUAACCGAAAGU | 0.002603599 |
| SEQ ID NO: 884 | Tab3-221 | hsa-miR-100* | CAAGCUUGUAUCUAUAGGUAUG | 0.002603599 |
| SEQ ID NO: 885 | Tab3-222 | hsa-miR-100 | AACCCGUAGAUCCGAACUUGUG | 0.002749246 |
| SEQ ID NO: 636 | Tab3-223 | hsa-miR-1912 | UACCCAGGAGCAUGCAGUGUGAA | 0.002827701 |
| SEQ ID NO: 82 | Tab3-224 | hsa-miR-671-3p | UCCGGUUCUCAGGGUCCUCCACC | 0.002849005 |
| SEQ ID NO: 652 | Tab3-225 | hsa-miR-188-3p | CUCCCACAUGCAGGGUUUGCA | 0.002862454 |
| SEQ ID NO: 313 | Tab3-226 | hsa-miR-509-5p | UACUGCAGACAGUGGCAAUCA | 0.002942393 |
| SEQ ID NO: 757 | Tab3-227 | hsa-miR-1299 | UUCUGGAAUUCUGUGUGAGGGA | 0.002964854 |
| SEQ ID NO: 473 | Tab3-228 | hsa-miR-32* | CAAUUUAGUGUGUGUGAUAUUU | 0.003001636 |
| SEQ ID NO: 247 | Tab3-229 | hsa-miR-539 | GGAGAAAUUAUCCUUGGUGUGU | 0.003006519 |
| SEQ ID NO: 825 | Tab3-230 | hsa-miR-1246 | AAUGGAUUUUUGGAGCAGG | 0.003196732 |
| SEQ ID NO: 540 | Tab3-231 | hsa-miR-223 | UGUCAGUUUGUCAAAUACCCCA | 0.003196732 |
| SEQ ID NO: 219 | Tab3-232 | hsa-miR-548p | UAGCAAAAACUGCAGUUACUUU | 0.0032184 |
| SEQ ID NO: 625 | Tab3-233 | hsa-miR-193b* | CGGGGUUUUGAGGGCGAGAUGA | 0.003330517 |
| SEQ ID NO: 277 | Tab3-234 | hsa-miR-519c-5p | CUCUAGAGGGAAGCGCUUUCUG | 0.00333355 |
| SEQ ID NO: 198 | Tab3-235 | hsa-miR-566 | GGGCGCCUGUGAUCCCAAC | 0.00333355 |
| SEQ ID NO: 576 | Tab3-236 | hsa-miR-20b* | ACUGUAGUAGGGCACUUCCAG | 0.003339912 |
| SEQ ID NO: 869 | Tab3-237 | hsa-miR-10b | UACCCUGUAGAACCGAAUUUGUG | 0.003339912 |
| SEQ ID NO: 243 | Tab3-238 | hsa-miR-542-5p | UCGGGGAUCAUCAUGUCACGAGA | 0.003348905 |
| SEQ ID NO: 443 | Tab3-239 | hsa-miR-340* | UCCGUCUCAGGGAUCUUUAUAGC | 0.003367466 |
| SEQ ID NO: 723 | Tab3-240 | hsa-miR-140-3p | UACCACAGGGUAGAACCACGG | 0.003367466 |
| SEQ ID NO: 19 | Tab3-241 | hsa-miR-934 | UGUCUACUACUGGAGACACUGG | 0.003367466 |
| SEQ ID NO: 655 | Tab3-242 | hsa-miR-186* | GCCCAAAGGUGAAUUUUUGGG | 0.003414904 |
| SEQ ID NO: 106 | Tab3-243 | hsa-miR-647 | GUGGCUGCGUGGUGGGCACUCCUUC | 0.003450872 |
| SEQ ID NO: 795 | Tab3-244 | hsa-miR-1268 | CGGGCCGUGGUGGGGG | 0.003540983 |
| SEQ ID NO: 153 | Tab3-245 | hsa-miR-606 | AAACUACUGAAAAUCAAAGAU | 0.003608289 |
| SEQ ID NO: 287 | Tab3-246 | hsa-miR-518d-5p | CUCUAGAGGGAAGCACUUUCUG | 0.003675784 |
| SEQ ID NO: 475 | Tab3-247 | hsa-miR-31* | UGCUAUGCCAACAUAUUGCCAU | 0.003675784 |
| SEQ ID NO: 194 | Tab3-248 | hsa-miR-570 | CGAAAACAGCAAUUACCUUUGC | 0.003792356 |
| SEQ ID NO: 164 | Tab3-249 | hsa-miR-595 | GAAGUGCCGUGGUGUGUCU | 0.003992451 |
| SEQ ID NO: 25 | Tab3-250 | hsa-miR-92a-2* | GGGUGGGGAUUUGUUGCAUUAC | 0.004031824 |
| SEQ ID NO: 831 | Tab3-251 | hsa-miR-1238 | CUUCCUCGUCUGGGAUGGCCC | 0.004139974 |
| SEQ ID NO: 532 | Tab3-252 | hsa-miR-23a* | GGGGUUCCUGGGGAUGGGAUUU | 0.004171238 |
| SEQ ID NO: 499 | Tab3-253 | hsa-miR-301a | CAGUGCAAUAGUAUUGUCAAAGC | 0.004242433 |
| SEQ ID NO: 855 | Tab3-254 | hsa-miR-1203 | CCCGAGCCAGGAUGAUGCAGCUC | 0.004275602 |
| SEQ ID NO: 857 | Tab3-255 | hsa-miR-1201 | AGCCUGAUUAAACACAUGCUCUGA | 0.004342912 |
| SEQ ID NO: 188 | Tab3-256 | hsa-miR-575 | GAGCCAGUUGGACAGGAGC | 0.00452256 |

FIG. 30A (Cont.)

| | | | | |
|---|---|---|---|---|
| SEQ ID NO: 125 | Tab3-257 | hsa-miR-629 | UGGGUUUACGUUGGGAGAACU | 0,004603144 |
| SEQ ID NO: 334 | Tab3-258 | hsa-miR-497 | CAGCAGCACACUGUGGUUUGU | 0,004688632 |
| SEQ ID NO: 267 | Tab3-259 | hsa-miR-520d-5p | CUACAAAGGGAAGCCCUUUC | 0,004816748 |
| SEQ ID NO: 180 | Tab3-260 | hsa-miR-582-3p | UAACUGGUUGAACAACUGAACC | 0,004828213 |
| SEQ ID NO: 504 | Tab3-261 | hsa-miR-29b-1* | GCUGGUUUCAUAUGGUGGUUUAGA | 0,004859643 |
| SEQ ID NO: 734 | Tab3-262 | hsa-miR-135a* | UAUAGGGAUUGGAGCCGUGGCG | 0,005256651 |
| SEQ ID NO: 109 | Tab3-263 | hsa-miR-644 | AGUGUGGCUUUCUUAGAGC | 0,005475847 |
| SEQ ID NO: 762 | Tab3-264 | hsa-miR-1295 | UUAGGGCCGAGAUCUGGGUGA | 0,00555437 |
| SEQ ID NO: 321 | Tab3-265 | hsa-miR-505 | CGUCAACACUUGCUGGUUUCCU | 0,005940665 |
| SEQ ID NO: 80 | Tab3-266 | hsa-miR-675 | UGGUGCGGAGAGGGCCCACAGUG | 0,00611489 |
| SEQ ID NO: 505 | Tab3-267 | hsa-miR-29b | UAGCACCAUUUGAAAUCAGUGUU | 0,006128436 |
| SEQ ID NO: 792 | Tab3-268 | hsa-miR-1271 | CUUGGCACCUAGCAAGCACUCA | 0,006259889 |
| SEQ ID NO: 724 | Tab3-269 | hsa-miR-139-5p | UCUACAGUGCACGUGUCUCCAG | 0,006371888 |
| SEQ ID NO: 37 | Tab3-270 | hsa-miR-891a | UGCAACGAACCUGAGCCACUGA | 0,006500774 |
| SEQ ID NO: 291 | Tab3-271 | hsa-miR-518b | CAAAGCGCUCCCCUUUAGAGGU | 0,006500774 |
| SEQ ID NO: 782 | Tab3-272 | hsa-miR-1278 | UAGUACUGUGCAUAUCAUCUAU | 0,006834012 |
| SEQ ID NO: 730 | Tab3-273 | hsa-miR-136* | CAUCAUCGUCUCAAAUGAGUCU | 0,006980604 |
| SEQ ID NO: 256 | Tab3-274 | hsa-miR-524-5p | CUACAAAGGGAAGCACUUUCUC | 0,0071312 |
| SEQ ID NO: 868 | Tab3-275 | hsa-miR-10b* | ACAGAUUCGAUUCUAGGGGAAU | 0,00727873 |
| SEQ ID NO: 802 | Tab3-276 | hsa-miR-1261 | AUGGAUAAGGCUUUGGCUU | 0,007729932 |
| SEQ ID NO: 699 | Tab3-277 | hsa-miR-148b | UCAGUGCAUCACAGAACUUUGU | 0,007756079 |
| SEQ ID NO: 444 | Tab3-278 | hsa-miR-340 | UUAUAAAGCAAUGAGACUGAUU | 0,007881577 |
| SEQ ID NO: 29 | Tab3-279 | hsa-miR-922 | GCAGCAGAGAAUAGGACUACGUC | 0,007900544 |
| SEQ ID NO: 333 | Tab3-280 | hsa-miR-497* | CAAACCACACUGUGGUGUUAGA | 0,0079145 |
| SEQ ID NO: 223 | Tab3-281 | hsa-miR-548l | AAAAGUAAUUGCGGGUUUUGUC | 0,0079145 |
| SEQ ID NO: 813 | Tab3-282 | hsa-miR-1257 | AGUGAAUGAUGGGUUCGAGC | 0,00819578 |
| SEQ ID NO: 345 | Tab3-283 | hsa-miR-489 | GUGACAUCACAUAUACGGCAGC | 0,008406705 |
| SEQ ID NO: 514 | Tab3-284 | hsa-miR-28-5p | AAGGAGCUCACAGUCUAUUGAG | 0,00853656 |
| SEQ ID NO: 889 | Tab3-285 | hsa-let-7g* | CUGUACAGGCCACUGCCUUGC | 0,008689089 |
| SEQ ID NO: 353 | Tab3-286 | hsa-miR-485-3p | GUCAUACACGGCUCUCCUCUCU | 0,009101856 |
| SEQ ID NO: 634 | Tab3-287 | hsa-miR-1914 | CCCUGUGCCCGGCCCACUUCUG | 0,009156653 |
| SEQ ID NO: 161 | Tab3-288 | hsa-miR-598 | UACGUCAUCGUUGUCAUCGUCA | 0,00927381 |
| SEQ ID NO: 376 | Tab3-289 | hsa-miR-432 | UCUUGGAGUAGGUCAUUGGGUGG | 0,009415303 |
| SEQ ID NO: 503 | Tab3-290 | hsa-miR-29b-2* | CUGGUUUCACAUGGUGGCUUAG | 0,009415303 |
| SEQ ID NO: 299 | Tab3-291 | hsa-miR-516b | AUCUGGAGGUAAGAAGCACUUU | 0,009415303 |
| SEQ ID NO: 231 | Tab3-292 | hsa-miR-548d-5p | AAAAGUAAUUGUGGUUUUUGCC | 0,009415303 |
| SEQ ID NO: 529 | Tab3-293 | hsa-miR-24 | UGGCUCAGUUCAGCAGGAACAG | 0,009431431 |

FIG. 30A (Cont.)

| | | | | |
|---|---|---|---|---|
| SEQ ID NO: 265 | Tab3-294 | hsa-miR-520f | AAGUGCUUCCUUUUAGAGGGUU | 0.009431431 |
| SEQ ID NO: 637 | Tab3-295 | hsa-miR-1911* | CACCAGGCAUUGUGGUCUCC | 0.009521603 |
| SEQ ID NO: 405 | Tab3-296 | hsa-miR-377 | AUCACAGAAAGGCAAGUUUUGU | 0.009655715 |
| SEQ ID NO: 70 | Tab3-297 | hsa-miR-744 | UGCGGGGCUAGGGCUAACAGCA | 0.00982757 |
| SEQ ID NO: 375 | Tab3-298 | hsa-miR-432* | CUGGAUGGCUCCUCCAUGUCU | 0.00982757 |
| SEQ ID NO: 836 | Tab3-299 | hsa-miR-1231 | GUGUCUGGGACAGCUGC | 0.009943694 |
| SEQ ID NO: 619 | Tab3-300 | hsa-miR-196a* | CGGCAACAAGAAACUGCCUGAG | 0.010358087 |
| SEQ ID NO: 48 | Tab3-301 | hsa-miR-877 | GUAGAGGAGAUGGCGCAGGG | 0.010358087 |
| SEQ ID NO: 157 | Tab3-302 | hsa-miR-602 | GACACGGGCGACAGCUGCGCCC | 0.01036271 |
| SEQ ID NO: 446 | Tab3-303 | hsa-miR-33b | GUGCAUUGCUGUUGCAUUGC | 0.01088038 |
| SEQ ID NO: 365 | Tab3-304 | hsa-miR-450b-5p | UUUUGCAAUAUGUUCCUGAAUA | 0.01102843 |
| SEQ ID NO: 159 | Tab3-305 | hsa-miR-600 | ACUUACAGACAAGAGCCUUGCUC | 0.011188478 |
| SEQ ID NO: 120 | Tab3-306 | hsa-miR-633 | CUAAUAGUAUCUACCACAAUAAA | 0.011272357 |
| SEQ ID NO: 767 | Tab3-307 | hsa-miR-1291 | UGGCCCUGACUGAAGACCAGCAGU | 0.011291095 |
| SEQ ID NO: 527 | Tab3-308 | hsa-miR-24-2* | UGCCUACUGAGCUGAAAACACAG | 0.011862023 |
| SEQ ID NO: 641 | Tab3-309 | hsa-miR-191 | CAACGGAAUCCCAAAAGCAGCUG | 0.011866098 |
| SEQ ID NO: 861 | Tab3-310 | hsa-miR-1184 | CCUGCAGCGACUUGAUGGCUUCC | 0.011898092 |
| SEQ ID NO: 151 | Tab3-311 | hsa-miR-608 | AGGGGUGGUGUUGGGACAGCUCCGU | 0.011909056 |
| SEQ ID NO: 349 | Tab3-312 | hsa-miR-487a | AAUCAUACAGGGACAUCCAGUU | 0.012242788 |
| SEQ ID NO: 669 | Tab3-313 | hsa-miR-181c | AACAUUCAACCUGUCGGUGAGU | 0.012327318 |
| SEQ ID NO: 156 | Tab3-314 | hsa-miR-603 | CACACACUGCAAUUACUUUUGC | 0.012469728 |
| SEQ ID NO: 823 | Tab3-315 | hsa-miR-1248 | ACCUCUGUAUAAGCACUGUGCUAAA | 0.012469728 |
| SEQ ID NO: 103 | Tab3-316 | hsa-miR-650 | AGGAGGCAGCGCUCUCAGGAC | 0.012469728 |
| SEQ ID NO: 238 | Tab3-317 | hsa-miR-548a-3p | CAAAACUGGCAAUUACUUUUGC | 0.012832596 |
| SEQ ID NO: 75 | Tab3-318 | hsa-miR-7-1* | CAACAAAUCACAGUCUGCCAUA | 0.012878342 |
| SEQ ID NO: 502 | Tab3-319 | hsa-miR-29c | UAGCACCAUUUGAAAUCGGUUA | 0.013179817 |
| SEQ ID NO: 455 | Tab3-320 | hsa-miR-335* | UUUUUCAUUAUUGCUCCUGACC | 0.013316997 |
| SEQ ID NO: 337 | Tab3-321 | hsa-miR-494 | UGAAACAUACACGGGAAACCUC | 0.013575461 |
| SEQ ID NO: 43 | Tab3-322 | hsa-miR-886-5p | CGGGUCGGAGUUAGCUCAAGCGG | 0.01358313 |
| SEQ ID NO: 344 | Tab3-323 | hsa-miR-490-3p | CAACCUGGAGGACUCCAUGCUG | 0.014155737 |
| SEQ ID NO: 590 | Tab3-324 | hsa-miR-202* | UUCCUAUGCAUAUACUUCUUUG | 0.015015233 |
| SEQ ID NO: 105 | Tab3-325 | hsa-miR-648 | AAGUGUGCAGGGCACUGGU | 0.015429411 |
| SEQ ID NO: 292 | Tab3-326 | hsa-miR-518a-5p | CUGCAAAGGGAAGCCCUUUC | 0.015596349 |
| SEQ ID NO: 686 | Tab3-327 | hsa-miR-154 | UAGGUUAUCCGUGUUGCCUUCG | 0.015607109 |
| SEQ ID NO: 89 | Tab3-328 | hsa-miR-663 | AGGCGGGGCGCCGCGGGACCGC | 0.015665014 |
| SEQ ID NO: 603 | Tab3-329 | hsa-miR-199b-5p | CCCAGUGUUUAGACUAUCUGUUC | 0.015665014 |
| SEQ ID NO: 496 | Tab3-330 | hsa-miR-302a* | ACUUAAACGUGGAUGUACUUGCU | 0.015665014 |

FIG. 30A (Cont.)

| | | | | |
|---|---|---|---|---|
| SEQ ID NO: 130 | Tab3-331 | hsa-miR-625* | GACUAUAGAACUUCCCCUCA | 0.015665014 |
| SEQ ID NO: 269 | Tab3-332 | hsa-miR-520c-5p | CUCUAGAGGGAAGCACUUUCUG | 0.015790761 |
| SEQ ID NO: 416 | Tab3-333 | hsa-miR-373 | GAAGUGCUUCGAUUUUGGGGUGU | 0.015815092 |
| SEQ ID NO: 419 | Tab3-334 | hsa-miR-371-3p | AAGUGCCGCCAUCUUUUGAGUGU | 0.015947766 |
| SEQ ID NO: 447 | Tab3-335 | hsa-miR-33a* | CAAUGUUCCAGCUGAGUGCAUCAC | 0.016127044 |
| SEQ ID NO: 716 | Tab3-336 | hsa-miR-143* | GGUGCAGUGCUGCAUCUCUGGU | 0.016127044 |
| SEQ ID NO: 275 | Tab3-337 | hsa-miR-519e | AAGUGCCUCCUUUUAGAGUGUU | 0.01680014 |
| SEQ ID NO: 739 | Tab3-338 | hsa-miR-1324 | CCAGACAGAAUUCUAUGCACUUUC | 0.016818458 |
| SEQ ID NO: 187 | Tab3-339 | hsa-miR-576-3p | AAGAUGUGGAAAAAAUUGGAAUC | 0.016884828 |
| SEQ ID NO: 391 | Tab3-340 | hsa-miR-410 | AAUAUAACACAGAUGGCCUGU | 0.017021437 |
| SEQ ID NO: 396 | Tab3-341 | hsa-miR-382 | GAAGUUGUUCGUGGUGGAUUCG | 0.017043589 |
| SEQ ID NO: 259 | Tab3-342 | hsa-miR-523 | GAACGCGCUUCCCUAUAGAGGGU | 0.017043589 |
| SEQ ID NO: 58 | Tab3-343 | hsa-miR-769-3p | CUGGGAUCUCCGGGGUCUUUGCUGGA | 0.017114892 |
| SEQ ID NO: 293 | Tab3-344 | hsa-miR-518a-3p | GAAAGCGCUUCCCUUUGCUGGA | 0.017228948 |
| SEQ ID NO: 845 | Tab3-345 | hsa-miR-1224-5p | GUGAGGACUCGGGAGGUGG | 0.017228948 |
| SEQ ID NO: 651 | Tab3-346 | hsa-miR-188-5p | CAUCCCUUGCAUGGUGGAGGG | 0.017228948 |
| SEQ ID NO: 184 | Tab3-347 | hsa-miR-578 | CUUCUUGUGCUCUAGGAUUGU | 0.017839504 |
| SEQ ID NO: 812 | Tab3-348 | hsa-miR-1258 | AGUUAGGAUUAGGUCGUGGAA | 0.018195157 |
| SEQ ID NO: 241 | Tab3-349 | hsa-miR-544 | AUUCUGCAUUUUUAGCAAGUUC | 0.018278326 |
| SEQ ID NO: 789 | Tab3-350 | hsa-miR-127-3p | UCGGAUCCGUCUGAGCUUGGCU | 0.018801139 |
| SEQ ID NO: 706 | Tab3-351 | hsa-miR-146b-5p | UGAGAACUGAAUUCCAUAGGCU | 0.019249696 |
| SEQ ID NO: 359 | Tab3-352 | hsa-miR-454* | ACCCUAUCAAUAUUGUCUCUGC | 0.020191984 |
| SEQ ID NO: 390 | Tab3-353 | hsa-miR-411 | UAGUAGACCGUAUAGCGUACG | 0.020466494 |
| SEQ ID NO: 305 | Tab3-354 | hsa-miR-513c | UUCUCAAGGAGGUGUCGUUUAU | 0.020841482 |
| SEQ ID NO: 252 | Tab3-355 | hsa-miR-526b | CUCUUGAGGGAAGCACUUUCUGU | 0.021022835 |
| SEQ ID NO: 844 | Tab3-356 | hsa-miR-1225-3p | UGAGCCCCUGUGCCGCCCCCAG | 0.021154067 |
| SEQ ID NO: 250 | Tab3-357 | hsa-miR-527 | CUGCAAAGGGAAGCCCUUUC | 0.02116498 |
| SEQ ID NO: 498 | Tab3-358 | hsa-miR-301b | CAGUGCAAUGAUAUUGUCAAAGC | 0.021213589 |
| SEQ ID NO: 467 | Tab3-359 | hsa-miR-323-5p | AGGUGGUCCGUGGCGCGUUCGC | 0.021328204 |
| SEQ ID NO: 770 | Tab3-360 | hsa-miR-1289 | UGGAGUCCAGGAAUCUGCAUUU | 0.021465538 |
| SEQ ID NO: 111 | Tab3-361 | hsa-miR-642 | GUCCCUCUCCAAAUGUGUCUUG | 0.021465538 |
| SEQ ID NO: 667 | Tab3-362 | hsa-miR-181d | AACAUUCAUUGUUGUCGGUGGGU | 0.021821939 |
| SEQ ID NO: 196 | Tab3-363 | hsa-miR-568 | AUGUAUAAAUGUAUACACAC | 0.022475334 |
| SEQ ID NO: 595 | Tab3-364 | hsa-miR-200b | UAAUACUGCCUGGUAAUGAUGA | 0.022684652 |
| SEQ ID NO: 642 | Tab3-365 | hsa-miR-190b | UGAUAUGUUUGAUAUGGGUU | 0.022972797 |
| SEQ ID NO: 445 | Tab3-366 | hsa-miR-33b* | CAGUGCCUCGGCAGUGCAGCCC | 0.023088725 |
| SEQ ID NO: 648 | Tab3-367 | hsa-miR-18b | UAAGGUGCAUCUAGUGCAGUUAG | 0.023129304 |

FIG. 30A (Cont.)

| | | | | |
|---|---|---|---|---|
| SEQ ID NO: 423 | Tab3-368 | hsa-miR-367* | ACUGUUGCUAAUAUGCAACUCU | 0.024297853 |
| SEQ ID NO: 266 | Tab3-369 | hsa-miR-520e | AAAGUGCUUCCUUUUUGAGGG | 0.024728573 |
| SEQ ID NO: 283 | Tab3-370 | hsa-miR-518f* | CUCUAGAGGGAAGCACUUUCUC | 0.025299963 |
| SEQ ID NO: 78 | Tab3-371 | hsa-miR-7 | UGGAAGACUAGUGAUUUUGUUGU | 0.025392522 |
| SEQ ID NO: 437 | Tab3-372 | hsa-miR-34a* | CAAUCAGCAAGUAUACUGCCCU | 0.025397185 |
| SEQ ID NO: 708 | Tab3-373 | hsa-miR-146a* | CCCUGAAAUUCAGUUCUUCAG | 0.026808003 |
| SEQ ID NO: 661 | Tab3-374 | hsa-miR-183 | UAUGGCACUGGUAGAAUUCACU | 0.026808003 |
| SEQ ID NO: 474 | Tab3-375 | hsa-miR-32 | UAUUGCACAUUACUAAGUUGCA | 0.027331241 |
| SEQ ID NO: 458 | Tab3-376 | hsa-miR-331-3p | GCCCCUGGGCCUAUCCUAGAA | 0.027447394 |
| SEQ ID NO: 226 | Tab3-377 | hsa-miR-548i | AAAAGUAAUUGCGGAUUUUGCC | 0.027524999 |
| SEQ ID NO: 720 | Tab3-378 | hsa-miR-141* | CAUCUUCCAGUACAGUGUUGGA | 0.028945087 |
| SEQ ID NO: 456 | Tab3-379 | hsa-miR-335 | UCAAGAGCAAUAACGAAAAAUGU | 0.030110337 |
| SEQ ID NO: 71 | Tab3-380 | hsa-miR-720 | UCUCGCUGGGGCCUCCA | 0.032476019 |
| SEQ ID NO: 102 | Tab3-381 | hsa-miR-651 | UUUAGGAUAAGCUUGACUUUUG | 0.032748562 |
| SEQ ID NO: 328 | Tab3-382 | hsa-miR-500* | AUGCACCUGGGCAAGGAUUCUG | 0.033818608 |
| SEQ ID NO: 544 | Tab3-383 | hsa-miR-221 | AGCUACAUUGUCUGCUGGGUUUC | 0.033929369 |
| SEQ ID NO: 735 | Tab3-384 | hsa-miR-135a | UAUGGCUUUUUAUUCCUAUGUGA | 0.034082155 |
| SEQ ID NO: 97 | Tab3-385 | hsa-miR-655 | AUAAUACAUGGUUAACCUCUUU | 0.034428041 |
| SEQ ID NO: 680 | Tab3-386 | hsa-miR-15b | UAGCAGCACAUCAUGGUUUACA | 0.034927549 |
| SEQ ID NO: 261 | Tab3-387 | hsa-miR-522 | AAAAGUUCCCUUUAGAGUGU | 0.035340642 |
| SEQ ID NO: 763 | Tab3-388 | hsa-miR-1294 | UGUGAGGUUGGCAUUGUUGUCU | 0.035340642 |
| SEQ ID NO: 722 | Tab3-389 | hsa-miR-140-5p | CAGUGGUUUUACCCUAUGGUAG | 0.035363673 |
| SEQ ID NO: 22 | Tab3-390 | hsa-miR-93 | CAAAGUGCUGUUCGUGCAGGUAG | 0.035783523 |
| SEQ ID NO: 751 | Tab3-391 | hsa-miR-1306 | ACGUUGGCUCUGGUGGUG | 0.035993897 |
| SEQ ID NO: 371 | Tab3-392 | hsa-miR-449b | AGGCAGUGUAUUGUUAGCUGGC | 0.036070502 |
| SEQ ID NO: 863 | Tab3-393 | hsa-miR-1182 | GAGGGUCUUGGGAGGGAUGUGAC | 0.036416775 |
| SEQ ID NO: 36 | Tab3-394 | hsa-miR-891b | UGCAACUACCUGAGUCAUUGA | 0.036619787 |
| SEQ ID NO: 508 | Tab3-395 | hsa-miR-299-5p | UGGUUUACCGUCCCACAUACAU | 0.036910836 |
| SEQ ID NO: 484 | Tab3-396 | hsa-miR-30b* | CUGGGAGGUGAAUGAUUUACUUC | 0.037170128 |
| SEQ ID NO: 819 | Tab3-397 | hsa-miR-1252 | AGAAGGAAAUGAAUUCAUUUA | 0.037774803 |
| SEQ ID NO: 848 | Tab3-398 | hsa-miR-1307 | UGGAGUGUGACAAUGGUGUUUG | 0.038889568 |
| SEQ ID NO: 750 | Tab3-399 | hsa-miR-122 | ACUCGGCGUGCGGGUCGUCGUG | 0.038932493 |
| SEQ ID NO: 482 | Tab3-400 | hsa-miR-30c-1* | CUGGGAGAGGGUUGUUUACUCC | 0.039698475 |
| SEQ ID NO: 765 | Tab3-401 | hsa-miR-1293 | UGGGUGGUCUGGAGAUUUGUGC | 0.040197985 |
| SEQ ID NO: 340 | Tab3-402 | hsa-miR-492 | AGGACCUGCGGGACAAGAUUCUU | 0.040391709 |
| SEQ ID NO: 202 | Tab3-403 | hsa-miR-561 | CAAAGUUUAAGAUCCUUGAAGU | 0.041117397 |
| SEQ ID NO: 703 | Tab3-404 | hsa-miR-1471 | GCCCGCGUGUGGAGCCAGGUGU | 0.041180996 |

FIG. 30A (Cont.)

| | | | | |
|---|---|---|---|---|
| SEQ ID NO: 399 | Tab3-405 | hsa-miR-380 | UAUGUAAUAUGGUCCACAUCUU | 0.041347806 |
| SEQ ID NO: 623 | Tab3-406 | hsa-miR-194* | CCAGUGGGGCUGCUGUUAUCUG | 0.041347806 |
| SEQ ID NO: 278 | Tab3-407 | hsa-miR-519c-3p | AAAGUGCAUCUUUUAGAGGAU | 0.041347806 |
| SEQ ID NO: 166 | Tab3-408 | hsa-miR-593 | UGUCUCUGCUGGGGUUUCU | 0.04224774 |
| SEQ ID NO: 240 | Tab3-409 | hsa-miR-545 | UCAGCAAACAUUAUUGUGUGC | 0.04655147 |
| SEQ ID NO: 388 | Tab3-410 | hsa-miR-412 | ACUUCACCUGGUCCACUAGCCGU | 0.047280565 |
| SEQ ID NO: 418 | Tab3-411 | hsa-miR-371-5p | ACUCAAACUGUGGGGGCACU | 0.047963215 |
| SEQ ID NO: 433 | Tab3-412 | hsa-miR-34c-5p | AGGCAGUGUAGUUAGCUGAUUGC | 0.048522241 |
| SEQ ID NO: 380 | Tab3-413 | hsa-miR-425* | AUCGGGAAUGUCGUUCCGCCC | 0.04916331 |
| SEQ ID NO: 204 | Tab3-414 | hsa-miR-558 | UGAGCUGCUGUACCAAAAU | 0.049579821 |
| SEQ ID NO: 175 | Tab3-415 | hsa-miR-586 | UAUGCAUUGUAUUUUUAGGUCC | 0.051621465 |
| SEQ ID NO: 143 | Tab3-416 | hsa-miR-615-5p | GGGGGUCCCCGGUGCUCGGAUC | 0.052553507 |
| SEQ ID NO: 150 | Tab3-417 | hsa-miR-609 | AGGGUGUUUCUCUCAUCUCU | 0.05348473 |
| SEQ ID NO: 489 | Tab3-418 | hsa-miR-302e | UAAGUGCUUCCAUGCUU | 0.05348473 |
| SEQ ID NO: 209 | Tab3-419 | hsa-miR-554 | GCUAGUCCUGACUCAGCCAGU | 0.054137289 |
| SEQ ID NO: 233 | Tab3-420 | hsa-miR-548c-5p | AAAAGUAAUUGCGGUUUUUGCC | 0.054172939 |
| SEQ ID NO: 620 | Tab3-421 | hsa-miR-196a | UAGGUAGUUUCAUGUUGUUGGG | 0.05479446 |
| SEQ ID NO: 494 | Tab3-422 | hsa-miR-302b* | ACUUUAACAUGGAAGUGCUUUC | 0.055043262 |
| SEQ ID NO: 818 | Tab3-423 | hsa-miR-1253 | AGAGAAGAAGAUCAGCCUGCA | 0.055289116 |
| SEQ ID NO: 244 | Tab3-424 | hsa-miR-542-3p | UGUGACAGAUUGAUAACUGAAA | 0.05734066 |
| SEQ ID NO: 222 | Tab3-425 | hsa-miR-548m | CAAAGGUAUUGUGGUUUUG | 0.057442266 |
| SEQ ID NO: 408 | Tab3-426 | hsa-miR-376a* | GUAGAUUCUCCUUCUAUGAGUA | 0.057442266 |
| SEQ ID NO: 752 | Tab3-427 | hsa-miR-1305 | UUUUCAACUCUAAUGGGAGAGA | 0.057551435 |
| SEQ ID NO: 607 | Tab3-428 | hsa-miR-198 | GGUCCAGAGGGGAGGGAGGUUC | 0.058096461 |
| SEQ ID NO: 510 | Tab3-429 | hsa-miR-298 | AGCAGAAGCAGGGAGGUUCUCCCA | 0.058096461 |
| SEQ ID NO: 883 | Tab3-430 | hsa-miR-101 | UACAGUACUGUGAUAACUGAA | 0.058945538 |
| SEQ ID NO: 271 | Tab3-431 | hsa-miR-520b | AAAGUGCUUCCUUUUUAGAGGG | 0.05901194 |
| SEQ ID NO: 700 | Tab3-432 | hsa-miR-148a* | AAAGUUCUGAGACACUCCGACU | 0.059266202 |
| SEQ ID NO: 303 | Tab3-433 | hsa-miR-515-3p | GAGUGCCUUCUUUUGGAGCGUU | 0.059458365 |
| SEQ ID NO: 687 | Tab3-434 | hsa-miR-1539 | UCCUGCGCGUCCCAGAUGCC | 0.059632476 |
| SEQ ID NO: 34 | Tab3-435 | hsa-miR-892b | CACUGGCUCCUUUCUGGGUAGA | 0.060215178 |
| SEQ ID NO: 155 | Tab3-436 | hsa-miR-604 | AGGCUGCGGAAUUCAGGAC | 0.061682723 |
| SEQ ID NO: 594 | Tab3-437 | hsa-miR-200b* | CAUCUUACUGGGCAGCAUUGGA | 0.062068926 |
| SEQ ID NO: 875 | Tab3-438 | hsa-miR-106a* | CUGACUAAGCACUUCUUAC | 0.062973904 |
| SEQ ID NO: 404 | Tab3-439 | hsa-miR-377* | AGAGGUUGCCCUUGGUGAAUUC | 0.064215489 |
| SEQ ID NO: 672 | Tab3-440 | hsa-miR-181a* | ACCAUCGACCGUUGAUUGUACC | 0.064215489 |
| SEQ ID NO: 335 | Tab3-441 | hsa-miR-496 | UGAGUAUUACAUGGCCAAUCUC | 0.064215489 |

FIG. 30A (Cont.)

| SEQ ID NO | Tab3 | miRNA | Sequence | Value |
|---|---|---|---|---|
| SEQ ID NO: 790 | Tab3-442 | hsa-miR-1273 | GGGCGACAAAGCAAGACUCUUUCUU | 0,064468384 |
| SEQ ID NO: 288 | Tab3-443 | hsa-miR-518d-3p | CAAAGCGCUUCCCUUUGGAGC | 0,06632784 |
| SEQ ID NO: 367 | Tab3-444 | hsa-miR-450a | UUUUGCGAUGGUUUCCUAAUAU | 0,067009273 |
| SEQ ID NO: 295 | Tab3-445 | hsa-miR-517b | UCGUGCAUCCCUUUAGAGUGUU | 0,068375909 |
| SEQ ID NO: 385 | Tab3-446 | hsa-miR-423-3p | AGCUCGGUCUGAGGCCCCUCAGU | 0,068444366 |
| SEQ ID NO: 572 | Tab3-447 | hsa-miR-211 | UUCCCUUUGUCAUCCUUCGCCU | 0,069008916 |
| SEQ ID NO: 780 | Tab3-448 | hsa-miR-128 | UCACAGUGAACCGGUCUCUUU | 0,069942451 |
| SEQ ID NO: 216 | Tab3-449 | hsa-miR-550 | AGUGCCUGAGGGAGUAAGAGCCC | 0,069942451 |
| SEQ ID NO: 749 | Tab3-450 | hsa-miR-1308 | GCAUGGGUGGUUCAGUGG | 0,070845841 |
| SEQ ID NO: 427 | Tab3-451 | hsa-miR-363* | CGGGUGGAUCACGAUGCAAUUU | 0,072452961 |
| SEQ ID NO: 413 | Tab3-452 | hsa-miR-374a* | CUUAUCAGAUUGUAUUGUAAU | 0,073774496 |
| SEQ ID NO: 403 | Tab3-453 | hsa-miR-378 | ACUGGACUUGGAGUCAGAAGG | 0,074988782 |
| SEQ ID NO: 827 | Tab3-454 | hsa-miR-1244 | AAGUAGUUGGUUUGUAUGAGAUGGUU | 0,075272705 |
| SEQ ID NO: 710 | Tab3-455 | hsa-miR-1469 | CUCGGCGCGGGCGGGUGGGCUCC | 0,075376133 |
| SEQ ID NO: 115 | Tab3-456 | hsa-miR-638 | AGGGAUCGCGGGCGGGUGGGCCU | 0,075381067 |
| SEQ ID NO: 174 | Tab3-457 | hsa-miR-587 | UUUCCAUAGGUGAUGAGUCAC | 0,077386173 |
| SEQ ID NO: 168 | Tab3-458 | hsa-miR-591 | AGACCAUGGGUUCUCAUUGU | 0,078228809 |
| SEQ ID NO: 695 | Tab3-459 | hsa-miR-150 | UCUCCCAACCCUUGUACCAGUG | 0,082451447 |
| SEQ ID NO: 270 | Tab3-460 | hsa-miR-520c-3p | AAAGUGCUUCCUUUUAGAGGGU | 0,084519835 |
| SEQ ID NO: 121 | Tab3-461 | hsa-miR-632 | GUGUCUGCUUCCUGUGGGA | 0,084519835 |
| SEQ ID NO: 513 | Tab3-462 | hsa-miR-296-3p | GAGGGUUGGGUGGAGGCUCUCC | 0,084519835 |
| SEQ ID NO: 476 | Tab3-463 | hsa-miR-31 | AGGCAAGAUGCUGGCAUAGCU | 0,085596635 |
| SEQ ID NO: 273 | Tab3-464 | hsa-miR-520a-3p | AAAGUGCUUCCCUUUGGACUGU | 0,086680013 |
| SEQ ID NO: 807 | Tab3-465 | hsa-miR-125b-1* | ACGGGUUAGGCUCUUGGGAGCU | 0,086772679 |
| SEQ ID NO: 395 | Tab3-466 | hsa-miR-383 | AGAUCACAAGGUGAUUGUGGCU | 0,086772679 |
| SEQ ID NO: 50 | Tab3-467 | hsa-miR-7-2* | CAACAAAUCCCAGUCUACCUAA | 0,087185854 |
| SEQ ID NO: 728 | Tab3-468 | hsa-miR-876-3p | UGGAUGGUUUACAAAGUAAUCA | 0,087328958 |
| SEQ ID NO: 373 | Tab3-469 | hsa-miR-138 | AGCUGGUGUUGUGAAUCAGGCCG | 0,087693721 |
| SEQ ID NO: 479 | Tab3-470 | hsa-miR-448 | UUGCAUAUGUAGGAUGUCCCAU | 0,089443508 |
| SEQ ID NO: 491 | Tab3-471 | hsa-miR-30d* | CUUUCAGUCAGAUGUUUGCUGC | 0,093708624 |
| SEQ ID NO: 851 | Tab3-472 | hsa-miR-302d | UAAGUGCUUCCAUGUUUGAGUGU | 0,094169783 |
| SEQ ID NO: 224 | Tab3-473 | hsa-miR-1207-3p | UCAGCUGGCCCUCAUUUC | 0,094256962 |
| SEQ ID NO: 601 | Tab3-474 | hsa-miR-548k | AAAAGUACUUGCGGAUUUUGCU | 0,094319585 |
| SEQ ID NO: 853 | Tab3-475 | hsa-miR-19a* | AGUUUUGCAUAGUUGCACUACA | 0,094359637 |
| SEQ ID NO: 764 | Tab3-476 | hsa-miR-1205 | UCUGCAGGGUUUGCUUUGAG | 0,094359637 |
| SEQ ID NO: 853 | Tab3-477 | hsa-miR-129-3p | AAGCCCUUACCCCAAAAAGCAU | 0,094359637 |
| SEQ ID NO: 835 | Tab3-478 | hsa-miR-1233 | UGAGCCCUGUCCUCCCGCAG | 0,094359637 |

FIG. 30A (Cont.)

| | | | | |
|---|---|---|---|---|
| SEQ ID NO: 862 | Tab3-479 | hsa-miR-1183 | CACUGUAGGUGAUGGUGAGAGAGUGGGCA | 0.094359637 |
| SEQ ID NO: 435 | Tab3-480 | hsa-miR-34b* | UAGGCAGUGUCAUUAGCUGAUUG | 0.094621754 |
| SEQ ID NO: 133 | Tab3-481 | hsa-miR-624 | CACAAGGUAUUGGUAUACCU | 0.094654501 |
| SEQ ID NO: 897 | Tab3-482 | hsa-let-7d | AGAGGUAGUAGGUUGCAUAGUU | 0.09785891 |
| SEQ ID NO: 522 | Tab3-483 | hsa-miR-26a-2* | CCUAUUCUUGAUUACUUGUUUC | 0.09785891 |
| SEQ ID NO: 718 | Tab3-484 | hsa-miR-142-5p | CAUAAAGUAGAAAGCACUACU | 0.09785891 |
| SEQ ID NO: 235 | Tab3-485 | hsa-miR-548b-5p | AAAAGUAAUUGUGGUUUUGGCC | 0.101011376 |
| SEQ ID NO: 116 | Tab3-486 | hsa-miR-637 | ACUGGGGCUUUCGGGCUCUGCGU | 0.101011376 |
| SEQ ID NO: 768 | Tab3-487 | hsa-miR-1290 | UGGAUUUUUGGAUCAGGGA | 0.10485473 |
| SEQ ID NO: 84 | Tab3-488 | hsa-miR-668 | UGUCACUCGUCUGGCCCACUAC | 0.10485473 |
| SEQ ID NO: 185 | Tab3-489 | hsa-miR-577 | UAGAUAAAAUAUUGGUACCUG | 0.10485473 |
| SEQ ID NO: 843 | Tab3-490 | hsa-miR-1225-5p | GUGGGUACGGGCCCAGUGGGGGG | 0.107406409 |
| SEQ ID NO: 205 | Tab3-491 | hsa-miR-557 | GUUUGCACGGGUGGGCCUUGUCU | 0.109024925 |
| SEQ ID NO: 811 | Tab3-492 | hsa-miR-1259 | AUAUAUGACAUGAUUAGCUUU | 0.109107385 |
| SEQ ID NO: 685 | Tab3-493 | hsa-miR-154* | AAUCAUACACGGUUGACCUAUU | 0.110065504 |
| SEQ ID NO: 519 | Tab3-494 | hsa-miR-27a | UUCACAGUGGCUAAGUUCCGC | 0.11233289 |
| SEQ ID NO: 450 | Tab3-495 | hsa-miR-339-3p | UGAGCGCCUCGACGACAGAGCCG | 0.113090501 |
| SEQ ID NO: 301 | Tab3-496 | hsa-miR-516a-3p | UGCUUCCUUUCAGAGGGU | 0.115495765 |
| SEQ ID NO: 549 | Tab3-497 | hsa-miR-22 | AAGCUGCCAGUUGAAGAACUGU | 0.116684713 |
| SEQ ID NO: 879 | Tab3-498 | hsa-miR-103-as | UCAUAGCCCUGUACAAUGCUGCU | 0.116925675 |
| SEQ ID NO: 268 | Tab3-499 | hsa-miR-520d-3p | AAAGUGCUUCUCUUUGGUGGGU | 0.117125191 |
| SEQ ID NO: 829 | Tab3-500 | hsa-miR-124* | CGUUCACAGCGGACCUUGAU | 0.120529663 |
| SEQ ID NO: 731 | Tab3-501 | hsa-miR-136 | ACUCCAUUUGUUUUGAUGAUGA | 0.121319184 |
| SEQ ID NO: 465 | Tab3-502 | hsa-miR-324-5p | CGCAUCCCCUAGGGCAUUGGUGU | 0.122688746 |
| SEQ ID NO: 428 | Tab3-503 | hsa-miR-363 | AAUUGCACGGUAUCCAUCUGUA | 0.123157006 |
| SEQ ID NO: 401 | Tab3-504 | hsa-miR-379 | UGGUAGACUAUGGAACGUAGG | 0.123652444 |
| SEQ ID NO: 39 | Tab3-505 | hsa-miR-889 | UUAAUAUCGGACAACCAUUGU | 0.123652444 |
| SEQ ID NO: 207 | Tab3-506 | hsa-miR-556-3p | AUAUUACCAUUGGCUCAUCUUU | 0.123652444 |
| SEQ ID NO: 859 | Tab3-507 | hsa-miR-1197 | UAGGACACAUGGUCUACUUCU | 0.127244847 |
| SEQ ID NO: 126 | Tab3-508 | hsa-miR-628-5p | AUGCUGACAUAUUUACUAGAGG | 0.128885467 |
| SEQ ID NO: 690 | Tab3-509 | hsa-miR-153 | UUGCAUAGUCACAAAAGUGAUC | 0.130887102 |
| SEQ ID NO: 217 | Tab3-510 | hsa-miR-549 | UGACAACUAUGGAUGAGCUCU | 0.131108565 |
| SEQ ID NO: 232 | Tab3-511 | hsa-miR-548d-3p | CAAAAACCACAGUUUCUUUUGC | 0.131334473 |
| SEQ ID NO: 90 | Tab3-512 | hsa-miR-662 | UCCCACGUUGUGUGCCCAGCAG | 0.132120784 |
| SEQ ID NO: 12 | Tab3-513 | hsa-miR-941 | CACCCGGAGCCAUUCUGAGCCUC | 0.132120784 |
| SEQ ID NO: 858 | Tab3-514 | hsa-miR-1200 | CUCCUGAGCCAUUCUGAGCCUC | 0.133983172 |
| SEQ ID NO: 327 | Tab3-515 | hsa-miR-501-3p | AAUGCACCCGGCAAGGAUUCU | 0.134458335 |

FIG. 30A (Cont.)

| | | | | |
|---|---|---|---|---|
| SEQ ID NO: 317 | Tab3-516 | hsa-miR-508-3p | UGAUUGUAGCCUUUUGGAGUAGA | 0,135872697 |
| SEQ ID NO: 178 | Tab3-517 | hsa-miR-583 | CAAAGAGGAAGGUCCCAUUAC | 0,136329908 |
| SEQ ID NO: 298 | Tab3-518 | hsa-miR-516b* | UGCUUCCUUUCAGAGGGU | 0,136546941 |
| SEQ ID NO: 195 | Tab3-519 | hsa-miR-569 | AGUUAAUGAAUCCUGAAAGU | 0,138347214 |
| SEQ ID NO: 366 | Tab3-520 | hsa-miR-450b-3p | UUGGGAUCAUUUGCAUCCAUA | 0,143719324 |
| SEQ ID NO: 864 | Tab3-521 | hsa-miR-1181 | CCGUCGCCGCCACCCGAGCCG | 0,143719324 |
| SEQ ID NO: 203 | Tab3-522 | hsa-miR-559 | UAAAGUAAAUAUGCACCAAAA | 0,143719324 |
| SEQ ID NO: 212 | Tab3-523 | hsa-miR-551b* | GAAAUCAAGCGUGGGUGAGACC | 0,144409374 |
| SEQ ID NO: 663 | Tab3-524 | hsa-miR-1826 | AUUGAUCAACACUUCGAACGCAAU | 0,145319246 |
| SEQ ID NO: 846 | Tab3-525 | hsa-miR-1224-3p | CCCCACCUCCUCUCUCUCAG | 0,149912449 |
| SEQ ID NO: 137 | Tab3-526 | hsa-miR-620 | AUGGAGAUAGAUAUAGAAAU | 0,150635822 |
| SEQ ID NO: 740 | Tab3-527 | hsa-miR-1323 | UCAAAAACUGAGGGGCAUUUUCU | 0,150635822 |
| SEQ ID NO: 394 | Tab3-528 | hsa-miR-384 | AUUCCUAGAAAUUGUACACUCAGGC | 0,150635822 |
| SEQ ID NO: 698 | Tab3-529 | hsa-miR-148b* | AAGUUCUGUUAUACACUCAGGC | 0,152425384 |
| SEQ ID NO: 245 | Tab3-530 | hsa-miR-541* | AAAGGAUUCUGCUGUCGGUCCCACU | 0,153021282 |
| SEQ ID NO: 877 | Tab3-531 | hsa-miR-105* | ACGGAUGUUUGAGCAUGUGCUA | 0,153045731 |
| SEQ ID NO: 587 | Tab3-532 | hsa-miR-205 | UCCUUCAUUCCACCGGAGUCUG | 0,155057992 |
| SEQ ID NO: 149 | Tab3-533 | hsa-miR-610 | UGCUAAAUGUGUGCUGGGA | 0,155408243 |
| SEQ ID NO: 411 | Tab3-534 | hsa-miR-374b* | CUUAGCAGGUUGUAUUAUCAUU | 0,156044356 |
| SEQ ID NO: 38 | Tab3-535 | hsa-miR-890 | UACUGGAAAGGCAUCAGUUG | 0,158558135 |
| SEQ ID NO: 646 | Tab3-536 | hsa-miR-190 | UGAUAUGUUUGAUAUAUUAGGU | 0,161334747 |
| SEQ ID NO: 891 | Tab3-537 | hsa-let-7f-2* | CUAUACAGUCUACUGUCUUUCC | 0,16167196 |
| SEQ ID NO: 707 | Tab3-538 | hsa-miR-146b-3p | UGCCCUGUGGACUCAGUUCUGG | 0,16167196 |
| SEQ ID NO: 76 | Tab3-539 | hsa-miR-708* | CAACUAGACUGUGAGCUUCUAG | 0,162687128 |
| SEQ ID NO: 653 | Tab3-540 | hsa-miR-187* | GGCUACAACACAGGACCCGGGC | 0,163682894 |
| SEQ ID NO: 379 | Tab3-541 | hsa-miR-429 | UAAUACUGUCUGGUAAAACCGU | 0,164068789 |
| SEQ ID NO: 554 | Tab3-542 | hsa-miR-218-1* | AUGGUUCCGUCAAGCACCAUGG | 0,164645322 |
| SEQ ID NO: 108 | Tab3-543 | hsa-miR-645 | UCUAGGCUGGUACUGCUGA | 0,166358148 |
| SEQ ID NO: 547 | Tab3-544 | hsa-miR-220a | CCACACCGUAUCUGACACUUU | 0,166358148 |
| SEQ ID NO: 683 | Tab3-545 | hsa-miR-155* | CUCCUACAUAUUAGCAUUAACA | 0,166358148 |
| SEQ ID NO: 13 | Tab3-546 | hsa-miR-940 | AAGGCAGGGCCCCCGCUCCCC | 0,169101572 |
| SEQ ID NO: 778 | Tab3-547 | hsa-miR-1281 | UCGCCUCCUGCCUCCAGAGUA | 0,170945654 |
| SEQ ID NO: 758 | Tab3-548 | hsa-miR-1298 | UUCAUUCGGCUGUCCAGAUGUA | 0,171244212 |
| SEQ ID NO: 511 | Tab3-549 | hsa-miR-297 | AUGCAUGUGUACUGUGUCUGC | 0,180420095 |
| SEQ ID NO: 747 | Tab3-550 | hsa-miR-130a* | UUCACAUUGUGCUACUGUCUGC | 0,180840669 |
| SEQ ID NO: 746 | Tab3-551 | hsa-miR-130b | CAGUGCAAUGAUGAAAGGGCAU | 0,180840669 |
| SEQ ID NO: 550 | Tab3-552 | hsa-miR-219-5p | UGAUUGUCCAAACGCAAUUCU | 0,182347116 |

FIG. 30A (Cont.)

| | | | |
|---|---|---|---|
| SEQ ID NO: 533 | Tab3-553 | hsa-miR-23a | AUCACAUUGCCAGGGAUUUCC | 0,183467922 |
| SEQ ID NO: 9 | Tab3-554 | hsa-miR-944 | AAAUUAUUGUACAUCGGAUGAG | 0,185726121 |
| SEQ ID NO: 88 | Tab3-555 | hsa-miR-663b | GGUGGCCCGGCCGUGCCUGAGG | 0,186333665 |
| SEQ ID NO: 449 | Tab3-556 | hsa-miR-339-5p | UCCCUGUCCUCCAGGAGCUCACG | 0,186333665 |
| SEQ ID NO: 754 | Tab3-557 | hsa-miR-1303 | UUUAGAGACGGGGUCUUGCUCU | 0,1909372 |
| SEQ ID NO: 312 | Tab3-558 | hsa-miR-510 | UACUCAGGAGAGUGGCAAUCAC | 0,191367108 |
| SEQ ID NO: 800 | Tab3-559 | hsa-miR-1263 | AUGGUACCCUGGCAUACUAGGU | 0,192928136 |
| SEQ ID NO: 51 | Tab3-560 | hsa-miR-875-5p | UAUACCUCAGUUUUAUCAGGUG | 0,194638271 |
| SEQ ID NO: 114 | Tab3-561 | hsa-miR-639 | AUCGCUGCGGUUGCGAGCGCUGU | 0,198959623 |
| SEQ ID NO: 894 | Tab3-562 | hsa-let-7e* | CUAUACGGCCUCCUAGCUUUCC | 0,199973185 |
| SEQ ID NO: 214 | Tab3-563 | hsa-miR-551a | GCGACCCACUCUGGUUUCA | 0,20034621 |
| SEQ ID NO: 793 | Tab3-564 | hsa-miR-1270 | CUGGAGAUAUGGAAGAGCUGUGU | 0,202575991 |
| SEQ ID NO: 442 | Tab3-565 | hsa-miR-342-3p | UCUCACACAGAAAUCGCACCCGU | 0,206125296 |
| SEQ ID NO: 5 | Tab3-566 | hsa-miR-98 | UGAGGUAGUAAGUUGUAUUGUU | 0,209648127 |
| SEQ ID NO: 760 | Tab3-567 | hsa-miR-1296 | UUAGGGCCCUGGCUGCCUCCAUCCC | 0,211553377 |
| SEQ ID NO: 464 | Tab3-568 | hsa-miR-325 | CCUAGUAGGUGUCCAGUAAGUGU | 0,211675684 |
| SEQ ID NO: 453 | Tab3-569 | hsa-miR-337-5p | GAACGGCUUCAUACAGGAGUU | 0,212483009 |
| SEQ ID NO: 599 | Tab3-570 | hsa-miR-19b-1* | AGUUUUGCAGGUUUGCAUCCAGC | 0,212483009 |
| SEQ ID NO: 351 | Tab3-571 | hsa-miR-486-3p | UCUCACACAGAGCUCACAGAGAU | 0,216769986 |
| SEQ ID NO: 497 | Tab3-572 | hsa-miR-302a | UAAGUGCUUCCAUGUUUUGGUGA | 0,226651356 |
| SEQ ID NO: 85 | Tab3-573 | hsa-miR-665 | ACCAGGAGGCUGAGGCCCCU | 0,226651356 |
| SEQ ID NO: 201 | Tab3-574 | hsa-miR-562 | AAAGUAGCUGUACCAUUUGC | 0,227449479 |
| SEQ ID NO: 347 | Tab3-575 | hsa-miR-488 | UUGAAAGGCUAUUUCUUGGUC | 0,230737842 |
| SEQ ID NO: 847 | Tab3-576 | hsa-miR-122* | AACGCCAUUAUCACACUAAAUA | 0,232955196 |
| SEQ ID NO: 69 | Tab3-577 | hsa-miR-744* | CUGUUGCCACUAACCUCAACCU | 0,23343122 |
| SEQ ID NO: 262 | Tab3-578 | hsa-miR-521 | AACGCACUUCCCUUUAGAGUGU | 0,235152837 |
| SEQ ID NO: 338 | Tab3-579 | hsa-miR-493* | UUGUACAUGGUAGGCUUUCAUU | 0,23701706 |
| SEQ ID NO: 573 | Tab3-580 | hsa-miR-210 | CUGUGCGUGUGACAGCGGCUGA | 0,244151854 |
| SEQ ID NO: 665 | Tab3-581 | hsa-miR-182* | UGGUUCUAGACUUGCCAACUA | 0,244633628 |
| SEQ ID NO: 304 | Tab3-582 | hsa-miR-514 | AUUGACACUUCUGUGAGUAGA | 0,244967603 |
| SEQ ID NO: 555 | Tab3-583 | hsa-miR-218 | UUGUGCUUGAUCUAACCAUGU | 0,245527555 |
| SEQ ID NO: 148 | Tab3-584 | hsa-miR-611 | GCGAGGACCCCUCGGGGUCUGAC | 0,248111953 |
| SEQ ID NO: 81 | Tab3-585 | hsa-miR-671-5p | AGGAAGCCCUGGAGGGGCUGGAG | 0,253638712 |
| SEQ ID NO: 68 | Tab3-586 | hsa-miR-758 | UUUGUGACCUGGUCCACUAACC | 0,253638712 |
| SEQ ID NO: 361 | Tab3-587 | hsa-miR-453 | AGGGUGUCCGGUGUGAGUUCGCA | 0,254405503 |
| SEQ ID NO: 727 | Tab3-588 | hsa-miR-138-1* | GCUACUUCACAACACCAGGGCC | 0,254962662 |
| SEQ ID NO: 518 | Tab3-589 | hsa-miR-27a* | AGGGCUUAGCUGCUUGUGAGCA | 0,256857752 |

FIG. 30A (Cont.)

| | | | | |
|---|---|---|---|---|
| SEQ ID NO: 629 | Tab3-590 | hsa-miR-192* | CUGCCAAUUCCAUAGGUCACAG | 0.257982036 |
| SEQ ID NO: 729 | Tab3-591 | hsa-miR-137 | UUAUUGCUUAAGAAUACGCGUAG | 0.258611277 |
| SEQ ID NO: 372 | Tab3-592 | hsa-miR-449a | UGGCAGUGUAUUGUUAGCUGGU | 0.258611277 |
| SEQ ID NO: 904 | Tab3-593 | hsa-let-7a | UGAGGUAGUAGGUUGUAUAGUU | 0.259502492 |
| SEQ ID NO: 668 | Tab3-594 | hsa-miR-181c* | AACCAUCGACCGUUGAUUGUAGUGGAC | 0.263193986 |
| SEQ ID NO: 339 | Tab3-595 | hsa-miR-493 | UGAAGGUCUACUGUGUGCCAGG | 0.263193986 |
| SEQ ID NO: 644 | Tab3-596 | hsa-miR-1909 | CGCAGGGGCCGGGUGCUCACCG | 0.263343534 |
| SEQ ID NO: 434 | Tab3-597 | hsa-miR-34c-3p | AAUCACUAACCACACGGCCAGG | 0.266363835 |
| SEQ ID NO: 581 | Tab3-598 | hsa-miR-208a | AUAAGACGAGCAAAAAGCUUGU | 0.271610114 |
| SEQ ID NO: 824 | Tab3-599 | hsa-miR-1247 | ACCCGUCCCGUUCGUCCCGGA | 0.272234705 |
| SEQ ID NO: 169 | Tab3-600 | hsa-miR-590-5p | GAGCUUAUUCAUAAAAGUGCAG | 0.27673256 |
| SEQ ID NO: 662 | Tab3-601 | hsa-miR-1827 | UGAGGCAGUAGAUUGAAU | 0.277254214 |
| SEQ ID NO: 486 | Tab3-602 | hsa-miR-30a* | CUUUCAGUCGGAUGUUUGCAGC | 0.280009151 |
| SEQ ID NO: 654 | Tab3-603 | hsa-miR-187 | UCGUGUCUUGUGUUGCAGCCGG | 0.288084056 |
| SEQ ID NO: 697 | Tab3-604 | hsa-miR-149 | UCUGGCUCCGUGUCUUCACUCCC | 0.288935778 |
| SEQ ID NO: 741 | Tab3-605 | hsa-miR-1322 | GAUGAUGCUGAUGUGCUG | 0.288935778 |
| SEQ ID NO: 459 | Tab3-606 | hsa-miR-330-5p | UCUCUGGGCCUGUGUCUUAGGC | 0.289611258 |
| SEQ ID NO: 77 | Tab3-607 | hsa-miR-708 | AAGGAGCUUACAAUCUAGCUGGG | 0.294728042 |
| SEQ ID NO: 436 | Tab3-608 | hsa-miR-34b | CAAUCACUAACUCCACUGCCAU | 0.305121961 |
| SEQ ID NO: 666 | Tab3-609 | hsa-miR-182 | UUUGGCAAUGGUAGAACUCACACU | 0.305361349 |
| SEQ ID NO: 422 | Tab3-610 | hsa-miR-369-3p | AAUAAUACAUGGUUGAUCUU | 0.305361349 |
| SEQ ID NO: 517 | Tab3-611 | hsa-miR-27b | UUCACAGUGGCUAAGUUCUGC | 0.307154957 |
| SEQ ID NO: 493 | Tab3-612 | hsa-miR-302c | UAAGUGCUUCCAUGUUUCAGUGG | 0.308809111 |
| SEQ ID NO: 506 | Tab3-613 | hsa-miR-29a* | ACUGAUUUCUUUUGGUGUUCAG | 0.309065617 |
| SEQ ID NO: 99 | Tab3-614 | hsa-miR-654-3p | UAUGUCUGCUGACCAUCACCUU | 0.310892061 |
| SEQ ID NO: 546 | Tab3-615 | hsa-miR-220b | CCACCACCGUGUCUGACACUG | 0.313278431 |
| SEQ ID NO: 814 | Tab3-616 | hsa-miR-1256 | AGGCAUUGACUUCUCACUAGCU | 0.313278431 |
| SEQ ID NO: 633 | Tab3-617 | hsa-miR-1914* | GGAGGGGUCCCGCACUGGGAGG | 0.321714781 |
| SEQ ID NO: 903 | Tab3-618 | hsa-let-7a* | CUAUACAAUCUACUGUCUUUC | 0.321714781 |
| SEQ ID NO: 816 | Tab3-619 | hsa-miR-1255a | AGGAUGAGCAAAGAAAGUAGAUU | 0.321714781 |
| SEQ ID NO: 899 | Tab3-620 | hsa-let-7c | UGAGGUAGUAGGUUGUAUGGUU | 0.322804927 |
| SEQ ID NO: 725 | Tab3-621 | hsa-miR-139-3p | GGAGACGCGGCCCUGUUGGAGU | 0.328857016 |
| SEQ ID NO: 363 | Tab3-622 | hsa-miR-452 | AACUGUUUGCAGAGGAAACUGA | 0.328857016 |
| SEQ ID NO: 294 | Tab3-623 | hsa-miR-517c | AUCGUGCAUCCUUUUAGAGUGU | 0.328857016 |
| SEQ ID NO: 213 | Tab3-624 | hsa-miR-551b | GCGACCCAUACUUGGUUUCAG | 0.329135716 |
| SEQ ID NO: 193 | Tab3-625 | hsa-miR-571 | UGAGUUGGCCAUCUGAGUGAG | 0.329135716 |
| SEQ ID NO: 769 | Tab3-626 | hsa-miR-129* | AAGCCCUUACCCCAAAAAGUAU | 0.333071731 |

FIG. 30A (Cont.)

| | | | |
|---|---|---|---|
| SEQ ID NO: 336 | Tab3-627 | hsa-miR-495 | AAACAAACAUGGUGCACUUCUU | 0.338368855 |
| SEQ ID NO: 509 | Tab3-628 | hsa-miR-299-3p | UAUGUGGGAUGGUAAACCGCUU | 0.340967267 |
| SEQ ID NO: 616 | Tab3-629 | hsa-miR-197 | UUCACCACCUUCUCCACCAGC | 0.344635402 |
| SEQ ID NO: 230 | Tab3-630 | hsa-miR-548e | AAAACGAGACUACUUUUGCA | 0.36881696 |
| SEQ ID NO: 145 | Tab3-631 | hsa-miR-614 | GAACGCCUGUUCUUGCCAGGUGG | 0.370471328 |
| SEQ ID NO: 806 | Tab3-632 | hsa-miR-125b-2* | UCACAAGUCAGGCUCUUGGGAC | 0.371077072 |
| SEQ ID NO: 457 | Tab3-633 | hsa-miR-331-5p | CUAGGUAUGGUCCCAGGGAUCC | 0.372381817 |
| SEQ ID NO: 383 | Tab3-634 | hsa-miR-424 | CAGCAGCAAUUCAUGUUUUGAA | 0.372381817 |
| SEQ ID NO: 677 | Tab3-635 | hsa-miR-16-1* | CCAGUAUUAAACUGUGCUGCUGA | 0.374401904 |
| SEQ ID NO: 784 | Tab3-636 | hsa-miR-1276 | UAAAGAGCCCUGUGGGAGACA | 0.377421941 |
| SEQ ID NO: 197 | Tab3-637 | hsa-miR-567 | AGUAUGUUCUUCCAGGACAGAAC | 0.377938327 |
| SEQ ID NO: 870 | Tab3-638 | hsa-miR-10a* | CAAAUUCGUAUCUAGGGGAAUA | 0.381790819 |
| SEQ ID NO: 208 | Tab3-639 | hsa-miR-555 | AGGGUAAGCUGAACCUCUGAU | 0.383236834 |
| SEQ ID NO: 10 | Tab3-640 | hsa-miR-943 | CUGACUGUUGCCGUCCUCCAG | 0.385639767 |
| SEQ ID NO: 46 | Tab3-641 | hsa-miR-885-3p | AGGCAGCGGGGUGUAGUGGAUA | 0.385639767 |
| SEQ ID NO: 488 | Tab3-642 | hsa-miR-302f | UAAUUGCUUCCAUGUUU | 0.392187078 |
| SEQ ID NO: 775 | Tab3-643 | hsa-miR-1284 | UCUAUACAGACCCUGGCUUUUC | 0.392187078 |
| SEQ ID NO: 692 | Tab3-644 | hsa-miR-151-5p | UCGAGGAGCUCACAGUCUAGU | 0.392187078 |
| SEQ ID NO: 290 | Tab3-645 | hsa-miR-518c | CAAAGCGCUUCUCUUUAGAGUGU | 0.39689513 |
| SEQ ID NO: 409 | Tab3-646 | hsa-miR-376a | AUCAUAGAGGAAAAUCCACGU | 0.397271664 |
| SEQ ID NO: 229 | Tab3-647 | hsa-miR-548f | AAAACUGUAAUUACUUUU | 0.399652164 |
| SEQ ID NO: 492 | Tab3-648 | hsa-miR-302c* | UUUAACAUGGGGUACCUGCUG | 0.400749085 |
| SEQ ID NO: 95 | Tab3-649 | hsa-miR-657 | GGCAGGUUCUCACCCUCUCUAGG | 0.407448428 |
| SEQ ID NO: 771 | Tab3-650 | hsa-miR-1288 | UGGACUGCCCUGAUCUGGAGA | 0.407448428 |
| SEQ ID NO: 647 | Tab3-651 | hsa-miR-18b* | UGCCCUAAAUGCCCCUUCUGGC | 0.414121138 |
| SEQ ID NO: 781 | Tab3-652 | hsa-miR-1279 | UCAUAUUGCUUCUUUCU | 0.415219054 |
| SEQ ID NO: 141 | Tab3-653 | hsa-miR-616* | ACUCAAAACCCUUCAGUGACUU | 0.416884401 |
| SEQ ID NO: 210 | Tab3-654 | hsa-miR-553 | AAAACGGUGAGAUUUUGUUU | 0.417692108 |
| SEQ ID NO: 640 | Tab3-655 | hsa-miR-191* | GCUGCGCUUGGAUUUCGUCCCC | 0.417692108 |
| SEQ ID NO: 128 | Tab3-656 | hsa-miR-627 | GUGAGUCUACACCUCUUUGGGUGAA | 0.421665365 |
| SEQ ID NO: 40 | Tab3-657 | hsa-miR-888* | GACUGACUGGUUGACCAGAGGGG | 0.424935372 |
| SEQ ID NO: 736 | Tab3-658 | hsa-miR-134 | UGUGACUGGUUGACCAGAGGGG | 0.428299118 |
| SEQ ID NO: 834 | Tab3-659 | hsa-miR-1234 | UCGGCCUGACCACCCACAC | 0.428299118 |
| SEQ ID NO: 542 | Tab3-660 | hsa-miR-222 | AGCUACAUCUGGCUACUGGGU | 0.428299118 |
| SEQ ID NO: 412 | Tab3-661 | hsa-miR-374b | AUAUAAUACAACCUGCUAAGUG | 0.437464901 |
| SEQ ID NO: 873 | Tab3-662 | hsa-miR-106b* | CCGCACUGUGGGUACUUGCUGC | 0.439932697 |
| SEQ ID NO: 181 | Tab3-663 | hsa-miR-581 | UCUUGUGUUCUCUAGAUCAGU | 0.440952014 |

FIG. 30A (Cont.)

| | | | |
|---|---|---|---|
| SEQ ID NO: 755 | Tab3-664 | hsa-miR-1302 | UUGGGACAUACUUAUGCUAAA | 0.449342226 |
| SEQ ID NO: 852 | Tab3-665 | hsa-miR-1206 | UGUUCAUGUAGAUGUUUAAGC | 0.451742296 |
| SEQ ID NO: 318 | Tab3-666 | hsa-miR-507 | UUUUGCACCUUUUGGAGUGAA | 0.453181931 |
| SEQ ID NO: 400 | Tab3-667 | hsa-miR-379* | UAUGUAACAUGGUCCACUAACU | 0.454253475 |
| SEQ ID NO: 15 | Tab3-668 | hsa-miR-938 | UGCCCUUAAAGGUGAACCCAGU | 0.460321239 |
| SEQ ID NO: 562 | Tab3-669 | hsa-miR-212 | UAACAGUCUCCAGUCACGGCC | 0.460792512 |
| SEQ ID NO: 850 | Tab3-670 | hsa-miR-1207-5p | UGGCAGGGAGGCUGGGAGGGG | 0.460792512 |
| SEQ ID NO: 311 | Tab3-671 | hsa-miR-511 | GUGUCUUUUGCUCUGCAGUCA | 0.460792512 |
| SEQ ID NO: 893 | Tab3-672 | hsa-let-7f | UGAGGUAGAUUGUAUAGUU | 0.466298032 |
| SEQ ID NO: 284 | Tab3-673 | hsa-miR-518f | GAAAGCGCUUCUCUUUAGAGG | 0.467251122 |
| SEQ ID NO: 639 | Tab3-674 | hsa-miR-1910 | CCAGUCCUGUGCCUGCCGCCU | 0.467481996 |
| SEQ ID NO: 602 | Tab3-675 | hsa-miR-19a | UGUGCAAAUCUAUGCAAAACUGA | 0.474755766 |
| SEQ ID NO: 717 | Tab3-676 | hsa-miR-143 | UGAGAUGAAGCACUGUAGCUC | 0.476138161 |
| SEQ ID NO: 606 | Tab3-677 | hsa-miR-199a-3p | ACAGUAGUCUGCACAUUGGUUA | 0.476970958 |
| SEQ ID NO: 694 | Tab3-678 | hsa-miR-150* | CUGGUACAGGCCUGGGGGACAG | 0.478022588 |
| SEQ ID NO: 761 | Tab3-679 | hsa-miR-129-5p | CUUUUUGCGGUCUGGGCUUGC | 0.478022588 |
| SEQ ID NO: 539 | Tab3-680 | hsa-miR-223* | CGUAUUUGACAAGCUGAGUU | 0.478022588 |
| SEQ ID NO: 523 | Tab3-681 | hsa-miR-26a-1* | CCUAUUCUGGUUACUUGCACG | 0.481070985 |
| SEQ ID NO: 7 | Tab3-682 | hsa-miR-96 | UUUGGCACUAGCACAUUUUGCU | 0.49217503 |
| SEQ ID NO: 147 | Tab3-683 | hsa-miR-612 | GCUGGGCAGGGCUUCUGAGCUCCUU | 0.500260946 |
| SEQ ID NO: 192 | Tab3-684 | hsa-miR-572 | GUCCGCUGCGGCGGCGGCCCA | 0.501661675 |
| SEQ ID NO: 179 | Tab3-685 | hsa-miR-582-5p | UUACAGUUGUUCAACCAGUUACU | 0.505541335 |
| SEQ ID NO: 854 | Tab3-686 | hsa-miR-1204 | UCGUGGGCCUGGUUCACUUACG | 0.507435386 |
| SEQ ID NO: 357 | Tab3-687 | hsa-miR-455-5p | UAUGUGCCUUUGGACUACAUCG | 0.511363367 |
| SEQ ID NO: 93 | Tab3-688 | hsa-miR-659 | CUUGGUUCAGGGAGGGUCCCA | 0.511587065 |
| SEQ ID NO: 138 | Tab3-689 | hsa-miR-619 | GACCUGGACAUGUUUGUGCCAGU | 0.512295752 |
| SEQ ID NO: 96 | Tab3-690 | hsa-miR-656 | AAUAUUAUACAGUCAACCUCU | 0.516305395 |
| SEQ ID NO: 18 | Tab3-691 | hsa-miR-935 | CCAGUUACCGCUUCCGCUACCGC | 0.523625437 |
| SEQ ID NO: 52 | Tab3-692 | hsa-miR-875-3p | CCUGGAAACACUGAGGUUGUG | 0.526762182 |
| SEQ ID NO: 350 | Tab3-693 | hsa-miR-486-5p | UCCUGUACUGAGCUGCCCCGAG | 0.527194038 |
| SEQ ID NO: 251 | Tab3-694 | hsa-miR-526b* | GAAAGUGCUUCCUUUUAGAGGC | 0.531170223 |
| SEQ ID NO: 589 | Tab3-695 | hsa-miR-203 | GUGAAAUGUAAUUACUUUUGUAC | 0.545791792 |
| SEQ ID NO: 228 | Tab3-696 | hsa-miR-548g | AAAACUGUAAUUACUUUUGUAC | 0.549535107 |
| SEQ ID NO: 354 | Tab3-697 | hsa-miR-484 | UCAGGCUCAGUCCCCUCCCGAU | 0.549535107 |
| SEQ ID NO: 420 | Tab3-698 | hsa-miR-370 | GCCUGCUGGGGUGAACCUGGU | 0.549535107 |
| SEQ ID NO: 227 | Tab3-699 | hsa-miR-548h | AAAAGUAAUCGCGGUUUUUGUC | 0.549535107 |
| SEQ ID NO: 766 | Tab3-700 | hsa-miR-1292 | UGGGAACGGGUUCCGGCAGACGCUG | 0.552941581 |

FIG. 30A (Cont.)

| | | | | |
|---|---|---|---|---|
| SEQ ID NO: 631 | Tab3-701 | hsa-miR-1915* | ACCUUGCCUUGCUGCCCGGGCC | 0.553317998 |
| SEQ ID NO: 308 | Tab3-702 | hsa-miR-513a-3p | UAAAUUUCACCUUUCUGAGAAGG | 0.553317998 |
| SEQ ID NO: 485 | Tab3-703 | hsa-miR-30b | UGUAAACAUCCUACACUCAGCU | 0.555658341 |
| SEQ ID NO: 575 | Tab3-704 | hsa-miR-21 | UAGCUUAUCAGACUGAUGUUGA | 0.557379323 |
| SEQ ID NO: 461 | Tab3-705 | hsa-miR-329 | AACACACCUGGUUAACCUCUUU | 0.559795841 |
| SEQ ID NO: 898 | Tab3-706 | hsa-let-7c* | UAGAGUUACACCCUGGGAGUUA | 0.56374786 |
| SEQ ID NO: 33 | Tab3-707 | hsa-miR-9 | UCUUUGGUUAUCUAGCUGUAUGA | 0.566126339 |
| SEQ ID NO: 56 | Tab3-708 | hsa-miR-770-5p | UCCAGUACCACGUGUCAGGGCCA | 0.566126339 |
| SEQ ID NO: 688 | Tab3-709 | hsa-miR-1538 | CGGCCCGGGCUGCUGCUGUUCCU | 0.566126339 |
| SEQ ID NO: 470 | Tab3-710 | hsa-miR-320c | AAAAGCUGGGUUGAGAGGGU | 0.57074302 |
| SEQ ID NO: 901 | Tab3-711 | hsa-let-7b | UGAGGUAGUAGGUUGUGUGGUU | 0.572775803 |
| SEQ ID NO: 360 | Tab3-712 | hsa-miR-454 | UAGUGCAAUAUUGCUUAUAGGGU | 0.576066985 |
| SEQ ID NO: 61 | Tab3-713 | hsa-miR-766 | ACUCCAGCCCCACAGGCAAGGCUCAGC | 0.57643543 |
| SEQ ID NO: 325 | Tab3-714 | hsa-miR-502-3p | AAUGCACCUGGGCAAGGAUUCA | 0.577328998 |
| SEQ ID NO: 538 | Tab3-715 | hsa-miR-224 | CAAGUCACUAGUGGUUCCGUU | 0.579047469 |
| SEQ ID NO: 239 | Tab3-716 | hsa-miR-545* | UCAGUAAAUGUUUAUUAGAUGA | 0.580627899 |
| SEQ ID NO: 170 | Tab3-717 | hsa-miR-590-3p | UAAUUUUAUGUAUAAGCUAGU | 0.5824926 |
| SEQ ID NO: 100 | Tab3-718 | hsa-miR-653 | GUGUUGAAACAAUCUCUACUG | 0.5902417 |
| SEQ ID NO: 759 | Tab3-719 | hsa-miR-1297 | UUCAAGUAAUUCAGGUG | 0.599492517 |
| SEQ ID NO: 643 | Tab3-720 | hsa-miR-1909* | UGAGUGCCGGUGCCUGCCCUG | 0.603792487 |
| SEQ ID NO: 160 | Tab3-721 | hsa-miR-599 | GUUGUGUCAGUUUAUCAAAC | 0.603792487 |
| SEQ ID NO: 237 | Tab3-722 | hsa-miR-548a-5p | AAAAGUAAUUGCGAGUUUUACC | 0.605108744 |
| SEQ ID NO: 352 | Tab3-723 | hsa-miR-485-5p | AGAGGCUGGCCGUGAUGAAUUC | 0.608260427 |
| SEQ ID NO: 866 | Tab3-724 | hsa-miR-1179 | AAGCAUUCUUUCAUUGGUUGG | 0.619116969 |
| SEQ ID NO: 377 | Tab3-725 | hsa-miR-431* | CAGGUCGUCUGCAGGGCUUCU | 0.619585313 |
| SEQ ID NO: 310 | Tab3-726 | hsa-miR-512-3p | AAGUGCUGUCAUAGCUGAGGUC | 0.627369668 |
| SEQ ID NO: 886 | Tab3-727 | hsa-miR-1 | UGGAAUGUAAAGAAGUAUGUAU | 0.631432714 |
| SEQ ID NO: 521 | Tab3-728 | hsa-miR-26b | UUCAAGUAAUUCAGGAUAGGU | 0.632997371 |
| SEQ ID NO: 838 | Tab3-729 | hsa-miR-1228* | GUGGGCGGGGGCAGGUGUGUG | 0.637667559 |
| SEQ ID NO: 41 | Tab3-730 | hsa-miR-888 | UACUCAAAAAGCUGUCAGUCA | 0.639546866 |
| SEQ ID NO: 28 | Tab3-731 | hsa-miR-924 | AGAGCUUGUGAUGUCUUGC | 0.644497156 |
| SEQ ID NO: 815 | Tab3-732 | hsa-miR-1255b | CGGAUGAGCAAAGAAAGUGGUU | 0.646289734 |
| SEQ ID NO: 726 | Tab3-733 | hsa-miR-138-2* | GCUAUUUCACGACACCAGGGUU | 0.656991553 |
| SEQ ID NO: 878 | Tab3-734 | hsa-miR-105 | UCAAAUGCUCAGACUCCUGUGGU | 0.661395251 |
| SEQ ID NO: 466 | Tab3-735 | hsa-miR-324-3p | ACUGCCCCAGGUGCUGCUGG | 0.664797331 |
| SEQ ID NO: 415 | Tab3-736 | hsa-miR-373* | ACUCAAAAUGGGGGCUUUCC | 0.668554979 |
| SEQ ID NO: 392 | Tab3-737 | hsa-miR-409-5p | AGGUUACCCGAGCAACUUUGCAU | 0.671790846 |

FIG. 30A (Cont.)

| SEQ ID NO: 110 | Tab3-738 | hsa-miR-643 | ACUUGUAUGCUAGCUCAGGUAG | 0.679112161 |
|---|---|---|---|---|
| SEQ ID NO: 144 | Tab3-739 | hsa-miR-615-3p | UCCGAGCCUGGGUCUCCCUCUU | 0.680034841 |
| SEQ ID NO: 307 | Tab3-740 | hsa-miR-513a-5p | UUCACAGGGAGGUGUCAU | 0.683356445 |
| SEQ ID NO: 296 | Tab3-741 | hsa-miR-517a | AUCGUGCAUCCCUUAGAGUGU | 0.689923149 |
| SEQ ID NO: 645 | Tab3-742 | hsa-miR-1908 | CGGCGGGACGCGCGAUUGGUC | 0.700008298 |
| SEQ ID NO: 154 | Tab3-743 | hsa-miR-605 | UAAAUCCAUGUGCCUUCUCCU | 0.704403249 |
| SEQ ID NO: 454 | Tab3-744 | hsa-miR-337-3p | CUCCUAUAUGAUGCCUUUCUUC | 0.705870018 |
| SEQ ID NO: 31 | Tab3-745 | hsa-miR-920 | GGGGAGCUGUGGAAGCAGUA | 0.705870018 |
| SEQ ID NO: 783 | Tab3-746 | hsa-miR-1277 | UACGUAGAUAUAUAUGUAUUU | 0.705913362 |
| SEQ ID NO: 406 | Tab3-747 | hsa-miR-376c | AACAUAGAGGAAAUUCCACGU | 0.707187857 |
| SEQ ID NO: 621 | Tab3-748 | hsa-miR-195* | CCAAUAUUGGCUGUGCUGCUCC | 0.707187857 |
| SEQ ID NO: 892 | Tab3-749 | hsa-let-7f-1* | CUAUACAAUCUAUUGCCUUCCC | 0.707187857 |
| SEQ ID NO: 592 | Tab3-750 | hsa-miR-200c* | CGUCUUACCCAGCAGUGUUUGG | 0.712604267 |
| SEQ ID NO: 796 | Tab3-751 | hsa-miR-1267 | CCUGUUGAAGUGUAAUCCCCA | 0.714203251 |
| SEQ ID NO: 673 | Tab3-752 | hsa-miR-181a | AACAUUCAACCUGUCGGUGAGU | 0.721536345 |
| SEQ ID NO: 384 | Tab3-753 | hsa-miR-423-5p | UGAGGGGCAGAGAGCGAGACUUU | 0.724048336 |
| SEQ ID NO: 628 | Tab3-754 | hsa-miR-193a-3p | AACUGGCCUACACAAAGUCCCAGU | 0.725298742 |
| SEQ ID NO: 91 | Tab3-755 | hsa-miR-661 | UGCCUGGGUCUCUGGCCUGCGCGU | 0.725744562 |
| SEQ ID NO: 598 | Tab3-756 | hsa-miR-19b-2* | AGUUUUGCAGGUUUGCAUUUCA | 0.729534568 |
| SEQ ID NO: 810 | Tab3-757 | hsa-miR-125a-3p | ACAGGUGAGGUUCUUGGGAGCC | 0.735107149 |
| SEQ ID NO: 744 | Tab3-758 | hsa-miR-132 | UAACAGUCUACAGCCAUGGUCG | 0.735871055 |
| SEQ ID NO: 658 | Tab3-759 | hsa-miR-185 | UGGAGAGAAAGGCAGUUCCUGA | 0.735871055 |
| SEQ ID NO: 53 | Tab3-760 | hsa-miR-874 | CUGCCCUGGCCCGAGGGACCGA | 0.743106794 |
| SEQ ID NO: 704 | Tab3-761 | hsa-miR-1470 | GCCCUCCGCCGUGCACCCCG | 0.743490263 |
| SEQ ID NO: 481 | Tab3-762 | hsa-miR-30c-2* | CUGGGAGAAGGCUGUUUACUCU | 0.743490263 |
| SEQ ID NO: 381 | Tab3-763 | hsa-miR-425 | AAUGACACGAUCACUCCCGUUGA | 0.743954974 |
| SEQ ID NO: 772 | Tab3-764 | hsa-miR-1287 | UGCUGGAUCAGUGGUUCGAGUC | 0.750313474 |
| SEQ ID NO: 748 | Tab3-765 | hsa-miR-130a | CAGUGCAAUGUUAAAAGGGCAU | 0.774019054 |
| SEQ ID NO: 248 | Tab3-766 | hsa-miR-532-5p | CAUGCCUUGAGUGUAGGACCGU | 0.776612731 |
| SEQ ID NO: 774 | Tab3-767 | hsa-miR-1285 | UCUGGGCAACAAAGUGAGACCU | 0.790533365 |
| SEQ ID NO: 319 | Tab3-768 | hsa-miR-506 | UAAGGCACCCUUCUGAGUAGA | 0.790533365 |
| SEQ ID NO: 57 | Tab3-769 | hsa-miR-769-5p | UGAGACCUCUGGGUUCUGAGCU | 0.790533365 |
| SEQ ID NO: 421 | Tab3-770 | hsa-miR-369-5p | AGAUCGACCGUGUUAUAUUCGC | 0.790533365 |
| SEQ ID NO: 140 | Tab3-771 | hsa-miR-617 | AGACUUCCCAUUUGAAGGUGGC | 0.790533365 |
| SEQ ID NO: 794 | Tab3-772 | hsa-miR-1269 | CUGGACUGAGCCGUGCUACUGG | 0.790533365 |
| SEQ ID NO: 190 | Tab3-773 | hsa-miR-574-3p | CACGCUCAUGCACACACCCACA | 0.790533365 |
| SEQ ID NO: 322 | Tab3-774 | hsa-miR-504 | AGACCCUGGUCUGCACUCUAUC | 0.790533365 |

FIG. 30A (Cont.)

| | | | | |
|---|---|---|---|---|
| SEQ ID NO: 364 | Tab3-775 | hsa-miR-451 | AAACCGUUACCAUUACUGAGUU | 0.791416201 |
| SEQ ID NO: 895 | Tab3-776 | hsa-let-7e | UGAGGUAGGAGGUUGUAUAGUU | 0.79316116 |
| SEQ ID NO: 414 | Tab3-777 | hsa-miR-374a | UUAUAAUACAACCUGAUAAGUG | 0.794795605 |
| SEQ ID NO: 17 | Tab3-778 | hsa-miR-936 | ACAGUAGAGGGAGGAAUGCAG | 0.794795605 |
| SEQ ID NO: 104 | Tab3-779 | hsa-miR-649 | AAACCUGUGUUGUUCAAGAGUC | 0.798824757 |
| SEQ ID NO: 551 | Tab3-780 | hsa-miR-219-2-3p | AGAAUUGUGGCUGGACAUCUGU | 0.801093702 |
| SEQ ID NO: 280 | Tab3-781 | hsa-miR-519b-3p | AAAGUGCAUCCUUUUAGAGGUU | 0.801839871 |
| SEQ ID NO: 681 | Tab3-782 | hsa-miR-15a* | CAGGCCAUAUUGUGCUGCCUCA | 0.801839871 |
| SEQ ID NO: 21 | Tab3-783 | hsa-miR-93* | ACUGCUGAGCUAGCACUUCCCG | 0.8067541 |
| SEQ ID NO: 890 | Tab3-784 | hsa-let-7g | UGAGGUAGUAGUUUGUACAGUU | 0.809879811 |
| SEQ ID NO: 560 | Tab3-785 | hsa-miR-214* | UGCCUGUCUACACUUGCUGUGC | 0.815503909 |
| SEQ ID NO: 134 | Tab3-786 | hsa-miR-623 | AUCCCUUGCAGGGGCUGUUGGGU | 0.815503909 |
| SEQ ID NO: 123 | Tab3-787 | hsa-miR-630 | AGUAUUCUGUACCAGGGAAGGU | 0.815503909 |
| SEQ ID NO: 86 | Tab3-788 | hsa-miR-664* | ACUGGCUAGGGAAAAUGAUUGGAU | 0.820404153 |
| SEQ ID NO: 452 | Tab3-789 | hsa-miR-338-3p | UCCAGCAUCAGUGAUUUUGUUG | 0.827454646 |
| SEQ ID NO: 221 | Tab3-790 | hsa-miR-548n | CAAAAGUAAUGUGGAUUUUGU | 0.827454646 |
| SEQ ID NO: 626 | Tab3-791 | hsa-miR-193b | AACUGGCCCUCAAAGUCCCGCU | 0.893379901 |
| SEQ ID NO: 638 | Tab3-792 | hsa-miR-1911 | UGAGUACCGCCAUGUCUGUUGGG | 0.893379901 |
| SEQ ID NO: 60 | Tab3-793 | hsa-miR-767-3p | UCUGCUCAUACCCCAUGUCCUUUCU | 0.84339326 |
| SEQ ID NO: 139 | Tab3-794 | hsa-miR-618 | AAACUCUACUGUCCUUCUGAGU | 0.84339326 |
| SEQ ID NO: 604 | Tab3-795 | hsa-miR-199b-3p | ACAGUAGUCUGCACAUUGGUUA | 0.84763149 |
| SEQ ID NO: 678 | Tab3-796 | hsa-miR-16 | UAGCAGCACGUAAAUAUUGGCG | 0.84763149 |
| SEQ ID NO: 286 | Tab3-797 | hsa-miR-518e | AAAGCGCUUCCCUUCAGAGUG | 0.852530001 |
| SEQ ID NO: 490 | Tab3-798 | hsa-miR-302d* | ACUUUAACAUGGAGGCACUUGC | 0.864673616 |
| SEQ ID NO: 659 | Tab3-799 | hsa-miR-184 | UGGACGGAGAACUGAUAAGGGU | 0.854495627 |
| SEQ ID NO: 860 | Tab3-800 | hsa-miR-1185 | AGAGGAUACCCUUUGUAUGUU | 0.85584286 |
| SEQ ID NO: 189 | Tab3-801 | hsa-miR-574-5p | UGAGUGUGUGUGUGUGAGUGUGU | 0.858857177 |
| SEQ ID NO: 463 | Tab3-802 | hsa-miR-326 | CCUCUGGGGCCCUUCCUCCAG | 0.858857177 |
| SEQ ID NO: 732 | Tab3-803 | hsa-miR-135b* | AUGUAGGGCUAAAAGCCAUGGG | 0.857719333 |
| SEQ ID NO: 635 | Tab3-804 | hsa-miR-1913 | UCUGCCCCUCCGCUGCUGCCA | 0.858295351 |
| SEQ ID NO: 129 | Tab3-805 | hsa-miR-626 | AGCUGUCUGAAAAUGUCUU | 0.859538258 |
| SEQ ID NO: 526 | Tab3-806 | hsa-miR-25 | CAUUGCACUUGUCUCGGUCUGA | 0.865191301 |
| SEQ ID NO: 753 | Tab3-807 | hsa-miR-1304 | UUUGAGGCUACAGUGAGAUGUG | 0.866285197 |
| SEQ ID NO: 632 | Tab3-808 | hsa-miR-1915 | CCCCAGGGCGACGCGGCGGG | 0.866456075 |
| SEQ ID NO: 211 | Tab3-809 | hsa-miR-552 | AACAGGUGACUGGUUAGACAA | 0.872182845 |
| SEQ ID NO: 16 | Tab3-810 | hsa-miR-937 | AUCCGCGCUCUGACUAUAAUGCC | 0.877021406 |
| SEQ ID NO: 805 | Tab3-811 | hsa-miR-126 | UCGUACCGUGAGUAAUAAUGCG | |

FIG. 30A (Cont.)

| | | | | |
|---|---|---|---|---|
| SEQ ID NO: 8 | Tab3-812 | hsa-miR-95 | UUCAACGGGUAUUUAUUGAGCA | 0.877021406 |
| SEQ ID NO: 696 | Tab3-813 | hsa-miR-149* | AGGGAGGGACGGCGGGGCUGUGC | 0.890152786 |
| SEQ ID NO: 682 | Tab3-814 | hsa-miR-15a | UAGCAGCACAUAAUGGUUUGUG | 0.894544386 |
| SEQ ID NO: 117 | Tab3-815 | hsa-miR-636 | UGUGCUUGCUCGUCCCGCCCGCA | 0.894544386 |
| SEQ ID NO: 888 | Tab3-816 | hsa-let-7i | UGAGGUAGUAGUUUGUGCUGUU | 0.894544386 |
| SEQ ID NO: 417 | Tab3-817 | hsa-miR-372 | AAAGUGCUGCGACAUUUGAGCGU | 0.899908908 |
| SEQ ID NO: 234 | Tab3-818 | hsa-miR-548c-3p | CAAAAAUCUCAAUUACUUUUGC | 0.903764082 |
| SEQ ID NO: 162 | Tab3-819 | hsa-miR-697 | UGUGUCACUCGAUGACCACUGU | 0.916000918 |
| SEQ ID NO: 389 | Tab3-820 | hsa-miR-411* | UAUGUAACACGGUCCACUAACC | 0.916160139 |
| SEQ ID NO: 263 | Tab3-821 | hsa-miR-520h | ACAAAGUGCUUCCCUUUAGAGU | 0.916679661 |
| SEQ ID NO: 119 | Tab3-822 | hsa-miR-634 | AACCAGCACCCCAACUUUGGAC | 0.917663393 |
| SEQ ID NO: 472 | Tab3-823 | hsa-miR-320a | AAAAGCUGGGUUGAGAGGGCGA | 0.918968059 |
| SEQ ID NO: 530 | Tab3-824 | hsa-miR-23b* | UGGGUUCCUGGCAUGCUGAUUU | 0.920840603 |
| SEQ ID NO: 330 | Tab3-825 | hsa-miR-499-5p | UUAAGACUUGCAGUGAUGUUU | 0.921464415 |
| SEQ ID NO: 200 | Tab3-826 | hsa-miR-563 | AGGUUGACAUACGUUUCC | 0.921464415 |
| SEQ ID NO: 176 | Tab3-827 | hsa-miR-585 | UGGGCGUAUCUGUAUGCUA | 0.926842881 |
| SEQ ID NO: 451 | Tab3-828 | hsa-miR-338-5p | AACAAUAUCCUGGUGCUGAGUG | 0.927612831 |
| SEQ ID NO: 799 | Tab3-829 | hsa-miR-1264 | CAAGCUUAUUUGAGCACCUGUU | 0.931048035 |
| SEQ ID NO: 837 | Tab3-830 | hsa-miR-1229 | CUCUCACCACUGCCCUCCACAG | 0.932531804 |
| SEQ ID NO: 689 | Tab3-831 | hsa-miR-1537 | AAAACGCUCUAGAUUACAGUUGU | 0.932590664 |
| SEQ ID NO: 439 | Tab3-832 | hsa-miR-346 | UGUCUGCCCGCAUGCCUGCCUCU | 0.932888437 |
| SEQ ID NO: 249 | Tab3-833 | hsa-miR-532-3p | CCUCCCACACCCAAGGCUUGCA | 0.934194634 |
| SEQ ID NO: 552 | Tab3-834 | hsa-miR-219-1-3p | AGAGUUGAGUCUGGACGUCCCG | 0.939788562 |
| SEQ ID NO: 142 | Tab3-835 | hsa-miR-616 | AGUCAUUGGAGGGUUUGAGCAG | 0.939788562 |
| SEQ ID NO: 871 | Tab3-836 | hsa-miR-10a | UACCCUGUAGAUCCGAAUUUGUG | 0.939788562 |
| SEQ ID NO: 236 | Tab3-837 | hsa-miR-876-5p | UGGAUUUCUUUGUGAAUCACCA | 0.941350652 |
| SEQ ID NO: 257 | Tab3-838 | hsa-miR-548b-3p | CAAGAACCUCAGUUGCUUUUGU | 0.941943081 |
| SEQ ID NO: 163 | Tab3-839 | hsa-miR-346 | GAAGGGCGUCCCUUUGGAGU | 0.943929692 |
| SEQ ID NO: 691 | Tab3-840 | hsa-miR-524-3p | AAGCCUGCAUGACAGAACUGG | 0.945417238 |
| SEQ ID NO: 524 | Tab3-841 | hsa-miR-596 | UCAGUGCAUGACAGAACUGG | 0.95229716 |
| SEQ ID NO: 882 | Tab3-842 | hsa-miR-152 | UCAGUGCAUGACAGAACUUGG | 0.95229716 |
| SEQ ID NO: 183 | Tab3-843 | hsa-miR-26a | UUCAAGUAAUCCAGGAUAGGCU | 0.953614772 |
| SEQ ID NO: 468 | Tab3-844 | hsa-miR-101* | CAGUUAUCACAGUGCUGAUGCU | 0.958800374 |
| SEQ ID NO: 348 | Tab3-845 | hsa-miR-579 | UUCAUUUGGUAUAAACCGCGAUU | 0.958800374 |
| SEQ ID NO: 101 | Tab3-846 | hsa-miR-323-3p | CACAUUACACGGUCGACCUCU | 0.958800374 |
| SEQ ID NO: 242 | Tab3-847 | hsa-miR-487b | AAUCGUACAGGGUCAUCCACUU | 0.958800374 |
| SEQ ID NO: 242 | Tab3-848 | hsa-miR-652 | AAUGGCGCCACUAGGGUUGUG | 0.958800374 |
| | | hsa-miR-543 | AAACAUUCGCGGUGCACUUCUU | 0.960414751 |

FIG. 30A (Cont.)

| SEQ ID NO | Tab | miRNA | Sequence | Value |
|---|---|---|---|---|
| SEQ ID NO: 191 | Tab3-849 | hsa-miR-573 | CUGAAGUGAUGUGUAACUGAUCAG | 0.96534592 |
| SEQ ID NO: 591 | Tab3-850 | hsa-miR-202 | AGAGGUAUAGGGCAUGGGAA | 0.969136434 |
| SEQ ID NO: 525 | Tab3-851 | hsa-miR-25* | AGGCGGAGACUUGGGCAAUUG | 0.96926941 |
| SEQ ID NO: 112 | Tab3-852 | hsa-miR-641 | AAAGACAUAGGAUGAGUCACCUC | 0.970377712 |
| SEQ ID NO: 387 | Tab3-853 | hsa-miR-421 | AUCAACAGACAUUAAUUGGGCGC | 0.970377712 |
| SEQ ID NO: 27 | Tab3-854 | hsa-miR-92a | UAUUGCACUUGUCCCGGCCUGU | 0.970377712 |
| SEQ ID NO: 276 | Tab3-855 | hsa-miR-519d | CAAAGUGCCUCCCUUUAGAGUG | 0.9707701494 |
| SEQ ID NO: 471 | Tab3-856 | hsa-miR-320b | AAAAGCUGGGUUGAGAGGGCAA | 0.9755531937 |
| SEQ ID NO: 702 | Tab3-857 | hsa-miR-147b | GUGUGCGGAAAUGCUUCUGCUA | 0.97838546 |
| SEQ ID NO: 469 | Tab3-858 | hsa-miR-320d | AAAAGCUGGGUUGAGAGGA | 0.9811494 |
| SEQ ID NO: 30 | Tab3-859 | hsa-miR-921 | CUAGUGAGGGACAGAACCAGGAUUC | 0.992561443 |
| SEQ ID NO: 867 | Tab3-860 | hsa-miR-1178 | UUGCUCACUGUUCUUCCCUAG | 0.992561443 |
| SEQ ID NO: 92 | Tab3-861 | hsa-miR-660 | UACCCAUUGCAUAUCGGAGUUG | 0.992561443 |
| SEQ ID NO: 332 | Tab3-862 | hsa-miR-498 | UUUCAAGCCAGGGGGCGUUUUUC | 0.994281938 |
| SEQ ID NO: 3 | Tab3-863 | hsa-miR-99a* | CAAGCUCGCUUCUAUGGGUCUG | 0.999657232 |

FIG. 30B

| SEQ ID NO | miRNA | Sequence | mean rang | median | qmedian | log median | test raw p | test adj p |
|---|---|---|---|---|---|---|---|---|
| SEQ ID NO: 809 | hsa-miR-125a-5p | ucccugagacccuuuaaccuguga | 151 | 354 | 0.427 | -0.852 | 1.269E-10 | 1.825E-08 |
| SEQ ID NO: 329 | hsa-miR-500 | uaauccuugcuaccuggugaga | 213 | 460 | 0.463 | -0.771 | 3.584E-08 | 1.546E-06 |
| SEQ ID NO: 746 | hsa-miR-130b | cagugcaaugaugaaagggcau | 1463 | 661 | 2.213 | 0.794 | 3.761E-08 | 1.546E-06 |
| SEQ ID NO: 4 | hsa-miR-99a | aacccguagauccgaucuugug | 102 | 219 | 0.466 | -0.763 | 4.767E-08 | 1.819E-06 |
| SEQ ID NO: 430 | hsa-miR-362-3p | aacacaccuauucaaggauuca | 204 | 423 | 0.482 | -0.730 | 1.144E-04 | 6.537E-04 |
| SEQ ID NO: 890 | hsa-let-7g | ugagguaguaguuuguacaguu | 294 | 629 | 0.467 | -0.761 | 4.378E-03 | 1.426E-02 |
| SEQ ID NO: 895 | hsa-let-7e | ugagguaggagguuguauaguu | 141 | 330 | 0.427 | -0.852 | 1.316E-02 | 3.483E-02 |
| SEQ ID NO: 431 | hsa-miR-361-5p | uuaucagaauccagggguac | 418 | 756 | 0.552 | -0.593 | 1.501E-09 | 1.440E-07 |
| SEQ ID NO: 460 | hsa-miR-330-3p | gcaaagcacacggccugcagaga | 377 | 215 | 1.750 | 0.560 | 5.035E-09 | 3.621E-07 |
| SEQ ID NO: 701 | hsa-miR-148a | ucagugcacuacagaacuuugu | 950 | 523 | 1.817 | 0.597 | 1.896E-08 | 9.624E-07 |
| SEQ ID NO: 165 | hsa-miR-593* | aggcaccagcaggcauugcucagc | 288 | 180 | 1.600 | 0.470 | 2.815E-08 | 1.350E-06 |
| SEQ ID NO: 788 | hsa-miR-1274a | gucccuguucaggcgcua | 142 | 258 | 0.551 | -0.596 | 5.086E-08 | 1.829E-06 |
| SEQ ID NO: 382 | hsa-miR-424* | caaaacguaggcgcugcuau | 110 | 208 | 0.530 | -0.634 | 5.924E-08 | 1.966E-06 |
| SEQ ID NO: 136 | hsa-miR-621 | ggcuagcagcagcgcauuaccu | 332 | 183 | 1.810 | 0.593 | 3.121E-07 | 8.688E-06 |
| SEQ ID NO: 429 | hsa-miR-362-5p | aaucccuugaaccuaggugugagu | 126 | 245 | 0.517 | -0.661 | 6.427E-07 | 1.353E-05 |
| SEQ ID NO: 622 | hsa-miR-195 | uagcagcacagaaauauuggc | 620 | 423 | 1.464 | 0.381 | 7.164E-07 | 1.472E-05 |
| SEQ ID NO: 478 | hsa-miR-30e | uguaaacauccuugacuggaag | 241 | 464 | 0.520 | -0.653 | 7.936E-07 | 1.557E-05 |
| SEQ ID NO: 444 | hsa-miR-340 | uuauaaagcaaugacugauu | 140 | 224 | 0.627 | -0.467 | 8.845E-07 | 1.624E-05 |
| SEQ ID NO: 861 | hsa-miR-1184 | ccugcaggggacuugauggcuucc | 176 | 106 | 1.665 | 0.510 | 1.314E-06 | 2.139E-05 |
| SEQ ID NO: 327 | hsa-miR-501-3p | aaugcacccgggcaggaaucu | 372 | 241 | 1.547 | 0.436 | 1.752E-06 | 2.701E-05 |
| SEQ ID NO: 362 | hsa-miR-452* | cucaucugcaaagaaguaagug | 291 | 194 | 1.502 | 0.407 | 2.451E-06 | 3.647E-05 |
| SEQ ID NO: 216 | hsa-miR-550 | agugccugagggaguaagagcc | 114 | 161 | 0.705 | -0.350 | 2.644E-06 | 3.741E-05 |
| SEQ ID NO: 386 | hsa-miR-422a | acuggacuugccuagggucagaaggc | 139 | 274 | 0.507 | -0.679 | 2.837E-06 | 3.950E-05 |
| SEQ ID NO: 756 | hsa-miR-1301 | uugcagcugccuggggagugacuuc | 202 | 121 | 1.673 | 0.514 | 3.475E-06 | 4.760E-05 |
| SEQ ID NO: 872 | hsa-miR-107 | agcagcauuguacaggggcuauca | 1305 | 675 | 1.933 | 0.659 | 3.938E-06 | 5.150E-05 |
| SEQ ID NO: 855 | hsa-miR-1202 | cccggaggcugaugucagcagc | 198 | 127 | 1.562 | 0.446 | 4.200E-06 | 5.254E-05 |
| SEQ ID NO: 856 | hsa-miR-1203 | gugccagucgcugaugugggg | 208 | 147 | 1.420 | 0.350 | 5.171E-06 | 6.127E-05 |
| SEQ ID NO: 59 | hsa-miR-767-5p | ugcaccauggguugucugagcaug | 157 | 111 | 1.414 | 0.347 | 6.199E-06 | 7.217E-05 |
| SEQ ID NO: 300 | hsa-miR-516a-5p | uucucugagaaagagcacuuuc | 193 | 111 | 1.744 | 0.556 | 7.731E-06 | 8.307E-05 |
| SEQ ID NO: 98 | hsa-miR-654-5p | uggugggccgcagaacaugugc | 181 | 126 | 1.437 | 0.363 | 7.993E-06 | 8.369E-05 |
| SEQ ID NO: 465 | hsa-miR-324-5p | cgcaucccuagggcauuggugu | 332 | 468 | 0.709 | -0.343 | 8.049E-06 | 8.369E-05 |
| SEQ ID NO: 475 | hsa-miR-31* | ugcuaugccaacauauuggccau | 171 | 109 | 1.573 | 0.453 | 8.487E-06 | 8.720E-05 |
| SEQ ID NO: 487 | hsa-miR-30a | uguaaacauccucgacuggaag | 323 | 636 | 0.508 | -0.677 | 1.189E-05 | 1.140E-04 |
| SEQ ID NO: 302 | hsa-miR-515-5p | uucuccaaaagaaagcacuuuug | 161 | 112 | 1.440 | 0.365 | 1.573E-05 | 1.414E-04 |
| SEQ ID NO: 440 | hsa-miR-345 | gcugacucccuaguccaggcuc | 108 | 157 | 0.689 | -0.372 | 1.959E-05 | 1.708E-04 |
| SEQ ID NO: 315 | hsa-miR-509-3-5p | uacugcagacguggcaaucaug | 212 | 162 | 1.305 | 0.266 | 2.191E-05 | 1.854E-04 |

FIG. 30B (Cont.)

| | | | | | | | |
|---|---|---|---|---|---|---|---|
| SEQ ID NO: 649 | hsa-miR-18a* | acugcccuaagugucucuucugg | 192 | | 0.507 | -0.680 | 2.378E-05 | 1.973E-04 |
| SEQ ID NO: 107 | hsa-miR-846 | aagcagcugcucugagc | 206 | 379 | 1.322 | 0.279 | 2.457E-05 | 2.019E-04 |
| SEQ ID NO: 636 | hsa-miR-1912 | uaccagagaugcaguguga | 152 | 156 | 1.399 | 0.336 | 3.249E-05 | 2.552E-04 |
| SEQ ID NO: 313 | hsa-miR-509-5p | uacugcagacagugccaauca | 213 | 109 | 1.435 | 0.361 | 3.442E-05 | 2.621E-04 |
| SEQ ID NO: 887 | hsa-let-7i* | cugcaaguacugccuugcu | 226 | 148 | 1.779 | 0.576 | 3.604E-05 | 2.658E-04 |
| SEQ ID NO: 600 | hsa-miR-19b | ugugcaaauccaugcaaaacuga | 10422 | 127 | 0.802 | -0.221 | 3.870E-05 | 2.807E-04 |
| SEQ ID NO: 199 | hsa-miR-564 | aggcacgugucagcagc | 157 | 13000 | 1.303 | 0.264 | 4.042E-05 | 2.907E-04 |
| SEQ ID NO: 297 | hsa-miR-517* | ccucuagauggaagcacugucu | 165 | 120 | 1.443 | 0.367 | 4.581E-05 | 3.241E-04 |
| SEQ ID NO: 787 | hsa-miR-1274b | ucccuguccggcgcca | 770 | 114 | 0.590 | -0.528 | 4.731E-05 | 3.293E-04 |
| SEQ ID NO: 559 | hsa-miR-215 | augaccuaugaaugacagac | 375 | 1305 | 0.678 | -0.388 | 6.282E-05 | 4.066E-04 |
| SEQ ID NO: 446 | hsa-miR-33b | gugcaugcuguugcaugc | 172 | 553 | 1.315 | 0.274 | 8.142E-05 | 4.880E-04 |
| SEQ ID NO: 578 | hsa-miR-20a* | acugcauuaugagcacuuaaag | 139 | 131 | 1.317 | 0.275 | 1.054E-04 | 6.103E-04 |
| SEQ ID NO: 709 | hsa-miR-146a | ugagaacugaauuccaugggu | 193 | 106 | 0.609 | -0.496 | 1.176E-04 | 6.593E-04 |
| SEQ ID NO: 101 | hsa-miR-652 | aauggcgccacuagggguugu | 1113 | 316 | 0.686 | -0.376 | 1.443E-04 | 7.833E-04 |
| SEQ ID NO: 360 | hsa-miR-454 | uagugcaauauugcuuauagggu | 114 | 1621 | 0.626 | -0.469 | 1.529E-04 | 8.197E-04 |
| SEQ ID NO: 674 | hsa-miR-17* | acugcagugaaggauauguag | 541 | 183 | 1.320 | 0.277 | 1.851E-04 | 9.622E-04 |
| SEQ ID NO: 498 | hsa-miR-301b | cagugcaaugauauugucaaagc | 182 | 410 | 1.332 | 0.286 | 2.447E-04 | 1.228E-03 |
| SEQ ID NO: 385 | hsa-miR-423-3p | agcucggucugaggccccucagu | 1105 | 137 | 0.682 | -0.383 | 3.178E-04 | 1.562E-03 |
| SEQ ID NO: 20 | hsa-miR-933 | ugugcgcaggagaccucuccc | 175 | 1621 | 1.249 | 0.222 | 3.388E-04 | 1.652E-03 |
| SEQ ID NO: 87 | hsa-miR-664 | uauucauuuauccccagccuaca | 273 | 140 | 0.527 | -0.641 | 5.277E-04 | 2.498E-03 |
| SEQ ID NO: 127 | hsa-miR-628-3p | ucuaguaagaguggcagugca | 152 | 518 | 0.749 | -0.289 | 5.681E-04 | 2.664E-03 |
| SEQ ID NO: 881 | hsa-miR-103 | agcagcauuguacaggggcuauga | 6845 | 203 | 1.982 | 0.684 | 6.944E-04 | 3.222E-03 |
| SEQ ID NO: 403 | hsa-miR-378 | acuggacuuggagucagaagg | 259 | 3453 | 0.718 | -0.331 | 1.549E-03 | 6.364E-03 |
| SEQ ID NO: 323 | hsa-miR-503 | uagcagcgggaacaguucugcag | 260 | 361 | 1.078 | 0.075 | 1.627E-03 | 6.579E-03 |
| SEQ ID NO: 635 | hsa-miR-1913 | ucugccccucgcugcugcca | 359 | 241 | 1.398 | 0.335 | 1.680E-03 | 6.745E-03 |
| SEQ ID NO: 292 | hsa-miR-518a-5p | cugcaaagggaagcccuuuc | 164 | 257 | 1.288 | 0.253 | 1.871E-03 | 7.266E-03 |
| SEQ ID NO: 250 | hsa-miR-527 | cugcaaagggaagcccuuuc | 156 | 127 | 1.366 | 0.312 | 1.978E-03 | 7.555E-03 |
| SEQ ID NO: 428 | hsa-miR-363 | aauugcacgguauccaucugua | 3453 | 114 | 1.372 | 0.316 | 2.291E-03 | 8.467E-03 |
| SEQ ID NO: 680 | hsa-miR-15b | uagcagcacaucauggguuuaca | 13583 | 2518 | 1.133 | 0.125 | 2.909E-03 | 1.016E-02 |
| SEQ ID NO: 888 | hsa-let-7i | ugagguaguaguuugugcuguu | 513 | 11992 | 0.536 | -0.624 | 3.091E-03 | 1.067E-02 |
| SEQ ID NO: 480 | hsa-miR-30d | uguaaacauccccgacuggaag | 7722 | 957 | 0.786 | -0.240 | 3.138E-03 | 1.079E-02 |
| SEQ ID NO: 875 | hsa-miR-106a* | cugcaauguaagcacuucuac | 132 | 9818 | 1.041 | 0.040 | 3.556E-03 | 1.203E-02 |
| SEQ ID NO: 61 | hsa-miR-766 | acucccacagcccacagcccuac | 491 | 127 | 1.453 | 0.374 | 3.626E-03 | 1.222E-02 |
| SEQ ID NO: 630 | hsa-miR-192 | cugaccuaugaauugacagcc | 5652 | 338 | 0.859 | -0.152 | 3.977E-03 | 1.310E-02 |
| SEQ ID NO: 345 | hsa-miR-489 | gugacaucauauacggcagc | 155 | 6578 | 0.977 | -0.023 | 4.648E-03 | 1.486E-02 |
| SEQ ID NO: 529 | hsa-miR-24 | uggcucucagguccagagaacag | 1762 | 159 | 1.280 | 0.246 | 5.818E-03 | 1.813E-02 |
| SEQ ID NO: 834 | hsa-miR-1234 | ucggccugaccacccccac | 699 | 1377 | 1.987 | 0.687 | 6.711E-03 | 2.025E-02 |

FIG. 30B (Cont.)

| | | | | | | | | |
|---|---|---|---|---|---|---|---|---|
| SEQ ID NO: 248 | hsa-miR-532-5p | caugccuugagugucaggacgu | 211 | 268 | 0.788 | -0.238 | 7.143E-03 | 2.126E-02 |
| SEQ ID NO: 577 | hsa-miR-20b | caaagugcucauagugcaguag | 2820 | 1919 | 1.470 | 0.385 | 7.198E-03 | 2.135E-02 |
| SEQ ID NO: 27 | hsa-miR-92a | uauugcacuugucccggccugu | 11992 | 15762 | 0.761 | -0.273 | 7.282E-03 | 2.152E-02 |
| SEQ ID NO: 328 | hsa-miR-500* | augcaccuggcaaggauucug | 250 | 224 | 1.118 | 0.112 | 7.577E-03 | 2.209E-02 |
| SEQ ID NO: 542 | hsa-miR-222 | agcuacaucugcuacuggu | 445 | 543 | 0.820 | -0.199 | 7.573E-03 | 2.209E-02 |
| SEQ ID NO: 89 | hsa-miR-663 | aggcgggcgccgcggaccgc | 349 | 291 | 1.199 | 0.182 | 7.574E-03 | 2.209E-02 |
| SEQ ID NO: 75 | hsa-miR-7-1* | caacaaaucacagucugccaua | 288 | 361 | 0.799 | -0.225 | 8.993E-03 | 2.545E-02 |
| SEQ ID NO: 450 | hsa-miR-339-3p | ugagcgccucgacgacagagccg | 279 | 240 | 1.165 | 0.153 | 9.277E-03 | 2.616E-02 |
| SEQ ID NO: 723 | hsa-miR-140-3p | uaccacagguagaaccacg | 24753 | 24753 | 1.000 | 0.000 | 9.716E-03 | 2.714E-02 |
| SEQ ID NO: 897 | hsa-let-7d | agagguaguaggguugcauaguu | 1987 | 3002 | 0.662 | -0.413 | 1.142E-02 | 3.120E-02 |
| SEQ ID NO: 80 | hsa-miR-675 | uggugcggagaggguugagga | 138 | 234 | 0.590 | -0.528 | 1.316E-02 | 3.483E-02 |
| SEQ ID NO: 469 | hsa-miR-320d | aaaagcuggguugagga | 908 | 714 | 1.271 | 0.240 | 1.323E-02 | 3.492E-02 |
| SEQ ID NO: 249 | hsa-miR-532-3p | ccucccacaccaaggcuugca | 4406 | 3002 | 1.468 | 0.384 | 1.433E-02 | 3.734E-02 |
| SEQ ID NO: 652 | hsa-miR-188-3p | cucccaaugcaggguugca | 129 | 127 | 1.022 | 0.022 | 1.537E-02 | 3.923E-02 |
| SEQ ID NO: 527 | hsa-miR-24-2* | ugccuacugagcugaaacag | 147 | 146 | 1.006 | 0.006 | 1.559E-02 | 3.968E-02 |
| SEQ ID NO: 669 | hsa-miR-181c | aacauucaaccugucggugagu | 126 | 179 | 0.708 | -0.346 | 1.676E-02 | 4.180E-02 |
| SEQ ID NO: 663 | hsa-miR-1826 | auugaucggacacauucgaacgcaau | 195 | 160 | 1.224 | 0.202 | 1.899E-02 | 4.709E-02 |
| SEQ ID NO: 23 | hsa-miR-92b* | agggacggacgcggugcagug | 132 | 191 | 0.689 | -0.372 | 2.039E-02 | 4.986E-02 |
| SEQ ID NO: 477 | hsa-miR-30e* | cuuucagucggauguuuacagc | 39 | 105 | 0.373 | -0.985 | 2.035E-12 | 1.756E-09 |
| SEQ ID NO: 656 | hsa-miR-186 | caaagaauucuccuuuggggcu | 34 | 209 | 0.161 | -1.828 | 3.218E-11 | 6.943E-09 |
| SEQ ID NO: 462 | hsa-miR-328 | cuggccccucucugcccuccgu | 57 | 180 | 0.318 | -1.147 | 2.661E-11 | 6.943E-09 |
| SEQ ID NO: 125 | hsa-miR-629 | ugggutuuacguuggagaacu | 58 | 203 | 0.284 | -1.259 | 4.191E-11 | 7.233E-09 |
| SEQ ID NO: 426 | hsa-miR-365 | uaaugcccuaaaaauccuuau | 64 | 166 | 0.386 | -0.952 | 2.112E-10 | 2.603E-08 |
| SEQ ID NO: 660 | hsa-miR-183* | gugaauuaccgaagggccuuucg | 85 | 199 | 0.424 | -0.857 | 4.830E-09 | 3.621E-07 |
| SEQ ID NO: 131 | hsa-miR-625 | aggggaaaguucuauaguc | 59 | 190 | 0.309 | -1.173 | 1.014E-08 | 6.734E-07 |
| SEQ ID NO: 387 | hsa-miR-421 | aucaacagacauuaauugggc | 87 | 193 | 0.450 | -0.798 | 5.639E-08 | 1.947E-06 |
| SEQ ID NO: 253 | hsa-miR-526a | cucuagagggaagcacuuucg | 140 | 55 | 2.546 | 0.935 | 3.223E-07 | 8.692E-06 |
| SEQ ID NO: 246 | hsa-miR-541 | uguugggcacagaaucuggacu | 106 | 51 | 2.071 | 0.728 | 3.855E-07 | 9.785E-06 |
| SEQ ID NO: 287 | hsa-miR-518d-5p | cucuagagggaagcacuucug | 158 | 76 | 2.076 | 0.730 | 4.116E-07 | 1.015E-05 |
| SEQ ID NO: 896 | hsa-let-7d* | cuauacgaccugcugccuuucu | 59 | 183 | 0.319 | -1.141 | 1.203E-06 | 1.997E-05 |
| SEQ ID NO: 773 | hsa-miR-1286 | ugcaggaccaagaugagcci | 120 | 55 | 2.180 | 0.779 | 1.193E-06 | 1.997E-05 |
| SEQ ID NO: 842 | hsa-miR-1226 | ucaccagcccuguguuccccuag | 49 | 102 | 0.483 | -0.728 | 1.874E-06 | 2.838E-05 |
| SEQ ID NO: 719 | hsa-miR-142-3p | uguaguguuuacuacuuuaugga | 18 | 109 | 0.166 | -1.793 | 2.526E-06 | 3.695E-05 |
| SEQ ID NO: 747 | hsa-miR-130a* | uucacauugugcuacugucugc | 53 | 106 | 0.498 | -0.697 | 3.652E-06 | 4.925E-05 |
| SEQ ID NO: 627 | hsa-miR-193a-5p | ugggucuuugcgggagaguga | 55 | 138 | 0.400 | -0.915 | 4.156E-06 | 5.254E-05 |
| SEQ ID NO: 548 | hsa-miR-22* | aguucaguggcaagcuuua | 47 | 122 | 0.382 | -0.961 | 4.928E-06 | 6.076E-05 |
| SEQ ID NO: 762 | hsa-miR-1295 | uuaggccgcagaucuggguga | 113 | 55 | 2.050 | 0.718 | 6.486E-06 | 7.270E-05 |

FIG. 30B (Cont.)

| | | | | | | |
|---|---|---|---|---|---|---|
| SEQ ID NO: 778 | hsa-miR-1281 | ucgccuccuccucuccc | 68 | 0.364 | -1.011 | 1.222E-05 | 1.159E-04 |
| SEQ ID NO: 393 | hsa-miR-409-3p | gaauguugcucggugaaccccu | 36 | 188 | -1.201 | 3.360E-05 | 2.589E-04 |
| SEQ ID NO: 326 | hsa-miR-501-5p | aauccuuugucccuggugaga | 40 | 119 | -1.024 | 3.791E-05 | 2.772E-04 |
| SEQ ID NO: 402 | hsa-miR-378* | cuccugacuccaggucccugugu | 51 | 111 | 0.476 | -0.741 | 7.773E-05 | 4.724E-04 |
| SEQ ID NO: 664 | hsa-miR-1825 | uccagugcccucuccucc | 46 | 107 | 0.455 | -0.788 | 1.162E-04 | 6.593E-04 |
| SEQ ID NO: 78 | hsa-miR-7 | uggaagacuagugauuuuguugu | 31 | 102 | 0.245 | -1.407 | 1.173E-04 | 6.593E-04 |
| SEQ ID NO: 177 | hsa-miR-584 | uuauggguuugccugggacugag | 84 | 127 | 0.418 | -0.871 | 3.186E-04 | 1.562E-03 |
| SEQ ID NO: 786 | hsa-miR-1275 | gugggggaggcugc | 60 | 201 | 0.500 | -0.694 | 2.082E-03 | 7.836E-03 |
| SEQ ID NO: 865 | hsa-miR-1180 | uuuccggcucgcugggugugu | 62 | 120 | 0.433 | -0.837 | 6.705E-03 | 2.025E-02 |
| SEQ ID NO: 846 | hsa-miR-1224-3p | cccaccucucucucuccuccag | 95 | 144 | 0.489 | -0.716 | 1.571E-02 | 3.988E-02 |
| SEQ ID NO: 260 | hsa-miR-522* | cucuagagggaagcgcuuucug | 132 | 195 | 1.609 | 0.476 | 4.838E-07 | 1.128E-05 |
| SEQ ID NO: 277 | hsa-miR-519c-5p | cucuagagggaagcgcuuucug | 130 | 82 | 1.891 | 0.637 | 5.167E-07 | 1.173E-05 |
| SEQ ID NO: 543 | hsa-miR-221* | accuggcauacaauugagauuu | 104 | 69 | 1.890 | 0.637 | 5.438E-07 | 1.197E-05 |
| SEQ ID NO: 791 | hsa-miR-1272 | gaugauggcagcaaauucugaaa | 129 | 55 | 1.573 | 0.453 | 8.508E-07 | 1.611E-05 |
| SEQ ID NO: 841 | hsa-miR-1226* | gugagggcaugcaggccuggaugggg | 187 | 82 | 1.998 | 0.692 | 1.105E-06 | 1.947E-05 |
| SEQ ID NO: 739 | hsa-miR-1324 | ccagacagaauucuaugcacuuuc | 127 | 93 | 1.565 | 0.448 | 1.744E-06 | 2.701E-05 |
| SEQ ID NO: 378 | hsa-miR-431 | ugucuugcaggccgucauga | 176 | 81 | 1.797 | 0.586 | 5.098E-06 | 6.127E-05 |
| SEQ ID NO: 574 | hsa-miR-21* | caacaccaguccgaugggcugu | 102 | 98 | 1.670 | 0.513 | 6.372E-06 | 7.236E-05 |
| SEQ ID NO: 172 | hsa-miR-589 | ugagaaccacgucugcucugag | 79 | 61 | 0.624 | -0.472 | 7.686E-06 | 8.307E-05 |
| SEQ ID NO: 272 | hsa-miR-520a-5p | cuccagagggaaguacuuucu | 100 | 127 | 1.692 | 0.526 | 7.797E-06 | 8.307E-05 |
| SEQ ID NO: 544 | hsa-miR-221 | agcuacauuugucugcugggguuuc | 81 | 59 | 0.516 | -0.662 | 9.855E-06 | 9.889E-05 |
| SEQ ID NO: 148 | hsa-miR-611 | gcgagagaccccugugagaacagggg | 100 | 157 | 1.592 | 0.465 | 1.021E-05 | 1.013E-04 |
| SEQ ID NO: 797 | hsa-miR-1266 | ccucuccagggcuuguagaauaugag | 111 | 63 | 1.531 | 0.426 | 1.035E-05 | 1.015E-04 |
| SEQ ID NO: 206 | hsa-miR-556-5p | gaugaggggaagcgcuuauuuug | 117 | 72 | 1.599 | 0.469 | 1.298E-05 | 1.218E-04 |
| SEQ ID NO: 279 | hsa-miR-519b-5p | cucuagagggaagcgcuuucug | 128 | 73 | 1.726 | 0.546 | 1.570E-05 | 1.414E-04 |
| SEQ ID NO: 283 | hsa-miR-518f* | cucuagagggaagcacuuuuc | 123 | 74 | 1.517 | 0.417 | 1.549E-05 | 1.414E-04 |
| SEQ ID NO: 820 | hsa-miR-1251 | acuucaguagcugccaagggcu | 128 | 81 | 1.375 | 0.319 | 1.949E-05 | 1.708E-04 |
| SEQ ID NO: 671 | hsa-miR-181a-2* | accacugaccuugacugacc | 87 | 93 | 0.545 | -0.607 | 3.184E-05 | 2.544E-04 |
| SEQ ID NO: 171 | hsa-miR-589* | ucagaacaaaugccguuccaga | 83 | 160 | 0.690 | -0.372 | 3.282E-05 | 2.552E-04 |
| SEQ ID NO: 619 | hsa-miR-196a* | cggcaacaagaaacugccugag | 139 | 121 | 1.517 | 0.417 | 4.165E-05 | 2.970E-04 |
| SEQ ID NO: 37 | hsa-miR-891a | ugcaacgaaccugagccacuga | 92 | 1.444 | 0.368 | 4.649E-05 | 3.262E-04 |
| SEQ ID NO: 240 | hsa-miR-545 | ucaacaaacauuuauuugugc | 114 | 79 | 1.707 | 0.535 | 4.909E-05 | 3.336E-04 |
| SEQ ID NO: 556 | hsa-miR-217 | uacugcaucaggaacugauugga | 116 | 68 | 1.593 | 0.465 | 5.232E-05 | 3.500E-04 |
| SEQ ID NO: 188 | hsa-miR-575 | gagccaguuggacuggage | 141 | 89 | 1.425 | 0.354 | 6.361E-05 | 4.066E-04 |
| SEQ ID NO: 281 | hsa-miR-519a* | cucuagagggaagcgcuuuucu | 127 | 89 | 1.646 | 0.498 | 6.515E-05 | 4.104E-04 |
| SEQ ID NO: 882 | hsa-miR-101* | caguuaucacagugggcucaugcu | 142 | 86 | 0.619 | -0.480 | 7.614E-05 | 4.675E-04 |
| SEQ ID NO: 316 | hsa-miR-508-5p | uacuccagagggcuucacucaug | 69 | 112 | 1.877 | 0.630 | 7.639E-05 | 4.675E-04 |

FIG. 30B (Cont.)

| | | | | | | | | |
|---|---|---|---|---|---|---|---|---|
| SEQ ID NO: 29 | hsa-miR-922 | gcagcagaauaggacuagcguc | 126 | 78 | 1,622 | 0.484 | 7.857E-05 | 4.742E-04 |
| SEQ ID NO: 776 | hsa-miR-1283 | ucuacaaaggaaagcguuucu | 109 | 73 | 1,487 | 0.397 | 9.312E-05 | 5.467E-04 |
| SEQ ID NO: 118 | hsa-miR-635 | acuugggcacuaaugggauaauguc | 101 | 79 | 1,271 | 0.240 | 1.087E-04 | 6.256E-04 |
| SEQ ID NO: 173 | hsa-miR-588 | uuggccacaaugguuagaac | 119 | 91 | 1,307 | 0.268 | 1.284E-04 | 7.055E-04 |
| SEQ ID NO: 545 | hsa-miR-220c | acacaggcguugugaagacu | 103 | 68 | 1,518 | 0.418 | 1.506E-04 | 8.123E-04 |
| SEQ ID NO: 750 | hsa-miR-1307 | acucggcuggcgucggucgug | 57 | 109 | 0.526 | -0.643 | 1.745E-04 | 9.238E-04 |
| SEQ ID NO: 558 | hsa-miR-216a | uaaucucagcuggcaacccuga | 142 | 92 | 1,543 | 0.433 | 1.801E-04 | 9.419E-04 |
| SEQ ID NO: 42 | hsa-miR-887 | gugaacgggcgccauccgagg | 103 | 74 | 1,383 | 0.324 | 2.368E-04 | 1.195E-03 |
| SEQ ID NO: 219 | hsa-miR-548p | uagcaaaacugcaguuacuuu | 113 | 98 | 1,159 | 0.147 | 3.772E-04 | 1.809E-03 |
| SEQ ID NO: 840 | hsa-miR-1227 | cgugccccuuuucccag | 64 | 106 | 0.604 | -0.505 | 8.472E-04 | 3.808E-03 |
| SEQ ID NO: 679 | hsa-miR-15b* | cgaaucauuaucgcucua | 65 | 124 | 0.526 | -0.642 | 9.174E-04 | 4.081E-03 |
| SEQ ID NO: 48 | hsa-miR-877 | guagaggagaugcgcagg | 60 | 102 | 0.587 | -0.533 | 9.539E-04 | 4.222E-03 |
| SEQ ID NO: 258 | hsa-miR-523* | cucuagagggaagcgcuuucug | 119 | 89 | 1,340 | 0.292 | 1.404E-03 | 5.883E-03 |
| SEQ ID NO: 341 | hsa-miR-491-5p | aguggggaacccuuccaugagg | 92 | 157 | 0.586 | -0.535 | 1.632E-03 | 6.579E-03 |
| SEQ ID NO: 785 | hsa-miR-127-5p | cugaagcucagagggcucugau | 126 | 92 | 1,368 | 0.314 | 1.631E-03 | 6.579E-03 |
| SEQ ID NO: 832 | hsa-miR-1237 | uccuucugcuccgucccccag | 80 | 130 | 0.613 | -0.489 | 1.798E-03 | 7.054E-03 |
| SEQ ID NO: 343 | hsa-miR-490-5p | ccauggacgcgguggaugcc | 130 | 97 | 1,350 | 0.300 | 1.878E-03 | 7.266E-03 |
| SEQ ID NO: 830 | hsa-miR-124 | uaaggcacgcggugaagcc | 103 | 67 | 1,538 | 0.431 | 2.296E-03 | 8.467E-03 |
| SEQ ID NO: 285 | hsa-miR-518e* | cucuagagggaagcgcuuucug | 138 | 91 | 1,521 | 0.419 | 2.573E-03 | 9.289E-03 |
| SEQ ID NO: 124 | hsa-miR-629* | guucuccaacgcuaagcccagc | 94 | 160 | 0.584 | -0.538 | 3.223E-03 | 1.104E-02 |
| SEQ ID NO: 593 | hsa-miR-200c | uaauacugccgguaaugauga | 93 | 121 | 0.766 | -0.267 | 3.474E-03 | 1.185E-02 |
| SEQ ID NO: 336 | hsa-miR-495 | aaacaaacaugcacuuucu | 66 | 120 | 0.548 | -0.602 | 4.486E-03 | 1.443E-02 |
| SEQ ID NO: 677 | hsa-miR-16-1* | ccaguauuaacugcugcuga | 74 | 107 | 0.690 | -0.370 | 5.771E-03 | 1.804E-02 |
| SEQ ID NO: 448 | hsa-miR-33a | gugcauugguagcauuguca | 103 | 72 | 1,426 | 0.355 | 6.836E-03 | 2.049E-02 |
| SEQ ID NO: 156 | hsa-miR-603 | cacacacugcaauuacuuugc | 114 | 92 | 1,240 | 0.215 | 7.104E-03 | 2.121E-02 |
| SEQ ID NO: 655 | hsa-miR-186* | gcccaaaggugaauuuuuggg | 102 | 72 | 1,418 | 0.349 | 7.753E-03 | 2.253E-02 |
| SEQ ID NO: 703 | hsa-miR-1471 | gccgguguggagcaggugu | 110 | 80 | 1,381 | 0.323 | 8.374E-03 | 2.417E-02 |
| SEQ ID NO: 557 | hsa-miR-216b | aaaucucugcaggcaaauga | 121 | 93 | 1,300 | 0.262 | 9.424E-03 | 2.649E-02 |
| SEQ ID NO: 103 | hsa-miR-650 | aggaggcagcgcucuaggac | 124 | 93 | 1,331 | 0.286 | 1.002E-02 | 2.789E-02 |
| SEQ ID NO: 333 | hsa-miR-497* | caaaccacacugugaga | 102 | 82 | 1,235 | 0.211 | 1.148E-02 | 3.127E-02 |
| SEQ ID NO: 106 | hsa-miR-647 | guugcugcacucacuuc | 68 | 19 | 3,528 | 1,261 | 1.385E-02 | 8.536E-07 |
| SEQ ID NO: 707 | hsa-miR-146b-3p | ugcccuggaccucaguucgg | 55 | 14 | 3,792 | 1,333 | 1.641E-08 | 8.996E-07 |
| SEQ ID NO: 274 | hsa-miR-519e* | uucuccaaaaggagcacuuuc | 60 | 2 | 26,548 | 3,279 | 1.668E-08 | 8.996E-07 |
| SEQ ID NO: 182 | hsa-miR-580 | uugagaaugaaucauuagg | 43 | 7 | 6,321 | 1,844 | 3.657E-06 | 1.546E-06 |
| SEQ ID NO: 500 | hsa-miR-300 | uauacaaggcagaacucucucu | 48 | 7 | 7,104 | 1,961 | 8.709E-08 | 2.784E-06 |
| SEQ ID NO: 54 | hsa-miR-873 | gcaggaacuguagaguccu | 64 | 28 | 2,330 | 0.846 | 1.118E-07 | 3.446E-06 |
| SEQ ID NO: 356 | hsa-miR-483-3p | ucacucccucuccccgucu | 21 | 86 | 0.243 | -1,413 | 3.578E-07 | 9.358E-06 |

FIG. 30B (Cont.)

| | | | | | | | | |
|---|---|---|---|---|---|---|---|---|
| SEQ ID NO: 547 | hsa-miR-220a | ccacaccguaucucugacacuuu | 61 | 15 | 4,049 | 1,398 | 5,546E-07 | 1,197E-05 |
| SEQ ID NO: 814 | hsa-miR-1256 | aggcauugacuucucacuagcu | 67 | 30 | 2,247 | 0,809 | 7,812E-07 | 1,557E-05 |
| SEQ ID NO: 503 | hsa-miR-29b-2* | cugguuucacauggugcuuag | 36 | 98 | 0,368 | -0,998 | 1,202E-06 | 1,997E-05 |
| SEQ ID NO: 306 | hsa-miR-513b | uucacaaggauggugucauuuau | 46 | 9 | 5,030 | 1,615 | 3,856E-06 | 5,119E-05 |
| SEQ ID NO: 496 | hsa-miR-302a* | acuuaaaaacguggauguacugcu | 43 | 16 | 2,760 | 1,015 | 6,272E-06 | 7,217E-05 |
| SEQ ID NO: 501 | hsa-miR-29c* | ugaccgauuucuccugguguuc | 1 | 61 | 0,021 | -3,861 | 6,635E-06 | 7,341E-05 |
| SEQ ID NO: 854 | hsa-miR-1204 | ucuggccuguccuccauuau | 18 | 1 | 18,300 | 2,907 | 1,061E-05 | 1,029E-04 |
| SEQ ID NO: 282 | hsa-miR-519a | aaagugcauccuuuuagagugu | 31 | 3 | 10,102 | 2,313 | 1,468E-05 | 1,363E-04 |
| SEQ ID NO: 299 | hsa-miR-516b | aucuggaguaagaagcacuuu | 35 | 1 | 34,823 | 3,550 | 1,893E-05 | 1,684E-04 |
| SEQ ID NO: 252 | hsa-miR-526b | cucugaggaagcacuuucugu | 38 | 10 | 3,868 | 1,353 | 2,297E-05 | 1,925E-04 |
| SEQ ID NO: 155 | hsa-miR-604 | aggcugcgaauucagac | 89 | 36 | 2,453 | 0,897 | 3,256E-05 | 2,552E-04 |
| SEQ ID NO: 264 | hsa-miR-520g | acaaagugcuucccuuuagagugu | 48 | 12 | 3,874 | 1,354 | 3,492E-05 | 2,621E-04 |
| SEQ ID NO: 538 | hsa-miR-224 | caagucacuagugguuccguu | 47 | 2 | 21,069 | 3,048 | 3,475E-05 | 2,621E-04 |
| SEQ ID NO: 3 | hsa-miR-99a* | caagcucgcuucuauggucug | 34 | 11 | 3,028 | 1,108 | 5,997E-05 | 3,921E-04 |
| SEQ ID NO: 594 | hsa-miR-200b* | caucuacuggcagcauugga | 68 | 27 | 2,493 | 0,913 | 6,344E-05 | 4,066E-04 |
| SEQ ID NO: 352 | hsa-miR-485-5p | agaggcugccguaugaauuc | 47 | 20 | 2,372 | 0,864 | 6,503E-05 | 4,104E-04 |
| SEQ ID NO: 38 | hsa-miR-890 | uacuugaaggcaucagug | 37 | 4 | 10,003 | 2,303 | 7,517E-05 | 4,675E-04 |
| SEQ ID NO: 267 | hsa-miR-520d-5p | cuacaaaggaagccuuuc | 60 | 28 | 2,161 | 0,771 | 8,260E-05 | 4,916E-04 |
| SEQ ID NO: 823 | hsa-miR-1248 | accuucuguauaagcacugugcuaaa | 21 | 57 | 0,373 | -0,988 | 8,650E-05 | 5,113E-04 |
| SEQ ID NO: 256 | hsa-miR-524-5p | cuacaaaggaagcacuuucuc | 50 | 20 | 2,504 | 0,918 | 1,249E-04 | 6,910E-04 |
| SEQ ID NO: 826 | hsa-miR-1245 | aagugaucuaaaggccuacau | 44 | 14 | 3,065 | 1,120 | 1,363E-04 | 7,444E-04 |
| SEQ ID NO: 700 | hsa-miR-148a* | aaagguucugagacacucgacu | 25 | 58 | 0,424 | -0,857 | 1,915E-04 | 9,896E-04 |
| SEQ ID NO: 8 | hsa-miR-95 | uucaacgguauuuauugagca | 16 | 1 | 16,191 | 2,784 | 2,163E-04 | 1,105E-03 |
| SEQ ID NO: 401 | hsa-miR-379 | ugguagacuauggaacuagg | 8 | 1 | 8,393 | 2,127 | 2,261E-04 | 1,148E-03 |
| SEQ ID NO: 45 | hsa-miR-885-5p | uccauuacacuacccugcucu | 23 | 59 | 0,398 | -0,920 | 2,962E-04 | 1,478E-03 |
| SEQ ID NO: 35 | hsa-miR-892a | cacuguccuuucugcguag | 3 | 31 | 0,100 | -2,307 | 3,406E-04 | 1,652E-03 |
| SEQ ID NO: 894 | hsa-let-7e* | cuauacggccucccuuagucuuu | 10 | 1 | 9,754 | 2,278 | 3,668E-04 | 1,768E-03 |
| SEQ ID NO: 555 | hsa-miR-218 | uugugcuugaucuaaccaugu | 33 | 4 | 9,051 | 2,203 | 4,015E-04 | 1,914E-03 |
| SEQ ID NO: 55 | hsa-miR-802 | caguaacaaagauucaucccuugu | 60 | 28 | 2,170 | 0,775 | 6,535E-04 | 3,049E-03 |
| SEQ ID NO: 359 | hsa-miR-454* | acccuaucaauauugucucugc | 13 | 44 | 0,295 | -1,221 | 7,426E-04 | 3,409E-03 |
| SEQ ID NO: 438 | hsa-miR-34a | uggcaguguguuaguuguguugu | 21 | 66 | 0,317 | -1,149 | 7,848E-04 | 3,584E-03 |
| SEQ ID NO: 796 | hsa-miR-1267 | ccuguuqaaguguguauauccca | 41 | 15 | 2,715 | 0,999 | 1,009E-03 | 4,443E-03 |
| SEQ ID NO: 421 | hsa-miR-369-5p | agaucgaccguguuauauucgc | 31 | 6 | 4,863 | 1,582 | 1,254E-03 | 5,331E-03 |
| SEQ ID NO: 422 | hsa-miR-369-3p | aauaauacauggugaucuuu | 16 | 1 | 16,170 | 2,783 | 1,253E-03 | 5,331E-03 |
| SEQ ID NO: 310 | hsa-miR-512-3p | aagugcucauagcugaggc | 36 | 1 | 36,059 | 3,585 | 1,498E-03 | 6,213E-03 |
| SEQ ID NO: 60 | hsa-miR-767-3p | ucugcucuauacccaugguuucu | 44 | 19 | 2,264 | 0,817 | 1,534E-03 | 6,335E-03 |
| SEQ ID NO: 166 | hsa-miR-593 | ugucucugcuggguuucu | 14 | 1 | 13,767 | 2,622 | 1,611E-03 | 6,579E-03 |

FIG. 30B (Cont.)

| | | | | | | |
|---|---|---|---|---|---|---|
| SEQ ID NO: 481 | hsa-miR-30c-2* | cugggagaaggcugcuuuacucu | 22 | 22,273 | 3,103 | 1,745E-03 | 6,910E-03 |
| SEQ ID NO: 419 | hsa-miR-371-3p | aagugccgccaucuuugagugu | 34 | 2,378 | 0,866 | 2,088E-03 | 7,836E-03 |
| SEQ ID NO: 509 | hsa-miR-299-3p | uauguggauguaaaccgcuu | 14 | 13,831 | 2,627 | 2,073E-03 | 7,836E-03 |
| SEQ ID NO: 520 | hsa-miR-26b* | ccguuccauuacuuggcuc | 1 | 0,032 | -3,438 | 2,129E-03 | 7,920E-03 |
| SEQ ID NO: 595 | hsa-miR-200b | uaauacugccugguaaugauga | 45 | 2,530 | 0,928 | 2,315E-03 | 8,502E-03 |
| SEQ ID NO: 806 | hsa-miR-125b-2* | ucacaagucaggcucuugggac | 19 | 21,504 | 3,068 | 2,447E-03 | 8,910E-03 |
| SEQ ID NO: 860 | hsa-miR-1185 | agaggauacccuuuguauguu | 32 | 10,991 | 2,397 | 2,666E-03 | 9,507E-03 |
| SEQ ID NO: 892 | hsa-let-7f-1* | cuauacaaucuauugccuuccc | 11 | 3,756 | 1,323 | 2,687E-03 | 9,541E-03 |
| SEQ ID NO: 763 | hsa-miR-1294 | ugugaguugcauuguugucu | 34 | 9,161 | 2,215 | 2,767E-03 | 9,785E-03 |
| SEQ ID NO: 877 | hsa-miR-105* | acggauguuugagcaugugcua | 9 | 8,283 | 2,114 | 2,936E-03 | 1,022E-02 |
| SEQ ID NO: 721 | hsa-miR-141 | uaacacugucugguaaagaugg | 8 | 2,228 | 0,801 | 2,958E-03 | 1,025E-02 |
| SEQ ID NO: 804 | hsa-miR-126* | cauuauuacuuuuggcuacgcg | 39 | 0,075 | -2,591 | 3,533E-03 | 1,200E-02 |
| SEQ ID NO: 229 | hsa-miR-548f | aaaaacugcuaauuacuuuu | 17 | 2,704 | 0,995 | 3,756E-03 | 1,251E-02 |
| SEQ ID NO: 737 | hsa-miR-133b | uuuggucccccuucaaccagcua | 2 | 0,358 | -1,027 | 4,353E-03 | 1,426E-02 |
| SEQ ID NO: 688 | hsa-miR-1538 | cggccggccugcugcucuguccu | 31 | 2,185 | 0,782 | 4,966E-03 | 1,564E-02 |
| SEQ ID NO: 251 | hsa-miR-526b* | gaaagugcuucccuuuuagagc | 18 | 13,267 | 2,585 | 5,989E-03 | 1,853E-02 |
| SEQ ID NO: 11 | hsa-miR-942 | ucuucucuguuuuggccaugug | 52 | 0,318 | -1,146 | 6,567E-03 | 2,003E-02 |
| SEQ ID NO: 361 | hsa-miR-453 | agguugccguggagucgca | 33 | 2,801 | 1,030 | 6,756E-03 | 2,032E-02 |
| SEQ ID NO: 662 | hsa-miR-1827 | ugaggcaguagaaugaau | 1 | 23,397 | 3,153 | 1,010E-02 | 2,802E-02 |
| SEQ ID NO: 232 | hsa-miR-548d-3p | caaaaaccacaguuucuuuugc | 50 | 2,957 | 1,084 | 1,035E-02 | 2,853E-02 |
| SEQ ID NO: 132 | hsa-miR-624* | uaguaccagucacuguguca | 7 | 0,285 | -1,256 | 1,112E-02 | 3,057E-02 |
| SEQ ID NO: 278 | hsa-miR-519c-3p | aaagugcaucuuuuuagaggau | 16 | 2,132 | 0,757 | 1,135E-02 | 3,110E-02 |
| SEQ ID NO: 591 | hsa-miR-202 | agagguauaaggcaugggaa | 72 | 15,381 | 2,733 | 1,189E-02 | 3,226E-02 |
| SEQ ID NO: 28 | hsa-miR-924 | agagucuugcaugucugc | 18 | 12,663 | 2,539 | 1,255E-02 | 3,375E-02 |
| SEQ ID NO: 377 | hsa-miR-431* | cagucgucuugcagggcuucc | 21 | 3,267 | 1,184 | 1,386E-02 | 3,643E-02 |
| SEQ ID NO: 129 | hsa-miR-626 | agcugucugaaaaugucuu | 35 | 2,148 | 0,765 | 1,473E-02 | 3,795E-02 |
| SEQ ID NO: 322 | hsa-miR-504 | agacccuggucugcacucuauc | 46 | 3,182 | 1,157 | 1,579E-02 | 3,995E-02 |
| SEQ ID NO: 109 | hsa-miR-644 | aguuggcuuucucuuagagc | 21 | 3,402 | 1,224 | 1,670E-02 | 4,179E-02 |
| SEQ ID NO: 541 | hsa-miR-222* | cucaguagccaguaguagguaguccu | 38 | 1,759 | 0,565 | 4,847E-08 | 1,819E-06 |
| SEQ ID NO: 516 | hsa-miR-27b* | agagcuuagcugauuggugaac | 25 | 1,984 | 0,685 | 2,012E-07 | 5,787E-06 |
| SEQ ID NO: 849 | hsa-miR-1208 | ucacuguucagacaggcgga | 61 | 1,922 | 0,653 | 1,997E-07 | 5,787E-06 |
| SEQ ID NO: 254 | hsa-miR-525-5p | cuccagagggaucgcacuuucu | 61 | 1,889 | 0,636 | 8,585E-07 | 1,611E-05 |
| SEQ ID NO: 346 | hsa-miR-488* | cccagauaauugcacucuca | 94 | 1,662 | 0,508 | 9,857E-07 | 1,772E-05 |
| SEQ ID NO: 309 | hsa-miR-512-5p | cacucagccuugagggcacuuuc | 81 | 1,735 | 0,551 | 1,517E-06 | 2,425E-05 |
| SEQ ID NO: 738 | hsa-miR-133a | uuuggucccccuucaaccagcug | 72 | 0,531 | -0,633 | 2,639E-06 | 3,741E-05 |
| SEQ ID NO: 424 | hsa-miR-367 | aauugcacuuuagcaauguga | 53 | 1,617 | 0,481 | 5,183E-06 | 6,127E-05 |
| SEQ ID NO: 388 | hsa-miR-412 | acuucaccugguccacuagccgu | 50 | 1,642 | 0,496 | 2,185E-05 | 1,854E-04 |

FIG. 30B (Cont.)

| | | | | | | | |
|---|---|---|---|---|---|---|---|
| SEQ ID NO: 597 | hsa-miR-200a | uaacacugucugguaacgaugu | 90 | 51 | 1,764 | 0,567 | 2,522E-05 | 2,053E-04 |
| SEQ ID NO: 344 | hsa-miR-490-3p | caaccuggaggacauuuacuagag | 87 | 58 | 1,504 | 0,408 | 4,814E-05 | 3,323E-04 |
| SEQ ID NO: 126 | hsa-miR-628-5p | augcugacauauuuacuagagg | 78 | 58 | 1,332 | 0,287 | 4,851E-05 | 3,323E-04 |
| SEQ ID NO: 853 | hsa-miR-1205 | ucugcaggguuugcuuugag | 71 | 43 | 1,639 | 0,494 | 5,188E-05 | 3,498E-04 |
| SEQ ID NO: 884 | hsa-miR-100* | caagcuuguaucuauaaguaug | 62 | 33 | 1,894 | 0,639 | 5,557E-05 | 3,689E-04 |
| SEQ ID NO: 637 | hsa-miR-1911* | caccaggcaugugguccc | 85 | 53 | 1,591 | 0,464 | 5,992E-05 | 3,921E-04 |
| SEQ ID NO: 198 | hsa-miR-566 | ggcgccuggaucccaac | 86 | 61 | 1,421 | 0,351 | 7,625E-05 | 4,675E-04 |
| SEQ ID NO: 642 | hsa-miR-190b | ugauauguuugauaugggu | 1 | 1 | 1,000 | 0,000 | 1,233E-04 | 6,865E-04 |
| SEQ ID NO: 52 | hsa-miR-875-3p | ccuggaaacacugaggunugu | 52 | 30 | 1,748 | 0,559 | 1,724E-04 | 9,184E-04 |
| SEQ ID NO: 159 | hsa-miR-600 | acuuacagacaagagccuugcuc | 73 | 43 | 1,682 | 0,520 | 1,788E-04 | 9,408E-04 |
| SEQ ID NO: 435 | hsa-miR-34b* | uaggcaguguauuagcugauug | 44 | 24 | 1,873 | 0,628 | 2,152E-04 | 1,105E-03 |
| SEQ ID NO: 374 | hsa-miR-433 | aucaugggcuccucggugu | 67 | 42 | 1,576 | 0,455 | 3,059E-04 | 1,517E-03 |
| SEQ ID NO: 836 | hsa-miR-1231 | gugucuggggacagcugc | 82 | 55 | 1,496 | 0,403 | 5,297E-04 | 2,498E-03 |
| SEQ ID NO: 407 | hsa-miR-376b | aucauagaggaaauccauguu | 61 | 41 | 1,482 | 0,394 | 7,341E-04 | 3,388E-03 |
| SEQ ID NO: 168 | hsa-miR-591 | agaccagguucuucauugu | 53 | 32 | 1,684 | 0,521 | 8,128E-04 | 3,692E-03 |
| SEQ ID NO: 289 | hsa-miR-518c* | ucucuggagggaagcacuuucug | 52 | 32 | 1,646 | 0,498 | 8,194E-04 | 3,702E-03 |
| SEQ ID NO: 782 | hsa-miR-1278 | uagucugcauaucaucuau | 54 | 42 | 1,285 | 0,250 | 9,113E-04 | 4,075E-03 |
| SEQ ID NO: 670 | hsa-miR-181b | aacauuugucauugucgguggu | 48 | 92 | 0,520 | -0,654 | 1,032E-03 | 4,523E-03 |
| SEQ ID NO: 95 | hsa-miR-657 | ggcagggucgauucaccccucucuagg | 59 | 32 | 1,854 | 0,618 | 1,066E-03 | 4,646E-03 |
| SEQ ID NO: 486 | hsa-miR-30a* | cuuucagucgauccccuuuagcagc | 40 | 26 | 1,520 | 0,419 | 1,086E-03 | 4,708E-03 |
| SEQ ID NO: 255 | hsa-miR-525-3p | gaaggcgcuucccccuuuuagagcg | 58 | 45 | 1,288 | 0,253 | 1,135E-03 | 4,897E-03 |
| SEQ ID NO: 40 | hsa-miR-888* | gacugacaccucuuuuggugaa | 47 | 31 | 1,525 | 0,422 | 1,150E-03 | 4,938E-03 |
| SEQ ID NO: 400 | hsa-miR-379* | uauguaacaugguccacuaacu | 54 | 32 | 1,696 | 0,528 | 1,275E-03 | 5,395E-03 |
| SEQ ID NO: 149 | hsa-miR-610 | ugagcuaaaugugugccagga | 50 | 43 | 1,161 | 0,150 | 1,438E-03 | 5,996E-03 |
| SEQ ID NO: 90 | hsa-miR-662 | ucccacguuggugccagcag | 52 | 83 | 0,624 | -0,472 | 1,690E-03 | 6,751E-03 |
| SEQ ID NO: 212 | hsa-miR-551b* | gaaacuggccguggggugagacc | 37 | 61 | 0,615 | -0,486 | 1,714E-03 | 6,817E-03 |
| SEQ ID NO: 353 | hsa-miR-485-3p | gucauacacggcucucucucu | 52 | 86 | 0,609 | -0,497 | 1,762E-03 | 6,942E-03 |
| SEQ ID NO: 771 | hsa-miR-1288 | uggacugcccugaucuggaga | 55 | 87 | 0,634 | -0,456 | 1,832E-03 | 7,155E-03 |
| SEQ ID NO: 220 | hsa-miR-548o | ccaaaacugcaguuacuuugc | 100 | 72 | 1,387 | 0,327 | 1,931E-03 | 7,439E-03 |
| SEQ ID NO: 365 | hsa-miR-450b-5p | uuuugcaauaugunuccugaaua | 61 | 49 | 1,253 | 0,225 | 1,953E-03 | 7,491E-03 |
| SEQ ID NO: 488 | hsa-miR-302f | uaauugcuucccauguu | 1 | 1 | 1,456 | 0,376 | 2,070E-03 | 7,836E-03 |
| SEQ ID NO: 167 | hsa-miR-592 | uugugucauaugcgaugugu | 45 | 25 | 1,801 | 0,589 | 2,126E-03 | 7,920E-03 |
| SEQ ID NO: 427 | hsa-miR-363* | cggugaucacgaugcaauuu | 62 | 47 | 1,337 | 0,290 | 2,382E-03 | 8,712E-03 |
| SEQ ID NO: 337 | hsa-miR-494 | ugaaacauacacggaaacuc | 55 | 91 | 0,610 | -0,494 | 2,519E-03 | 9,135E-03 |
| SEQ ID NO: 858 | hsa-miR-1200 | cuccugagccauucggagcccuc | 75 | 55 | 1,368 | 0,314 | 2,608E-03 | 9,377E-03 |
| SEQ ID NO: 397 | hsa-miR-381 | uauacaaggcaagcucucugu | 87 | 57 | 1,529 | 0,425 | 2,642E-03 | 9,460E-03 |
| SEQ ID NO: 112 | hsa-miR-641 | aaagacauaaggauagaguccccuc | 58 | 35 | 1,677 | 0,517 | 2,798E-03 | 9,856E-03 |

FIG. 30B (Cont.)

| | | | | | | | |
|---|---|---|---|---|---|---|---|
| SEQ ID NO: 769 | hsa-miR-129* | aagccuuuaccccaaaaguau | 45 | 68 | 0,659 | -0,417 | 2,858E-03 | 1,003E-02 |
| SEQ ID NO: 712 | hsa-miR-145* | ggauuccuggaaauacuguucu | 60 | 32 | 1,895 | 0,639 | 3,676E-03 | 1,234E-02 |
| SEQ ID NO: 56 | hsa-miR-770-5p | uccaguaccacgugucagggca | 54 | 47 | 1,157 | 0,146 | 3,738E-03 | 1,250E-02 |
| SEQ ID NO: 36 | hsa-miR-891b | ugcaacuuaccugagucauuga | 95 | 59 | 1,614 | 0,478 | 3,780E-03 | 1,255E-02 |
| SEQ ID NO: 288 | hsa-miR-518d-3p | caaagcgcuuccuuuggagc | 80 | 60 | 1,335 | 0,289 | 3,893E-03 | 1,287E-02 |
| SEQ ID NO: 69 | hsa-miR-744* | cuguugccacuaaccucaaccu | 40 | 70 | 0,563 | -0,575 | 4,376E-03 | 1,426E-02 |
| SEQ ID NO: 228 | hsa-miR-549g | aaaacuguaauuacuuuuguac | 26 | 47 | 0,561 | -0,579 | 4,407E-03 | 1,430E-02 |
| SEQ ID NO: 852 | hsa-miR-1206 | uguucaugugaugguuuaagc | 59 | 43 | 1,354 | 0,303 | 4,438E-03 | 1,435E-02 |
| SEQ ID NO: 395 | hsa-miR-383 | agaucagaaggugauuguugcu | 49 | 32 | 1,550 | 0,438 | 4,729E-03 | 1,506E-02 |
| SEQ ID NO: 238 | hsa-miR-548a-3p | caaaacuggcaauuacuuuugc | 70 | 59 | 1,175 | 0,161 | 4,905E-03 | 1,553E-02 |
| SEQ ID NO: 105 | hsa-miR-648 | aagugcaggcacuggu | 47 | 26 | 1,780 | 0,577 | 5,678E-03 | 1,782E-02 |
| SEQ ID NO: 828 | hsa-miR-1243 | aacuggaucaauuauauaggagug | 50 | 31 | 1,624 | 0,485 | 5,922E-03 | 1,838E-02 |
| SEQ ID NO: 19 | hsa-miR-934 | ugucuacuacuggagacacugg | 87 | 61 | 1,430 | 0,358 | 6,156E-03 | 1,897E-02 |
| SEQ ID NO: 473 | hsa-miR-32* | caauuagugugugugauauuu | 28 | 51 | 0,548 | -0,601 | 6,522E-03 | 2,000E-02 |
| SEQ ID NO: 243 | hsa-miR-542-5p | ucggggaucaucaugucacgaga | 84 | 69 | 1,216 | 0,196 | 6,535E-03 | 2,000E-02 |
| SEQ ID NO: 349 | hsa-miR-487a | aaucauacagggacaauccagu | 64 | 52 | 1,230 | 0,207 | 6,647E-03 | 2,020E-02 |
| SEQ ID NO: 82 | hsa-miR-671-3p | uccgguucucagggcuccacc | 36 | 59 | 0,622 | -0,474 | 7,405E-03 | 2,181E-02 |
| SEQ ID NO: 213 | hsa-miR-551b | gcgacccauacuugguucag | 73 | 61 | 1,208 | 0,189 | 8,327E-03 | 2,411E-02 |
| SEQ ID NO: 62 | hsa-miR-765 | ugggagagaaggaaggugaug | 49 | 82 | 0,598 | -0,514 | 8,475E-03 | 2,438E-02 |
| SEQ ID NO: 437 | hsa-miR-34a* | caaucagcaaguauacugccu | 90 | 84 | 1,074 | 0,071 | 8,690E-03 | 2,491E-02 |
| SEQ ID NO: 110 | hsa-miR-643 | acuugauagcucauccauag | 37 | 61 | 0,619 | -0,480 | 8,811E-03 | 2,516E-02 |
| SEQ ID NO: 366 | hsa-miR-450b-3p | uugggaucauuugcauccaua | 33 | 18 | 1,825 | 0,602 | 8,836E-03 | 2,516E-02 |
| SEQ ID NO: 783 | hsa-miR-1277 | uacuagaauauauuuagcauuu | 53 | 44 | 1,211 | 0,192 | 9,675E-03 | 2,711E-02 |
| SEQ ID NO: 241 | hsa-miR-544 | auugcauuuuuaggcucgauu | 37 | 20 | 1,832 | 0,606 | 1,026E-02 | 2,838E-02 |
| SEQ ID NO: 143 | hsa-miR-615-5p | ggggucccggucccagggauc | 48 | 72 | 0,675 | -0,393 | 1,197E-02 | 3,239E-02 |
| SEQ ID NO: 580 | hsa-miR-208b | auaagacgaacaaaagguuugu | 60 | 45 | 1,338 | 0,291 | 1,283E-02 | 3,428E-02 |
| SEQ ID NO: 634 | hsa-miR-1914 | cccugugccggccacuuucg | 52 | 31 | 1,674 | 0,515 | 1,280E-02 | 3,428E-02 |
| SEQ ID NO: 705 | hsa-miR-147 | gugugugggaaagcuucugc | 29 | 56 | 0,521 | -0,652 | 1,389E-02 | 3,643E-02 |
| SEQ ID NO: 152 | hsa-miR-607 | guucaaauccagaaucuauaac | 81 | 64 | 1,261 | 0,232 | 1,437E-02 | 3,734E-02 |
| SEQ ID NO: 133 | hsa-miR-624 | cacaagguauuggguauuaccu | 52 | 30 | 1,733 | 0,550 | 1,470E-02 | 3,795E-02 |
| SEQ ID NO: 113 | hsa-miR-640 | augaccaggaaccugcucu | 99 | 76 | 1,303 | 0,265 | 1,469E-02 | 3,795E-02 |
| SEQ ID NO: 687 | hsa-miR-1539 | uccugcgcguccccagaugccc | 81 | 73 | 1,111 | 0,106 | 1,499E-02 | 3,851E-02 |
| SEQ ID NO: 770 | hsa-miR-1289 | uggagucccaggaaucugcauuuu | 93 | 73 | 1,263 | 0,234 | 1,510E-02 | 3,867E-02 |
| SEQ ID NO: 178 | hsa-miR-583 | caaagaggaaggucccauuac | 47 | 26 | 1,767 | 0,569 | 1,630E-02 | 4,112E-02 |
| SEQ ID NO: 324 | hsa-miR-502-5p | auccuugcuaucugggugca | 10 | 20 | 0,508 | -0,678 | 1,662E-02 | 4,170E-02 |
| SEQ ID NO: 789 | hsa-miR-127-3p | ucggaucgucucgaguuggcu | 53 | 36 | 1,464 | 0,382 | 1,658E-02 | 4,170E-02 |
| SEQ ID NO: 217 | hsa-miR-549 | ugaacaacuauggaugagcucu | 51 | 53 | 0,960 | -0,041 | 1,745E-02 | 4,340E-02 |

FIG. 30B (Cont.)

| | | | | | | | |
|---|---|---|---|---|---|---|---|
| SEQ ID NO: 464 | hsa-miR-325 | ccuaguaggugccaguaagugu | 52 | 31 | 1,693 | 0,526 | 1,913E-02 | 4,711E-02 |
| SEQ ID NO: 752 | hsa-miR-1305 | uuuucaacucuaaugggagaga | 90 | 76 | 1,180 | 0,166 | 1,916E-02 | 4,711E-02 |
| SEQ ID NO: 293 | hsa-miR-518a-3p | gaaagcgcuucccuuugcugga | 53 | 46 | 1,162 | 0,150 | 1,953E-02 | 4,788E-02 |
| SEQ ID NO: 713 | hsa-miR-145 | guccaguuuuucccaggaauccc | 131 | 343 | 0,381 | -0,966 | 7,727E-10 | 8,335E-08 |
| SEQ ID NO: 605 | hsa-miR-199a-5p | cccaguguucagacuaccuguuc | 236 | 513 | 0,459 | -0,778 | 3,027E-05 | 2,441E-04 |
| SEQ ID NO: 531 | hsa-miR-23b | aucacauugccagggauuacc | 3147 | 4406 | 0,714 | -0,337 | 4,636E-07 | 1,111E-05 |
| SEQ ID NO: 706 | hsa-miR-146b-5p | ugagaacuggaauuccauaggcu | 101 | 188 | 0,539 | -0,618 | 9,021E-06 | 9,159E-05 |
| SEQ ID NO: 334 | hsa-miR-497 | cagcagcacagacaggcagu | 167 | 123 | 1,357 | 0,305 | 2,131E-05 | 1,839E-04 |
| SEQ ID NO: 561 | hsa-miR-214 | acagcaggcacagacaggcagu | 296 | 177 | 1,668 | 0,511 | 3,531E-05 | 2,627E-04 |
| SEQ ID NO: 899 | hsa-let-7c | ugagguaguagguuguauggguu | 423 | 661 | 0,640 | -0,446 | 1,342E-03 | 5,648E-03 |
| SEQ ID NO: 507 | hsa-miR-29a | uagcaccaucugaaaucacuu | 702 | 920 | 0,763 | -0,271 | 4,499E-03 | 1,443E-02 |
| SEQ ID NO: 661 | hsa-miR-183 | uauggcacugguggaauucacu | 324 | 416 | 0,780 | -0,249 | 4,914E-03 | 1,553E-02 |
| SEQ ID NO: 519 | hsa-miR-27a | uucacaguggcuaaguucgc | 259 | 406 | 0,637 | -0,451 | 8,862E-03 | 2,516E-02 |
| SEQ ID NO: 456 | hsa-miR-335 | ucaagagcaauaacgaaaaaugu | 449 | 538 | 0,834 | -0,182 | 1,219E-02 | 3,287E-02 |
| SEQ ID NO: 805 | hsa-miR-126 | ucguaccgugaguaauaaugcg | 1604 | 2208 | 0,726 | -0,320 | 1,287E-02 | 3,428E-02 |
| SEQ ID NO: 718 | hsa-miR-142-5p | cauaaaguguacuucugauacu | 752 | 970 | 0,776 | -0,254 | 1,396E-02 | 3,652E-02 |
| SEQ ID NO: 441 | hsa-miR-342-5p | aggggugcuaucugugauuga | 85 | 200 | 0,423 | -0,862 | 2,885E-11 | 6,943E-09 |
| SEQ ID NO: 684 | hsa-miR-155 | uuaaugcuaaucgugauagggu | 84 | 169 | 0,495 | -0,704 | 4,133E-06 | 5,254E-05 |
| SEQ ID NO: 358 | hsa-miR-455-3p | gcaguccauggcauauacac | 169 | 92 | 1,843 | 0,611 | 4,775E-09 | 3,621E-07 |
| SEQ ID NO: 869 | hsa-miR-10b | uacccuguagaaccgaauuugug | 50 | 18 | 2,804 | 1,031 | 9,673E-05 | 5,640E-04 |
| SEQ ID NO: 626 | hsa-miR-193b | aacuggcccucaaaguccccgcu | 56 | 88 | 0,632 | -0,459 | 1,916E-02 | 4,711E-02 |

Figure 31

| number of best miRNAs | Accuracy | Specificity | Sensitivity |
|---|---|---|---|
| 2 | 0,81 | 0,8 | 0,82 |
| 4 | 0,85 | 0,8 | 0,9 |
| 6 | 0,89 | 0,86 | 0,92 |
| 8 | 0,9 | 0,89 | 0,9 |
| 10 | 0,92 | 0,92 | 0,93 |
| 12 | 0,94 | 0,95 | 0,93 |
| 14 | 0,93 | 0,92 | 0,94 |
| 16 | 0,94 | 0,93 | 0,95 |
| 18 | 0,95 | 0,93 | 0,97 |
| 20 | 0,95 | 0,96 | 0,95 |
| 22 | 0,97 | 0,96 | 0,98 |
| 24 | 0,95 | 0,95 | 0,95 |
| 26 | 0,97 | 0,98 | 0,95 |
| 28 | 0,96 | 0,96 | 0,96 |
| 30 | 0,97 | 0,98 | 0,96 |
| 32 | 0,96 | 0,97 | 0,96 |
| 34 | 0,98 | 0,98 | 0,98 |
| 36 | 0,97 | 0,98 | 0,96 |
| 38 | 0,98 | 0,99 | 0,97 |
| 40 | 0,98 | 0,98 | 0,97 |

Figures 32A and 32B

| SEQ ID NO | Disease details |
|---|---|
| SEQ ID NO: 329, 746, 430, 431, 460, 165, 788, 382, 136, 429, 444, 861, 327, 362, 216, 386, 756, 872, 855, 856, 59, 300, 98, 475, 302, 315, 649, 107, 636, 313, 887, 600, 199, 297, 787, 559, 446, 578, 709, 101, 360, 674, 498, 20, 87, 127, 881, 323, 635, 292, 250, 428, 888, 480, 875, 61, 630, 345, 834, 27, 328, 89, 75, 450, 723, 80, 469, 249, 652, 527, 669, 663, 23, 656, 125, 660, 131, 387, 253, 246, 287, 896, 773, 842, 719, 747, 627, 548, 762, 778, 393, 326, 402, 664, 78, 177, 786, 865, 846, 260, 277, 543, 791, 841, 739, 378, 574, 172, 272, 148, 797, 206, 279, 283, 820, 671, 171, 619, 37, 240, 556, 188, 281, 882, 316, 29, 776, 118, 173, 545, 750, 558, 42, 219, 840, 679, 48, 258, 341, 785, 832, 343, 830, 285, 124, 336, 677, 448, 156, 655, 703, 557, 103, 333, 106, 707, 274, 182, 500, 54, 356, 547, 814, 503, 306, 496, 501, 854, 282, 299, 252, 155, 264, 3, 594, 352, 38, 267, 823, 256, 826, 700, 401, 45, 35, 894, 55, 359, 438, 796, 421, 422, 310, 60, 166, 481, 419, 509, 520, 595, 806, 860, 892, 763, 877, 721, 804, 229, 688, 251, 11, 361, 662, 232, 132, 278, 591, 28, 377, 129, 322, 109, 541, 516, 849, 254, 346, 309, 738, 424, 388, 597, 344, 126, 853, 884, 637, 198, 642, 52, 159, 435, 374, 836, 407, 168, 289, 782, 670, 95, 255, 40, 400, 149, 90, 212, 353, 771, 220, 365, 488, 167, 427, 337, 858, 397, 112, 769, 712, 56, 36, 288, 69, 228, 852, 238, 105, 828, 19, 473, 243, 349, 82, 213, 62, 437, 110, 366, 783, 241, 143, 580, 634, 705, 152, 133, 113, 687, 770, 178, 324, 217, 464, 752, 293 | Skin Cancer (305 miRNAs) A |
| SEQ ID NO: 809, 329, 746, 4, 430, 890, 895, 431, 460, 701, 165, 788, 382, 136, 429, 622, 478, 444, 861, 327, 362, 216, 386, 756, 872, 855, 856, 59, 300, 98, 465, 475, 487, 302, 440, 315, 649, 107, 636, 313, 887, 600, 199, 297, 787, 559, 446, 578, 709, 101, 360, 674, 498, 385, 20, 87, 127, 881, 403, 323, 635, 292, 250, 428, 680, 888, 480, 875, 61, 630, 345, 529, 834, 248, 577, 27, 328, 542, 89, 75, 450, 723, 897, 80, 469, 249, 652, 527, 669, 663, 23, 477, 656, 462, 125, 426, 660, 131, 387, 253, 246, 287, 896, 773, 842, 719, 747, 627, 548, 762, 778, 393, 326, 402, 664, 78, 177, 786, 865, 846, 260, 277, 543, 791, 841, 739, 378, 574, 172, 272, 544, 148, 797, 206, 279, 283, 820, 671, 171, 619, 37, 240, 556, 188, 281, 882, 316, 29, 776, 118, 173, 545, 750, 558, 42, 219, 840, 679, 48, 258, 341, 785, 832, 343, 830, 285, 124, 593, 336, 677, 448, 156, 655, 703, 557, 103, 333, 106, 707, 274, 182, 500, 54, 356, 547, 814, 503, 306, 496, 501, 854, 282, 299, 252, 155, 264, 538, 3, 594, 352, 38, 267, 823, 256, 826, 700, 8, 401, 45, 35, 894, 555, 55, 359, 438, 796, 421, 422, 310, 60, 166, 481, 419, 509, 520, 595, 806, 860, 892, 763, 877, 721, 804, 229, 737, 688, 251, 11, 361, 662, 232, 132, 278, 591, 28, 377, 129, 322, 109, 541, 516, 849, 254, 346, 309, 738, 424, 388, 597, 344, 126, 853, 884, 637, 198, 642, 52, 159, 435, 374, 836, 407, 168, 289, 782, 670, 95, 486, 255, 40, 400, 149, 90, 212, 353, 771, 220, 365, 488, 167, 427, 337, 858, 397, 112, 769, 712, 56, 36, 288, 69, 228, 852, 395, 238, 105, 828, 19, 473, 243, 349, 82, 213, 62, 437, 110, 366, 783, 241, 143, 580, 634, 705, 152, 133, 113, 687, 770, 178, 324, 789, 217, 464, 752, 293 | Melanoma (335 miRNAs) B |

FIG. 33A

| Signature | SEQ-ID Nos | miRNA-identifiers | Acc | Spec | Sens |
|---|---|---|---|---|---|
| M1 | SEQ ID NO: 809, SEQ ID NO: 329, SEQ ID NO: 746 | hsa-miR-125a-5p, hsa-miR-500, hsa-miR-130b | 86% | 83% | 89% |
| M2 | SEQ ID NO: 746, SEQ ID NO: 4, SEQ ID NO: 430 | hsa-miR-130b, hsa-miR-99a, hsa-miR-362-3p | 83% | 80% | 87% |
| M3 | SEQ ID NO: 430, SEQ ID NO: 890, SEQ ID NO: 895 | hsa-miR-362-3p, hsa-let-7g, hsa-let-7e | 67% | 52% | 82% |
| M4 | SEQ ID NO: 895, SEQ ID NO: 431, SEQ ID NO: 460 | hsa-let-7e, hsa-miR-361-5p, hsa-miR-330-3p | 84% | 73% | 95% |
| M5 | SEQ ID NO: 460, SEQ ID NO: 701, SEQ ID NO: 165 | hsa-miR-330-3p, hsa-miR-148a, hsa-miR-593* | 90% | 81% | 99% |
| M6 | SEQ ID NO: 165, SEQ ID NO: 788, SEQ ID NO: 382 | hsa-miR-593*, hsa-miR-1274a, hsa-miR-424* | 88% | 80% | 97% |
| M7 | SEQ ID NO: 382, SEQ ID NO: 136, SEQ ID NO: 429 | hsa-miR-424*, hsa-miR-621, hsa-miR-362-5p | 85% | 74% | 95% |
| M8 | SEQ ID NO: 429, SEQ ID NO: 622, SEQ ID NO: 478 | hsa-miR-362-5p, hsa-miR-195, hsa-miR-30e | 77% | 66% | 88% |
| M9 | SEQ ID NO: 478, SEQ ID NO: 444, SEQ ID NO: 861 | hsa-miR-30e, hsa-miR-340, hsa-miR-1184 | 76% | 63% | 88% |
| M10 | SEQ ID NO: 861, SEQ ID NO: 327, SEQ ID NO: 362 | hsa-miR-1184, hsa-miR-501-3p, hsa-miR-452* | 84% | 76% | 92% |
| M11 | SEQ ID NO: 362, SEQ ID NO: 216, SEQ ID NO: 386 | hsa-miR-452*, hsa-miR-550, hsa-miR-422a | 75% | 67% | 84% |
| M12 | SEQ ID NO: 386, SEQ ID NO: 756, SEQ ID NO: 872 | hsa-miR-422a, hsa-miR-1301, hsa-miR-107 | 91% | 88% | 93% |
| M13 | SEQ ID NO: 872, SEQ ID NO: 856, SEQ ID NO: 300 | hsa-miR-107, hsa-miR-1202, hsa-miR-516a-5p | 85% | 80% | 89% |
| M14 | SEQ ID NO: 856, SEQ ID NO: 59, SEQ ID NO: 300 | hsa-miR-1202, hsa-miR-767-5p, hsa-miR-516a-5p | 82% | 66% | 98% |
| M15 | SEQ ID NO: 300, SEQ ID NO: 98, SEQ ID NO: 465 | hsa-miR-516a-5p, hsa-miR-654-5p, hsa-miR-324-5p | 84% | 72% | 95% |
| M16 | SEQ ID NO: 809, SEQ ID NO: 329, SEQ ID NO: 746, SEQ ID NO: 4, SEQ ID NO: 430 | hsa-miR-125a-5p, hsa-miR-500, hsa-miR-130b, hsa-miR-99a, hsa-miR-362-3p | 85% | 81% | 89% |

FIG. 33A (Cont.)

| | | | | | |
|---|---|---|---|---|---|
| M17 | SEQ ID NO: 746, SEQ ID NO: 4, SEQ ID NO: 430, SEQ ID NO: 890, SEQ ID NO: 895 | hsa-miR-130b, hsa-miR-99a, hsa-miR-362-3p, hsa-let-7g, hsa-let-7e | 82% | 78% | 87% |
| M18 | SEQ ID NO: 430, SEQ ID NO: 890, SEQ ID NO: 895, SEQ ID NO: 431, SEQ ID NO: 460 | hsa-miR-362-3p, hsa-let-7g, hsa-let-7e, hsa-miR-361-5p, hsa-miR-330-3p | 83% | 75% | 91% |
| M19 | SEQ ID NO: 890, SEQ ID NO: 895, SEQ ID NO: 431, SEQ ID NO: 460, SEQ ID NO: 701 | hsa-let-7g, hsa-let-7e, hsa-miR-361-5p, hsa-miR-330-3p, hsa-miR-148a | 92% | 85% | 99% |
| M20 | SEQ ID NO: 431, SEQ ID NO: 460, SEQ ID NO: 701, SEQ ID NO: 165, SEQ ID NO: 788 | hsa-miR-361-5p, hsa-miR-330-3p, hsa-miR-148a, hsa-miR-593*, hsa-miR-1274a | 95% | 89% | 100% |
| M21 | SEQ ID NO: 701, SEQ ID NO: 165, SEQ ID NO: 788, SEQ ID NO: 382, SEQ ID NO: 136 | hsa-miR-148a, hsa-miR-593*, hsa-miR-1274a, hsa-miR-424*, hsa-miR-621 | 93% | 91% | 96% |
| M22 | SEQ ID NO: 165, SEQ ID NO: 788, SEQ ID NO: 382, SEQ ID NO: 136, SEQ ID NO: 429, SEQ ID NO: 622 | hsa-miR-593*, hsa-miR-1274a, hsa-miR-424*, hsa-miR-621, hsa-miR-362-5p, hsa-miR-195 | 86% | 76% | 96% |
| M23 | SEQ ID NO: 136, SEQ ID NO: 429, SEQ ID NO: 622, SEQ ID NO: 478, SEQ ID NO: 444, SEQ ID NO: 861 | hsa-miR-621, hsa-miR-362-5p, hsa-miR-195, hsa-miR-30e, hsa-miR-340, hsa-miR-1184 | 82% | 71% | 94% |
| M24 | SEQ ID NO: 478, SEQ ID NO: 444, SEQ ID NO: 861, SEQ ID NO: 327, SEQ ID NO: 362, SEQ ID NO: 216 | hsa-miR-30e, hsa-miR-340, hsa-miR-1184, hsa-miR-501-3p, hsa-miR-452*, hsa-miR-550 | 83% | 75% | 91% |
| M25 | SEQ ID NO: 327, SEQ ID NO: 362, SEQ ID NO: 216, SEQ ID NO: 386, SEQ ID NO: 756, SEQ ID NO: 872 | hsa-miR-501-3p, hsa-miR-452*, hsa-miR-550, hsa-miR-422a, hsa-miR-1301, hsa-miR-107 | 93% | 90% | 96% |
| M26 | SEQ ID NO: 386, SEQ ID NO: 756, SEQ ID NO: 872, SEQ ID NO: 855, SEQ ID NO: 856, SEQ ID NO: 59 | hsa-miR-422a, hsa-miR-1301, hsa-miR-107, hsa-miR-1203, hsa-miR-1202, hsa-miR-767-5p | 88% | 83% | 93% |
| M27 | SEQ ID NO: 855, SEQ ID NO: 856, SEQ ID NO: 59, SEQ ID NO: 300, SEQ ID NO: 98, SEQ ID NO: 465 | hsa-miR-1203, hsa-miR-1202, hsa-miR-767-5p, hsa-miR-516a-5p, hsa-miR-654-5p, hsa-miR-324-5p | 83% | 70% | 95% |
| M28 | SEQ ID NO: 300, SEQ ID NO: 98, SEQ ID NO: 465, SEQ ID NO: 475, SEQ ID NO: 487, SEQ ID NO: 302 | hsa-miR-516a-5p, hsa-miR-654-5p, hsa-miR-324-5p, hsa-miR-31*, hsa-miR-30a, hsa-miR-515-5p | 87% | 79% | 95% |

FIG. 33A (Cont.)

| | | | | | |
|---|---|---|---|---|---|
| M29 | SEQ ID NO: 475, SEQ ID NO: 487, SEQ ID NO: 302, SEQ ID NO: 440, SEQ ID NO: 315, SEQ ID NO: 649 | hsa-miR-31*, hsa-miR-30a, hsa-miR-515-5p, hsa-miR-345, hsa-miR-509-3-5p, hsa-miR-18a* | 86% | 78% | 93% |
| M30 | SEQ ID NO: 440, SEQ ID NO: 315, SEQ ID NO: 649, SEQ ID NO: 107, SEQ ID NO: 636, SEQ ID NO: 313 | hsa-miR-345, hsa-miR-509-3-5p, hsa-miR-18a*, hsa-miR-646, hsa-miR-1912, hsa-miR-509-5p | 78% | 69% | 87% |
| M31 | SEQ ID NO: 809, SEQ ID NO: 329, SEQ ID NO: 746, SEQ ID NO: 4, SEQ ID NO: 430, SEQ ID NO: 890, SEQ ID NO: 895, SEQ ID NO: 431, SEQ ID NO: 460, SEQ ID NO: 701 | hsa-miR-125a-5p, hsa-miR-500, hsa-miR-130b, hsa-miR-99a, hsa-miR-362-3p, hsa-let-7g, hsa-let-7e, hsa-miR-361-5p, hsa-miR-330-3p, hsa-miR-148a | 94% | 91% | 97% |
| M32 | SEQ ID NO: 890, SEQ ID NO: 895, SEQ ID NO: 431, SEQ ID NO: 460, SEQ ID NO: 701, SEQ ID NO: 165, SEQ ID NO: 788, SEQ ID NO: 382, SEQ ID NO: 136, SEQ ID NO: 429, SEQ ID NO: 622 | hsa-let-7g, hsa-let-7e, hsa-miR-361-5p, hsa-miR-330-3p, hsa-miR-148a, hsa-miR-593*, hsa-miR-1274a, hsa-miR-424*, hsa-miR-621, hsa-miR-362-5p, hsa-miR-195 | 95% | 93% | 97% |
| M33 | SEQ ID NO: 788, SEQ ID NO: 382, SEQ ID NO: 136, SEQ ID NO: 429, SEQ ID NO: 622, SEQ ID NO: 478, SEQ ID NO: 444, SEQ ID NO: 861, SEQ ID NO: 327, SEQ ID NO: 362 | hsa-miR-1274a, hsa-miR-424*, hsa-miR-621, hsa-miR-362-5p, hsa-miR-195, hsa-miR-30e, hsa-miR-340, hsa-miR-1184, hsa-miR-501-3p, hsa-miR-452* | 90% | 83% | 96% |
| M34 | SEQ ID NO: 478, SEQ ID NO: 444, SEQ ID NO: 861, SEQ ID NO: 327, SEQ ID NO: 362, SEQ ID NO: 216, SEQ ID NO: 386, SEQ ID NO: 756, SEQ ID NO: 872, SEQ ID NO: 855 | hsa-miR-30e, hsa-miR-340, hsa-miR-1184, hsa-miR-501-3p, hsa-miR-452*, hsa-miR-550, hsa-miR-422a, hsa-miR-1301, hsa-miR-107, hsa-miR-1203 | 90% | 88% | 92% |
| M35 | SEQ ID NO: 216, SEQ ID NO: 386, SEQ ID NO: 756, SEQ ID NO: 872, SEQ ID NO: 855, SEQ ID NO: 856, SEQ ID NO: 59, SEQ ID NO: 300, SEQ ID NO: 98, SEQ ID NO: 465 | hsa-miR-550, hsa-miR-422a, hsa-miR-1301, hsa-miR-107, hsa-miR-1203, hsa-miR-1202, hsa-miR-767-5p, hsa-miR-516a-5p, hsa-miR-654-5p, hsa-miR-324-5p | 92% | 89% | 94% |
| M36 | SEQ ID NO: 856, SEQ ID NO: 59, SEQ ID NO: 300, SEQ ID NO: 98, SEQ ID NO: 465, SEQ ID NO: 475, SEQ ID NO: 487, SEQ ID NO: 302, SEQ ID NO: 440, SEQ ID NO: 315 | hsa-miR-1202, hsa-miR-767-5p, hsa-miR-516a-5p, hsa-miR-654-5p, hsa-miR-324-5p, hsa-miR-31*, hsa-miR-30a, hsa-miR-515-5p, hsa-miR-345, hsa-miR-509-3-5p | 85% | 78% | 92% |

FIG. 33A (Cont.)

| | | | | | |
|---|---|---|---|---|---|
| M37 | SEQ ID NO: 475, SEQ ID NO: 487, SEQ ID NO: 302, SEQ ID NO: 440, SEQ ID NO: 315, SEQ ID NO: 649, SEQ ID NO: 107, SEQ ID NO: 636, SEQ ID NO: 313, SEQ ID NO: 887 | hsa-miR-31*, hsa-miR-30a, hsa-miR-515-5p, hsa-miR-345, hsa-miR-509-3-5p, hsa-miR-18a*, hsa-miR-646, hsa-miR-1912, hsa-miR-509-5p, hsa-let-7i* | 88% | 84% | 93% |
| M38 | SEQ ID NO: 649, SEQ ID NO: 107, SEQ ID NO: 636, SEQ ID NO: 313, SEQ ID NO: 887, SEQ ID NO: 600, SEQ ID NO: 199, SEQ ID NO: 297, SEQ ID NO: 787, SEQ ID NO: 559 | hsa-miR-18a*, hsa-miR-646, hsa-miR-1912, hsa-miR-509-5p, hsa-let-7i*, hsa-miR-19b, hsa-miR-564, hsa-miR-517*, hsa-miR-1274b, hsa-miR-215 | 87% | 82% | 93% |
| M39 | SEQ ID NO: 600, SEQ ID NO: 199, SEQ ID NO: 297, SEQ ID NO: 787, SEQ ID NO: 559, SEQ ID NO: 446, SEQ ID NO: 578, SEQ ID NO: 709, SEQ ID NO: 101, SEQ ID NO: 360 | hsa-miR-19b, hsa-miR-564, hsa-miR-517*, hsa-miR-1274b, hsa-miR-215, hsa-miR-33b, hsa-miR-20a*, hsa-miR-146a, hsa-miR-652, hsa-miR-454 | 88% | 83% | 92% |
| M40 | SEQ ID NO: 809, SEQ ID NO: 746, SEQ ID NO: 430, SEQ ID NO: 895, SEQ ID NO: 460 | hsa-miR-125a-5p, hsa-miR-130b, hsa-miR-362-3p, hsa-let-7e, hsa-miR-330-3p | 85% | 84% | 87% |
| M41 | SEQ ID NO: 4, SEQ ID NO: 890, SEQ ID NO: 431, SEQ ID NO: 701, SEQ ID NO: 788 | hsa-miR-99a, hsa-let-7g, hsa-miR-361-5p, hsa-miR-148a, hsa-miR-1274a | 95% | 90% | 99% |
| M42 | SEQ ID NO: 431, SEQ ID NO: 701, SEQ ID NO: 788, SEQ ID NO: 136, SEQ ID NO: 622 | hsa-miR-361-5p, hsa-miR-148a, hsa-miR-1274a, hsa-miR-621, hsa-miR-195 | 91% | 84% | 98% |
| M43 | SEQ ID NO: 809, SEQ ID NO: 329, SEQ ID NO: 4 | hsa-miR-125a-5p, hsa-miR-500, hsa-miR-99a | 85% | 80% | 90% |
| M44 | SEQ ID NO: 4, SEQ ID NO: 430, SEQ ID NO: 431 | hsa-miR-99a, hsa-miR-362-3p, hsa-miR-361-5p | 79% | 71% | 88% |
| M45 | SEQ ID NO: 431, SEQ ID NO: 460, SEQ ID NO: 701 | hsa-miR-361-5p, hsa-miR-330-3p, hsa-miR-148a | 92% | 86% | 97% |
| M46 | SEQ ID NO: 701, SEQ ID NO: 165, SEQ ID NO: 788 | hsa-miR-148a, hsa-miR-593*, hsa-miR-1274a | 91% | 82% | 100% |
| M47 | SEQ ID NO: 788, SEQ ID NO: 382, SEQ ID NO: 136 | hsa-miR-1274a, hsa-miR-424*, hsa-miR-621 | 88% | 79% | 97% |
| M48 | SEQ ID NO: 136, SEQ ID NO: 429, SEQ ID NO: 622 | hsa-miR-621, hsa-miR-362-5p, hsa-miR-195 | 80% | 71% | 88% |

FIG. 33A (Cont.)

| | | | | | |
|---|---|---|---|---|---|
| M49 | SEQ ID NO: 622, SEQ ID NO: 478, SEQ ID NO: 444 | hsa-miR-195, hsa-miR-30e, hsa-miR-340 | 79% | 64% | 93% |
| M50 | SEQ ID NO: 444, SEQ ID NO: 861, SEQ ID NO: 362 | hsa-miR-340, hsa-miR-1184, hsa-miR-452* | 79% | 69% | 88% |
| M51 | SEQ ID NO: 362, SEQ ID NO: 386, SEQ ID NO: 756 | hsa-miR-452*, hsa-miR-422a, hsa-miR-1301 | 83% | 77% | 88% |
| M52 | SEQ ID NO: 756, SEQ ID NO: 872, SEQ ID NO: 855 | hsa-miR-1301, hsa-miR-107, hsa-miR-1203 | 88% | 83% | 94% |
| M53 | SEQ ID NO: 855, SEQ ID NO: 856, SEQ ID NO: 59 | hsa-miR-1203, hsa-miR-1202, hsa-miR-767-5p | 80% | 64% | 96% |
| M54 | SEQ ID NO: 59, SEQ ID NO: 300, SEQ ID NO: 98 | hsa-miR-767-5p, hsa-miR-516a-5p, hsa-miR-654-5p | 83% | 71% | 95% |
| M55 | SEQ ID NO: 98, SEQ ID NO: 487, SEQ ID NO: 440 | hsa-miR-654-5p, hsa-miR-30a, hsa-miR-345 | 81% | 76% | 86% |
| M56 | SEQ ID NO: 487, SEQ ID NO: 302, SEQ ID NO: 440 | hsa-miR-30a, hsa-miR-515-5p, hsa-miR-345 | 86% | 81% | 91% |
| M57 | SEQ ID NO: 440, SEQ ID NO: 315, SEQ ID NO: 649 | hsa-miR-345, hsa-miR-509-3-5p, hsa-miR-18a* | 76% | 69% | 83% |
| M58 | SEQ ID NO: 809, SEQ ID NO: 329, SEQ ID NO: 4, SEQ ID NO: 430, SEQ ID NO: 431 | hsa-miR-125a-5p, hsa-miR-500, hsa-miR-99a, hsa-miR-362-3p, hsa-miR-361-5p | 83% | 82% | 85% |
| M59 | SEQ ID NO: 4, SEQ ID NO: 430, SEQ ID NO: 431, SEQ ID NO: 460, SEQ ID NO: 701 | hsa-miR-99a, hsa-miR-362-3p, hsa-miR-361-5p, hsa-miR-330-3p, hsa-miR-148a | 95% | 91% | 98% |
| M60 | SEQ ID NO: 431, SEQ ID NO: 460, SEQ ID NO: 701, SEQ ID NO: 165, SEQ ID NO: 788 | hsa-miR-361-5p, hsa-miR-330-3p, hsa-miR-148a, hsa-miR-593*, hsa-miR-1274a | 94% | 88% | 100% |
| M61 | SEQ ID NO: 460, SEQ ID NO: 701, SEQ ID NO: 165, SEQ ID NO: 788, SEQ ID NO: 382 | hsa-miR-330-3p, hsa-miR-148a, hsa-miR-593*, hsa-miR-1274a, hsa-miR-424* | 94% | 93% | 96% |
| M62 | SEQ ID NO: 165, SEQ ID NO: 788, SEQ ID NO: 382, SEQ ID NO: 136, SEQ ID NO: 429 | hsa-miR-593*, hsa-miR-1274a, hsa-miR-424*, hsa-miR-621, hsa-miR-362-5p | 87% | 78% | 97% |
| M63 | SEQ ID NO: 382, SEQ ID NO: 136, SEQ ID NO: 429, SEQ ID NO: 622, SEQ ID NO: 478 | hsa-miR-424*, hsa-miR-621, hsa-miR-362-5p, hsa-miR-195, hsa-miR-30e | 83% | 75% | 91% |

FIG. 33A (Cont.)

| | | | | | |
|---|---|---|---|---|---|
| M64 | SEQ ID NO: 136, SEQ ID NO: 429, SEQ ID NO: 622, SEQ ID NO: 478, SEQ ID NO: 444, SEQ ID NO: 861 | hsa-miR-621, hsa-miR-362-5p, hsa-miR-195, hsa-miR-30e, hsa-miR-340, hsa-miR-1184 | 83% | 72% | 93% |
| M65 | SEQ ID NO: 478, SEQ ID NO: 444, SEQ ID NO: 861, SEQ ID NO: 362, SEQ ID NO: 386, SEQ ID NO: 756 | hsa-miR-30e, hsa-miR-340, hsa-miR-1184, hsa-miR-452*, hsa-miR-422a, hsa-miR-1301 | 85% | 80% | 90% |
| M66 | SEQ ID NO: 362, SEQ ID NO: 386, SEQ ID NO: 756, SEQ ID NO: 872, SEQ ID NO: 855, SEQ ID NO: 856 | hsa-miR-452*, hsa-miR-422a, hsa-miR-1301, hsa-miR-107, hsa-miR-1203, hsa-miR-1202 | 87% | 83% | 91% |
| M67 | SEQ ID NO: 872, SEQ ID NO: 855, SEQ ID NO: 856, SEQ ID NO: 59, SEQ ID NO: 300, SEQ ID NO: 98 | hsa-miR-107, hsa-miR-1203, hsa-miR-1202, hsa-miR-767-5p, hsa-miR-516a-5p, hsa-miR-654-5p | 83% | 74% | 93% |
| M68 | SEQ ID NO: 59, SEQ ID NO: 300, SEQ ID NO: 98, SEQ ID NO: 475, SEQ ID NO: 487, SEQ ID NO: 302 | hsa-miR-767-5p, hsa-miR-516a-5p, hsa-miR-654-5p, hsa-miR-31*, hsa-miR-30a, hsa-miR-515-5p | 88% | 77% | 100% |
| M69 | SEQ ID NO: 475, SEQ ID NO: 487, SEQ ID NO: 302, SEQ ID NO: 440, SEQ ID NO: 315, SEQ ID NO: 649 | hsa-miR-31*, hsa-miR-30a, hsa-miR-515-5p, hsa-miR-345, hsa-miR-509-3-5p, hsa-miR-18a* | 86% | 79% | 93% |
| M70 | SEQ ID NO: 440, SEQ ID NO: 315, SEQ ID NO: 649, SEQ ID NO: 107, SEQ ID NO: 636, SEQ ID NO: 313 | hsa-miR-345, hsa-miR-509-3-5p, hsa-miR-18a*, hsa-miR-646, hsa-miR-1912, hsa-miR-509-5p | 79% | 71% | 87% |
| M71 | SEQ ID NO: 107, SEQ ID NO: 636, SEQ ID NO: 313, SEQ ID NO: 887, SEQ ID NO: 600, SEQ ID NO: 199 | hsa-miR-646, hsa-miR-1912, hsa-miR-509-5p, hsa-let-7i*, hsa-miR-19b, hsa-miR-564 | 83% | 76% | 91% |
| M72 | SEQ ID NO: 887, SEQ ID NO: 600, SEQ ID NO: 199, SEQ ID NO: 297, SEQ ID NO: 787, SEQ ID NO: 559 | hsa-let-7i*, hsa-miR-19b, hsa-miR-564, hsa-miR-517*, hsa-miR-1274b, hsa-miR-215 | 83% | 80% | 86% |
| M73 | SEQ ID NO: 809, SEQ ID NO: 329, SEQ ID NO: 4, SEQ ID NO: 430, SEQ ID NO: 431, SEQ ID NO: 460, SEQ ID NO: 701, SEQ ID NO: 165, SEQ ID NO: 788, SEQ ID NO: 382 | hsa-miR-125a-5p, hsa-miR-500, hsa-miR-99a, hsa-miR-362-3p, hsa-miR-361-5p, hsa-miR-330-3p, hsa-miR-148a, hsa-miR-593*, hsa-miR-1274a, hsa-miR-424* | 94% | 91% | 98% |

FIG. 33A (Cont.)

| | | | | | |
|---|---|---|---|---|---|
| M74 | SEQ ID NO: 460, SEQ ID NO: 701, SEQ ID NO: 165, SEQ ID NO: 788, SEQ ID NO: 382, SEQ ID NO: 136, SEQ ID NO: 429, SEQ ID NO: 622, SEQ ID NO: 478, SEQ ID NO: 444, SEQ ID NO: 861 | hsa-miR-330-3p, hsa-miR-148a, hsa-miR-593*, hsa-miR-1274a, hsa-miR-424*, hsa-miR-621, hsa-miR-362-5p, hsa-miR-195, hsa-miR-30e, hsa-miR-340, hsa-miR-1184 | 90% | 83% | 96% |
| M75 | SEQ ID NO: 429, SEQ ID NO: 622, SEQ ID NO: 478, SEQ ID NO: 444, SEQ ID NO: 861, SEQ ID NO: 362, SEQ ID NO: 386, SEQ ID NO: 756, SEQ ID NO: 872, SEQ ID NO: 855 | hsa-miR-362-5p, hsa-miR-195, hsa-miR-30e, hsa-miR-340, hsa-miR-1184, hsa-miR-452*, hsa-miR-422a, hsa-miR-1301, hsa-miR-107, hsa-miR-1203 | 87% | 82% | 92% |
| M76 | SEQ ID NO: 362, SEQ ID NO: 386, SEQ ID NO: 756, SEQ ID NO: 872, SEQ ID NO: 855, SEQ ID NO: 856, SEQ ID NO: 59, SEQ ID NO: 300, SEQ ID NO: 98, SEQ ID NO: 475 | hsa-miR-452*, hsa-miR-422a, hsa-miR-1301, hsa-miR-107, hsa-miR-1203, hsa-miR-1202, hsa-miR-767-5p, hsa-miR-516a-5p, hsa-miR-654-5p, hsa-miR-31* | 90% | 89% | 91% |
| M77 | SEQ ID NO: 856, SEQ ID NO: 59, SEQ ID NO: 300, SEQ ID NO: 98, SEQ ID NO: 475, SEQ ID NO: 487, SEQ ID NO: 302, SEQ ID NO: 440, SEQ ID NO: 315, SEQ ID NO: 649 | hsa-miR-1202, hsa-miR-767-5p, hsa-miR-516a-5p, hsa-miR-654-5p, hsa-miR-31*, hsa-miR-30a, hsa-miR-515-5p, hsa-miR-345, hsa-miR-509-3-5p, hsa-miR-18a* | 86% | 79% | 94% |
| M78 | SEQ ID NO: 487, SEQ ID NO: 302, SEQ ID NO: 440, SEQ ID NO: 315, SEQ ID NO: 649, SEQ ID NO: 107, SEQ ID NO: 636, SEQ ID NO: 313, SEQ ID NO: 887, SEQ ID NO: 600 | hsa-miR-30a, hsa-miR-515-5p, hsa-miR-345, hsa-miR-509-3-5p, hsa-miR-18a*, hsa-miR-646, hsa-miR-1912, hsa-miR-509-5p, hsa-let-7i*, hsa-miR-19b | 87% | 81% | 94% |
| M79 | SEQ ID NO: 107, SEQ ID NO: 636, SEQ ID NO: 313, SEQ ID NO: 887, SEQ ID NO: 600, SEQ ID NO: 199, SEQ ID NO: 297, SEQ ID NO: 787, SEQ ID NO: 559, SEQ ID NO: 446 | hsa-miR-646, hsa-miR-1912, hsa-miR-509-5p, hsa-let-7i*, hsa-miR-19b, hsa-miR-564, hsa-miR-517*, hsa-miR-1274b, hsa-miR-215, hsa-miR-33b | 86% | 80% | 91% |
| M80 | SEQ ID NO: 199, SEQ ID NO: 297, SEQ ID NO: 787, SEQ ID NO: 559, SEQ ID NO: 446, SEQ ID NO: 578, SEQ ID NO: 709, SEQ ID NO: 101, SEQ ID NO: 360, SEQ ID NO: 674 | hsa-miR-564, hsa-miR-517*, hsa-miR-1274b, hsa-miR-215, hsa-miR-33b, hsa-miR-20a*, hsa-miR-146a, hsa-miR-652, hsa-miR-454, hsa-miR-17* | 87% | 82% | 92% |

FIG. 33A (Cont.)

| | | | | | |
|---|---|---|---|---|---|
| M81 | SEQ ID NO: 578, SEQ ID NO: 709, SEQ ID NO: 101, SEQ ID NO: 360, SEQ ID NO: 674, SEQ ID NO: 498, SEQ ID NO: 385, SEQ ID NO: 20, SEQ ID NO: 87, SEQ ID NO: 127 | hsa-miR-20a*, hsa-miR-146a, hsa-miR-652, hsa-miR-454, hsa-miR-17*, hsa-miR-301b, hsa-miR-423-3p, hsa-miR-933, hsa-miR-664, hsa-miR-628-3p | 86% | 81% | 92% |
| M82 | SEQ ID NO: 809, SEQ ID NO: 4, SEQ ID NO: 431, SEQ ID NO: 701, SEQ ID NO: 788 | hsa-miR-125a-5p, hsa-miR-99a, hsa-miR-361-5p, hsa-miR-148a, hsa-miR-1274a | 93% | 89% | 96% |
| M83 | SEQ ID NO: 430, SEQ ID NO: 460, SEQ ID NO: 165, SEQ ID NO: 382, SEQ ID NO: 429 | hsa-miR-362-3p, hsa-miR-330-3p, hsa-miR-593*, hsa-miR-424*, hsa-miR-362-5p | 87% | 77% | 97% |
| M84 | SEQ ID NO: 165, SEQ ID NO: 382, SEQ ID NO: 429, SEQ ID NO: 478, SEQ ID NO: 861 | hsa-miR-593*, hsa-miR-424*, hsa-miR-362-5p, hsa-miR-30e, hsa-miR-1184 | 85% | 79% | 91% |

FIG. 33B

| Signatures | SEQ ID Nos | miRNA-Identifiers | Acc | Spec | Sens |
|---|---|---|---|---|---|
| S1 | SEQ ID NO: 329, SEQ ID NO: 746, SEQ ID NO: 430 | hsa-miR-500, hsa-miR-130b, hsa-miR-362-3p | 81% | 81% | 81% |
| S2 | SEQ ID NO: 430, SEQ ID NO: 431, SEQ ID NO: 460 | hsa-miR-362-3p, hsa-miR-361-5p, hsa-miR-330-3p | 81% | 75% | 88% |
| S3 | SEQ ID NO: 460, SEQ ID NO: 165, SEQ ID NO: 788 | hsa-miR-330-3p, hsa-miR-593*, hsa-miR-1274a | 86% | 73% | 99% |
| S4 | SEQ ID NO: 788, SEQ ID NO: 382, SEQ ID NO: 136 | hsa-miR-1274a, hsa-miR-424*, hsa-miR-621 | 87% | 78% | 97% |
| S5 | SEQ ID NO: 136, SEQ ID NO: 429, SEQ ID NO: 444 | hsa-miR-621, hsa-miR-362-5p, hsa-miR-340 | 83% | 70% | 97% |
| S6 | SEQ ID NO: 444, SEQ ID NO: 861, SEQ ID NO: 327 | hsa-miR-340, hsa-miR-1184, hsa-miR-501-3p | 81% | 72% | 89% |
| S7 | SEQ ID NO: 327, SEQ ID NO: 362, SEQ ID NO: 216 | hsa-miR-501-3p, hsa-miR-452*, hsa-miR-550 | 82% | 76% | 89% |
| S8 | SEQ ID NO: 216, SEQ ID NO: 386, SEQ ID NO: 756 | hsa-miR-550, hsa-miR-422a, hsa-miR-1301 | 83% | 78% | 88% |
| S9 | SEQ ID NO: 756, SEQ ID NO: 872, SEQ ID NO: 855 | hsa-miR-1301, hsa-miR-107, hsa-miR-1203 | 88% | 82% | 95% |
| S10 | SEQ ID NO: 855, SEQ ID NO: 856, SEQ ID NO: 59 | hsa-miR-1203, hsa-miR-1202, hsa-miR-767-5p | 80% | 64% | 96% |
| S11 | SEQ ID NO: 59, SEQ ID NO: 300, SEQ ID NO: 98 | hsa-miR-767-5p, hsa-miR-516a-5p, hsa-miR-654-5p | 84% | 72% | 95% |
| S12 | SEQ ID NO: 98, SEQ ID NO: 475, SEQ ID NO: 302 | hsa-miR-654-5p, hsa-miR-31*, hsa-miR-515-5p | 88% | 79% | 97% |
| S13 | SEQ ID NO: 302, SEQ ID NO: 649, SEQ ID NO: 636 | hsa-miR-515-5p, hsa-miR-18a*, hsa-miR-1912 | 84% | 73% | 94% |
| S14 | SEQ ID NO: 649, SEQ ID NO: 107, SEQ ID NO: 636 | hsa-miR-18a*, hsa-miR-646, hsa-miR-1912 | 79% | 71% | 87% |
| S15 | SEQ ID NO: 636, SEQ ID NO: 313, SEQ ID NO: 887 | hsa-miR-1912, hsa-miR-509-5p, hsa-let-7i* | 78% | 65% | 91% |
| S16 | SEQ ID NO: 329, SEQ ID NO: 746, SEQ ID NO: 430, SEQ ID NO: 431, SEQ ID NO: 460 | hsa-miR-500, hsa-miR-130b, hsa-miR-362-3p, hsa-miR-361-5p, hsa-miR-330-3p | 91% | 92% | 91% |

FIG. 33B (Cont.)

| | | | | | |
|---|---|---|---|---|---|
| S17 | SEQ ID NO: 430, SEQ ID NO: 431, SEQ ID NO: 460, SEQ ID NO: 165, SEQ ID NO: 788 | hsa-miR-362-3p, hsa-miR-361-5p, hsa-miR-330-3p, hsa-miR-593*, hsa-miR-1274a | 86% | 80% | 92% |
| S18 | SEQ ID NO: 460, SEQ ID NO: 165, SEQ ID NO: 788, SEQ ID NO: 382, SEQ ID NO: 136 | hsa-miR-330-3p, hsa-miR-593*, hsa-miR-1274a, hsa-miR-424*, hsa-miR-621 | 88% | 80% | 97% |
| S19 | SEQ ID NO: 165, SEQ ID NO: 788, SEQ ID NO: 382, SEQ ID NO: 136, SEQ ID NO: 429 | hsa-miR-593*, hsa-miR-1274a, hsa-miR-424*, hsa-miR-621, hsa-miR-362-5p | 87% | 77% | 96% |
| S20 | SEQ ID NO: 382, SEQ ID NO: 136, SEQ ID NO: 429, SEQ ID NO: 444, SEQ ID NO: 861 | hsa-miR-424*, hsa-miR-621, hsa-miR-362-5p, hsa-miR-340, hsa-miR-1184 | 88% | 79% | 96% |
| S21 | SEQ ID NO: 429, SEQ ID NO: 444, SEQ ID NO: 861, SEQ ID NO: 327, SEQ ID NO: 362 | hsa-miR-362-5p, hsa-miR-340, hsa-miR-1184, hsa-miR-501-3p, hsa-miR-452* | 87% | 75% | 99% |
| S22 | SEQ ID NO: 444, SEQ ID NO: 861, SEQ ID NO: 327, SEQ ID NO: 362, SEQ ID NO: 216, SEQ ID NO: 386 | hsa-miR-340, hsa-miR-1184, hsa-miR-501-3p, hsa-miR-452*, hsa-miR-550, hsa-miR-422a | 85% | 81% | 88% |
| S23 | SEQ ID NO: 362, SEQ ID NO: 216, SEQ ID NO: 386, SEQ ID NO: 756, SEQ ID NO: 872, SEQ ID NO: 855 | hsa-miR-452*, hsa-miR-550, hsa-miR-422a, hsa-miR-1301, hsa-miR-107, hsa-miR-1203 | 88% | 84% | 91% |
| S24 | SEQ ID NO: 756, SEQ ID NO: 872, SEQ ID NO: 855, SEQ ID NO: 856, SEQ ID NO: 59, SEQ ID NO: 300 | hsa-miR-1301, hsa-miR-107, hsa-miR-1203, hsa-miR-1202, hsa-miR-767-5p, hsa-miR-516a-5p | 85% | 75% | 95% |
| S25 | SEQ ID NO: 856, SEQ ID NO: 59, SEQ ID NO: 300, SEQ ID NO: 98, SEQ ID NO: 475, SEQ ID NO: 302 | hsa-miR-1202, hsa-miR-767-5p, hsa-miR-516a-5p, hsa-miR-654-5p, hsa-miR-31*, hsa-miR-515-5p | 87% | 76% | 99% |
| S26 | SEQ ID NO: 98, SEQ ID NO: 475, SEQ ID NO: 302, SEQ ID NO: 315, SEQ ID NO: 649, SEQ ID NO: 107 | hsa-miR-654-5p, hsa-miR-31*, hsa-miR-515-5p, hsa-miR-509-3-5p, hsa-miR-18a*, hsa-miR-646 | 85% | 74% | 96% |
| S27 | SEQ ID NO: 315, SEQ ID NO: 649, SEQ ID NO: 107, SEQ ID NO: 636, SEQ ID NO: 313, SEQ ID NO: 887 | hsa-miR-509-3-5p, hsa-miR-18a*, hsa-miR-646, hsa-miR-1912, hsa-miR-509-5p, hsa-let-7i* | 82% | 73% | 91% |
| S28 | SEQ ID NO: 636, SEQ ID NO: 313, SEQ ID NO: 887, SEQ ID NO: 600, SEQ ID NO: 199, SEQ ID NO: 297 | hsa-miR-1912, hsa-miR-509-5p, hsa-let-7i*, hsa-miR-19b, hsa-miR-564, hsa-miR-517* | 84% | 75% | 93% |

FIG. 33B (Cont.)

| | | | | | |
|---|---|---|---|---|---|
| S29 | SEQ ID NO: 600, SEQ ID NO: 199, SEQ ID NO: 297, SEQ ID NO: 787, SEQ ID NO: 559, SEQ ID NO: 446 | hsa-miR-19b, hsa-miR-564, hsa-miR-517*, hsa-miR-1274b, hsa-miR-215, hsa-miR-33b | 83% | 76% | 91% |
| S30 | SEQ ID NO: 787, SEQ ID NO: 559, SEQ ID NO: 446, SEQ ID NO: 578, SEQ ID NO: 709, SEQ ID NO: 101 | hsa-miR-1274b, hsa-miR-215, hsa-miR-33b, hsa-miR-20a*, hsa-miR-146a, hsa-miR-652 | 84% | 78% | 91% |
| S31 | SEQ ID NO: 329, SEQ ID NO: 746, SEQ ID NO: 430, SEQ ID NO: 431, SEQ ID NO: 460, SEQ ID NO: 165, SEQ ID NO: 788, SEQ ID NO: 382, SEQ ID NO: 136, SEQ ID NO: 429 | hsa-miR-500, hsa-miR-130b, hsa-miR-362-3p, hsa-miR-361-5p, hsa-miR-330-3p, hsa-miR-593*, hsa-miR-1274a, hsa-miR-424*, hsa-miR-621, hsa-miR-362-5p | 94% | 92% | 96% |
| S32 | SEQ ID NO: 165, SEQ ID NO: 788, SEQ ID NO: 382, SEQ ID NO: 136, SEQ ID NO: 429, SEQ ID NO: 444, SEQ ID NO: 861, SEQ ID NO: 327, SEQ ID NO: 362, SEQ ID NO: 216, SEQ ID NO: 386 | hsa-miR-593*, hsa-miR-1274a, hsa-miR-424*, hsa-miR-621, hsa-miR-362-5p, hsa-miR-340, hsa-miR-1184, hsa-miR-501-3p, hsa-miR-452*, hsa-miR-550, hsa-miR-422a | 91% | 88% | 94% |
| S33 | SEQ ID NO: 861, SEQ ID NO: 327, SEQ ID NO: 362, SEQ ID NO: 216, SEQ ID NO: 386, SEQ ID NO: 756, SEQ ID NO: 872, SEQ ID NO: 855, SEQ ID NO: 856, SEQ ID NO: 59 | hsa-miR-1184, hsa-miR-501-3p, hsa-miR-452*, hsa-miR-550, hsa-miR-422a, hsa-miR-1301, hsa-miR-107, hsa-miR-1203, hsa-miR-1202, hsa-miR-767-5p | 92% | 89% | 95% |
| S34 | SEQ ID NO: 756, SEQ ID NO: 872, SEQ ID NO: 855, SEQ ID NO: 856, SEQ ID NO: 59, SEQ ID NO: 300, SEQ ID NO: 98, SEQ ID NO: 475, SEQ ID NO: 302, SEQ ID NO: 315 | hsa-miR-1301, hsa-miR-107, hsa-miR-1203, hsa-miR-1202, hsa-miR-767-5p, hsa-miR-516a-5p, hsa-miR-654-5p, hsa-miR-31*, hsa-miR-515-5p, hsa-miR-509-3-5p | 92% | 88% | 96% |
| S35 | SEQ ID NO: 300, SEQ ID NO: 98, SEQ ID NO: 475, SEQ ID NO: 302, SEQ ID NO: 315, SEQ ID NO: 649, SEQ ID NO: 107, SEQ ID NO: 636, SEQ ID NO: 313, SEQ ID NO: 887 | hsa-miR-516a-5p, hsa-miR-654-5p, hsa-miR-31*, hsa-miR-515-5p, hsa-miR-509-3-5p, hsa-miR-18a*, hsa-miR-646, hsa-miR-1912, hsa-miR-509-5p, hsa-let-7i* | 88% | 79% | 96% |
| S36 | SEQ ID NO: 649, SEQ ID NO: 107, SEQ ID NO: 636, SEQ ID NO: 313, SEQ ID NO: 887, SEQ ID NO: 600, SEQ ID NO: 199, SEQ ID NO: 297, SEQ ID NO: 787, SEQ ID NO: 559 | hsa-miR-18a*, hsa-miR-646, hsa-miR-1912, hsa-miR-509-5p, hsa-let-7i*, hsa-miR-19b, hsa-miR-564, hsa-miR-517*, hsa-miR-1274b, hsa-miR-215 | 87% | 80% | 94% |

FIG. 33B (Cont.)

| | | | | | |
|---|---|---|---|---|---|
| S37 | SEQ ID NO: 600, SEQ ID NO: 199, SEQ ID NO: 297, SEQ ID NO: 787, SEQ ID NO: 559, SEQ ID NO: 446, SEQ ID NO: 578, SEQ ID NO: 709, SEQ ID NO: 101, SEQ ID NO: 360 | hsa-miR-19b, hsa-miR-564, hsa-miR-517*, hsa-miR-1274b, hsa-miR-215, hsa-miR-33b, hsa-miR-20a*, hsa-miR-146a, hsa-miR-652, hsa-miR-454 | 88% | 83% | 92% |
| S38 | SEQ ID NO: 446, SEQ ID NO: 578, SEQ ID NO: 709, SEQ ID NO: 101, SEQ ID NO: 360, SEQ ID NO: 674, SEQ ID NO: 498, SEQ ID NO: 20, SEQ ID NO: 87, SEQ ID NO: 127 | hsa-miR-33b, hsa-miR-20a*, hsa-miR-146a, hsa-miR-652, hsa-miR-454, hsa-miR-17*, hsa-miR-301b, hsa-miR-933, hsa-miR-664, hsa-miR-628-3p | 87% | 79% | 94% |
| S39 | SEQ ID NO: 674, SEQ ID NO: 498, SEQ ID NO: 20, SEQ ID NO: 87, SEQ ID NO: 127, SEQ ID NO: 881, SEQ ID NO: 323, SEQ ID NO: 635, SEQ ID NO: 292, SEQ ID NO: 250 | hsa-miR-17*, hsa-miR-301b, hsa-miR-933, hsa-miR-664, hsa-miR-628-3p, hsa-miR-103, hsa-miR-503, hsa-miR-1913, hsa-miR-518a-5p, hsa-miR-527 | 83% | 78% | 88% |
| S40 | SEQ ID NO: 329, SEQ ID NO: 430, SEQ ID NO: 460, SEQ ID NO: 788, SEQ ID NO: 136 | hsa-miR-500, hsa-miR-362-3p, hsa-miR-330-3p, hsa-miR-1274a, hsa-miR-621 | 88% | 83% | 92% |
| S41 | SEQ ID NO: 431, SEQ ID NO: 165, SEQ ID NO: 382, SEQ ID NO: 429, SEQ ID NO: 861 | hsa-miR-361-5p, hsa-miR-593*, hsa-miR-424*, hsa-miR-362-5p, hsa-miR-1184 | 88% | 86% | 89% |
| S42 | SEQ ID NO: 382, SEQ ID NO: 429, SEQ ID NO: 861, SEQ ID NO: 362, SEQ ID NO: 386 | hsa-miR-424*, hsa-miR-362-5p, hsa-miR-1184, hsa-miR-452*, hsa-miR-422a | 83% | 75% | 91% |

```
                              SEQUENCE LISTING

<160> NUMBER OF SEQ ID NOS: 965

<210> SEQ ID NO 1
<211> LENGTH: 22
<212> TYPE: RNA
<213> ORGANISM: Homo sapiens

<400> SEQUENCE: 1
caagcucgug ucugugggguc cg                                              22

<210> SEQ ID NO 2
<211> LENGTH: 22
<212> TYPE: RNA
<213> ORGANISM: Homo sapiens

<400> SEQUENCE: 2
cacccguaga accgaccuug cg                                               22

<210> SEQ ID NO 3
<211> LENGTH: 22
<212> TYPE: RNA
<213> ORGANISM: Homo sapiens

<400> SEQUENCE: 3
caagcucgcu ucuauggguc ug                                               22

<210> SEQ ID NO 4
<211> LENGTH: 22
<212> TYPE: RNA
<213> ORGANISM: Homo sapiens

<400> SEQUENCE: 4
aacccguaga uccgaucuug ug                                               22

<210> SEQ ID NO 5
<211> LENGTH: 22
<212> TYPE: RNA
<213> ORGANISM: Homo sapiens

<400> SEQUENCE: 5
ugagguagua aguuguauug uu                                               22

<210> SEQ ID NO 6
<211> LENGTH: 22
<212> TYPE: RNA
<213> ORGANISM: Homo sapiens

<400> SEQUENCE: 6
aaucaugugc agugccaaua ug                                               22

<210> SEQ ID NO 7
<211> LENGTH: 23
<212> TYPE: RNA
<213> ORGANISM: Homo sapiens

<400> SEQUENCE: 7
uuuggcacua gcacauuuuu gcu                                              23
```

```
<210> SEQ ID NO 8
<211> LENGTH: 22
<212> TYPE: RNA
<213> ORGANISM: Homo sapiens

<400> SEQUENCE: 8
uucaacgggu auuuauugag ca                                              22

<210> SEQ ID NO 9
<211> LENGTH: 22
<212> TYPE: RNA
<213> ORGANISM: Homo sapiens

<400> SEQUENCE: 9
aaauuauugu acaucggaug ag                                              22

<210> SEQ ID NO 10
<211> LENGTH: 21
<212> TYPE: RNA
<213> ORGANISM: Homo sapiens

<400> SEQUENCE: 10
cugacuguug ccguccucca g                                               21

<210> SEQ ID NO 11
<211> LENGTH: 22
<212> TYPE: RNA
<213> ORGANISM: Homo sapiens

<400> SEQUENCE: 11
ucuucucugu uuuggccaug ug                                              22

<210> SEQ ID NO 12
<211> LENGTH: 23
<212> TYPE: RNA
<213> ORGANISM: Homo sapiens

<400> SEQUENCE: 12
cacccggcug ugugcacaug ugc                                             23

<210> SEQ ID NO 13
<211> LENGTH: 21
<212> TYPE: RNA
<213> ORGANISM: Homo sapiens

<400> SEQUENCE: 13
aaggcagggc ccccgcuccc c                                               21

<210> SEQ ID NO 14
<211> LENGTH: 24
<212> TYPE: RNA
<213> ORGANISM: Homo sapiens

<400> SEQUENCE: 14 ugggagcug aggcucuggg ggug                                             24

<210> SEQ ID NO 15
<211> LENGTH: 22
<212> TYPE: RNA
<213> ORGANISM: Homo sapiens

<400> SEQUENCE: 15
ugcccuuaaa ggugaaccca gu                                              22
```

```
<210> SEQ ID NO 16
<211> LENGTH: 22
<212> TYPE: RNA
<213> ORGANISM: Homo sapiens

<400> SEQUENCE: 16
auccgcgcuc ugacucucug cc                                          22

<210> SEQ ID NO 17
<211> LENGTH: 22
<212> TYPE: RNA
<213> ORGANISM: Homo sapiens

<400> SEQUENCE: 17
acaguagagg gaggaaucgc ag                                          22

<210> SEQ ID NO 18
<211> LENGTH: 23
<212> TYPE: RNA
<213> ORGANISM: Homo sapiens

<400> SEQUENCE: 18
ccaguuaccg cuuccgcuac cgc                                         23

<210> SEQ ID NO 19
<211> LENGTH: 22
<212> TYPE: RNA
<213> ORGANISM: Homo sapiens

<400> SEQUENCE: 19
ugucuacuac uggagacacu gg                                          22

<210> SEQ ID NO 20
<211> LENGTH: 22
<212> TYPE: RNA
<213> ORGANISM: Homo sapiens

<400> SEQUENCE: 20
ugugcgcagg gagaccucuc cc                                          22

<210> SEQ ID NO 21
<211> LENGTH: 22
<212> TYPE: RNA
<213> ORGANISM: Homo sapiens

<400> SEQUENCE: 21
acugcugagc uagcacuucc cg                                          22

<210> SEQ ID NO 22
<211> LENGTH: 23
<212> TYPE: RNA
<213> ORGANISM: Homo sapiens

<400> SEQUENCE: 22 caaagucug uucgugcagg uag                                          23

<210> SEQ ID NO 23
<211> LENGTH: 22
<212> TYPE: RNA
<213> ORGANISM: Homo sapiens

<400> SEQUENCE: 23
```
agggacggga cgcggugcag ug                                          22

<210> SEQ ID NO 24
<211> LENGTH: 22
<212> TYPE: RNA
<213> ORGANISM: Homo sapiens

<400> SEQUENCE: 24
uauugcacuc gucccggccu cc                                          22

<210> SEQ ID NO 25
<211> LENGTH: 22
<212> TYPE: RNA
<213> ORGANISM: Homo sapiens

<400> SEQUENCE: 25
ggguggggau uuguugcauu ac                                          22

<210> SEQ ID NO 26
<211> LENGTH: 23
<212> TYPE: RNA
<213> ORGANISM: Homo sapiens

<400> SEQUENCE: 26
agguugggau cgguugcaau gcu                                         23

<210> SEQ ID NO 27
<211> LENGTH: 22
<212> TYPE: RNA
<213> ORGANISM: Homo sapiens

<400> SEQUENCE: 27
uauugcacuu gucccggccu gu                                          22

<210> SEQ ID NO 28
<211> LENGTH: 20
<212> TYPE: RNA
<213> ORGANISM: Homo sapiens

<400> SEQUENCE: 28
agagucuugu gaugucuugc                                             20

<210> SEQ ID NO 29
<211> LENGTH: 23
<212> TYPE: RNA
<213> ORGANISM: Homo sapiens

<400> SEQUENCE: 29
gcagcagaga auaggacuac guc                                         23

<210> SEQ ID NO 30
<211> LENGTH: 25
<212> TYPE: RNA
<213> ORGANISM: Homo sapiens

<400> SEQUENCE: 30
cuagugaggg acagaaccag gauuc                                       25

<210> SEQ ID NO 31
<211> LENGTH: 20
<212> TYPE: RNA
<213> ORGANISM: Homo sapiens

<400> SEQUENCE: 31

```
gggagcugu ggaagcagua                                         20

<210> SEQ ID NO 32
<211> LENGTH: 22
<212> TYPE: RNA
<213> ORGANISM: Homo sapiens

<400> SEQUENCE: 32
auaaagcuag auaaccgaaa gu                                     22

<210> SEQ ID NO 33
<211> LENGTH: 23
<212> TYPE: RNA
<213> ORGANISM: Homo sapiens

<400> SEQUENCE: 33
ucuuugguua ucuagcugua uga                                    23

<210> SEQ ID NO 34
<211> LENGTH: 22
<212> TYPE: RNA
<213> ORGANISM: Homo sapiens

<400> SEQUENCE: 34
cacuggcucc uuucgggua ga                                      22

<210> SEQ ID NO 35
<211> LENGTH: 21
<212> TYPE: RNA
<213> ORGANISM: Homo sapiens

<400> SEQUENCE: 35
cacugugucc uuucugcgua g                                      21

<210> SEQ ID NO 36
<211> LENGTH: 22
<212> TYPE: RNA
<213> ORGANISM: Homo sapiens

<400> SEQUENCE: 36
ugcaacuuac cugagucauu ga                                     22

<210> SEQ ID NO 37
<211> LENGTH: 22
<212> TYPE: RNA
<213> ORGANISM: Homo sapiens

<400> SEQUENCE: 37
ugcaacgaac cugagccacu ga                                     22

<210> SEQ ID NO 38
<211> LENGTH: 21
<212> TYPE: RNA
<213> ORGANISM: Homo sapiens

<400> SEQUENCE: 38
uacuuggaaa ggcaucaguu g                                      21

<210> SEQ ID NO 39
<211> LENGTH: 21
<212> TYPE: RNA
<213> ORGANISM: Homo sapiens
```

```
<400> SEQUENCE: 39
uuaauaucgg acaaccauug u                                        21

<210> SEQ ID NO 40
<211> LENGTH: 22
<212> TYPE: RNA
<213> ORGANISM: Homo sapiens

<400> SEQUENCE: 40
gacugacacc ucuuugggug aa                                       22

<210> SEQ ID NO 41
<211> LENGTH: 21
<212> TYPE: RNA
<213> ORGANISM: Homo sapiens

<400> SEQUENCE: 41
uacucaaaaa gcugucaguc a                                        21

<210> SEQ ID NO 42
<211> LENGTH: 22
<212> TYPE: RNA
<213> ORGANISM: Homo sapiens

<400> SEQUENCE: 42
gugaacgggc gccaucccga gg                                       22

<210> SEQ ID NO 43
<211> LENGTH: 23
<212> TYPE: RNA
<213> ORGANISM: Homo sapiens

<400> SEQUENCE: 43
cgggucggag uuagcucaag cgg                                      23

<210> SEQ ID NO 44
<211> LENGTH: 21
<212> TYPE: RNA
<213> ORGANISM: Homo sapiens

<400> SEQUENCE: 44
cgcgggugcu uacugacccu u                                        21

<210> SEQ ID NO 45
<211> LENGTH: 22
<212> TYPE: RNA
<213> ORGANISM: Homo sapiens

<400> SEQUENCE: 45
uccauuacac uacccugccu cu                                       22

<210> SEQ ID NO 46
<211> LENGTH: 22
<212> TYPE: RNA
<213> ORGANISM: Homo sapiens

<400> SEQUENCE: 46
aggcagcggg guguagugga ua                                       22

<210> SEQ ID NO 47
<211> LENGTH: 21
<212> TYPE: RNA
<213> ORGANISM: Homo sapiens
```

```
<400> SEQUENCE: 47
uccucuucuc ccuccuccca g                                              21

<210> SEQ ID NO 48
<211> LENGTH: 20
<212> TYPE: RNA
<213> ORGANISM: Homo sapiens

<400> SEQUENCE: 48
guagaggaga uggcgcaggg                                                20

<210> SEQ ID NO 49
<211> LENGTH: 22
<212> TYPE: RNA
<213> ORGANISM: Homo sapiens

<400> SEQUENCE: 49
uggauuucuu ugugaaucac ca                                             22

<210> SEQ ID NO 50
<211> LENGTH: 22
<212> TYPE: RNA
<213> ORGANISM: Homo sapiens

<400> SEQUENCE: 50
uggugguuua caaaguaauu ca                                             22

<210> SEQ ID NO 51
<211> LENGTH: 22
<212> TYPE: RNA
<213> ORGANISM: Homo sapiens

<400> SEQUENCE: 51
uauaccucag uuuuaucagg ug                                             22

<210> SEQ ID NO 52
<211> LENGTH: 21
<212> TYPE: RNA
<213> ORGANISM: Homo sapiens

<400> SEQUENCE: 52
ccuggaaaca cugagguugu g                                              21

<210> SEQ ID NO 53
<211> LENGTH: 22
<212> TYPE: RNA
<213> ORGANISM: Homo sapiens

<400> SEQUENCE: 53
cugcccuggc ccgagggacc ga                                             22

<210> SEQ ID NO 54
<211> LENGTH: 21
<212> TYPE: RNA
<213> ORGANISM: Homo sapiens

<400> SEQUENCE: 54
gcaggaacuu gugagucucc u                                              21

<210> SEQ ID NO 55
<211> LENGTH: 23
<212> TYPE: RNA
```

<213> ORGANISM: Homo sapiens

<400> SEQUENCE: 55
caguaacaaa gauucauccu ugu                                            23

<210> SEQ ID NO 56
<211> LENGTH: 23
<212> TYPE: RNA
<213> ORGANISM: Homo sapiens

<400> SEQUENCE: 56
uccaguacca cgugucaggg cca                                            23

<210> SEQ ID NO 57
<211> LENGTH: 22
<212> TYPE: RNA
<213> ORGANISM: Homo sapiens

<400> SEQUENCE: 57
ugagaccucu ggguucugag cu                                             22

<210> SEQ ID NO 58
<211> LENGTH: 23
<212> TYPE: RNA
<213> ORGANISM: Homo sapiens

<400> SEQUENCE: 58
cugggaucuc cggggucuug guu                                            23

<210> SEQ ID NO 59
<211> LENGTH: 23
<212> TYPE: RNA
<213> ORGANISM: Homo sapiens

<400> SEQUENCE: 59
ugcaccaugg uugucugagc aug                                            23

<210> SEQ ID NO 60
<211> LENGTH: 23
<212> TYPE: RNA
<213> ORGANISM: Homo sapiens

<400> SEQUENCE: 60
ucugcucaua ccccaugguu ucu                                            23

<210> SEQ ID NO 61
<211> LENGTH: 22
<212> TYPE: RNA
<213> ORGANISM: Homo sapiens

<400> SEQUENCE: 61
acuccagccc cacagccuca gc                                             22

<210> SEQ ID NO 62
<211> LENGTH: 21
<212> TYPE: RNA
<213> ORGANISM: Homo sapiens

<400> SEQUENCE: 62
uggaggagaa ggaaggugau g                                              21

<210> SEQ ID NO 63
<211> LENGTH: 22

```
<212> TYPE: RNA
<213> ORGANISM: Homo sapiens

<400> SEQUENCE: 63
gcaggugcuc acuguccuc cu                                          22

<210> SEQ ID NO 64
<211> LENGTH: 22
<212> TYPE: RNA
<213> ORGANISM: Homo sapiens

<400> SEQUENCE: 64
ggggcugggg ccggggccga gc                                         22

<210> SEQ ID NO 65
<211> LENGTH: 22
<212> TYPE: RNA
<213> ORGANISM: Homo sapiens

<400> SEQUENCE: 65
gcagcagggu gaaacugaca ca                                         22

<210> SEQ ID NO 66
<211> LENGTH: 20
<212> TYPE: RNA
<213> ORGANISM: Homo sapiens

<400> SEQUENCE: 66
cggcucuggg ucugugggga                                            20

<210> SEQ ID NO 67
<211> LENGTH: 22
<212> TYPE: RNA
<213> ORGANISM: Homo sapiens

<400> SEQUENCE: 67
gcagagugca aacaauuuug ac                                         22

<210> SEQ ID NO 68
<211> LENGTH: 22
<212> TYPE: RNA
<213> ORGANISM: Homo sapiens

<400> SEQUENCE: 68
uuugugaccu gguccacuaa cc                                         22

<210> SEQ ID NO 69
<211> LENGTH: 22
<212> TYPE: RNA
<213> ORGANISM: Homo sapiens

<400> SEQUENCE: 69
cuguugccac uaaccucaac cu                                         22

<210> SEQ ID NO 70
<211> LENGTH: 22
<212> TYPE: RNA
<213> ORGANISM: Homo sapiens

<400> SEQUENCE: 70
ugcggggcua gggcuaacag ca                                         22

<210> SEQ ID NO 71
```

```
<211> LENGTH: 17
<212> TYPE: RNA
<213> ORGANISM: Homo sapiens

<400> SEQUENCE: 71
ucucgcuggg gccucca                                                        17

<210> SEQ ID NO 72
<211> LENGTH: 22
<212> TYPE: RNA
<213> ORGANISM: Homo sapiens

<400> SEQUENCE: 72
caacaaaucc cagucuaccu aa                                                  22

<210> SEQ ID NO 73
<211> LENGTH: 21
<212> TYPE: RNA
<213> ORGANISM: Homo sapiens

<400> SEQUENCE: 73
cuuccgcccc gccgggcguc g                                                   21

<210> SEQ ID NO 74
<211> LENGTH: 22
<212> TYPE: RNA
<213> ORGANISM: Homo sapiens

<400> SEQUENCE: 74
gggacccagg gagagacgua ag                                                  22

<210> SEQ ID NO 75
<211> LENGTH: 22
<212> TYPE: RNA
<213> ORGANISM: Homo sapiens

<400> SEQUENCE: 75
caacaaauca cagucugcca ua                                                  22

<210> SEQ ID NO 76
<211> LENGTH: 22
<212> TYPE: RNA
<213> ORGANISM: Homo sapiens

<400> SEQUENCE: 76
caacuagacu gugagcuucu ag                                                  22

<210> SEQ ID NO 77
<211> LENGTH: 23
<212> TYPE: RNA
<213> ORGANISM: Homo sapiens

<400> SEQUENCE: 77
aaggagcuua caaucuagcu ggg                                                 23

<210> SEQ ID NO 78
<211> LENGTH: 23
<212> TYPE: RNA
<213> ORGANISM: Homo sapiens

<400> SEQUENCE: 78
uggaagacua gugauuuugu ugu                                                 23
```

-continued

```
<210> SEQ ID NO 79
<211> LENGTH: 20
<212> TYPE: RNA
<213> ORGANISM: Homo sapiens

<400> SEQUENCE: 79
cuguaugccc ucaccgcuca                                                    20

<210> SEQ ID NO 80
<211> LENGTH: 23
<212> TYPE: RNA
<213> ORGANISM: Homo sapiens

<400> SEQUENCE: 80
uggugcggag agggcccaca gug                                                23

<210> SEQ ID NO 81
<211> LENGTH: 23
<212> TYPE: RNA
<213> ORGANISM: Homo sapiens

<400> SEQUENCE: 81
aggaagcccu ggaggggcug gag                                                23

<210> SEQ ID NO 82
<211> LENGTH: 21
<212> TYPE: RNA
<213> ORGANISM: Homo sapiens

<400> SEQUENCE: 82
uccgguucuc agggcuccac c                                                  21

<210> SEQ ID NO 83
<211> LENGTH: 20
<212> TYPE: RNA
<213> ORGANISM: Homo sapiens

<400> SEQUENCE: 83
gucccugagu guauguggug                                                    20

<210> SEQ ID NO 84
<211> LENGTH: 23
<212> TYPE: RNA
<213> ORGANISM: Homo sapiens

<400> SEQUENCE: 84
ugucacucgg cucggcccac uac                                                23

<210> SEQ ID NO 85
<211> LENGTH: 20
<212> TYPE: RNA
<213> ORGANISM: Homo sapiens

<400> SEQUENCE: 85
accaggaggc ugaggcsccu                                                    20

<210> SEQ ID NO 86
<211> LENGTH: 24
<212> TYPE: RNA
<213> ORGANISM: Homo sapiens

<400> SEQUENCE: 86
acuggcuagg gaaaaugauu ggau                                               24
```

```
<210> SEQ ID NO 87
<211> LENGTH: 23
<212> TYPE: RNA
<213> ORGANISM: Homo sapiens

<400> SEQUENCE: 87
uauucauuua ucccagccu aca                                            23

<210> SEQ ID NO 88
<211> LENGTH: 22
<212> TYPE: RNA
<213> ORGANISM: Homo sapiens

<400> SEQUENCE: 88
gguggcccgg ccgugccuga gg                                            22

<210> SEQ ID NO 89
<211> LENGTH: 22
<212> TYPE: RNA
<213> ORGANISM: Homo sapiens

<400> SEQUENCE: 89
aggcggggcg ccgcgggacc gc                                            22

<210> SEQ ID NO 90
<211> LENGTH: 21
<212> TYPE: RNA
<213> ORGANISM: Homo sapiens

<400> SEQUENCE: 90
ucccacguug uggcccagca g                                             21

<210> SEQ ID NO 91
<211> LENGTH: 24
<212> TYPE: RNA
<213> ORGANISM: Homo sapiens

<400> SEQUENCE: 91
ugccuggguc ucuggccugc gcgu                                          24

<210> SEQ ID NO 92
<211> LENGTH: 22
<212> TYPE: RNA
<213> ORGANISM: Homo sapiens

<400> SEQUENCE: 92
uacccauugc auaucggagu ug                                            22

<210> SEQ ID NO 93
<211> LENGTH: 22
<212> TYPE: RNA
<213> ORGANISM: Homo sapiens

<400> SEQUENCE: 93
cuugguucag ggaggguccc ca                                            22

<210> SEQ ID NO 94
<211> LENGTH: 25
<212> TYPE: RNA
<213> ORGANISM: Homo sapiens

<400> SEQUENCE: 94
ggcggaggga aguagguccg uuggu                                         25
```

```
<210> SEQ ID NO 95
<211> LENGTH: 23
<212> TYPE: RNA
<213> ORGANISM: Homo sapiens

<400> SEQUENCE: 95
ggcagguucu cacccucucu agg                                           23

<210> SEQ ID NO 96
<211> LENGTH: 21
<212> TYPE: RNA
<213> ORGANISM: Homo sapiens

<400> SEQUENCE: 96
aauauuauac agucaaccuc u                                             21

<210> SEQ ID NO 97
<211> LENGTH: 22
<212> TYPE: RNA
<213> ORGANISM: Homo sapiens

<400> SEQUENCE: 97
auaauacaug guuaaccucu uu                                            22

<210> SEQ ID NO 98
<211> LENGTH: 22
<212> TYPE: RNA
<213> ORGANISM: Homo sapiens

<400> SEQUENCE: 98
uggugggccg cagaacaugu gc                                            22

<210> SEQ ID NO 99
<211> LENGTH: 22
<212> TYPE: RNA
<213> ORGANISM: Homo sapiens

<400> SEQUENCE: 99
uaugucugcu gaccaucacc uu                                            22

<210> SEQ ID NO 100
<211> LENGTH: 21
<212> TYPE: RNA
<213> ORGANISM: Homo sapiens

<400> SEQUENCE: 100
guguugaaac aaucucuacu g                                             21

<210> SEQ ID NO 101
<211> LENGTH: 21
<212> TYPE: RNA
<213> ORGANISM: Homo sapiens

<400> SEQUENCE: 101
aauggcgcca cuaggguugu g                                             21

<210> SEQ ID NO 102
<211> LENGTH: 22
<212> TYPE: RNA
<213> ORGANISM: Homo sapiens

<400> SEQUENCE: 102
```
uuuaggauaa gcuugacuuu ug					22

<210> SEQ ID NO 103
<211> LENGTH: 21
<212> TYPE: RNA
<213> ORGANISM: Homo sapiens

<400> SEQUENCE: 103
aggaggcagc gcucucagga c					21

<210> SEQ ID NO 104
<211> LENGTH: 22
<212> TYPE: RNA
<213> ORGANISM: Homo sapiens

<400> SEQUENCE: 104
aaaccugugu uguucaagag uc				22

<210> SEQ ID NO 105
<211> LENGTH: 19
<212> TYPE: RNA
<213> ORGANISM: Homo sapiens

<400> SEQUENCE: 105
aagugugcag ggcacuggu					19

<210> SEQ ID NO 106
<211> LENGTH: 21
<212> TYPE: RNA
<213> ORGANISM: Homo sapiens

<400> SEQUENCE: 106
guggcugcac ucacuuccuu c					21

<210> SEQ ID NO 107
<211> LENGTH: 19
<212> TYPE: RNA
<213> ORGANISM: Homo sapiens

<400> SEQUENCE: 107
aagcagcugc cucugaggc					19

<210> SEQ ID NO 108
<211> LENGTH: 19
<212> TYPE: RNA
<213> ORGANISM: Homo sapiens

<400> SEQUENCE: 108
ucuaggcugg uacugcuga					19

<210> SEQ ID NO 109
<211> LENGTH: 19
<212> TYPE: RNA
<213> ORGANISM: Homo sapiens

<400> SEQUENCE: 109
aguguggcuu ucuuagagc					19

<210> SEQ ID NO 110
<211> LENGTH: 22
<212> TYPE: RNA
<213> ORGANISM: Homo sapiens

<400> SEQUENCE: 110

-continued acuuguaugc uagcucaggu ag                                          22

<210> SEQ ID NO 111
<211> LENGTH: 22
<212> TYPE: RNA
<213> ORGANISM: Homo sapiens

<400> SEQUENCE: 111
gucccucucc aaaugugucu ug                                          22

<210> SEQ ID NO 112
<211> LENGTH: 24
<212> TYPE: RNA
<213> ORGANISM: Homo sapiens

<400> SEQUENCE: 112
aaagacauag gauagaguca ccuc                                        24

<210> SEQ ID NO 113
<211> LENGTH: 21
<212> TYPE: RNA
<213> ORGANISM: Homo sapiens

<400> SEQUENCE: 113
augauccagg aaccugccuc u                                           21

<210> SEQ ID NO 114
<211> LENGTH: 23
<212> TYPE: RNA
<213> ORGANISM: Homo sapiens

<400> SEQUENCE: 114
aucgcugcgg uugcgagcgc ugu                                         23

<210> SEQ ID NO 115
<211> LENGTH: 25
<212> TYPE: RNA
<213> ORGANISM: Homo sapiens

<400> SEQUENCE: 115
agggaucgcg ggcgggguggc ggccu                                      25

<210> SEQ ID NO 116
<211> LENGTH: 24
<212> TYPE: RNA
<213> ORGANISM: Homo sapiens

<400> SEQUENCE: 116 acuggggcu uucgggcucu gcgu                                         24

<210> SEQ ID NO 117
<211> LENGTH: 23
<212> TYPE: RNA
<213> ORGANISM: Homo sapiens

<400> SEQUENCE: 117
ugugcuugcu cgucccgccc gca                                         23

<210> SEQ ID NO 118
<211> LENGTH: 23
<212> TYPE: RNA
<213> ORGANISM: Homo sapiens

<400> SEQUENCE: 118
acuugggcac ugaaacaaug ucc                                               23

<210> SEQ ID NO 119
<211> LENGTH: 22
<212> TYPE: RNA
<213> ORGANISM: Homo sapiens

<400> SEQUENCE: 119
aaccagcacc ccaacuuugg ac                                                22

<210> SEQ ID NO 120
<211> LENGTH: 23
<212> TYPE: RNA
<213> ORGANISM: Homo sapiens

<400> SEQUENCE: 120
cuaauaguau cuaccacaau aaa                                               23

<210> SEQ ID NO 121
<211> LENGTH: 19
<212> TYPE: RNA
<213> ORGANISM: Homo sapiens

<400> SEQUENCE: 121
gugucugcuu ccuguggga                                                    19

<210> SEQ ID NO 122
<211> LENGTH: 21
<212> TYPE: RNA
<213> ORGANISM: Homo sapiens

<400> SEQUENCE: 122
agaccuggcc cagaccucag c                                                 21

<210> SEQ ID NO 123
<211> LENGTH: 22
<212> TYPE: RNA
<213> ORGANISM: Homo sapiens

<400> SEQUENCE: 123
aguauucugu accagggaag gu                                                22

<210> SEQ ID NO 124
<211> LENGTH: 22
<212> TYPE: RNA
<213> ORGANISM: Homo sapiens

<400> SEQUENCE: 124
guucucccaa cguaagccca gc                                                22

<210> SEQ ID NO 125
<211> LENGTH: 21
<212> TYPE: RNA
<213> ORGANISM: Homo sapiens

<400> SEQUENCE: 125
uggguuuacg uugggagaac u                                                 21

<210> SEQ ID NO 126
<211> LENGTH: 22
<212> TYPE: RNA
<213> ORGANISM: Homo sapiens

```
<400> SEQUENCE: 126
augcugacau auuuacuaga gg                                              22

<210> SEQ ID NO 127
<211> LENGTH: 21
<212> TYPE: RNA
<213> ORGANISM: Homo sapiens

<400> SEQUENCE: 127
ucuaguaaga guggcagucg a                                               21

<210> SEQ ID NO 128
<211> LENGTH: 22
<212> TYPE: RNA
<213> ORGANISM: Homo sapiens

<400> SEQUENCE: 128
gugagucucu aagaaaagag ga                                              22

<210> SEQ ID NO 129
<211> LENGTH: 19
<212> TYPE: RNA
<213> ORGANISM: Homo sapiens

<400> SEQUENCE: 129
agcugucuga aaaugucuu                                                  19

<210> SEQ ID NO 130
<211> LENGTH: 22
<212> TYPE: RNA
<213> ORGANISM: Homo sapiens

<400> SEQUENCE: 130
gacuauagaa cuuccccu ca                                                22

<210> SEQ ID NO 131
<211> LENGTH: 21
<212> TYPE: RNA
<213> ORGANISM: Homo sapiens

<400> SEQUENCE: 131 aggggaaag uucuauaguc c                                                21

<210> SEQ ID NO 132
<211> LENGTH: 22
<212> TYPE: RNA
<213> ORGANISM: Homo sapiens

<400> SEQUENCE: 132
uaguaccagu accuuguguu ca                                              22

<210> SEQ ID NO 133
<211> LENGTH: 21
<212> TYPE: RNA
<213> ORGANISM: Homo sapiens

<400> SEQUENCE: 133
cacaagguau ugguauuacc u                                               21

<210> SEQ ID NO 134
<211> LENGTH: 23
<212> TYPE: RNA
```

-continued

```
<213> ORGANISM: Homo sapiens

<400> SEQUENCE: 134
aucccuugca ggggcuguug ggu                                                23

<210> SEQ ID NO 135
<211> LENGTH: 21
<212> TYPE: RNA
<213> ORGANISM: Homo sapiens

<400> SEQUENCE: 135
acagucugcu gagguuggag c                                                  21

<210> SEQ ID NO 136
<211> LENGTH: 21
<212> TYPE: RNA
<213> ORGANISM: Homo sapiens

<400> SEQUENCE: 136
ggcuagcaac agcgcuuacc u                                                  21

<210> SEQ ID NO 137
<211> LENGTH: 20
<212> TYPE: RNA
<213> ORGANISM: Homo sapiens

<400> SEQUENCE: 137
auggagauag auauagaaau                                                    20

<210> SEQ ID NO 138
<211> LENGTH: 24
<212> TYPE: RNA
<213> ORGANISM: Homo sapiens

<400> SEQUENCE: 138
gaccuggaca uguuugugcc cagu                                               24

<210> SEQ ID NO 139
<211> LENGTH: 23
<212> TYPE: RNA
<213> ORGANISM: Homo sapiens

<400> SEQUENCE: 139
aaacucuacu uguccuucug agu                                                23

<210> SEQ ID NO 140
<211> LENGTH: 22
<212> TYPE: RNA
<213> ORGANISM: Homo sapiens

<400> SEQUENCE: 140
agacuuccca uuugaaggug gc                                                 22

<210> SEQ ID NO 141
<211> LENGTH: 22
<212> TYPE: RNA
<213> ORGANISM: Homo sapiens

<400> SEQUENCE: 141
acucaaaacc cuucagugac uu                                                 22

<210> SEQ ID NO 142
<211> LENGTH: 22
```

```
<212> TYPE: RNA
<213> ORGANISM: Homo sapiens

<400> SEQUENCE: 142
agucauugga gggguuugagc ag                                          22

<210> SEQ ID NO 143
<211> LENGTH: 22
<212> TYPE: RNA
<213> ORGANISM: Homo sapiens

<400> SEQUENCE: 143 ggggguccc ggugcucgga uc                                            22

<210> SEQ ID NO 144
<211> LENGTH: 22
<212> TYPE: RNA
<213> ORGANISM: Homo sapiens

<400> SEQUENCE: 144
uccgagccug ggucucccuc uu                                           22

<210> SEQ ID NO 145
<211> LENGTH: 23
<212> TYPE: RNA
<213> ORGANISM: Homo sapiens

<400> SEQUENCE: 145
gaacgccugu ucuugccagg ugg                                          23

<210> SEQ ID NO 146
<211> LENGTH: 20
<212> TYPE: RNA
<213> ORGANISM: Homo sapiens

<400> SEQUENCE: 146
aggaauguuc cuucuuugcc                                              20

<210> SEQ ID NO 147
<211> LENGTH: 25
<212> TYPE: RNA
<213> ORGANISM: Homo sapiens

<400> SEQUENCE: 147
gcugggcagg gcuucugagc uccuu                                        25

<210> SEQ ID NO 148
<211> LENGTH: 23
<212> TYPE: RNA
<213> ORGANISM: Homo sapiens

<400> SEQUENCE: 148
gcgaggaccc cucggggucu gac                                          23

<210> SEQ ID NO 149
<211> LENGTH: 21
<212> TYPE: RNA
<213> ORGANISM: Homo sapiens

<400> SEQUENCE: 149
ugagcuaaau gugugcuggg a                                            21

<210> SEQ ID NO 150
```

```
<211> LENGTH: 20
<212> TYPE: RNA
<213> ORGANISM: Homo sapiens

<400> SEQUENCE: 150
aggguguuuc ucucaucucu                                                    20

<210> SEQ ID NO 151
<211> LENGTH: 25
<212> TYPE: RNA
<213> ORGANISM: Homo sapiens

<400> SEQUENCE: 151
aggggugguc uugggacagc uccgu                                              25

<210> SEQ ID NO 152
<211> LENGTH: 21
<212> TYPE: RNA
<213> ORGANISM: Homo sapiens

<400> SEQUENCE: 152
guucaaaucc agaucuauaa c                                                  21

<210> SEQ ID NO 153
<211> LENGTH: 21
<212> TYPE: RNA
<213> ORGANISM: Homo sapiens

<400> SEQUENCE: 153
aaacuacuga aaaucaaaga u                                                  21

<210> SEQ ID NO 154
<211> LENGTH: 23
<212> TYPE: RNA
<213> ORGANISM: Homo sapiens

<400> SEQUENCE: 154
uaaaucccau ggugccuucu ccu                                                23

<210> SEQ ID NO 155
<211> LENGTH: 19
<212> TYPE: RNA
<213> ORGANISM: Homo sapiens

<400> SEQUENCE: 155
aggcugcgga auucaggac                                                     19

<210> SEQ ID NO 156
<211> LENGTH: 22
<212> TYPE: RNA
<213> ORGANISM: Homo sapiens

<400> SEQUENCE: 156
cacacacugc aauuacuuuu gc                                                 22

<210> SEQ ID NO 157
<211> LENGTH: 23
<212> TYPE: RNA
<213> ORGANISM: Homo sapiens

<400> SEQUENCE: 157
gacacgggcg acagcugcgg ccc                                                23
```

```
<210> SEQ ID NO 158
<211> LENGTH: 22
<212> TYPE: RNA
<213> ORGANISM: Homo sapiens

<400> SEQUENCE: 158
uggucuagga uuguuggagg ag                                              22

<210> SEQ ID NO 159
<211> LENGTH: 23
<212> TYPE: RNA
<213> ORGANISM: Homo sapiens

<400> SEQUENCE: 159
acuuacagac aagagccuug cuc                                             23

<210> SEQ ID NO 160
<211> LENGTH: 20
<212> TYPE: RNA
<213> ORGANISM: Homo sapiens

<400> SEQUENCE: 160
guugugucag uuuaucaaac                                                 20

<210> SEQ ID NO 161
<211> LENGTH: 22
<212> TYPE: RNA
<213> ORGANISM: Homo sapiens

<400> SEQUENCE: 161
uacgucaucg uugucaucgu ca                                              22

<210> SEQ ID NO 162
<211> LENGTH: 22
<212> TYPE: RNA
<213> ORGANISM: Homo sapiens

<400> SEQUENCE: 162
ugugucacuc gaugaccacu gu                                              22

<210> SEQ ID NO 163
<211> LENGTH: 21
<212> TYPE: RNA
<213> ORGANISM: Homo sapiens

<400> SEQUENCE: 163
aagccugccc ggcuccucgg g                                               21

<210> SEQ ID NO 164
<211> LENGTH: 21
<212> TYPE: RNA
<213> ORGANISM: Homo sapiens

<400> SEQUENCE: 164
gaagugugcc gugguguguc u                                               21

<210> SEQ ID NO 165
<211> LENGTH: 25
<212> TYPE: RNA
<213> ORGANISM: Homo sapiens

<400> SEQUENCE: 165
aggcaccagc caggcauugc ucagc                                           25
```

<210> SEQ ID NO 166
<211> LENGTH: 19
<212> TYPE: RNA
<213> ORGANISM: Homo sapiens

<400> SEQUENCE: 166
ugucucugcu gggguuucu                                                    19

<210> SEQ ID NO 167
<211> LENGTH: 22
<212> TYPE: RNA
<213> ORGANISM: Homo sapiens

<400> SEQUENCE: 167
uugugucaau augcgaugau gu                                                22

<210> SEQ ID NO 168
<211> LENGTH: 20
<212> TYPE: RNA
<213> ORGANISM: Homo sapiens

<400> SEQUENCE: 168
agaccauggg uucucauugu                                                   20

<210> SEQ ID NO 169
<211> LENGTH: 22
<212> TYPE: RNA
<213> ORGANISM: Homo sapiens

<400> SEQUENCE: 169
gagcuuauuc auaaaagugc ag                                                22

<210> SEQ ID NO 170
<211> LENGTH: 21
<212> TYPE: RNA
<213> ORGANISM: Homo sapiens

<400> SEQUENCE: 170
uaauuuuaug uauaagcuag u                                                 21

<210> SEQ ID NO 171
<211> LENGTH: 24
<212> TYPE: RNA
<213> ORGANISM: Homo sapiens

<400> SEQUENCE: 171
ucagaacaaa ugccgguucc caga                                              24

<210> SEQ ID NO 172
<211> LENGTH: 22
<212> TYPE: RNA
<213> ORGANISM: Homo sapiens

<400> SEQUENCE: 172
ugagaaccac gucugcucug ag                                                22

<210> SEQ ID NO 173
<211> LENGTH: 21
<212> TYPE: RNA
<213> ORGANISM: Homo sapiens

<400> SEQUENCE: 173
uuggccacaa uggguuagaa c                                                 21

<210> SEQ ID NO 174
<211> LENGTH: 21
<212> TYPE: RNA
<213> ORGANISM: Homo sapiens

<400> SEQUENCE: 174
uuuccauagg ugaugaguca c                                     21

<210> SEQ ID NO 175
<211> LENGTH: 22
<212> TYPE: RNA
<213> ORGANISM: Homo sapiens

<400> SEQUENCE: 175
uaugcauugu auuuuaggu cc                                     22

<210> SEQ ID NO 176
<211> LENGTH: 19
<212> TYPE: RNA
<213> ORGANISM: Homo sapiens

<400> SEQUENCE: 176
ugggcguauc uguaugcua                                        19

<210> SEQ ID NO 177
<211> LENGTH: 22
<212> TYPE: RNA
<213> ORGANISM: Homo sapiens

<400> SEQUENCE: 177
uuaugguuug ccugggacug ag                                    22

<210> SEQ ID NO 178
<211> LENGTH: 21
<212> TYPE: RNA
<213> ORGANISM: Homo sapiens

<400> SEQUENCE: 178
caaagaggaa ggucccauua c                                     21

<210> SEQ ID NO 179
<211> LENGTH: 23
<212> TYPE: RNA
<213> ORGANISM: Homo sapiens

<400> SEQUENCE: 179
uuacaguugu ucaaccaguu acu                                   23

<210> SEQ ID NO 180
<211> LENGTH: 22
<212> TYPE: RNA
<213> ORGANISM: Homo sapiens

<400> SEQUENCE: 180
uaacugguug aacaacugaa cc                                    22

<210> SEQ ID NO 181
<211> LENGTH: 21
<212> TYPE: RNA
<213> ORGANISM: Homo sapiens

<400> SEQUENCE: 181
ucuuguguuc ucuagaucag u                                                    21

<210> SEQ ID NO 182
<211> LENGTH: 22
<212> TYPE: RNA
<213> ORGANISM: Homo sapiens

<400> SEQUENCE: 182
uugagaauga ugaaucauua gg                                                   22

<210> SEQ ID NO 183
<211> LENGTH: 23
<212> TYPE: RNA
<213> ORGANISM: Homo sapiens

<400> SEQUENCE: 183
uucauuuggu auaaaccgcg auu                                                  23

<210> SEQ ID NO 184
<211> LENGTH: 21
<212> TYPE: RNA
<213> ORGANISM: Homo sapiens

<400> SEQUENCE: 184
cuucuugugc ucuaggauug u                                                    21

<210> SEQ ID NO 185
<211> LENGTH: 21
<212> TYPE: RNA
<213> ORGANISM: Homo sapiens

<400> SEQUENCE: 185
uagauaaaau auugguaccu g                                                    21

<210> SEQ ID NO 186
<211> LENGTH: 22
<212> TYPE: RNA
<213> ORGANISM: Homo sapiens

<400> SEQUENCE: 186
auucuaauuu cuccacgucu uu                                                   22

<210> SEQ ID NO 187
<211> LENGTH: 22
<212> TYPE: RNA
<213> ORGANISM: Homo sapiens

<400> SEQUENCE: 187
aagaugugga aaaauuggaa uc                                                   22

<210> SEQ ID NO 188
<211> LENGTH: 19
<212> TYPE: RNA
<213> ORGANISM: Homo sapiens

<400> SEQUENCE: 188
gagccaguug gacaggagc                                                       19

<210> SEQ ID NO 189
<211> LENGTH: 23
<212> TYPE: RNA
<213> ORGANISM: Homo sapiens

<400> SEQUENCE: 189

```
ugagugugug ugugugagug ugu                                            23

<210> SEQ ID NO 190
<211> LENGTH: 22
<212> TYPE: RNA
<213> ORGANISM: Homo sapiens

<400> SEQUENCE: 190
cacgcucaug cacacaccca ca                                             22

<210> SEQ ID NO 191
<211> LENGTH: 24
<212> TYPE: RNA
<213> ORGANISM: Homo sapiens

<400> SEQUENCE: 191
cugaagugau guguaacuga ucag                                           24

<210> SEQ ID NO 192
<211> LENGTH: 20
<212> TYPE: RNA
<213> ORGANISM: Homo sapiens

<400> SEQUENCE: 192
guccgcucgg cgguggccca                                                20

<210> SEQ ID NO 193
<211> LENGTH: 21
<212> TYPE: RNA
<213> ORGANISM: Homo sapiens

<400> SEQUENCE: 193
ugaguuggcc aucugaguga g                                              21

<210> SEQ ID NO 194
<211> LENGTH: 22
<212> TYPE: RNA
<213> ORGANISM: Homo sapiens

<400> SEQUENCE: 194
cgaaaacagc aauuaccuuu gc                                             22

<210> SEQ ID NO 195
<211> LENGTH: 21
<212> TYPE: RNA
<213> ORGANISM: Homo sapiens

<400> SEQUENCE: 195
aguuaaugaa uccuggaaag u                                              21

<210> SEQ ID NO 196
<211> LENGTH: 20
<212> TYPE: RNA
<213> ORGANISM: Homo sapiens

<400> SEQUENCE: 196
auguauaaau guauacacac                                                20

<210> SEQ ID NO 197
<211> LENGTH: 23
<212> TYPE: RNA
<213> ORGANISM: Homo sapiens
```

<400> SEQUENCE: 197
aguauguucu uccaggacag aac                                        23

<210> SEQ ID NO 198
<211> LENGTH: 19
<212> TYPE: RNA
<213> ORGANISM: Homo sapiens

<400> SEQUENCE: 198
gggcgccugu gaucccaac                                             19

<210> SEQ ID NO 199
<211> LENGTH: 19
<212> TYPE: RNA
<213> ORGANISM: Homo sapiens

<400> SEQUENCE: 199
aggcacggug ucagcaggc                                             19

<210> SEQ ID NO 200
<211> LENGTH: 19
<212> TYPE: RNA
<213> ORGANISM: Homo sapiens

<400> SEQUENCE: 200
agguugacau acguuuccc                                             19

<210> SEQ ID NO 201
<211> LENGTH: 20
<212> TYPE: RNA
<213> ORGANISM: Homo sapiens

<400> SEQUENCE: 201
aaaguagcug uaccauuugc                                            20

<210> SEQ ID NO 202
<211> LENGTH: 22
<212> TYPE: RNA
<213> ORGANISM: Homo sapiens

<400> SEQUENCE: 202
caaaguuuaa gauccuugaa gu                                         22

<210> SEQ ID NO 203
<211> LENGTH: 21
<212> TYPE: RNA
<213> ORGANISM: Homo sapiens

<400> SEQUENCE: 203
uaaaguaaau augcaccaaa a                                          21

<210> SEQ ID NO 204
<211> LENGTH: 19
<212> TYPE: RNA
<213> ORGANISM: Homo sapiens

<400> SEQUENCE: 204
ugagcugcug uaccaaaau                                             19

<210> SEQ ID NO 205
<211> LENGTH: 23
<212> TYPE: RNA
<213> ORGANISM: Homo sapiens

```
<400> SEQUENCE: 205
guuugcacgg gugggccuug ucu                                              23

<210> SEQ ID NO 206
<211> LENGTH: 22
<212> TYPE: RNA
<213> ORGANISM: Homo sapiens

<400> SEQUENCE: 206
gaugagcuca uuguaauaug ag                                               22

<210> SEQ ID NO 207
<211> LENGTH: 22
<212> TYPE: RNA
<213> ORGANISM: Homo sapiens

<400> SEQUENCE: 207
auauuaccau uagcucaucu uu                                               22

<210> SEQ ID NO 208
<211> LENGTH: 21
<212> TYPE: RNA
<213> ORGANISM: Homo sapiens

<400> SEQUENCE: 208
aggguaagcu gaaccucuga u                                                21

<210> SEQ ID NO 209
<211> LENGTH: 21
<212> TYPE: RNA
<213> ORGANISM: Homo sapiens

<400> SEQUENCE: 209
gcuaguccug acucagccag u                                                21

<210> SEQ ID NO 210
<211> LENGTH: 21
<212> TYPE: RNA
<213> ORGANISM: Homo sapiens

<400> SEQUENCE: 210
aaaacgguga gauuuuguuu u                                                21

<210> SEQ ID NO 211
<211> LENGTH: 21
<212> TYPE: RNA
<213> ORGANISM: Homo sapiens

<400> SEQUENCE: 211
aacaggugac ugguuagaca a                                                21

<210> SEQ ID NO 212
<211> LENGTH: 22
<212> TYPE: RNA
<213> ORGANISM: Homo sapiens

<400> SEQUENCE: 212
gaaaucaagc gugggugaga cc                                               22

<210> SEQ ID NO 213
<211> LENGTH: 21
<212> TYPE: RNA
```

<213> ORGANISM: Homo sapiens

<400> SEQUENCE: 213
gcgacccaua cuugguuuca g                                             21

<210> SEQ ID NO 214
<211> LENGTH: 21
<212> TYPE: RNA
<213> ORGANISM: Homo sapiens

<400> SEQUENCE: 214
gcgacccacu cuugguuucc a                                             21

<210> SEQ ID NO 215
<211> LENGTH: 22
<212> TYPE: RNA
<213> ORGANISM: Homo sapiens

<400> SEQUENCE: 215
ugucuuacuc ccucaggcac au                                            22

<210> SEQ ID NO 216
<211> LENGTH: 23
<212> TYPE: RNA
<213> ORGANISM: Homo sapiens

<400> SEQUENCE: 216
agugccugag ggaguaagag ccc                                           23

<210> SEQ ID NO 217
<211> LENGTH: 21
<212> TYPE: RNA
<213> ORGANISM: Homo sapiens

<400> SEQUENCE: 217
ugacaacuau ggaugagcuc u                                             21

<210> SEQ ID NO 218
<211> LENGTH: 22
<212> TYPE: RNA
<213> ORGANISM: Homo sapiens

<400> SEQUENCE: 218
gcuggugcaa aaguaauggc gg                                            22

<210> SEQ ID NO 219
<211> LENGTH: 22
<212> TYPE: RNA
<213> ORGANISM: Homo sapiens

<400> SEQUENCE: 219
uagcaaaaac ugcaguuacu uu                                            22

<210> SEQ ID NO 220
<211> LENGTH: 22
<212> TYPE: RNA
<213> ORGANISM: Homo sapiens

<400> SEQUENCE: 220
ccaaaacugc aguuacuuuu gc                                            22

<210> SEQ ID NO 221
<211> LENGTH: 22

<212> TYPE: RNA
<213> ORGANISM: Homo sapiens

<400> SEQUENCE: 221
caaaaguaau uguggauuuu gu                                          22

<210> SEQ ID NO 222
<211> LENGTH: 21
<212> TYPE: RNA
<213> ORGANISM: Homo sapiens

<400> SEQUENCE: 222
caaagguauu ugggguuuuu g                                           21

<210> SEQ ID NO 223
<211> LENGTH: 22
<212> TYPE: RNA
<213> ORGANISM: Homo sapiens

<400> SEQUENCE: 223
aaaaguauuu gcggguuuug uc                                          22

<210> SEQ ID NO 224
<211> LENGTH: 22
<212> TYPE: RNA
<213> ORGANISM: Homo sapiens

<400> SEQUENCE: 224
aaaaguacuu gcggauuuug cu                                          22

<210> SEQ ID NO 225
<211> LENGTH: 22
<212> TYPE: RNA
<213> ORGANISM: Homo sapiens

<400> SEQUENCE: 225
aaaaguaauu gcggucuuug gu                                          22

<210> SEQ ID NO 226
<211> LENGTH: 22
<212> TYPE: RNA
<213> ORGANISM: Homo sapiens

<400> SEQUENCE: 226
aaaaguaauu gcggauuuug cc                                          22

<210> SEQ ID NO 227
<211> LENGTH: 22
<212> TYPE: RNA
<213> ORGANISM: Homo sapiens

<400> SEQUENCE: 227
aaaaguaauc gcgguuuug uc                                           22

<210> SEQ ID NO 228
<211> LENGTH: 22
<212> TYPE: RNA
<213> ORGANISM: Homo sapiens

<400> SEQUENCE: 228
aaaacuguaa uuacuuuugu ac                                          22

<210> SEQ ID NO 229

```
<211> LENGTH: 19
<212> TYPE: RNA
<213> ORGANISM: Homo sapiens

<400> SEQUENCE: 229
aaaaacugua auuacuuuu                                                19

<210> SEQ ID NO 230
<211> LENGTH: 22
<212> TYPE: RNA
<213> ORGANISM: Homo sapiens

<400> SEQUENCE: 230
aaaaacugag acuacuuuug ca                                            22

<210> SEQ ID NO 231
<211> LENGTH: 22
<212> TYPE: RNA
<213> ORGANISM: Homo sapiens

<400> SEQUENCE: 231
aaaaguaauu gugguuuuug cc                                            22

<210> SEQ ID NO 232
<211> LENGTH: 22
<212> TYPE: RNA
<213> ORGANISM: Homo sapiens

<400> SEQUENCE: 232
caaaaaccac aguuucuuuu gc                                            22

<210> SEQ ID NO 233
<211> LENGTH: 22
<212> TYPE: RNA
<213> ORGANISM: Homo sapiens

<400> SEQUENCE: 233
aaaaguaauu gcgguuuuug cc                                            22

<210> SEQ ID NO 234
<211> LENGTH: 22
<212> TYPE: RNA
<213> ORGANISM: Homo sapiens

<400> SEQUENCE: 234
caaaaaucuc aauuacuuuu gc                                            22

<210> SEQ ID NO 235
<211> LENGTH: 22
<212> TYPE: RNA
<213> ORGANISM: Homo sapiens

<400> SEQUENCE: 235
aaaaguaauu gugguuuugg cc                                            22

<210> SEQ ID NO 236
<211> LENGTH: 22
<212> TYPE: RNA
<213> ORGANISM: Homo sapiens

<400> SEQUENCE: 236
caagaaccuc aguugcuuuu gu                                            22
```

```
<210> SEQ ID NO 237
<211> LENGTH: 22
<212> TYPE: RNA
<213> ORGANISM: Homo sapiens

<400> SEQUENCE: 237
aaaaguaauu gcgaguuuua cc                                              22

<210> SEQ ID NO 238
<211> LENGTH: 22
<212> TYPE: RNA
<213> ORGANISM: Homo sapiens

<400> SEQUENCE: 238
caaaacuggc aauuacuuuu gc                                              22

<210> SEQ ID NO 239
<211> LENGTH: 22
<212> TYPE: RNA
<213> ORGANISM: Homo sapiens

<400> SEQUENCE: 239
ucaguaaaug uuuauuagau ga                                              22

<210> SEQ ID NO 240
<211> LENGTH: 22
<212> TYPE: RNA
<213> ORGANISM: Homo sapiens

<400> SEQUENCE: 240
ucagcaaaca uuuauugugu gc                                              22

<210> SEQ ID NO 241
<211> LENGTH: 22
<212> TYPE: RNA
<213> ORGANISM: Homo sapiens

<400> SEQUENCE: 241
auucugcauu uuuagcaagu uc                                              22

<210> SEQ ID NO 242
<211> LENGTH: 22
<212> TYPE: RNA
<213> ORGANISM: Homo sapiens

<400> SEQUENCE: 242
aaacauucgc ggugcacuuc uu                                              22

<210> SEQ ID NO 243
<211> LENGTH: 23
<212> TYPE: RNA
<213> ORGANISM: Homo sapiens

<400> SEQUENCE: 243
ucggggauca ucaugucacg aga                                             23

<210> SEQ ID NO 244
<211> LENGTH: 22
<212> TYPE: RNA
<213> ORGANISM: Homo sapiens

<400> SEQUENCE: 244
ugugacagau ugauaacuga aa                                              22
```

```
<210> SEQ ID NO 245
<211> LENGTH: 25
<212> TYPE: RNA
<213> ORGANISM: Homo sapiens

<400> SEQUENCE: 245
aaaggauucu gcugucgguc ccacu                                              25

<210> SEQ ID NO 246
<211> LENGTH: 22
<212> TYPE: RNA
<213> ORGANISM: Homo sapiens

<400> SEQUENCE: 246
uggugggcac agaaucugga cu                                                 22

<210> SEQ ID NO 247
<211> LENGTH: 22
<212> TYPE: RNA
<213> ORGANISM: Homo sapiens

<400> SEQUENCE: 247
ggagaaauua uccuuggugu gu                                                 22

<210> SEQ ID NO 248
<211> LENGTH: 22
<212> TYPE: RNA
<213> ORGANISM: Homo sapiens

<400> SEQUENCE: 248
caugccuuga guguaggacc gu                                                 22

<210> SEQ ID NO 249
<211> LENGTH: 22
<212> TYPE: RNA
<213> ORGANISM: Homo sapiens

<400> SEQUENCE: 249
ccucccacac ccaaggcuug ca                                                 22

<210> SEQ ID NO 250
<211> LENGTH: 20
<212> TYPE: RNA
<213> ORGANISM: Homo sapiens

<400> SEQUENCE: 250
cugcaaaggg aagcccuuuc                                                    20

<210> SEQ ID NO 251
<211> LENGTH: 22
<212> TYPE: RNA
<213> ORGANISM: Homo sapiens

<400> SEQUENCE: 251
gaaagugcuu ccuuuuagag gc                                                 22

<210> SEQ ID NO 252
<211> LENGTH: 23
<212> TYPE: RNA
<213> ORGANISM: Homo sapiens

<400> SEQUENCE: 252
cucuugaggg aagcacuuuc ugu                                                23
```

<210> SEQ ID NO 253
<211> LENGTH: 22
<212> TYPE: RNA
<213> ORGANISM: Homo sapiens

<400> SEQUENCE: 253
cucuagaggg aagcacuuuc ug                                              22

<210> SEQ ID NO 254
<211> LENGTH: 21
<212> TYPE: RNA
<213> ORGANISM: Homo sapiens

<400> SEQUENCE: 254
cuccagaggg augcacuuuc u                                               21

<210> SEQ ID NO 255
<211> LENGTH: 22
<212> TYPE: RNA
<213> ORGANISM: Homo sapiens

<400> SEQUENCE: 255
gaaggcgcuu cccuuuagag cg                                              22

<210> SEQ ID NO 256
<211> LENGTH: 22
<212> TYPE: RNA
<213> ORGANISM: Homo sapiens

<400> SEQUENCE: 256
cuacaaaggg aagcacuuuc uc                                              22

<210> SEQ ID NO 257
<211> LENGTH: 21
<212> TYPE: RNA
<213> ORGANISM: Homo sapiens

<400> SEQUENCE: 257
gaaggcgcuu cccuuuggag u                                               21

<210> SEQ ID NO 258
<211> LENGTH: 22
<212> TYPE: RNA
<213> ORGANISM: Homo sapiens

<400> SEQUENCE: 258
cucuagaggg aagcgcuuuc ug                                              22

<210> SEQ ID NO 259
<211> LENGTH: 23
<212> TYPE: RNA
<213> ORGANISM: Homo sapiens

<400> SEQUENCE: 259
gaacgcgcuu cccuauagag ggu                                             23

<210> SEQ ID NO 260
<211> LENGTH: 22
<212> TYPE: RNA
<213> ORGANISM: Homo sapiens

<400> SEQUENCE: 260

```
cucuagaggg aagcgcuuuc ug                                              22

<210> SEQ ID NO 261
<211> LENGTH: 22
<212> TYPE: RNA
<213> ORGANISM: Homo sapiens

<400> SEQUENCE: 261
aaaaugguuc ccuuuagagu gu                                              22

<210> SEQ ID NO 262
<211> LENGTH: 22
<212> TYPE: RNA
<213> ORGANISM: Homo sapiens

<400> SEQUENCE: 262
aacgcacuuc ccuuuagagu gu                                              22

<210> SEQ ID NO 263
<211> LENGTH: 22
<212> TYPE: RNA
<213> ORGANISM: Homo sapiens

<400> SEQUENCE: 263
acaaagugcu ucccuuuaga gu                                              22

<210> SEQ ID NO 264
<211> LENGTH: 24
<212> TYPE: RNA
<213> ORGANISM: Homo sapiens

<400> SEQUENCE: 264
acaaagugcu ucccuuuaga gugu                                            24

<210> SEQ ID NO 265
<211> LENGTH: 22
<212> TYPE: RNA
<213> ORGANISM: Homo sapiens

<400> SEQUENCE: 265
aagugcuucc uuuuagaggg uu                                              22

<210> SEQ ID NO 266
<211> LENGTH: 21
<212> TYPE: RNA
<213> ORGANISM: Homo sapiens

<400> SEQUENCE: 266
aaagugcuuc cuuuuugagg g                                               21

<210> SEQ ID NO 267
<211> LENGTH: 20
<212> TYPE: RNA
<213> ORGANISM: Homo sapiens

<400> SEQUENCE: 267
cuacaaaggg aagcccuuuc                                                 20

<210> SEQ ID NO 268
<211> LENGTH: 22
<212> TYPE: RNA
<213> ORGANISM: Homo sapiens

<400> SEQUENCE: 268
```

```
aaagugcuuc ucuuggugg gu                                                22

<210> SEQ ID NO 269
<211> LENGTH: 22
<212> TYPE: RNA
<213> ORGANISM: Homo sapiens

<400> SEQUENCE: 269
cucuagaggg aagcacuuuc ug                                               22

<210> SEQ ID NO 270
<211> LENGTH: 22
<212> TYPE: RNA
<213> ORGANISM: Homo sapiens

<400> SEQUENCE: 270
aaagugcuuc cuuuuagagg gu                                               22

<210> SEQ ID NO 271
<211> LENGTH: 21
<212> TYPE: RNA
<213> ORGANISM: Homo sapiens

<400> SEQUENCE: 271
aaagugcuuc cuuuuagagg g                                                21

<210> SEQ ID NO 272
<211> LENGTH: 21
<212> TYPE: RNA
<213> ORGANISM: Homo sapiens

<400> SEQUENCE: 272
cuccagaggg aaguacuuuc u                                                21

<210> SEQ ID NO 273
<211> LENGTH: 22
<212> TYPE: RNA
<213> ORGANISM: Homo sapiens

<400> SEQUENCE: 273
aaagugcuuc ccuuuggacu gu                                               22

<210> SEQ ID NO 274
<211> LENGTH: 22
<212> TYPE: RNA
<213> ORGANISM: Homo sapiens

<400> SEQUENCE: 274
uucuccaaaa gggagcacuu uc                                               22

<210> SEQ ID NO 275
<211> LENGTH: 22
<212> TYPE: RNA
<213> ORGANISM: Homo sapiens

<400> SEQUENCE: 275
aagugccucc uuuuagagug uu                                               22

<210> SEQ ID NO 276
<211> LENGTH: 22
<212> TYPE: RNA
<213> ORGANISM: Homo sapiens
```

```
<400> SEQUENCE: 276
caaagugccu cccuuuagag ug                                              22

<210> SEQ ID NO 277
<211> LENGTH: 22
<212> TYPE: RNA
<213> ORGANISM: Homo sapiens

<400> SEQUENCE: 277
cucuagaggg aagcgcuuuc ug                                              22

<210> SEQ ID NO 278
<211> LENGTH: 22
<212> TYPE: RNA
<213> ORGANISM: Homo sapiens

<400> SEQUENCE: 278
aaagugcauc uuuuuagagg au                                              22

<210> SEQ ID NO 279
<211> LENGTH: 22
<212> TYPE: RNA
<213> ORGANISM: Homo sapiens

<400> SEQUENCE: 279
cucuagaggg aagcgcuuuc ug                                              22

<210> SEQ ID NO 280
<211> LENGTH: 22
<212> TYPE: RNA
<213> ORGANISM: Homo sapiens

<400> SEQUENCE: 280
aaagugcauc cuuuuagagg uu                                              22

<210> SEQ ID NO 281
<211> LENGTH: 22
<212> TYPE: RNA
<213> ORGANISM: Homo sapiens

<400> SEQUENCE: 281
cucuagaggg aagcgcuuuc ug                                              22

<210> SEQ ID NO 282
<211> LENGTH: 22
<212> TYPE: RNA
<213> ORGANISM: Homo sapiens

<400> SEQUENCE: 282
aaagugcauc cuuuuagagu gu                                              22

<210> SEQ ID NO 283
<211> LENGTH: 22
<212> TYPE: RNA
<213> ORGANISM: Homo sapiens

<400> SEQUENCE: 283
cucuagaggg aagcacuuuc uc                                              22

<210> SEQ ID NO 284
<211> LENGTH: 21
<212> TYPE: RNA
<213> ORGANISM: Homo sapiens
```

```
<400> SEQUENCE: 284
gaaagcgcuu cucuuuagag g                                    21

<210> SEQ ID NO 285
<211> LENGTH: 22
<212> TYPE: RNA
<213> ORGANISM: Homo sapiens

<400> SEQUENCE: 285
cucuagaggg aagcgcuuuc ug                                   22

<210> SEQ ID NO 286
<211> LENGTH: 21
<212> TYPE: RNA
<213> ORGANISM: Homo sapiens

<400> SEQUENCE: 286
aaagcgcuuc ccuucagagu g                                    21

<210> SEQ ID NO 287
<211> LENGTH: 22
<212> TYPE: RNA
<213> ORGANISM: Homo sapiens

<400> SEQUENCE: 287
cucuagaggg aagcacuuuc ug                                   22

<210> SEQ ID NO 288
<211> LENGTH: 21
<212> TYPE: RNA
<213> ORGANISM: Homo sapiens

<400> SEQUENCE: 288
caaagcgcuu cccuuggag c                                     21

<210> SEQ ID NO 289
<211> LENGTH: 23
<212> TYPE: RNA
<213> ORGANISM: Homo sapiens

<400> SEQUENCE: 289
ucucuggagg gaagcacuuu cug                                  23

<210> SEQ ID NO 290
<211> LENGTH: 23
<212> TYPE: RNA
<213> ORGANISM: Homo sapiens

<400> SEQUENCE: 290
caaagcgcuu cucuuuagag ugu                                  23

<210> SEQ ID NO 291
<211> LENGTH: 22
<212> TYPE: RNA
<213> ORGANISM: Homo sapiens

<400> SEQUENCE: 291
caaagcgcuc cccuuuagag gu                                   22

<210> SEQ ID NO 292
<211> LENGTH: 20
<212> TYPE: RNA
```

<213> ORGANISM: Homo sapiens

<400> SEQUENCE: 292
cugcaaaggg aagcccuuuc                                        20

<210> SEQ ID NO 293
<211> LENGTH: 22
<212> TYPE: RNA
<213> ORGANISM: Homo sapiens

<400> SEQUENCE: 293
gaaagcgcuu cccuuugcug ga                                     22

<210> SEQ ID NO 294
<211> LENGTH: 22
<212> TYPE: RNA
<213> ORGANISM: Homo sapiens

<400> SEQUENCE: 294
aucgugcauc cuuuuagagu gu                                     22

<210> SEQ ID NO 295
<211> LENGTH: 22
<212> TYPE: RNA
<213> ORGANISM: Homo sapiens

<400> SEQUENCE: 295
ucgugcaucc cuuuagagug uu                                     22

<210> SEQ ID NO 296
<211> LENGTH: 22
<212> TYPE: RNA
<213> ORGANISM: Homo sapiens

<400> SEQUENCE: 296
aucgugcauc ccuuuagagu gu                                     22

<210> SEQ ID NO 297
<211> LENGTH: 22
<212> TYPE: RNA
<213> ORGANISM: Homo sapiens

<400> SEQUENCE: 297
ccucuagaug gaagcacugu cu                                     22

<210> SEQ ID NO 298
<211> LENGTH: 18
<212> TYPE: RNA
<213> ORGANISM: Homo sapiens

<400> SEQUENCE: 298
ugcuuccuuu cagagggu                                          18

<210> SEQ ID NO 299
<211> LENGTH: 22
<212> TYPE: RNA
<213> ORGANISM: Homo sapiens

<400> SEQUENCE: 299
aucuggaggu aagaagcacu uu                                     22

<210> SEQ ID NO 300
<211> LENGTH: 23

```
<212> TYPE: RNA
<213> ORGANISM: Homo sapiens

<400> SEQUENCE: 300
uucucgagga aagaagcacu uuc                                          23

<210> SEQ ID NO 301
<211> LENGTH: 18
<212> TYPE: RNA
<213> ORGANISM: Homo sapiens

<400> SEQUENCE: 301
ugcuuccuuu cagagggu                                                18

<210> SEQ ID NO 302
<211> LENGTH: 24
<212> TYPE: RNA
<213> ORGANISM: Homo sapiens

<400> SEQUENCE: 302
uucuccaaaa gaaagcacuu ucug                                         24

<210> SEQ ID NO 303
<211> LENGTH: 22
<212> TYPE: RNA
<213> ORGANISM: Homo sapiens

<400> SEQUENCE: 303
gagugccuuc uuuuggagcg uu                                           22

<210> SEQ ID NO 304
<211> LENGTH: 21
<212> TYPE: RNA
<213> ORGANISM: Homo sapiens

<400> SEQUENCE: 304
auugacacuu cugugaguag a                                            21

<210> SEQ ID NO 305
<211> LENGTH: 22
<212> TYPE: RNA
<213> ORGANISM: Homo sapiens

<400> SEQUENCE: 305
uucucaagga ggugucguuu au                                           22

<210> SEQ ID NO 306
<211> LENGTH: 22
<212> TYPE: RNA
<213> ORGANISM: Homo sapiens

<400> SEQUENCE: 306
uucacaagga ggugucauuu au                                           22

<210> SEQ ID NO 307
<211> LENGTH: 18
<212> TYPE: RNA
<213> ORGANISM: Homo sapiens

<400> SEQUENCE: 307
uucacaggga ggugucau                                                18

<210> SEQ ID NO 308
```

```
<211> LENGTH: 23
<212> TYPE: RNA
<213> ORGANISM: Homo sapiens

<400> SEQUENCE: 308
uaaauuucac cuuucugaga agg                                              23

<210> SEQ ID NO 309
<211> LENGTH: 23
<212> TYPE: RNA
<213> ORGANISM: Homo sapiens

<400> SEQUENCE: 309
cacucagccu ugagggcacu uuc                                              23

<210> SEQ ID NO 310
<211> LENGTH: 22
<212> TYPE: RNA
<213> ORGANISM: Homo sapiens

<400> SEQUENCE: 310
aagugcuguc auagcugagg uc                                               22

<210> SEQ ID NO 311
<211> LENGTH: 21
<212> TYPE: RNA
<213> ORGANISM: Homo sapiens

<400> SEQUENCE: 311
gugucuuuug cucugcaguc a                                                21

<210> SEQ ID NO 312
<211> LENGTH: 22
<212> TYPE: RNA
<213> ORGANISM: Homo sapiens

<400> SEQUENCE: 312
uacucaggag aguggcaauc ac                                               22

<210> SEQ ID NO 313
<211> LENGTH: 21
<212> TYPE: RNA
<213> ORGANISM: Homo sapiens

<400> SEQUENCE: 313
uacugcagac aguggcaauc a                                                21

<210> SEQ ID NO 314
<211> LENGTH: 22
<212> TYPE: RNA
<213> ORGANISM: Homo sapiens

<400> SEQUENCE: 314
ugauugguac gucugugggu ag                                               22

<210> SEQ ID NO 315
<211> LENGTH: 22
<212> TYPE: RNA
<213> ORGANISM: Homo sapiens

<400> SEQUENCE: 315
uacugcagac guggcaauca ug                                               22
```

```
<210> SEQ ID NO 316
<211> LENGTH: 23
<212> TYPE: RNA
<213> ORGANISM: Homo sapiens

<400> SEQUENCE: 316
uacuccagag ggcgucacuc aug                                              23

<210> SEQ ID NO 317
<211> LENGTH: 23
<212> TYPE: RNA
<213> ORGANISM: Homo sapiens

<400> SEQUENCE: 317
ugauuguagc cuuuuggagu aga                                              23

<210> SEQ ID NO 318
<211> LENGTH: 21
<212> TYPE: RNA
<213> ORGANISM: Homo sapiens

<400> SEQUENCE: 318
uuuugcaccu uuuggaguga a                                                21

<210> SEQ ID NO 319
<211> LENGTH: 21
<212> TYPE: RNA
<213> ORGANISM: Homo sapiens

<400> SEQUENCE: 319
uaaggcaccc uucugaguag a                                                21

<210> SEQ ID NO 320
<211> LENGTH: 22
<212> TYPE: RNA
<213> ORGANISM: Homo sapiens

<400> SEQUENCE: 320
gggagccagg aaguauugau gu                                               22

<210> SEQ ID NO 321
<211> LENGTH: 22
<212> TYPE: RNA
<213> ORGANISM: Homo sapiens

<400> SEQUENCE: 321
cgucaacacu ugcugguuuc cu                                               22

<210> SEQ ID NO 322
<211> LENGTH: 22
<212> TYPE: RNA
<213> ORGANISM: Homo sapiens

<400> SEQUENCE: 322
agacccuggu cugcacucua uc                                               22

<210> SEQ ID NO 323
<211> LENGTH: 23
<212> TYPE: RNA
<213> ORGANISM: Homo sapiens

<400> SEQUENCE: 323
uagcagcggg aacaguucug cag                                              23
```

```
<210> SEQ ID NO 324
<211> LENGTH: 21
<212> TYPE: RNA
<213> ORGANISM: Homo sapiens

<400> SEQUENCE: 324
auccuugcua ucugggugcu a                                              21

<210> SEQ ID NO 325
<211> LENGTH: 22
<212> TYPE: RNA
<213> ORGANISM: Homo sapiens

<400> SEQUENCE: 325
aaugcaccug ggcaaggauu ca                                             22

<210> SEQ ID NO 326
<211> LENGTH: 22
<212> TYPE: RNA
<213> ORGANISM: Homo sapiens

<400> SEQUENCE: 326
aauccuuugu cccuggguga ga                                             22

<210> SEQ ID NO 327
<211> LENGTH: 22
<212> TYPE: RNA
<213> ORGANISM: Homo sapiens

<400> SEQUENCE: 327
aaugcacccg ggcaaggauu cu                                             22

<210> SEQ ID NO 328
<211> LENGTH: 22
<212> TYPE: RNA
<213> ORGANISM: Homo sapiens

<400> SEQUENCE: 328
augcaccugg gcaaggauuc ug                                             22

<210> SEQ ID NO 329
<211> LENGTH: 23
<212> TYPE: RNA
<213> ORGANISM: Homo sapiens

<400> SEQUENCE: 329
uaauccuugc uaccuggguug aga                                           23

<210> SEQ ID NO 330
<211> LENGTH: 21
<212> TYPE: RNA
<213> ORGANISM: Homo sapiens

<400> SEQUENCE: 330
uuaagacuug cagugauguu u                                              21

<210> SEQ ID NO 331
<211> LENGTH: 22
<212> TYPE: RNA
<213> ORGANISM: Homo sapiens

<400> SEQUENCE: 331
aacaucacag caagucugug cu                                             22
```

<210> SEQ ID NO 332
<211> LENGTH: 23
<212> TYPE: RNA
<213> ORGANISM: Homo sapiens

<400> SEQUENCE: 332
uuucaagcca gggggcguuu uuc                                                23

<210> SEQ ID NO 333
<211> LENGTH: 22
<212> TYPE: RNA
<213> ORGANISM: Homo sapiens

<400> SEQUENCE: 333
caaaccacac uguggguuua ga                                                 22

<210> SEQ ID NO 334
<211> LENGTH: 21
<212> TYPE: RNA
<213> ORGANISM: Homo sapiens

<400> SEQUENCE: 334
cagcagcaca cuguggguug u                                                  21

<210> SEQ ID NO 335
<211> LENGTH: 22
<212> TYPE: RNA
<213> ORGANISM: Homo sapiens

<400> SEQUENCE: 335
ugaguauuac auggccaauc uc                                                 22

<210> SEQ ID NO 336
<211> LENGTH: 22
<212> TYPE: RNA
<213> ORGANISM: Homo sapiens

<400> SEQUENCE: 336
aaacaaacau ggugcacuuc uu                                                 22

<210> SEQ ID NO 337
<211> LENGTH: 22
<212> TYPE: RNA
<213> ORGANISM: Homo sapiens

<400> SEQUENCE: 337
ugaaacauac acgggaaacc uc                                                 22

<210> SEQ ID NO 338
<211> LENGTH: 22
<212> TYPE: RNA
<213> ORGANISM: Homo sapiens

<400> SEQUENCE: 338
uuguacaugg uaggcuuuca uu                                                 22

<210> SEQ ID NO 339
<211> LENGTH: 22
<212> TYPE: RNA
<213> ORGANISM: Homo sapiens

<400> SEQUENCE: 339
ugaaggucua cugugugcca gg                                       22

<210> SEQ ID NO 340
<211> LENGTH: 23
<212> TYPE: RNA
<213> ORGANISM: Homo sapiens

<400> SEQUENCE: 340
aggaccugcg ggacaagauu cuu                                      23

<210> SEQ ID NO 341
<211> LENGTH: 22
<212> TYPE: RNA
<213> ORGANISM: Homo sapiens

<400> SEQUENCE: 341 agugggaac ccuuccauga gg                                        22

<210> SEQ ID NO 342
<211> LENGTH: 22
<212> TYPE: RNA
<213> ORGANISM: Homo sapiens

<400> SEQUENCE: 342
cuuaugcaag auucccuucu ac                                       22

<210> SEQ ID NO 343
<211> LENGTH: 20
<212> TYPE: RNA
<213> ORGANISM: Homo sapiens

<400> SEQUENCE: 343
ccauggaucu ccaggugggu                                          20

<210> SEQ ID NO 344
<211> LENGTH: 22
<212> TYPE: RNA
<213> ORGANISM: Homo sapiens

<400> SEQUENCE: 344
caaccuggag gacuccaugc ug                                       22

<210> SEQ ID NO 345
<211> LENGTH: 22
<212> TYPE: RNA
<213> ORGANISM: Homo sapiens

<400> SEQUENCE: 345
gugacaucac auauacggca gc                                       22

<210> SEQ ID NO 346
<211> LENGTH: 21
<212> TYPE: RNA
<213> ORGANISM: Homo sapiens

<400> SEQUENCE: 346
cccagauaau ggcacucuca a                                        21

<210> SEQ ID NO 347
<211> LENGTH: 21
<212> TYPE: RNA
<213> ORGANISM: Homo sapiens

<400> SEQUENCE: 347

-continued

| | |
|---|---|
| uugaaaggcu auuucuuggu c | 21 |

<210> SEQ ID NO 348
<211> LENGTH: 22
<212> TYPE: RNA
<213> ORGANISM: Homo sapiens

<400> SEQUENCE: 348

| | |
|---|---|
| aaucguacag ggucauccac uu | 22 |

<210> SEQ ID NO 349
<211> LENGTH: 22
<212> TYPE: RNA
<213> ORGANISM: Homo sapiens

<400> SEQUENCE: 349

| | |
|---|---|
| aaucauacag ggacauccag uu | 22 |

<210> SEQ ID NO 350
<211> LENGTH: 22
<212> TYPE: RNA
<213> ORGANISM: Homo sapiens

<400> SEQUENCE: 350

| | |
|---|---|
| uccuguacug agcugccccg ag | 22 |

<210> SEQ ID NO 351
<211> LENGTH: 21
<212> TYPE: RNA
<213> ORGANISM: Homo sapiens

<400> SEQUENCE: 351

| | |
|---|---|
| cggggcagcu caguacagga u | 21 |

<210> SEQ ID NO 352
<211> LENGTH: 22
<212> TYPE: RNA
<213> ORGANISM: Homo sapiens

<400> SEQUENCE: 352

| | |
|---|---|
| agaggcuggc cgugaugaau uc | 22 |

<210> SEQ ID NO 353
<211> LENGTH: 22
<212> TYPE: RNA
<213> ORGANISM: Homo sapiens

<400> SEQUENCE: 353

| | |
|---|---|
| gucauacacg gcucuccucu cu | 22 |

<210> SEQ ID NO 354
<211> LENGTH: 22
<212> TYPE: RNA
<213> ORGANISM: Homo sapiens

<400> SEQUENCE: 354

| | |
|---|---|
| ucaggcucag uccccucccg au | 22 |

<210> SEQ ID NO 355
<211> LENGTH: 22
<212> TYPE: RNA
<213> ORGANISM: Homo sapiens

```
<400> SEQUENCE: 355
aagacgggag gaaagaaggg ag                                              22

<210> SEQ ID NO 356
<211> LENGTH: 21
<212> TYPE: RNA
<213> ORGANISM: Homo sapiens

<400> SEQUENCE: 356
ucacuccucu ccucccgucu u                                               21

<210> SEQ ID NO 357
<211> LENGTH: 22
<212> TYPE: RNA
<213> ORGANISM: Homo sapiens

<400> SEQUENCE: 357
uaugugccuu uggacuacau cg                                              22

<210> SEQ ID NO 358
<211> LENGTH: 21
<212> TYPE: RNA
<213> ORGANISM: Homo sapiens

<400> SEQUENCE: 358 gcagccaug ggcauauaca c                                                21

<210> SEQ ID NO 359
<211> LENGTH: 22
<212> TYPE: RNA
<213> ORGANISM: Homo sapiens

<400> SEQUENCE: 359
acccuaucaa uauugucucu gc                                              22

<210> SEQ ID NO 360
<211> LENGTH: 23
<212> TYPE: RNA
<213> ORGANISM: Homo sapiens

<400> SEQUENCE: 360
uagugcaaua uugcuuauag ggu                                             23

<210> SEQ ID NO 361
<211> LENGTH: 23
<212> TYPE: RNA
<213> ORGANISM: Homo sapiens

<400> SEQUENCE: 361
agguuguccg uggugaguuc gca                                             23

<210> SEQ ID NO 362
<211> LENGTH: 22
<212> TYPE: RNA
<213> ORGANISM: Homo sapiens

<400> SEQUENCE: 362
cucaucugca aagaaguaag ug                                              22

<210> SEQ ID NO 363
<211> LENGTH: 22
<212> TYPE: RNA
<213> ORGANISM: Homo sapiens
```

```
<400> SEQUENCE: 363
aacuguuugc agaggaaacu ga                                          22

<210> SEQ ID NO 364
<211> LENGTH: 22
<212> TYPE: RNA
<213> ORGANISM: Homo sapiens

<400> SEQUENCE: 364
aaaccguuac cauuacugag uu                                          22

<210> SEQ ID NO 365
<211> LENGTH: 22
<212> TYPE: RNA
<213> ORGANISM: Homo sapiens

<400> SEQUENCE: 365
uuuugcaaua uguccugaa ua                                           22

<210> SEQ ID NO 366
<211> LENGTH: 22
<212> TYPE: RNA
<213> ORGANISM: Homo sapiens

<400> SEQUENCE: 366
uugggaucau uuugcaucca ua                                          22

<210> SEQ ID NO 367
<211> LENGTH: 22
<212> TYPE: RNA
<213> ORGANISM: Homo sapiens

<400> SEQUENCE: 367
uuuugcgaug uguccuaau au                                           22

<210> SEQ ID NO 368
<211> LENGTH: 23
<212> TYPE: RNA
<213> ORGANISM: Homo sapiens

<400> SEQUENCE: 368
uugcuaguug cacuccucuc ugu                                         23

<210> SEQ ID NO 369
<211> LENGTH: 25
<212> TYPE: RNA
<213> ORGANISM: Homo sapiens

<400> SEQUENCE: 369
uaggcagugu auugcuagcg gcugu                                       25

<210> SEQ ID NO 370
<211> LENGTH: 22
<212> TYPE: RNA
<213> ORGANISM: Homo sapiens

<400> SEQUENCE: 370
cagccacaac uacccugcca cu                                          22

<210> SEQ ID NO 371
<211> LENGTH: 22
<212> TYPE: RNA
```

<213> ORGANISM: Homo sapiens

<400> SEQUENCE: 371
aggcagugua uuguuagcug gc					22

<210> SEQ ID NO 372
<211> LENGTH: 22
<212> TYPE: RNA
<213> ORGANISM: Homo sapiens

<400> SEQUENCE: 372
uggcagugua uuguuagcug gu					22

<210> SEQ ID NO 373
<211> LENGTH: 22
<212> TYPE: RNA
<213> ORGANISM: Homo sapiens

<400> SEQUENCE: 373
uugcauaugu aggaugucccc au					22

<210> SEQ ID NO 374
<211> LENGTH: 22
<212> TYPE: RNA
<213> ORGANISM: Homo sapiens

<400> SEQUENCE: 374
aucaugaugg gcuccucggu gu					22

<210> SEQ ID NO 375
<211> LENGTH: 21
<212> TYPE: RNA
<213> ORGANISM: Homo sapiens

<400> SEQUENCE: 375
cuggauggcu ccuccauguc u					21

<210> SEQ ID NO 376
<211> LENGTH: 23
<212> TYPE: RNA
<213> ORGANISM: Homo sapiens

<400> SEQUENCE: 376
ucuuggagua ggucauuggg ugg					23

<210> SEQ ID NO 377
<211> LENGTH: 22
<212> TYPE: RNA
<213> ORGANISM: Homo sapiens

<400> SEQUENCE: 377
caggucgucu ugcagggcuu cu					22

<210> SEQ ID NO 378
<211> LENGTH: 21
<212> TYPE: RNA
<213> ORGANISM: Homo sapiens

<400> SEQUENCE: 378
ugucuugcag gccgucaugc a					21

<210> SEQ ID NO 379
<211> LENGTH: 22

<212> TYPE: RNA
<213> ORGANISM: Homo sapiens

<400> SEQUENCE: 379
uaauacuguc ugguaaaacc gu                                    22

<210> SEQ ID NO 380
<211> LENGTH: 22
<212> TYPE: RNA
<213> ORGANISM: Homo sapiens

<400> SEQUENCE: 380
aucgggaaug ucguguccgc cc                                    22

<210> SEQ ID NO 381
<211> LENGTH: 23
<212> TYPE: RNA
<213> ORGANISM: Homo sapiens

<400> SEQUENCE: 381
aaugacacga ucacucccgu uga                                   23

<210> SEQ ID NO 382
<211> LENGTH: 21
<212> TYPE: RNA
<213> ORGANISM: Homo sapiens

<400> SEQUENCE: 382
caaaacguga ggcgcugcua u                                     21

<210> SEQ ID NO 383
<211> LENGTH: 22
<212> TYPE: RNA
<213> ORGANISM: Homo sapiens

<400> SEQUENCE: 383
cagcagcaau ucauguuuug aa                                    22

<210> SEQ ID NO 384
<211> LENGTH: 23
<212> TYPE: RNA
<213> ORGANISM: Homo sapiens

<400> SEQUENCE: 384
ugaggggcag agagcgagac uuu                                   23

<210> SEQ ID NO 385
<211> LENGTH: 23
<212> TYPE: RNA
<213> ORGANISM: Homo sapiens

<400> SEQUENCE: 385
agcucggucu gaggccccuc agu                                   23

<210> SEQ ID NO 386
<211> LENGTH: 22
<212> TYPE: RNA
<213> ORGANISM: Homo sapiens

<400> SEQUENCE: 386
acuggacuua gggucagaag gc                                    22

<210> SEQ ID NO 387

```
<211> LENGTH: 23
<212> TYPE: RNA
<213> ORGANISM: Homo sapiens

<400> SEQUENCE: 387
aucaacagac auuaauuggg cgc                                              23

<210> SEQ ID NO 388
<211> LENGTH: 23
<212> TYPE: RNA
<213> ORGANISM: Homo sapiens

<400> SEQUENCE: 388
acuucaccug guccacuagc cgu                                              23

<210> SEQ ID NO 389
<211> LENGTH: 22
<212> TYPE: RNA
<213> ORGANISM: Homo sapiens

<400> SEQUENCE: 389
uauguaacac gguccacuaa cc                                               22

<210> SEQ ID NO 390
<211> LENGTH: 21
<212> TYPE: RNA
<213> ORGANISM: Homo sapiens

<400> SEQUENCE: 390
uaguagaccg uauagcguac g                                                21

<210> SEQ ID NO 391
<211> LENGTH: 21
<212> TYPE: RNA
<213> ORGANISM: Homo sapiens

<400> SEQUENCE: 391
aauauaacac agauggccug u                                                21

<210> SEQ ID NO 392
<211> LENGTH: 23
<212> TYPE: RNA
<213> ORGANISM: Homo sapiens

<400> SEQUENCE: 392
agguuacccg agcaacuuug cau                                              23

<210> SEQ ID NO 393
<211> LENGTH: 22
<212> TYPE: RNA
<213> ORGANISM: Homo sapiens

<400> SEQUENCE: 393
gaauguugcu cggugaaccc cu                                               22

<210> SEQ ID NO 394
<211> LENGTH: 20
<212> TYPE: RNA
<213> ORGANISM: Homo sapiens

<400> SEQUENCE: 394
auuccuagaa auuguucaua                                                  20
```

```
<210> SEQ ID NO 395
<211> LENGTH: 22
<212> TYPE: RNA
<213> ORGANISM: Homo sapiens

<400> SEQUENCE: 395
agaucagaag gugauugugg cu                                              22

<210> SEQ ID NO 396
<211> LENGTH: 22
<212> TYPE: RNA
<213> ORGANISM: Homo sapiens

<400> SEQUENCE: 396
gaaguuguuc gugguggauu cg                                              22

<210> SEQ ID NO 397
<211> LENGTH: 22
<212> TYPE: RNA
<213> ORGANISM: Homo sapiens

<400> SEQUENCE: 397
uauacaaggg caagcucucu gu                                              22

<210> SEQ ID NO 398
<211> LENGTH: 22
<212> TYPE: RNA
<213> ORGANISM: Homo sapiens

<400> SEQUENCE: 398
ugguugacca uagaacaugc gc                                              22

<210> SEQ ID NO 399
<211> LENGTH: 22
<212> TYPE: RNA
<213> ORGANISM: Homo sapiens

<400> SEQUENCE: 399
uauguaauau gguccacauc uu                                              22

<210> SEQ ID NO 400
<211> LENGTH: 22
<212> TYPE: RNA
<213> ORGANISM: Homo sapiens

<400> SEQUENCE: 400
uauguaacau gguccacuaa cu                                              22

<210> SEQ ID NO 401
<211> LENGTH: 21
<212> TYPE: RNA
<213> ORGANISM: Homo sapiens

<400> SEQUENCE: 401
ugguagacua uggaacguag g                                               21

<210> SEQ ID NO 402
<211> LENGTH: 22
<212> TYPE: RNA
<213> ORGANISM: Homo sapiens

<400> SEQUENCE: 402
cuccugacuc cagguccugu gu                                              22
```

```
<210> SEQ ID NO 403
<211> LENGTH: 21
<212> TYPE: RNA
<213> ORGANISM: Homo sapiens

<400> SEQUENCE: 403
acuggacuug gagucagaag g                                              21

<210> SEQ ID NO 404
<211> LENGTH: 22
<212> TYPE: RNA
<213> ORGANISM: Homo sapiens

<400> SEQUENCE: 404
agagguugcc cuuggugaau uc                                             22

<210> SEQ ID NO 405
<211> LENGTH: 22
<212> TYPE: RNA
<213> ORGANISM: Homo sapiens

<400> SEQUENCE: 405
aucacacaaa ggcaacuuuu gu                                             22

<210> SEQ ID NO 406
<211> LENGTH: 21
<212> TYPE: RNA
<213> ORGANISM: Homo sapiens

<400> SEQUENCE: 406
aacauagagg aaauuccacg u                                              21

<210> SEQ ID NO 407
<211> LENGTH: 22
<212> TYPE: RNA
<213> ORGANISM: Homo sapiens

<400> SEQUENCE: 407
aucauagagg aaaauccaug uu                                             22

<210> SEQ ID NO 408
<211> LENGTH: 22
<212> TYPE: RNA
<213> ORGANISM: Homo sapiens

<400> SEQUENCE: 408
guagauucuc cuucuaugag ua                                             22

<210> SEQ ID NO 409
<211> LENGTH: 21
<212> TYPE: RNA
<213> ORGANISM: Homo sapiens

<400> SEQUENCE: 409
aucauagagg aaaauccacg u                                              21

<210> SEQ ID NO 410
<211> LENGTH: 22
<212> TYPE: RNA
<213> ORGANISM: Homo sapiens

<400> SEQUENCE: 410
uuuguucguu cggcucgcgu ga                                             22
```

<210> SEQ ID NO 411
<211> LENGTH: 22
<212> TYPE: RNA
<213> ORGANISM: Homo sapiens

<400> SEQUENCE: 411
cuuagcaggu uguauuauca uu                                              22

<210> SEQ ID NO 412
<211> LENGTH: 22
<212> TYPE: RNA
<213> ORGANISM: Homo sapiens

<400> SEQUENCE: 412
auauaauaca accugcuaag ug                                              22

<210> SEQ ID NO 413
<211> LENGTH: 22
<212> TYPE: RNA
<213> ORGANISM: Homo sapiens

<400> SEQUENCE: 413
cuuaucagau uguauuguaa uu                                              22

<210> SEQ ID NO 414
<211> LENGTH: 22
<212> TYPE: RNA
<213> ORGANISM: Homo sapiens

<400> SEQUENCE: 414
uuauaauaca accugauaag ug                                              22

<210> SEQ ID NO 415
<211> LENGTH: 22
<212> TYPE: RNA
<213> ORGANISM: Homo sapiens

<400> SEQUENCE: 415
acucaaaaug ggggcgcuuu cc                                              22

<210> SEQ ID NO 416
<211> LENGTH: 23
<212> TYPE: RNA
<213> ORGANISM: Homo sapiens

<400> SEQUENCE: 416
gaagugcuuc gauuuugggg ugu                                             23

<210> SEQ ID NO 417
<211> LENGTH: 23
<212> TYPE: RNA
<213> ORGANISM: Homo sapiens

<400> SEQUENCE: 417
aaagugcugc gacauuugag cgu                                             23

<210> SEQ ID NO 418
<211> LENGTH: 20
<212> TYPE: RNA
<213> ORGANISM: Homo sapiens

<400> SEQUENCE: 418
acucaaacug uggggcacu                   20

<210> SEQ ID NO 419
<211> LENGTH: 23
<212> TYPE: RNA
<213> ORGANISM: Homo sapiens

<400> SEQUENCE: 419
aagugccgcc aucuuugag ugu               23

<210> SEQ ID NO 420
<211> LENGTH: 22
<212> TYPE: RNA
<213> ORGANISM: Homo sapiens

<400> SEQUENCE: 420
gccugcuggg guggaaccug gu               22

<210> SEQ ID NO 421
<211> LENGTH: 22
<212> TYPE: RNA
<213> ORGANISM: Homo sapiens

<400> SEQUENCE: 421
agaucgaccg uguuauauuc gc               22

<210> SEQ ID NO 422
<211> LENGTH: 21
<212> TYPE: RNA
<213> ORGANISM: Homo sapiens

<400> SEQUENCE: 422
aauaauacau gguugaucuu u                21

<210> SEQ ID NO 423
<211> LENGTH: 22
<212> TYPE: RNA
<213> ORGANISM: Homo sapiens

<400> SEQUENCE: 423
acuguugcua auaugcaacu cu               22

<210> SEQ ID NO 424
<211> LENGTH: 22
<212> TYPE: RNA
<213> ORGANISM: Homo sapiens

<400> SEQUENCE: 424
aauugcacuu uagcaauggu ga               22

<210> SEQ ID NO 425
<211> LENGTH: 22
<212> TYPE: RNA
<213> ORGANISM: Homo sapiens

<400> SEQUENCE: 425
agggacuuuc aggggcagcu gu               22

<210> SEQ ID NO 426
<211> LENGTH: 22
<212> TYPE: RNA
<213> ORGANISM: Homo sapiens

<400> SEQUENCE: 426
uaaugccccu aaaaauccuu au                                              22

<210> SEQ ID NO 427
<211> LENGTH: 22
<212> TYPE: RNA
<213> ORGANISM: Homo sapiens

<400> SEQUENCE: 427
cggguggauc acgaugcaau uu                                              22

<210> SEQ ID NO 428
<211> LENGTH: 22
<212> TYPE: RNA
<213> ORGANISM: Homo sapiens

<400> SEQUENCE: 428
aauugcacgg uauccaucug ua                                              22

<210> SEQ ID NO 429
<211> LENGTH: 24
<212> TYPE: RNA
<213> ORGANISM: Homo sapiens

<400> SEQUENCE: 429
aauccuugga accaggugu gagu                                             24

<210> SEQ ID NO 430
<211> LENGTH: 22
<212> TYPE: RNA
<213> ORGANISM: Homo sapiens

<400> SEQUENCE: 430
aacacaccua uucaaggauu ca                                              22

<210> SEQ ID NO 431
<211> LENGTH: 22
<212> TYPE: RNA
<213> ORGANISM: Homo sapiens

<400> SEQUENCE: 431
uuaucagaau cuccaggggu ac                                              22

<210> SEQ ID NO 432
<211> LENGTH: 23
<212> TYPE: RNA
<213> ORGANISM: Homo sapiens

<400> SEQUENCE: 432 uccccaggu gugauucuga uuu                                              23

<210> SEQ ID NO 433
<211> LENGTH: 23
<212> TYPE: RNA
<213> ORGANISM: Homo sapiens

<400> SEQUENCE: 433
aggcagugua guuagcugau ugc                                             23

<210> SEQ ID NO 434
<211> LENGTH: 22
<212> TYPE: RNA
<213> ORGANISM: Homo sapiens

```
<400> SEQUENCE: 434
aaucacuaac cacacggcca gg                                              22

<210> SEQ ID NO 435
<211> LENGTH: 23
<212> TYPE: RNA
<213> ORGANISM: Homo sapiens

<400> SEQUENCE: 435
uaggcagugu cauuagcuga uug                                             23

<210> SEQ ID NO 436
<211> LENGTH: 22
<212> TYPE: RNA
<213> ORGANISM: Homo sapiens

<400> SEQUENCE: 436
caaucacuaa cuccacugcc au                                              22

<210> SEQ ID NO 437
<211> LENGTH: 22
<212> TYPE: RNA
<213> ORGANISM: Homo sapiens

<400> SEQUENCE: 437
caaucagcaa guauacugcc cu                                              22

<210> SEQ ID NO 438
<211> LENGTH: 22
<212> TYPE: RNA
<213> ORGANISM: Homo sapiens

<400> SEQUENCE: 438
uggcaguguc uuagcugguu gu                                              22

<210> SEQ ID NO 439
<211> LENGTH: 23
<212> TYPE: RNA
<213> ORGANISM: Homo sapiens

<400> SEQUENCE: 439
ugucugcccg caugccugcc ucu                                             23

<210> SEQ ID NO 440
<211> LENGTH: 22
<212> TYPE: RNA
<213> ORGANISM: Homo sapiens

<400> SEQUENCE: 440
gcugacuccu aguccagggc uc                                              22

<210> SEQ ID NO 441
<211> LENGTH: 21
<212> TYPE: RNA
<213> ORGANISM: Homo sapiens

<400> SEQUENCE: 441
aggggugcua ucugugauug a                                               21

<210> SEQ ID NO 442
<211> LENGTH: 23
<212> TYPE: RNA
<213> ORGANISM: Homo sapiens
```

```
<400> SEQUENCE: 442
ucucacacag aaaucgcacc cgu                                           23

<210> SEQ ID NO 443
<211> LENGTH: 22
<212> TYPE: RNA
<213> ORGANISM: Homo sapiens

<400> SEQUENCE: 443
uccgucucag uuacuuuaua gc                                            22

<210> SEQ ID NO 444
<211> LENGTH: 22
<212> TYPE: RNA
<213> ORGANISM: Homo sapiens

<400> SEQUENCE: 444
uuauaaagca augagacuga uu                                            22

<210> SEQ ID NO 445
<211> LENGTH: 22
<212> TYPE: RNA
<213> ORGANISM: Homo sapiens

<400> SEQUENCE: 445
cagugccucg gcagugcagc cc                                            22

<210> SEQ ID NO 446
<211> LENGTH: 20
<212> TYPE: RNA
<213> ORGANISM: Homo sapiens

<400> SEQUENCE: 446
gugcauugcu guugcauugc                                               20

<210> SEQ ID NO 447
<211> LENGTH: 22
<212> TYPE: RNA
<213> ORGANISM: Homo sapiens

<400> SEQUENCE: 447
caauguuucc acagugcauc ac                                            22

<210> SEQ ID NO 448
<211> LENGTH: 21
<212> TYPE: RNA
<213> ORGANISM: Homo sapiens

<400> SEQUENCE: 448
gugcauugua guugcauugc a                                             21

<210> SEQ ID NO 449
<211> LENGTH: 23
<212> TYPE: RNA
<213> ORGANISM: Homo sapiens

<400> SEQUENCE: 449
ucccuguccu ccaggagcuc acg                                           23

<210> SEQ ID NO 450
<211> LENGTH: 23
<212> TYPE: RNA
```

<213> ORGANISM: Homo sapiens

<400> SEQUENCE: 450
ugagcgccuc gacgacagag ccg                                          23

<210> SEQ ID NO 451
<211> LENGTH: 22
<212> TYPE: RNA
<213> ORGANISM: Homo sapiens

<400> SEQUENCE: 451
aacaauaucc uggugcugag ug                                           22

<210> SEQ ID NO 452
<211> LENGTH: 22
<212> TYPE: RNA
<213> ORGANISM: Homo sapiens

<400> SEQUENCE: 452
uccagcauca gugauuuugu ug                                           22

<210> SEQ ID NO 453
<211> LENGTH: 21
<212> TYPE: RNA
<213> ORGANISM: Homo sapiens

<400> SEQUENCE: 453
gaacggcuuc auacaggagu u                                            21

<210> SEQ ID NO 454
<211> LENGTH: 22
<212> TYPE: RNA
<213> ORGANISM: Homo sapiens

<400> SEQUENCE: 454
cuccuauaug augccuuucu uc                                           22

<210> SEQ ID NO 455
<211> LENGTH: 22
<212> TYPE: RNA
<213> ORGANISM: Homo sapiens

<400> SEQUENCE: 455
uuuuucauua uugcuccuga cc                                           22

<210> SEQ ID NO 456
<211> LENGTH: 23
<212> TYPE: RNA
<213> ORGANISM: Homo sapiens

<400> SEQUENCE: 456
ucaagagcaa uaacgaaaaa ugu                                          23

<210> SEQ ID NO 457
<211> LENGTH: 22
<212> TYPE: RNA
<213> ORGANISM: Homo sapiens

<400> SEQUENCE: 457
cuagguaugg ucccagggau cc                                           22

<210> SEQ ID NO 458
<211> LENGTH: 21

```
<212> TYPE: RNA
<213> ORGANISM: Homo sapiens

<400> SEQUENCE: 458
gccccugggc cuauccuaga a                                            21

<210> SEQ ID NO 459
<211> LENGTH: 22
<212> TYPE: RNA
<213> ORGANISM: Homo sapiens

<400> SEQUENCE: 459
ucucugggcc ugugucuuag gc                                           22

<210> SEQ ID NO 460
<211> LENGTH: 23
<212> TYPE: RNA
<213> ORGANISM: Homo sapiens

<400> SEQUENCE: 460
gcaaagcaca cggccugcag aga                                          23

<210> SEQ ID NO 461
<211> LENGTH: 22
<212> TYPE: RNA
<213> ORGANISM: Homo sapiens

<400> SEQUENCE: 461
aacacaccug guuaaccucu uu                                           22

<210> SEQ ID NO 462
<211> LENGTH: 22
<212> TYPE: RNA
<213> ORGANISM: Homo sapiens

<400> SEQUENCE: 462
cuggcccucu cugcccuucc gu                                           22

<210> SEQ ID NO 463
<211> LENGTH: 20
<212> TYPE: RNA
<213> ORGANISM: Homo sapiens

<400> SEQUENCE: 463
ccucugggcc cuuccuccag                                              20

<210> SEQ ID NO 464
<211> LENGTH: 23
<212> TYPE: RNA
<213> ORGANISM: Homo sapiens

<400> SEQUENCE: 464
ccuaguaggu guccaguaag ugu                                          23

<210> SEQ ID NO 465
<211> LENGTH: 23
<212> TYPE: RNA
<213> ORGANISM: Homo sapiens

<400> SEQUENCE: 465
cgcauccccu agggcauugg ugu                                          23

<210> SEQ ID NO 466
```

-continued

```
<211> LENGTH: 20
<212> TYPE: RNA
<213> ORGANISM: Homo sapiens

<400> SEQUENCE: 466
acugccccag gugcugcugg                                                   20

<210> SEQ ID NO 467
<211> LENGTH: 22
<212> TYPE: RNA
<213> ORGANISM: Homo sapiens

<400> SEQUENCE: 467
aggugguccg uggcgcguuc gc                                                22

<210> SEQ ID NO 468
<211> LENGTH: 21
<212> TYPE: RNA
<213> ORGANISM: Homo sapiens

<400> SEQUENCE: 468
cacauuacac ggucgaccuc u                                                 21

<210> SEQ ID NO 469
<211> LENGTH: 19
<212> TYPE: RNA
<213> ORGANISM: Homo sapiens

<400> SEQUENCE: 469
aaaagcuggg uugagagga                                                    19

<210> SEQ ID NO 470
<211> LENGTH: 20
<212> TYPE: RNA
<213> ORGANISM: Homo sapiens

<400> SEQUENCE: 470
aaaagcuggg uugagagggu                                                   20

<210> SEQ ID NO 471
<211> LENGTH: 22
<212> TYPE: RNA
<213> ORGANISM: Homo sapiens

<400> SEQUENCE: 471
aaaagcuggg uugagagggc aa                                                22

<210> SEQ ID NO 472
<211> LENGTH: 22
<212> TYPE: RNA
<213> ORGANISM: Homo sapiens

<400> SEQUENCE: 472
aaaagcuggg uugagagggc ga                                                22

<210> SEQ ID NO 473
<211> LENGTH: 22
<212> TYPE: RNA
<213> ORGANISM: Homo sapiens

<400> SEQUENCE: 473
caauuuagug ugugugauau uu                                                22
```

```
<210> SEQ ID NO 474
<211> LENGTH: 22
<212> TYPE: RNA
<213> ORGANISM: Homo sapiens

<400> SEQUENCE: 474
uauugcacau uacuaaguug ca                                              22

<210> SEQ ID NO 475
<211> LENGTH: 22
<212> TYPE: RNA
<213> ORGANISM: Homo sapiens

<400> SEQUENCE: 475
ugcuaugcca acauauugcc au                                              22

<210> SEQ ID NO 476
<211> LENGTH: 21
<212> TYPE: RNA
<213> ORGANISM: Homo sapiens

<400> SEQUENCE: 476
aggcaagaug cuggcauagc u                                               21

<210> SEQ ID NO 477
<211> LENGTH: 22
<212> TYPE: RNA
<213> ORGANISM: Homo sapiens

<400> SEQUENCE: 477
cuuucagucg gauguuuaca gc                                              22

<210> SEQ ID NO 478
<211> LENGTH: 22
<212> TYPE: RNA
<213> ORGANISM: Homo sapiens

<400> SEQUENCE: 478
uguaaacauc cuugacugga ag                                              22

<210> SEQ ID NO 479
<211> LENGTH: 22
<212> TYPE: RNA
<213> ORGANISM: Homo sapiens

<400> SEQUENCE: 479
cuuucaguca gauguuugcu gc                                              22

<210> SEQ ID NO 480
<211> LENGTH: 22
<212> TYPE: RNA
<213> ORGANISM: Homo sapiens

<400> SEQUENCE: 480
uguaaacauc cccgacugga ag                                              22

<210> SEQ ID NO 481
<211> LENGTH: 22
<212> TYPE: RNA
<213> ORGANISM: Homo sapiens

<400> SEQUENCE: 481
cugggagaag gcuguuuacu cu                                              22
```

```
<210> SEQ ID NO 482
<211> LENGTH: 22
<212> TYPE: RNA
<213> ORGANISM: Homo sapiens

<400> SEQUENCE: 482
cugggagagg guuguuuacu cc                                              22

<210> SEQ ID NO 483
<211> LENGTH: 23
<212> TYPE: RNA
<213> ORGANISM: Homo sapiens

<400> SEQUENCE: 483
uguaaacauc cuacacucuc agc                                             23

<210> SEQ ID NO 484
<211> LENGTH: 22
<212> TYPE: RNA
<213> ORGANISM: Homo sapiens

<400> SEQUENCE: 484
cugggaggug gauguuuacu uc                                              22

<210> SEQ ID NO 485
<211> LENGTH: 22
<212> TYPE: RNA
<213> ORGANISM: Homo sapiens

<400> SEQUENCE: 485
uguaaacauc cuacacucag cu                                              22

<210> SEQ ID NO 486
<211> LENGTH: 22
<212> TYPE: RNA
<213> ORGANISM: Homo sapiens

<400> SEQUENCE: 486
cuuucagucg gauguuugca gc                                              22

<210> SEQ ID NO 487
<211> LENGTH: 22
<212> TYPE: RNA
<213> ORGANISM: Homo sapiens

<400> SEQUENCE: 487
uguaaacauc cucgacugga ag                                              22

<210> SEQ ID NO 488
<211> LENGTH: 17
<212> TYPE: RNA
<213> ORGANISM: Homo sapiens

<400> SEQUENCE: 488
uaauugcuuc cauguuu                                                    17

<210> SEQ ID NO 489
<211> LENGTH: 17
<212> TYPE: RNA
<213> ORGANISM: Homo sapiens

<400> SEQUENCE: 489
uaagugcuuc caugcuu                                                    17
```

```
<210> SEQ ID NO 490
<211> LENGTH: 22
<212> TYPE: RNA
<213> ORGANISM: Homo sapiens

<400> SEQUENCE: 490
acuuuaacau ggaggcacuu gc                                              22

<210> SEQ ID NO 491
<211> LENGTH: 23
<212> TYPE: RNA
<213> ORGANISM: Homo sapiens

<400> SEQUENCE: 491
uaagugcuuc cauguuugag ugu                                             23

<210> SEQ ID NO 492
<211> LENGTH: 22
<212> TYPE: RNA
<213> ORGANISM: Homo sapiens

<400> SEQUENCE: 492
uuuaacaugg ggguaccugc ug                                              22

<210> SEQ ID NO 493
<211> LENGTH: 23
<212> TYPE: RNA
<213> ORGANISM: Homo sapiens

<400> SEQUENCE: 493
uaagugcuuc cauguuucag ugg                                             23

<210> SEQ ID NO 494
<211> LENGTH: 22
<212> TYPE: RNA
<213> ORGANISM: Homo sapiens

<400> SEQUENCE: 494
acuuuaacau ggaagugcuu uc                                              22

<210> SEQ ID NO 495
<211> LENGTH: 23
<212> TYPE: RNA
<213> ORGANISM: Homo sapiens

<400> SEQUENCE: 495
uaagugcuuc cauguuuuag uag                                             23

<210> SEQ ID NO 496
<211> LENGTH: 23
<212> TYPE: RNA
<213> ORGANISM: Homo sapiens

<400> SEQUENCE: 496
acuuaaacgu ggauguacuu gcu                                             23

<210> SEQ ID NO 497
<211> LENGTH: 23
<212> TYPE: RNA
<213> ORGANISM: Homo sapiens

<400> SEQUENCE: 497
```

```
uaagugcuuc cauguuugg uga                                              23

<210> SEQ ID NO 498
<211> LENGTH: 23
<212> TYPE: RNA
<213> ORGANISM: Homo sapiens

<400> SEQUENCE: 498
cagugcaaug auauugucaa agc                                             23

<210> SEQ ID NO 499
<211> LENGTH: 23
<212> TYPE: RNA
<213> ORGANISM: Homo sapiens

<400> SEQUENCE: 499
cagugcaaua guauugucaa agc                                             23

<210> SEQ ID NO 500
<211> LENGTH: 22
<212> TYPE: RNA
<213> ORGANISM: Homo sapiens

<400> SEQUENCE: 500
uauacaaggg cagacucucu cu                                              22

<210> SEQ ID NO 501
<211> LENGTH: 22
<212> TYPE: RNA
<213> ORGANISM: Homo sapiens

<400> SEQUENCE: 501
ugaccgauuu cuccuggugu uc                                              22

<210> SEQ ID NO 502
<211> LENGTH: 22
<212> TYPE: RNA
<213> ORGANISM: Homo sapiens

<400> SEQUENCE: 502
uagcaccauu ugaaaucggu ua                                              22

<210> SEQ ID NO 503
<211> LENGTH: 22
<212> TYPE: RNA
<213> ORGANISM: Homo sapiens

<400> SEQUENCE: 503
cugguuucac augguggcuu ag                                              22

<210> SEQ ID NO 504
<211> LENGTH: 24
<212> TYPE: RNA
<213> ORGANISM: Homo sapiens

<400> SEQUENCE: 504
gcugguuuca uauggugguu uaga                                            24

<210> SEQ ID NO 505
<211> LENGTH: 23
<212> TYPE: RNA
<213> ORGANISM: Homo sapiens

<400> SEQUENCE: 505
```

-continued

| | |
|---|---|
| uagcaccauu ugaaaucagu guu | 23 |

<210> SEQ ID NO 506
<211> LENGTH: 22
<212> TYPE: RNA
<213> ORGANISM: Homo sapiens

<400> SEQUENCE: 506

| | |
|---|---|
| acugauuucu uuuggguguuc ag | 22 |

<210> SEQ ID NO 507
<211> LENGTH: 22
<212> TYPE: RNA
<213> ORGANISM: Homo sapiens

<400> SEQUENCE: 507

| | |
|---|---|
| uagcaccauc ugaaaucggu ua | 22 |

<210> SEQ ID NO 508
<211> LENGTH: 22
<212> TYPE: RNA
<213> ORGANISM: Homo sapiens

<400> SEQUENCE: 508

| | |
|---|---|
| ugguuuaccg ucccacauac au | 22 |

<210> SEQ ID NO 509
<211> LENGTH: 22
<212> TYPE: RNA
<213> ORGANISM: Homo sapiens

<400> SEQUENCE: 509

| | |
|---|---|
| uaugugggau gguaaaccgc uu | 22 |

<210> SEQ ID NO 510
<211> LENGTH: 24
<212> TYPE: RNA
<213> ORGANISM: Homo sapiens

<400> SEQUENCE: 510

| | |
|---|---|
| agcagaagca gggagguucu ccca | 24 |

<210> SEQ ID NO 511
<211> LENGTH: 21
<212> TYPE: RNA
<213> ORGANISM: Homo sapiens

<400> SEQUENCE: 511

| | |
|---|---|
| auguaugugu gcaugugcau g | 21 |

<210> SEQ ID NO 512
<211> LENGTH: 21
<212> TYPE: RNA
<213> ORGANISM: Homo sapiens

<400> SEQUENCE: 512

| | |
|---|---|
| agggcccccc cucaauccug u | 21 |

<210> SEQ ID NO 513
<211> LENGTH: 22
<212> TYPE: RNA
<213> ORGANISM: Homo sapiens

```
<400> SEQUENCE: 513
gaggguuggg uggaggcucu cc                                            22

<210> SEQ ID NO 514
<211> LENGTH: 22
<212> TYPE: RNA
<213> ORGANISM: Homo sapiens

<400> SEQUENCE: 514
aaggagcuca cagucuauug ag                                            22

<210> SEQ ID NO 515
<211> LENGTH: 22
<212> TYPE: RNA
<213> ORGANISM: Homo sapiens

<400> SEQUENCE: 515
cacuagauug ugagcuccug ga                                            22

<210> SEQ ID NO 516
<211> LENGTH: 22
<212> TYPE: RNA
<213> ORGANISM: Homo sapiens

<400> SEQUENCE: 516
agagcuuagc ugauugguga ac                                            22

<210> SEQ ID NO 517
<211> LENGTH: 21
<212> TYPE: RNA
<213> ORGANISM: Homo sapiens

<400> SEQUENCE: 517
uucacagugg cuaaguucug c                                             21

<210> SEQ ID NO 518
<211> LENGTH: 22
<212> TYPE: RNA
<213> ORGANISM: Homo sapiens

<400> SEQUENCE: 518
agggcuuagc ugcuugugag ca                                            22

<210> SEQ ID NO 519
<211> LENGTH: 21
<212> TYPE: RNA
<213> ORGANISM: Homo sapiens

<400> SEQUENCE: 519
uucacagugg cuaaguuccg c                                             21

<210> SEQ ID NO 520
<211> LENGTH: 22
<212> TYPE: RNA
<213> ORGANISM: Homo sapiens

<400> SEQUENCE: 520
ccuguucucc auuacuuggc uc                                            22

<210> SEQ ID NO 521
<211> LENGTH: 21
<212> TYPE: RNA
<213> ORGANISM: Homo sapiens
```

<400> SEQUENCE: 521
uucaaguaau ucaggauagg u                                          21

<210> SEQ ID NO 522
<211> LENGTH: 22
<212> TYPE: RNA
<213> ORGANISM: Homo sapiens

<400> SEQUENCE: 522
ccuauucuug auuacuuguu uc                                         22

<210> SEQ ID NO 523
<211> LENGTH: 22
<212> TYPE: RNA
<213> ORGANISM: Homo sapiens

<400> SEQUENCE: 523
ccuauucuug guuacuugca cg                                         22

<210> SEQ ID NO 524
<211> LENGTH: 22
<212> TYPE: RNA
<213> ORGANISM: Homo sapiens

<400> SEQUENCE: 524
uucaaguaau ccaggauagg cu                                         22

<210> SEQ ID NO 525
<211> LENGTH: 21
<212> TYPE: RNA
<213> ORGANISM: Homo sapiens

<400> SEQUENCE: 525
aggcggagac uugggcaauu g                                          21

<210> SEQ ID NO 526
<211> LENGTH: 22
<212> TYPE: RNA
<213> ORGANISM: Homo sapiens

<400> SEQUENCE: 526
cauugcacuu gucucggucu ga                                         22

<210> SEQ ID NO 527
<211> LENGTH: 22
<212> TYPE: RNA
<213> ORGANISM: Homo sapiens

<400> SEQUENCE: 527
ugccuacuga gcugaaacac ag                                         22

<210> SEQ ID NO 528
<211> LENGTH: 22
<212> TYPE: RNA
<213> ORGANISM: Homo sapiens

<400> SEQUENCE: 528
ugccuacuga gcugauauca gu                                         22

<210> SEQ ID NO 529
<211> LENGTH: 22
<212> TYPE: RNA

<213> ORGANISM: Homo sapiens

<400> SEQUENCE: 529
uggcucaguu cagcaggaac ag  22

<210> SEQ ID NO 530
<211> LENGTH: 22
<212> TYPE: RNA
<213> ORGANISM: Homo sapiens

<400> SEQUENCE: 530
uggguuccug gcaugcugau uu  22

<210> SEQ ID NO 531
<211> LENGTH: 21
<212> TYPE: RNA
<213> ORGANISM: Homo sapiens

<400> SEQUENCE: 531
aucacauugc cagggauuac c  21

<210> SEQ ID NO 532
<211> LENGTH: 22
<212> TYPE: RNA
<213> ORGANISM: Homo sapiens

<400> SEQUENCE: 532
gggguuccug gggaugggau uu  22

<210> SEQ ID NO 533
<211> LENGTH: 21
<212> TYPE: RNA
<213> ORGANISM: Homo sapiens

<400> SEQUENCE: 533
aucacauugc cagggauuuc c  21

<210> SEQ ID NO 534
<211> LENGTH: 22
<212> TYPE: RNA
<213> ORGANISM: Homo sapiens

<400> SEQUENCE: 534
gagagcagug uguguugccu gg  22

<210> SEQ ID NO 535
<211> LENGTH: 21
<212> TYPE: RNA
<213> ORGANISM: Homo sapiens

<400> SEQUENCE: 535
ugacagcgcc cugccuggcu c  21

<210> SEQ ID NO 536
<211> LENGTH: 22
<212> TYPE: RNA
<213> ORGANISM: Homo sapiens

<400> SEQUENCE: 536
ucugcaagug ucagaggcga gg  22

<210> SEQ ID NO 537
<211> LENGTH: 23

```
<212> TYPE: RNA
<213> ORGANISM: Homo sapiens

<400> SEQUENCE: 537
aaaauggugc ccuagugacu aca                                          23

<210> SEQ ID NO 538
<211> LENGTH: 21
<212> TYPE: RNA
<213> ORGANISM: Homo sapiens

<400> SEQUENCE: 538
caagucacua gugguuccgu u                                            21

<210> SEQ ID NO 539
<211> LENGTH: 22
<212> TYPE: RNA
<213> ORGANISM: Homo sapiens

<400> SEQUENCE: 539
cguguauuug acaagcugag uu                                           22

<210> SEQ ID NO 540
<211> LENGTH: 22
<212> TYPE: RNA
<213> ORGANISM: Homo sapiens

<400> SEQUENCE: 540
ugucaguuug ucaaauaccc ca                                           22

<210> SEQ ID NO 541
<211> LENGTH: 22
<212> TYPE: RNA
<213> ORGANISM: Homo sapiens

<400> SEQUENCE: 541
cucaguagcc aguguagauc cu                                           22

<210> SEQ ID NO 542
<211> LENGTH: 21
<212> TYPE: RNA
<213> ORGANISM: Homo sapiens

<400> SEQUENCE: 542
agcuacaucu ggcuacuggg u                                            21

<210> SEQ ID NO 543
<211> LENGTH: 22
<212> TYPE: RNA
<213> ORGANISM: Homo sapiens

<400> SEQUENCE: 543
accuggcaua caauguagau uu                                           22

<210> SEQ ID NO 544
<211> LENGTH: 23
<212> TYPE: RNA
<213> ORGANISM: Homo sapiens

<400> SEQUENCE: 544
agcuacauug ucugcugggu uuc                                          23

<210> SEQ ID NO 545
```

```
<211> LENGTH: 22
<212> TYPE: RNA
<213> ORGANISM: Homo sapiens

<400> SEQUENCE: 545
acacagggcu guugugaaga cu                                          22

<210> SEQ ID NO 546
<211> LENGTH: 21
<212> TYPE: RNA
<213> ORGANISM: Homo sapiens

<400> SEQUENCE: 546
ccaccaccgu gucugacacu u                                           21

<210> SEQ ID NO 547
<211> LENGTH: 21
<212> TYPE: RNA
<213> ORGANISM: Homo sapiens

<400> SEQUENCE: 547
ccacaccgua ucugacacuu u                                           21

<210> SEQ ID NO 548
<211> LENGTH: 22
<212> TYPE: RNA
<213> ORGANISM: Homo sapiens

<400> SEQUENCE: 548
aguucuucag uggcaagcuu ua                                          22

<210> SEQ ID NO 549
<211> LENGTH: 22
<212> TYPE: RNA
<213> ORGANISM: Homo sapiens

<400> SEQUENCE: 549
aagcugccag uugaagaacu gu                                          22

<210> SEQ ID NO 550
<211> LENGTH: 21
<212> TYPE: RNA
<213> ORGANISM: Homo sapiens

<400> SEQUENCE: 550
ugauugucca aacgcaauuc u                                           21

<210> SEQ ID NO 551
<211> LENGTH: 22
<212> TYPE: RNA
<213> ORGANISM: Homo sapiens

<400> SEQUENCE: 551
agaauugugg cuggacaucu gu                                          22

<210> SEQ ID NO 552
<211> LENGTH: 22
<212> TYPE: RNA
<213> ORGANISM: Homo sapiens

<400> SEQUENCE: 552
agaguugagu cuggacgucc cg                                          22
```

```
<210> SEQ ID NO 553
<211> LENGTH: 22
<212> TYPE: RNA
<213> ORGANISM: Homo sapiens

<400> SEQUENCE: 553
caugguucug ucaagcaccg cg                                              22

<210> SEQ ID NO 554
<211> LENGTH: 22
<212> TYPE: RNA
<213> ORGANISM: Homo sapiens

<400> SEQUENCE: 554
augguuccgu caagcaccau gg                                              22

<210> SEQ ID NO 555
<211> LENGTH: 21
<212> TYPE: RNA
<213> ORGANISM: Homo sapiens

<400> SEQUENCE: 555
uugugcuuga ucuaaccaug u                                               21

<210> SEQ ID NO 556
<211> LENGTH: 23
<212> TYPE: RNA
<213> ORGANISM: Homo sapiens

<400> SEQUENCE: 556
uacugcauca ggaacugauu gga                                             23

<210> SEQ ID NO 557
<211> LENGTH: 22
<212> TYPE: RNA
<213> ORGANISM: Homo sapiens

<400> SEQUENCE: 557
aaaucucugc aggcaaaugu ga                                              22

<210> SEQ ID NO 558
<211> LENGTH: 22
<212> TYPE: RNA
<213> ORGANISM: Homo sapiens

<400> SEQUENCE: 558
uaaucucagc uggcaacugu ga                                              22

<210> SEQ ID NO 559
<211> LENGTH: 21
<212> TYPE: RNA
<213> ORGANISM: Homo sapiens

<400> SEQUENCE: 559
augaccuaug aauugacaga c                                               21

<210> SEQ ID NO 560
<211> LENGTH: 22
<212> TYPE: RNA
<213> ORGANISM: Homo sapiens

<400> SEQUENCE: 560
ugccugucua cacuugcugu gc                                              22
```

```
<210> SEQ ID NO 561
<211> LENGTH: 22
<212> TYPE: RNA
<213> ORGANISM: Homo sapiens

<400> SEQUENCE: 561
acagcaggca cagacaggca gu                                              22

<210> SEQ ID NO 562
<211> LENGTH: 21
<212> TYPE: RNA
<213> ORGANISM: Homo sapiens

<400> SEQUENCE: 562
uaacagucuc cagucacggc c                                               21

<210> SEQ ID NO 563
<211> LENGTH: 21
<212> TYPE: RNA
<213> ORGANISM: Homo sapiens

<400> SEQUENCE: 563
uguucucuuu gccaaggaca g                                               21

<210> SEQ ID NO 564
<211> LENGTH: 21
<212> TYPE: RNA
<213> ORGANISM: Homo sapiens

<400> SEQUENCE: 564
ccucccaugc caagaacucc c                                               21

<210> SEQ ID NO 565
<211> LENGTH: 21
<212> TYPE: RNA
<213> ORGANISM: Homo sapiens

<400> SEQUENCE: 565
gguucuuagc auaggagguc u                                               21

<210> SEQ ID NO 566
<211> LENGTH: 22
<212> TYPE: RNA
<213> ORGANISM: Homo sapiens

<400> SEQUENCE: 566
caucagaauu cauggaggcu ag                                              22

<210> SEQ ID NO 567
<211> LENGTH: 22
<212> TYPE: RNA
<213> ORGANISM: Homo sapiens

<400> SEQUENCE: 567
agcuuccaug acuccugaug ga                                              22

<210> SEQ ID NO 568
<211> LENGTH: 21
<212> TYPE: RNA
<213> ORGANISM: Homo sapiens

<400> SEQUENCE: 568
cgagccucaa gcaagggacu u                                               21
```

```
<210> SEQ ID NO 569
<211> LENGTH: 22
<212> TYPE: RNA
<213> ORGANISM: Homo sapiens

<400> SEQUENCE: 569
uagucccuuc cuugaagcgg uc                                            22

<210> SEQ ID NO 570
<211> LENGTH: 21
<212> TYPE: RNA
<213> ORGANISM: Homo sapiens

<400> SEQUENCE: 570
auuugugcuu ggcucuguca c                                             21

<210> SEQ ID NO 571
<211> LENGTH: 22
<212> TYPE: RNA
<213> ORGANISM: Homo sapiens

<400> SEQUENCE: 571
uuggggaaac ggccgcugag ug                                            22

<210> SEQ ID NO 572
<211> LENGTH: 22
<212> TYPE: RNA
<213> ORGANISM: Homo sapiens

<400> SEQUENCE: 572
uucccuuugu cauccuucgc cu                                            22

<210> SEQ ID NO 573
<211> LENGTH: 22
<212> TYPE: RNA
<213> ORGANISM: Homo sapiens

<400> SEQUENCE: 573
cugugcgugu gacagcggcu ga                                            22

<210> SEQ ID NO 574
<211> LENGTH: 21
<212> TYPE: RNA
<213> ORGANISM: Homo sapiens

<400> SEQUENCE: 574
caacaccagu cgaugggcug u                                             21

<210> SEQ ID NO 575
<211> LENGTH: 22
<212> TYPE: RNA
<213> ORGANISM: Homo sapiens

<400> SEQUENCE: 575
uagcuuauca gacugauguu ga                                            22

<210> SEQ ID NO 576
<211> LENGTH: 22
<212> TYPE: RNA
<213> ORGANISM: Homo sapiens

<400> SEQUENCE: 576
```
acuguaguau gggcacuucc ag                                                22

<210> SEQ ID NO 577
<211> LENGTH: 23
<212> TYPE: RNA
<213> ORGANISM: Homo sapiens

<400> SEQUENCE: 577
caaagugcuc auagugcagg uag                                               23

<210> SEQ ID NO 578
<211> LENGTH: 22
<212> TYPE: RNA
<213> ORGANISM: Homo sapiens

<400> SEQUENCE: 578
acugcauuau gagcacuuaa ag                                                22

<210> SEQ ID NO 579
<211> LENGTH: 23
<212> TYPE: RNA
<213> ORGANISM: Homo sapiens

<400> SEQUENCE: 579
uaaagugcuu auagugcagg uag                                               23

<210> SEQ ID NO 580
<211> LENGTH: 22
<212> TYPE: RNA
<213> ORGANISM: Homo sapiens

<400> SEQUENCE: 580
auaagacgaa caaaagguuu gu                                                22

<210> SEQ ID NO 581
<211> LENGTH: 22
<212> TYPE: RNA
<213> ORGANISM: Homo sapiens

<400> SEQUENCE: 581
auaagacgag caaaaagcuu gu                                                22

<210> SEQ ID NO 582
<211> LENGTH: 22
<212> TYPE: RNA
<213> ORGANISM: Homo sapiens

<400> SEQUENCE: 582
uggaauguaa ggaagugugu gg                                                22

<210> SEQ ID NO 583
<211> LENGTH: 23
<212> TYPE: RNA
<213> ORGANISM: Homo sapiens

<400> SEQUENCE: 583
cuguaauaua aauuuaauuu auu                                               23

<210> SEQ ID NO 584
<211> LENGTH: 23
<212> TYPE: RNA
<213> ORGANISM: Homo sapiens

<400> SEQUENCE: 584

-continued

| | |
|---|---|
| guguuaauua aaccucuauu uac | 23 |

<210> SEQ ID NO 585
<211> LENGTH: 20
<212> TYPE: RNA
<213> ORGANISM: Homo sapiens

<400> SEQUENCE: 585

| | |
|---|---|
| uguuuugaua acaguaaugu | 20 |

<210> SEQ ID NO 586
<211> LENGTH: 21
<212> TYPE: RNA
<213> ORGANISM: Homo sapiens

<400> SEQUENCE: 586

| | |
|---|---|
| gauuucagug gagugaaguu c | 21 |

<210> SEQ ID NO 587
<211> LENGTH: 22
<212> TYPE: RNA
<213> ORGANISM: Homo sapiens

<400> SEQUENCE: 587

| | |
|---|---|
| uccuucauuc caccggaguc ug | 22 |

<210> SEQ ID NO 588
<211> LENGTH: 22
<212> TYPE: RNA
<213> ORGANISM: Homo sapiens

<400> SEQUENCE: 588

| | |
|---|---|
| uucccuuugu cauccuaugc cu | 22 |

<210> SEQ ID NO 589
<211> LENGTH: 22
<212> TYPE: RNA
<213> ORGANISM: Homo sapiens

<400> SEQUENCE: 589

| | |
|---|---|
| gugaaauguu uaggaccacu ag | 22 |

<210> SEQ ID NO 590
<211> LENGTH: 22
<212> TYPE: RNA
<213> ORGANISM: Homo sapiens

<400> SEQUENCE: 590

| | |
|---|---|
| uuccuaugca uauacuucuu ug | 22 |

<210> SEQ ID NO 591
<211> LENGTH: 20
<212> TYPE: RNA
<213> ORGANISM: Homo sapiens

<400> SEQUENCE: 591

| | |
|---|---|
| agagguauag ggcaugggaa | 20 |

<210> SEQ ID NO 592
<211> LENGTH: 22
<212> TYPE: RNA
<213> ORGANISM: Homo sapiens

```
<400> SEQUENCE: 592
cgucuuaccc agcaguguuu gg                                              22

<210> SEQ ID NO 593
<211> LENGTH: 23
<212> TYPE: RNA
<213> ORGANISM: Homo sapiens

<400> SEQUENCE: 593
uaauacugcc ggguaaugau gga                                             23

<210> SEQ ID NO 594
<211> LENGTH: 22
<212> TYPE: RNA
<213> ORGANISM: Homo sapiens

<400> SEQUENCE: 594
caucuuacug ggcagcauug ga                                              22

<210> SEQ ID NO 595
<211> LENGTH: 22
<212> TYPE: RNA
<213> ORGANISM: Homo sapiens

<400> SEQUENCE: 595
uaauacugcc ugguaaugau ga                                              22

<210> SEQ ID NO 596
<211> LENGTH: 22
<212> TYPE: RNA
<213> ORGANISM: Homo sapiens

<400> SEQUENCE: 596
caucuuaccg gacagugcug ga                                              22

<210> SEQ ID NO 597
<211> LENGTH: 22
<212> TYPE: RNA
<213> ORGANISM: Homo sapiens

<400> SEQUENCE: 597
uaacacuguc ugguaacgau gu                                              22

<210> SEQ ID NO 598
<211> LENGTH: 22
<212> TYPE: RNA
<213> ORGANISM: Homo sapiens

<400> SEQUENCE: 598
aguuuugcag guuugcauuu ca                                              22

<210> SEQ ID NO 599
<211> LENGTH: 23
<212> TYPE: RNA
<213> ORGANISM: Homo sapiens

<400> SEQUENCE: 599
aguuuugcag guuugcaucc agc                                             23

<210> SEQ ID NO 600
<211> LENGTH: 23
<212> TYPE: RNA
<213> ORGANISM: Homo sapiens
```

-continued

```
<400> SEQUENCE: 600
ugugcaaauc caugcaaaac uga                                              23

<210> SEQ ID NO 601
<211> LENGTH: 22
<212> TYPE: RNA
<213> ORGANISM: Homo sapiens

<400> SEQUENCE: 601
aguuuugcau aguugcacua ca                                               22

<210> SEQ ID NO 602
<211> LENGTH: 23
<212> TYPE: RNA
<213> ORGANISM: Homo sapiens

<400> SEQUENCE: 602
ugugcaaauc uaugcaaaac uga                                              23

<210> SEQ ID NO 603
<211> LENGTH: 23
<212> TYPE: RNA
<213> ORGANISM: Homo sapiens

<400> SEQUENCE: 603
cccaguguuu agacuaucug uuc                                              23

<210> SEQ ID NO 604
<211> LENGTH: 22
<212> TYPE: RNA
<213> ORGANISM: Homo sapiens

<400> SEQUENCE: 604
acaguagucu gcacauuggu ua                                               22

<210> SEQ ID NO 605
<211> LENGTH: 23
<212> TYPE: RNA
<213> ORGANISM: Homo sapiens

<400> SEQUENCE: 605
cccaguguuc agacuaccug uuc                                              23

<210> SEQ ID NO 606
<211> LENGTH: 22
<212> TYPE: RNA
<213> ORGANISM: Homo sapiens

<400> SEQUENCE: 606
acaguagucu gcacauuggu ua                                               22

<210> SEQ ID NO 607
<211> LENGTH: 22
<212> TYPE: RNA
<213> ORGANISM: Homo sapiens

<400> SEQUENCE: 607
gguccagagg ggagauaggu uc                                               22

<210> SEQ ID NO 608
<211> LENGTH: 22
<212> TYPE: RNA
```

```
<213> ORGANISM: Homo sapiens

<400> SEQUENCE: 608
cucccacugc uucacuugac ua                                          22

<210> SEQ ID NO 609
<211> LENGTH: 21
<212> TYPE: RNA
<213> ORGANISM: Homo sapiens

<400> SEQUENCE: 609
gguuuggucc uagccuuucu a                                           21

<210> SEQ ID NO 610
<211> LENGTH: 22
<212> TYPE: RNA
<213> ORGANISM: Homo sapiens

<400> SEQUENCE: 610
gauuagggug cuuagcuguu aa                                          22

<210> SEQ ID NO 611
<211> LENGTH: 20
<212> TYPE: RNA
<213> ORGANISM: Homo sapiens

<400> SEQUENCE: 611
ccuccugccc uccuugcugu                                             20

<210> SEQ ID NO 612
<211> LENGTH: 25
<212> TYPE: RNA
<213> ORGANISM: Homo sapiens

<400> SEQUENCE: 612
cccccacaac cgcgcuugac uagcu                                       25

<210> SEQ ID NO 613
<211> LENGTH: 23
<212> TYPE: RNA
<213> ORGANISM: Homo sapiens

<400> SEQUENCE: 613
ugguuguagu ccgugcgaga aua                                         23

<210> SEQ ID NO 614
<211> LENGTH: 19
<212> TYPE: RNA
<213> ORGANISM: Homo sapiens

<400> SEQUENCE: 614
accgugcaaa gguagcaua                                              19

<210> SEQ ID NO 615
<211> LENGTH: 22
<212> TYPE: RNA
<213> ORGANISM: Homo sapiens

<400> SEQUENCE: 615
ucaggccagg cacaguggcu ca                                          22

<210> SEQ ID NO 616
<211> LENGTH: 22
```

```
<212> TYPE: RNA
<213> ORGANISM: Homo sapiens

<400> SEQUENCE: 616
uucaccaccu ucuccaccca gc                                              22

<210> SEQ ID NO 617
<211> LENGTH: 22
<212> TYPE: RNA
<213> ORGANISM: Homo sapiens

<400> SEQUENCE: 617
ucgacagcac gacacugccu uc                                              22

<210> SEQ ID NO 618
<211> LENGTH: 22
<212> TYPE: RNA
<213> ORGANISM: Homo sapiens

<400> SEQUENCE: 618
uagguaguuu ccuguuguug gg                                              22

<210> SEQ ID NO 619
<211> LENGTH: 22
<212> TYPE: RNA
<213> ORGANISM: Homo sapiens

<400> SEQUENCE: 619
cggcaacaag aaacugccug ag                                              22

<210> SEQ ID NO 620
<211> LENGTH: 22
<212> TYPE: RNA
<213> ORGANISM: Homo sapiens

<400> SEQUENCE: 620
uagguaguuu cauguuguug gg                                              22

<210> SEQ ID NO 621
<211> LENGTH: 22
<212> TYPE: RNA
<213> ORGANISM: Homo sapiens

<400> SEQUENCE: 621
ccaauauugg cugugcugcu cc                                              22

<210> SEQ ID NO 622
<211> LENGTH: 21
<212> TYPE: RNA
<213> ORGANISM: Homo sapiens

<400> SEQUENCE: 622
uagcagcaca gaaauauugg c                                               21

<210> SEQ ID NO 623
<211> LENGTH: 22
<212> TYPE: RNA
<213> ORGANISM: Homo sapiens

<400> SEQUENCE: 623 ccagugggc ugcuguuauc ug                                               22

<210> SEQ ID NO 624
```

```
<211> LENGTH: 22
<212> TYPE: RNA
<213> ORGANISM: Homo sapiens

<400> SEQUENCE: 624
uguaacagca acuccaugug ga                                              22

<210> SEQ ID NO 625
<211> LENGTH: 22
<212> TYPE: RNA
<213> ORGANISM: Homo sapiens

<400> SEQUENCE: 625
cgggguuuug agggcgagau ga                                              22

<210> SEQ ID NO 626
<211> LENGTH: 22
<212> TYPE: RNA
<213> ORGANISM: Homo sapiens

<400> SEQUENCE: 626
aacuggcccu caaagucccg cu                                              22

<210> SEQ ID NO 627
<211> LENGTH: 22
<212> TYPE: RNA
<213> ORGANISM: Homo sapiens

<400> SEQUENCE: 627
ugggucuuug cgggcgagau ga                                              22

<210> SEQ ID NO 628
<211> LENGTH: 22
<212> TYPE: RNA
<213> ORGANISM: Homo sapiens

<400> SEQUENCE: 628
aacuggccua caaagucccca gu                                             22
```

```
aacuggccua caaagucccca gu
```

Actually re-reading: `aacuggccua caaagucccca gu` length 22.

```
<210> SEQ ID NO 629
<211> LENGTH: 22
<212> TYPE: RNA
<213> ORGANISM: Homo sapiens

<400> SEQUENCE: 629
cugccaauuc cauaggucac ag                                              22

<210> SEQ ID NO 630
<211> LENGTH: 21
<212> TYPE: RNA
<213> ORGANISM: Homo sapiens

<400> SEQUENCE: 630
cugaccuaug aauugacagc c                                               21

<210> SEQ ID NO 631
<211> LENGTH: 22
<212> TYPE: RNA
<213> ORGANISM: Homo sapiens

<400> SEQUENCE: 631
accuugccuu gcugcccggg cc                                              22
```

```
<210> SEQ ID NO 632
<211> LENGTH: 20
<212> TYPE: RNA
<213> ORGANISM: Homo sapiens

<400> SEQUENCE: 632
ccccagggcg acgcggcggg                                                   20

<210> SEQ ID NO 633
<211> LENGTH: 22
<212> TYPE: RNA
<213> ORGANISM: Homo sapiens

<400> SEQUENCE: 633 ggagggucc cgcacuggga gg                                                 22

<210> SEQ ID NO 634
<211> LENGTH: 22
<212> TYPE: RNA
<213> ORGANISM: Homo sapiens

<400> SEQUENCE: 634
cccugugccc ggcccacuuc ug                                                22

<210> SEQ ID NO 635
<211> LENGTH: 22
<212> TYPE: RNA
<213> ORGANISM: Homo sapiens

<400> SEQUENCE: 635
ucugcccccu ccgcugcugc ca                                                22

<210> SEQ ID NO 636
<211> LENGTH: 22
<212> TYPE: RNA
<213> ORGANISM: Homo sapiens

<400> SEQUENCE: 636
uacccagagc augcagugug aa                                                22

<210> SEQ ID NO 637
<211> LENGTH: 20
<212> TYPE: RNA
<213> ORGANISM: Homo sapiens

<400> SEQUENCE: 637
caccaggcau uguggucucc                                                   20

<210> SEQ ID NO 638
<211> LENGTH: 23
<212> TYPE: RNA
<213> ORGANISM: Homo sapiens

<400> SEQUENCE: 638
ugaguaccgc caugucuguu ggg                                               23

<210> SEQ ID NO 639
<211> LENGTH: 21
<212> TYPE: RNA
<213> ORGANISM: Homo sapiens

<400> SEQUENCE: 639
ccaguccugu gccugccgcc u                                                 21
```

<210> SEQ ID NO 640
<211> LENGTH: 22
<212> TYPE: RNA
<213> ORGANISM: Homo sapiens

<400> SEQUENCE: 640
gcugcgcuug gauuucgucc cc                                              22

<210> SEQ ID NO 641
<211> LENGTH: 23
<212> TYPE: RNA
<213> ORGANISM: Homo sapiens

<400> SEQUENCE: 641
caacggaauc ccaaaagcag cug                                             23

<210> SEQ ID NO 642
<211> LENGTH: 21
<212> TYPE: RNA
<213> ORGANISM: Homo sapiens

<400> SEQUENCE: 642
ugauauguuu gauauugggu u                                               21

<210> SEQ ID NO 643
<211> LENGTH: 21
<212> TYPE: RNA
<213> ORGANISM: Homo sapiens

<400> SEQUENCE: 643
ugagugccgg ugccugcccu g                                               21

<210> SEQ ID NO 644
<211> LENGTH: 22
<212> TYPE: RNA
<213> ORGANISM: Homo sapiens

<400> SEQUENCE: 644
cgcaggggcc gggugcucac cg                                              22

<210> SEQ ID NO 645
<211> LENGTH: 21
<212> TYPE: RNA
<213> ORGANISM: Homo sapiens

<400> SEQUENCE: 645
cggcggggac ggcgauuggu c                                               21

<210> SEQ ID NO 646
<211> LENGTH: 22
<212> TYPE: RNA
<213> ORGANISM: Homo sapiens

<400> SEQUENCE: 646
ugauauguuu gauauauuag gu                                              22

<210> SEQ ID NO 647
<211> LENGTH: 22
<212> TYPE: RNA
<213> ORGANISM: Homo sapiens

<400> SEQUENCE: 647
ugcccuaaau gccccuucug gc                                              22

<210> SEQ ID NO 648
<211> LENGTH: 23
<212> TYPE: RNA
<213> ORGANISM: Homo sapiens

<400> SEQUENCE: 648
uaaggugcau cuagugcagu uag                                              23

<210> SEQ ID NO 649
<211> LENGTH: 23
<212> TYPE: RNA
<213> ORGANISM: Homo sapiens

<400> SEQUENCE: 649
acugcccuaa gugcuccuuc ugg                                              23

<210> SEQ ID NO 650
<211> LENGTH: 23
<212> TYPE: RNA
<213> ORGANISM: Homo sapiens

<400> SEQUENCE: 650
uaaggugcau cuagugcaga uag                                              23

<210> SEQ ID NO 651
<211> LENGTH: 21
<212> TYPE: RNA
<213> ORGANISM: Homo sapiens

<400> SEQUENCE: 651
caucccuugc augguggagg g                                                21

<210> SEQ ID NO 652
<211> LENGTH: 21
<212> TYPE: RNA
<213> ORGANISM: Homo sapiens

<400> SEQUENCE: 652
cucccacaug caggguuugc a                                                21

<210> SEQ ID NO 653
<211> LENGTH: 22
<212> TYPE: RNA
<213> ORGANISM: Homo sapiens

<400> SEQUENCE: 653
ggcuacaaca caggacccgg gc                                               22

<210> SEQ ID NO 654
<211> LENGTH: 22
<212> TYPE: RNA
<213> ORGANISM: Homo sapiens

<400> SEQUENCE: 654
ucgugucuug uguugcagcc gg                                               22

<210> SEQ ID NO 655
<211> LENGTH: 22
<212> TYPE: RNA
<213> ORGANISM: Homo sapiens

<400> SEQUENCE: 655

```
gcccaaaggu gaauuuuuug gg                                      22

<210> SEQ ID NO 656
<211> LENGTH: 22
<212> TYPE: RNA
<213> ORGANISM: Homo sapiens

<400> SEQUENCE: 656
caaagaauuc uccuuuuggg cu                                      22

<210> SEQ ID NO 657
<211> LENGTH: 22
<212> TYPE: RNA
<213> ORGANISM: Homo sapiens

<400> SEQUENCE: 657
aggggcuggc uuccucugg uc                                       22

<210> SEQ ID NO 658
<211> LENGTH: 22
<212> TYPE: RNA
<213> ORGANISM: Homo sapiens

<400> SEQUENCE: 658
uggagagaaa ggcaguuccu ga                                      22

<210> SEQ ID NO 659
<211> LENGTH: 22
<212> TYPE: RNA
<213> ORGANISM: Homo sapiens

<400> SEQUENCE: 659
uggacggaga acugauaagg gu                                      22

<210> SEQ ID NO 660
<211> LENGTH: 22
<212> TYPE: RNA
<213> ORGANISM: Homo sapiens

<400> SEQUENCE: 660
gugaauuacc gaagggccau aa                                      22

<210> SEQ ID NO 661
<211> LENGTH: 22
<212> TYPE: RNA
<213> ORGANISM: Homo sapiens

<400> SEQUENCE: 661
uauggcacug guagaauuca cu                                      22

<210> SEQ ID NO 662
<211> LENGTH: 18
<212> TYPE: RNA
<213> ORGANISM: Homo sapiens

<400> SEQUENCE: 662
ugaggcagua gauugaau                                           18

<210> SEQ ID NO 663
<211> LENGTH: 27
<212> TYPE: RNA
<213> ORGANISM: Homo sapiens

<400> SEQUENCE: 663
```

-continued

| | |
|---|---|
| auugaucauc gacacuucga acgcaau | 27 |

<210> SEQ ID NO 664
<211> LENGTH: 18
<212> TYPE: RNA
<213> ORGANISM: Homo sapiens

<400> SEQUENCE: 664

| | |
|---|---|
| uccagugccc uccucucc | 18 |

<210> SEQ ID NO 665
<211> LENGTH: 21
<212> TYPE: RNA
<213> ORGANISM: Homo sapiens

<400> SEQUENCE: 665

| | |
|---|---|
| ugguucuaga cuugccaacu a | 21 |

<210> SEQ ID NO 666
<211> LENGTH: 24
<212> TYPE: RNA
<213> ORGANISM: Homo sapiens

<400> SEQUENCE: 666

| | |
|---|---|
| uuuggcaaug guagaacuca cacu | 24 |

<210> SEQ ID NO 667
<211> LENGTH: 23
<212> TYPE: RNA
<213> ORGANISM: Homo sapiens

<400> SEQUENCE: 667

| | |
|---|---|
| aacauucauu guugucggug ggu | 23 |

<210> SEQ ID NO 668
<211> LENGTH: 22
<212> TYPE: RNA
<213> ORGANISM: Homo sapiens

<400> SEQUENCE: 668

| | |
|---|---|
| aaccaucgac cguugagugg ac | 22 |

<210> SEQ ID NO 669
<211> LENGTH: 22
<212> TYPE: RNA
<213> ORGANISM: Homo sapiens

<400> SEQUENCE: 669

| | |
|---|---|
| aacauucaac cugucgguga gu | 22 |

<210> SEQ ID NO 670
<211> LENGTH: 23
<212> TYPE: RNA
<213> ORGANISM: Homo sapiens

<400> SEQUENCE: 670

| | |
|---|---|
| aacauucauu gcugucggug ggu | 23 |

<210> SEQ ID NO 671
<211> LENGTH: 22
<212> TYPE: RNA
<213> ORGANISM: Homo sapiens

```
<400> SEQUENCE: 671
accacugacc guugacugua cc                                              22

<210> SEQ ID NO 672
<211> LENGTH: 22
<212> TYPE: RNA
<213> ORGANISM: Homo sapiens

<400> SEQUENCE: 672
accaucgacc guugauugua cc                                              22

<210> SEQ ID NO 673
<211> LENGTH: 23
<212> TYPE: RNA
<213> ORGANISM: Homo sapiens

<400> SEQUENCE: 673
aacauucaac gcugucggug agu                                             23

<210> SEQ ID NO 674
<211> LENGTH: 22
<212> TYPE: RNA
<213> ORGANISM: Homo sapiens

<400> SEQUENCE: 674
acugcaguga aggcacuugu ag                                              22

<210> SEQ ID NO 675
<211> LENGTH: 23
<212> TYPE: RNA
<213> ORGANISM: Homo sapiens

<400> SEQUENCE: 675
caaagugcuu acagugcagg uag                                             23

<210> SEQ ID NO 676
<211> LENGTH: 22
<212> TYPE: RNA
<213> ORGANISM: Homo sapiens

<400> SEQUENCE: 676
ccaauauuac ugugcugcuu ua                                              22

<210> SEQ ID NO 677
<211> LENGTH: 22
<212> TYPE: RNA
<213> ORGANISM: Homo sapiens

<400> SEQUENCE: 677
ccaguauuaa cugugcugcu ga                                              22

<210> SEQ ID NO 678
<211> LENGTH: 22
<212> TYPE: RNA
<213> ORGANISM: Homo sapiens

<400> SEQUENCE: 678
uagcagcacg uaaauauugg cg                                              22

<210> SEQ ID NO 679
<211> LENGTH: 22
<212> TYPE: RNA
<213> ORGANISM: Homo sapiens
```

```
<400> SEQUENCE: 679
cgaaucauua uuugcugcuc ua                                              22

<210> SEQ ID NO 680
<211> LENGTH: 22
<212> TYPE: RNA
<213> ORGANISM: Homo sapiens

<400> SEQUENCE: 680
uagcagcaca ucaugguuua ca                                              22

<210> SEQ ID NO 681
<211> LENGTH: 22
<212> TYPE: RNA
<213> ORGANISM: Homo sapiens

<400> SEQUENCE: 681
caggccauau ugugcugccu ca                                              22

<210> SEQ ID NO 682
<211> LENGTH: 22
<212> TYPE: RNA
<213> ORGANISM: Homo sapiens

<400> SEQUENCE: 682
uagcagcaca uaaugguuug ug                                              22

<210> SEQ ID NO 683
<211> LENGTH: 22
<212> TYPE: RNA
<213> ORGANISM: Homo sapiens

<400> SEQUENCE: 683
cuccuacaua uuagcauuaa ca                                              22

<210> SEQ ID NO 684
<211> LENGTH: 23
<212> TYPE: RNA
<213> ORGANISM: Homo sapiens

<400> SEQUENCE: 684
uuaaugcuaa ucgugauagg ggu                                             23

<210> SEQ ID NO 685
<211> LENGTH: 22
<212> TYPE: RNA
<213> ORGANISM: Homo sapiens

<400> SEQUENCE: 685
aaucauacac gguugaccua uu                                              22

<210> SEQ ID NO 686
<211> LENGTH: 22
<212> TYPE: RNA
<213> ORGANISM: Homo sapiens

<400> SEQUENCE: 686
uagguuaucc guguugccuu cg                                              22

<210> SEQ ID NO 687
<211> LENGTH: 21
<212> TYPE: RNA
```

-continued

<213> ORGANISM: Homo sapiens

<400> SEQUENCE: 687
uccugcgcgu cccagaugcc c                                            21

<210> SEQ ID NO 688
<211> LENGTH: 23
<212> TYPE: RNA
<213> ORGANISM: Homo sapiens

<400> SEQUENCE: 688
cggcccgggc ugcugcuguu ccu                                          23

<210> SEQ ID NO 689
<211> LENGTH: 22
<212> TYPE: RNA
<213> ORGANISM: Homo sapiens

<400> SEQUENCE: 689
aaaaccgucu aguuacaguu gu                                           22

<210> SEQ ID NO 690
<211> LENGTH: 22
<212> TYPE: RNA
<213> ORGANISM: Homo sapiens

<400> SEQUENCE: 690
uugcauaguc acaaaaguga uc                                           22

<210> SEQ ID NO 691
<211> LENGTH: 21
<212> TYPE: RNA
<213> ORGANISM: Homo sapiens

<400> SEQUENCE: 691
ucagugcaug acagaacuug g                                            21

<210> SEQ ID NO 692
<211> LENGTH: 21
<212> TYPE: RNA
<213> ORGANISM: Homo sapiens

<400> SEQUENCE: 692
ucgaggagcu cacagucuag u                                            21

<210> SEQ ID NO 693
<211> LENGTH: 21
<212> TYPE: RNA
<213> ORGANISM: Homo sapiens

<400> SEQUENCE: 693
cuagacugaa gcuccuugag g                                            21

<210> SEQ ID NO 694
<211> LENGTH: 22
<212> TYPE: RNA
<213> ORGANISM: Homo sapiens

<400> SEQUENCE: 694
cugguacagg ccuggggggac ag                                          22

<210> SEQ ID NO 695
<211> LENGTH: 22

```
<212> TYPE: RNA
<213> ORGANISM: Homo sapiens

<400> SEQUENCE: 695
ucucccaacc cuuguaccag ug                                              22

<210> SEQ ID NO 696
<211> LENGTH: 21
<212> TYPE: RNA
<213> ORGANISM: Homo sapiens

<400> SEQUENCE: 696
agggagggac gggggcugug c                                               21

<210> SEQ ID NO 697
<211> LENGTH: 23
<212> TYPE: RNA
<213> ORGANISM: Homo sapiens

<400> SEQUENCE: 697
ucuggcuccg ugucuucacu ccc                                             23

<210> SEQ ID NO 698
<211> LENGTH: 22
<212> TYPE: RNA
<213> ORGANISM: Homo sapiens

<400> SEQUENCE: 698
aaguucuguu auacacucag gc                                              22

<210> SEQ ID NO 699
<211> LENGTH: 22
<212> TYPE: RNA
<213> ORGANISM: Homo sapiens

<400> SEQUENCE: 699
ucagugcauc acagaacuuu gu                                              22

<210> SEQ ID NO 700
<211> LENGTH: 22
<212> TYPE: RNA
<213> ORGANISM: Homo sapiens

<400> SEQUENCE: 700
aaaguucuga gacacuccga cu                                              22

<210> SEQ ID NO 701
<211> LENGTH: 22
<212> TYPE: RNA
<213> ORGANISM: Homo sapiens

<400> SEQUENCE: 701
ucagugcacu acagaacuuu gu                                              22

<210> SEQ ID NO 702
<211> LENGTH: 22
<212> TYPE: RNA
<213> ORGANISM: Homo sapiens

<400> SEQUENCE: 702
gugugcggaa augcuucugc ua                                              22

<210> SEQ ID NO 703
```

```
<211> LENGTH: 22
<212> TYPE: RNA
<213> ORGANISM: Homo sapiens

<400> SEQUENCE: 703
gcccgcgugu ggagccaggu gu                                              22

<210> SEQ ID NO 704
<211> LENGTH: 21
<212> TYPE: RNA
<213> ORGANISM: Homo sapiens

<400> SEQUENCE: 704
gcccuccgcc cgugcacccc g                                               21

<210> SEQ ID NO 705
<211> LENGTH: 20
<212> TYPE: RNA
<213> ORGANISM: Homo sapiens

<400> SEQUENCE: 705
guguguggaa augcuucugc                                                 20

<210> SEQ ID NO 706
<211> LENGTH: 22
<212> TYPE: RNA
<213> ORGANISM: Homo sapiens

<400> SEQUENCE: 706
ugagaacuga auuccauagg cu                                              22

<210> SEQ ID NO 707
<211> LENGTH: 22
<212> TYPE: RNA
<213> ORGANISM: Homo sapiens

<400> SEQUENCE: 707
ugcccugugg acucaguucu gg                                              22

<210> SEQ ID NO 708
<211> LENGTH: 22
<212> TYPE: RNA
<213> ORGANISM: Homo sapiens

<400> SEQUENCE: 708
ccucugaaau ucaguucuuc ag                                              22

<210> SEQ ID NO 709
<211> LENGTH: 22
<212> TYPE: RNA
<213> ORGANISM: Homo sapiens

<400> SEQUENCE: 709
ugagaacuga auuccauggg uu                                              22

<210> SEQ ID NO 710
<211> LENGTH: 22
<212> TYPE: RNA
<213> ORGANISM: Homo sapiens

<400> SEQUENCE: 710
cucggcgcgg ggcgcgggcu cc                                              22
```

```
<210> SEQ ID NO 711
<211> LENGTH: 21
<212> TYPE: RNA
<213> ORGANISM: Homo sapiens

<400> SEQUENCE: 711
cuccguuugc cuguuucgcu g                                                   21

<210> SEQ ID NO 712
<211> LENGTH: 22
<212> TYPE: RNA
<213> ORGANISM: Homo sapiens

<400> SEQUENCE: 712
ggauuccugg aaauacuguu cu                                                  22

<210> SEQ ID NO 713
<211> LENGTH: 23
<212> TYPE: RNA
<213> ORGANISM: Homo sapiens

<400> SEQUENCE: 713
guccaguuuu cccaggaauc ccu                                                 23

<210> SEQ ID NO 714
<211> LENGTH: 22
<212> TYPE: RNA
<213> ORGANISM: Homo sapiens

<400> SEQUENCE: 714
ggauaucauc auauacugua ag                                                  22

<210> SEQ ID NO 715
<211> LENGTH: 20
<212> TYPE: RNA
<213> ORGANISM: Homo sapiens

<400> SEQUENCE: 715
uacaguauag augauguacu                                                     20

<210> SEQ ID NO 716
<211> LENGTH: 22
<212> TYPE: RNA
<213> ORGANISM: Homo sapiens

<400> SEQUENCE: 716
ggugcagugc ugcaucucug gu                                                  22

<210> SEQ ID NO 717
<211> LENGTH: 21
<212> TYPE: RNA
<213> ORGANISM: Homo sapiens

<400> SEQUENCE: 717
ugagaugaag cacuguagcu c                                                   21

<210> SEQ ID NO 718
<211> LENGTH: 21
<212> TYPE: RNA
<213> ORGANISM: Homo sapiens

<400> SEQUENCE: 718
cauaaaguag aaagcacuac u                                                   21
```

<210> SEQ ID NO 719
<211> LENGTH: 23
<212> TYPE: RNA
<213> ORGANISM: Homo sapiens

<400> SEQUENCE: 719
uguaguguuu ccuacuuuau gga                                    23

<210> SEQ ID NO 720
<211> LENGTH: 22
<212> TYPE: RNA
<213> ORGANISM: Homo sapiens

<400> SEQUENCE: 720
caucuuccag uacaguguug ga                                     22

<210> SEQ ID NO 721
<211> LENGTH: 22
<212> TYPE: RNA
<213> ORGANISM: Homo sapiens

<400> SEQUENCE: 721
uaacacuguc ugguaaagau gg                                     22

<210> SEQ ID NO 722
<211> LENGTH: 22
<212> TYPE: RNA
<213> ORGANISM: Homo sapiens

<400> SEQUENCE: 722
cagugguuuu acccuauggu ag                                     22

<210> SEQ ID NO 723
<211> LENGTH: 21
<212> TYPE: RNA
<213> ORGANISM: Homo sapiens

<400> SEQUENCE: 723
uaccacaggg uagaaccacg g                                      21

<210> SEQ ID NO 724
<211> LENGTH: 22
<212> TYPE: RNA
<213> ORGANISM: Homo sapiens

<400> SEQUENCE: 724
ucuacagugc acgugucucc ag                                     22

<210> SEQ ID NO 725
<211> LENGTH: 22
<212> TYPE: RNA
<213> ORGANISM: Homo sapiens

<400> SEQUENCE: 725
ggagacgcgg cccuguugga gu                                     22

<210> SEQ ID NO 726
<211> LENGTH: 22
<212> TYPE: RNA
<213> ORGANISM: Homo sapiens

<400> SEQUENCE: 726
gcuauuucac gacaccaggg uu                                     22

```
<210> SEQ ID NO 727
<211> LENGTH: 22
<212> TYPE: RNA
<213> ORGANISM: Homo sapiens

<400> SEQUENCE: 727
gcuacuucac aacaccaggg cc                                              22

<210> SEQ ID NO 728
<211> LENGTH: 23
<212> TYPE: RNA
<213> ORGANISM: Homo sapiens

<400> SEQUENCE: 728
agcugguguu gugaaucagg ccg                                             23

<210> SEQ ID NO 729
<211> LENGTH: 23
<212> TYPE: RNA
<213> ORGANISM: Homo sapiens

<400> SEQUENCE: 729
uuauugcuua agaauacgcg uag                                             23

<210> SEQ ID NO 730
<211> LENGTH: 22
<212> TYPE: RNA
<213> ORGANISM: Homo sapiens

<400> SEQUENCE: 730
caucaucguc ucaaaugagu cu                                              22

<210> SEQ ID NO 731
<211> LENGTH: 23
<212> TYPE: RNA
<213> ORGANISM: Homo sapiens

<400> SEQUENCE: 731
acuccauuug uuuugaugau gga                                             23

<210> SEQ ID NO 732
<211> LENGTH: 22
<212> TYPE: RNA
<213> ORGANISM: Homo sapiens

<400> SEQUENCE: 732
auguagggcu aaaagccaug gg                                              22

<210> SEQ ID NO 733
<211> LENGTH: 23
<212> TYPE: RNA
<213> ORGANISM: Homo sapiens

<400> SEQUENCE: 733
uauggcuuuu cauuccuaug uga                                             23

<210> SEQ ID NO 734
<211> LENGTH: 22
<212> TYPE: RNA
<213> ORGANISM: Homo sapiens

<400> SEQUENCE: 734
```

```
uauagggauu ggagccgugg cg                                          22

<210> SEQ ID NO 735
<211> LENGTH: 23
<212> TYPE: RNA
<213> ORGANISM: Homo sapiens

<400> SEQUENCE: 735
uauggcuuuu uauuccuaug uga                                         23

<210> SEQ ID NO 736
<211> LENGTH: 22
<212> TYPE: RNA
<213> ORGANISM: Homo sapiens

<400> SEQUENCE: 736
ugugacuggu ugaccagagg gg                                          22

<210> SEQ ID NO 737
<211> LENGTH: 22
<212> TYPE: RNA
<213> ORGANISM: Homo sapiens

<400> SEQUENCE: 737
uuuggucccc uucaaccagc ua                                          22

<210> SEQ ID NO 738
<211> LENGTH: 22
<212> TYPE: RNA
<213> ORGANISM: Homo sapiens

<400> SEQUENCE: 738
uuuggucccc uucaaccagc ug                                          22

<210> SEQ ID NO 739
<211> LENGTH: 24
<212> TYPE: RNA
<213> ORGANISM: Homo sapiens

<400> SEQUENCE: 739
ccagacagaa uucuaugcac uuuc                                        24

<210> SEQ ID NO 740
<211> LENGTH: 22
<212> TYPE: RNA
<213> ORGANISM: Homo sapiens

<400> SEQUENCE: 740
ucaaaacuga ggggcauuuu cu                                          22

<210> SEQ ID NO 741
<211> LENGTH: 19
<212> TYPE: RNA
<213> ORGANISM: Homo sapiens

<400> SEQUENCE: 741
gaugaugcug cugaugcug                                              19

<210> SEQ ID NO 742
<211> LENGTH: 18
<212> TYPE: RNA
<213> ORGANISM: Homo sapiens

<400> SEQUENCE: 742
```

-continued cagggaggug aaugugau                                                    18

<210> SEQ ID NO 743
<211> LENGTH: 22
<212> TYPE: RNA
<213> ORGANISM: Homo sapiens

<400> SEQUENCE: 743
accguggcuu ucgauuguua cu                                               22

<210> SEQ ID NO 744
<211> LENGTH: 22
<212> TYPE: RNA
<213> ORGANISM: Homo sapiens

<400> SEQUENCE: 744
uaacagucua cagccauggu cg                                               22

<210> SEQ ID NO 745
<211> LENGTH: 21
<212> TYPE: RNA
<213> ORGANISM: Homo sapiens

<400> SEQUENCE: 745
acucuuuccc uguugcacua c                                                21

<210> SEQ ID NO 746
<211> LENGTH: 22
<212> TYPE: RNA
<213> ORGANISM: Homo sapiens

<400> SEQUENCE: 746
cagugcaaug augaaagggc au                                               22

<210> SEQ ID NO 747
<211> LENGTH: 22
<212> TYPE: RNA
<213> ORGANISM: Homo sapiens

<400> SEQUENCE: 747
uucacauugu gcuacugucu gc                                               22

<210> SEQ ID NO 748
<211> LENGTH: 22
<212> TYPE: RNA
<213> ORGANISM: Homo sapiens

<400> SEQUENCE: 748
cagugcaaug uuaaaagggc au                                               22

<210> SEQ ID NO 749
<211> LENGTH: 18
<212> TYPE: RNA
<213> ORGANISM: Homo sapiens

<400> SEQUENCE: 749
gcaugggugg uucagugg                                                    18

<210> SEQ ID NO 750
<211> LENGTH: 22
<212> TYPE: RNA
<213> ORGANISM: Homo sapiens

<400> SEQUENCE: 750
acucggcgug gcgucggucg ug                                          22

<210> SEQ ID NO 751
<211> LENGTH: 18
<212> TYPE: RNA
<213> ORGANISM: Homo sapiens

<400> SEQUENCE: 751
acguuggcuc uggugguG                                               18

<210> SEQ ID NO 752
<211> LENGTH: 22
<212> TYPE: RNA
<213> ORGANISM: Homo sapiens

<400> SEQUENCE: 752
uuuucaacuc uaaugggaga ga                                          22

<210> SEQ ID NO 753
<211> LENGTH: 22
<212> TYPE: RNA
<213> ORGANISM: Homo sapiens

<400> SEQUENCE: 753
uuugaggcua cagugagaug ug                                          22

<210> SEQ ID NO 754
<211> LENGTH: 22
<212> TYPE: RNA
<213> ORGANISM: Homo sapiens

<400> SEQUENCE: 754
uuuagagacg gggucuugcu cu                                          22

<210> SEQ ID NO 755
<211> LENGTH: 21
<212> TYPE: RNA
<213> ORGANISM: Homo sapiens

<400> SEQUENCE: 755
uugggacaua cuuaugcuaa a                                           21

<210> SEQ ID NO 756
<211> LENGTH: 24
<212> TYPE: RNA
<213> ORGANISM: Homo sapiens

<400> SEQUENCE: 756
uugcagcugc cugggaguga cuuc                                        24

<210> SEQ ID NO 757
<211> LENGTH: 22
<212> TYPE: RNA
<213> ORGANISM: Homo sapiens

<400> SEQUENCE: 757
uucuggaauu cugugugagg ga                                          22

<210> SEQ ID NO 758
<211> LENGTH: 22
<212> TYPE: RNA
<213> ORGANISM: Homo sapiens -continued

```
<400> SEQUENCE: 758
uucauucggc uguccagaug ua                                    22

<210> SEQ ID NO 759
<211> LENGTH: 17
<212> TYPE: RNA
<213> ORGANISM: Homo sapiens

<400> SEQUENCE: 759
uucaaguaau ucaggug                                          17

<210> SEQ ID NO 760
<211> LENGTH: 22
<212> TYPE: RNA
<213> ORGANISM: Homo sapiens

<400> SEQUENCE: 760
uuagggcccu ggcuccaucu cc                                    22

<210> SEQ ID NO 761
<211> LENGTH: 21
<212> TYPE: RNA
<213> ORGANISM: Homo sapiens

<400> SEQUENCE: 761 cuuuugcgg ucugggcuug c                                      21

<210> SEQ ID NO 762
<211> LENGTH: 21
<212> TYPE: RNA
<213> ORGANISM: Homo sapiens

<400> SEQUENCE: 762
uuaggccgca gaucugggug a                                     21

<210> SEQ ID NO 763
<211> LENGTH: 22
<212> TYPE: RNA
<213> ORGANISM: Homo sapiens

<400> SEQUENCE: 763
ugugagguug gcauuguugu cu                                    22

<210> SEQ ID NO 764
<211> LENGTH: 22
<212> TYPE: RNA
<213> ORGANISM: Homo sapiens

<400> SEQUENCE: 764
aagcccuuac cccaaaaagc au                                    22

<210> SEQ ID NO 765
<211> LENGTH: 22
<212> TYPE: RNA
<213> ORGANISM: Homo sapiens

<400> SEQUENCE: 765 ugggugggucu ggagauuugu gc                                   22

<210> SEQ ID NO 766
<211> LENGTH: 25
<212> TYPE: RNA
```

```
<213> ORGANISM: Homo sapiens

<400> SEQUENCE: 766
ugggaacggg uuccggcaga cgcug                                      25

<210> SEQ ID NO 767
<211> LENGTH: 24
<212> TYPE: RNA
<213> ORGANISM: Homo sapiens

<400> SEQUENCE: 767
uggcccugac ugaagaccag cagu                                       24

<210> SEQ ID NO 768
<211> LENGTH: 19
<212> TYPE: RNA
<213> ORGANISM: Homo sapiens

<400> SEQUENCE: 768
uggauuuuug gaucaggga                                             19

<210> SEQ ID NO 769
<211> LENGTH: 22
<212> TYPE: RNA
<213> ORGANISM: Homo sapiens

<400> SEQUENCE: 769
aagcccuuac cccaaaaagu au                                         22

<210> SEQ ID NO 770
<211> LENGTH: 23
<212> TYPE: RNA
<213> ORGANISM: Homo sapiens

<400> SEQUENCE: 770
uggaguccag gaaucugcau uuu                                        23

<210> SEQ ID NO 771
<211> LENGTH: 21
<212> TYPE: RNA
<213> ORGANISM: Homo sapiens

<400> SEQUENCE: 771
uggacugccc ugaucuggag a                                          21

<210> SEQ ID NO 772
<211> LENGTH: 22
<212> TYPE: RNA
<213> ORGANISM: Homo sapiens

<400> SEQUENCE: 772
ugcuggauca gugguucgag uc                                         22

<210> SEQ ID NO 773
<211> LENGTH: 21
<212> TYPE: RNA
<213> ORGANISM: Homo sapiens

<400> SEQUENCE: 773
ugcaggacca agaugagccc u                                          21

<210> SEQ ID NO 774
<211> LENGTH: 22
```

```
<212> TYPE: RNA
<213> ORGANISM: Homo sapiens

<400> SEQUENCE: 774
ucugggcaac aaagugagac cu                                              22

<210> SEQ ID NO 775
<211> LENGTH: 22
<212> TYPE: RNA
<213> ORGANISM: Homo sapiens

<400> SEQUENCE: 775
ucuauacaga cccuggcuuu uc                                              22

<210> SEQ ID NO 776
<211> LENGTH: 22
<212> TYPE: RNA
<213> ORGANISM: Homo sapiens

<400> SEQUENCE: 776
ucuacaaagg aaagcgcuuu cu                                              22

<210> SEQ ID NO 777
<211> LENGTH: 20
<212> TYPE: RNA
<213> ORGANISM: Homo sapiens

<400> SEQUENCE: 777
ucguuugccu uuucugcuu                                                  20

<210> SEQ ID NO 778
<211> LENGTH: 17
<212> TYPE: RNA
<213> ORGANISM: Homo sapiens

<400> SEQUENCE: 778
ucgccuccuc cucuccc                                                    17

<210> SEQ ID NO 779
<211> LENGTH: 17
<212> TYPE: RNA
<213> ORGANISM: Homo sapiens

<400> SEQUENCE: 779
ucccaccgcu gccaccc                                                    17

<210> SEQ ID NO 780
<211> LENGTH: 21
<212> TYPE: RNA
<213> ORGANISM: Homo sapiens

<400> SEQUENCE: 780
ucacagugaa ccggucucuu u                                               21

<210> SEQ ID NO 781
<211> LENGTH: 17
<212> TYPE: RNA
<213> ORGANISM: Homo sapiens

<400> SEQUENCE: 781
ucauauugcu ucuuucu                                                    17

<210> SEQ ID NO 782
```

```
<211> LENGTH: 22
<212> TYPE: RNA
<213> ORGANISM: Homo sapiens

<400> SEQUENCE: 782
uaguacugug cauaucaucu au                                              22

<210> SEQ ID NO 783
<211> LENGTH: 22
<212> TYPE: RNA
<213> ORGANISM: Homo sapiens

<400> SEQUENCE: 783
uacguagaua uauauguauu uu                                              22

<210> SEQ ID NO 784
<211> LENGTH: 20
<212> TYPE: RNA
<213> ORGANISM: Homo sapiens

<400> SEQUENCE: 784
uaaagagccc uguggagaca                                                 20

<210> SEQ ID NO 785
<211> LENGTH: 22
<212> TYPE: RNA
<213> ORGANISM: Homo sapiens

<400> SEQUENCE: 785
cugaagcuca gagggcucug au                                              22

<210> SEQ ID NO 786
<211> LENGTH: 17
<212> TYPE: RNA
<213> ORGANISM: Homo sapiens

<400> SEQUENCE: 786 guggggaga ggcuguc                                                     17

<210> SEQ ID NO 787
<211> LENGTH: 17
<212> TYPE: RNA
<213> ORGANISM: Homo sapiens

<400> SEQUENCE: 787
ucccuguucg ggcgcca                                                    17

<210> SEQ ID NO 788
<211> LENGTH: 18
<212> TYPE: RNA
<213> ORGANISM: Homo sapiens

<400> SEQUENCE: 788
gucccuguuc aggcgcca                                                   18

<210> SEQ ID NO 789
<211> LENGTH: 22
<212> TYPE: RNA
<213> ORGANISM: Homo sapiens

<400> SEQUENCE: 789
ucggauccgu cugagcuugg cu                                              22
```

```
<210> SEQ ID NO 790
<211> LENGTH: 25
<212> TYPE: RNA
<213> ORGANISM: Homo sapiens

<400> SEQUENCE: 790
gggcgacaaa gcaagacucu uucuu                                         25

<210> SEQ ID NO 791
<211> LENGTH: 26
<212> TYPE: RNA
<213> ORGANISM: Homo sapiens

<400> SEQUENCE: 791
gaugaugaug gcagcaaauu cugaaa                                        26

<210> SEQ ID NO 792
<211> LENGTH: 22
<212> TYPE: RNA
<213> ORGANISM: Homo sapiens

<400> SEQUENCE: 792
cuuggcaccu agcaagcacu ca                                            22

<210> SEQ ID NO 793
<211> LENGTH: 23
<212> TYPE: RNA
<213> ORGANISM: Homo sapiens

<400> SEQUENCE: 793
cuggagauau ggaagagcug ugu                                           23

<210> SEQ ID NO 794
<211> LENGTH: 22
<212> TYPE: RNA
<213> ORGANISM: Homo sapiens

<400> SEQUENCE: 794
cuggacugag ccgugcuacu gg                                            22

<210> SEQ ID NO 795
<211> LENGTH: 18
<212> TYPE: RNA
<213> ORGANISM: Homo sapiens

<400> SEQUENCE: 795
cgggcguggu gguggggg                                                 18

<210> SEQ ID NO 796
<211> LENGTH: 21
<212> TYPE: RNA
<213> ORGANISM: Homo sapiens

<400> SEQUENCE: 796
ccuguugaag uguaaucccc a                                             21

<210> SEQ ID NO 797
<211> LENGTH: 23
<212> TYPE: RNA
<213> ORGANISM: Homo sapiens

<400> SEQUENCE: 797
ccucagggcu guagaacagg gcu                                           23
```

<210> SEQ ID NO 798
<211> LENGTH: 22
<212> TYPE: RNA
<213> ORGANISM: Homo sapiens

<400> SEQUENCE: 798
caggaugugg ucaaguguug uu                                              22

<210> SEQ ID NO 799
<211> LENGTH: 23
<212> TYPE: RNA
<213> ORGANISM: Homo sapiens

<400> SEQUENCE: 799
caagucuuau uugagcaccu guu                                             23

<210> SEQ ID NO 800
<211> LENGTH: 22
<212> TYPE: RNA
<213> ORGANISM: Homo sapiens

<400> SEQUENCE: 800
augguacccu ggcauacuga gu                                              22

<210> SEQ ID NO 801
<211> LENGTH: 22
<212> TYPE: RNA
<213> ORGANISM: Homo sapiens

<400> SEQUENCE: 801
augggugaau uuguagaagg au                                              22

<210> SEQ ID NO 802
<211> LENGTH: 19
<212> TYPE: RNA
<213> ORGANISM: Homo sapiens

<400> SEQUENCE: 802
auggauaagg cuuuggcuu                                                  19

<210> SEQ ID NO 803
<211> LENGTH: 18
<212> TYPE: RNA
<213> ORGANISM: Homo sapiens

<400> SEQUENCE: 803
aucccaccuc ugccacca                                                   18

<210> SEQ ID NO 804
<211> LENGTH: 21
<212> TYPE: RNA
<213> ORGANISM: Homo sapiens

<400> SEQUENCE: 804
cauuauuacu uuugguacgc g                                               21

<210> SEQ ID NO 805
<211> LENGTH: 22
<212> TYPE: RNA
<213> ORGANISM: Homo sapiens

<400> SEQUENCE: 805
ucguaccgug aguaauaaug cg                                              22

```
<210> SEQ ID NO 806
<211> LENGTH: 22
<212> TYPE: RNA
<213> ORGANISM: Homo sapiens

<400> SEQUENCE: 806
ucacaaguca ggcucuuggg ac                                          22

<210> SEQ ID NO 807
<211> LENGTH: 22
<212> TYPE: RNA
<213> ORGANISM: Homo sapiens

<400> SEQUENCE: 807
acggguuagg cucuugggag cu                                          22

<210> SEQ ID NO 808
<211> LENGTH: 22
<212> TYPE: RNA
<213> ORGANISM: Homo sapiens

<400> SEQUENCE: 808
ucccugagac ccuaacuugu ga                                          22

<210> SEQ ID NO 809
<211> LENGTH: 24
<212> TYPE: RNA
<213> ORGANISM: Homo sapiens

<400> SEQUENCE: 809
ucccugagac ccuuuaaccu guga                                        24

<210> SEQ ID NO 810
<211> LENGTH: 22
<212> TYPE: RNA
<213> ORGANISM: Homo sapiens

<400> SEQUENCE: 810
acaggugagg uucuugggag cc                                          22

<210> SEQ ID NO 811
<211> LENGTH: 21
<212> TYPE: RNA
<213> ORGANISM: Homo sapiens

<400> SEQUENCE: 811
auauaugaug acuuagcuuu u                                           21

<210> SEQ ID NO 812
<211> LENGTH: 21
<212> TYPE: RNA
<213> ORGANISM: Homo sapiens

<400> SEQUENCE: 812
aguuaggauu aggucgugga a                                           21

<210> SEQ ID NO 813
<211> LENGTH: 21
<212> TYPE: RNA
<213> ORGANISM: Homo sapiens

<400> SEQUENCE: 813
```

```
agugaaugau ggguucugac c                                              21

<210> SEQ ID NO 814
<211> LENGTH: 22
<212> TYPE: RNA
<213> ORGANISM: Homo sapiens

<400> SEQUENCE: 814
aggcauugac uucucacuag cu                                             22

<210> SEQ ID NO 815
<211> LENGTH: 22
<212> TYPE: RNA
<213> ORGANISM: Homo sapiens

<400> SEQUENCE: 815
cggaugagca aagaaagugg uu                                             22

<210> SEQ ID NO 816
<211> LENGTH: 23
<212> TYPE: RNA
<213> ORGANISM: Homo sapiens

<400> SEQUENCE: 816
aggaugagca aagaaaguag auu                                            23

<210> SEQ ID NO 817
<211> LENGTH: 24
<212> TYPE: RNA
<213> ORGANISM: Homo sapiens

<400> SEQUENCE: 817
agccuggaag cuggagccug cagu                                           24

<210> SEQ ID NO 818
<211> LENGTH: 21
<212> TYPE: RNA
<213> ORGANISM: Homo sapiens

<400> SEQUENCE: 818
agagaagaag aucagccugc a                                              21

<210> SEQ ID NO 819
<211> LENGTH: 22
<212> TYPE: RNA
<213> ORGANISM: Homo sapiens

<400> SEQUENCE: 819
agaaggaaau ugaauucauu ua                                             22

<210> SEQ ID NO 820
<211> LENGTH: 21
<212> TYPE: RNA
<213> ORGANISM: Homo sapiens

<400> SEQUENCE: 820
acucuagcug ccaaaggcgc u                                              21

<210> SEQ ID NO 821
<211> LENGTH: 21
<212> TYPE: RNA
<213> ORGANISM: Homo sapiens

<400> SEQUENCE: 821
```

```
acggugcugg auguggccuu u                                          21

<210> SEQ ID NO 822
<211> LENGTH: 22
<212> TYPE: RNA
<213> ORGANISM: Homo sapiens

<400> SEQUENCE: 822
acgcccuucc ccccuucuu ca                                          22

<210> SEQ ID NO 823
<211> LENGTH: 27
<212> TYPE: RNA
<213> ORGANISM: Homo sapiens

<400> SEQUENCE: 823
accuucuugu auaagcacug ugcuaaa                                    27

<210> SEQ ID NO 824
<211> LENGTH: 22
<212> TYPE: RNA
<213> ORGANISM: Homo sapiens

<400> SEQUENCE: 824
acccgucccg uucgucccg ga                                          22

<210> SEQ ID NO 825
<211> LENGTH: 19
<212> TYPE: RNA
<213> ORGANISM: Homo sapiens

<400> SEQUENCE: 825
aauggauuuu uggagcagg                                             19

<210> SEQ ID NO 826
<211> LENGTH: 21
<212> TYPE: RNA
<213> ORGANISM: Homo sapiens

<400> SEQUENCE: 826
aagugaucua aaggccuaca u                                          21

<210> SEQ ID NO 827
<211> LENGTH: 26
<212> TYPE: RNA
<213> ORGANISM: Homo sapiens

<400> SEQUENCE: 827
aaguaguugg uuuguaugag augguu                                     26

<210> SEQ ID NO 828
<211> LENGTH: 22
<212> TYPE: RNA
<213> ORGANISM: Homo sapiens

<400> SEQUENCE: 828
aacuggauca auuauaggag ug                                         22

<210> SEQ ID NO 829
<211> LENGTH: 22
<212> TYPE: RNA
<213> ORGANISM: Homo sapiens
```

```
<400> SEQUENCE: 829
cguguucaca gcggaccuug au                                                    22

<210> SEQ ID NO 830
<211> LENGTH: 20
<212> TYPE: RNA
<213> ORGANISM: Homo sapiens

<400> SEQUENCE: 830
uaaggcacgc ggugaaugcc                                                       20

<210> SEQ ID NO 831
<211> LENGTH: 20
<212> TYPE: RNA
<213> ORGANISM: Homo sapiens

<400> SEQUENCE: 831
cuuccucguc ugucugcccc                                                       20

<210> SEQ ID NO 832
<211> LENGTH: 21
<212> TYPE: RNA
<213> ORGANISM: Homo sapiens

<400> SEQUENCE: 832
uccuucugcu ccguccccca g                                                     21

<210> SEQ ID NO 833
<211> LENGTH: 22
<212> TYPE: RNA
<213> ORGANISM: Homo sapiens

<400> SEQUENCE: 833
ccucuucccc uugucucucc ag                                                    22

<210> SEQ ID NO 834
<211> LENGTH: 22
<212> TYPE: RNA
<213> ORGANISM: Homo sapiens

<400> SEQUENCE: 834
ucggccugac cacccacccc ac                                                    22

<210> SEQ ID NO 835
<211> LENGTH: 20
<212> TYPE: RNA
<213> ORGANISM: Homo sapiens

<400> SEQUENCE: 835
ugagcccugu ccucccgcag                                                       20

<210> SEQ ID NO 836
<211> LENGTH: 20
<212> TYPE: RNA
<213> ORGANISM: Homo sapiens

<400> SEQUENCE: 836
gugucugggc ggacagcugc                                                       20

<210> SEQ ID NO 837
<211> LENGTH: 23
<212> TYPE: RNA
<213> ORGANISM: Homo sapiens
```

<400> SEQUENCE: 837
cucucaccac ugcccuccca cag                                    23

<210> SEQ ID NO 838
<211> LENGTH: 21
<212> TYPE: RNA
<213> ORGANISM: Homo sapiens

<400> SEQUENCE: 838
gugggcgggg gcaggugugu g                                      21

<210> SEQ ID NO 839
<211> LENGTH: 20
<212> TYPE: RNA
<213> ORGANISM: Homo sapiens

<400> SEQUENCE: 839
ucacaccugc cucgccccc                                         20

<210> SEQ ID NO 840
<211> LENGTH: 20
<212> TYPE: RNA
<213> ORGANISM: Homo sapiens

<400> SEQUENCE: 840
cgugccaccc uuuucccag                                         20

<210> SEQ ID NO 841
<211> LENGTH: 26
<212> TYPE: RNA
<213> ORGANISM: Homo sapiens

<400> SEQUENCE: 841
gugagggcau gcaggccugg augggg                                 26

<210> SEQ ID NO 842
<211> LENGTH: 22
<212> TYPE: RNA
<213> ORGANISM: Homo sapiens

<400> SEQUENCE: 842
ucaccagccc uguguucccu ag                                     22

<210> SEQ ID NO 843
<211> LENGTH: 22
<212> TYPE: RNA
<213> ORGANISM: Homo sapiens

<400> SEQUENCE: 843
guggguacgg cccagugggg gg                                     22

<210> SEQ ID NO 844
<211> LENGTH: 22
<212> TYPE: RNA
<213> ORGANISM: Homo sapiens

<400> SEQUENCE: 844 ugagcccug ugccgccccc ag                                      22

<210> SEQ ID NO 845
<211> LENGTH: 19
<212> TYPE: RNA

```
<213> ORGANISM: Homo sapiens

<400> SEQUENCE: 845
gugaggacuc gggaggugg                                           19

<210> SEQ ID NO 846
<211> LENGTH: 21
<212> TYPE: RNA
<213> ORGANISM: Homo sapiens

<400> SEQUENCE: 846
ccccaccucc ucucuccuca g                                        21

<210> SEQ ID NO 847
<211> LENGTH: 22
<212> TYPE: RNA
<213> ORGANISM: Homo sapiens

<400> SEQUENCE: 847
aacgccauua ucacacuaaa ua                                       22

<210> SEQ ID NO 848
<211> LENGTH: 22
<212> TYPE: RNA
<213> ORGANISM: Homo sapiens

<400> SEQUENCE: 848
uggaguguga caauguguu ug                                        22

<210> SEQ ID NO 849
<211> LENGTH: 20
<212> TYPE: RNA
<213> ORGANISM: Homo sapiens

<400> SEQUENCE: 849
ucacuguuca gacaggcgga                                          20

<210> SEQ ID NO 850
<211> LENGTH: 21
<212> TYPE: RNA
<213> ORGANISM: Homo sapiens

<400> SEQUENCE: 850
uggcagggag gcugggaggg g                                        21

<210> SEQ ID NO 851
<211> LENGTH: 18
<212> TYPE: RNA
<213> ORGANISM: Homo sapiens

<400> SEQUENCE: 851
ucagcuggcc cucauuuc                                            18

<210> SEQ ID NO 852
<211> LENGTH: 21
<212> TYPE: RNA
<213> ORGANISM: Homo sapiens

<400> SEQUENCE: 852
uguucaugua gauguuuaag c                                        21

<210> SEQ ID NO 853
<211> LENGTH: 20
```

```
<212> TYPE: RNA
<213> ORGANISM: Homo sapiens

<400> SEQUENCE: 853
ucugcagggu uugcuuugag                                              20

<210> SEQ ID NO 854
<211> LENGTH: 21
<212> TYPE: RNA
<213> ORGANISM: Homo sapiens

<400> SEQUENCE: 854
ucguggccug gucuccauua u                                            21

<210> SEQ ID NO 855
<211> LENGTH: 21
<212> TYPE: RNA
<213> ORGANISM: Homo sapiens

<400> SEQUENCE: 855
cccggagcca ggaugcagcu c                                            21

<210> SEQ ID NO 856
<211> LENGTH: 21
<212> TYPE: RNA
<213> ORGANISM: Homo sapiens

<400> SEQUENCE: 856
gugccagcug cagugggga g                                             21

<210> SEQ ID NO 857
<211> LENGTH: 24
<212> TYPE: RNA
<213> ORGANISM: Homo sapiens

<400> SEQUENCE: 857
agccugauua aacacaugcu cuga                                         24

<210> SEQ ID NO 858
<211> LENGTH: 22
<212> TYPE: RNA
<213> ORGANISM: Homo sapiens

<400> SEQUENCE: 858
cuccugagcc auucugagcc uc                                           22

<210> SEQ ID NO 859
<211> LENGTH: 21
<212> TYPE: RNA
<213> ORGANISM: Homo sapiens

<400> SEQUENCE: 859
uaggacacau ggucuacuuc u                                            21

<210> SEQ ID NO 860
<211> LENGTH: 21
<212> TYPE: RNA
<213> ORGANISM: Homo sapiens

<400> SEQUENCE: 860
agaggauacc cuuuguaugu u                                            21

<210> SEQ ID NO 861
```

```
<211> LENGTH: 23
<212> TYPE: RNA
<213> ORGANISM: Homo sapiens

<400> SEQUENCE: 861
ccugcagcga cuugauggcu ucc                                               23

<210> SEQ ID NO 862
<211> LENGTH: 27
<212> TYPE: RNA
<213> ORGANISM: Homo sapiens

<400> SEQUENCE: 862
cacuguaggu gauggugaga gugggca                                           27

<210> SEQ ID NO 863
<211> LENGTH: 23
<212> TYPE: RNA
<213> ORGANISM: Homo sapiens

<400> SEQUENCE: 863
gagggucuug ggagggaugu gac                                               23

<210> SEQ ID NO 864
<211> LENGTH: 21
<212> TYPE: RNA
<213> ORGANISM: Homo sapiens

<400> SEQUENCE: 864
ccgucgccgc cacccgagcc g                                                 21

<210> SEQ ID NO 865
<211> LENGTH: 22
<212> TYPE: RNA
<213> ORGANISM: Homo sapiens

<400> SEQUENCE: 865
uuuccggcuc gcguggugu gu                                                 22

<210> SEQ ID NO 866
<211> LENGTH: 21
<212> TYPE: RNA
<213> ORGANISM: Homo sapiens

<400> SEQUENCE: 866
aagcauucuu ucauugguug g                                                 21

<210> SEQ ID NO 867
<211> LENGTH: 21
<212> TYPE: RNA
<213> ORGANISM: Homo sapiens

<400> SEQUENCE: 867
uugcucacug uucuucccua g                                                 21

<210> SEQ ID NO 868
<211> LENGTH: 22
<212> TYPE: RNA
<213> ORGANISM: Homo sapiens

<400> SEQUENCE: 868
acagauucga uucuagggga au                                                22
```

```
<210> SEQ ID NO 869
<211> LENGTH: 23
<212> TYPE: RNA
<213> ORGANISM: Homo sapiens

<400> SEQUENCE: 869
uacccuguag aaccgaauuu gug                                              23

<210> SEQ ID NO 870
<211> LENGTH: 22
<212> TYPE: RNA
<213> ORGANISM: Homo sapiens

<400> SEQUENCE: 870
caaauucgua ucuaggggaa ua                                               22

<210> SEQ ID NO 871
<211> LENGTH: 23
<212> TYPE: RNA
<213> ORGANISM: Homo sapiens

<400> SEQUENCE: 871
uacccuguag auccgaauuu gug                                              23

<210> SEQ ID NO 872
<211> LENGTH: 23
<212> TYPE: RNA
<213> ORGANISM: Homo sapiens

<400> SEQUENCE: 872
agcagcauug uacagggcua uca                                              23

<210> SEQ ID NO 873
<211> LENGTH: 22
<212> TYPE: RNA
<213> ORGANISM: Homo sapiens

<400> SEQUENCE: 873
ccgcacugug gguacuugcu gc                                               22

<210> SEQ ID NO 874
<211> LENGTH: 21
<212> TYPE: RNA
<213> ORGANISM: Homo sapiens

<400> SEQUENCE: 874
uaaagugcug acagugcaga u                                                21

<210> SEQ ID NO 875
<211> LENGTH: 22
<212> TYPE: RNA
<213> ORGANISM: Homo sapiens

<400> SEQUENCE: 875
cugcaaugua agcacuucuu ac                                               22

<210> SEQ ID NO 876
<211> LENGTH: 23
<212> TYPE: RNA
<213> ORGANISM: Homo sapiens

<400> SEQUENCE: 876
aaaagugcuu acagugcagg uag                                              23
```

```
<210> SEQ ID NO 877
<211> LENGTH: 22
<212> TYPE: RNA
<213> ORGANISM: Homo sapiens

<400> SEQUENCE: 877
acggauguuu gagcaugugc ua                                                  22

<210> SEQ ID NO 878
<211> LENGTH: 23
<212> TYPE: RNA
<213> ORGANISM: Homo sapiens

<400> SEQUENCE: 878
ucaaaugcuc agacuccugu ggu                                                 23

<210> SEQ ID NO 879
<211> LENGTH: 23
<212> TYPE: RNA
<213> ORGANISM: Homo sapiens

<400> SEQUENCE: 879
ucauagcccu guacaaugcu gcu                                                 23

<210> SEQ ID NO 880
<211> LENGTH: 23
<212> TYPE: RNA
<213> ORGANISM: Homo sapiens

<400> SEQUENCE: 880
agcuucuuua cagugcugcc uug                                                 23

<210> SEQ ID NO 881
<211> LENGTH: 23
<212> TYPE: RNA
<213> ORGANISM: Homo sapiens

<400> SEQUENCE: 881
agcagcauug uacagggcua uga                                                 23

<210> SEQ ID NO 882
<211> LENGTH: 22
<212> TYPE: RNA
<213> ORGANISM: Homo sapiens

<400> SEQUENCE: 882
caguuaucac agugcugaug cu                                                  22

<210> SEQ ID NO 883
<211> LENGTH: 21
<212> TYPE: RNA
<213> ORGANISM: Homo sapiens

<400> SEQUENCE: 883
uacaguacug ugauaacuga a                                                   21

<210> SEQ ID NO 884
<211> LENGTH: 22
<212> TYPE: RNA
<213> ORGANISM: Homo sapiens

<400> SEQUENCE: 884
caagcuugua ucuauaggua ug                                                  22
```

```
<210> SEQ ID NO 885
<211> LENGTH: 22
<212> TYPE: RNA
<213> ORGANISM: Homo sapiens

<400> SEQUENCE: 885
aacccguaga uccgaacuug ug                                              22

<210> SEQ ID NO 886
<211> LENGTH: 22
<212> TYPE: RNA
<213> ORGANISM: Homo sapiens

<400> SEQUENCE: 886
uggaauguaa agaaguaugu au                                              22

<210> SEQ ID NO 887
<211> LENGTH: 22
<212> TYPE: RNA
<213> ORGANISM: Homo sapiens

<400> SEQUENCE: 887
cugcgcaagc uacugccuug cu                                              22

<210> SEQ ID NO 888
<211> LENGTH: 22
<212> TYPE: RNA
<213> ORGANISM: Homo sapiens

<400> SEQUENCE: 888
ugagguagua guuugugcug uu                                              22

<210> SEQ ID NO 889
<211> LENGTH: 21
<212> TYPE: RNA
<213> ORGANISM: Homo sapiens

<400> SEQUENCE: 889
cuguacaggc cacugccuug c                                               21

<210> SEQ ID NO 890
<211> LENGTH: 22
<212> TYPE: RNA
<213> ORGANISM: Homo sapiens

<400> SEQUENCE: 890
ugagguagua guuuguacag uu                                              22

<210> SEQ ID NO 891
<211> LENGTH: 22
<212> TYPE: RNA
<213> ORGANISM: Homo sapiens

<400> SEQUENCE: 891
cuauacaguc uacugucuuu cc                                              22

<210> SEQ ID NO 892
<211> LENGTH: 22
<212> TYPE: RNA
<213> ORGANISM: Homo sapiens

<400> SEQUENCE: 892
```
cuauacaauc uauugccuuc cc                                             22

<210> SEQ ID NO 893
<211> LENGTH: 22
<212> TYPE: RNA
<213> ORGANISM: Homo sapiens

<400> SEQUENCE: 893
ugagguagua gauuguauag uu                                             22

<210> SEQ ID NO 894
<211> LENGTH: 22
<212> TYPE: RNA
<213> ORGANISM: Homo sapiens

<400> SEQUENCE: 894
cuauacggcc uccuagcuuu cc                                             22

<210> SEQ ID NO 895
<211> LENGTH: 22
<212> TYPE: RNA
<213> ORGANISM: Homo sapiens

<400> SEQUENCE: 895
ugagguagga gguuguauag uu                                             22

<210> SEQ ID NO 896
<211> LENGTH: 22
<212> TYPE: RNA
<213> ORGANISM: Homo sapiens

<400> SEQUENCE: 896
cuauacgacc ugcugccuuu cu                                             22

<210> SEQ ID NO 897
<211> LENGTH: 22
<212> TYPE: RNA
<213> ORGANISM: Homo sapiens

<400> SEQUENCE: 897
agagguagua gguugcauag uu                                             22

<210> SEQ ID NO 898
<211> LENGTH: 22
<212> TYPE: RNA
<213> ORGANISM: Homo sapiens

<400> SEQUENCE: 898
uagaguuaca cccugggagu ua                                             22

<210> SEQ ID NO 899
<211> LENGTH: 22
<212> TYPE: RNA
<213> ORGANISM: Homo sapiens

<400> SEQUENCE: 899
ugagguagua gguuguaugg uu                                             22

<210> SEQ ID NO 900
<211> LENGTH: 22
<212> TYPE: RNA
<213> ORGANISM: Homo sapiens

<400> SEQUENCE: 900

-continued

| | |
|---|---|
| cuauacaacc uacugccuuc cc | 22 |

<210> SEQ ID NO 901
<211> LENGTH: 22
<212> TYPE: RNA
<213> ORGANISM: Homo sapiens

<400> SEQUENCE: 901

| | |
|---|---|
| ugagguagua gguugugugg uu | 22 |

<210> SEQ ID NO 902
<211> LENGTH: 22
<212> TYPE: RNA
<213> ORGANISM: Homo sapiens

<400> SEQUENCE: 902

| | |
|---|---|
| cuguacagcc uccuagcuuu cc | 22 |

<210> SEQ ID NO 903
<211> LENGTH: 21
<212> TYPE: RNA
<213> ORGANISM: Homo sapiens

<400> SEQUENCE: 903

| | |
|---|---|
| cuauacaauc uacugucuuu c | 21 |

<210> SEQ ID NO 904
<211> LENGTH: 22
<212> TYPE: RNA
<213> ORGANISM: Homo sapiens

<400> SEQUENCE: 904

| | |
|---|---|
| ugagguagua gguuguauag uu | 22 |

<210> SEQ ID NO 905
<211> LENGTH: 22
<212> TYPE: RNA
<213> ORGANISM: Homo sapiens

<400> SEQUENCE: 905

| | |
|---|---|
| uaauacugcc ugguaaugau ga | 22 |

<210> SEQ ID NO 906
<211> LENGTH: 21
<212> TYPE: RNA
<213> ORGANISM: Homo sapiens

<400> SEQUENCE: 906

| | |
|---|---|
| cucuccucuc cuaaccucgc u | 21 |

<210> SEQ ID NO 907
<211> LENGTH: 23
<212> TYPE: RNA
<213> ORGANISM: Homo sapiens

<400> SEQUENCE: 907

| | |
|---|---|
| agucgagagu gggagaagag cgg | 23 |

<210> SEQ ID NO 908
<211> LENGTH: 19
<212> TYPE: RNA
<213> ORGANISM: Homo sapiens

```
<400> SEQUENCE: 908
aaaaccgucu aguuacagu                                                    19

<210> SEQ ID NO 909
<211> LENGTH: 23
<212> TYPE: RNA
<213> ORGANISM: Homo sapiens

<400> SEQUENCE: 909
cucagugaug aaaacuuugu cca                                               23

<210> SEQ ID NO 910
<211> LENGTH: 21
<212> TYPE: RNA
<213> ORGANISM: Homo sapiens

<400> SEQUENCE: 910
guugccuuuu uguucccaug c                                                 21

<210> SEQ ID NO 911
<211> LENGTH: 21
<212> TYPE: RNA
<213> ORGANISM: Homo sapiens

<400> SEQUENCE: 911
uaggcaccaa aaagcaacaa c                                                 21

<210> SEQ ID NO 912
<211> LENGTH: 21
<212> TYPE: RNA
<213> ORGANISM: Homo sapiens

<400> SEQUENCE: 912
gcugcaccgg agacugggua a                                                 21

<210> SEQ ID NO 913
<211> LENGTH: 21
<212> TYPE: RNA
<213> ORGANISM: Homo sapiens

<400> SEQUENCE: 913
uacccagucu ccggugcagc c                                                 21

<210> SEQ ID NO 914
<211> LENGTH: 24
<212> TYPE: RNA
<213> ORGANISM: Homo sapiens

<400> SEQUENCE: 914
uuccucugau gacuuccugu uagu                                              24

<210> SEQ ID NO 915
<211> LENGTH: 21
<212> TYPE: RNA
<213> ORGANISM: Homo sapiens

<400> SEQUENCE: 915
uggaacugag gaucugagga a                                                 21

<210> SEQ ID NO 916
<211> LENGTH: 21
<212> TYPE: RNA
<213> ORGANISM: Homo sapiens
```

```
<400> SEQUENCE: 916
aguggcaaag ucuuuccaua u                                              21

<210> SEQ ID NO 917
<211> LENGTH: 22
<212> TYPE: RNA
<213> ORGANISM: Homo sapiens

<400> SEQUENCE: 917
uuagcucagc gguuacuucg ac                                             22

<210> SEQ ID NO 918
<211> LENGTH: 21
<212> TYPE: RNA
<213> ORGANISM: Homo sapiens

<400> SEQUENCE: 918
caagcaaccu gucuggguug u                                              21

<210> SEQ ID NO 919
<211> LENGTH: 19
<212> TYPE: RNA
<213> ORGANISM: Homo sapiens

<400> SEQUENCE: 919
uaacgcauaa uauggacau                                                 19

<210> SEQ ID NO 920
<211> LENGTH: 21
<212> TYPE: RNA
<213> ORGANISM: Homo sapiens

<400> SEQUENCE: 920
auguccauau uauggguuag u                                              21

<210> SEQ ID NO 921
<211> LENGTH: 21
<212> TYPE: RNA
<213> ORGANISM: Homo sapiens

<400> SEQUENCE: 921
caguugcuag uugcacuccu c                                              21

<210> SEQ ID NO 922
<211> LENGTH: 21
<212> TYPE: RNA
<213> ORGANISM: Homo sapiens

<400> SEQUENCE: 922
aggcagugua uugcuagcgg c                                              21

<210> SEQ ID NO 923
<211> LENGTH: 21
<212> TYPE: RNA
<213> ORGANISM: Homo sapiens

<400> SEQUENCE: 923
aguucuugcc ugguuucucu a                                              21

<210> SEQ ID NO 924
<211> LENGTH: 18
<212> TYPE: RNA
```

```
<213> ORGANISM: Homo sapiens

<400> SEQUENCE: 924
ucugcauugc cagggauu                                              18

<210> SEQ ID NO 925
<211> LENGTH: 19
<212> TYPE: RNA
<213> ORGANISM: Homo sapiens

<400> SEQUENCE: 925
uagcuuuaga gacugagag                                             19

<210> SEQ ID NO 926
<211> LENGTH: 23
<212> TYPE: RNA
<213> ORGANISM: Homo sapiens

<400> SEQUENCE: 926
ugagacaggc uuaugcugcu auc                                        23

<210> SEQ ID NO 927
<211> LENGTH: 21
<212> TYPE: RNA
<213> ORGANISM: Homo sapiens

<400> SEQUENCE: 927
agcagcauga accugucuca c                                          21

<210> SEQ ID NO 928
<211> LENGTH: 21
<212> TYPE: RNA
<213> ORGANISM: Homo sapiens

<400> SEQUENCE: 928
ccggcggcag ggguggcacc g                                          21

<210> SEQ ID NO 929
<211> LENGTH: 20
<212> TYPE: RNA
<213> ORGANISM: Homo sapiens

<400> SEQUENCE: 929
gccuuaggag aaaguuucug                                            20

<210> SEQ ID NO 930
<211> LENGTH: 19
<212> TYPE: RNA
<213> ORGANISM: Homo sapiens

<400> SEQUENCE: 930
uccuaaggca gucccugga                                             19

<210> SEQ ID NO 931
<211> LENGTH: 21
<212> TYPE: RNA
<213> ORGANISM: Homo sapiens

<400> SEQUENCE: 931
aaggucgccc ucaaggugac c                                          21

<210> SEQ ID NO 932
<211> LENGTH: 21
```

```
<212> TYPE: RNA
<213> ORGANISM: Homo sapiens

<400> SEQUENCE: 932
augccuggga guugcgaucu g                                              21

<210> SEQ ID NO 933
<211> LENGTH: 21
<212> TYPE: RNA
<213> ORGANISM: Homo sapiens

<400> SEQUENCE: 933
uggaguuaaa gacuuuuucu c                                              21

<210> SEQ ID NO 934
<211> LENGTH: 24
<212> TYPE: RNA
<213> ORGANISM: Homo sapiens

<400> SEQUENCE: 934
cagagaauag uuuaaauuag aauc                                           24

<210> SEQ ID NO 935
<211> LENGTH: 23
<212> TYPE: RNA
<213> ORGANISM: Homo sapiens

<400> SEQUENCE: 935
ugcaacuuac ugagggcuuu gaa                                            23

<210> SEQ ID NO 936
<211> LENGTH: 21
<212> TYPE: RNA
<213> ORGANISM: Homo sapiens

<400> SEQUENCE: 936
uggggutuug caguccuuag c                                              21

<210> SEQ ID NO 937
<211> LENGTH: 21
<212> TYPE: RNA
<213> ORGANISM: Homo sapiens

<400> SEQUENCE: 937
agacacuaua cgagucauau a                                              21

<210> SEQ ID NO 938
<211> LENGTH: 21
<212> TYPE: RNA
<213> ORGANISM: Homo sapiens

<400> SEQUENCE: 938
auaggacuca uauagugcca g                                              21

<210> SEQ ID NO 939
<211> LENGTH: 22
<212> TYPE: RNA
<213> ORGANISM: Homo sapiens

<400> SEQUENCE: 939
auccccagau acaauggaca au                                             22

<210> SEQ ID NO 940
```

-continued

```
<211> LENGTH: 23
<212> TYPE: RNA
<213> ORGANISM: Homo sapiens

<400> SEQUENCE: 940
uucaccuguu agccugucca gag                                              23

<210> SEQ ID NO 941
<211> LENGTH: 23
<212> TYPE: RNA
<213> ORGANISM: Homo sapiens

<400> SEQUENCE: 941
ugacagcgcc cugccuggcu cgg                                              23

<210> SEQ ID NO 942
<211> LENGTH: 23
<212> TYPE: RNA
<213> ORGANISM: Homo sapiens

<400> SEQUENCE: 942
agcgcgggcu gagcgcugcc agu                                              23

<210> SEQ ID NO 943
<211> LENGTH: 22
<212> TYPE: RNA
<213> ORGANISM: Homo sapiens

<400> SEQUENCE: 943
uauacuacau auaauauaug ua                                               22

<210> SEQ ID NO 944
<211> LENGTH: 22
<212> TYPE: RNA
<213> ORGANISM: Homo sapiens

<400> SEQUENCE: 944
uauacuacau auaauauaug ua                                               22

<210> SEQ ID NO 945
<211> LENGTH: 23
<212> TYPE: RNA
<213> ORGANISM: Homo sapiens

<400> SEQUENCE: 945
uagcaccauc ugaaaucggu uau                                              23

<210> SEQ ID NO 946
<211> LENGTH: 22
<212> TYPE: RNA
<213> ORGANISM: Homo sapiens

<400> SEQUENCE: 946
gugcaaaagu caucacgguu uu                                               22

<210> SEQ ID NO 947
<211> LENGTH: 21
<212> TYPE: RNA
<213> ORGANISM: Homo sapiens

<400> SEQUENCE: 947
accgcgauga cuuuugcauc a                                                21
```

```
<210> SEQ ID NO 948
<211> LENGTH: 23
<212> TYPE: RNA
<213> ORGANISM: Homo sapiens

<400> SEQUENCE: 948
ucaccgcggu cuuuccucc cac                                              23

<210> SEQ ID NO 949
<211> LENGTH: 21
<212> TYPE: RNA
<213> ORGANISM: Homo sapiens

<400> SEQUENCE: 949
uuggggaaac ggccgcugag u                                               21

<210> SEQ ID NO 950
<211> LENGTH: 21
<212> TYPE: RNA
<213> ORGANISM: Homo sapiens

<400> SEQUENCE: 950
uccucccaug ccaagaacuc c                                               21

<210> SEQ ID NO 951
<211> LENGTH: 21
<212> TYPE: RNA
<213> ORGANISM: Homo sapiens

<400> SEQUENCE: 951
gguucuuagc auaggagguc u                                               21

<210> SEQ ID NO 952
<211> LENGTH: 22
<212> TYPE: RNA
<213> ORGANISM: Homo sapiens

<400> SEQUENCE: 952
cugcgugucc cuaggugagg gg                                              22

<210> SEQ ID NO 953
<211> LENGTH: 22
<212> TYPE: RNA
<213> ORGANISM: Homo sapiens

<400> SEQUENCE: 953
ggcacagggc gaguggaaag aa                                              22

<210> SEQ ID NO 954
<211> LENGTH: 22
<212> TYPE: RNA
<213> ORGANISM: Homo sapiens

<400> SEQUENCE: 954
ucacuaccug acaauacagu au                                              22

<210> SEQ ID NO 955
<211> LENGTH: 22
<212> TYPE: RNA
<213> ORGANISM: Homo sapiens

<400> SEQUENCE: 955
ugcuguauug ucagguagug au                                              22
```

```
<210> SEQ ID NO 956
<211> LENGTH: 24
<212> TYPE: RNA
<213> ORGANISM: Homo sapiens

<400> SEQUENCE: 956
uggaggugau gaacugucug agcc                                              24

<210> SEQ ID NO 957
<211> LENGTH: 21
<212> TYPE: RNA
<213> ORGANISM: Homo sapiens

<400> SEQUENCE: 957
ugcguguccc gccuguuccc u                                                 21

<210> SEQ ID NO 958
<211> LENGTH: 24
<212> TYPE: RNA
<213> ORGANISM: Homo sapiens

<400> SEQUENCE: 958
ugugcugauu gucacguucu gauu                                              24

<210> SEQ ID NO 959
<211> LENGTH: 24
<212> TYPE: RNA
<213> ORGANISM: Homo sapiens

<400> SEQUENCE: 959
acagaugaug aacuuauuga cggg                                              24

<210> SEQ ID NO 960
<211> LENGTH: 23
<212> TYPE: RNA
<213> ORGANISM: Homo sapiens

<400> SEQUENCE: 960
accuuccucu ccaugggucu uuc                                               23

<210> SEQ ID NO 961
<211> LENGTH: 22
<212> TYPE: RNA
<213> ORGANISM: Homo sapiens

<400> SEQUENCE: 961
agacccauug aggagaaggu uc                                                22

<210> SEQ ID NO 962
<211> LENGTH: 21
<212> TYPE: RNA
<213> ORGANISM: Homo sapiens

<400> SEQUENCE: 962
uucucaagag ggaggcaauc a                                                 21

<210> SEQ ID NO 963
<211> LENGTH: 18
<212> TYPE: RNA
<213> ORGANISM: Homo sapiens

<400> SEQUENCE: 963
uugagaagga ggcugcug                                                     18
```

```
<210> SEQ ID NO 964
<211> LENGTH: 20
<212> TYPE: RNA
<213> ORGANISM: Homo sapiens

<400> SEQUENCE: 964
cuguaugccc ucaccgcuca                                              20

<210> SEQ ID NO 965
<211> LENGTH: 21
<212> TYPE: RNA
<213> ORGANISM: Homo sapiens

<400> SEQUENCE: 965
gucagcggag gaaaagaaac u                                            21
```

MIRNA FINGERPRINT IN THE DIAGNOSIS OF DISEASES

This application is a divisional of U.S. Ser. No. 13/376,225 filed Feb. 24, 2012, which is a 35 U.S.C. 371 National Phase Entry Application from PCT/EP2010/057944, filed Jun. 7, 2010, which claims the benefit of U.S. Provisional Applications Nos. 61/184,452 filed Jun. 5, 2009, 61/213,971 filed Aug. 3, 2009, 61/287,521 filed Dec. 17, 2009 and European Patent Application No. 09015668.8 filed on Dec. 17, 2009, the disclosures of which are incorporated herein in their entirety by reference.

BACKGROUND OF THE INVENTION

MicroRNAs (miRNA) are a recently discovered class of small non-coding RNAs (17-14 nucleotides). Due to their function as regulators of gene expression they play a critical role both in physiological and in pathological processes, such as cancer (Calin and Croce 2006; Esquela-Kerscher and Slack 2006; Zhang, Pan et al. 2007; Sassen, Miska et al. 2008).

There is increasing evidence that miRNAs are not only found in tissues but also in human blood both as free circulating nucleic acids (also called circulating miRNAs) and in mononuclear cells. A recent proof-of-principle study demonstrated miRNA expression pattern in pooled blood sera and pooled blood cells, both in healthy individuals and in cancer patients including patients with lung cancer (Chen, Ba et al. 2008). In addition, a remarkable stability of miRNAs in human sera was recently demonstrated (Chen, Ba et al. 2008; Gilad, Meiri et al. 2008). These findings make miRNA a potential tool for diagnostics for various types of diseases based on blood analysis.

Lung cancer is the leading cause of cancer death worldwide (Jemal, Siegel et al. 2008). Its five-year survival rate is among the lowest of all cancer types and is markedly correlated to the stage at the time of diagnosis (Scott, Howington et al. 2007). Using currently existing techniques, more than two-thirds of lung cancers are diagnosed at late stages, when the relative survival rate is low (Henschke and Yankelevitz 2008). This reality calls for the search of new biomarkers that are able to catch lung cancer while it is still small and locally defined.

Multiple sclerosis (MS, also known as disseminated sclerosis or encephalomyelitis disseminata) is an inflammatory autoimmune disease of the central nervous system (CNS). Causing MS appears to be a combination of immunological, genetic and environmental factors. It is a chronic demyelinating disease, which primarily affects young adults and is characterized by a highly variable course. The heterogeneous presentation of MS is characterized by a variety of clinical problems arising from multiple regions of demyelination and inflammation along axonal pathways. The signs and symptoms of MS are determined by the location of the affected regions.

Mostly, the disease begins in the third or fourth decade of life. Its initial course is characterized by acute episodes of neurological dysfunction, such as decreased vision, followed by subsequent recovery. This course is known as relapsing-remitting MS. Over time, the improvement after attacks may be incomplete and the relapsing-remitting course may evolve into one of increasing progression of disability, termed secondary progressive MS.

The diagnosis of MS generally relies on the presence of a neurological problem that remits and then returns at an unrelated site. This is confirmed by magnetic resonance imaging (MRI) or functional evidence of lesions in a particular pathway by abnormal evoked potentials. The histological hallmark of MS at postmortem exam is multiple lesions at different sites showing loss of myelin and infiltration by a characteristic complement of inflammatory cells.

The key to identifying predictive markers is a deeper understanding of the factors that underlie the therapeutic response. Identification of biomarkers will in turn allow for stratification of MS patients for their response to a specific treatment, ultimately leading to improved therapeutic benefits and a personalized treatment approach for MS patients.

Identification of reliable biomarkers in MS sclerosis patients bears the potential for an improved MS diagnosis, monitoring the disease activity and progression and also to evaluate response to treatments. The field of biomarker discovery has gradually shifted from the aim to find the perfect surrogate marker to the construction of composite markers with higher performances, taking advantage of technologies allowing unbiased screening, including microarray analyses. However, suitable biomarker sets allowing for a non-invasive diagnosis of MS based on peripheral profiles have not been detected, so far.

The three most common skin cancers are basal cell cancer, squamous cell cancer, and melanoma, each of which is named after the type of skin cell from which it arises. Skin cancer generally develops in the epidermis (the outermost layer of skin), so a tumor is usually clearly visible. This makes most skin cancers detectable in the early stages. Melanoma is less common than basal cell carcinoma and squamous cell carcinoma, but it is the most serious. Non-melanoma skin cancers are the most common skin cancers, and the majority of these are basal cell carcinomas (BCC). These are usually localized growths caused by excessive cumulative exposure to the sun and do not tend to spread. Basal cell carcinomas are present on sun-exposed areas of the skin, especially the face. They rarely metastasize, and rarely cause death. They are easily treated with surgery or radiation. Squamous cell carcinomas (SCC) are common, but much less common than basal cell cancers. They metastasize more frequently than BCCs. Even then, the metastasis rate is quite low, with the exception of SCCs of the lip, ear, and in immunosuppressed patients. Melanomas are the least frequent of the 3 common skin cancers. They frequently metastasize, and are deadly once spread.

Malignant melanoma represent the most aggressive form of skin cancer. The number of melanoma cases continues to increase in incidence, according to the World Health Organization (WHO) faster than that of any other type of cancer. Melanoma accounts for about 4% of skin cancer cases but for as many as 74% of all skin cancer deaths. The probability of surviving 5 years after the diagnosis drops to as low as 5% for advanced melanomas, or to even complete fatality (stage IV).

Currently, there is no promising standard therapy available for the treatment of melanomas in advanced stages. In order to improve prognosis and have a significant impact on decreasing mortality rates it is crucial to recognize this malignancy in its earliest forms. Considering metastasis to distinct organs happens very early in the progression of this disease, current research focuses on the development and improvement of early detection strategies. Only early surgical removal of the primary tumor increases the chance for the recovery of patients suffering from melanoma.

Thus, although various markers have been proposed to indicate specific types of disorders such as cancer, MS or melanoma such as malignant melanoma, there is still a need for more efficient and effective methods and compositions for the diagnosis of diseases.

SUMMARY OF THE INVENTION

The present invention provides novel methods for diagnosing diseases based on the determination of specific miRNAs that have altered expression levels in disease states compared to healthy controls or altered expression levels in a condition 1 (biological state or health state 1) compared to a condition 2 (biological state or health state 2).

Further, the present invention provides novel methods for diagnosing diseases based on the determination of specific miRNAs that have altered expression levels in disease states compared to healthy or other relevant controls. The present invention particularly provides novel methods for the diagnosis and/or prognosis and/or monitoring of melanoma or related diseases in human individuals based on miRNA analysis from samples derived from blood.

Definitions miRNA microRNAs (miRNA or μRNA) are single-stranded RNA molecules of ~21-23 nucleotides in length, which regulate gene expression. miRNAs are encoded by genes from whose DNA they are transcribed but miRNAs are not translated into protein (i.e. they are non-coding RNAs). The genes encoding miRNAs are much longer than the processed mature miRNA molecule; miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide or passenger strand, is degraded as a RISC substrate. Therefore the miRNA*s are derived from the same hairpin structure like the "normal" miRNAs. So if the "normal" miRNA is then later called the "mature miRNA" or "guided strand", the miRNA* is the passenger strand.

miRNA* (See Also Above "miRNA")

The miRNA*s, also known as the anti-guide or passenger strand, are mostly complementary to the guide strand, but there are usually single-stranded overhangs on each end, there is usually one or a few mispairs and there are sometimes extra or missing bases causing single-stranded "bubbles. The miRNA*s are likely to act in a regulatory fashion as the miRNAs. It is understood that according to the present invention the term "miRNA" also includes the term "miRNA*".

MiRNA-(Expression) Profile or miRNA Fingerprint

A miRNA-Profile represents the collection of expression levels of a plurality of miRNAs, therefore it is a quantitative measure of individual miRNA expression levels. Hereby, each miRNA is represented by a numerical value. The higher the value of an individual miRNA the higher is the expression level of this miRNA. A miRNA-profile is obtained from the RNA of a biological sample. The are various technologies to determine a miRNA-Profile, e.g. microarrays, RT-PCR, Next Generation Sequencing. As a starting material for analysis, RNA or total-RNA or any fraction thereof can be used. The plurality of miRNAs that are determined by a miRNA-profile can range from a selection of one up to all known miRNAs.

Pre-determined Set of miRNAs or miRNA Signature

The pre-determined set of miRNAs or miRNA signature is understood in the present invention as a fixed defined set of miRNAs which is able to differentiate between a condition 1 and another condition 2. e.g. when condition 1 is lung cancer and condition 2 is normal control, the corresponding pre-determined set of miRNAs is able to differentiate between a samples derived from a lung cancer patient or a normal control patient. Alternatively, condition 1 is lung cancer and condition 2 is multiple sclerosis, the corresponding pre-determined set of miRNAs is able to differentiate between a lung cancer patient and a multiple sclerosis patient. In order to be able to perform the sample analysis it is required that, e.g. on the matrix that will be used to determine a miRNA profile, these fixed defined set of miRNAs have to be represented by capture probes that are defined by the pre-determined set of miRNAs. For example, when the predetermined set of miRNAs for diagnosing lung cancer from healthy controls consists of 25 miRNAs, probes capable for detecting these 25 miRNAs have to be implemented for performing the diagnostic analysis.

Common miRNA Signature Profile

A common miRNA signature profile is understood in the present invention as a non-fixed defined set of miRNAs or non-coding RNAs which is able to differentiate between a condition 1 and another condition 2. The common miRNA or non-coding RNA signature profile is calculated "on-the-fly" from a plurality of miRNA-profiles that are stored, e.g. in database. The common miRNA signature profile which is able to differentiate between a condition 1 and another condition 2 is changing as soon as an new profile is added to the database which is relevant to either to state of health 1 or another condition 2. In this respect it is different from a predetermined set of miRNAs (see above). Furthermore, the basis for generating the common miRNA signature profile—hence the miRNA profiles stored in the database—is generated from capture probes, e.g. on a matrix that is representing as much as possible different capture probes for detecting as much as possible, ideally all known, miRNAs.

Non-coding RNA

A non-coding RNA (ncRNA) is a functional RNA molecule that is not translated into a protein. Less-frequently used synonyms are non-protein-coding RNA (npcRNA), non-messenger RNA (nmRNA), small non-messenger RNA (snmRNA), functional RNA (fRNA). The term small RNA (sRNA) is often used for bacterial ncRNAs. The DNA sequence from which a non-coding RNA is transcribed as the end product is often called an RNA gene or non-coding RNA gene.

Non-coding RNA genes include highly abundant and functionally important RNAs such as transfer RNA (tRNA) and ribosomal RNA (rRNA), as well as RNAs such as snoRNAs, microRNAs, siRNAs and piRNAs and the long ncRNAs that include examples such as Xist and HOTAIR (see here for a more complete list of ncRNAs). The number of ncRNAs encoded within the human genome is unknown, however recent transcriptomic and bioinformatic studies suggest the existence of thousands of ncRNAs. Since most of the newly identified ncRNAs have not been validated for their function, it is possible that many are non-functional.

Condition

A condition (biological state or health state) is understood in the present invention as status of a subject that can be described by physical, mental or social criteria. It includes as well so-called "healthy" and "diseased" conditions, therefore it is not limited to the WHO definition of health as "a state of complete physical, mental, and social well-being and not merely the absence of disease or infirmity." but includes disease and infirmity. For the definition of diseases comprised, e.g. by the conditions of the present invention, it is referred to the international classification of diseases (ICD) of the WHO (http://www.who.int/classifications/icd/en/index.html). When 2 or more conditions are compared according to the present invention, it is understood that this is possible for all conditions that can be defined and is not limited to a comparison of a disease versus healthy and extends to multi-way comparisons. Examples for comparison are, but not limited to:

Pairwise Comparisons:
- lung cancer vs. healthy control, pancreatic cancer vs. healthy control
- lung cancer vs. pancreatic cancer, lung cancer vs. multiple sclerosis
- lung cancer WHO grade 1 vs. lung cancer WHO grade 2
- lung cancer WHO grade 1 metastasing vs. lung cancer WHO grade 1 non-metastasing
- Morbus Crohn vs. collitis
- Pancreatic cancer vs. pancreatitis Multi-Way Comparisons:
- Lung cancer vs. pancreatic cancer vs. multiple sclerosis
- Pancreas cancer vs. pancreatitis vs. lung cancer WHO grade 1 non-metastasing A "biological sample" in terms of the invention means a sample of biological tissue or fluid. Examples of biological samples are sections of tissues, blood, blood fractions, plasma, serum, urine or samples from other peripheral sources, or cell cultures, cell colonies of even single cells, or a collection of single cells. Furthermore, also pools or mixture of the above mentioned samples may be employed. A biological sample may be provided by removing a sample of cells from a subject, but can also be provided by using a previously isolated sample. For example, a tissue sample can be removed from a subject suspected of having a disease by conventional biopsy techniques. In a preferred embodiment, a blood sample is taken from the subject. In one embodiment, the blood or tissue sample is obtained from the subject prior to initiation of radiotherapy, chemotherapy or other therapeutic treatment. According to the invention, the biological sample preferably is a blood, plasma or PBMC (peripheral blood mononuclear cell) or a serum sample. Further, it is also preferred to use blood cells, e.g. PBMC, erythrocytes, leukocytes or thrombocytes.

A biological sample from a patient means a sample from a subject suspected to be affected by a disease, or is at risk, or has the disease. As used herein, the term "subject" refers to any mammal, including both human and other mammals. Preferably, the methods of the present invention are applied to human subjects.

Subject-matter of the invention is a method for diagnosing a disease, particularly skin cancer such as melanoma, basal cell carcinoma, or squamous cell carcinoma, or related diseases comprising the steps (a) determining an expression profile of a predetermined set of miRNAs in a biological sample from a patient; and
(b) comparing said expression profile to a reference expression profile, wherein the comparison of said determined expression profile to said reference expression profile allows for the diagnosis of the disease.

In step (a) of the above method of the invention, an expression profile of a predetermined set of miRNAs is determined. The determination may be carried out by any convenient means for determining nucleic acids. For expression profiling, qualitative, semi-quantitative and preferably quantitative detection methods can be used. A variety of techniques are well known to those of skill in the art. In particular, the determination may comprise nucleic acid hybridization and/or nucleic acid amplification steps.

Nucleic acid hybridization may for example be performed using a solid phase nucleic acid biochip array, in particular a microarray, beads, or in situ hybridization. The miRNA microarray technology affords the analysis of a complex biological sample for all expressed miRNAs. Nucleotides with complementarity to the corresponding miRNAs are spotted or synthesized on coated carriers. E.g. miRNAs isolated from the sample of interest are labelled, e.g. fluorescently labelled, so that upon hybridization of the miRNAs to the complementary sequences on the carrier the resulting signal indicates the occurrence of a distinct miRNA. Preferably, microarray methods are employed that do not require labeling of the miRNAs prior to hybridization (FIGS. 3-4) and start directly from total RNA input. On one miRNA microarray, preferably the whole predetermined set of miRNAs can be analyzed. Even more preferably a predetermined subset of miRNAs leading to sufficient performance (e.g. accuracy, specificity, sensitivity) regarding diagnosis of the disease/clinical condition may be analyzed. Examples of preferred hybridization assays are shown in FIGS. 1-4. The design of exemplary miRNA capture probes for use in hybridization assays is depicted in FIGS. 5 and 6.

Further, quantitative real-time polymerase chain reaction (qRT-PCR) can be used to detect miRNAs or sets of miRNAs, especially very low abundant miRNAs. Furthermore, bead-based assays, e.g. the luminex platform are also suitable.

Alternative methods for obtaining expression profiles may also contain sequencing, next generation sequencing or mass spectroscopy.

The predetermined set of miRNAs in step (a) of the above method of the invention depends on the disease/clinical condition to be diagnosed. The inventors found out that single miRNA biomarkers lack sufficient accuracy, specificity and sensitivity, and therefore it is preferred to analyze more complex miRNA expression patterns, so-called miRNA signatures. The predetermined set of miRNAs comprises one or more, preferably a larger number of miRNAs (miRNA signatures) that are differentially regulated in samples of a patient affected by a particular disease compared to healthy or other relevant controls. In certain embodiments, e.g. wherein Luminex, RT-PCR or qRT-PCR are employed to measure the predetermined sets of miRNAs, it is preferred that smaller subsets, e.g. of from 3, 4 or 5 and up to 10, 20, 30 or 50 miRNAs are analyzed.

The expression profile determined in the above step (a) is subsequently compared to a reference expression profile in the above step (b). The reference expression profile is the expression profile of the same set of miRNAs in a biological sample originating from the same source as the biological sample from a patient but e.g. obtained from a healthy subject. Preferably, both the reference expression profile and the expression profile of the above step (a) are determined in a blood, plasma, or including whole blood, plasma, serum or fractions thereof, or in a sample of peripheral blood mononuclear cells, erythrocytes, leukocytes and/or thrombocytes. It is understood that the reference expression profile is not necessarily obtained from a single healthy subject but may be an average expression profile of a plurality of healthy subjects. It is preferred to use a reference expression profile obtained from a person of the same gender, and a similar age as the patient. It is also understood that the reference expression profile is not necessarily determined for each test. Appropriate reference profiles stored in databases may also be used. These stored reference profiles may, e.g. be derived from previous tests. The relevant reference profile may also be a mathematical function or an algorithm which has been developed on the basis of a plurality of reference profiles and allows a diagnosis.

The above method of the invention is suitable for diagnosing any diseases for which a differential expression of miRNAs compared to healthy or other relevant controls exists. In particular, the method may be used for diagnosing cancer including bladder cancer, brain cancer, breast cancer, colon cancer, endometrium cancer, gastrointestinal stromal cancer, glioma, head- and neck cancer, kidney cancer, leukemia, liver cancer, lung cancer, lymph node cancer, skin cancer such as melanoma or non-melanoma skin cancer, meninges cancer, ovarian cancer, pancreas cancer, prostate cancer, sarcoma, stomach cancer, testicular cancer, thyroid cancer, thymus cancer and Wilm's tumor. The diagnosis may comprise determining type, rate and/or stage of cancer. The course of the disease and the success of therapy such as chemotherapy may be monitored. The method of the invention provides a prognosis on the survivor rate and enables to determine a patient's response to drugs.

In addition to cancer, also different types of diseases may be diagnosed by means of the above method of the invention, if the disease state is correlated with a differential expression of miRNAs compared to a healthy control. For example the disease may be Alzheimer's disease, multiple sclerosis, melanoma, Morbus Crohn and cardiovascular diseases. The inventors found out that also these diseases are correlated with a specific expression profile of miRNAs.

Figure 9:
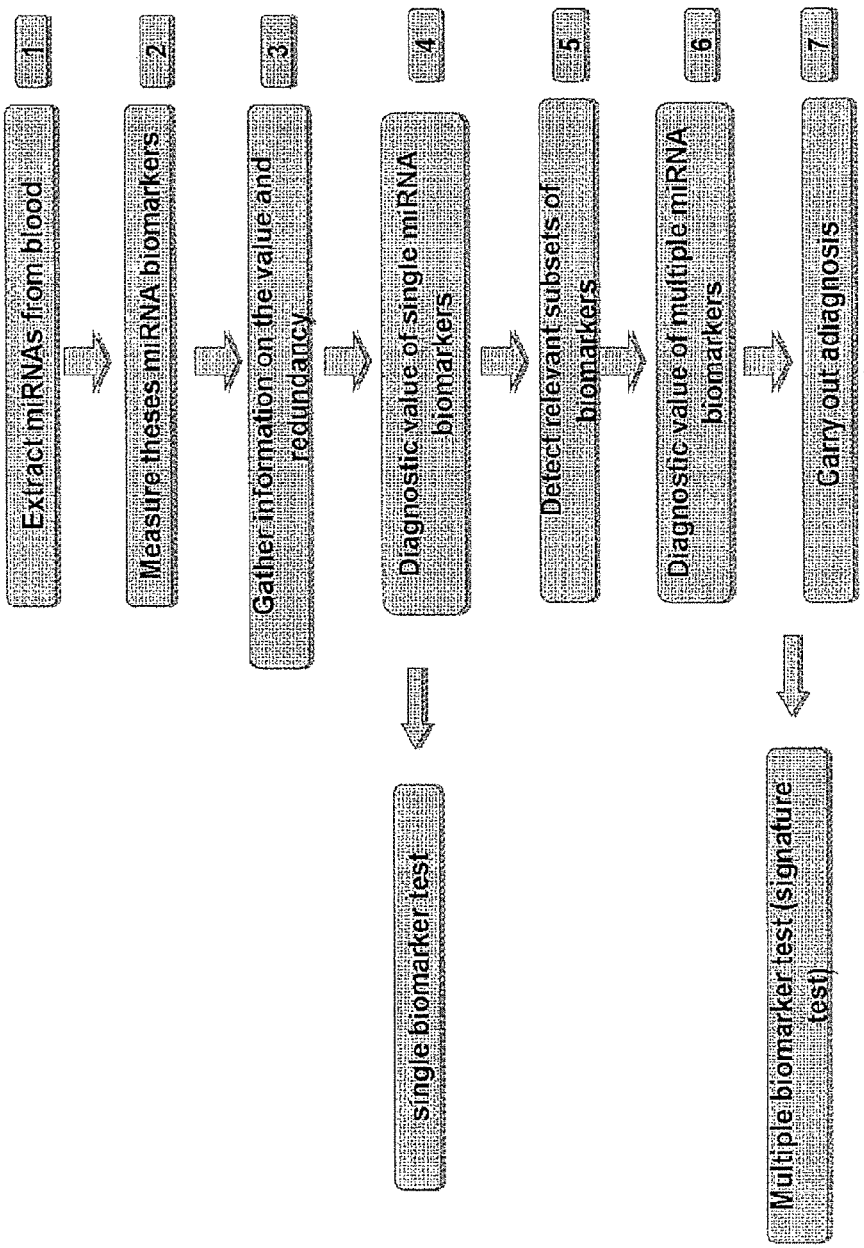

The inventors succeeded in developing a generally applicable approach to arrive at miRNA signatures that are correlated with a particular disease. The general workflow is depicted in FIG. 9. In more detail, the following steps are accomplished:

1. miRNAs are extracted from a biological sample of a patient, preferably a blood or serum or urine sample or a sample comprising erythrocytes, leukocytes or thrombocytes, using suitable kits/purification methods. From these samples preferably the RNA-fraction is used for analysis.
2. The respective samples are measured using experimental techniques. These techniques include but are not restricted to:
   Array based approaches
   Real time quantitative polymerase chain reaction
   bead based assays (e.g. Luminex)
   Sequencing
   Next Generation Sequencing
   Mass Spectroscopy
3. Mathematical approaches are applied to gather information on the value and the redundancy of single biomarkers. These methods include, but are not restricted to:
   basic mathematic approaches (e.g. Fold Quotients, Signal to Noise ratios, Correlation)
   statistical methods as hypothesis tests (e.g. t-test, Wilcoxon-Mann-Whitney test), the Area under the Receiver operator Characteristics Curve
   Information Theory approaches, (e.g. the Mutual Information, Cross-entropy)
   Probability theory (e.g. joint and conditional probabilities)
   Combinations and modifications of the previously mentioned examples
4. The information collected in 3) are used to estimate for each biomarker the diagnostic content or value. Usually, however, this diagnostic value is too small to get a highly accurate diagnosis with accuracy rates, specificities and sensitivities beyond the 90% barrier. Please note that the diagnostic content for our miRNAs can be found in the attached Figures. These Figures include the miRNAs with the sequences, the fold quotient, the mutual information and the significance value as computed by a t-test.
5. Thus statistical learning/machine learning/bioinformatics/ computational approaches are applied to define subsets of biomarkers that are tailored for the detection of diseases. These techniques includes but are not restricted to
   Wrapper subset selection techniques (e.g. forward step-wise, backward step-wise, combinatorial approaches, optimization approaches)
   Filter subset selection methods (e.g. the methods mentioned in 3)
   Principal Component Analysis
   Combinations and modifications of such methods (e.g. hybrid approaches)
6. The diagnostic content of each detected set can be estimated by mathematical and/or computational techniques to define the diagnostic information content of subsets.
7. The subsets, detected in step 5, which may range from only a small number (at least two) to all measured biomarkers is then used to carry out a diagnosis. To this end, statistical learning/machine learning/bioinformatics/ computational approaches are applied that include but are not restricted to any type of supervised or unsupervised analysis:
   Classification techniques (e.g. naïve Bayes, Linear Discriminant Analysis, Quadratic Discriminant Analysis Neural Nets, Tree based approaches, Support Vector Machines, Nearest Neighbour Approaches)
   Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression)
   Clustering techniques (e.g. k-means clustering, hierarchical clustering, PCA)
   Adaptations, extensions, and combinations of the previously mentioned approaches The inventors surprisingly found out that the described approach yields in miRNA signatures that provide high diagnostic accuracy, specificity and sensitivity in the determination of diseases.

According to a preferred embodiment of the invention, the disease to be determined is lung cancer, e.g. lung carcinoid, lung pleural mesothelioma or lung squamous cell carcinoma, in particular non-small cell lung carcinoma.

The inventors succeeded in determining miRNAs that are differentially regulated in samples from lung cancer patients as compared to healthy controls. A complete overview of all miRNAs that are found to be differentially regulated in blood samples of lung cancer patients is provided in the tables shown in FIGS. 10A, 10B and 11A. In the tables shown in FIGS. 10A, 10B and 11A, the miRNAs that are found to be differentially regulated are sorted in the order of their mutual information and in the order of their t-test significance as described in more detail below. Mutual information (MI) (Shannon, 1984) is an adequate measure to estimate the overall diagnostic information content of single biomarkers (Keller, Ludwig et al., 2006). According to the invention mutual information is considered as the reduction in uncertainty about the class labels "0" for controls and "1" for tumor samples due to the knowledge of the miRNA expression. The higher the value of the MI of a miRNA, the higher is the diagnostic content of the respective miRNA. The computation of the MI of each miRNA is explained in the experimental section below.

The miRNAs that provide the highest mutual information in samples from lung cancer patients compared to healthy controls are hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p, hsa-miR-324-3p (group (a)).

Figure 12:

Further, the measured miRNA profiles in samples from lung cancer patients compared to healthy controls were classified according to their significance in t-tests as described in more detail in the experimental section. The miRNAs that performed best according to the t-test results are hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p, hsa-miR-93* (group (b)). A comparison of a subset of 15 of these miRNAs is depicted in FIG. 12.

The miRNAs given above that have been grouped in the order of their performance in the t-tests or in the order of their MI-values provide the highest diagnostic power. Thus, preferably the predetermined set of miRNAs for the diagnosis of lung cancer comprises one or more nucleic acids selected from the above groups (a) and (b) of miRNAs. The predetermined set of miRNAs should preferably comprise at least 7, preferably at least 10, 15, 20 or 24 of the indicated nucleic acids. Most preferably, all of the above indicated miRNAs are included in the predetermined set of miRNAs. It is particularly preferred to include the 24, 20, 15, 10 or at least 7 of the first mentioned miRNAs in the order of their performance in the t-tests or of their MI-values. A comparison of the results obtained by determining 4, 8, 10, 16, 20, 24, 28 or 40 miRNAs provided in FIG. 13A-G shows that the accuracy of the diagnosis is improved, the more miRNAs are measured.

In a particularly preferred embodiment of the method of the invention, the predetermined set of miRNAs for diagnosis of lung cancer includes the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

In a further particularly preferred embodiment of the method of the invention, the miRNAs are selected from the miRNAs shown in FIG. 11A. Preferably, the predetermined set of miRNAs for the diagnosis of multiple sclerosis comprises one or more nucleic acids selected from the deregulated miRNAs presented in the tables in FIG. 10A, 10B or 11A. The predetermined set of miRNAs should preferably comprise at least 7, preferably at least 10, 15, 20 or 24 of the indicated nucleic acids. It is particularly preferred to include the 24, 20, 15, 10 or at least 7 of the first mentioned miRNAs according to their order in the tables in FIG. 10A, 10B or 11A.

In a still further embodiment, the predetermined set of miRNA molecules for the diagnosis of lung cancer comprises at least one preferred signature as shown in FIG. 11B. It should be noted that preferred diagnostic sets may also comprise one or more miRNAs of the miRNAs disclosed FIG. 11B, and any combination of the miRNAs together with one or more further diagnostically relevant miRNA from FIGS. 10A, 10B and 11A. Preferred predetermined sets of miRNA molecules based on FIG. 11B comprise at least 3, 4, 5, 6, 7, 8, 9 or 10 miRNAs and up to 10, 15 or 20 or more miRNAs.

For the diagnosis of different types of diseases, such as for a different type of cancer, a different predetermined set of miRNAs should be determined in step (a) of the method of the invention. The relevant miRNA signatures can be obtained according to the workflow depicted in FIG. 9 and as explained above.

According to another preferred embodiment of the invention, the disease to be determined is multiple sclerosis. Surprisingly, the inventors found out that miRNAs are differentially regulated in samples from MS patients as compared to health controls. A complete overview of all miRNAs that are found to be differentially regulated in blood samples of multiple sclerosis patients is provided in the table shown in FIGS. 18A, B and C. In one embodiment, 193 miRNAs were found to be significantly deregulated in blood cells of MS patients as compared to controls (FIG. 18A). In a further embodiment—based on additional information—165 miRNAs were found to be significantly deregulated in blood cells of MS patients as compared to controls (FIG. 18B). In a still further embodiment, 308 miRNAs were found to be significantly deregulated in blood cells of MS patients as compared to controls (FIG. 18C).

Preferably, the predetermined set of miRNAs for the diagnosis of multiple sclerosis comprises one or more nucleic acids selected from the deregulated miRNAs presented in the tables in FIG. 18A, 18B or 18C. The predetermined set of miRNAs should preferably comprise at least 7, preferably at least 10, 15, 20 or 24 of the indicated nucleic acids. It is particularly preferred to include the 24, 20, 15, 10 or at least 7 of the first mentioned miRNAs according to their order in the tables in FIG. 18A, 18B or 18C, preferably except hsa-miR-148a, hsa-mi18b, hsa-miR-96, hsa-miR-96, hsa-miR-599, hsa-miR-493, hsa-miR184, hsa-miR-193a.

Thus, preferably the predetermined set of miRNAs for the diagnosis of MS comprises one or more nucleic acids selected from the 24 most deregulated miRNAs hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p. Preferably, the predetermined set of miRNAs comprises at least 7, preferably at least 10, 15, 20 or all of the above-indicated nucleic acids. Most preferably, the predetermined set of miRNAs comprises those miRNAs that were most significantly deregulated: hsa-miR-145, hsa-miR-186, hsa-miR-664, hsa-miR-584, hsa-miR-20b, hsa-miR-223, hsa-miR-422a, hsa-miR-142-3p, hsa-let-7c.

In another embodiment, the predetermined set of miRNAs for the diagnosis of MS comprises at least one preferred signature 1-84 as shown in FIG. 18D. It should be noted that preferred diagnostic sets may also comprise one or more miRNAs of the miRNAs disclosed in FIG. 18D and any combination of the miRNAs together with one or more further diagnostically relevant miRNA from FIG. 18A, 18B or 18C. Preferred predetermined sets of miRNA molecules based on FIG. 18D comprise at least 3, 4, 5, 6, 7, 8, 9 or 10 miRNAs and up to 10, 15, or 20 or more miRNAs.

According to another preferred embodiment of the invention, the disease to be determined is melanoma. Surprisingly, the inventors found out that miRNAs are differentially regulated in samples from melanoma patients as compared to healthy controls. A complete overview of all miRNAs that are found to be differentially regulated in blood samples of melanoma patients is provided in the tables shown in FIG. 30A. In one embodiment 863 miRNAs, particularly the first 414 miRNAs, were found to be significantly deregulated in blood cells of melanoma patients as compared to the controls. The first 414 miRNAs are statistically of high relevance (p<0.05).

In a further embodiment, —based on additional information—353 miRNAs were found to be significantly deregulated in blood cells of melanoma patients as compared to controls (FIG. 30B).

Preferably, the predetermined set of miRNAs for the diagnosis of melanoma comprises one or more nucleic acids selected from the deregulated miRNAs presented in the table in FIG. 30A or 30B.

In a further embodiment, the measured miRNA profiles were classified using statistical learning approaches in order to compute accuracy, specificity, and sensitivity for the diagnosis of melanoma as described in more detail in the experimental section. The miRNAs that performed best for the diagnosis of melanoma according to their accuracy, specificity, and sensitivity are hsa-let-7d, hsa-miR-145, hsa-miR-664, hsa-miR-378*, hsa-miR-365, hsa-miR-328, hsa-miR-422a, hsa-miR-17*, hsa-miR-342-5p, hsa-miR-151-3p, hsa-miR-361-3p, hsa-miR-30a, hsa-miR-181-2*, hsa-miR-30e, hsa-miR-1227, hsa-let-7b*, hsa-miR-34a, hsa-miR-1301, hsa-miR-584, and hsa-miR-1286.

In a further embodiment the predetermined set of miRNAs for the diagnosis of melanoma comprises one or more miRNAs selected from the group consisting of hsa-miR-186, hsa-let-7d*, hsa-miR-18a*, hsa-miR-145, hsa-miR-99a, hsa-miR-664, hsa-miR-501-5p, hsa-miR-378*, hsa-miR-29c*, hsa-miR-1280, hsa-miR-365, hsa-miR-1249, hsa-miR-328, hsa-miR-422a, hsa-miR-30d, and hsa-miR-17*.

In still another embodiment, the predetermined set of miRNAs for the diagnosis of melanoma comprises one ore more miRNAs selected from the group consisting of hsa-miR-452*, hsa-miR-216a, hsa-miR-186, hsa-let-7d*, hsa-miR-17*, hsa-miR-646, hsa-miR-217, hsa-miR-621, hsa-miR-517*, hsa-miR-99a, hsa-miR-664, hsa-miR-593*, hsa-miR-18a*, hsa-miR-145, hsa-miR-1280, hsa-let-7i*, hsa-miR-422a, hsa-miR-330-3p, hsa-miR-767-5p, hsa-miR-183*, hsa-miR-1249, hsa-miR-20b, hsa-miR-509-3-5p, hsa-miR-519b-5p, hsa-miR-362-3p, hsa-miR-501-5p, hsa-miR-378*, hsa-miR-365, hsa-miR-151-3p, hsa-miR-342-5p, hsa-miR-328, hsa-miR-181a-2*, hsa-miR-518e*, hsa-miR-362-5p, hsa-miR-584, hsa-miR-550*, hsa-miR-30a, hsa-miR-221*, hsa-miR-361-3p, hsa-miR-625, hsa-miR-146a, hsa-miR-214, hsa-miR-106b, hsa-miR-18a, hsa-miR-30e*, hsa-miR-125a-5p, hsa-miR-142-3p, hsa-miR-107, hsa-miR-20a, hsa-miR-22* and hsa-miR-199a-5p.

In a further embodiment the present invention allows the detection of skin cancer, i.e. melanoma and non-melanoma skin cancer. FIG. 32A shows a list of especially preferred miRNAs suitable for the diagnosis of skin cancer, e.g. melanoma and non-melanoma skin cancer. FIG. 32B shows a list of especially preferred miRNAs suitable for the diagnosis of melanoma. The invention encompasses preferably the use of at least one miRNA from thoses lists, e.g. at least 5, preferably at least 10, 15, 20, 25, 30, 35, 40, 45 or more of those miRNAs.

In another embodiment, the predetermined set of miRNAs comprises at least one preferred signature 1 to 84 for the diagnosis of melanoma as shown in FIG. 33A. In another embodiment, the predetermined set of miRNAs comprises at least one preferred signature 1 to 42 as shown in FIG. 33B for the diagnosis of skin cancer includes melanoma and non-melanoma skin cancer. It should be noted that preferred diagnostic sets may also comprise one or more miRNAs of the miRNAs disclosed in FIGS. 33A and 33B and any combination of these miRNAs together with one or more further diagnostically relevant miRNA from FIGS. 30A, 30B, 32A and 32B. Preferred predetermined sets of miRNA molecules based on FIG. 33A or 33B comprise at least 3, 4, 5, 6, 7, 8, 9 or 10 miRNAs and up to 10, 15, 20 or more miRNAs.

Another embodiment of the present invention is a kit for diagnosing a disease, comprising means for determining an expression profile of a predetermined set of miRNAs in a biological sample, in particular in a blood, plasma and/or serum sample including whole blood, plasma, serum or fractions thereof, or in a sample comprising peripheral blood mononuclear cells, erythrocytes, leukocytes and/or thrombocytes. Preferably, one or more reference expression profiles are also provided which show the expression profile of the same set of miRNAs in the same type of biological sample, in particular in a blood and/or serum sample, obtained from one or more healthy subjects. A comparison to said reference expression profile(s) allows for the diagnosis of the disease.

The kit is preferably a test kit for detecting a predetermined set of miRNAs in sample by nucleic acid hybridisation and optionally amplification such as PCR or RT-PCR. The kit preferably comprises probes and/or primers for detecting a predetermined set of miRNAs. Further, the kit may comprise enzymes and reagents e.g. for the cDNA synthesis from miRNAs prior to qRT-PCR.

The kits for diagnosing diseases preferably comprise predetermined sets of miRNAs as described above, particularly for the diagnosis of lung cancer, multiple sclerosis and skin cancer, particularly melanoma as described above.

A kit for diagnosing lung cancer preferably comprises means for determining the expression profile of one or more miRNAs selected from the group (a) consisting of hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p and hsa-miR-324-3p.

According to another embodiment of the invention, the kit for diagnosing lung cancer preferably comprises means for determining the expression profile of one or more miRNAs selected from the group (b) consisting of hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p and hsa-miR-93*.

In a preferred embodiment, the kit comprises means for determining at least 7, preferably at least 10, 15, 20 or 24 miRNAs of the indicated groups of miRNAs. It is particularly preferred to include means for determining the 24, 20, 15, 10 or at least 7 of the first mentioned miRNAs in the order of their MI-values or their performance in the t-tests as shown in the tables in FIGS. 10A and 10B. Most preferably, means for determining all of the above indicated miRNAs are included in the kit for diagnosing lung cancer. The kit is particularly suitable for diagnosing lung cancer in a blood and/or serum sample or in a sample comprising erythrocytes, leukocytes and/or thrombocytes.

In a particularly preferred embodiment, the kit for the diagnosis of lung cancer comprises means for determining the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

Further, a kit for the diagnosis of lung cancer may comprise means for determining miRNAs selected from the miRNAs shown in FIGS. 11A and 11B as described above.

Another preferred embodiment of the present invention is a kit for diagnosing multiple sclerosis, comprising means for determining the expression profile of one or more miRNAs presented in the table in FIGS. 18A, B, C and D as described above.

Preferably the kit may comprise one or more miRNAs selected from the group consisting of hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p.

In a preferred embodiment the kit comprises means for determining at least seven, preferably at least 10, 15, 20 or all of the indicated miRNAs. It is particularly preferred to include means for determining the 24, 20, 15, 10 or at least 7 first mentioned miRNAs in the order of their diagnostic significance as represented by their order in the tables in FIG. 18A, 18B or 18C. Further, the kit may comprise means for determining the expression profile of a predetermined set of miRNAs based on FIG. 18D as described above.

The kit for diagnosing MS is particularly suitable for diagnosing MS in a blood, plasma and/or serum sample or in a sample comprising peripheral blood mononuclear cells, erythrocytes, leukocytes and/or thrombocytes.

Another preferred embodiment of the invention is a kit for diagnosing melanoma, or skin cancer including melanoma and non-melanoma skin cancer comprising means for determining the expression profile of one or more miRNAs presented in the table in FIGS. 30A and 30B, preferably one or more miRNAs selected from the group of hsa-let-7d, hsa-miR-145, hsa-miR-664, hsa-miR-378*, hsa-miR-365, hsa-miR-328, hsa-miR-422a, hsa-miR-17*, hsa-miR-342-5p, hsa-miR-151-3p, hsa-miR-361-3p, hsa-miR-30a, hsa-miR-181-2*, hsa-miR-30e, hsa-miR-1227, hsa-let-7b*, hsa-miR-34a, hsa-miR-1301, hsa-miR-584, and hsa-miR-1286 (see FIG. 31).

In a particularly preferred embodiment, the kit for diagnosing melanoma comprises means for determining the miRNAs hsa-miR-452*, hsa-miR-216a, hsa-miR-186, hsa-let-7d*, hsa-miR-17*, hsa-miR-646, hsa-miR-217, hsa-miR-621, hsa-miR-517*, hsa-miR-99a, hsa-miR-664, hsa-miR-593*, hsa-miR-18a*, hsa-miR-145, hsa-miR-1280, hsa-let-7i*, hsa-miR-422a, hsa-miR-330-3p, hsa-miR-767-5p, hsa-miR-183*, hsa-miR-1249, hsa-miR-20b, hsa-miR-509-3-5p, hsa-miR-519b-5p, hsa-miR-362-3p, hsa-miR-501-5p, hsa-miR-378*, hsa-miR-365, hsa-miR-151-3p, hsa-miR-342-5p, hsa-miR-328, hsa-miR-181a-2*, hsa-miR-518e*, hsa-miR-362-5p, hsa-miR-584, hsa-miR-550*, hsa-miR-30a, hsa-miR-221*, hsa-miR-361-3p, hsa-miR-625, hsa-miR-146a, hsa-miR-214, hsa-miR-106b, hsa-miR-18a, hsa-miR-30e*, hsa-miR-125a-5p, hsa-miR-142-3p, hsa-miR-107, hsa-miR-20a, hsa-miR-22* and hsa-miR-199a-5p.

In another particularly preferred embodiment, the kit for diagnosing melanoma comprises means for determining the miRNAs hsa-miR-186, hsa-let-7d*, hsa-miR-18a*, hsa-miR-145, hsa-miR-99a, hsa-miR-664, hsa-miR-501-5p, hsa-miR-378*, hsa-miR-29c*, hsa-miR-1280, hsa-miR-365, hsa-miR-1249, hsa-miR-328, hsa-miR-422a, hsa-miR-30d, and hsa-miR-17*.

In another preferred embodiment, the kit comprises means for determining at least 7, preferably at least 10, 15, 20, 25, 30, 35, 40, 45, or all of the indicated miRNAs. It is particularly preferred to include means for determining the 24, 20, 15, 10 or at least 7 first mentioned miRNAs in the order of the diagnostic significance as represented by their order in the table of FIG. 30A or 30B.

Further, the kit may comprise means for determining the expression profile of a predetermined set of miRNAs based on FIGS. 32A, 32B, 33A and 33B as described above.

The kit for diagnosing melanoma or skin cancer including melanoma and non-melanoma skin cancer is particularly suitable for diagnosing melanoma in a blood, plasma and/or serum sample or in a sample comprising erythrocytes, leukocytes and/or thrombocytes.

In a further embodiment the means for determining a predetermined set of miRNAs may be RT-PCR/qRT-PCR (real time polymerase chain reaction). The workflow for RT-PCR/qRT-PCR may include the following steps: (i) extracting the total RNA from a blood sample, e.g. whole blood, serum, or plasma, of a human subject, e.g. a human subject with unknown clinical condition, e.g. healthy person or patient suffering from a disease (e.g. skin cancer, melanoma, lung cancer multiple sclerosis), and obtaining cDNA samples by an RNA reverse transcription (RT) reaction using miRNA-specific primers; or collecting a blood sample, e.g. whole blood, serum, or plasma, from a human and conducting reverse transcriptase reaction using miRNA-specific primers with blood, e.g. whole blood, serum, or plasma, being a buffer so as to prepare cDNA samples, (ii) designing miRNA-specific cDNA forward primers and providing universal reverse primers to amplify the cDNA via polymerase chain reaction (PCR), (iii) adding a labeled, e.g. fluorescent probe to conduct PCR, and (iv) detecting and comparing the variation in levels of miRNAs in the blood sample, e.g. whole blood, serum, or plasma, relative to those of miRNAs in normal (control) blood, e.g. whole blood, serum, or plasma, sample. A variety of kits and protocols to determine an expression profile by real time polymerase chain reaction (RT-PCR) such as real time quantitative PCR (RT-qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300.

The means for determining a predetermined set of miRNAs may for example comprise a microarray comprising miRNA-specific oligonucleotide probes. In a preferred embodiment, the microarray comprises miRNA-specific oligonucleotide probes for the detection of miRNAs. Depending on the intended use of the microarray in the diagnosis or prognosis of a particular disease, probes for detecting different miRNAs may be included. A microarray for use in the diagnostic of lung cancer preferably comprises miRNA-specific oligonucleotide probes for one or more miRNAs selected from the group consisting of:

(a) hsa-miR-361-5p, hsa-miR-23b, hsa-miR-126, hsa-miR-527, hsa-miR-29a, hsa-let-7i, hsa-miR-19a, hsa-miR-28-5p, hsa-miR-185*, hsa-miR-23a, hsa-miR-1914*, hsa-miR-29c, hsa-miR-505*, hsa-let-7d, hsa-miR-378, hsa-miR-29b, hsa-miR-604, hsa-miR-29b, hsa-let-7b, hsa-miR-299-3p, hsa-miR-423-3p, hsa-miR-18a*, hsa-miR-1909, hsa-let-7c, hsa-miR-15a, hsa-miR-425, hsa-miR-93*, hsa-miR-665, hsa-miR-30e, hsa-miR-339-3p, hsa-miR-1307, hsa-miR-625*, hsa-miR-193a-5p, hsa-miR-130b, hsa-miR-17*, hsa-miR-574-5p and hsa-miR-324-3p or (b) hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p and hsa-miR-93*.

In a preferred embodiment, the microarray comprises oligonucleotide probes for determining at least 7, preferably at least 10, 15, 20 or 24 of the miRNAs of the indicated groups (a) and (b) of miRNAs. It is particularly preferred to include oligonucleotide probes for determining the 24, 20, 15, 10 or at least 7 of the first mentioned miRNAs in the order of their MI-values or their performance in the t-tests as shown in the tables in FIGS. 10A and 10B.

Further, the array may comprise probes for determining miRNAs as shown in FIGS. 11A and 11B as described above.

Most preferably, oligonucleotide probes for determining all of the above indicated miRNAs of groups (a) or (b) are included in the microarray for diagnosing lung cancer.

In a particularly preferred embodiment, the microarray for use in the diagnosis of lung cancer comprises oligonucleotide probes for determining the miRNAs hsa-miR-126, hsa-miR-423-5p, hsa-let-7i, hsa-let-7d, hsa-miR-22, hsa-miR-15a, hsa-miR-98, hsa-miR-19a, hsa-miR-574-5p, hsa-miR-324-3p, hsa-miR-20b, hsa-miR-25, hsa-miR-195, hsa-let-7e, hsa-let-7c, hsa-let-7f, hsa-let-7a, hsa-let-7g, hsa-miR-140-3p, hsa-miR-339-5p, hsa-miR-361-5p, hsa-miR-1283, hsa-miR-18a* and hsa-miR-26b.

A microarray intended for use in the diagnosis of multiple sclerosis preferably comprises miRNA specific oligonucleotide probes for one or more miRNAs presented in the tables in FIGS. 18A, 18B and 18C, preferably for one or more miRNAs selected from the group consisting of hsa-miR-145, hsa-miR-186, hsa-miR-664, hsa-miR-584, hsa-miR-20b, hsa-miR-223, hsa-miR-422a, hsa-miR-142-3p, hsa-let-7c, hsa-miR-151-3p, hsa-miR-491-5p, hsa-miR-942, hsa-miR-361-3p, hsa-miR-22*, hsa-miR-140-5p, hsa-miR-216a, hsa-miR-1275, hsa-miR-367, hsa-miR-146a, hsa-miR-598, hsa-miR-613, hsa-miR-18a*, hsa-miR-302b, hsa-miR-501-5p.

In a preferred embodiment the microarray comprises oligonucleotide probes for determining at least 7, preferably at least 10, 15, 20 or all of the indicated miRNAs. It is particularly preferred to include oligonucleotide probes for determining the most significant miRNAs, which is represented by their order in the tables depicted in FIGS. 18A, 18B and 18C.

Further, the array may comprise oligonucleotide probes for determining miRNAs as shown in FIG. 18D as described above.

The microarray can comprise oligonucleotide probes obtained from known or predicted miRNA sequences. The array may contain different oligonucleotide probes for each miRNA, for example one containing the active mature sequence and another being specific for the precursor of the miRNA. The array may also contain controls such as one or more sequences differing from the human orthologs by only a few bases, which can serve as controls for hybridization stringency conditions. It is also possible to include viral miRNAs or putative miRNAs as predicted from bioinformatic tools. Further, it is possible to include appropriate controls for non-specific hybridization on the microarray.

A microarray intended for use in the diagnosis of melanoma preferably comprises miRNA-specific oligonucleotide probes for one or more miRNAs presented in the table of FIG. 30A or 30B, preferably one or more miRNAs selected from the group consisting of hsa-let-7d, hsa-miR-145, hsa-miR-664, hsa-miR-378*, hsa-miR-365, hsa-miR-328, hsa-miR-422a, hsa-miR-17*, hsa-miR-342-5p, hsa-miR-151-3p, hsa-miR-361-3p, hsa-miR-30a, hsa-miR-181-2*, hsa-miR-30e, hsa-miR-1227, hsa-let-7b*, hsa-miR-34a, hsa-miR-1301, hsa-miR-584, and hsa-miR-1286 (FIG. 31).

In another preferred embodiment, the microarray for use in the diagnosis of melanoma comprises oligonucleotide probes for determining the miRNAs hsa-miR-452*, hsa-miR-216a, hsa-miR-186, hsa-let-7d*, hsa-miR-17*, hsa-miR-646, hsa-miR-217, hsa-miR-621, hsa-miR-517*, hsa-miR-99a, hsa-miR-664, hsa-miR-593*, hsa-miR-18a*, hsa-miR-145, hsa-miR-1280, hsa-let-7i*, hsa-miR-422a, hsa-miR-330-3p, hsa-miR-767-5p, hsa-miR-183*, hsa-miR-1249, hsa-miR-20b, hsa-miR-509-3-5p, hsa-miR-519b-5p, hsa-miR-362-3p, hsa-miR-501-5p, hsa-miR-378*, hsa-miR-365, hsa-miR-151-3p, hsa-miR-342-5p, hsa-miR-328, hsa-miR-181a-2*, hsa-miR-518e*, hsa-miR-362-5p, hsa-miR-584, hsa-miR-550*, hsa-miR-30a, hsa-miR-221*, hsa-miR-361-3p, hsa-miR-625, hsa-miR-146a, hsa-miR-214, hsa-miR-106b, hsa-miR-18a, hsa-miR-30e*, hsa-miR-125a-5p, hsa-miR-142-3p, hsa-miR-107, hsa-miR-20a, hsa-miR-22* and hsa-miR-199a-5p.

In another preferred embodiment, the microarray for use in the diagnosis of melanoma comprises oligonucleotide probes for determining the miRNAs hsa-miR-186, hsa-let-7d*, hsa-miR-18a*, hsa-miR-145, hsa-miR-99a, hsa-miR-664, hsa-miR-501-5p, hsa-miR-378*, hsa-miR-29c*, hsa-miR-1280, hsa-miR-365, hsa-miR-1249, hsa-miR-328, hsa-miR-422a, hsa-miR-30d, and hsa-miR-17*.

Further, the microarray may comprise oligonucleotide probes for determining the miRNAs as shown in FIGS. 32A, 32B, 33A and 33B as described above.

The invention also relates to sets of oligo- or polynucleotides for diagnosing lung cancer comprising the sequences of at least 5, preferably at least 7, 10, 15, 20 or all of the indicated miRNAs and/or the complement of such sequences. It is particularly preferred to include oligo- or polynucleotides for detecting the most significant miRNAs which are represented by the order in the table depicted in FIGS. 10A and 10B. Further, it is preferred to include oligo- or polynucleotides for detecting the miRNAs as shown in FIGS. 11A and 11B.

The invention also relates to sets of oligo- or polynucleotides for diagnosing multiple sclerosis comprising the sequences of at least 5, preferably at least 7, 10, 15, 20 or all of the indicated miRNAs, and/or the complement of such sequences. It is particularly preferred to include oligo- or polynucleotides of the most significant miRNAs, which are represented by their order in the table depicted in FIG. 18A, 18B or 18C. In a further embodiment, the set includes oligo- or polynucleotides for detecting the miRNAs based on FIG. 18D as described above.

The invention also relates to sets of oligo- or polynucleotides for diagnosing melanoma or skin cancer including melanoma and non-melanoma skin cancer comprising the sequences of at least 5, preferably at least 7, 10, 15, 20 or all of the indicated miRNAs, and/or the complement of such sequences. It is particularly preferred to include oligo- or polynucleotides of the most significant miRNAs which are represented by the order in the tables depicted in FIGS. 30A and 30B. In a further embodiment, the set includes oligo- or polynucleotides of the miRNAs based on FIGS. 32A, 32B, 33A and 33B as described above.

The oligo- or polynucleotides preferably have a length of 10, 15 or 20 and up to 30, 40, 50, 100 or more nucleotides. The term "oligo- or polynucleotides" includes single- or double-stranded molecules, RNA molecules, DNA molecules or nucleic acid analogs such as PNA or LNA.

Another embodiment of the present invention relates to a method for diagnosing and/or predicting the health state in a subject or for the assessment of a clinical condition of a patient.

For a manifold of human diseases, including cancer, molecular diagnostics methods have been developed over the past decades. However, only a small percentage of those tests has made its way into the clinical practice.

Recent developments have shown that there is a tendency towards smaller sets of biomarkers for the detection, including diagnosis and/or prognosis, of diseases. However, for single biomarkers and small biomarker sets, there is only a basic understanding whether these biomarkers are specific for only the single diseases or whether they occur in any other disease.

Therefore, the present inventors developed a novel class of diagnostic tests improving the current test scenarios. The inventors found out that a variety of diseases is correlated with a specific expression profile of miRNAs. In case a patient is affected by a particular disease, several miRNAs are present in larger amounts compared to a healthy normal control, whereas the amount of other miRNAs is decreased. Interestingly, the amount of some miRNAs is deregulated, i.e. increased or decreased, in more than one disease. The miRNA profile for a particular disease therefore shows conformity with the miRNA profile of other diseases in regard of individual miRNAs while other miRNAs show significant differences. If the expression profile of a large variety of miRNAs in a biological sample of a patient is measured, the comparison of the expression profile with a variety of reference expression profiles which are each characteristic for different diseases, or more generally the conditions, makes it possible to obtain information about the clinical condition of a certain patient and to determine, which disease(s) is/are present or absent in said patient.

A subject matter of this embodiment of the invention is a method for the assessment of a clinical condition of a patient comprising the steps
  (a) providing a biological sample from the patient,
  (b) determining a predetermined set of miRNAs in said sample to obtain a miRNA expression profile,
  (c) comparing said miRNA expression profile with a plurality of miRNA reference expression profiles characteristic for different diseases, and
  (d) assessing the clinical condition of the patient based on the comparison of step (c).

The inventors found out that the above method for the assessment of a clinical condition makes it possible to carry out an integrative diagnosis of a wide variety of diseases. Comparing a miRNA profile obtained from a biological sample of a patient whose clinical condition is not known with a plurality of reference profiles characteristic for different diseases enables the diagnosis of a wide variety of diseases with high specificity and sensitivity.

The set of miRNAs determined in the above step (b) preferably includes a large number of different miRNAs. It is particularly preferred to use at least 50, preferably at least 100, 200, 500 or 1,000 miRNAs. Most preferably, all known miRNAs are included in the set of miRNAs determined in step (b), for example the miRNAs disclosed in the Sequence Listing. Such a complex set of miRNA-biomarkers enables a diagnosis with higher specificity and sensitivity compared to single biomarkers or sets of only a few dozens of such markers.

The determination of the set of miRNAs can be done as described herein above. Preferably, the determination is done on an experimental platform which shows a high degree of automation to minimize experimental variations, measures results time- and cost-efficiently, measures results highly reproduceably and is suitable for measuring more than one sample at once in order to ensure a high throughput.

Step (c) of the above method of assessment of a clinical condition preferably includes a comparison of the miRNA profile measured for a patient with a large number of different miRNA reference profiles to provide information about the presence of as many different diseases as possible. The reference expression profiles may be laid down in a database, e.g. an internet database, a centralized or a decentralized database. The reference profiles do not necessarily have to include information about all miRNAs included in step (b), which are determined in the sample of the patient. It is, according to the invention, sufficient if the reference profile provides information on those miRNAs which are altered to a large extent compared to the condition of a healthy individual in case of the presence of a disease.

Preferably, an miRNA reference profile according to the invention provides information on miRNA expression characteristic for a particular disease in the same type of biological sample as used in step (b) for determining a predetermined set of miRNAs in a sample from a patient. This means that, if a patient with an unknown disease is to be classified with the analysis of a blood sample, the comparison is preferably made with miRNA reference expression profiles, which do also relate to the miRNA expression pattern in a blood sample.

The reference profiles characteristic for particular diseases provide information on one or more miRNAs, which are, in case of the disease, highly deregulated, for example strongly increased or decreased, as compared to a healthy condition. It is not necessary for the reference profiles to provide information about all miRNAs included in the set of biomarkers determined in step (b). However, the more miRNAs are included in the reference profile, the more precise the diagnosis will be. If, for example, a reference profile for lung cancer is included, it is preferred to include the characteristic miRNAs for lung cancer as disclosed hereinabove. Equivalently, it is preferred to include into a reference profile for multiple sclerosis the characteristic miRNAs for multiple sclerosis as described hereinabove as well. Alternatively, it is preferred to include into a reference profile for melanoma the characteristic miRNAs for melanoma as described hereinabove as well.

Examples for diseases that can be determined using the method for the assessment of a clinical condition disclosed above are lung cancer, multiple sclerosis, pancreatic cancer, melanoma and Wilm's tumor.

Another embodiment of this aspect of the invention is a kit for the assessment of a clinical condition of a patient comprising
(a) means for determining a predetermined set of miRNAs in a biological sample from a patient, and
(b) a plurality of miRNA reference expression profiles characteristic for different diseases.

The set of miRNAs to be determined in a biological sample from a patient preferably includes a large number of different miRNAs. It is particularly preferred to include all known miRNAs in the set of miRNAs to be determined. In each case, said predetermined set of miRNAs should include those miRNAs for which information is provided in the reference profiles characteristic for particular diseases. It is understood that only in case the set of miRNAs determined in a biological sample from a patient comprises those miRNAs included in the reference profile for a disease, a diagnosis regarding this particular disease can be provided.

The assessment of a clinical condition of a patient according to the invention is suitable for diagnosing any diseases which are correlated with a characteristic miRNA profile. Accordingly, the kit for the assessment of a clinical condition preferably includes reference profiles for a plurality of diseases that are correlated with a characteristic miRNA profile. It is understood that all miRNAs that are significantly deregulated in the disease states for which reference profiles are provided should be included in the set of miRNAs to be determined in a biological sample from a patient. If the kit for the assessment of a clinical condition of a patient should provide information regarding, e.g. lung cancer, a reference profile should be available providing information about the significantly deregulated miRNAs compared to a normal control individual. The miRNAs deregulated in case of lung cancer are as described as hereinabove. Similarly, in case the kit for the assessment of a clinical condition shall provide information on the presence of multiple sclerosis, a reference profile characteristic for multiple sclerosis should be included. Said reference profile preferably includes information on those miRNAs that are most significantly deregulated in the case of MS. The relevant miRNAs are as disclosed hereinabove. Similarly, in case the kit for the assessment of a clinical condition shall provide information on the presence of melanoma, a reference profile characteristic for melanoma should be included. Said reference profile preferably includes information on those miRNAs that are most significantly deregulated in the case of melanoma. The relevant miRNAs are as disclosed hereinabove.

Another embodiment of the present invention relates to a method of diagnosing and/or predicting the state of health of a subject comprising:
(a) providing a biological sample from the subject,
(b) providing a matrix that comprises at least one miRNA capture probe,
(c) contacting said total RNA with the matrix of step (b),
(d) determining the miRNA profile of said total RNA,
(e) comparing the miRNA profile of step (d) with the expression profile of a predetermined set of miRNAs, wherein each set is characteristic for a particular disease,
(f) calculating the probability value of said individual for each particular disease, and
(g) collecting the highest probability values determined in step (f) to diagnose and/or prognosis the health state of said individual.

In this method, a biological sample from a subject is provided and the complete expression profile of miRNAs is determined in that sample. In a preferred embodiment, the complete miRNA expression profile of the miRNAs depicted in the Sequence Listing is obtained. However, it is not excluded that the miRNA expression profile of further miRNAs is also determined in the biological sample from the subject including all miRNAs that are determined further in the future. The expression profile of the miRNAs in the biological sample of the subject is then compared to the expression profile of a predetermined set of miRNAs characteristic for a particular disease. This predetermined set of miRNAs may comprise miRNAs that are characteristic for multiple sclerosis, lung cancer and/or melanoma. In case the particular disease is multiple sclerosis, a preferred set of miRNAs comprises the miRNAs depicted in FIG. 18B. In case the particular disease is lung cancer, the preferred set of miRNAs is depicted in FIG. 10B. In case the particular disease is melanoma, the preferred set of miRNAs is depicted in FIG. 30A. The method does not exclude that predetermined sets of miRNAs that are characteristic for further diseases are included into the analysis.

Further in the method of diagnosing and/or predicting the state of health of a subject, the determined miRNA expression profile of the biological sample from the subject is further compared to the miRNA expression profile of a predetermined set of miRNAs characteristic for a variable number of particular diseases. The prediction regarding the state of health of the subject is the more precise the more diseases are included into the analysis. As already explained above, comparison of the miRNA expression profiles between the subject under investigation and the expression profile of the predetermined set of miRNAs characteristic for a particular disease is done as follows: As described above, the inventors have found that among all miRNAs that are known, a particular set of miRNAs is characteristic for a particular disease. Within this set of miRNAs, the expression of a particular miRNA is deregulated compared to the expression of the same miRNA derived from a sample from a healthy subject. Deregulated in the sense of the invention may comprise an increased level of expression compared to the same miRNA derived from a sample of a healthy person. Alternatively, "deregulated" may comprise a decreased level of expression of the same miRNA derived from a sample of a healthy subject. Thus, the method comprises the comparison whether a particular miRNA expression state determined in a biological subject from the sample shows the same deregulation than the miRNA of a predetermined set of miRNAs characteristic for a particular disease. This is done for all miRNAs in the sample from the subject for which the same miRNA has been included in the predetermined set of miRNAs characteristic for a particular disease. This analysis allows the calculation for the subject under investigation regarding the probability value for each particular disease included into the investigation and collection of the highest probability values allows for a diagnosis or prognosis regarding the health state of the subject.

In a further embodiment, the method of diagnosing or predicting the state of health of a subject results in a medical decision for said subject.

In a further embodiment, the miRNA expression profile of said subject and the expression profile of a predetermined set of miRNAs are stored in a database.

In a further embodiment, the probability value determined for each of the particular diseases is calculated by comparing the miRNA expression profile of said object to a reference expression profile as described herein. In a further embodiment, the matrix that comprises at least one miRNA capture probe is a microarray.

In a further embodiment, the biological sample from the subject comprises the total RNA. The total RNA may be labeled before contacting the total RNA with the matrix. Alternatively, the total RNA is not labeled before contacting said total RNA with the matrix.

In a further embodiment of the invention, contacting of said biological sample with the matrix comprises stringent hybridisation and/or polymerase-based primer extension. Alternatively, in case the matrix is a microarray as described herein, the contacting step of the biological sample with the microarray comprises an enzymatic reaction and/or a primer extension reaction.

In a further embodiment, the expression profiles are determined by RT-PCR, qRT-PCR or a Luminex-based assay.

A further embodiment of the invention relates to an apparatus for diagnosing or predicting the state of health of a subject comprising:
(a) database for storing a plurality of expression profiles of a predetermined set of miRNAs,
(b) means for generating an expression profile of a biological sample.

Preferably, the means comprises capture probes for at least one miRNA. In another preferred embodiment, the means are designed for parallel detection of a plurality of miRNAs molecules. The means may comprise a fluidic system, a detection system, means for input/injection of a biological sample, preferably total RNA from a subject, means for holding a matrix with a capture probe, means for connecting the sample input/injection matrix with a capture probe holding the fluidic system, means for hybridisation, enzymatic reactions and washing steps and/or means for heating and cooling of the reaction carried out on a matrix comprising a capture probe. Further, the means may comprise a PCR, RT-PCR, qRT-PCR, or Luminex-based system. In addition, the apparatus comprises a computer and an algorithm for comparing miRNA expression profiles and calculating the probability value.

Another embodiment of the invention is a method of diagnosing and/or predicting the state of health in a subject comprising the steps:
(a) providing a RNA sample from said subject,
(b) providing means for determining a plurality of miRNA and/or other non-coding RNA molecules, e.g. at least 4, 6, 8, 10, 20, 100, 1000, or 15000 and e.g. up to 1000, 10000, or 1000000 molecules, wherein the means may be matrix of capture probes,
(c) contacting the sample of (a) with the means, e.g. matrix of (b),
(d) determining the expression profile of a plurality of miRNAs and/or other non-coding RNAs in the sample of (a),
(e) providing a plurality of reference miRNA and/or other non-coding RNA expression profiles obtained from a plurality of different reference subjects representing a plurality of different conditions
(f) calculating a common signature profile from a combination of at least 2 conditions, represented by the corresponding expression profiles in step (e), wherein the common signature profile is a subset of miRNAs differentiating between the said at least 2 conditions,
(g) comparing the miRNA and/or other non-coding RNA profile of step (d) with a common signature profile of step (f), and
(h) calculating the probability value of said subject for the at least 2 conditions, and
(i) optionally repeating steps (f), (g) and (h) for at least another common signature profile, and/or
(g) optionally collecting the probability values for the particular common signature profiles to diagnose and/or predict the health state of said subject.

The term "state of health" includes at least one condition as defined above. It may also include a plurality of different conditions.

In preferred embodiments, the clinical conditions are related to lung cancer, multiple sclerosis, skin cancer or melanoma.

In the context of the invention it should be noted that all the methods described herein may be performed on other sources than miRNA, e.g. another non-coding RNAs, e.g. tRNAs, r-RNAs, siRNAs, and ncRNAs as described herein. In this case, the means, e.g matrix, capture probes etc. are designed in order to detect other non-coding RNAs, e.g. tRNAs, r-RNAs, siRNAs, and ncRNAs as described herein. The methods providing such probes are well known by a person skilled in the art.

The sample of the subject is the RNA source on which the expression analysis of the non-coding RNAs including miRNAs is conducted. The state of health of the subject may be unknown prior to analysis.

The matrix for performing the expression analysis may comprise a plurality of capture probes that are designed to detect a plurality of non-coding RNAs, including miRNAs. The higher the complexity of the capture probes on the matrix, i.e. the more non-coding RNAs, e.g. miRNAs, that can be detected by this matrix, the higher is the information content regarding the state of health of the analysis. In one embodiment of the present invention, the intention is to increase the amount of miRNAs or non-coding RNAs to the highest possible level. Today, the miRBase as an official repository of validated miRNAs lists approximately 1000 human miRNAs. Therefore, it is desirable to have all of these miRNAs being represented by a capture probe within/on a matrix. It is intended by the invention that the capture matrix comprising the capture probes is constantly updated and increased in its complexity as soon as new miRNAs or other non-coding RNAs become known.

The RNA sample that is brought into contact with the matrix comprising the capture probes is e.g. a total RNA sample or a subfraction that includes the non-coding RNAs and/or miRNAs of interest. The RNA sample may be obtained from a biological sample as defined herein. After bringing the RNA sample into contact with the matrix comprising the capture probes, an expression profile is determined, resulting in a numerical value for the capture probes representing the expression level of the non-coding RNAs and/or miRNAs of interest.

The non-coding and/or miRNA-profile of the subject is afterwards compared with a plurality of reference non-coding and/or miRNA-profiles. These reference profiles may be obtained from a plurality of subjects covering a plurality of defined conditions (including e.g. healthy controls and subjects suffering from different diseases). These reference profiles are e.g. stored in a database. Before the comparison from the plurality of reference profiles so-called common signature profiles are generated. A common signature profile is understood in the present invention as a non-fixed defined set of miRNAs or non-coding RNAs which is able to differentiate between a condition 1 and another condition 2 (or even more conditions). The common miRNA or non-coding RNA signature profile may be calculated "on-the-fly" from the plurality of reference miRNA- or non-coding RNA profiles that e.g. are stored in a database.

Next the non-coding and/or miRNA-profile of the subject is compared with a at least one, preferably with a plurality, most preferably with all possible common signature profiles. For each of the comparisons a probability may be calculated.

In case the common signature profile is able to differentiate between 2 conditions, there will be a first probability value for condition 1 (e.g. lung cancer) and a second probability value for condition 2 (e.g. multiple sclerosis), whereby both add up to an overall probability value of 1.

In case the common signature profile is able to differentiate between 3 conditions, there will be altogether 3 probability values, one for each state of health.

After comparison of the non-coding RNA profile, e.g. the miRNA-profile to a least one common signature profile and calculation of the corresponding probabilities, valuable information is obtained that can be used to determine the state of health of the subject. This information can be used for diagnosis or prognosis for that subject. The broader the range of common signature profiles employed for comparison, the broader is the range of information on the state of health generated for that subject.

The information obtained reflects for that subject e.g.:
(i) the probability to have lung cancer or be healthy
(ii) the probability to have lung cancer or multiple sclerosis
(iii) the probability to have multiple sclerosis or be healthy
(iv) etc.

It is important to note that the information obtained is not limited to the information for either i), ii) or iii) in the example, but to the comprehensive information of i), ii) and iii), etc. Therefore, the present invention provides a comprehensive information on the state of health for a subject. The comprehensiveness of information is only limited by the range of common signature profiles resulting from a plurality of different conditions. The more conditions are available, the broader is the range of information on the health state that can be generated from the RNA sample of the subject with, e.g. unknown state of health.

The inventors found out that the above methods for diagnosing and/or predicting a clinical condition or the state of health make it possible to carry out an integrative diagnosis of a wide variety of conditions, including diseases. Comparing a non-coding RNA, incl. miRNA, profile obtained from a biological sample of, e.g. a subject whose state of health is not known with a plurality of reference profiles characteristic for different conditions enables the diagnosis and/or prognosis of a state of health with high specificity and sensitivity.

The capture probes of the matrix in step (b) of the above method of diagnosing and/or predicting the state of health in a subject are preferably specific for a large number of different miRNAs or non-coding RNAs. It is particularly preferred to determine at least 4, 6, 8, 10, 20, 100, 1000, or 15000 and e.g. up to 1000, 10000, or 1000000 RNA molecules, by e.g. using a respective number of capture probes. Most preferably, specific probes for all known miRNAs and/or non-coding RNAs are included in step (b), for example the miRNAs disclosed in the table in the sequence listing. Such a complex set of miRNA-biomarkers enables a diagnosis and/or prognosis with higher specificity and sensitivity compared to single biomarkers or sets of only a few dozens of such markers.

A well established repository of validated miRNAs is the miRBase. The miRBase (www.mirbase.org) is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.

The determination of the miRNA reference profile representing a condition can be done as described herein above in the context of the determination of a predetermined set of miRNAs. Preferably, the determination is done on an experimental platform which shows a high degree of automation to minimize experimental variations, measures results time- and cost-efficiently, measures results highly reproducibly and is suitable for measuring more than one sample at once in order to ensure a high throughput.

Step (g) of the above method preferably includes a comparison of the miRNA profile measured for a subject with a large number of common signature profiles, obtained from different miRNA reference profiles to provide information for as many different conditions as possible. The reference expression profiles may be laid down in a database, e.g. an internet database, a centralized or a decentralized database. The reference profiles do not necessarily have to include information about all miRNAs determined in step (d). It is, according to the invention, sufficient if the reference profile provides information on those miRNA and/or non-coding RNA biomarkers which are altered to a large extent compared to the conditions to be compared (e.g. disease versus healthy control).

Preferably, a miRNA and/or non-coding RNA reference profile according to the above method of the invention provides information on miRNA and or non-coding RNA expression characteristic for a particular condition (e.g. disease) in the same type of biological sample as used in step (d) for determining the expression profile of a plurality of miRNAs in a sample from a patient. This means that, if a patient with an unknown state of health is to be classified with the analysis of a blood sample, the comparison is preferably made with miRNA and/or non-coding RNA reference expression profiles, which do also relate to the miRNA expression pattern in a blood sample.

The reference profiles characteristic for particular conditions (e.g. diseases) provide information on one or more miRNAs and/or non-coding RNA, which are, in case of a first condition (e.g. the disease), highly deregulated, for example strongly increased or decreased, as compared to another condition (e.g. healthy condition). It is not necessary for the reference profiles to provide information about all miRNAs included in the set of biomarkers determined in step (d). However, the more miRNAs are included in the reference profiles, the more precise the diagnosis will be. If, for example, a reference profile for lung cancer is included, it is preferred to include at least one characteristic miRNA, preferably a plurality of miRNAs, for the condition lung cancer as disclosed hereinabove. Equivalently, it is preferred to include into a reference profile for the condition multiple sclerosis at least one characteristic miRNA, preferably a plurality of miRNAs, for multiple sclerosis as described hereinabove as well. Alternatively, it is preferred to include into a reference profile for the condition melanoma at least one characteristic miRNA, preferably a plurality of miRNAs, for melanoma as described hereinabove as well.

Examples for conditions (e.g. diseases) that can be included into the method for diagnosing and/or predicting of a state of health of a subject disclosed above are lung cancer, multiple sclerosis, pancreatic cancer, melanoma and Wilm's tumor. The scope of the present invention is not limited to the above mentioned examples but is applicable to screening of a broad range of conditions including cancer (e.g. prostate, pancreatic, Wilms tumor, ovarian), cardiovascular diseases, infectious diseases (e.g. pancreatitis), inflammatory diseases (e.g. Chronic Obstructive Pulmonary Disease, Sarcoidosis, Paradontitis, Crohn's disease, collitis) or autoimmune diseases (e.g. rheumatoid arthritis).

Another embodiment of the present invention relates to a method of diagnosing and/or predicting the state of health of a subject comprising:
(a) providing a RNA sample from said subject,
(b) providing a means for determining a plurality of miRNA and/or non-coding RNA molecules, e.g. at least 4, 6, 8, 10, 20, 50, 100, or 200 and e.g. up to 1000, 10 000, or 1 000 000 molecules, wherein the means may be a matrix of capture probes,
(c) contacting the sample of (a) with the means of (b),
(d) determining the expression of a plurality of and/or non-coding RNAs in the sample of (a),
(e) comparing a predetermined subset of miRNAs and/or non-coding RNAs in said miRNA and/or non-coding RNA expression profile, wherein said subset is characteristic for a particular condition (e.g. disease) to a corresponding subset of miRNAs and/or non-coding RNAs in reference miRNA and/or non-coding RNA expression profiles obtained from a plurality of different reference subjects representing a plurality of different conditions including the particular disease,
(f) calculating the probability value of said subject for the particular condition (e.g. disease),
(g) optionally repeating steps (e) and (f) for at least one different particular condition (e.g. disease)
(h) optionally collecting the probability values for particular conditions (e.g. diseases) to diagnose and/or predict the health state of said subject.

Step (e) preferably comprises:
providing a plurality, e.g. at least 10, 50, 100 and e.g. up to 1000, 10.000 or 1000 000 reference miRNA and/or non-coding RNA expression profiles obtained from a plurality of different reference subjects representing a plurality of different conditions, selecting a subset of miRNAs and/or non-coding RNAs in the expression profile comprising a plurality of miRNAs and/or non-coding RNAs characteristic for the particular condition (e.g. disease), comparing the subset of miRNAs and/or non-coding RNAs in the subject to be analyzed and in at least two groups of reference subjects, wherein the first group of subjects suffers from the particular condition (e.g. disease) and the second group does not suffer from the particular condition (e.g. disease), wherein the second group may be healthy or may suffer from a different condition (e.g. disease)

In this method, a biological sample from a subject (patient) is provided and the complete expression profile of miRNAs and or non-coding RNAs is determined in that sample. In a preferred embodiment, the complete miRNA expression profile of the miRNAs depicted in the Sequence Listing is obtained. However, it is not excluded that the miRNA expression profile of further miRNAs and or non-coding RNAs also determined in the biological sample from the subject including all miRNAs and/or non-coding RNAs that are determined further in the future. The expression profile of the miRNAs in the biological sample of the subject is then compared to the expression profiles of a predetermined set of miRNAs characteristic for a particular condition (e.g. disease). This predetermined set of miRNAs may comprise miRNAs that are characteristic for multiple sclerosis, lung cancer and/or melanoma. In case the particular condition (e.g. disease) is multiple sclerosis, a preferred set of miRNAs comprises the miRNAs depicted in FIG. 18B, e.g. at least 1, 7, 10, 15, 20, 25, 30, 35, 40, 50, 75, 100 miRNAs of FIG. 18B. In case the particular condition, e.g. disease, lung cancer, the preferred set of miRNAs is depicted in FIG. 10B, at least 1, 7, 10, 15, 20, 25, 30, 35, 40, 50, 75, 100 miRNAs of FIG. 10B. In case the particular condition, e.g. disease is melanoma, the preferred set of miRNAs is depicted in FIG. 30A, at least 1, 7, 10, 15, 20, 25, 30, 35, 40, 50, 75, 100 miRNAs of FIG. 30A. The method does not exclude that predetermined sets of miRNAs that are characteristic for further diseases are included into the analysis.

Further in the method of diagnosing and/or predicting the state of health of a subject, the determined miRNA expression profile of the biological sample from the subject is further compared to the miRNA expression profile of a predetermined set of miRNAs characteristic for a variable number of particular conditions, e.g. diseases. The prediction regarding the state of health of the subject is the more precise the more conditions, e.g. diseases, are included into the analysis. As already explained above, comparison of the miRNA expression profiles between the subject under investigation and the expression profile of the predetermined set of miRNAs characteristic for a particular condition, e.g. disease, is done as follows: As described above, the inventors have found that among all miRNAs that are known, a particular set of miRNAs is characteristic for a particular condition, e.g. disease. Within this set of miRNAs, the expression of a particular miRNA is deregulated compared to the expression of the same miRNA derived from a sample from another condition, e.g. a healthy subject. Deregulated in the sense of the invention may comprise an increased level of expression compared to the same miRNA derived from a sample of a different condition, e.g. a healthy person. Alternatively, deregulated may comprise a decreased level of expression of the same miRNA derived from a sample of a different condition, e.g. a healthy subject. Thus, the method comprises the comparison whether a particular miRNA expression state determined in a biological subject from the sample shows the same deregulation than the miRNA of a predetermined set of miRNAs characteristic for a particular condition, e.g. disease. This is done for all miRNAs in the sample from the subject for which the same miRNA has been included in the predetermined set of miRNAs characteristic for a particular condition, e.g. disease. This analysis allows the calculation for the subject under investigation regarding the probability value for each particular condition, e.g. disease, included into the investigation and collection of the highest probability values allows for a diagnosis or prognosis regarding the health state of the individual.

In a further embodiment, the method of diagnosing or predicting the state of health of a subject results in a medical decision for said individual.

In a further embodiment, the miRNA expression profile of said subject and the expression profile of a predetermined set of miRNAs are stored in a database.

In a further embodiment, the probability value determined for each of the particular diseases is calculated by comparing the miRNA expression profile of said object to a reference expression profile as described herein. In a further embodiment, the matrix that comprises a plurality of miRNA and/or non-coding RNAs capture probes is a microarray.

In a further embodiment, the biological sample from the subject comprises the total RNA or a subfraction of the RNA sample. The RNA may be labeled before contacting the RNA with the matrix. Alternatively, the RNA is not labeled before contacting said RNA with the matrix.

In a further embodiment of the invention, contacting of said biological sample with the matrix comprises stringent hybridisation and/or polymerase-based primer extension. Alternatively, in case the matrix is a microarray as described herein, the contacting step of the biological sample with the microarray comprises an enzymatic reaction and/or a primer extension reaction.

A further embodiment of the invention relates to an apparatus for diagnosing or predicting the state of health of a subject comprising:
(a) database for storing a plurality of expression profiles,
b) means for generating an expression profile of a biological sample.

Preferably, the means comprises capture probes for miRNA and/or non-coding RNAs. In another preferred embodiment, the means are designed for parallel detection of a plurality of miRNAs and/or non-coding RNA molecules. The means may comprise a fluidic system, a detection system, means for input/injection of a biological sample, preferably RNA, total RNA or a subfraction of RNA from a subject, means for holding a matrix with a capture probe, means for connecting the sample input/injection matrix with a capture probe holding the fluidic system, means for hybridisation, enzymatic reactions and washing steps and/or means for heating and cooling of the reaction carried out on a matrix comprising a capture probe. In addition, the apparatus comprises a computer and an algorithm for comparing miRNA and/or non-coding RNA expression profiles and calculating the probability value.

The invention will now be illustrated by the following figures and the non-limiting experimental examples.

FIGURES

FIG. 1:
Scheme of a miRNA hybridization assay for use in the invention.
  miRNA capture probes consist of 1 miRNA probe sequence stretch that is linked to support via 3'-end or alternatively by 5'-end (not depicted here)
  the miRNA probe sequence stretches are complementary to miRNA target sequences
  each miRNA capture probe can bind 1 miRNA target sequences
  the miRNA target sequences are labeled prior to hybridisation (e.g. by biotin labeling)

Figure 2:
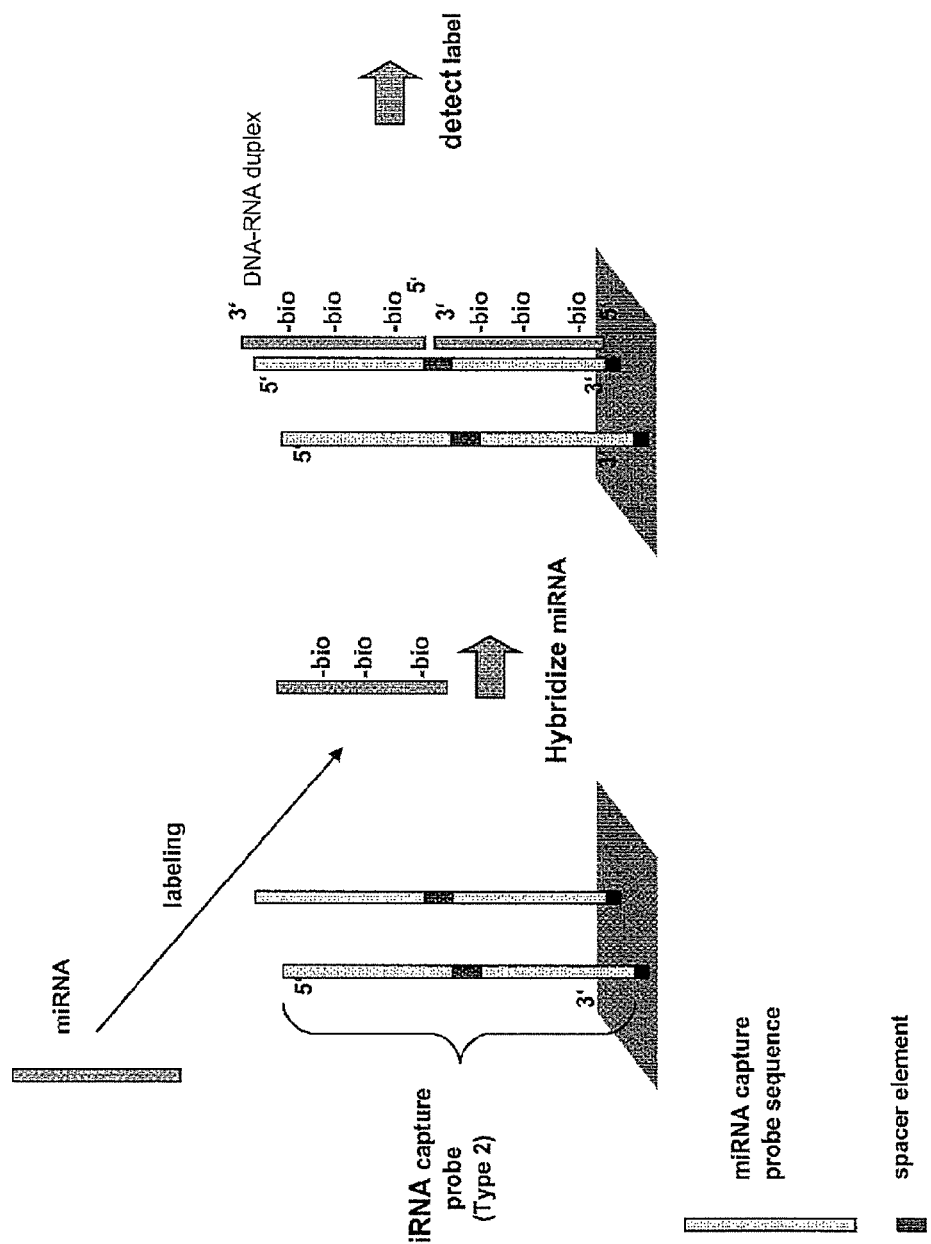

FIG. 2:
Scheme of an miRNA tandem hybridization assay for use in the invention
  miRNA capture probes consist of 2 DNA-based miRNA probe sequence stretches that are linked to each other by a spacer element
  the miRNA probe sequence stretches are complementary to miRNA target sequences
  each miRNA capture probe can bind 2 miRNA target sequences
  the spacer sequence consists of 0-8 nucleotides
  the miRNA target sequences are labeled prior to hybridisation (e.g. by biotin labeling)

Figure 3:
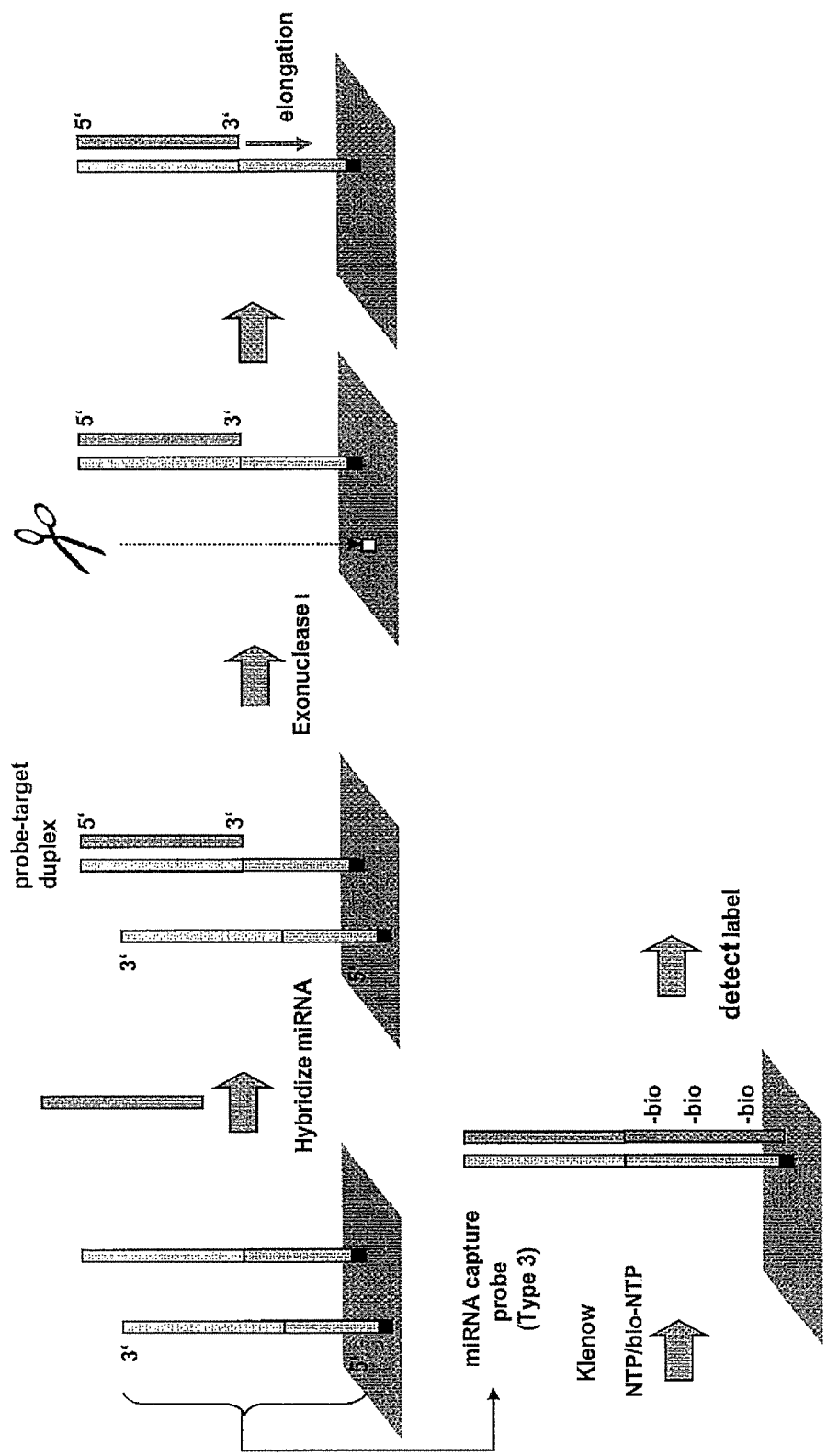
Figure 4:
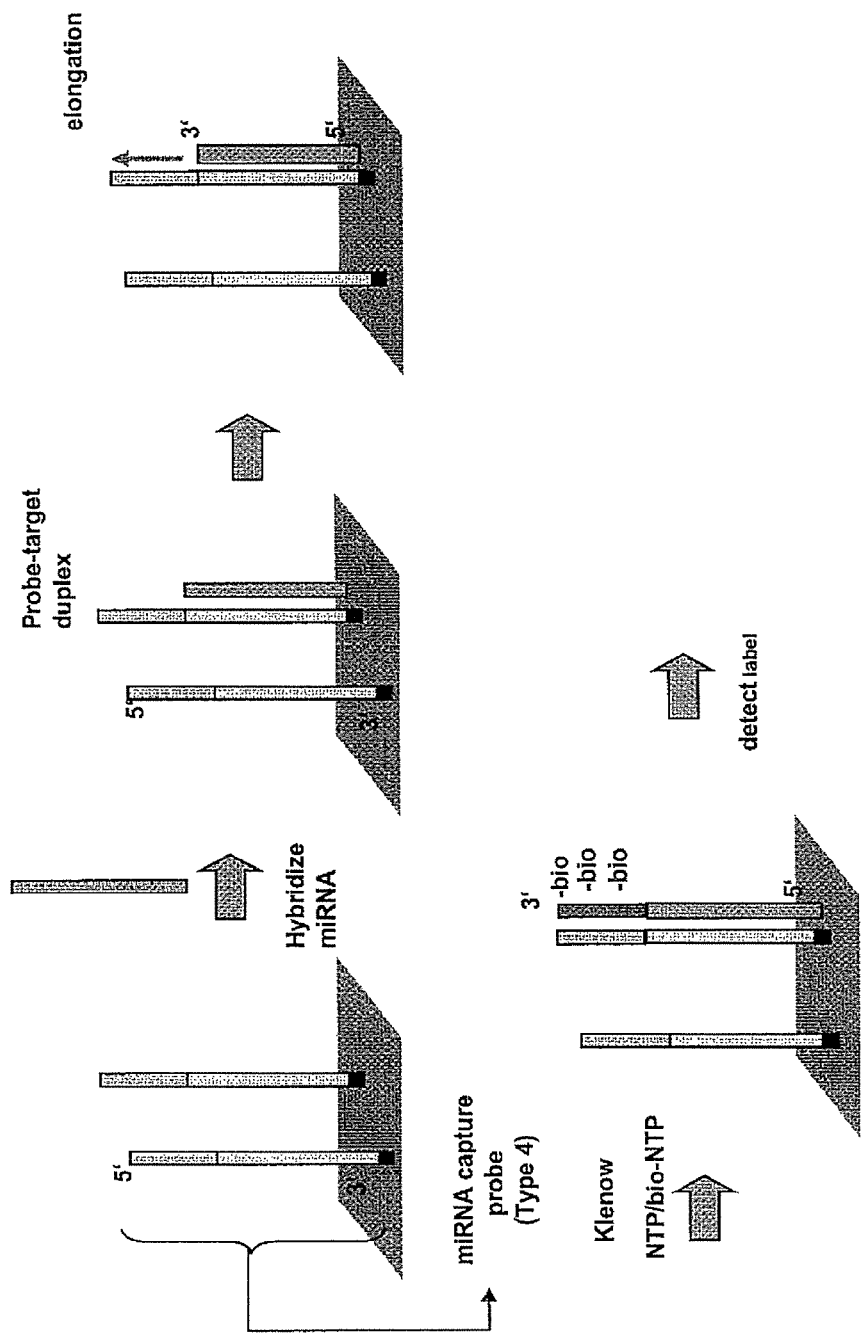

FIG. 3:
miRNA RAKE-Assay for use in the invention (PT Nelson et al., Nature Methods, 2004, 1(2), 1)
  the miRNA capture probes consist of one miRNA probe sequence stretch (green) and one elongation element (orange)
  probes are oriented 5'→3', presenting a free terminal 3'-OH
  the miRNA probe sequence stretch (green) is complementary to miRNA target sequences (dark green)
  the elongation sequences (orange) can be freely chosen and is typically between 1-12 nucleotides long, preferably a homomeric sequence
  each miRNA capture probe can bind 1 miRNA target sequences
  the miRNA target sequences are NOT labeled prior to hybridisation
  Labeling occurs after hybridisation during elongation by polymerase extention reaction
  Biochip is not reusable due to exonuclease treatment FIG. 4:
miRNA MPEA-Assay for use in the invention (Vorwerk S. et al., Microfluidic-based enzymatic on-chip labeling of miRNAs, N. Biotechnol. 2008; 25(2-3):142-9. Epub 2008 Aug. 20)
  the miRNA capture probes consist of one miRNA probe sequence stretch (green) and one elongation element (orange)
  probes are orientied 3'→5', presenting a free terminal 5'-OH the miRNA probe sequence stretch (green) is complementary to miRNA target sequences (dark green)
  the elongation sequences (orange) can be freely chosen and is typically between 1-12 nucleotides long, preferably a homomeric sequence
  each miRNA capture probe can bind 1 miRNA target sequences
  the miRNA target sequences are NOT labeled prior to hybridisation
  Labeling occurs after hybridisation during elongation by polymerase extention reaction
  Biochip is reusable after removal of target/elongated target FIG. 5:
miRNA capture probe design
Depicted is the design of a capture probe for the exemplary miRNA human mature miRNA let-7a (SEQ ID NO:904) for use in the various types of hybridization assays shown in FIGS. 1-4. SP=spacer element; EL=elongation element

FIG. 6:

Spacer Element.

Capture probes (SEQ ID NO:904) for use in e.g. a tandem hybridization assay as shown in FIG. 2 may comprise a spacer element SP. The spacer element represents a nucleotide sequence with n=0-12 nucleotides chosen on the basis of showing low complementarity to potential target sequences, therefore resulting in no to low degree of crosshybridization to target mixture. Preferably, n=0, i.e. there is no spacer between the 2 miRNA probe sequence stretches.

FIG. 7:

Elongation Element

A capture probe (SEQ ID NO:904), e.g. for use in a RAKE or MPEA assay as shown in FIGS. 3 and 4 may include an elongation element. The elongation element comprises a nucleotide sequence with N=0-30 nucleotides chosen on the basis of showing low complementarity to potential target sequences, therefore resulting in no to low degree of crosshybridization to target mixture. Preferred is a homomeric sequence stretch $-N_n$- with n=1-30, N=A or C, or T, or G. Especially preferred is a homomeric sequence stretch -Nn- with n=1-12, N=A or C, or T, or G.

FIG. 8:

Pearson Correlation Coefficient depending on the number of elongated nucleotides in capture probes in an MPEA assay.

FIG. 9:

Diagram describing the general approach for determining miRNA signatures for use as biomarkers in disease diagnosis.

FIG. 10A:

Overview of all miRNAs that are found to be differentially regulated in blood samples of lung cancer patients, grouped according to their mutual information (MI).

FIG. 10B:

Overview of all miRNAs that are found to be differentially regulated in blood samples of lung cancer patients, grouped according to their results in t-tests.

FIG. 11A:

Overview of preferred miRNAs that are found to be significantly differentially regulated in blood samples of lung cancer patients.

FIG. 11B:

Overview of preferred signatures/sets of miRNAs for the diagnosis of lung cancer with corresponding performance sets (in percent: acc=accuracy, spec=specificity, sens=sensitivity).

FIG. 12:

Expression of some relevant miRNAs for diagnosis of lung cancer. The bar-chart shows for 15 deregulated miRNAs the median value of cancer samples and normal samples. Here, blue bars correspond to cancer samples while red bars to controls.

FIGS. 13A-G:

Bar diagrams showing a classification of the accuracy, specificity and sensitivity of the diagnosis of lung cancer based on blood samples using different sizes of subsets of miRNAs. Blue bars represent accuracy, specificity and sensitivity of the diagnosis using the indicated biomarkers and red bars represent the results of the same experiments of random classifications. The relevant value is the population median (horizontal black lines inside the bars).

Figure 13A:
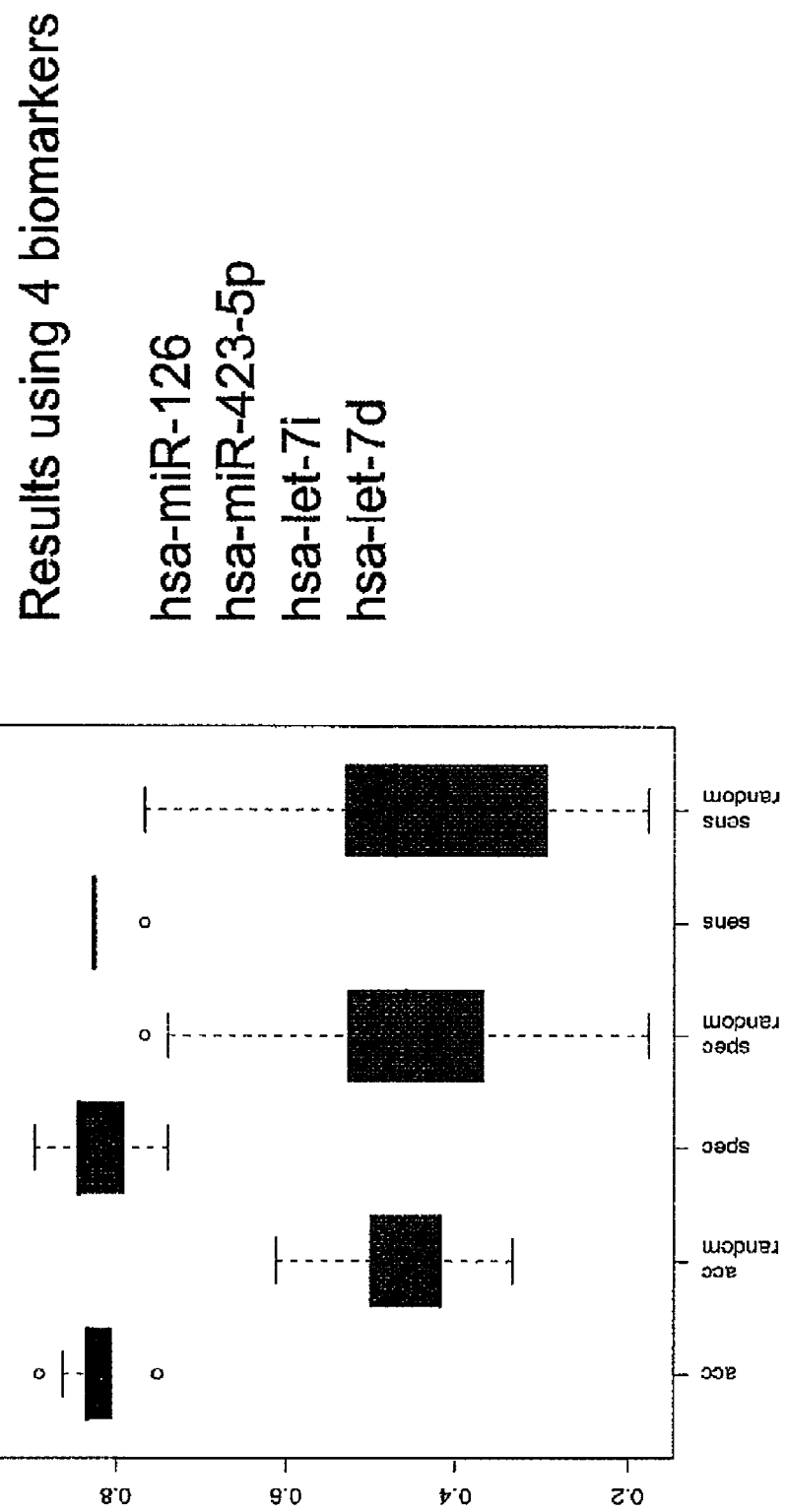
Figure 13B:
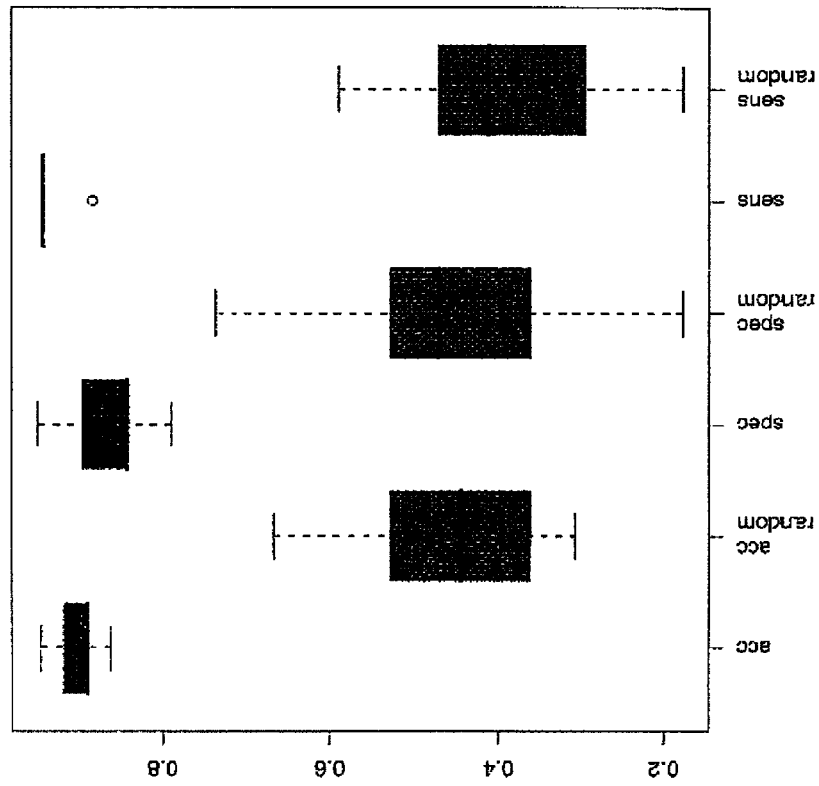
Figure 13C:
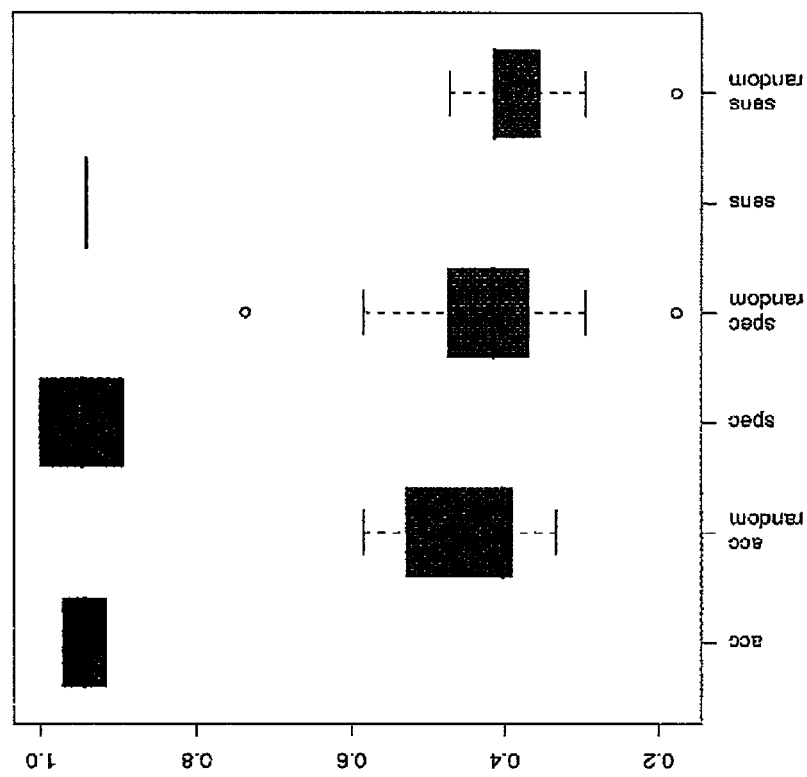
Figure 13D:
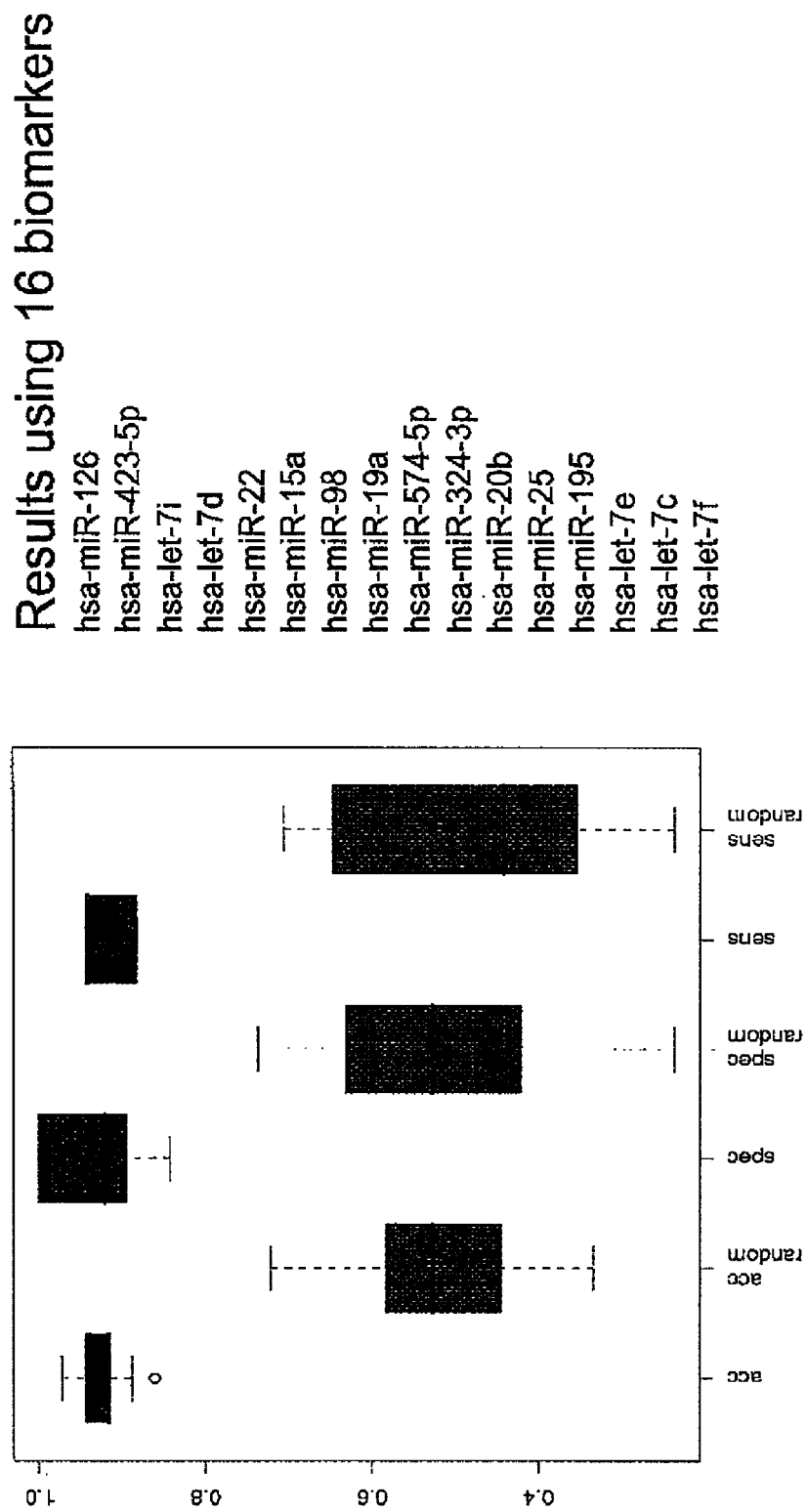
Figure 13E:
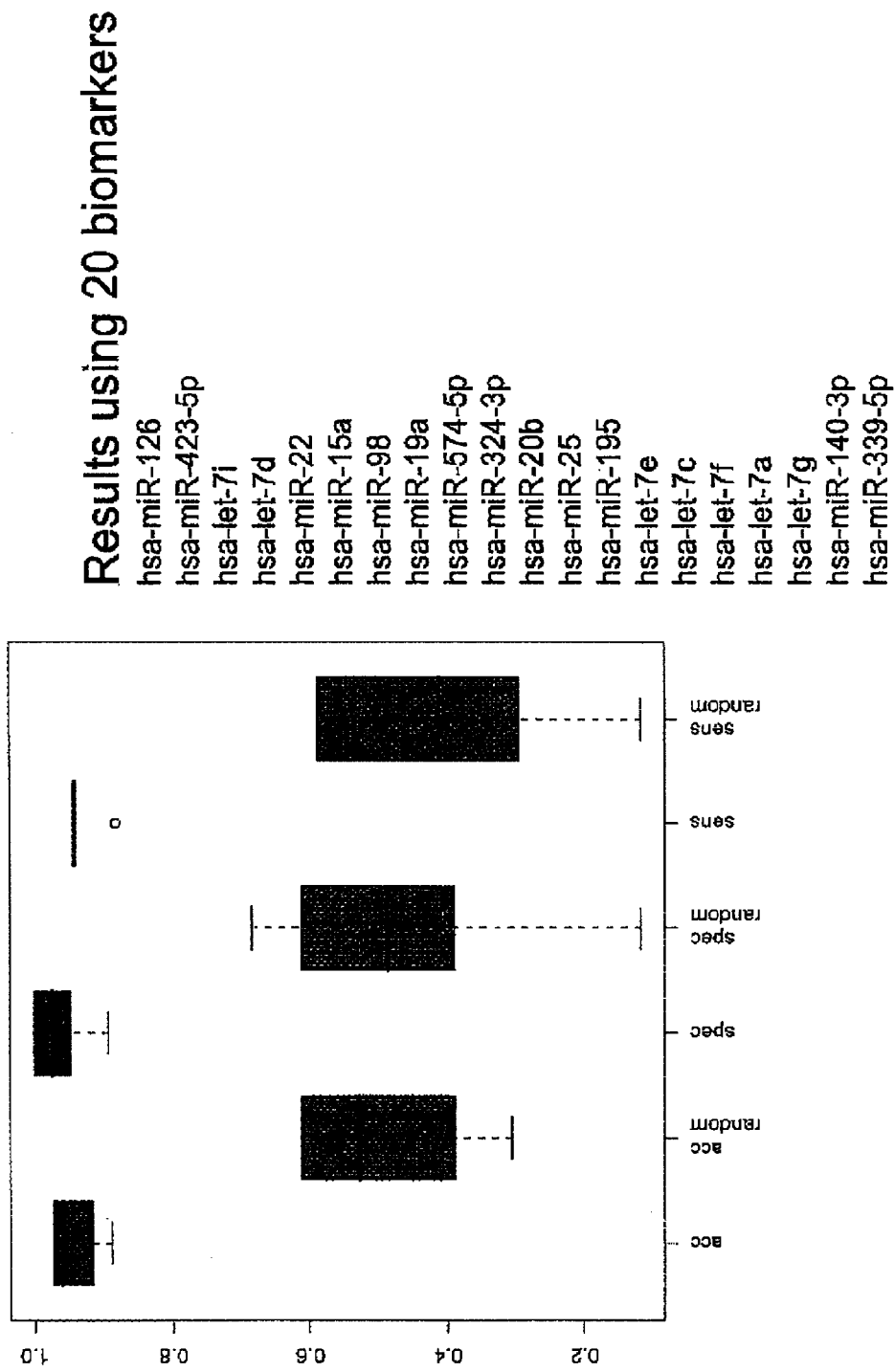
Figure 13F:
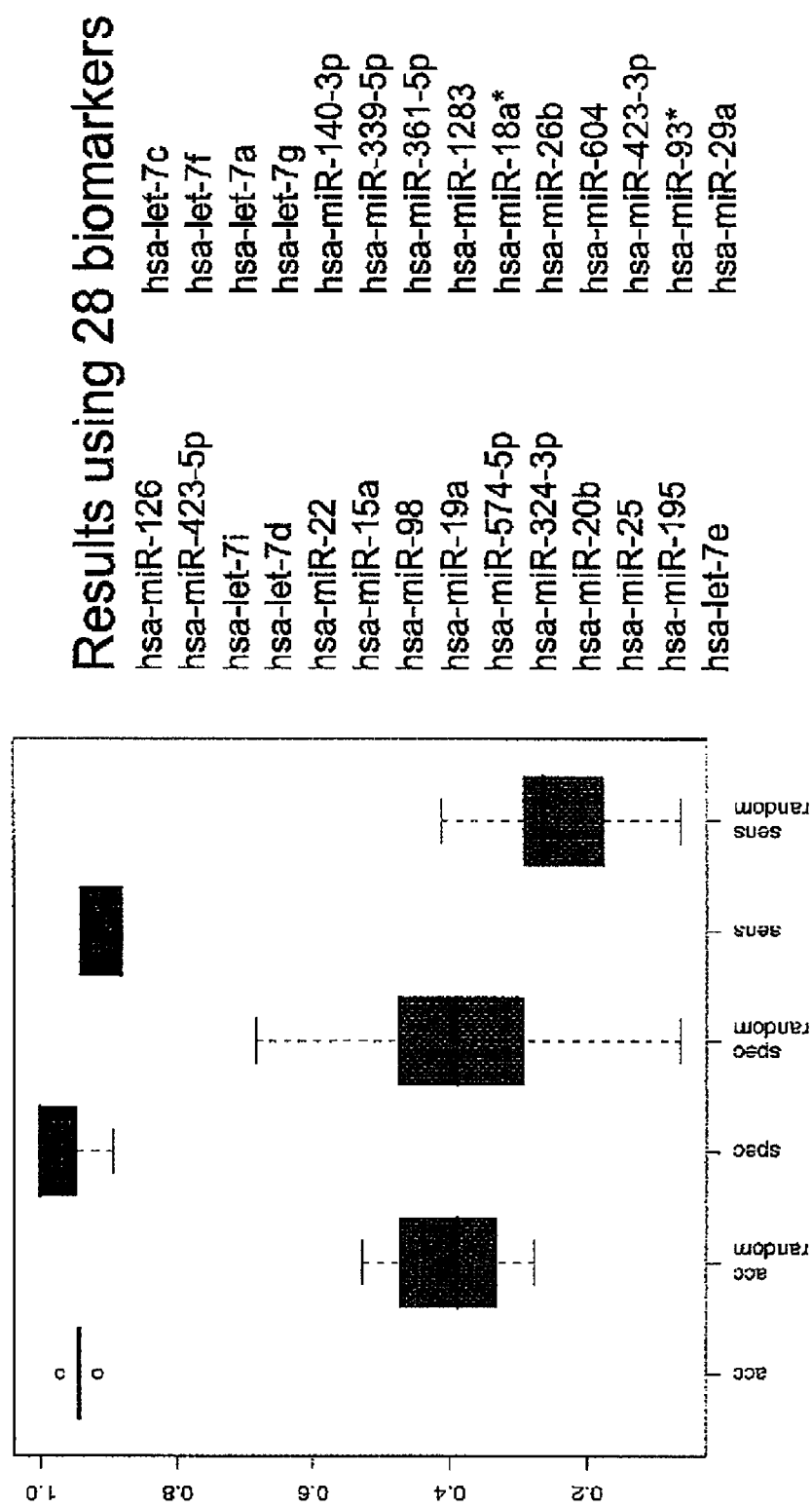
Figure 13G:
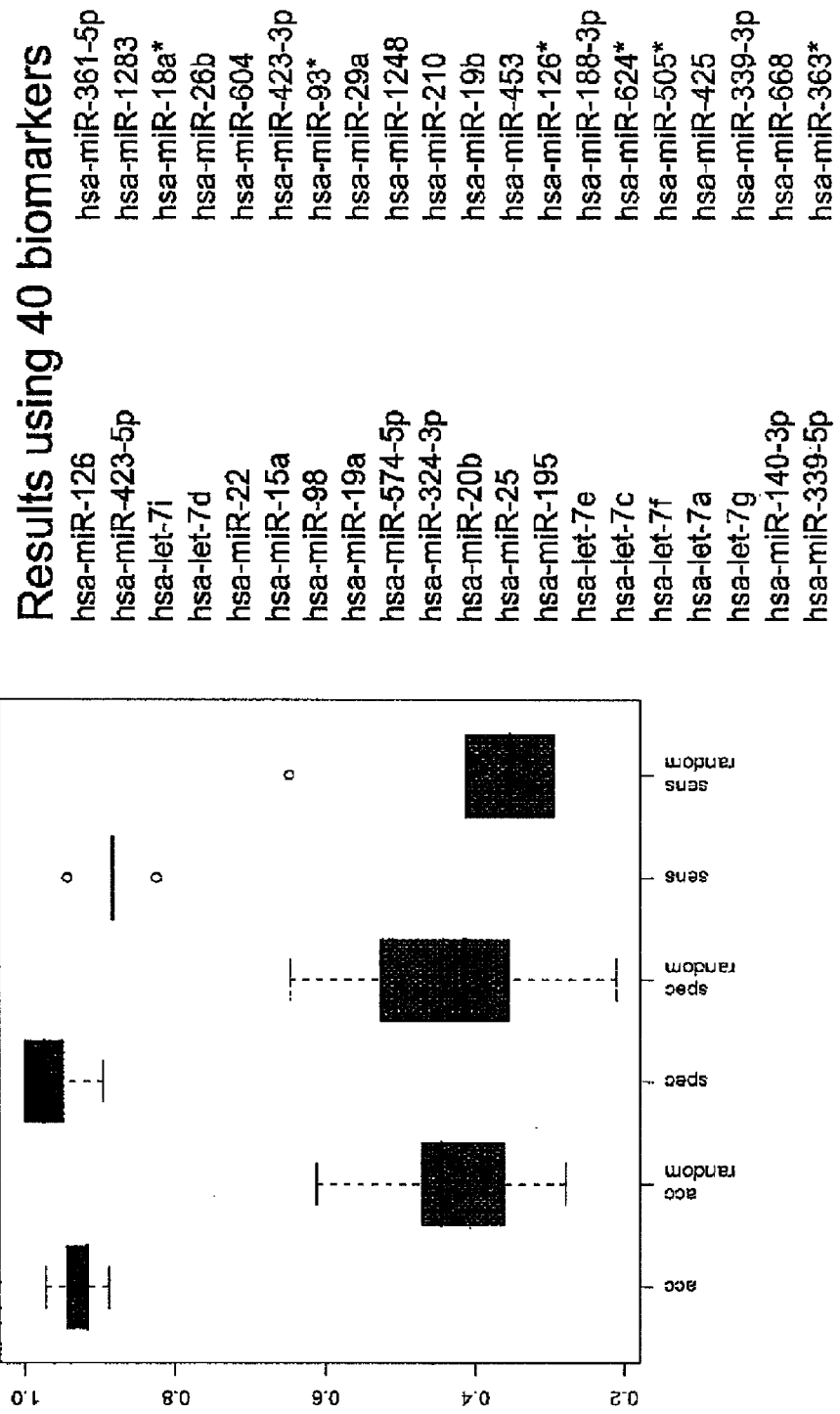

FIG. 13A: 4 biomarkers:

hsa-miR-126, hsa-miR-423-5p, hsa-let-7i and hsa-let-7d;

FIG. 13B: 8 biomarkers:

hsa-miR-126, hsa-miR-423-5p, hsa-let-7i; hsa-let-7d, hsa-miR-22, hsa-miR-15a, hsa-miR-98, and hsa-miR-19a;

FIG. 13C: 10 biomarkers:

hsa-miR-126, hsa-miR-423-5p, hsa-let-7i; hsa-let-7d, hsa-miR-22, hsa-miR-15a, hsa-miR-98, hsa-miR-19a, hsa-miR-574-5p, and hsa-miR-324-3p;

FIG. 13D: 16 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, and has-let-7f;

FIG. 13E: 20 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p and hsa-miR-339-5p;

FIG. 13F: 28 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p, hsa-miR-93*, and hsa-miR-29a;

FIG. 13G: 40 biomarkers:

hsa-miR-126, hsa-miR-423-5p, hsa-let-7i; hsa-let-7d, hsa-miR-22, hsa-miR-15a, hsa-miR-98, hsa-miR-19a; hsa-miR-574-5p; hsa-miR-324-3p, hsa-miR-20b, hsa-miR-25, hsa-miR-195, hsa-let-7e, hsa-let-7c, hsa-let-7f; hsa-let-7a, hsa-let-7g, hsa-miR-140-3p, hsa-miR-339-5p, hsa-miR-361-5p, hsa-miR-1283, hsa-miR-18a*, hsa-miR-26b, hsa-miR-604, hsa-miR-423-3p, hsa-miR-93*, hsa-miR-29a, hsa-miR-1248, hsa-miR-210, hsa-miR-19b, hsa-miR-453, hsa-miR-126*, hsa-miR-188-3p, hsa-miR-624*, hsa-miR-505*, hsa-miR-425, hsa-miR-339-3p, hsa-miR-668, and hsa-miR-363*.

FIG. 14:

Classification of lung cancer samples versus controls for two individual miRNAs (miR-126 and miR-196). Blue bars correspond to cancer samples, while red bars correspond to controls.

FIG. 15:

Lung cancer: Scatterplot of fold quotients of rt-qPCR (x-axis) and microarray experiments (y-axis).

FIG. 16:

Diagnosis of lung cancer. The mutual information of all miRNAs that have higher information content than the best permutation test (upper red line). The middle red line denotes the 95% quantile of the 1000 permutation tests and the bottom red line the mean of the permutation experiments, corresponding to the background MI.

FIG. 17:

Box plots of the classification accuracy, specificity and sensitivity of the set of 24 best miRNAs (obtained with radial basis function support vector machine). These miRNAs allow for the discrimination between blood cells of lung cancer patients and blood cells of controls with an accuracy of 95.4% [94.9%-95.9%], a specificity of 98.1% [97.3%-98.8%], and a sensitivity of 92.5% [91.8%-92.5%]. The permutation tests showed significantly decreased accuracy, specificity and sensitivity with 94.2% [47.2%-51.3%], 56.9% [54.5%-59.3%] and 40.6% [37.9%-43.4%], respectively, providing evidence that the obtained results are not due to an overfit of the statistical model on the miRNA fingerprints.

FIG. 18A:

Overview of all miRNAs that are found to be differentially regulated in blood samples of MS patients, grouped according to their diagnostic information represented by the respective area under the curve (AUC) value in receiver-operator characteristic curves. The first 193 entries represent miRNAs with t-test p-values <0.05.

FIG. 18B:

Overview of all miRNAs that are found to be differentially regulated in blood samples of MS patients, grouped according to their results in t-tests. The first 165 entries represent miRNAs with t-test p-values <0.05. The grouping is based on additional information derived from further patients (compared to FIG. 10A).

FIG. 18C:

A further list of 308 entries representing miRNAs with t-test p-values <0.05. The grouping is based on additional information derived from further patients (compared to FIGS. 18A and 18B).

FIG. 18D:

Overview of preferred signatures/sets of miRNAs for the diagnosis of multiple sclerosis (in percent: acc=accuracy, spec=specificity, sens=sensitivity).

FIG. 19:

Histogram plots of the logarithm of fold quotions, the raw t-test p-values and the adjusted p-values. The histogram plots show in the upper part a histogram of logarithmized fold changes, detailing a manifold up-regulated miRNAs in multiple sclerosis compared to healthy subjects. The middle and lower part of the Figure describe raw significance values and adjusted significance values providing evidence for a wide variety of deregulated miRNAs that are well suited for MS detection.

Figure 20A:
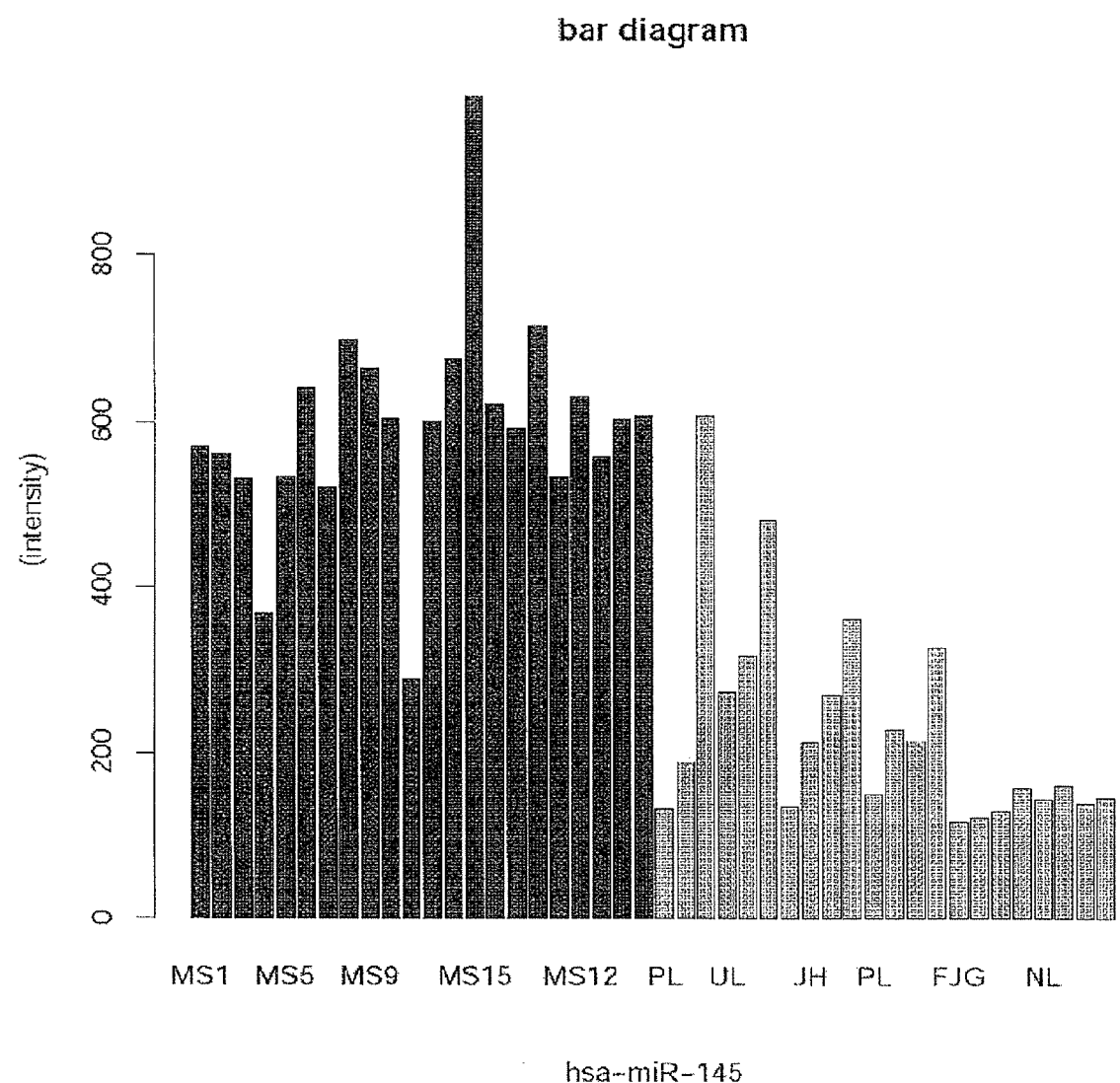
Figure 20B:
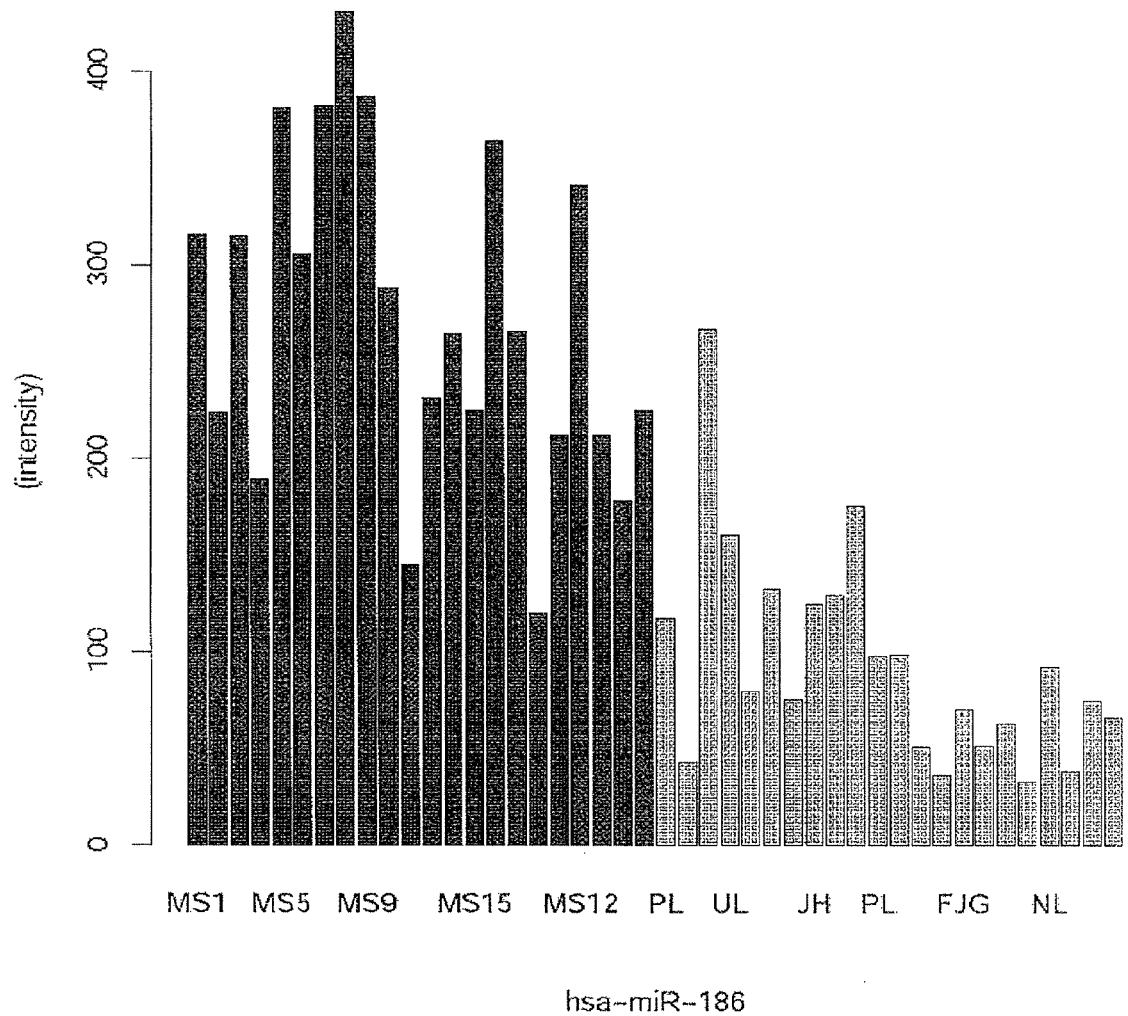

FIGS. 20A and 20B:

This Figure presents for two miRNAs, namely miR-145 and miR-186, the intensity values for all MS (left part) and control (right part) samples. Both miRNAs show a significant up-regulation in MS.

FIG. 21:

The Box-plots denote the accuracy, specificity and sensitivity of the diagnostic test of the invention (diagnosis of multiple sclerosis). In comparison, random classification results are shown, providing evidence for a decreased classification accuracy of about 50% (corresponding to random guessing). Furthermore, the graphic shows that the true classification scenario is more stable while the random classifications entail high variances.

FIG. 22:

This graph illustrates a disease network containing nodes for each disease as blue-coloured rhombs (lung cancer, multiple sclerosis, pancreatic cancer, melanoma and Wilm tumor). Additionally, it contains differentially colored and sized nodes, representing biomarker sets. The size of these nodes represents the number of biomarkers inside the set (additionally the number of biomarkers is given in side the corresponding circles). The color represents the information on the number of diseases that are significant for the biomarkers in the set. The nodes are connected to the respective diseases, e.g., each green colored node contains biomarkers, significant for two diseases and thus each green node is connected to two disease nodes. (blue=significant to one disease, rose=significant for 3 diseases, purple=significant to 5 diseases).

Figure 23A:
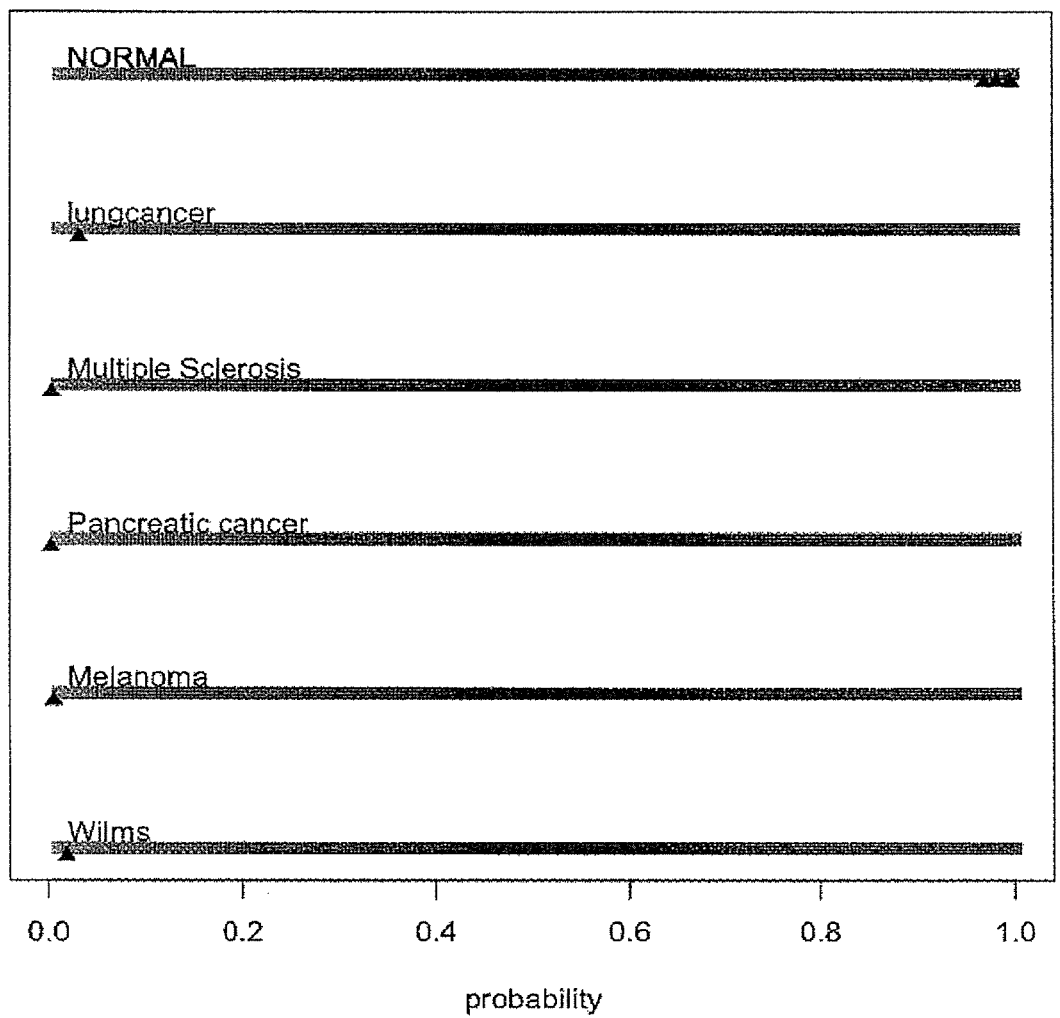
Figure 23B:
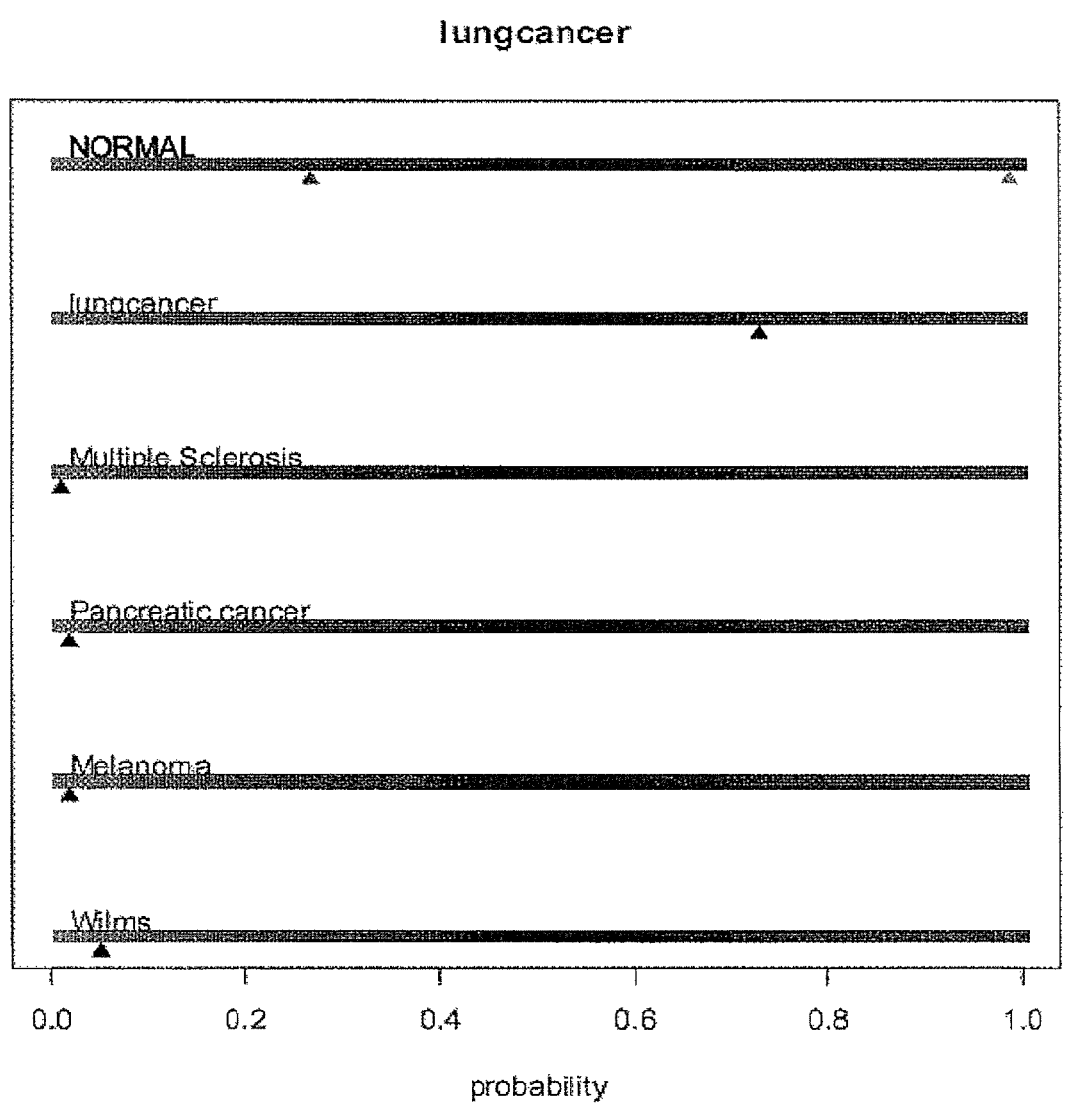
Figure 23C:
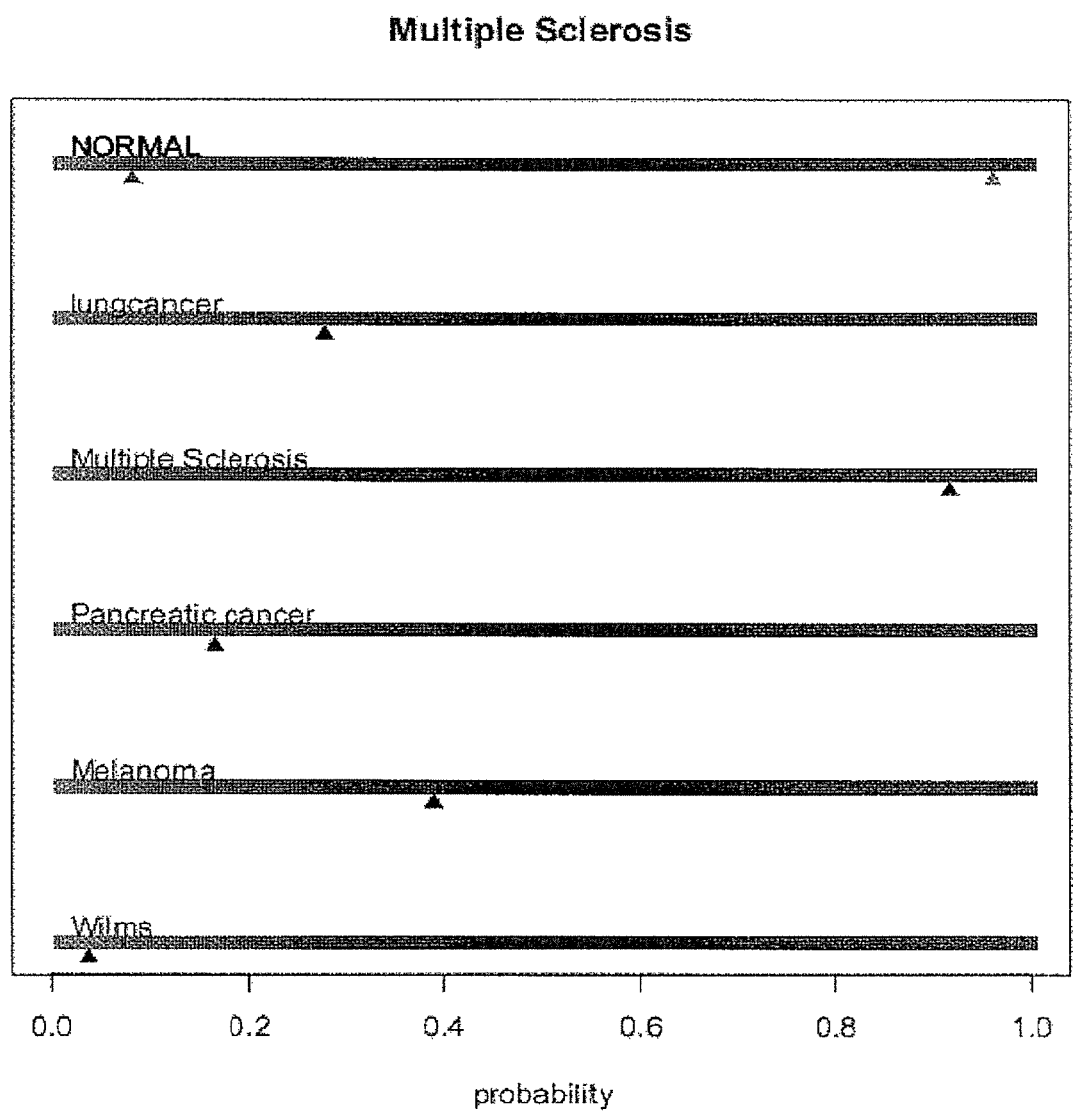

FIGS. 23A-C: The bar graphs in FIGS. 23A, B and C depict the disease probability for a "normal" individual (a), for an individual suffering from lung cancer (b) and for an individual suffering from multiple sclerosis (c).

Figure 24:
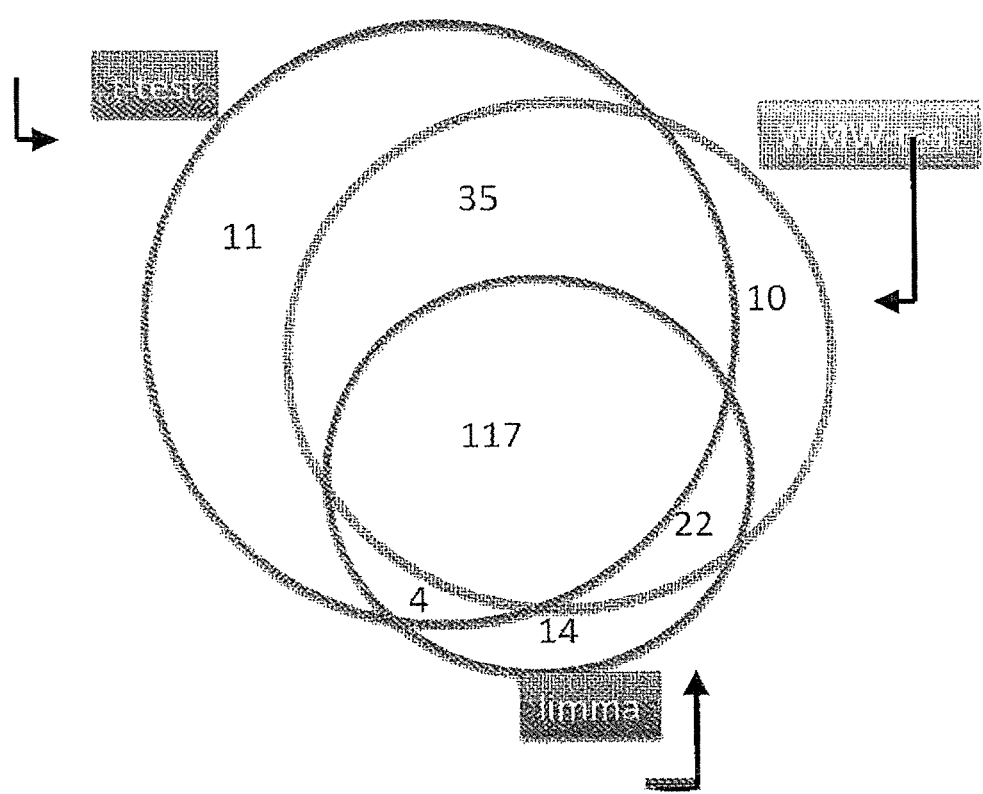

FIG. 24: Three-way Venn-diagram. The three circles represent the three tests used for classification (t-test, limma (empirical Bayes), Wilcoxon-Mann-Whitney) The numbers inside the circles and intersections of circles denotes the number of miRNAs significant with the intersecting tests.

FIG. 25:

Fold quotients in test and validation set. This figure presents the logarithm of fold quotients of miRNAs in the independently collected melanoma populations. The correlation of both fold quotients is 0.81.

FIG. 26:

Cluster dendrogram. This dendrogram presents the clustering in control 'C' samples, initially collected melanoma samples 'M' and melanoma samples in the validation set 'N'. This figure demonstrates that control samples seem to be different from the melanoma samples while the melanoma samples of both groups are rather mixed-up.

FIG. 27:

PCA plot. This figure shows the first versus the second principal component. Control samples can be clearly distinguished from melanoma samples while both melanoma populations do cluster together.

FIG. 28:

The blue (dark grey) boxes show the classification accuracy, specificity and sensitivity over the repeated cross-validation for the subset of 16 miRNAs in diagnosis of melanoma. The red (light grey) boxes show the respective accuracy, specificity and sensitivity for permutation test.

FIG. 29:

The logarithm of the quotient of the probability to be a melanoma sample and the probability to be a control sample for each control (C) and each melanoma (M) sample is given on the y-axis. If this quotient is greater than one (thus the logarithm greater zero) the sample is more likely to be a melanoma sample than a control sample.

FIGS. 30A and B:

Overview of miRNAs that are found to be differentially regulated in blood samples of melanoma patients, grouped accordingly to their results in t-tests.

FIG. 31:

Overview of some miRNAs classified according to their accuracy specificity, and sensitivity of the diagnosis of melanoma.

FIGS. 32A-B:

Overview of preferred miRNAs that are found to be differentially regulated in blood samples of skin cancer patients (FIG. 32A) or melanoma patients (FIG. 32B).

FIGS. 33A-B:

Overview of preferred signatures of miRNAs for the diagnosis of skin cancer S1-42 (FIG. 33B) or melanoma M 1-84 (FIG. 33A) respectively with acc=accuracy, spec=specificity, sens=sensitivity.

FIG. 34:

General overview of the method of diagnosing and/or predicting the state of health employing predetermined sets of miRNAs.

FIG. 35:

General overview of the method of diagnosing and/or predicting the state of health employing common signature profiles.

EXAMPLES

Example 1

Lung Cancer 1.1 Material and Methods
1.1.1 Samples

Blood samples were obtained with patients' informed consent. The patient samples stem from 17 patients with non-small cell lung carcinoma and normal controls. Normal samples were obtained from 19 different volunteers. More detailed information of patients and controls is given in Table 1.

TABLE 1

Detailed information on lung cancer patients and healthy control subjects

| blood donors | male | female |
|---|---|---|
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |
| lung cancer patients | | |
| number | 9 | 8 |
| average age | 67.4 | 60.6 |
| squamous cell lung cancer | 3 | 4 |
| adenocarcinoma | 6 | 1 |
| adenosquamous carcinoma | 0 | 1 |
| broncholaveolar carcinoma | 0 | 1 |
| typical carcinoid | 0 | 1 |
| healthy subjects | | |
| number | 7 | 12 |
| average age | 43.3 | 36.7 |

1.1.2 miRNA Microarray Screening

Blood of lung cancer patients and volunteers without known disease was extracted in PAXgene Blood RNA tubes (BD, Franklin Lakes, N.J. USA). For each blood donor, 5 ml of peripheral blood were obtained. Total RNA was extracted from blood cells using the miRNeasy Mini Kit (Qiagen GmbH, Hilden, Germany) and the RNA has been stored at −70° C. Samples were analyzed with the Geniom Realtime Analyzer (GRTA, febit gmbh, Heidelberg, Germany) using the Geniom Biochip miRNA *homo sapiens*. Each array contains 7 replicates of 866 miRNAs and miRNA star sequences as annotated in the Sanger mirBase 12.0 (Griffiths-Jones, Moxon et al. 2005; Griffiths-Jones, Saini et al. 2008). Sample labelling with Biotin has been carried out either by using the miRVANA™ miRNA Labelling Kit (Applied Biosystems Inc, Foster City, Calif. USA) or by multifluidic-based enzymatic on-chip labelling of miRNAs (MPEA (Vorwerk, Ganter et al. 2008), incorporated herein by reference).

Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values have been calculated corresponding to each replicate copy of mirBase on the array. Following background correction, the seven replicate intensity values of each miRNA were summarized by their median value. To normalize the data across different arrays, quantile normalization (Bolstad, Irizarry et al. 2003) was applied and all further analyses were carried out using the normalized and background subtracted intensity values.

1.1.3 Statistical Analysis

After having verified the normal distribution of the measured data, parametric t-tests (unpaired, two-tailed) were carried out for each miRNA separately, to detect miRNAs that show a different behavior in different groups of blood donors. The resulting p-values were adjusted for multiple testing by Benjamini-Hochberg (Hochberg 1988; Benjamini and Hochberg 1995) adjustment. Moreover, the Mutual Information (MI) (Shannon 1984) was computed as a measure to access the diagnostic value of single miRNA biomarkers. To this end, all biomarkers were transformed to z-scores and binned in three bins before the MI values of each biomarker, and the information whether the marker has been measured from a normal or lung cancer sample, was computed. In addition to the single biomarker analysis classification of samples using miRNA patterns was carried out using Support Vector Machines (SVM, (Vapnik 2000)) as implemented in the R (Team 2008) e1071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique a filter approach based on t-test was applied. In detail, the s miRNAs with lowest p-values were computed on the training set in each fold of the cross validation, where s was sampled from 1 to 866. The respective subset was used to train the SVM and to carry out the prediction of the test samples. As result, the mean accuracy, specificity, and sensitivity were calculated together with the 95% Confidence Intervals (95% CI) for each subset size. To check for overtraining permutation tests were applied. Here the class labels were sampled randomly and classifications were carried out using the permuted class labels. All statistical analyzes were performed using R (Team 2008).

1.2 Results
1.2.1 miRNA Experiments

The expression of 866 miRNAs and miRNA star sequences was analyzed in blood cells of 17 patients with NSCLC. As a control blood cells of 19 volunteers without known disease were used (see also Materials and Methods).

Following RNA isolation and labeling by miRVANA™ miRNA Labeling Kit, the miRNA expression profiles were measured by the Geniom Bioship miRNA *homo sapiens* in the GRTA (febit gmbh, Heidelberg). Following intensity value computation and quantile normalization of the miRNA profiles (Bolstad, Irizarry et al. 2003), a mean correlation value of 0.97 for technical replicates was determined by using purchased total RNA from Ambion (four heart and four liver replicates). For the biological replicates the different tumor samples were compared between each other and the different normal samples between each other. The biological replicates showed a mean correlation of 0.87 and a variance of 0.009.

1.2.2 Ruling Out the Influence of Age and Gender

To cross-check that age and gender do not have an influence on our analysis, t-tests were computed for the normal samples. In the case of males versus females there was no statistically significant deregulated miRNA. The most significant miRNA, hsa-miR-423, showed an adjusted significance level of 0.78.

To test for the influence of donor age the profiles obtained from samples obtained from the oldest versus youngest patients were compared by splitting the group in half based on age. Here, the most significant miRNA, miR-890, obtained an adjusted p-value of 0.87. As for gender, there were no deregulated miRNAs, thus providing evidence that age and gender do not have a substantial influence on the miRNA profiles.

1.2.3 Single Deregulated miRNAs

Hypothesis testing was applied to identify miRNAs deregulated in the blood cells of lung cancer patients as compared to the blood cells of the controls. Following verification of an approximately normal distribution, two-tailed unpaired t-tests were performed for each miRNA. The respective p-values were adjusted for multiple testing by the Benjamini-Hochberg approach (Hochberg 1988; Benjamini and Hochberg 1995). In total 27 miRNAs significantly deregulated in blood cells of lung cancer patients as compared to the controls were detected. A complete list of deregulated miRNAs is given in the tables in FIGS. 10A and 10B. The miRNAs that were most significantly deregulated included hsa-miR-126 with a p-value of 0.00003, hsa-let-7d with a p-value of 0.003, hsa-let-7i with a p-value of 0.003, and hsa-miR-423 with a p-value of 0.001 (FIG. 12). Other members of the let-7 family that were also found to be deregulated included hsa-let-7c, hsa-let-7e, hsa-let-7f, hsa-let-7g and hsa-let-7a. Besides miR-423, all above mentioned miRNAs were down-regulated in blood cells of lung cancer patients compared to blood cells of healthy subjects indicating an overall decreased miRNA repertoire.

To validate the findings, the miRNA profiling was repeated using an enzymatic on-chip labeling technique termed MPEA (Microfluidic-based enzymatic on-chip labeling of miRNAs) [24]. For this control experiment, 4 out of the 17 lung cancer patients and 10 of the controls were used. Hereby, 100 differentially regulated miRNAs were detected. The miRNAs that were most significantly deregulated include hsa-miR-1253 with a p-value of 0.001, hsa-miR-126 with a p-value of 0.006, hsa-let-7d with a p-value of 0.006, and hsa-let-7f with a p-value of 0.006. Of the previously identified 27 miRNAs 12 were detected to be significant in the second experiment, while the remaining miRNAs showed increased p-values. The correlation of fold changes was 0.62. Also other members of the let-7 family were confirmed as deregulated in blood cells of lung cancer patients. Furthermore, it was confirmed that the majority of the deregulated miRNAs were down-regulated in patients' blood samples. Here, 62% of the deregulated miRNAs showed decreased intensity values in lung cancer samples.

Figure 15:
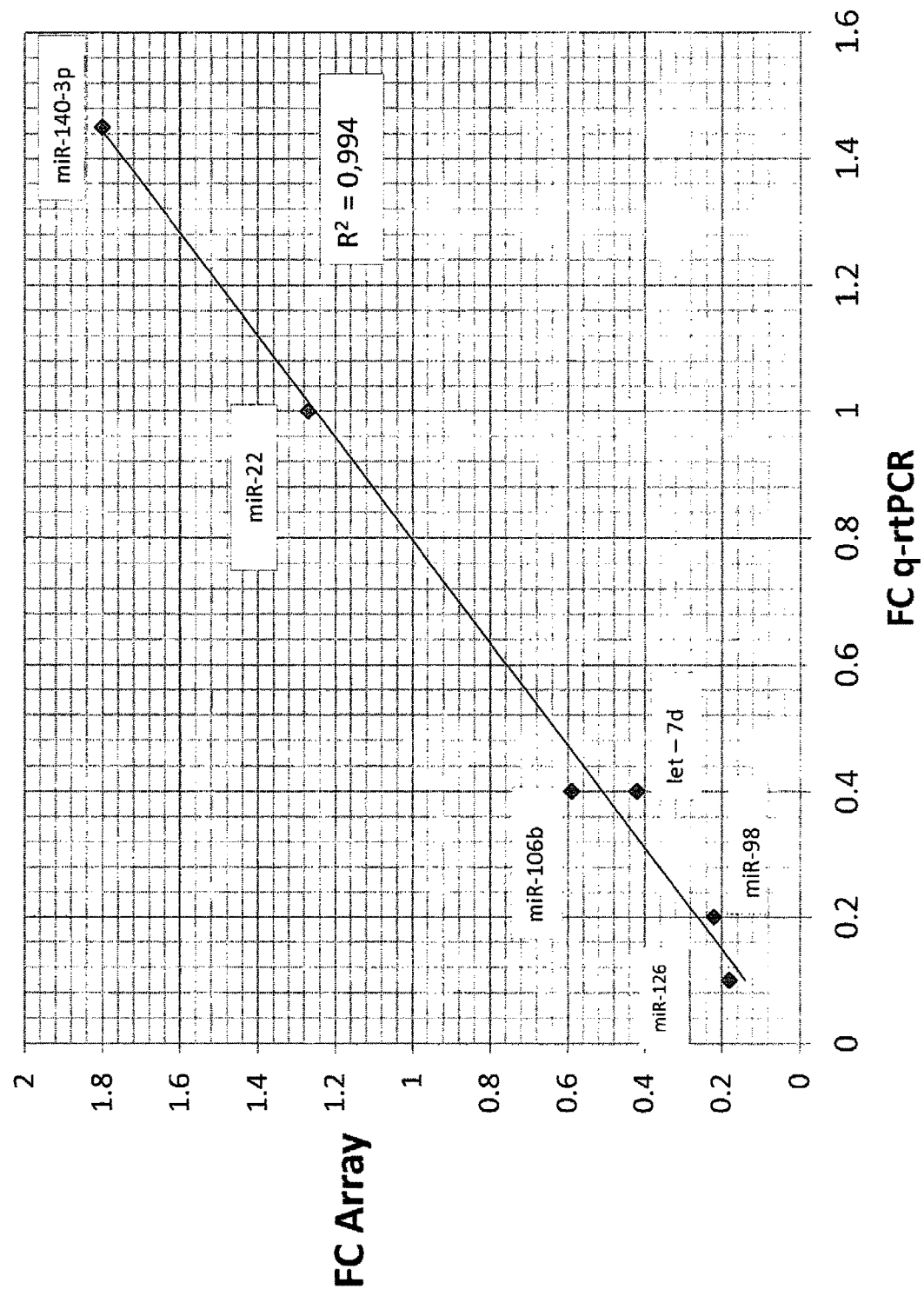

As a further control experiment an expression analysis by qRT-PCR was performed. As a test sample the fold changes of has-miR-106b, miR-98, miR-140-3p, let-7d, mir-126, and miR-22 were analyzed in blood cells of eight tumor patients and five controls. The fold quotients detected by the Geniom Biochip experiments agreed very well with the qRT-PCR experiments, as demonstrated by an excellent $R^2$ value of 0.994. The fold quotients are presented as a scatterplot together with the $R^2$ value and the regression line in FIG. 15.

1.2.4 Diagnostic Value of miRNA Biomarkers

Mutual Information (MI) (Shannon 1984) is an adequate measure to estimate the overall diagnostic information content of single biomarkers (Keller, Ludwig et al. 2006). In the present study, Mutual Information is considered as the reduction in uncertainty about the class labels '0' for controls and '1' for tumor samples due to the knowledge of the miRNA expression. The higher the value of the MI of a miRNA, the higher is the diagnostic content of the respective miRNA.

Figure 16:
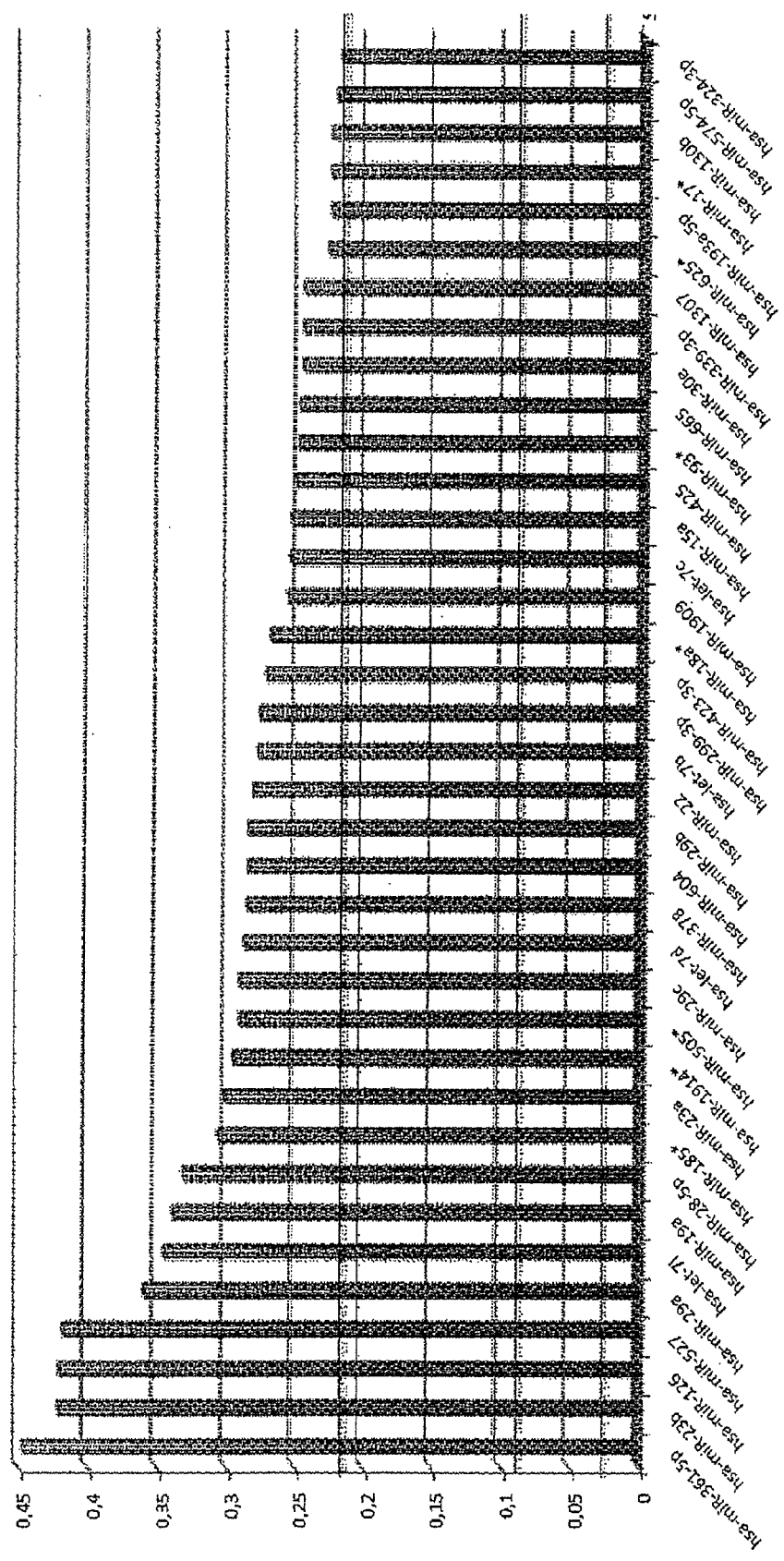

The MI of each miRNA with the class labels was computed. First, a permutation test was carried out to determine the background noise of the miRNAs, e.g. the random information content of each miRNA. 1000 miRNAs (with replacements) were randomly selected and the class labels were sampled for each miRNA. These permutation tests yielded a mean MI value of 0.029, a 95% quantile of 0.096 and a value of 0.217 for the highest random MI. Second, the MI values were calculated for the comparison between the miRNAs in blood cells of tumor patients and controls. The overall comparison of the 866 miRNAs yielded significantly increased MI values with a two-tailed p-value of $\leq 10^{-10}$ as shown by an unpaired Wilcoxon Mann-Whitney test (Wilcoxon 1945; Mann and Wilcoxon 1947). The miRNA hsa-miR-361-5p showed the highest MI with a value of 0.446. The miRNAs with the best significance values as computed by the t-test, namely hsa-miR-126 and hsa-miR-98, were also among the miRNAs showing the highest MI values. In total 37 miRNAs with MI values higher than the highest of 1000 permuted miRNAs and 200 miRNAs with MI values higher than the 95% quantile were detected (FIG. 16). A complete list of miRNAs, the respective MI and the enrichment compared to the background MI is provided in the table in FIG. 10A.

1.2.5 Evaluating Complex Fingerprints

Even single miRNAs with highest MI values are not sufficient to differentiate between blood cells of tumor patients as compared to controls with high specificity. For example, the has-miR-126 separates blood cells of tumor patients from blood cells of healthy individuals with a specificity of 68%, only. In order to improve the classification accuracy the predictive power of multiple miRNAs was combined by using statistical learning techniques. In detail, Support Vector Machines with different kernels (linear, polynomial, sigmoid, radial basis function) were applied to the data and a hypothesis test was carried out based subset selection as described in Material and Methods. To gain statistical significance 100 repetitions of 10-fold cross validation were carried out. Likewise, 100 repetitions for the permutation tests were computed.

Figure 17:
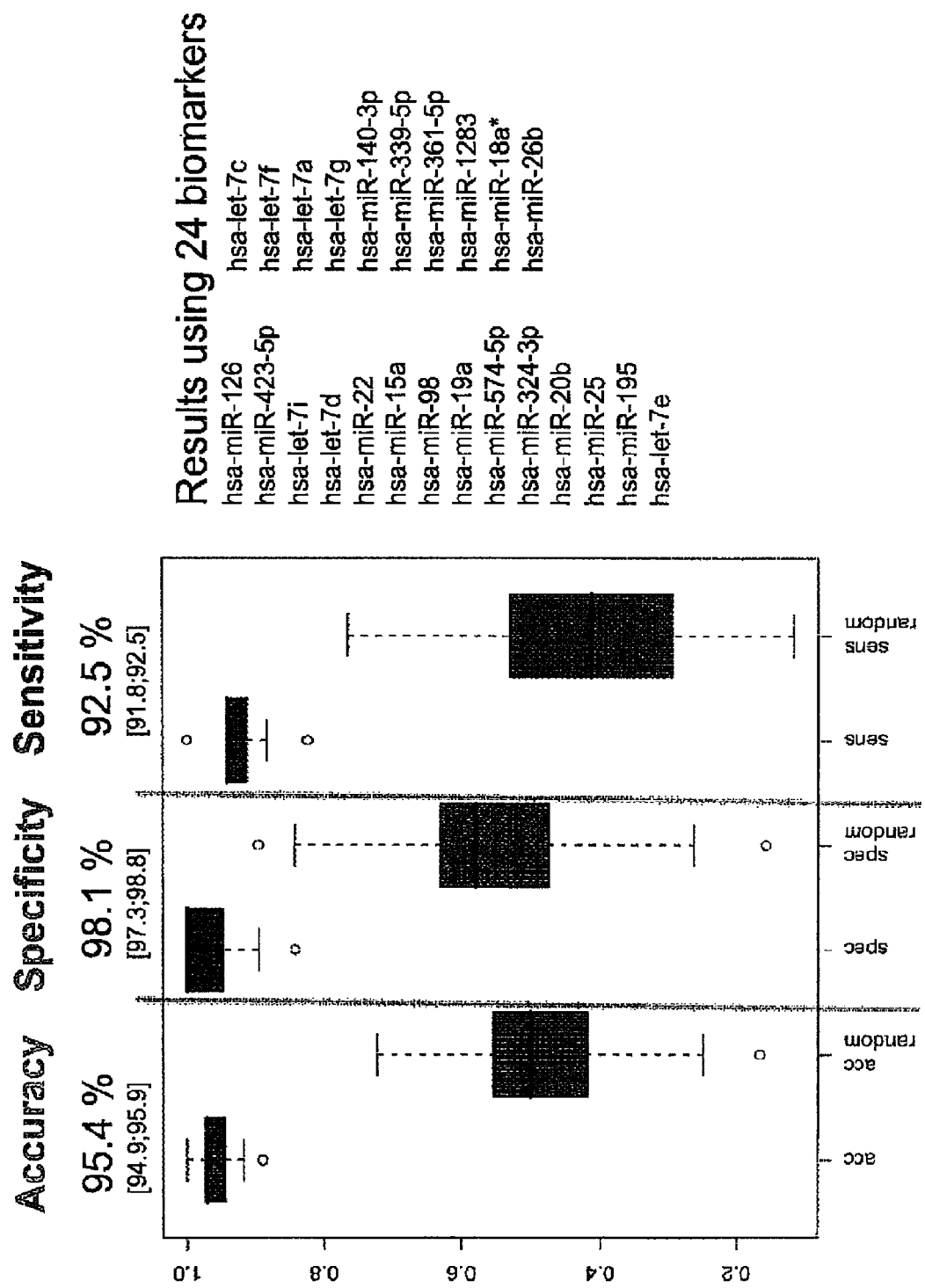

The best results were obtained with radial basis function Support Vector Machines and a subset of 24 miRNAs. These miRNAs allowed for the discrimination between blood cells of lung tumor patients and blood cells of controls with an accuracy of 95.4% [94.9%-95.9%], a specificity of 98.1% [97.3%-98.8%], and a sensitivity of 92.5% [91.8%-92.5%]. The permutation tests showed significantly decreased accuracy, specificity, and sensitivity with 49.2% [47.2%-51.3%], 56.9% [54.5%-59.3%] and 40.6% [37.9%-43.4%], respectively (FIG. 17), providing evidence that the obtained results are not due to an overfit of the statistical model on the miRNA fingerprints.

1.3 Discussion

While complex miRNA expression patterns have been reported for a huge variety of human tumors, information there was only one study analyzing miRNA expression in blood cells derived from tumor patients. In the following the present miRNA expression profiling is related to both the miRNA expression in blood cells and in cancer cells of non-small cell lung cancer patients. A significant down-regulation of has-miR-126 was found that was recently detected in blood cells of healthy individuals, but not in blood cells of lung cancer patients (Chen, Ba et al. 2008). Down-regulation of has-miR-126 was also found in lung cancer tissue in this study. Functional studies on has-miR-126 revealed this miRNA as a regulator of the endothelial expression of vascular cell adhesion molecule 1 (VCAM-1), which is an intercellular adhesion molecule expressed by endothelial cells focuses on the identification of miRNAs in serum of patients with cancer and other diseases or healthy controls. Since most miRNAs are expressed in both, serum and blood cells of healthy controls, most serum miRNAs are likely derived from circulating blood cells. Since there was only a weak correlation between the miRNA expression in serum and blood cell, miRNA expression appears to be deregulated in either serum or blood cells of cancer patients. The present experimental example focused on the analysis of miRNA expression in blood cells of non-small cell lung cancer patients and healthy controls. Significant downregulation of has-miR-126 was found that was recently detected in blood cells of healthy individuals, but not in blood cells of lung cancer patients (Harris, YamakuchiChen, Ba et al. 2008). Downregulation of has-miR-126 was also found in lung cancer tissue (Yanaihara, Caplen et al. 2006). Functional studies on has-miR-126 revealed this miRNA as regulator of the endothelial expression of vascular cell adhesion molecule 1 (VCAM-1), which is an intercellular adhesion molecule expressed by endothelial cells (Harris, Yamakuchi et al. 2008). hsa-miR-126 is also reported to be an inhibitor of cell invasion in non-small cell lung cancer cell lines, and down-regulation of this miRNA 126 might be a mechanism of lung cancer cells to evade these inhibitory effects (Crawford, Brawner et al. 2008). Members of the has-let-7 family that were found down-regulated in the present invention were the first miRNAs reported as de-regulated in lung cancer (Johnson, Grosshans et al. 2005). This down-regulation of the let-7 family in lung cancer was confirmed by several independent studies (Takamizawa, Konishi et al. 2004; Stahlhut Espinosa and Slack 2006; Tong 2006; Zhang, Wang et al. 2007; Williams 2008). The present data are also in agreement with a recent study showing the down-regulation of has-let-7a, has-let-7d, has-let-7f, has-let-7g, and has-let-7i in blood cells of lung cancer patients (Chen, Ba et al. 2008). Notably, down-regulation of let-7 in lung cancer was strongly associated with poor clinical outcome (Takamizawa, Konishi et al. 2004). The let-7 family members negatively regulate oncogene RAS (Johnson, Grosshans et al. 2005). The miRNA has-miR-22 that showed a high MI value and up-regulation in the present study, was recently also reported to be up-regulated in blood cells of lung cancer patients (Chen, Ba et al. 2008). The miRNA has-miR-19a that also showed a high MI value and up-regulation in the present study was reported to be up-regulated in lung cancer tissue (Hayashita, Osada et al. 2005; Calin and Croce 2006). In contrast, has-miR-20a, which is significantly down-regulated in the present experiments, was reported as up-regulated in lung cancer tissue (Hayashita, Osada et al. 2005; Calin and Croce 2006). The up-regulation of has-miR-20a was found in small-cell lung cancer cell lines, the present study investigated only NSCLC. In summary, there is a high degree of consistency between miRNA expression found in the peripheral blood cells of lung cancer patients and miRNA expression in lung cancer tissue (Takamizawa, Konishi et al. 2004; Hayashita, Osada et al. 2005; Lu, Getz et al. 2005; Calin and Croce 2006; Stahlhut Espinosa and Slack 2006; Tong 2006; Volinia, Calin et al. 2006; Yanaihara, Caplen et al. 2006; Zhang, Wang et al. 2007; Williams 2008).

Some of the deregulated miRNAs identified in the present invention are also reported as de-regulated in other cancer entities, e.g. has-miR-346 in gastritic cancer, has-miR-145 in bladder cancer, and has-miR-19a in hepatocellular carcinoma and B-cell leukemia (Alvarez-Garcia and Miska 2005; He, Thomson et al. 2005; Feitelson and Lee 2007; Guo, Huang et al. 2008; Ichimi, Enokida et al. 2009). In addition, miRNAs with high diagnostic potential e.g. high MI value, were found that were not yet related to cancer as for example has-miR-527 or has-mir-361-5p that were both up-regulated in blood cells of lung cancer patients.

Besides the deregulation of single miRNAs, the overall expression pattern of miRNAs in peripheral blood cells of lung cancer patients were analyzed in comparison to the pattern in blood cells of healthy controls. Recently, Chen et al. (Chen, Ba et al. 2008) reported a high correlation of 0.9205 between miRNA profiles in serum and miRNA profiles in blood cells, both in healthy individuals. The correlation of the miRNA profiles between serum and blood cells in lung cancer patients were significantly lower (0.4492). These results are indicative of deregulated miRNAs in blood and/or serum of patients and are in agreement with the present data that show the deregulation of miRNAs in the blood cells of lung carcinoma patients. These deregulated miRNAs can be used to differentiate patients with lung cancer from normal controls with high specificity and sensitivity. This is the first evidence for the diagnostic potential of miRNA expression profiles in peripheral blood cells of cancer patients and healthy individuals.

Example 2

Multiple Sclerosis 2.1 Material and Methods
2.1.1 Samples

Blood samples were obtained with patients' informed consent.

2.1.2 miRNA Microarray Screening

Blood of MS patients and volunteers without known disease was extracted in PAXgene Blood RNA tubes (BD, Franklin Lakes, N.J. USA). For each blood donor, 5 ml of peripheral blood were obtained. Total RNA was extracted from blood cells using the miRNeasy Mini Kit (Qiagen GmbH, Hilden, Germany) and the RNA has been stored at −70° C. Samples were analyzed with the Geniom Realtime Analyzer (GRTA, febit GmbH, Heidelberg, Germany) using the Geniom Biochip miRNA *homo sapiens*. Each array contains 7 replicates of 866 miRNAs and miRNA star sequences as annotated in the Sanger mirBase 12.0. Sample labelling with Biotine has been carried out by multifluidic-based enzymatic on-chip labelling of miRNAs (MPEA).

Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values have been calculated corresponding to each replicate copy of mirBase on the array. Following background correction, the seven replicate intensity values of each miRNA were summarized by their median value. To normalize the data across different arrays, quantile normalization was applied and all further analyses were carried out using the normalized and background subtracted intensity values.

2.1.3 Statistical Analysis

After having verified the normal distribution of the measured data, a parametric t-test (unpaired, two-tailed) was carried out for each miRNA separately, to detect miRNAs that show a different behavior in different groups of blood donors. The resulting p-values were adjusted for multiple testing by Benjamini-Hochberg adjustment.

To find relations of the detected miRNAs to other diseases the Human miRNA Disease Database was used. In more detail, a bipartite network was built where nodes correspond either to a miRNA or to a diseases. Only edges between miRNA and diseases nodes are allowed, where an edge between miRNA A and disease B means that the miRNA A is differentially regulated in disease B. Since for MS no deregulated miRNAs are known the node "MultipleSclerosis" was added to this network and linked to all miRNAs that were significant in the analysis.

In addition to the single biomarker analysis and network analysis, classification of samples using miRNA patterns was carried out using Support Vector Machines (SVM,) as implemented in the R e1071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique we applied a filter approach based on t-test. In detail, the s miRNAs with lowest p-values were computed on the training set in each fold of the cross validation, where s was sampled from 1 to 866. The respective subset was used to train the SVM and to carry out the prediction of the test samples. As result, the mean accuracy, specificity, and sensitivity were calculated together with the 95% Confidence Intervals (95% CI) for each subset size. To check for overtraining permutation tests were applied. Here the class labels were sampled randomly and classifications were carried out using the permuted class labels. All statistical analyzes were performed using R.

2.2 Results 2.2.1 miRNA Experiments

The expression of 866 miRNAs and miRNA star sequences was analyzed in blood cells of 22 patients with MS. As a control blood cells of 22 volunteers without known disease were used.

Following RNA isolation and the novel on-chip labeling technique, the miRNA expression profiles were measured by the Geniom Bioship miRNA homo sapiens in the GRTA (febit GmbH, Heidelberg). Following intensity value computation and quantile normalization of the miRNA profiles, a mean correlation value of 0.97 for technical replicates was determined by using purchased total RNA from Ambion (four heart and four liver replicates). For the biological replicates the different tumor samples were compared between each other and the different normal samples were compared between each other. The biological replicates showed a mean correlation of 0.87 and a variance of 0.009.

2.2.2 Ruling Out the Influence of Age and Gender

To cross-check that age and gender do not have an influence on our analysis, t-tests for the normal samples were computed. In the case of males versus females there were no statistically significant deregulated miRNA. The most significant miRNA, hsa-miR-423, showed an adjusted significance level of 0.78.

To test for the influence of donor age the profiles obtained from samples obtained from the oldest versus youngest patients were compared by splitting the group in half based on age. Here, the most significant miRNA, miR-890, obtained an adjusted p-value of 0.87. As for gender, there were no deregulated miRNAs, thus providing evidence that age and gender do not have a substantial influence on the miRNA profiles.

2.2.3 Single Deregulated miRNAs

Hypothesis testing was applied to identify miRNAs deregulated in the blood cells of MS patients as compared to the blood cells of the controls. Following verification of an approximately normal distribution, two-tailed unpaired t-tests were performed for each miRNA. The respective p-values were adjusted for multiple testing by the Benjamini-Hochberg approach. In total 193 miRNAs significantly deregulated in blood cells of MS patients as compared to the controls were detected. Histogram plots of the logarithm of fold quotients, the raw t-test p-values and the adjusted p-values are presented in FIG. 18B. A complete list of deregulated miRNAs is given in the Table in FIG. 18B. The miRNAs that were most significantly deregulated included hsa-miR-145 ($5.25*10^{-9}$), hsa-miR-186 ($3.42*10^{-7}$), hsa-miR-664 ($1.20*10^{-5}$), hsa-miR-20b ($1.98*10^{-5}$), hsa-miR-584 ($1.98*10^{-5}$), hsa-miR-223 ($2.14*10^{-5}$), hsa-miR-422a ($2.87*10^{-5}$), hsa-miR-142-3p ($3.01*10^{-5}$) and hsa-let-7c ($7.68*10^{-5}$). For the two best miRNAs, hsa-miR-186 and hsa-miR-145, bar-plots showing the intensity values for all MS and control samples are presented in FIGS. 20a and 20b.

Notably, all the above-mentioned miRNAs showed a significant up-regulation in MS besides miR-20b. Table 2 shows the 24 most deregulated miRNAs. Of these 91.7% were up-regulated in MS while 8.3% were down-regulated, providing evidence for an overall up-regulation of miRNAs in MS.

Additionally for the best miRNAs receiver operator characteristic curves (ROC) and the area under the curve value (AUC) were computed. The higher the AUC, the better the miRNA biomarker is, where a maximal value of 1 for miRNA A would mean that the highest control reactivity would be lower than the lowest MS intensity of miRNA A. For the best miRNA hsa-miR-145 an AUC value of 0.96 was obtained and four of the 44 samples were wrong classified (2 Ms sera as controls, so-called False Negatives, and 2 controls classified as MS samples, so-called False Positives).

TABLE 2

24 most significant miRNAs for MS

| miRNA | median g1 | median g2 | qmedian | Log (qmedian) | raw Pval | adj. Pval | AUC |
|---|---|---|---|---|---|---|---|
| hsa-miR-145 | 602.719 | 174.344 | 3.457 | 1.240 | 6.08E−12 | 5.25E−09 | 0.962 |
| hsa-miR-186 | 265.295 | 77.719 | 3.414 | 1.228 | 7.91E−10 | 3.42E−07 | 0.961 |
| hsa-miR-664 | 707.168 | 285.703 | 2.475 | 0.906 | 4.17E−08 | 1.20E−05 | 0.916 |
| hsa-miR-584 | 332.922 | 106.969 | 3.112 | 1.135 | 1.15E−07 | 1.98E−05 | 0.897 |
| hsa-miR-20b | 2689.207 | 5810.586 | 0.463 | −0.770 | 9.83E−08 | 1.98E−05 | 0.056 |
| hsa-miR-223 | 5118.574 | 2579.250 | 1.985 | 0.685 | 1.49E−07 | 2.14E−05 | 0.964 |
| hsa-miR-422a | 373.953 | 189.219 | 1.976 | 0.681 | 2.32E−07 | 2.87E−05 | 0.870 |
| hsa-miR-142-3p | 215.375 | 40.516 | 5.316 | 1.671 | 2.79E−07 | 3.01E−05 | 0.934 |
| hsa-let-7c | 1948.098 | 950.223 | 2.050 | 0.718 | 8.00E−07 | 7.68E−05 | 0.889 |
| hsa-miR-151-3p | 1021.363 | 571.344 | 1.788 | 0.581 | 1.81E−06 | 0.000156587 | 0.883 |
| hsa-miR-491-5p | 241.000 | 153.563 | 1.569 | 0.451 | 2.05E−06 | 0.000160884 | 0.876 |
| hsa-miR-942 | 112.969 | 38.094 | 2.966 | 1.087 | 5.09E−06 | 0.000366452 | 0.882 |
| hsa-miR-361-3p | 325.766 | 181.375 | 1.796 | 0.586 | 5.77E−06 | 0.000383235 | 0.852 |
| hsa-miR-22* | 178.938 | 103.844 | 1.723 | 0.544 | 6.24E−06 | 0.000385004 | 0.868 |
| hsa-miR-140-5p | 105.063 | 48.250 | 2.177 | 0.778 | 7.99E−06 | 0.000399262 | 0.874 |
| hsa-miR-216a | 202.219 | 315.828 | 0.640 | −0.446 | 8.24E−06 | 0.000399262 | 0.060 |
| hsa-miR-1275 | 210.203 | 116.969 | 1.797 | 0.586 | 7.04E−06 | 0.000399262 | 0.907 |
| hsa-miR-367 | 92.500 | 160.375 | 0.577 | −0.550 | 8.32E−06 | 0.000399262 | 0.138 |
| hsa-miR-146a | 470.359 | 271.342 | 1.733 | 0.550 | 9.61E−06 | 0.000437137 | 0.862 |
| hsa-miR-598 | 140.531 | 91.000 | 1.544 | 0.435 | 1.29E−05 | 0.000556416 | 0.841 |
| hsa-miR-613 | 60.781 | 19.000 | 3.199 | 1.163 | 1.67E−05 | 0.000687276 | 0.862 |
| hsa-miR-18a* | 490.891 | 233.672 | 2.101 | 0.742 | 2.02E−05 | 0.000794863 | 0.876 |
| hsa-miR-302b | 54.469 | 21.406 | 2.545 | 0.934 | 2.23E−05 | 0.000838901 | 0.855 |
| hsa-miR-501-5p | 139.938 | 79.563 | 1.759 | 0.565 | 2.60E−05 | 0.000936279 | 0.866 |

2.2.4 Relation to Other Diseases

Since there is no evidence for de-regulated miRNAs in MS patients in the literature, it was checked whether the detected 193 miRNAs are already related to other human diseases. To this end, the Human micro RNA Disease Database (HMDD) was grasped. This comprehensive database contains for over 100 human diseases information on deregulated miRNAs. Altogether, over 2000 relations are included in the HMDD. To analyze the respective data, a bipartite graph was created were nodes are either miRNAs or human diseases, and edges between a miRNA and a disease mean that the respective miRNA is deregulated in the respective disease.

Thereby, a network containing 452 nodes was created, 137 belonging to diseases and 315 to miRNAs. The network also contained 1617 unique edges (some relations between miRNAs and diseases have been published in multiple papers). As mentioned previously, MS is not included as disease in this network. Thus, the network was modified as followings: a disease node "MultipleSclerosis" was added and edges between this node and all significant miRNAs were created. Additionally, all disease nodes that are not linked to any MS miRNA and all miRNAs belonging only to removed disease nodes were removed. The novel network thus contains only those miRNAs that are significant in MS and other diseases and those that are significant in MS, only. This shrunken network contained 77 disease nodes together with the 193 significant miRNAs. Remarkably, only 43 of the 193 (22%) miRNAs were related to a disease other than MS while the remaining 78% miRNAs were only connected to MS. Of these 146 miRNAs, 36 were so-called star sequences.

Altogether, these results provide strong evidence that the detected complex miRNA profile is not disease specific but rather specific for MS.

2.2.5 Evaluating Complex Fingerprints

As discussed in Section 2.2.3, the best miRNA suffices to classify 20 of 22 MS samples and 20 of 22 control samples correctly. This obviously corresponds to a high specificity, sensitivity and accuracy of 90.8%. However, these results are not validated by a re-sampling technique as bootstrapping or cross-validation and are based only on a single marker.

In order to improve the already high classification accuracy and the statistical reliability the predictive power of multiple miRNAs was combined by using statistical learning techniques. In detail, Support Vector Machines with different kernels (linear, polynomial, sigmoid, radial basis function) were applied to the data and a hypothesis test based subset selection was carried out as described in Material and Methods. To gain statistical significance 100 repetitions of 10-fold cross validation were carried out. Likewise, 100 repetitions for the permutation tests were computed where samples with randomly assigned class labels were investigated.

The best results were obtained with radial basis function Support Vector Machines and a subset of 24 miRNAs (see Table 2). These miRNAs allowed for the discrimination between blood samples of MS patients and blood samples of controls with an accuracy of 95.5% a specificity of 95.5%, and a sensitivity of 95.5%.

Figure 21:
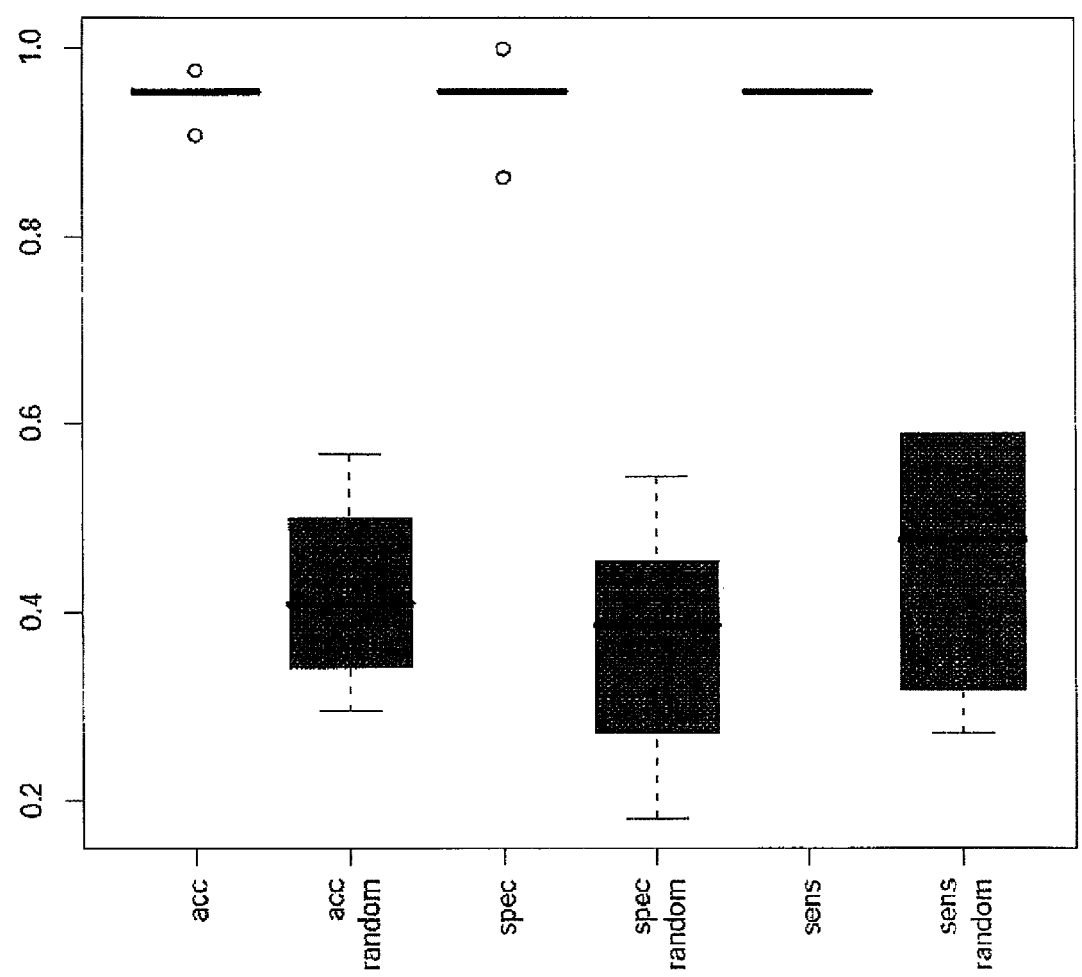
Figure 22:
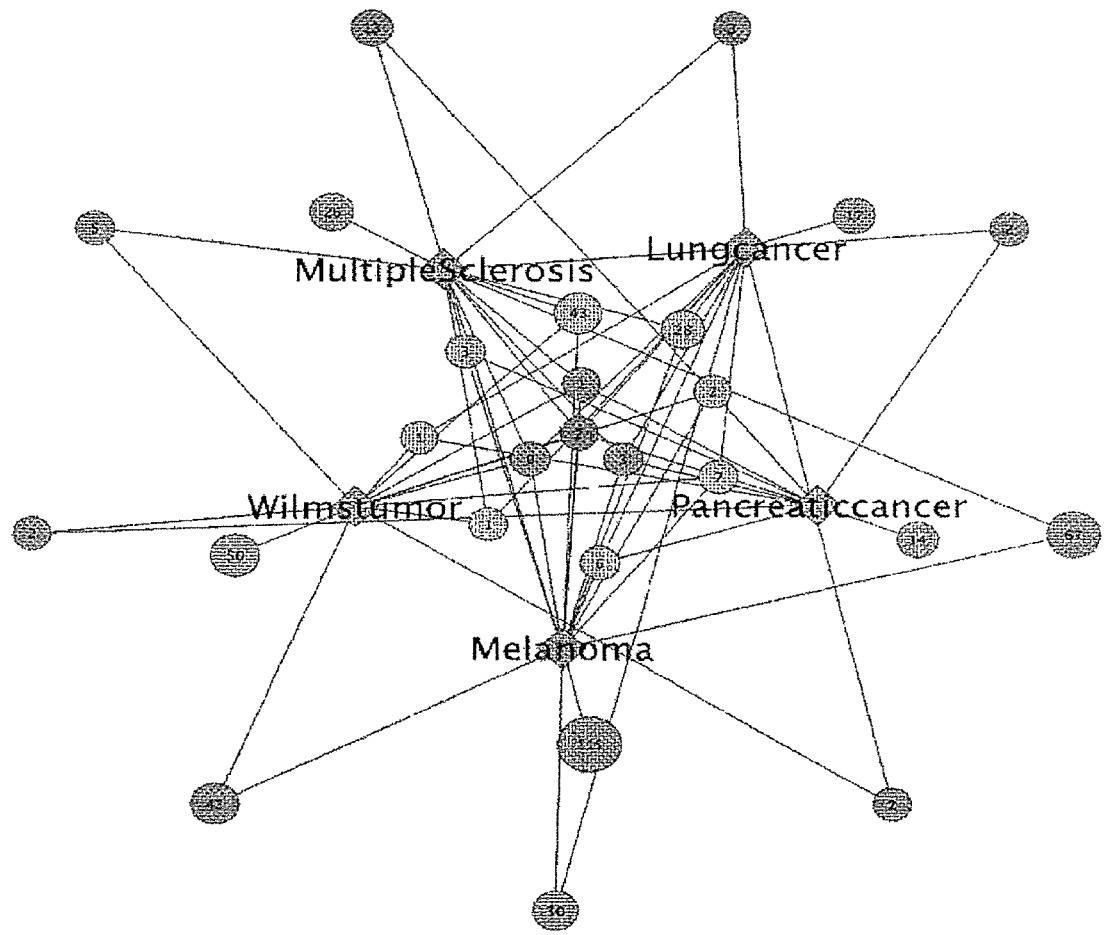

The permutation tests showed significantly decreased accuracy, specificity, and sensitivity rates, as detailed in FIG. 21. These results show that the obtained results are not due to an overfit of the statistical model on the miRNA fingerprints.

Additionally, it was checked whether the relevant miRNAs were linked to one of over 100 other diseases as annotated in the HMDD. Remarkable over 80% of the respective miRNAs have not been linked to other diseases, so far.

Example 3

Melanoma

3.1 Material and Methods
3.1.1 Samples

Participants of this study have given written informed consent. The patient blood samples stem from 35 patients with melanoma collected from two different groups and 21 normal controls. Normal samples were obtained from 21 different volunteers.

The patient samples include samples from various melanoma stages including from early stage (stage I) to late state melanomas (stage IV). The present invention enables therefore not only a diagnosis (e.g. early diagnosis) method but also a method for prognosis or progression of the disease.

3.1.2 miRNA Extraction and Microarray Screening

Blood of melanoma patients has been extracted as previously described (see above).

Samples were analyzed with the Geniom Realtime Analyzer (GRTA, febit gmbh, Heidelberg, Germany) using the Geniom Biochip miRNA *homo sapiens*. Each array contains 7 replicates of 866 miRNAs and miRNA star sequences as annotated in the Sanger miRBase 12.0. Sample labeling with Biotine has been carried out by microfluidic-based enzymatic on-chip labeling of miRNAs (MPEA).

Following hybridization for 16 hours at 42° C. the biochip was washed automatically and a program for signal enhancement was processed with the GRTA. The resulting detection pictures were evaluated using the Geniom Wizard Software. For each array, the median signal intensity was extracted from the raw data file such that for each miRNA seven intensity values have been calculated corresponding to each replicate copy of miRBase on the array. Following background correction, the seven replicate intensity values of each miRNA were summarized by their median value. To normalize the data across different arrays, quantile normalization was applied and all further analyses were carried out using the normalized and background subtracted intensity values.

3.1.3 Measures for Single Biomarker Analysis

First, we evaluated the measured biomarker profiles in order to detect miRNAs that show a different behavior in different groups of blood donors. To this end, we applied different statistical measures to monitor differences between these measures. The set of approaches contains parametric t-test (unpaired, two-tailed), Wilcoxon Mann-Whitney test (unpaired, two-tailed), a linear model with p-values computed by an empirical Bayes approach, the area under the receiver operator characteristics curve (AUC) and fold quotients. For all hypothesis tests, the resulting p-values were adjusted for multiple testing by Benjamini-Hochberg adjustment.

The detected sets of relevant biomarkers then have been compared using Venn diagrams.

3.1.4 Cluster Analysis and Principal Component Analysis

In order to detect clusters of miRNAs and samples, we carried out a hierarchical clustering approach. In more detail, we applied bottom up complete linkage clustering and used the Euclidian distance measure.

In addition to this approach, we also carried out a standard principal component analysis (PCA) and provide scatter plots of the first versus second PC.

3.1.5 Classification Analysis

In addition to the single biomarker analysis and unsupervised clustering we also carried out classification of samples using miRNA patterns by using Support Vector Machines (SVM) as implemented in the R e1071 package. In detail, different kernel (linear, polynomial, sigmoid, radial basis function) Support Vector Machines have been evaluated, where the cost parameter was sampled from 0.01 to 10 in decimal powers. The measured miRNA profiles were classified using 100 repetitions of standard 10-fold cross-validation. As a subset selection technique we applied a filter approach based on t-test. In detail, the s miRNAs with lowest p-values were computed on the training set in each fold of the cross validation, where s was sampled from 1 to 866. The respective subset was used to train the SVM and to carry out the prediction of the test samples. As result, the mean accuracy, specificity, and sensitivity were calculated together with the 95% Confidence Intervals (95% CI) for each subset size. To check for overtraining we applied permutation tests. Here we sampled the class labels randomly and carried out classifications using the permuted class labels. All statistical analyzes were performed using R.

3.2 Results

As described by McCarthy et al., there exists a disconnect between the mathematical and biological concepts of differential expression. On the one hand, fold-change cutoffs do not take the biological variability into account or guarantee reproducibility. In contrast, commonly applied hypothesis test are known to give high false discovery rates (FDRs) and are, especially in smaller samples, only weakly related to fold-changes. To gain improved statistical significance we decided to apply different scores to report deregulated miRNAs. First, we report differences between the detected sets and then report a consensus approach for differentially regulated miRNAs.

At first, we compared the three hypothesis tests as described in the materials and methods section. We considered all miRNAs with adjusted p-value of below 0.001 to be significant. The result of the three tests is presented as three-way Venn Diagram in FIG. 24. Here, 117 miRNAs were detected in all three tests, 35 additional for WMW test and t-test while not for empirical bayes approach, 22 for empirical bayes and for WMW test and 4 in the empirical bayes test and t-test. Taken together, these data show that the tests show a high concordance, given with 117 miRNAs the majority to be significant in all three tests. Our analysis showed also that the t-test detected the highest number of deregulated miRNAs. Interpreting the significant miRNAs carefully, we encountered problems of these tests that may lead to the reported high False Discovery Rates: 1) Given larger sample numbers and a low data variance, slight differences already lead to a significantly deregulated miRNA. 2) Related to this problem, given miRNAs that are low abundant and that can be differentiated only hardly from background noise may also lead to false positive biomarkers. To overcome this problem, we added two filters. The first one is a fold quotient filter, i.e., miRNAs must be changed at least 2-fold in their expression level. The second filter is a minimal expression level filter, i.e., the median value of the samples for one group must exceed 100. Both thresholds have been determined empirically. In summary, the combined analysis reported 51 deregulated miRNAs, of these, 21 were down-regulated in melanoma while 30 were up-regulated. All miRNAs are shown, sorted by their AUC value, in Table 3.

Most notably, the detected miRNAs usually are annotated as cancer related miRNAs. For example, miR-216a, the miRNA with second best AUC value has been described to be down-regulated in lung-neoplasms and is likewise more than 2-fold down-regulated in melanoma. miR-186, the up-regulated miRNA with highest AUC has been described to be up-regulated in pancreatic cancer. However, most studies published so far are significantly different in two points of our study: first, usually cancer tissue samples are profiled and second, only a subset of miRNAs has been screened in these studies, either by using qRT-PCR or array based techniques relying on older miRBase versions. Thus, our screening also showed significantly deregulated miRNAs that are not cancer or disease regulated since these have not been included in screenings so far. Only one example is miR-1280 that is up-regulated 2.5-fold in our studies.

Given the set of de-regulated miRNAs, we asked whether the fold quotients are the same in both measured miRNA populations. As already described, the 35 melanoma samples come from two different sources, split-up in a ratio of 1/3 versus 2/3, given 24 miRNAs initially collected and additional 11 miRNAs measured as independent validation set.

Figure 25:
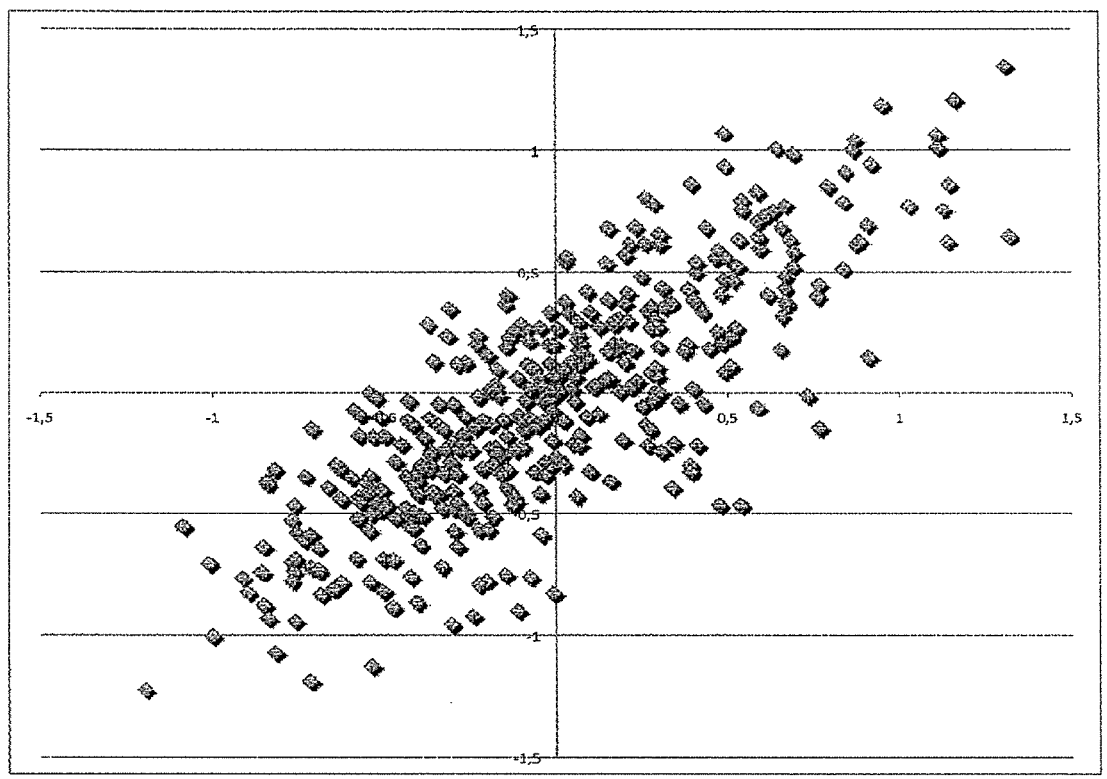

To reduce the noise in this analysis, we only considered miRNAs where both groups exceed a minimal expression level of 50, computed for both melanoma groups the fold quotient versus the controls and computed the correlation. The scatter-plot in FIG. 25 presents the logarithm of fold quotient of the initial group on the x-axis and of the validation group on the y-axis. The correlation of fold quotients between both melanoma populations was as high as 0.81, underlining the excellent reproducibility of the miRNA profiling.

Figure 26:
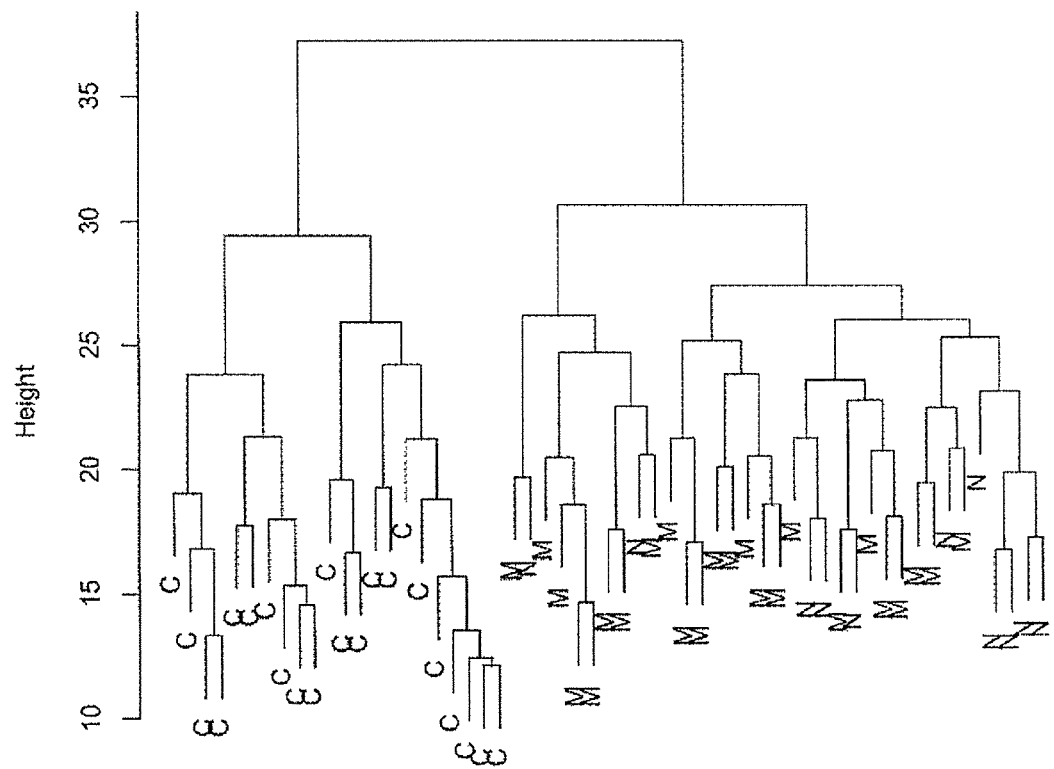

As next analysis, we asked whether the miRNA profiles could be clustered together. To this end, we applied hierarchical clustering as described in the Methods section. Since most of all miRNAs contribute rather noise than true signals to the clustering, we used only the 50 miRNAs with the overall highest data variance for clustering. The result is shown as dendrogram in FIG. 26. In this figure, control samples are denoted with 'C' while melanoma samples are denoted with 'M' for the initially screened set and 'N' for the validation set. This figure impressively demonstrates that control samples seem to be different from the melanoma samples while the melanoma samples of both groups do not cluster together but are rather mixed-up. Splitting the dendrogram in two groups and computing a contingency table we found that 21 of 21 controls belong to cluster 1 and 35 of 35 melanoma samples belong to cluster 2. Computing a significance value for this clustering using two-tailed Fisher's Exact test, we obtained a p-value of approx. $3*10^{-16}$.

Figure 27:
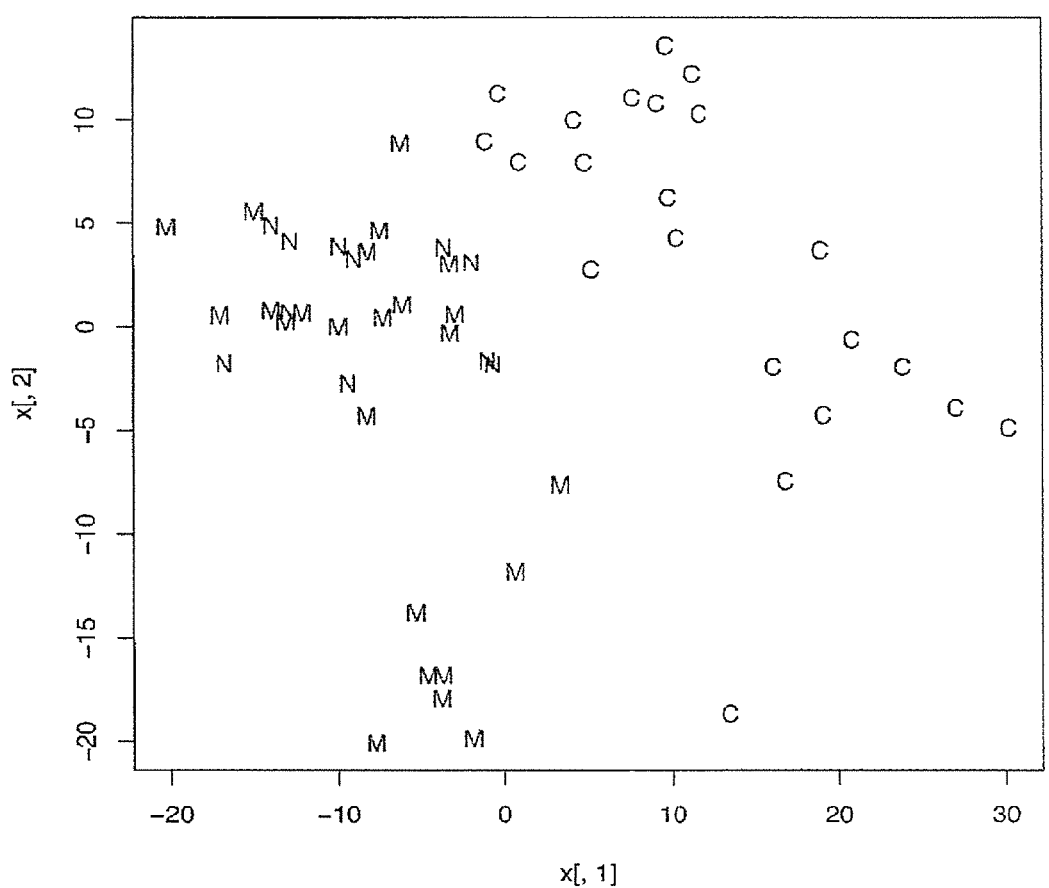

To provide a low-dimensional visualization of the high-dimensional data, we carried out a principal component analysis, as described in the Materials and Methods section. Investigating the eigenvalues of the first principal components, we found that the first component contained by far the highest overall data variance while the first and second principal component together contributed to approximately half of the overall variance. A plot of the first versus the second principal component is presented in FIG. 27. This plot contains the same labels as the cluster dendrogram in FIG. 26, i.e., control samples are denoted with 'C' while melanoma samples are denoted with 'M' or 'N' for the test and validation set respectively. This representation, compute using principal component analysis, confirmed the results as computed by hierarchical clustering. The control samples can be well differentiated from the melanoma samples while both melanoma populations mix up.

Now, we asked whether the results of the unsupervised cluster analysis can also be reproduced by a supervised statistical learning approach. To this end, we carried out a support vector machine classification together with a feature selection relying on t-test p-values. In more detail, we applied radial basis function support vector machines that have been evaluated using 10-fold cross-validation. The cross-validation runs have been repeated 100 times in order to get an estimation of the classification variance. To cross-check for data over-fit, we carried out 100 permutation tests, i.e., we applied the same statistical approach to a data set where the class labels melanoma and cancer have been randomly assigned.

Figure 28:
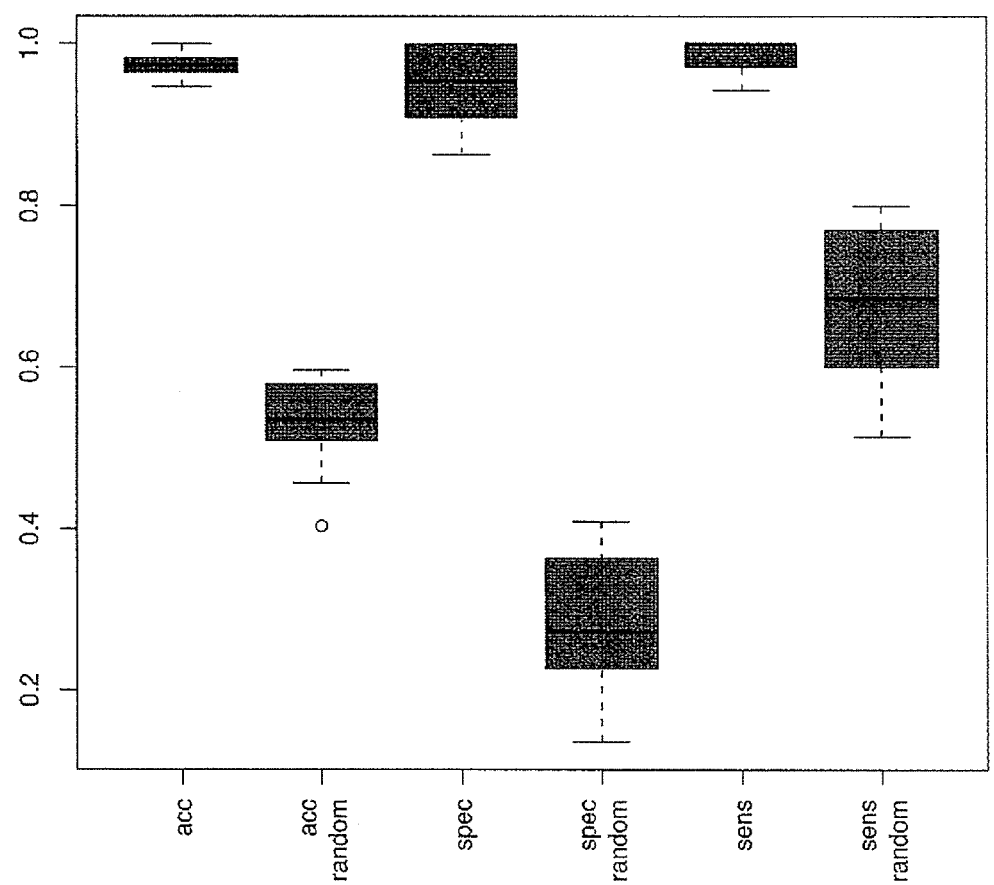

The best classification accuracy has been obtained by using the subset of 16 miRNAs consisting of hsa-miR-186, hsa-let-7d*, hsa-miR-18a*, hsa-miR-145, hsa-miR-99a, hsa-miR-664, hsa-miR-501-5p, hsa-miR-378*, hsa-miR-29c*, hsa-miR-1280, hsa-miR-365, hsa-miR-1249, hsa-miR-328, hsa-miR-422a, hsa-miR-30d, and hsa-miR-17*. By using these miRNAs, our classification approach reached a high accuracy, specificity and sensitivity of 97.4%, 95% and 98.9%. The results of all 100 cross-validation runs and 100 permutation tests are provided as box-plots in FIG. 28. Here, the blue (dark grey) boxes show the results of the cross-validation while the red (light grey) boxes show the significantly decreased (t-test p-value of $<10^{-10}$) accuracy of the permutation tests.

Figure 29:
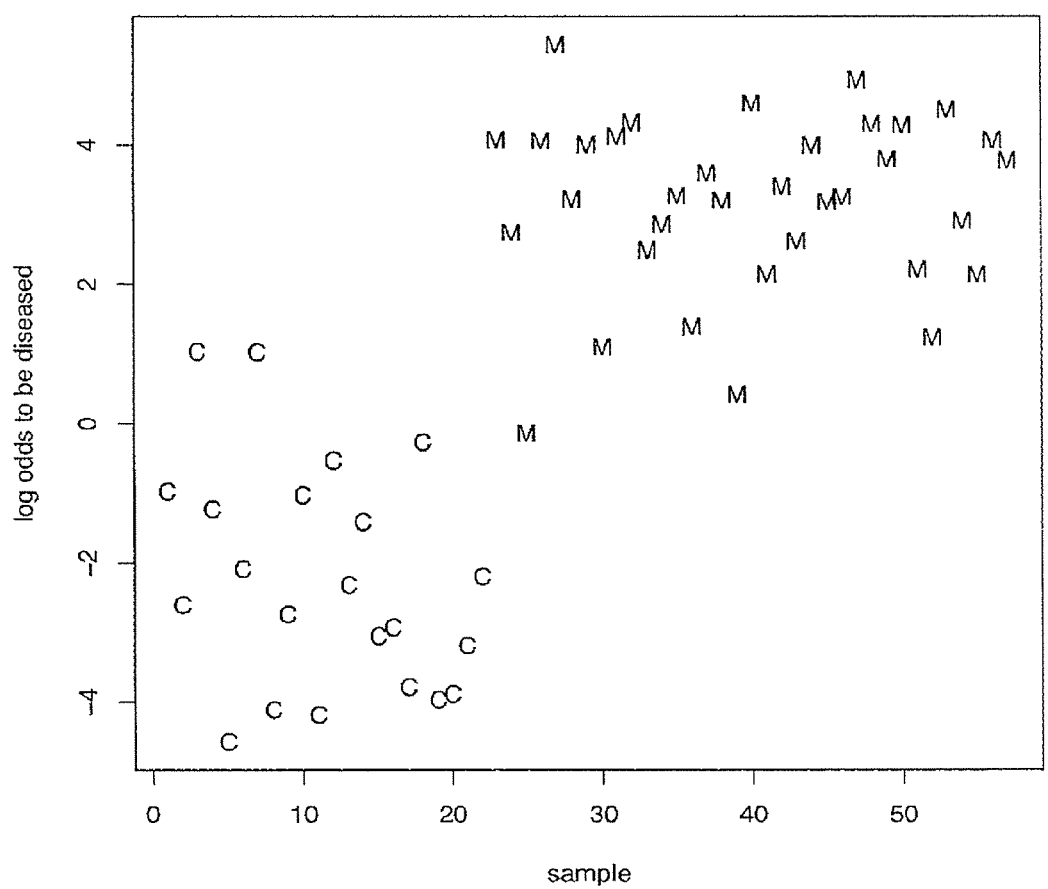
Figure 34:
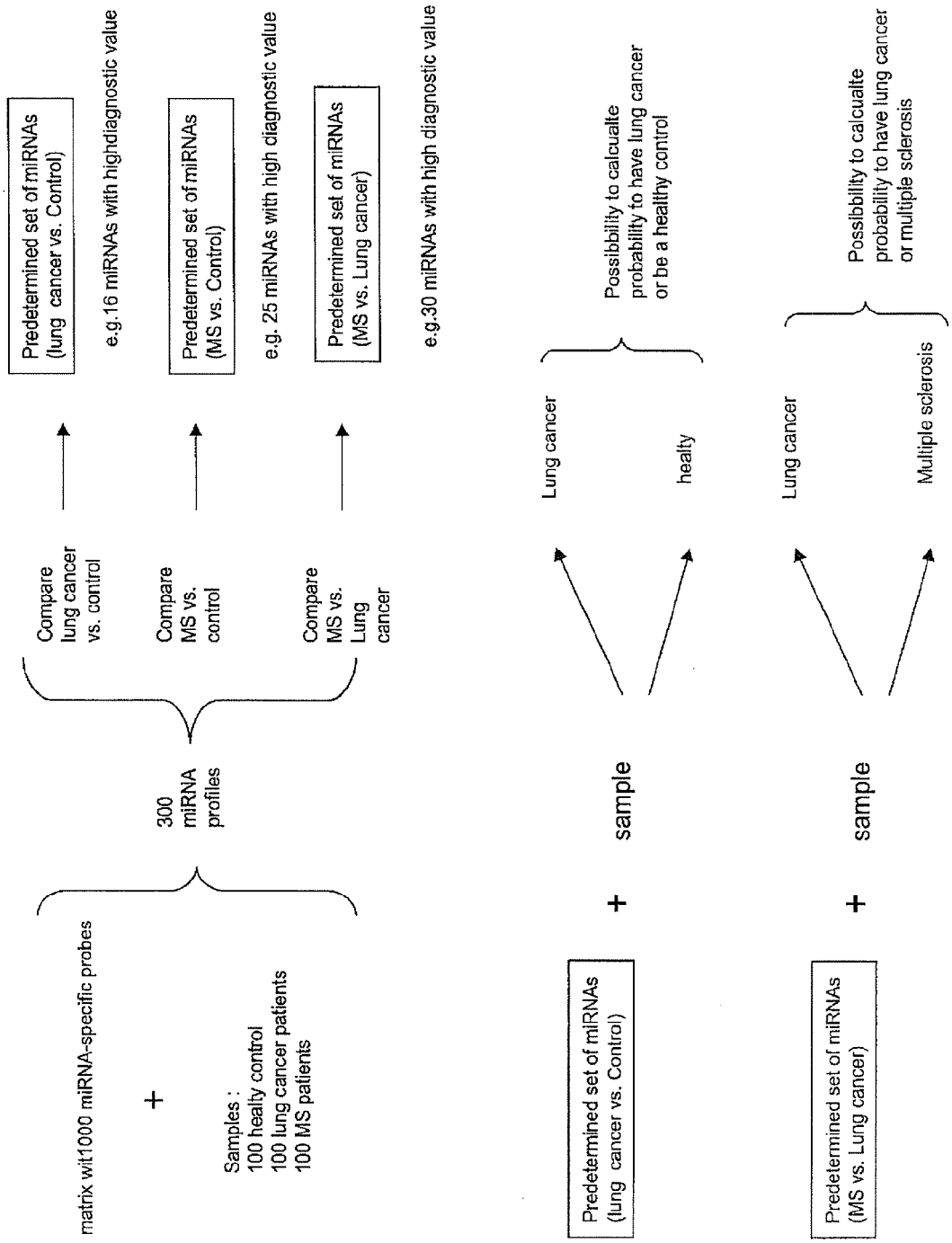
Figure 35:
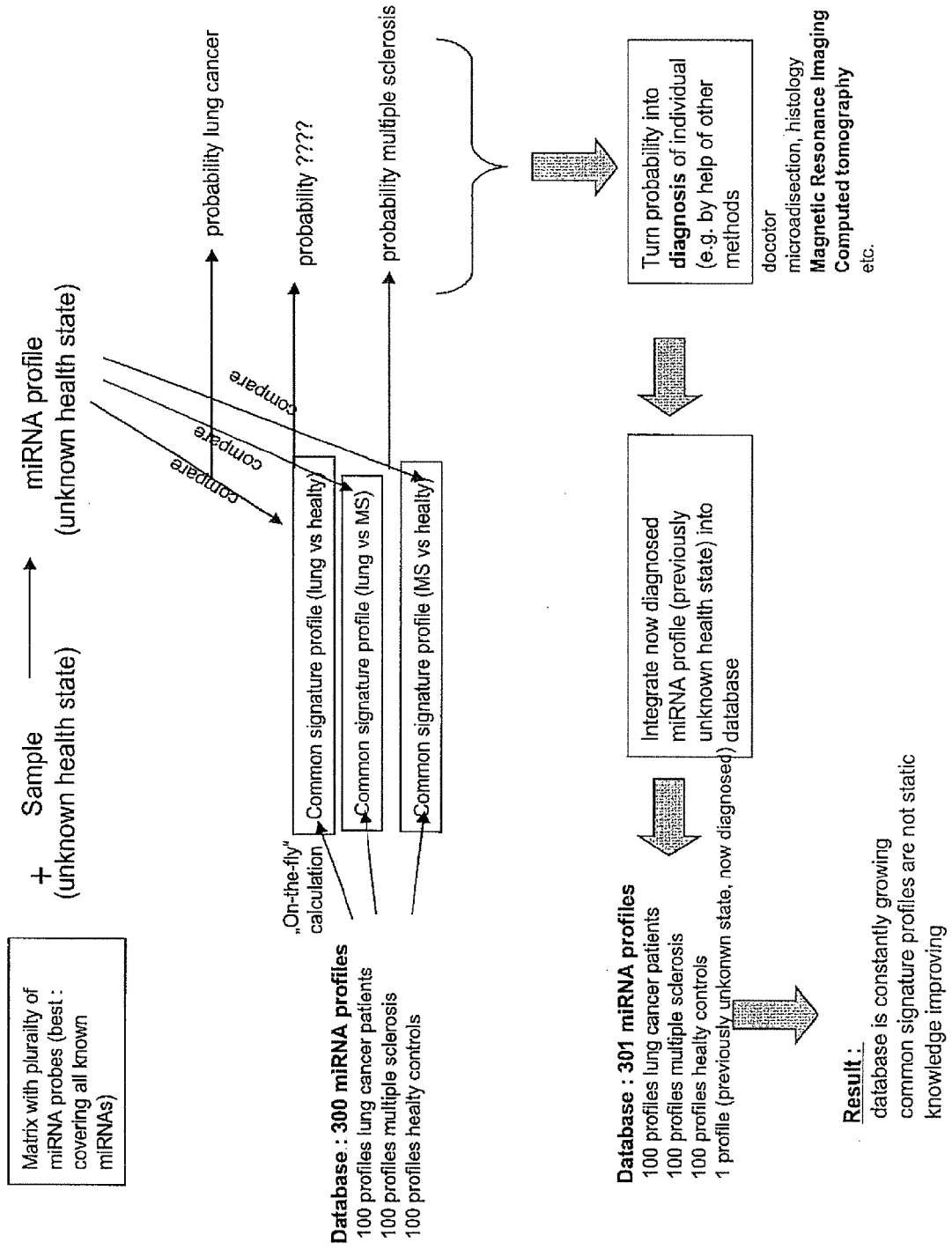

In FIG. 29, one of the classification results is presented. Here, the logarithm of the quotient of probabilities to be diseased and the probability to be a control are shown. The probabilities have been computed by the R implementation of the libsvm relying on the distance of the samples from the separating hyperplane. If the quotient of the probabilities is greater than one (thus the logarithm is greater zero) the sample is more likely to be a melanoma sample than a control sample. FIG. 29 clearly outlines that in general melanoma samples have logarithmized quotients of greater 0 while control samples have quotients of below 0.

TABLE 3

51 most significant miRNAs regulated in melanoma

| | median melanom | median normal | fold change | wmw adjp | ttest adjp | limma adjp | AUC |
|---|---|---|---|---|---|---|---|
| hsa-miR-452* | 189.7 | 633.3 | 0.3 | 0.000000 | 0.000460 | 0.000000 | 0.992 |
| hsa-miR-216a | 89.1 | 197.3 | 0.5 | 0.000001 | 0.000017 | 0.000039 | 0.978 |
| hsa-miR-186 | 206.5 | 26.2 | 7.9 | 0.000001 | 0.000000 | 0.000000 | 0.973 |
| hsa-let-7d* | 178.6 | 37.7 | 4.7 | 0.000001 | 0.000000 | 0.000000 | 0.960 |
| hsa-miR-17* | 433.5 | 941.8 | 0.5 | 0.000001 | 0.000000 | 0.000000 | 0.960 |
| hsa-miR-646 | 150.9 | 350.6 | 0.4 | 0.000001 | 0.000383 | 0.000000 | 0.959 |
| hsa-miR-217 | 86.3 | 183.8 | 0.5 | 0.000001 | 0.000548 | 0.000003 | 0.957 |
| hsa-miR-621 | 178.6 | 486.7 | 0.4 | 0.000001 | 0.000106 | 0.000000 | 0.954 |
| hsa-miR-517* | 109.9 | 230.8 | 0.5 | 0.000001 | 0.000215 | 0.000000 | 0.953 |
| hsa-miR-99a | 217.3 | 85.0 | 2.6 | 0.000002 | 0.000000 | 0.000000 | 0.947 |
| hsa-miR-664 | 557.0 | 173.0 | 3.2 | 0.000002 | 0.000000 | 0.000000 | 0.944 |
| hsa-miR-593* | 175.4 | 356.7 | 0.5 | 0.000002 | 0.000267 | 0.000000 | 0.942 |

TABLE 3-continued 51 most significant miRNAs regulated in melanoma

| | median melanom | median normal | fold change | wmw adjp | ttest adjp | limma adjp | AUC |
|---|---|---|---|---|---|---|---|
| hsa-miR-18a* | 397.4 | 135.0 | 2.9 | 0.000002 | 0.000000 | 0.000000 | 0.936 |
| hsa-miR-145 | 358.0 | 94.6 | 3.8 | 0.000002 | 0.000000 | 0.000000 | 0.936 |
| hsa-miR-1280 | 6779.6 | 2676.2 | 2.5 | 0.000002 | 0.000000 | 0.000000 | 0.933 |
| hsa-let-7i* | 122.8 | 281.4 | 0.4 | 0.000003 | 0.000452 | 0.000000 | 0.930 |
| hsa-miR-422a | 279.2 | 104.5 | 2.7 | 0.000004 | 0.000000 | 0.000000 | 0.923 |
| hsa-miR-330-3p | 213.1 | 443.2 | 0.5 | 0.000004 | 0.000522 | 0.000000 | 0.923 |
| hsa-miR-767-5p | 107.1 | 232.4 | 0.5 | 0.000004 | 0.000217 | 0.000001 | 0.922 |
| hsa-miR-183* | 195.9 | 87.7 | 2.2 | 0.000004 | 0.000001 | 0.000000 | 0.921 |
| hsa-miR-1249 | 144.8 | 46.1 | 3.1 | 0.000004 | 0.000000 | 0.000004 | 0.919 |
| hsa-miR-20b | 2163.5 | 5665.8 | 0.4 | 0.000004 | 0.000002 | 0.000001 | 0.919 |
| hsa-miR-509-3-5p | 157.0 | 371.4 | 0.4 | 0.000004 | 0.000459 | 0.000000 | 0.919 |
| hsa-miR-519b-5p | 72.5 | 155.1 | 0.5 | 0.000004 | 0.000029 | 0.000398 | 0.918 |
| hsa-miR-362-3p | 449.0 | 167.8 | 2.7 | 0.000004 | 0.000004 | 0.000000 | 0.917 |
| hsa-miR-501-5p | 106.5 | 27.8 | 3.8 | 0.000004 | 0.000000 | 0.000002 | 0.916 |
| hsa-miR-378* | 103.7 | 29.4 | 3.5 | 0.000004 | 0.000000 | 0.000002 | 0.916 |
| hsa-miR-365 | 160.5 | 65.1 | 2.5 | 0.000006 | 0.000000 | 0.000001 | 0.912 |
| hsa-miR-151-3p | 999.0 | 422.6 | 2.4 | 0.000006 | 0.000001 | 0.000000 | 0.909 |
| hsa-miR-342-5p | 196.8 | 92.1 | 2.1 | 0.000008 | 0.000001 | 0.000003 | 0.905 |
| hsa-miR-328 | 175.4 | 32.3 | 5.4 | 0.000008 | 0.000000 | 0.000001 | 0.904 |
| hsa-miR-181a-2* | 154.8 | 64.7 | 2.4 | 0.000016 | 0.000004 | 0.000004 | 0.892 |
| hsa-miR-518e* | 88.1 | 196.4 | 0.4 | 0.000019 | 0.000452 | 0.000586 | 0.888 |
| hsa-miR-362-5p | 245.4 | 119.5 | 2.1 | 0.000023 | 0.000008 | 0.000001 | 0.884 |
| hsa-miR-584 | 198.2 | 46.9 | 4.2 | 0.000023 | 0.000015 | 0.000008 | 0.883 |
| hsa-miR-550* | 808.5 | 313.8 | 2.6 | 0.000024 | 0.000026 | 0.000003 | 0.881 |
| hsa-miR-30a | 682.9 | 334.8 | 2.0 | 0.000027 | 0.000004 | 0.000002 | 0.879 |
| hsa-miR-221* | 54.3 | 113.8 | 0.5 | 0.000029 | 0.000106 | 0.000390 | 0.878 |
| hsa-miR-361-3p | 263.9 | 99.0 | 2.7 | 0.000033 | 0.000002 | 0.000003 | 0.875 |
| hsa-miR-625 | 185.8 | 63.3 | 2.9 | 0.000037 | 0.000017 | 0.000038 | 0.871 |
| hsa-miR-146a | 326.8 | 161.8 | 2.0 | 0.000037 | 0.000039 | 0.000003 | 0.871 |
| hsa-miR-214 | 172.3 | 383.4 | 0.4 | 0.000042 | 0.000376 | 0.000001 | 0.869 |
| hsa-miR-106b | 8639.8 | 18880.5 | 0.5 | 0.000044 | 0.000085 | 0.000019 | 0.867 |
| hsa-miR-18a | 1060.8 | 2560.0 | 0.4 | 0.000053 | 0.000742 | 0.000013 | 0.862 |
| hsa-miR-30e* | 101.7 | 47.8 | 2.1 | 0.000022 | 0.000005 | 0.000098 | 0.861 |
| hsa-miR-125a-5p | 370.8 | 147.4 | 2.5 | 0.000059 | 0.000033 | 0.000001 | 0.859 |
| hsa-miR-142-3p | 105.3 | 2.0 | 53.0 | 0.000082 | 0.000017 | 0.000009 | 0.851 |
| hsa-miR-107 | 725.8 | 1938.9 | 0.4 | 0.000092 | 0.000970 | 0.000034 | 0.849 |
| hsa-miR-20a | 3254.3 | 7282.8 | 0.4 | 0.000134 | 0.000159 | 0.000062 | 0.841 |
| hsa-miR-22* | 117.7 | 45.0 | 2.6 | 0.000193 | 0.000037 | 0.000138 | 0.832 |
| hsa-miR-199a-5p | 551.4 | 267.9 | 2.1 | 0.000201 | 0.000663 | 0.000042 | 0.831 |

3.3 Discussion

There is a good chance for recovery o patients suffering from melanoma if the primary lesion is detected very early. For patients with stage I melanoma the overall 5-year survival rate exceeds 90% but can fall below 10% for stage III or IV melanoma. A lot of efforts were undertaken in order to identify molecular biomarkers for melanoma detection before metastasis, which is an early event during melanoma progression. Because melanoma is a very heterogeneous disease, complex biomarker profiles would be best suited to monitor high-risk patients.

MiRNAs regulate more than one third of all human genes. It is evident that changes in the miRNA expression can lead to cancer development. Complex miRNA expression profiles may reflect the molecular changes leading to melanoma progression.

In our study we investigated the miRNA expression of currently all known human miRNAs and miRNA star sequences. Analyzing the miRNA expression in peripheral blood cells combines the advantages of the ease of obtaining blood with the avoidance of surgical interventions (skin biopsies) and of CT scans. We analyzed the miRNA expression in blood cells of two independent sets of melanoma patients and compared the expression profiles with that of healthy blood donors. Here we detected 51 differentially expressed miRNAs. A total of 30 miRNAs was upregulated in blood cells of melanoma patients, whereas 21 miRNAs were downregulated. Applying SVM with a feature subset selection method we were able to differentiate melanoma patients and healthy blood donors with high accuracy (97.4%) using a set of 16 miRNAs.

Example 4

Molecular Clinical Thermometer

For the molecular clinical thermometer, an arbitrary machine learning (feature extraction/classification/regression/clustering) technique can be applied. The workflow does not depend on the applied method that can be seen as a black box.

First, a sophisticated large set of samples for the diseases to be investigated has to be measured using a larger amount of biomarkers. This set, consisting of a p×n matrix where n is the number of samples and p the number of biomarkers, is commonly denoted as training data set.

Now, a combination of feature extraction and supervised learning techniques (the process can be also carried out with slight modifications using unsupervised techniques) is applied to generate a statistical model, which describes the training data well. Here, it is essential to control the model complexity in order to avoid so-called overtraining of the statistical models. Although, in general, multi-class cases can be carried out, we focus on two class comparisons, i.e., normal versus cancer 1, normal versus cancer 2, cancer 1 versus cancer 2.

Given the trained models and a new biomarker profile, the statistical model can be used to compute the probability for each class and this new sample. Only one example are support vector machines, where the distance of a sample to the separating hyperplane can be used to estimate the class probability via a regression approach. The specificity and sensitivity can be trade-off by shifting the probability threshold (which usually should be 0.5 or 50%).

The probabilities in the previously described step can be used to generate so-called disease probability plots (DPP). These plots contain for each class and a single sample the probabilities to belong to a certain class. In detail, each class is described by a colored line of length 100 (representing a percentage range), where the lower rate is colored green (representing small probabilities) and the higher range red (higher probabilities). For each class, an arrow marks the probability for the patient and the respective disease. For class "normal" the minimal and maximal probability to be normal are shown.

The DPPs thus allow for visualizing the complex statistical evaluation in a simple and well interpretable way.

REFERENCES

Alvarez-Garcia, I. and E. A. Miska (2005). "MicroRNA functions in animal development and human disease." *Development* 132(21): 4653-62.

Benjamini, Y. and Y. Hochberg (1995). "Controlling the false discovery rate: A practical and powerful approach to multiple testing." *J R Statist Soc B* 57: 289-300.

Bolstad, B. M., R. A. Irizarry, et al. (2003). "A comparison of normalization methods for high density oligonucleotide array data based on variance and bias." *Bioinformatics* 19(2): 185-93.

Calin, G. A. and C. M. Croce (2006). "MicroRNA-cancer connection: the beginning of a new tale." *Cancer Res* 66(15): 7390-4.

Calin, G. A. and C. M. Croce (2006). "MicroRNA signatures in human cancers." *Nat Rev Cancer* 6(11): 857-66.

Chen, X., Y. Ba, et al. (2008). "Characterization of microRNAs in serum: a novel class of biomarkers for diagnosis of cancer and other diseases." *Cell Res* 18(10): 997-1006.

Crawford, M., E. Brawner, et al. (2008). "MicroRNA-126 inhibits invasion in non-small cell lung carcinoma cell lines." *Biochem Biophys Res Commun* 373(4): 607-12.

Esquela-Kerscher, A. and F. J. Slack (2006). "Oncomirs—microRNAs with a role in cancer." *Nat Rev Cancer* 6(4): 259-69.

Feitelson, M. A. and J. Lee (2007). "Hepatitis B virus integration, fragile sites, and hepatocarcinogenesis." *Cancer Lett* 252(2): 157-70.

Gilad, S., E. Meiri, et al. (2008). "Serum microRNAs are promising novel biomarkers." *PLoS ONE* 3(9): e3148.

Griffiths-Jones, S., R. J. Grocock, et al. (2006). "miRBase: microRNA sequences, targets and gene nomenclature." *Nucleic Acids Res* 34(Database issue): D140-4.

Griffiths-Jones, S., S. Moxon, et al. (2005). "Rfam: annotating non-coding RNAs in complete genomes." *Nucleic Acids Res* 33(Database issue): D121-4.

Griffiths-Jones, S., H. K. Saini, et al. (2008). "miRBase: tools for microRNA genomics." *Nucleic Acids Res* 36(Database issue): D154-8.

Guo, L., Z. X. Huang, et al. (2008). "Differential Expression Profiles of microRNAs in NIH3T3 Cells in Response to UVB Irradiation." *Photochem Photobiol.*

Harris, T. A., M. Yamakuchi, et al. (2008). "MicroRNA-126 regulates endothelial expression of vascular cell adhesion molecule 1." *Proc Natl Acad Sci USA* 105(5): 1516-21.

Hayashita, Y., H. Osada, et al. (2005). "A polycistronic microRNA cluster, miR-17-92, is overexpressed in human lung cancers and enhances cell proliferation." *Cancer Res* 65(21): 9628-32.

He, L., J. M. Thomson, et al. (2005). "A microRNA polycistron as a potential human oncogene." *Nature* 435(7043): 828-33.

Henschke, C. I. and D. F. Yankelevitz (2008). "CT screening for lung cancer: update 2007." *Oncologist* 13(1): 65-78.

Hochberg, Y. (1988). "A sharper bonferroni procedure for multiple tests of significance." *Biometrica* 75: 185-193.

Ichimi, T., H. Enokida, et al. (2009). "Identification of novel microRNA targets based on microRNA signatures in bladder cancer." *Int J Cancer.*

Jemal, A., R. Siegel, et al. (2008). "Cancer statistics, 2008." *CA Cancer J Clin* 58(2): 71-96.

Johnson, S. M., H. Grosshans, et al. (2005). "RAS is regulated by the let-7 microRNA family." *Cell* 120(5): 635-47.

Keller, A., N. Ludwig, et al. (2006). "A minimally invasive multiple marker approach allows highly efficient detection of meningioma tumors." *BMC Bioinformatics* 7: 539.

Lee, R. C., R. L. Feinbaum, et al. (1993). "The *C. elegans* heterochronic gene lin-4 encodes small RNAs with antisense complementarity to lin-14." *Cell* 75(5): 843-54.

Lu, J., G. Getz, et al. (2005). "MicroRNA expression profiles classify human cancers." *Nature* 435(7043): 834-8.

Mann, H. and F. Wilcoxon (1947). "On a test whether one of two random variables is stochastically larger than the other." *Ann Mat Stat* 18: 50-60.

Sassen, S., E. A. Miska, et al. (2008). "MicroRNA: implications for cancer." *Virchows Arch* 452(1): 1-10.

Scott, W. J., J. Howington, et al. (2007). "Treatment of non-small cell lung cancer stage I and stage II: ACCP evidence-based clinical practice guidelines (2nd edition)." *Chest* 132(3 Suppl): 234S-242S.

Shannon, C. (1984). "A mathematical theory of communication." *The Bell System Technical Journal* 27: 623-656.

Stahlhut Espinosa, C. E. and F. J. Slack (2006). "The role of microRNAs in cancer." *Yale J Biol Med* 79(3-4): 131-40.

Takamizawa, J., H. Konishi, et al. (2004). "Reduced expression of the let-7 microRNAs in human lung cancers in association with shortened postoperative survival." *Cancer Res* 64(11): 3753-6.

Team, R. D. C. (2008). *R: A Language and Environment for Statistical Computing.* Vienna, Austria, R Foundation for Statistical Computing.

Tong, A. W. (2006). "Small RNAs and non-small cell lung cancer." *Curr Mol Med* 6(3): 339-49.

Vapnik, V. (2000). *The Nature of Statistical Learning Theory.*, Springer.

Volinia, S., G. A. Calin, et al. (2006). "A microRNA expression signature of human solid tumors defines cancer gene targets." *Proc Natl Acad Sci USA* 103(7): 2257-61.

Vorwerk, S., K. Ganter, et al. (2008). "Microfluidic-based enzymatic on-chip labeling of miRNAs." *N Biotechnol* 25(2-3): 142-9.

Wilcoxon, F. (1945). "Individual comparisons by ranking methods." *Biometric Bull* 1: 80-83.

Williams, A. E. (2008). "Functional aspects of animal microRNAs." *Cell Mol Life Sci* 65(4): 545-62.

Yanaihara, N., N. Caplen, et al. (2006). "Unique microRNA molecular profiles in lung cancer diagnosis and prognosis." *Cancer Cell* 9(3): 189-98.

Zhang, B., X. Pan, et al. (2007). "microRNAs as oncogenes and tumor suppressors." *Dev Biol* 302(1): 1-12.

Zhang, B., Q. Wang, et al. (2007). "MicroRNAs and their regulatory roles in animals and plants." *J Cell Physiol* 210(2): 279-89.

The invention claimed is:

1. A method of diagnosing and/or predicting the state of health in a subject comprising the steps:
   (a) providing a RNA sample from said subject, wherein said sample is a blood cell sample,
   (b) providing means for determining an expression profile for a plurality of miRNA and/or other non-coding RNA molecules, wherein said means are:
      (i) capture probes, wherein each capture probe comprises a sequence of at least partially complementary nucleotides to each miRNA of the plurality of miRNA or other non-coding RNA molecules, and an elongation sequence, or
      (ii) miRNA-specific primers, universal reverse primers and labeled probes to conduct a polymerase chain reaction
   (c1) determining the expression profile of a plurality of miRNAs and/or other noncoding RNAs in the sample of (a), by:
      (i) hybridizing the miRNAs and/or other non-coding RNA molecules in the sample of (a) with the means of (b)(i), and
      (ii) elongating the miRNAs and/or other non-coding RNA molecules of the sample with labeled nucleotides, and
      (iii) quantifying the labeled hybridized miRNA based on the label, or
   (c2) determining the expression profile of a plurality of miRNA and/or non-coding RNA molecules by:
      (i) obtaining cDNA samples by an RNA reverse transcription reaction using the miRNA-specific primers of (b)(ii), and
      (ii) amplifying the cDNA via polymerase chain reaction with miRNA-specific forward primers of (b)(ii), universal reverse primers of (b)(ii) and the labeled probe of (b)(ii) complementary to at least a portion of cDNA to be analyzed, and
      (iii) detecting levels of miRNAs on the basis of the labeled probe,
   (d) comparing a predetermined subset of miRNAs and/or other non-coding RNAs in said miRNA and/or other non-coding RNA expression profile, wherein said subset is characteristic for a particular condition to a corresponding subset of miRNAs and/or other non-coding RNAs in reference miRNA and/or non-coding RNA expression profiles obtained from a plurality of different reference subjects representing a plurality of different conditions, and
   (e) calculating the probability value of said subject for the particular conditions, and
   (f) optionally repeating steps (d) and (e) for at least one different particular condition, and/or
   (g) optionally collecting the probability values for the particular condition to diagnose and/or predict the health state of said subject.

2. The method of claim 1, wherein step (d) comprises:
   (a) Providing a plurality of reference miRNA and/or non-coding RNA expression profiles obtained from a plurality of different reference subjects representing a plurality of different conditions,
   (b) Selecting a subset of miRNAs and/or non-coding RNAs characteristic for a particular condition, and
   (c) Comparing the expression of a subset of miRNAs and/or non-coding RNAs in the subject to be analyzed and in at least 2 groups of reference subject, wherein the first group suffers from a particular condition (disease) and the second group does not suffer from the particular condition.

3. The method of claim 2, wherein the subjects of the second reference group may be healthy or may suffer from a different condition (disease).

4. The method of claim 1, wherein the condition or disease is cancer, a cardiovascular disease, an infectious disease, an inflammatory disease or an autoimmune disease.

5. The method of claim 1, wherein the means of step (b) are a matrix comprising a plurality of capture probes.

6. The method of claim 1, wherein the means of step (b) are means to conduct qRT-PCR.

7. The method of claim 1, wherein said blood cell sample is a mixture of erythrocytes, leukocytes and/or thrombocytes.

8. The method of claim 1 wherein the condition or disease is lung cancer, skin cancer, melanoma or multiple sclerosis.

9. A method of diagnosing and/or predicting the state of health in a subject comprising the steps:
   (a) providing a RNA sample from said subject, wherein said sample is a blood cell sample,
   (b) providing means for determining an expression profile for a plurality of miRNA and/or other non-coding RNA molecules, wherein said means are:

(i) capture probes, wherein each capture probe comprises a sequence of at least partially complementary nucleotides to each miRNA of the plurality of miRNA or other non-coding RNA molecules, and an elongation sequence, or
(ii) miRNA-specific primers, universal reverse primers and labeled probes to conduct a polymerase chain reaction (c1) determining the expression profile of a plurality of miRNAs and/or other noncoding RNAs in the sample of (a), by:
  (i) hybridizing the miRNAs and/or other non-coding RNA molecules in the sample of (a) with the means of (b)(i), and
  (ii) elongating the miRNAs and/or other non-coding RNA molecules of the sample with labeled nucleotides, and
  (iii) quantifying the labeled hybridized miRNA based on the label, or (c2) determining the expression profile of a plurality of miRNA and/or non-coding RNA molecules by:
  (i) obtaining cDNA samples by an RNA reverse transcription reaction using the miRNA-specific primers of (b)(ii), and
  (ii) amplifying the cDNA via polymerase chain reaction with miRNA-specific forward primers of (b)(ii), universal reverse primers of (b)(ii) and the labeled probe of (b)(ii) complementary to at least a portion of cDNA to be analyzed, and
  (iii) detecting levels of miRNAs on the basis of the labeled probe, (d) providing a plurality of miRNA and/or non-coding RNA reference expression profiles obtained from a plurality of different reference subjects representing a plurality of different conditions, (e) comparing the expression of a predetermined subset of miRNAs and/or other non-coding RNAs of the expression profile determined in step c1 or c2 to a corresponding predetermined subset of miRNAs and/or other non-coding miRNAs of the miRNA and/or non-coding RNA reference expression profiles, wherein said subset of miRNAs is characteristic for a particular condition, and (f) calculating the probability value of said subject for the particular conditions, and (g) optionally repeating steps (e) and (f) for at least one different particular condition, and/or (h) optionally collecting the probability values for the particular condition to diagnose and/or predict the health state of said subject.

10. The method of claim 9, wherein the condition or disease is cancer, a cardiovascular disease, an infectious disease, an inflammatory disease or an autoimmune disease.

11. The method of claim 9, wherein the means of step (c1) are a matrix comprising a plurality of capture probes.

12. The method of claim 9, wherein the means of step (c2) are means to conduct qRT-PCR.

13. The method of claim 9, wherein said blood cell sample is a mixture of erythrocytes, leukocytes and/or thrombocytes.

14. The method of claim 9 wherein the condition or disease is lung cancer, skin cancer, melanoma or multiple sclerosis.

15. The method of claim 9 wherein the predetermined set of miRNAs is representative of melanoma.

* * * * *